United States Patent
Kuehnert et al.

(10) Patent No.: US 10,807,989 B2
(45) Date of Patent: *Oct. 20, 2020

(54) 3-(CARBOXYMETHYL)-8-AMINO-2-OXO-1,3-DIAZA-SPIRO-[4.5]-DECANE DERIVATIVES

(71) Applicant: Grünenthal GmbH, Aachen (DE)

(72) Inventors: Sven Kuehnert, Dueren (DE); Rene Michael Koenigs, Erkelenz (DE); Florian Jakob, Aachen (DE); Achim Kless, Aachen (DE); Paul Ratcliffe, Aachen (DE); Ruth Jostock, Stolberg (DE); Thomas Koch, Stolberg (DE); Klaus Linz, Rheinbach (DE); Wolfgang Schroeder, Aachen (DE); Klaus Schiene, Juechen (DE); Anita Wegert, Aldenhoven (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/454,489

(22) Filed: Jun. 27, 2019

(65) Prior Publication Data

US 2019/0382407 A1 Dec. 19, 2019

Related U.S. Application Data

(63) Continuation of application No. 16/212,723, filed on Dec. 7, 2018, now abandoned, which is a continuation of application No. 15/980,181, filed on May 15, 2018, now abandoned, which is a continuation of application No. 15/405,919, filed on Jan. 13, 2017, now abandoned.

(30) Foreign Application Priority Data

Jan. 13, 2016 (EP) .................................. 16 151 014

(51) Int. Cl.
C07D 487/04 (2006.01)
C07K 5/062 (2006.01)
C07D 417/02 (2006.01)
C07D 413/12 (2006.01)
C07D 413/06 (2006.01)
C07D 409/12 (2006.01)
C07D 405/12 (2006.01)
C07D 405/06 (2006.01)
C07D 403/12 (2006.01)
C07D 403/06 (2006.01)
C07D 401/12 (2006.01)
C07D 401/06 (2006.01)
C07D 235/02 (2006.01)
C07D 417/12 (2006.01)

(52) U.S. Cl.
CPC ......... C07D 487/04 (2013.01); C07D 235/02 (2013.01); C07D 401/06 (2013.01); C07D 401/12 (2013.01); C07D 403/06 (2013.01); C07D 403/12 (2013.01); C07D 405/06 (2013.01); C07D 405/12 (2013.01); C07D 409/12 (2013.01); C07D 413/06 (2013.01); C07D 413/12 (2013.01); C07D 417/12 (2013.01); C07K 5/06026 (2013.01)

(58) Field of Classification Search
None
See application file for complete search history.

(56) References Cited

U.S. PATENT DOCUMENTS

| 5,698,567 | A | 12/1997 | Guillonneau et al. |
|---|---|---|---|
| 7,282,515 | B2 | 10/2007 | Meese et al. |
| 2004/0067930 | A1 | 4/2004 | Bhatti et al. |
| 2004/0192916 | A1 | 9/2004 | Buschmann et al. |
| 2006/0004034 | A1 | 1/2006 | Hinze et al. |
| 2007/0254904 | A1 | 11/2007 | Janssens et al. |
| 2008/0103183 | A1 | 5/2008 | Ackermann et al. |
| 2008/0249122 | A1 | 10/2008 | Bignan et al. |
| 2008/0287478 | A1 | 11/2008 | Hansen et al. |
| 2009/0247530 | A1 | 10/2009 | Nolte et al. |
| 2009/0253727 | A1 | 10/2009 | Goehring et al. |
| 2010/0331353 | A1 | 12/2010 | Schrimpf et al. |
| 2012/0029006 | A1 | 2/2012 | Linz et al. |
| 2017/0197919 | A1 | 7/2017 | Kuehnert et al. |
| 2017/0197947 | A1 | 7/2017 | Kuehnert et al. |
| 2017/0197949 | A1 | 7/2017 | Kuehnert et al. |
| 2017/0197970 | A1 | 7/2017 | Kuehnert et al. |
| 2017/0197971 | A1 | 7/2017 | Kuehnert et al. |
| 2018/0201616 | A1 | 7/2018 | Kuehnert et al. |
| 2018/0282341 | A1 | 10/2018 | Kuehnert et al. |
| 2019/0016735 | A1 | 1/2019 | Smith, II et al. |
| 2019/0016768 | A1 | 1/2019 | Chen et al. |
| 2019/0100497 | A1 | 4/2019 | Kuehnert et al. |
| 2019/0100515 | A1 | 4/2019 | Kuehnert et al. |
| 2019/0106429 | A1 | 4/2019 | Kuehnert et al. |
| 2019/0106430 | A1 | 4/2019 | Kuehnert et al. |
| 2020/0002319 | A1 | 1/2020 | Kuehnert et al. |

FOREIGN PATENT DOCUMENTS

| CL | 2003-02246 | 5/2004 |
|---|---|---|
| CL | 2009-00734 | 5/2009 |
| CL | 2013-00266 | 5/2013 |
| CL | 2018-01899 | 11/2013 |
| CL | 2018-01868 | 8/2018 |

(Continued)

OTHER PUBLICATIONS

Schroeder et al., "Functional plasticity of the N/OFQ-NOP receptor system determines analgesic properties of NOF receptor agonists", British Journal of Pharmacology, Apr. 15, 2014, pp. 3777-3800.

(Continued)

Primary Examiner — Po-Chih Chen
(74) Attorney, Agent, or Firm — Norris McLaughlin, P.A.

(57) ABSTRACT

The invention relates to 3-(carboxymethyl)-8-amino-2-oxo-1,3-diaza-spiro-[4.5]-decane derivatives, their preparation and their use in medicine, particularly in the treatment of pain.

31 Claims, No Drawings

(56) References Cited

FOREIGN PATENT DOCUMENTS

| | | |
|---|---|---|
| CL | 2018-01909 | 10/2018 |
| CL | 2018-01911 | 10/2018 |
| CL | 2018-01912 | 10/2018 |
| CL | 2018-01913 | 10/2018 |
| EP | 1401841 B1 | 8/2005 |
| EP | 1888596 B1 | 11/2006 |
| EP | 1893620 B1 | 11/2006 |
| EP | 2078718 A1 | 7/2009 |
| EP | 2411381 | 9/2010 |
| EP | 2598503 B1 | 2/2012 |
| EP | 2010531 B1 | 11/2017 |
| WO | 2004/043967 A1 | 5/2004 |
| WO | WO 2006/122769 A2 | 11/2006 |
| WO | WO 2006/122770 A1 | 11/2006 |
| WO | WO 2007/000325 A2 | 1/2007 |
| WO | WO 2007/124903 A1 | 11/2007 |
| WO | WO 2008/046758 A2 | 4/2008 |
| WO | 2009/118168 A1 | 10/2009 |
| WO | WO 2010/108651 A1 | 9/2010 |
| WO | 2012/013343 A1 | 2/2012 |
| WO | 2015/192039 A1 | 12/2015 |

OTHER PUBLICATIONS

Witkin et al., "The biology of Nociceptin/Orphanin FQ (N/OFQ) related to obesity, stress, anxiety, mood, and drug dependence", Pharmacology & Therapeutics 141, 2014, pp. 283-299, Elsevier.

Jenck et al., "Orphanin FQ acts as an anxiolytic to attenuate behavioral responses to stress", The National Academy of Sciences, Dec. 1997, pp. 14854-14858, vol. 94.

Mabrouk et al., "Stimulation of ö Opioid Receptor and Blockade of Nociceptin/Orphanin FQ Receptor Synergistically Attenuate Parkinsonism", The Journal of Neuroscience, Sep. 24, 2014, vol. 34, No. 19, pp. 12953-12962.

Pradhan et al., "The delta opioid receptor: an evolving target for the treatment of brain disorders", Trends in Pharmacologic ☐ I Sciences, CE Press, Oct. 2011, pp. 581-590, vol. 32, No. 10.

Gupta et al., "A Systematic Review of the Peripheral Analgesic Effects of Intraarticular Morphine", International Anesthesia Research Society, 2001, pp. 761-770, vol. 93.

Kalso et al., "No pain, no gain: clinical excellence and scientific rigour—lessons learned from IA morphine", International Association for the Study of Pain, 2002, pp. 269-275, vol. 98, Elsevier Science B.V.

Stein et al., "Attacking pain at its source: new perspectives on opioids", Nature Medicine, Aug. 2003, pp. 1003-1008, vol. 9, No. 8, Nature Publishing Group.

Zoellner et al., "Topical Fentanyl in a Randomized, Double-blind Study in Patients With Corneal Damage", Clin J Pain, Oct. 2008, pp. 690-696, vol. 24, No. 8, Lippincott Williams & Wilkins.

Bignan et al., "Recent advances towards the discovery of ORL-1 receptor agonists and antagonists", 2005, pp. 357-388, vol. 15, No. 4, Ashley Publications.

Chu et al.,Synthesis and DNA binding studies of bis-intercalators with a novel spiro-cyclic linker. Tetrahedron, 2006, 62, 5536-5548.

U.S. Appl. No. 15/405,485, filed Jan. 13, 2017.
U.S. Appl. No. 15/405,627, filed Jan. 13, 2017.
U.S. Appl. No. 15/405,896, filed Jan. 13, 2017.
U.S. Appl. No. 15/405,482, filed Jan. 13, 2017.
U.S. Appl. No. 15/923,948, filed Mar. 16, 2018.

Almutairy, B. et. al., "Development and Characterization of a Floating Drug Delivery System prepared via Hot-Melt Extrusion Technology Coupled with Pressurized CO2 for a Thermo-Labile API," University of Mississippi, 2016, AAPS, Nov. 2016.

3-(CARBOXYMETHYL)-8-AMINO-2-OXO-1,3-DIAZA-SPIRO-[4.5]-DECANE DERIVATIVES

This application is a continuation of U.S. Non-Provisional patent application Ser. No. 16/212,723, filed Dec. 7, 2018, which is a continuation of U.S. Non-Provisional patent application Ser. No. 15/980,181, filed May 15, 2018, abandoned, which is a continuation of U.S. Non-Provisional patent application Ser. No. 15/405,919, filed Jan. 13, 2017, abandoned, which claims foreign priority of European Patent Application No. 16 151 014.4, filed Jan. 13, 2016, the disclosures of which are incorporated herein by reference.

The invention relates to 3-(carboxymethyl)-8-amino-2-oxo-1,3-diaza-spiro-[4.5]-decane derivatives, their preparation and use in medicine, particularly in various neurological disorders, including but not limited to pain, neurodegenerative disorders, neuroinflammatory disorders, neuropsychiatric disorders, substance abuse/dependence.

Opioid receptors are a group of Gi/o protein-coupled receptors which are widely distributed in the human body. The opioid receptors are currently subdivided into four major classes, i.e. the three classical opioid receptors mu-opioid (MOP) receptor, kappa-opioid (KOP) receptor, and delta-opioid (DOP) receptor as well as the opioid receptor-like (ORL-1) receptor, which was more recently discovered based on its high homology with said classical opioid receptors. After identification of the endogenous ligand of the ORL-1 receptor, known as nociceptin/orphanin FQ, a highly basic 17 amino acid peptide isolated from tissue extracts in 1995, the ORL-1 receptor was renamed "nociceptin opioid peptide receptor" and abbreviated as "NOP-receptor".

The classical opioid receptors (MOP, KOP and DOP) as well as the NOP receptor are widely distributed/expressed in the human body, including in the brain, the spinal cord, on peripheral sensory neurons and the intestinal tract, wherein the distribution pattern differs between the different receptor classes.

Nociceptin acts at the molecular and cellular level in very much the same way as opioids. However, its pharmacological effects sometimes differ from, and even oppose those of opioids. NOP-receptor activation translates into a complex pharmacology of pain modulation, which, depending on route of administration, pain model and species involved, leads to either pronociceptive or antinociceptive activity. Furthermore, the NOP receptor system is upregulated under conditions of chronic pain. Systemic administration of selective NOP receptor agonists was found to exert a potent and efficacious analgesia in non-human primate models of acute and inflammatory pain in the absence of side effects. The activation of NOP receptors has been demonstrated to be devoid of reinforcing effects but to inhibit opioid-mediated reward in rodents and non-human primates (Review: Schroeder et al, Br J Pharmacol 2014; 171 (16): 3777-3800, and references therein).

Besides the involvement of the NOP receptor in nociception, results from preclinical experiments suggest that NOP receptor agonists might be useful inter alia in the treatment of neuropsychiatric disorders (Witkin et al, Pharmacology & Therapeutics, 141 (2014) 283-299; Jenck et al., Proc. Natl. Acad. Sci. USA 94, 1997, 14854-14858). Remarkably, the DOP receptor is also implicated to modulate not only pain but also neuropsychiatric disorders (Mabrouk et al, 2014; Pradhan et al., 2011).

Strong opioids acting at the MOP receptor site are widely used to treat moderate to severe acute and chronic pain. However, the therapeutic window of strong opioids is limited by severe side effects such as nausea and vomiting, constipation, dizziness, somnolence, respiratory depression, physical dependence and abuse. Furthermore, it is known that MOP receptor agonists show only reduced effectiveness under conditions of chronic and neuropathic pain.

It is known that some of the above mentioned side-effects of strong opioids are mediated by activation of classic opioid-receptors within the central nervous system. Furthermore, peripheral opioid receptors, when activated, can inhibit transmission of nociceptive signals shown in both, clinical and animal studies (Gupta et al., 2001; Kalso et al., 2002; Stein et al., 2003; Zollner et al., 2008).

Thus, to avoid CNS-mediated adverse effects after systemic administration, one approach has been to provide peripherally restricted opioid receptor ligands that do not easily cross the blood-brain barrier and therefore distribute poorly to the central nervous system (see for instance WO 2015/192039). Such peripherally acting compounds might combine effective analgesia with limited side-effects.

Another approach has been to provide compounds which interact with both the NOP receptor and the MOP receptor. Such compounds have for instance been described in WO 2004/043967, WO 2012/013343 and WO 2009/118168.

A further approach has been to provide multi-opioid receptor analgesics that modulate more than one of the opioid receptor subtypes to provide additive or synergistic analgesia and/or reduced side effects like abuse liability or tolerance.

On the one hand, it would be desirable to provide analgesics that selectively act on the NOP receptor system but less pronounced on the classic opioid receptor system, especially MOP receptor system, whereas it would be desirable to distinguish between central nervous activity and peripheral nervous activity. On the other hand, it would be desirable to provide analgesics that act on the NOP receptor system and also to a balanced degree on the MOP receptor system, whereas it would be desirable to distinguish between central nervous activity and peripheral nervous activity.

There is a need for medicaments which are effective in the treatment of pain and which have advantages compared to the compounds of the prior art. Where possible, such medicaments should contain such a small dose of active ingredient that satisfactory pain therapy can be ensured without the occurrence of intolerable treatment-emergent adverse events.

It is an object of the invention to provide pharmacologically active compounds, preferably analgesics that have advantages compared to the prior art.

This object has been achieved by the subject-matter of the patent claims.

A first aspect of the invention relates to 3-(carboxymethyl)-8-amino-2-oxo-1,3-diaza-spiro-[4.5]-decane derivatives according to general formula (I)

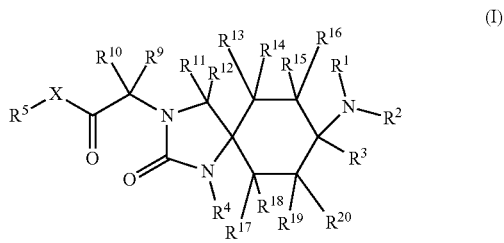

wherein

R¹ and R² independently of one another mean
—H;
—C₁-C₆-alkyl, linear or branched, saturated or unsaturated, unsubstituted or substituted with one, two, three or four substituents independently of one another selected from the group consisting of —F, —Cl, —Br, —I, —OH, —OCH₃, —CN and —CO₂CH₃;
a 3-12-membered cycloalkyl moiety, saturated or unsaturated, unsubstituted or substituted with one, two, three or four substituents independently of one another selected from the group consisting of —F, —Cl, —Br, —I, —OH, —OCH₃, —CN and —CO₂CH₃; wherein said 3-12-membered cycloalkyl moiety is optionally connected through —C₁-C₆-alkylene-, linear or branched, saturated or unsaturated, unsubstituted; or
a 3-12-membered heterocycloalkyl moiety, saturated or unsaturated, unsubstituted or substituted with one, two, three or four substituents independently of one another selected from the group consisting of —F, —Cl, —Br, —I, —OH, —OCH₃, —CN and —CO₂CH₃; wherein said 3-12-membered heterocycloalkyl moiety is optionally connected through —C₁-C₆-alkylene-, linear or branched, saturated or unsaturated, unsubstituted;
or
R¹ and R² together with the nitrogen atom to which they are attached form a ring and mean —(CH₂)₃₋₆—; —(CH₂)₂—O—(CH₂)₂—; or —(CH₂)₂—NR^A—(CH₂)₂—, wherein R^A means —H or —C₁-C₆-alkyl, linear or branched, saturated or unsaturated, unsubstituted or substituted with one, two, three or four substituents independently of one another selected from the group consisting of —F, —Cl, —Br and —I;
preferably with the proviso that R¹ and R² do not simultaneously mean —H;

R³ means
—C₁-C₆-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —C₁-C₆-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted; wherein said 3-12-membered heterocycloalkyl moiety is optionally connected through —C₁-C₆-alkylene-, linear or branched, saturated or unsaturated, unsubstituted, mono- or polysubstituted;
a 6-14-membered aryl moiety, unsubstituted, mono- or polysubstituted; wherein said 6-14-membered aryl moiety is optionally connected through —C₁-C₆-alkylene-, linear or branched, saturated or unsaturated, unsubstituted, mono- or polysubstituted; or
a 5-14-membered heteroaryl moiety, unsubstituted, mono- or polysubstituted; wherein said 5-14-membered heteroaryl moiety is optionally connected through —C₁-C₆-alkylene-, linear or branched, saturated or unsaturated, unsubstituted, mono- or polysubstituted;

R⁴ means
—H;
—C₁-C₆-alkyl, linear or branched, saturated or unsaturated, unsubstituted, mono- or polysubstituted; wherein said —C₁-C₆-alkyl is optionally connected through —C(=O)—, —C(=O)O—, or —S(=O)₂—;
a 3-12-membered cycloalkyl moiety, saturated or unsaturated, unsubstituted, mono- or polysubstituted; wherein said 3-12-membered cycloalkyl moiety is optionally connected through —C₁-C₆-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—CH₂—, or —S(=O)₂—;
a 3-12-membered heterocycloalkyl moiety, saturated or unsaturated, unsubstituted, mono- or polysubstituted; wherein said 3-12-membered heterocycloalkyl moiety is optionally connected through —C₁-C₆-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—CH₂—, or —S(=O)₂—;
a 6-14-membered aryl moiety, unsubstituted, mono- or polysubstituted; wherein said 6-14-membered aryl moiety is optionally connected through —C₁-C₆-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—CH₂—, or —S(=O)₂—; or
a 5-14-membered heteroaryl moiety, unsubstituted, mono- or polysubstituted; wherein said 5-14-membered heteroaryl moiety is optionally connected through —C₁-C₆-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—CH₂—, or —S(=O)₂—;

X means —O—, —S— or —NR⁶—;

R⁵ means
—H;
—C₁-C₆-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —C₁-C₆-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted; wherein said 3-12-membered heterocycloalkyl moiety is optionally connected through —C₁-C₆-alkylene-, linear or branched, saturated or unsaturated, unsubstituted, mono- or polysubstituted;
a 6-14-membered aryl moiety, unsubstituted, mono- or polysubstituted; wherein said 6-14-membered aryl moiety is optionally connected through —C₁-C₆-alkylene-, linear or branched, saturated or unsaturated, unsubstituted, mono- or polysubstituted; or
a 5-14-membered heteroaryl moiety, unsubstituted, mono- or polysubstituted; wherein said 5-14-membered heteroaryl moiety is optionally connected through —C₁-C₆-alkylene-, linear or branched, saturated or unsaturated, unsubstituted, mono- or polysubstituted;

in case X means NR⁶, R⁶ means
—H;
—C₁-C₆-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —C₁-C₆-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted;

wherein said 3-12-membered heterocycloalkyl moiety is optionally connected through —$C_1$-$C_6$-alkylene-, linear or branched, saturated or unsaturated, unsubstituted, mono- or polysubstituted;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

or in case X means $NR^6$, $R^5$ and $R^6$ together with the nitrogen atom to which they are attached form a 3-12-membered heterocycloalkyl moiety, saturated or unsaturated, unsubstituted, mono- or polysubstituted;

$R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —Cl, —Br, —I, —OH, or —$C_1$-$C_6$-alkyl, linear or branched, saturated or unsaturated, unsubstituted, mono- or polysubstituted;

wherein "mono- or polysubstituted" means that one or more hydrogen atoms are replaced by a substituent independently of one another selected from the group consisting of —F, —Cl, —Br, —I, —CN, —$R^{21}$, —C(=O)$R^{21}$, —C(=O)O$R^{21}$, —C(=O)N$R^{21}R^{22}$, —O—($CH_2CH_2$—O)$_{1\text{-}30}$—H, —O—($CH_2CH_2$—O)$_{1\text{-}30}$—$CH_3$, =O, —O$R^{21}$, —OC(=O)$R^{21}$, —OC(=O)O$R^{21}$, —OC(=O)N$R^{21}R^{22}$, —$NO_2$, —N$R^{21}R^{22}$, —N$R^{21}$—($CH_2$)$_{1\text{-}6}$—C(=O)$R^{22}$, —N$R^{21}$—($CH_2$)$_{1\text{-}6}$—C(=O)O$R^{22}$, —N$R^{23}$—($CH_2$)$_{1\text{-}6}$—C(=O)N$R^{21}R^{22}$, —N$R^{21}$C(=O)$R^{22}$, —N$R^{21}$C(=O)—O$R^{22}$, —N$R^{23}$C(=O)N$R^{21}R^{22}$, —N$R^{21}$S(=O)$_2R^{22}$, —S$R^{21}$, —S(=O)$R^{21}$, —S(=O)$_2R^{21}$, —S(=O)$_2$O$R^{21}$, and —S(=O)$_2$N$R^{21}R^{22}$;

wherein $R^{21}$, $R^{22}$ and $R^{23}$ independently of one another mean —H;

—$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —$NH_2$, and —O—$C_1$-$C_6$-alkyl;

a 3-12-membered cycloalkyl moiety, saturated or unsaturated, unsubstituted; wherein said 3-12-membered cycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 3-12-membered heterocycloalkyl moiety, saturated or unsaturated, unsubstituted; wherein said 3-12-membered heterocycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

or $R^{21}$ and $R^{22}$ within —C(=O)N$R^{21}R^{22}$, —OC(=O)N$R^{21}R^{22}$, —N$R^{21}R^{22}$, —N$R^{23}$—($CH_2$)$_{1\text{-}6}$—C(=O)N$R^{21}R^{22}$, —N$R^{23}$C(=O)N$R^{21}R^{22}$, or —S(=O)$_2$N$R^{21}R^{22}$ together with the nitrogen atom to which they are attached form a ring and mean —($CH_2$)$_{3\text{-}6}$—; —($CH_2$)$_2$—O—($CH_2$)$_2$—; or —($CH_2$)$_2$—N$R^B$—($CH_2$)$_2$—, wherein $R^B$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

or a physiologically acceptable salt thereof.

Preferably, aryl includes but is not limited to phenyl and naphthyl. Preferably, heteroaryl includes but is not limited to -1,2-benzodioxole, -pyrazinyl, -pyridazinyl, -pyridinyl, -pyrimidinyl, -thienyl, -imidazolyl, -benzimidazolyl, -thiazolyl, -1,3,4-thiadiazolyl, -benzothiazolyl, -oxazolyl, -benzoxazolyl, -pyrazolyl, -quinolinyl, -isoquinolinyl, -quinazolinyl, -indolyl, -indolinyl, -benzo[c][1,2,5]oxadiazolyl, -imidazo[1,2-a]pyrazinyl, or -1H-pyrrolo[2,3-b]pyridinyl. Preferably, cycloalkyl includes but is not limited to -cyclopropyl, -cyclobutyl, -cyclopentyl and -cyclohexyl. Preferably, heterocycloalkyl includes but is not limited to -aziridinyl, -azetidinyl, -pyrrolidinyl, -piperidinyl, -piperazinyl, -morpholinyl, -sulfamorpholinyl, -oxiridinyl, -oxetanyl, -tetrahydropyranyl, and -pyranyl.

When a moiety is connected through an asymmetric group such as —C(=O)O— or —C(=O)O—$CH_2$—, said asymmetric group may be arranged in either direction. For example, when $R^4$ is connected to the core structure through —C(=O)O—, the arrangement may be either $R^4$—C(=O)O— core or core —C(=O)O—$R^4$.

In preferred embodiments of the compound according to the invention, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —OH, or —$C_1$-$C_6$-alkyl; preferably —H.

In a preferred embodiment of the compound according to the invention, $R^1$ means —H; and $R^2$ means —$C_1$-$C_6$-alkyl, linear or branched, saturated or unsaturated, unsubstituted, mono- or polysubstituted. Preferably, $R^1$ means —H and $R^2$ means —$CH_3$.

In another preferred embodiment of the compound according to the invention, $R^1$ means —$CH_3$; and $R^2$ means —$C_1$-$C_6$-alkyl, linear or branched, saturated or unsaturated, unsubstituted, mono- or polysubstituted. Preferably, $R^1$ means —$CH_3$ and $R^2$ means —$CH_3$.

In still another preferred embodiment of the compound according to the invention, $R^1$ and $R^2$ together with the nitrogen atom to which they are attached form a ring and mean —($CH_2$)$_{3\text{-}6}$—. Preferably, $R^1$ and $R^2$ together with the nitrogen atom to which they are attached form a ring and mean —($CH_2$)$_3$—.

In yet another preferred embodiment, $R^1$ means —H or —$CH_3$; and $R^2$ means a 3-12-membered cycloalkyl moiety, saturated or unsaturated, unsubstituted; wherein said 3-12-membered cycloalkyl moiety is connected through —$CH_2$—, unsubstituted; preferably —$CH_2$-cycloalkyl, —$CH_2$-cyclobutyl or —$CH_2$-cyclopentyl; or $R^2$ means a 3-12-membered heterocycloalkyl moiety, saturated or unsubstituted, unsubstituted; wherein said 3-12-membered heterocycloalkyl moiety is connected through —CH$_2$—, unsubstituted; preferably —CH$_2$-oxetanyl or —CH$_2$-tetrahydrofuranyl.

In a preferred embodiment of the compound according to the invention, R$^3$ means —C$_1$-C$_6$-alkyl, linear or branched, saturated or unsaturated, unsubstituted, mono- or polysubstituted. Preferably, R$^3$ means —C$_1$-C$_6$-alkyl, linear or branched, saturated or unsaturated, unsubstituted or monosubstituted with —OCH$_3$.

In another preferred embodiment of the compound according to the invention, R$^3$ means a 6-14-membered aryl moiety, unsubstituted, mono- or polysubstituted, optionally connected through —C$_1$-C$_6$-alkylene-, linear or branched, saturated or unsaturated, unsubstituted. In a preferred embodiment, R$^3$ means -phenyl unsubstituted, mono- or polysubstituted. More preferably, R$^3$ means -phenyl unsubstituted, mono- or disubstituted with —F, —Cl, —CH$_3$, —CF$_3$, —OH, —OCH$_3$, —OCF$_3$ or —OCH$_2$OCH$_3$, preferably —F. In another preferred embodiment, R$^3$ means -benzyl unsubstituted, mono- or polysubstituted. More preferably, R$^3$ means -benzyl unsubstituted, mono- or disubstituted with —F, —Cl, —CH$_3$, —CF$_3$, —OH, —OCH$_3$, —OCF$_3$ or —OCH$_2$OCH$_3$, preferably —F.

In still another preferred embodiment of the compound according to the invention, R$^3$ means a 5-14-membered heteroaryl moiety, unsubstituted, mono- or polysubstituted. Preferably, R$^3$ means -thienyl or -pyridinyl, in each case unsubstituted, mono- or polysubstituted. More preferably, R$^3$ means -thienyl, -pyridinyl, -imidazolyl or benzimidazolyl, in each case unsubstituted or monosubstituted with —F, —Cl or —CH$_3$.

In a preferred embodiment of the compound according to the invention, R$^4$ means —H.

In another preferred embodiment of the compound according to the invention, R$^4$ means —C$_1$-C$_6$-alkyl, linear or branched, saturated or unsaturated, unsubstituted, mono- or polysubstituted. Preferably, R$^4$ means —C$_1$-C$_6$-alkyl, linear or branched, saturated or unsaturated, unsubstituted or monosubstituted with a substituent selected from the group consisting of —F, —Cl, —Br, —I, —CN, —CF$_3$, —OH, —O—C$_1$-C$_4$-alkyl, —OCF$_3$, —O—(CH$_2$CH$_2$—O)$_{1-30}$—H, —O—(CH$_2$CH$_2$—O)$_{1-30}$—CH$_3$, —OC(=O)C$_1$-C$_4$-alkyl, —C(=O)C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)NHC$_1$-C$_4$-alkylene-CN, —C(=O)NHC$_1$-C$_4$-alkylene-O—C$_1$-C$_4$-alkyl, —C(=O)N(C$_1$-C$_4$-alkyl)$_2$; —S(=O)C$_1$-C$_4$-alkyl, and —S(=O)$_2$C$_1$-C$_4$-alkyl; or with —C(=O)NR$^{21}$R$^{22}$ wherein R$^{21}$ and R$^{22}$ together with the nitrogen atom to which they are attached form a ring and mean —(CH$_2$)$_{3-6}$—, —(CH$_2$)$_2$—O—(CH$_2$)$_2$—, or —(CH$_2$)$_2$—NR$^B$—(CH$_2$)$_2$—, wherein R$^B$ means —H or —C$_1$-C$_6$-alkyl; or with —C(=O)NH-3-12-membered cycloalkyl, saturated or unsaturated, unsubstituted or monosubstituted with —F, —Cl, —Br, —I, —CN, or —OH; or with —C(=O)NH-3-12-membered heterocycloalkyl, saturated or unsaturated, unsubstituted or monosubstituted with —F, —Cl, —Br, —I, —CN, or —OH. More preferably, R$^4$ means —C$_1$-C$_6$-alkyl, linear or branched, saturated or unsaturated, unsubstituted or monosubstituted with —O—C$_1$-C$_4$-alkyl or —C(=O)N(C$_1$-C$_4$-alkyl)$_2$.

In still another preferred embodiment of the compound according to the invention, R$^4$ means a 3-12-membered cycloalkyl moiety, saturated or unsaturated, unsubstituted, mono- or polysubstituted; wherein the 3-12-membered cycloalkyl moiety is connected through —C$_1$-C$_6$-alkylene-, linear or branched, saturated or unsaturated, unsubstituted, mono- or polysubstituted. Preferably, R$^4$ means a 3-12-membered cycloalkyl moiety, saturated or unsaturated, unsubstituted, mono- or polysubstituted; wherein said 3-12-membered cycloalkyl moiety is connected through —CH$_2$— or —CH$_2$CH$_2$—. More preferably, R$^4$ means a 3-12-membered cycloalkyl moiety, saturated or unsaturated, unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said 3-12-membered cycloalkyl moiety is connected through —CH$_2$— or —CH$_2$CH$_2$—.

In a preferred embodiment of the compound according to the invention, R$^4$ means a 3-12-membered heterocycloalkyl moiety, saturated or unsaturated, unsubstituted, mono- or polysubstituted; wherein said 3-12-membered heterocycloalkyl moiety is connected through —C$_1$-C$_6$-alkylene-, linear or branched, saturated or unsaturated, unsubstituted, mono- or polysubstituted. Preferably, R$^4$ means a 3-12-membered heterocycloalkyl moiety, saturated or unsaturated, unsubstituted, mono- or polysubstituted; wherein said 3-12-membered heterocycloalkyl moiety is connected through —CH$_2$— or —CH$_2$CH$_2$—. More preferably, R$^4$ means -oxetanyl, -tetrahydrofuranyl or -tetrahydropyranyl, in each case unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said -oxetanyl, -tetrahydrofuranyl or -tetrahydropyranyl is connected through —CH$_2$— or —CH$_2$CH$_2$—.

In yet another preferred embodiment of the compound according to the invention, R$^4$ means a 6-14-membered aryl moiety, unsubstituted, mono- or polysubstituted; wherein said 6-14-membered aryl moiety is connected through —C$_1$-C$_6$-alkylene-, linear or branched, saturated or unsaturated, unsubstituted, mono- or polysubstituted. Preferably, R$^4$ means -phenyl, unsubstituted, mono- or polysubstituted; wherein said -phenyl is connected through —CH$_2$— or —CH$_2$CH$_2$—. More preferably, R$^4$ means -phenyl, unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$-C$_4$-alkyl, —C(=O)NH$_2$, —C(=O)NHC$_1$-C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said -phenyl is connected through —CH$_2$— or —CH$_2$CH$_2$—.

In a further preferred embodiment of the compound according to the invention, R$^4$ means a 5-14-membered heteroaryl moiety, unsubstituted, mono- or polysubstituted; wherein said 5-14-membered heteroaryl moiety is connected through —C$_1$-C$_6$-alkylene-, linear or branched, saturated or unsaturated, unsubstituted, mono- or polysubstituted. Preferably, R$^4$ means a 5-14-membered heteroaryl moiety, unsubstituted, mono- or polysubstituted; wherein said -phenyl is connected through —CH$_2$— or —CH$_2$CH$_2$—. More preferably, R$^4$ means -pyridinyl, -pyrimidinyl, -pyrazinyl, or -pyrazolinyl, in each case unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$—C$_4$-alkyl, —C(=O)NH$_2$, —C(=O)NHC$_1$—C$_4$-alkyl, —C(=O)N(C$_1$-C$_4$-alkyl)$_2$, —S(=O)C$_1$-C$_4$-alkyl and —S(=O)$_2$C$_1$-C$_4$-alkyl; wherein said -pyridinyl, -pyrimidinyl, -pyrazinyl, or -pyrazolinyl is connected through —CH$_2$— or —CH$_2$CH$_2$—.

In a preferred embodiment of the compound according to the invention, R$^5$ means —H.

In another preferred embodiment of the compound according to the invention, R$^5$ means —C$_1$-C$_6$-alkyl, linear or branched, saturated or unsaturated, unsubstituted, mono- or polysubstituted. Preferably, R$^5$ means —C$_1$-C$_6$-alkyl, linear or branched, saturated, unsubstituted, mono- or polysubstituted. More preferably, R$^5$ means —C$_1$-C$_6$-alkyl, linear or branched, unsubstituted or monosubstituted with a substituent selected from the group consisting of —F, —Cl, —Br, —I, —CN, —OH, —O—C$_1$-C$_4$-alkyl, —C(=O)OH, —C(=O)OC$_1$—C$_4$-alkyl, —C(=O)NH$_2$, —C(=O)NHC$_1$—C$_4$-alkyl, —C(=O)N(C$_1$-C$_4$-alkyl)$_2$, —S(=O)C$_1$-C$_4$-alkyl, —S(=O)$_2$C$_1$-C$_4$-alkyl, —C(=O)—C$_{3-12}$heterocycloalkyl, —NH—C(=O)—C$_1$-C$_4$-alkyl, —N(C$_1$-C$_4$-alkyl)$_2$ and NH—S(=O)$_2$—C$_1$-C$_4$-alkyl.

In still another preferred embodiment of the compound according to the invention, R$^5$ means a 3-12-membered cycloalkyl moiety, saturated or unsaturated, unsubstituted, mono- or polysubstituted, wherein said 3-12-membered cycloalkyl moiety is optionally connected through —C$_1$-C$_6$-alkylene-, linear or branched, saturated or unsaturated, unsubstituted, mono- or polysubstituted. Preferably, R$^5$ means a 3-6-membered cycloalkyl moiety, saturated, unsubstituted, mono- or polysubstituted, wherein said 3-12-membered cycloalkyl moiety is optionally connected through —C$_1$-C$_6$-alkylene-, linear or branched, saturated, unsubstituted; more preferably -cyclopropyl, -cyclobutyl, -cyclopentyl or -cyclohexyl, unsubstituted or monosubstituted with —F, —OH, —CN or —C$_1$-C$_4$-alkyl, wherein said -cyclopropyl, -cyclobutyl -cyclopentyl or -cyclohexyl is optionally connected through —CH$_2$— or —CH$_2$CH$_2$—.

In a preferred embodiment of the compound according to the invention, R$^5$ means a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted, mono- or polysubstituted. Preferably, R$^5$ means a 4-6-membered heterocycloalkyl moiety, saturated or unsaturated, unsubstituted, mono- or polysubstituted. More preferably, R$^5$ means -heterocyclobutyl or -tetrahydro-2H-thiopyranyl dioxide, unsubstituted.

In yet another preferred embodiment of the compound according to the invention, R$^5$ means a 5-14-membered heteroaryl moiety, unsubstituted, mono- or polysubstituted; wherein said 5-14-membered heteroaryl moiety is optionally connected through —C$_1$-C$_6$-alkylene-, linear or branched, saturated or unsaturated, unsubstituted, mono- or polysubstituted. Preferably, R$^5$ means a 5-6-membered heteroaryl moiety, unsubstituted, mono- or polysubstituted, wherein said 5-6-membered heteroaryl moiety is optionally connected through —CH$_2$—. More preferably, R$^5$ means a 5-6-membered heteroaryl moiety, unsubstituted or substituted with one, two, three or four substituents independently of one another selected from the group consisting of —F, —Cl, —Br, —I, —CN, —OH, —C$_1$-C$_4$-alkyl, —O—C$_1$-C$_4$-alkyl, —C(=O)OH, —C(=O)OC$_1$—C$_4$-alkyl, —C(=O)NH$_2$, —C(=O)NHC$_1$—C$_4$-alkyl, —C(=O)N(C$_1$-C$_4$-alkyl)$_2$, —S(=O)C$_1$-C$_4$-alkyl, —S(=O)$_2$C$_1$-C$_4$-alkyl and —S—C$_1$-C$_4$-alkyl, wherein said 5-6-membered heteroaryl moiety is optionally connected through —CH$_2$—. Still more preferably, R$^5$ means -oxazolyl, -isoxazolyl, -pyrazolyl, -pyridinyl, -pyridazinyl, -pyrazinyl, -thiazolyl, -thiadiazolyl, -imidazolyl or -pyrimidinyl, in each case unsubstituted or substituted with one, two, three or four substituents independently of one another selected from the group consisting of —F, —Cl, Br, —I, —CN, —OH, —C$_1$-C$_4$-alkyl, —O—C$_1$-C$_4$-alkyl, —C(=O)OH, —C(=O)OC$_1$—C$_4$-alkyl, —C(=O)NH$_2$, —C(=O)NHC$_1$—C$_4$-alkyl, —C(=O)N(C$_1$-C$_4$-alkyl)$_2$, S(=O)C$_1$-C$_4$-alkyl, —S(=O)$_2$C$_1$-C$_4$-alkyl and —S—C$_1$-C$_4$-alkyl, wherein said -oxazolyl, -isoxazolyl, -pyrazolyl, -pyridinyl, -pyridazinyl, -pyrazinyl, -thiazolyl, -thiadiazolyl, -imidazolyl or -pyrimidinyl is optionally connected through —CH$_2$—.

In a further preferred embodiment of the compound according to the invention, R$^5$ means a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted, mono- or polysubstituted. Preferably, R$^5$ means -phenyl, unsubstituted or substituted with one, two, three or four substituents independently of one another selected from the group consisting of —F, —Cl, Br, —I, —CN, —OH, —C$_1$-C$_4$-alkyl, —O—C$_1$-C$_4$-alkyl, —C(=O)OH, —C(=O)OC$_1$—C$_4$-alkyl, —C(=O)NH$_2$, —C(=O)NHC$_1$—C$_4$-alkyl, —C(=O)N(C$_1$-C$_4$-alkyl)$_2$, S(=O)C$_1$-C$_4$-alkyl, —S(=O)$_2$C$_1$-C$_4$-alkyl and —S—C$_1$-C$_4$-alkyl, wherein said -phenyl is optionally connected through —CH$_2$—.

In a preferred embodiment of the compound according to the invention, X means NR$^6$ and R$^5$ and R$^6$ together with the nitrogen atom to which they are attached form a 3-12-membered heterocycloalkyl moiety, saturated or unsaturated, unsubstituted, mono- or polysubstituted. Preferably, X means NR$^6$ and R$^5$ and R$^6$ together with the nitrogen atom to which they are attached form a 5-6-membered heterocycloalkyl moiety, saturated or unsaturated, unsubstituted, mono- or polysubstituted. More preferably, X means NR$^6$ and R$^5$ and R$^6$ together with the nitrogen atom to which they are attached form -pyrrolidinyl, -piperidinyl, -piperazinyl, -morpholinyl, -thiomorpholinyl, -thiomorpholinyl dioxide or -(methylsulfonyl)piperazinyl, in each case unsubstituted or substituted with one, two, three or four substituents independently of one another selected from the group consisting of =O, —OH, —CH$_2$—OH and —C(=O)NH$_2$, wherein said -pyrrolidinyl, -piperidinyl, piperazinyl, -morpholinyl, -thiomorpholinyl, -thiomorpholinyl dioxide or -(methylsulfonyl)piperazinyl is optionally condensed with an imidazole moiety, unsubstituted.

In a preferred embodiment of the compound according to the invention R$^5$ means

—H;

—C$_1$-C$_6$-alkyl, linear or branched, saturated or unsaturated, unsubstituted or substituted with one, two, three or four substituents independently of one another selected from the group consisting of —F, —Cl, —Br, —I, —CN, —O—CH$_3$, —O—(CH$_2$—CH$_2$—O)$_{1-10}$—H, —O—(CH$_2$CH$_2$—O)$_{1-10}$—CH$_3$, —C(=O)OH, —C(=O)OCH$_3$, —C(=O)NH$_2$, —C(=O)NHCH$_3$, —C(=O)N(CH$_3$)$_2$, —OH, —S(=O)CH$_3$, —S(=O)$_2$CH$_3$, unsubstituted —C(=O)-morpholinyl, —NH—C(=O)—CH$_3$, —N(CH$_3$)$_2$ and NH—S(=O)$_2$—CH$_3$;

-cyclopropyl, -cyclobutyl, -cyclopentyl or -cyclohexyl, unsubstituted or monosubstituted with —F, —OH, —CN or —CH₃, wherein said -cyclopropyl, -cyclobutyl, cyclopentyl or cyclohexyl is optionally connected through —CH₂— or —CH₂CH₂—;

-heterocyclobutyl, -heterocyclopentyl, or -heterocyclohexyl, in each case unsubstituted or substituted with one, two, three or four substituents independently of one another selected from the group consisting of —F, —Cl, —Br, —I, —CN, —O—CH₃, —O—(CH₂—CH₂—O)₁₋₁₀—H, —O—(CH₂CH₂—O)₁₋₁₀—CH₃, —C₁-C₄-alkyl, —C(=O)OH, —C(=O)OCH₃, —C(=O)NH₂, —C(=O)NHCH₃, —C(=O)N(CH₃)₂, =O, —OH, —SCH₃, —S(=O)CH₃, —S(=O)₂CH₃, unsubstituted —C(=O)-morpholinyl, —NH—C(=O)—CH₃, —N(CH₃)₂ and NH—S(=O)₂—CH₃; wherein said -heterocyclobutyl, -heterocyclopentyl, or -heterocyclohexyl is optionally connected through —CH₂— or —CH₂CH₂—;

-oxazolyl, -isoxazolyl, -pyrazolyl, -pyridinyl, -pyridazinyl, -pyrazinyl, -thiazolyl, -thiadiazolyl, -imidazolyl, -pyrimidinyl, or 5,6,7,8-tetrahydro-[1,2,4]triazolo[1,5-a]pyrazine, in each case unsubstituted or substituted with one, two, three or four substituents independently of one another selected from the group consisting of —F, —Cl, Br, —I, —CN, —OH, —CH₃, —O—CH₃, —C(=O)OH, —C(=O)OCH₃, —C(=O)NH₂, —C(=O)NHCH₃, —C(=O)N(CH₃)₂, S(=O)CH₃, —S(=O)₂CH₃ and —S—CH₃, wherein said -oxazolyl, -isoxazolyl, -pyrazolyl, -pyridinyl, -pyridazinyl, -pyrazinyl, -thiazolyl, -thiadiazolyl, -imidazolyl, -pyrimidinyl, or 5,6,7,8-tetrahydro-[1,2,4]triazolo[1,5-a]pyrazine is optionally connected through —CH₂—; or -phenyl, unsubstituted or substituted with one, two, three or four substituents independently of one another selected from the group consisting of —F, —Cl, Br, —I, —CN, —OH, —CH₃, —O—CH₃, —C(=O)OH, —C(=O)OCH₃, —C(=O)NH₂, —C(=O)NHCH₃, —C(=O)N(CH₃)₂, S(=O)CH₃, —S(=O)₂CH₃ and —S—CH₃, wherein said -phenyl is optionally connected through —CH₂—;

in case X means NR⁶, R⁶ means —H or —CH₃;

or in case X means NR⁶, R⁵ and R⁶ together with the nitrogen atom to which they are attached form a -pyrrolidinyl, -piperidinyl, -piperazinyl, -morpholinyl, -thiomorpholinyl, -thiomorpholinyl dioxide or -(methylsulfonyl)piperazinyl, in each case unsubstituted or substituted with one, two, three or four substituents independently of one another selected from the group consisting of =O, —OH, —CH₂—OH, —C(=O)NH₂, and —S(=O)₂CH₃, wherein said -pyrrolidinyl, -piperidinyl, -piperazinyl, -morpholinyl, -thiomorpholinyl, -thiomorpholinyl dioxide or -(methylsulfonyl) piperazinyl is optionally condensed with an imidazole moiety, unsubstituted;

In a preferred embodiment of the compound according to the invention, X means NR⁶ and R⁶ means —H or —C₁-C₆-alkyl, linear or branched, saturated or unsaturated, unsubstituted, mono- or polysubstituted. Preferably, R⁶ means —H or —CH₃.

In preferred embodiments, the compound according to the invention has a structure according to any of general formulas (II-A) to (VIII-C):

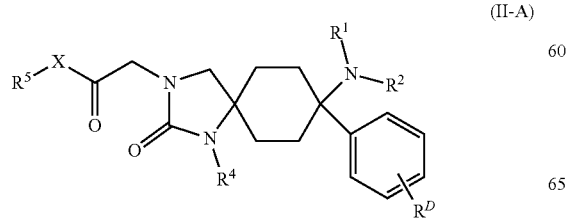
(II-A)

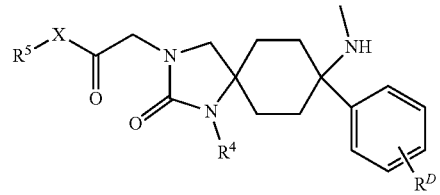
(II-B)

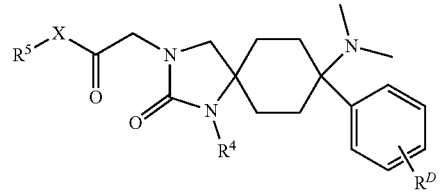
(II-C)

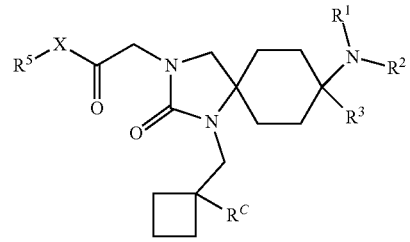
(III-A)

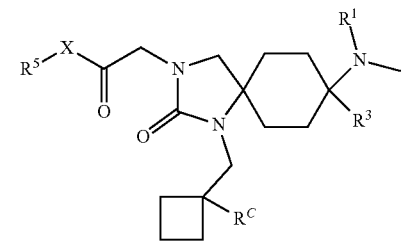
(III-B)

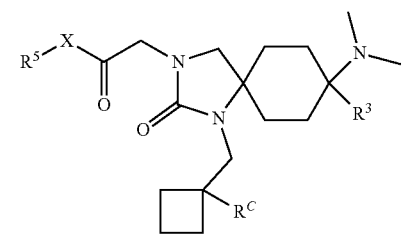
(III-C)

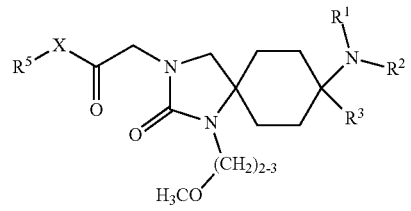
(IV-A)

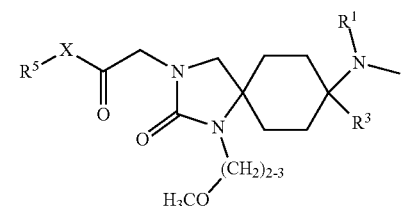
(IV-B)

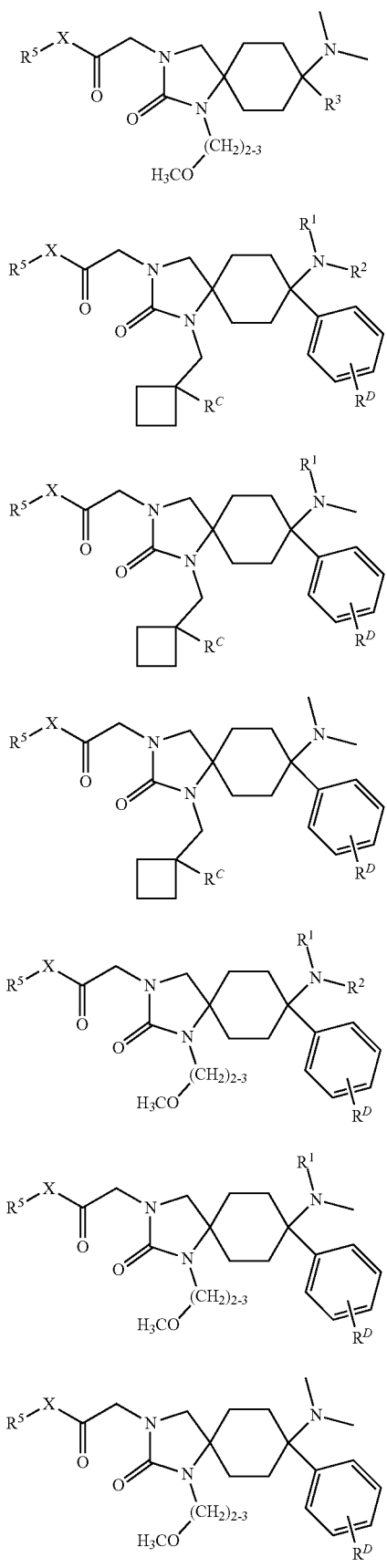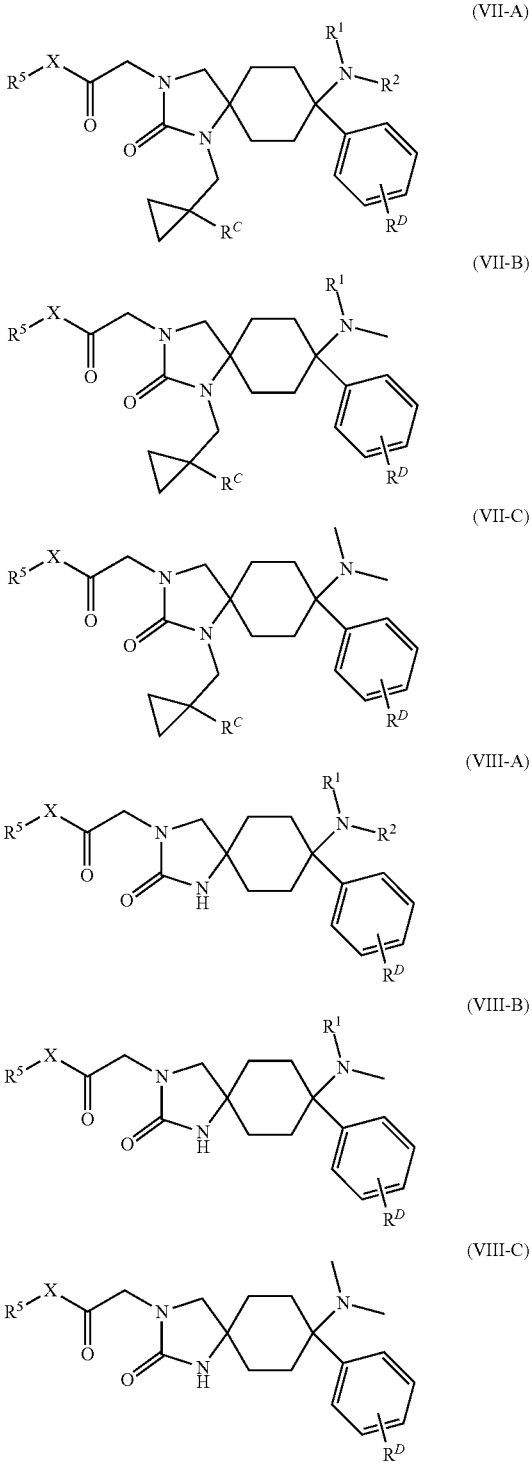
wherein in each case
$R^1$, $R^2$, $R^3$, $R^4$, $R^5$, $R^6$ and X are defined as above,
$R^C$ means —H, —OH, —F, —CN or —$C_1$-$C_4$-alkyl;
$R^D$ means —H or —F;
or a physiologically acceptable salt thereof.
Preferably, the substructure of the compounds according to general formula (I) represented by $R^5$, X, $R^9$ and $R^{10}$, i.e.

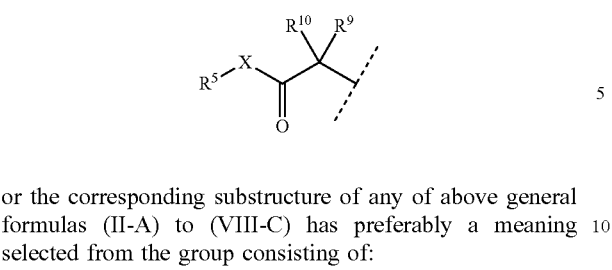
or the corresponding substructure of any of above general formulas (II-A) to (VIII-C) has preferably a meaning selected from the group consisting of:
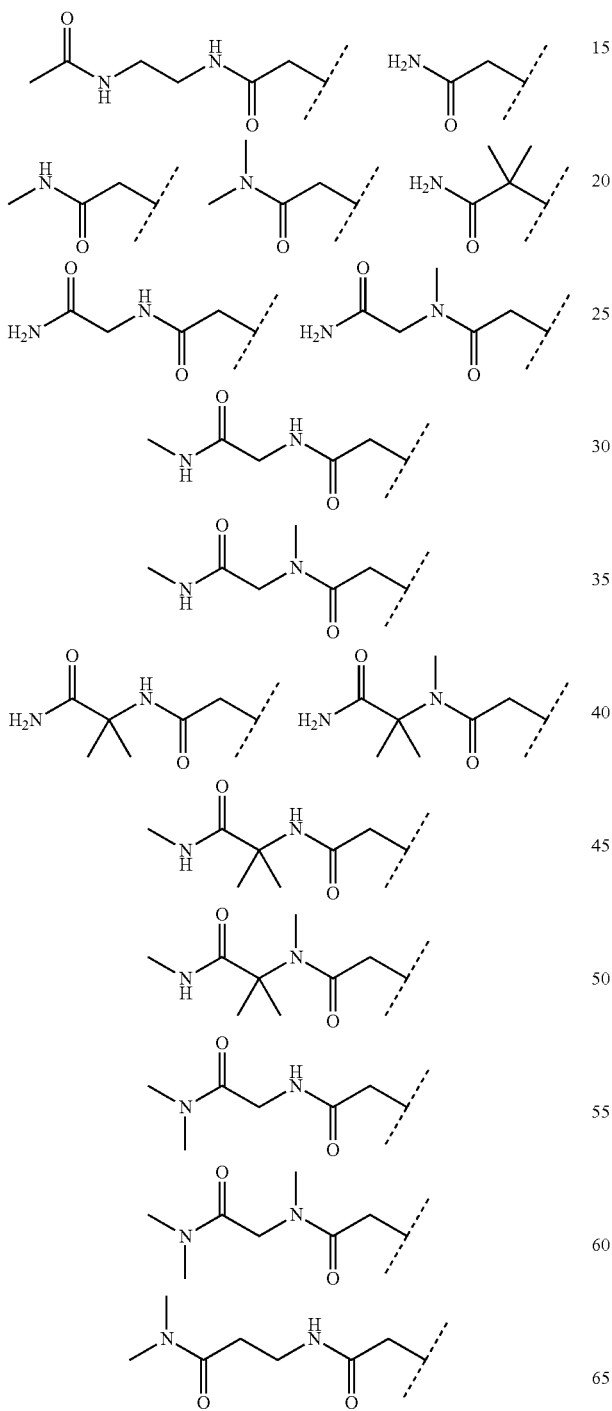
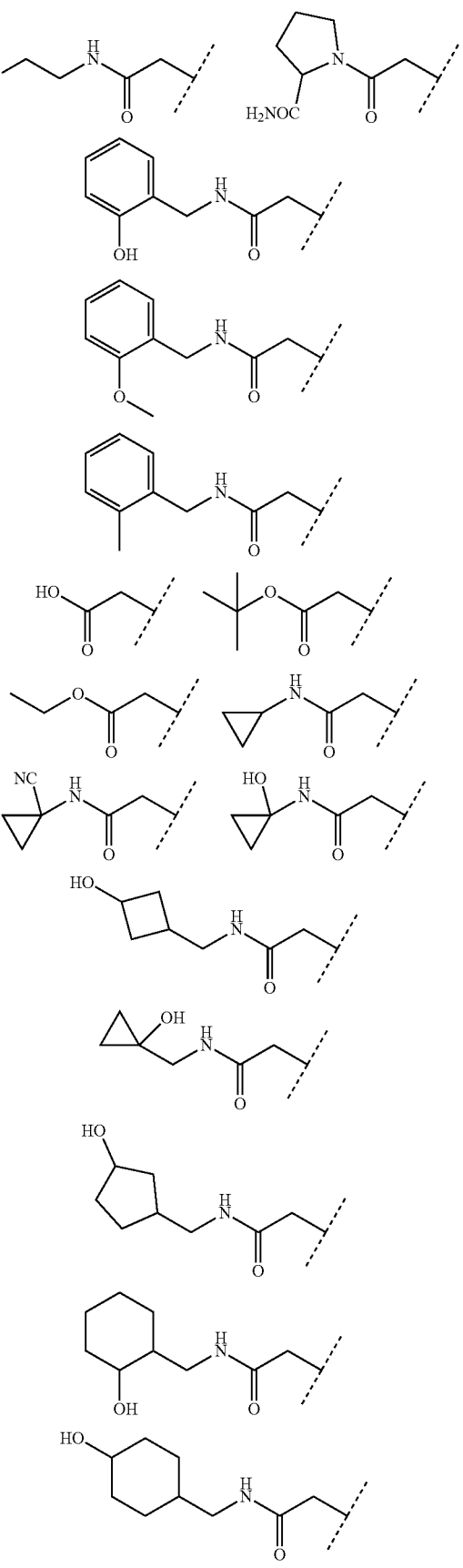

17
-continued
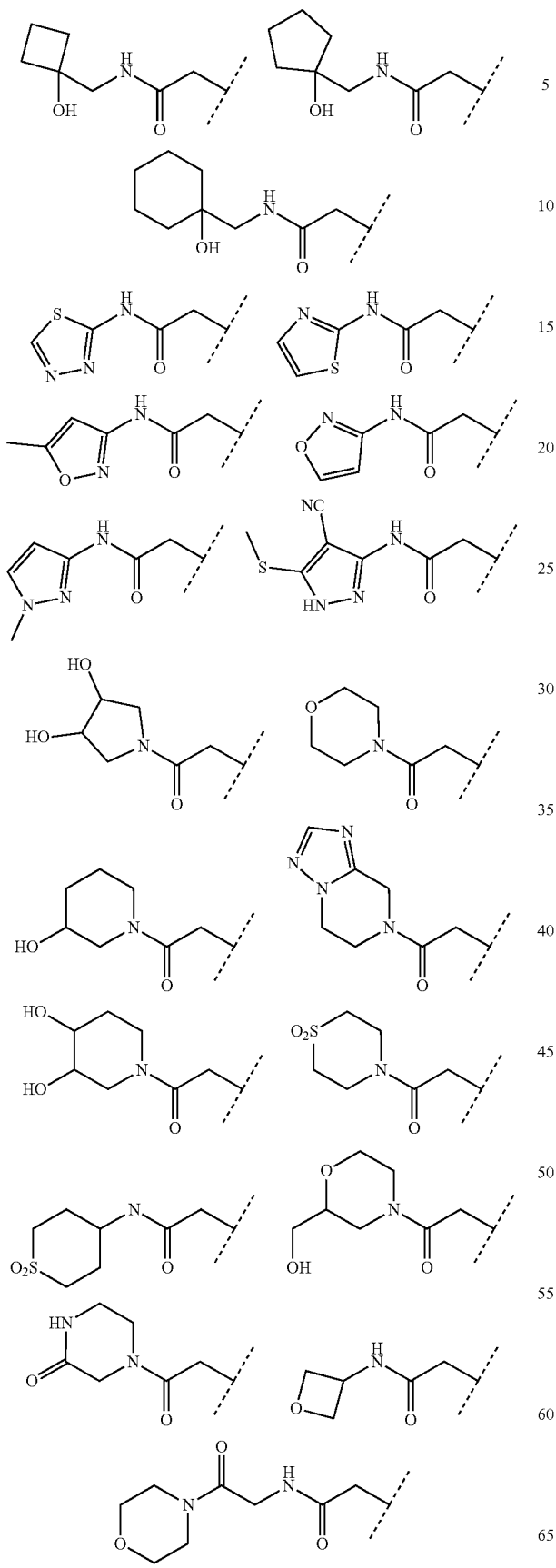
18
-continued
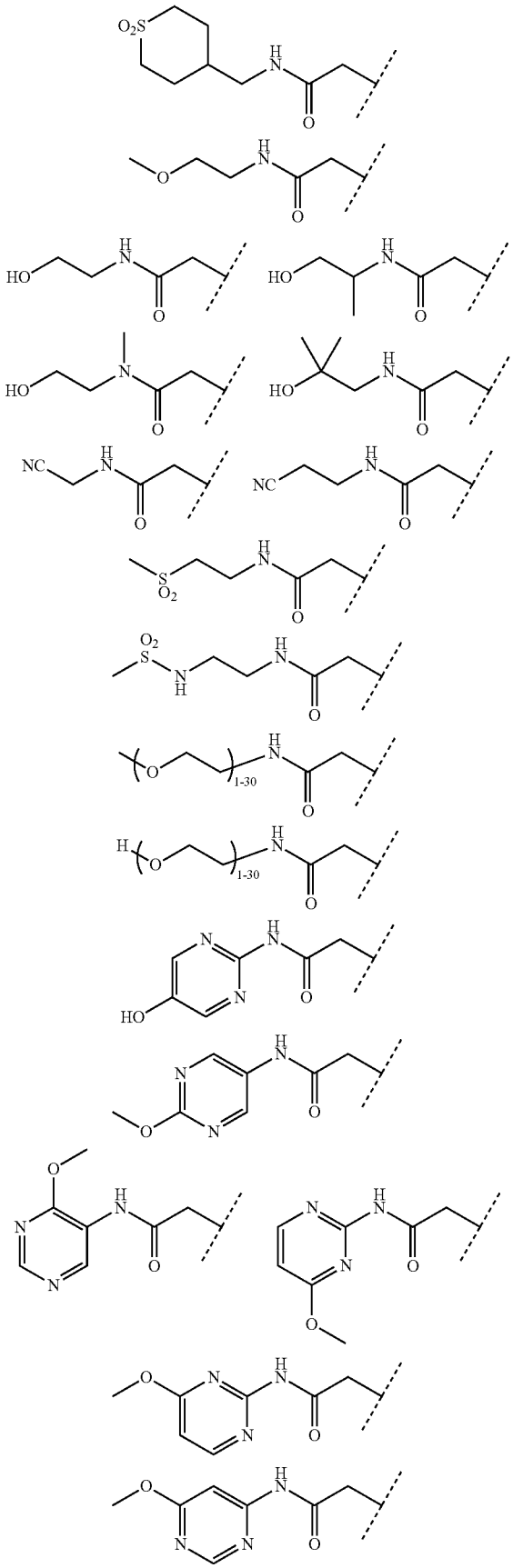

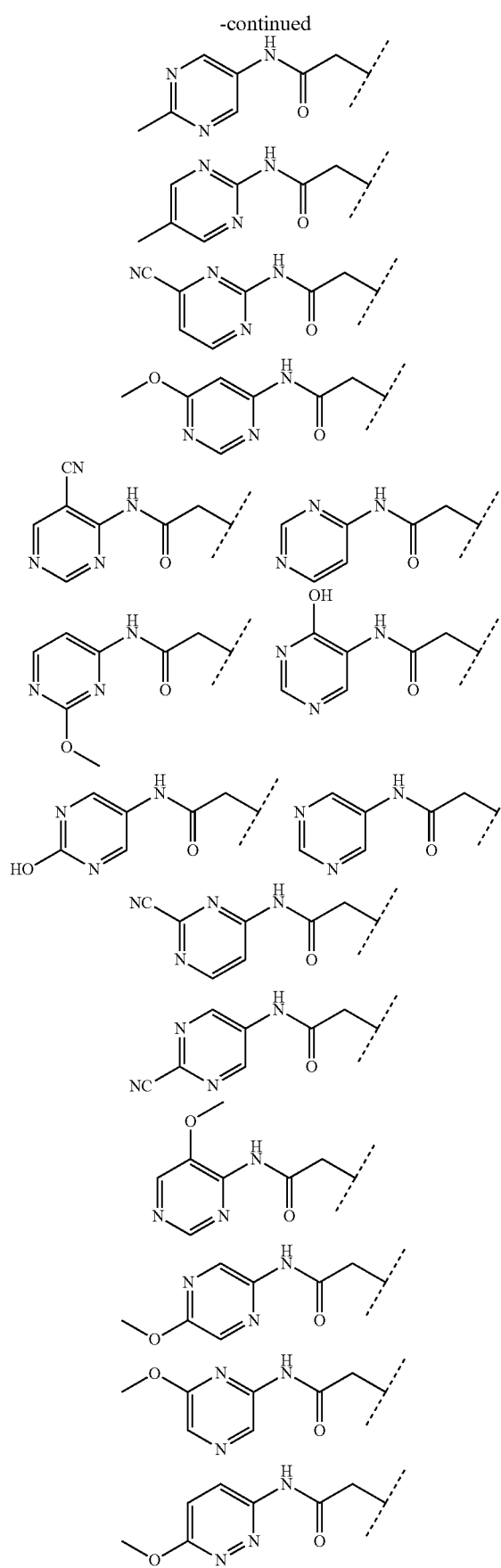
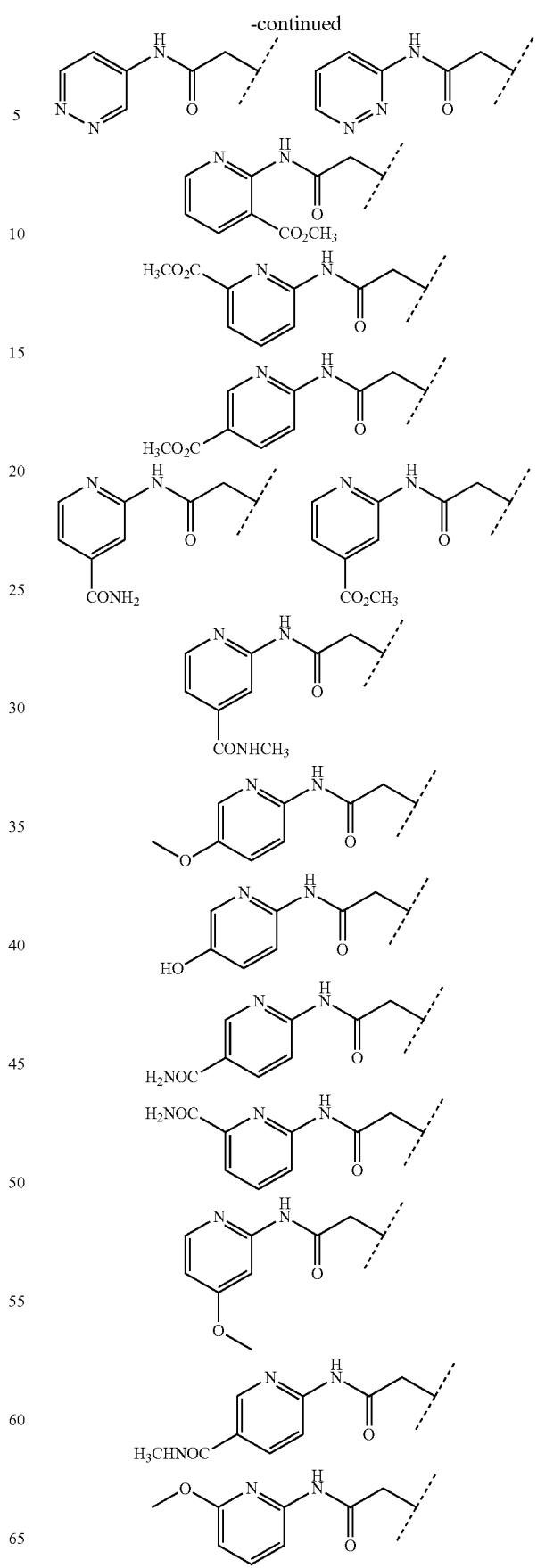

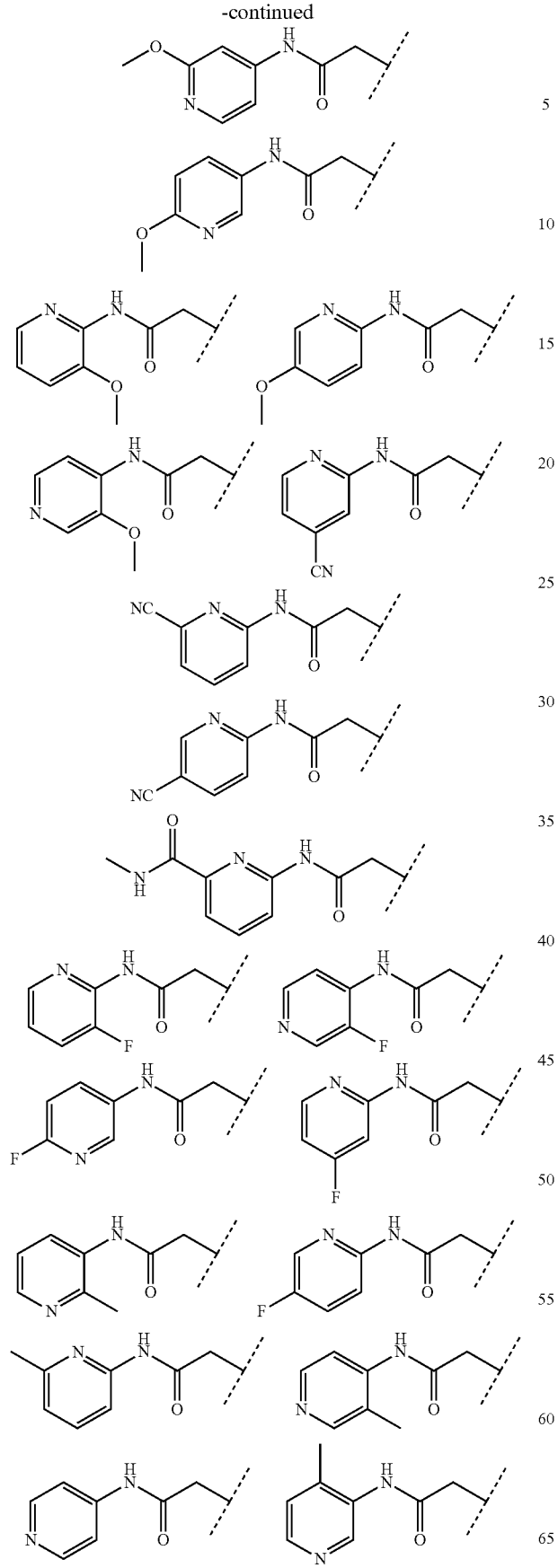
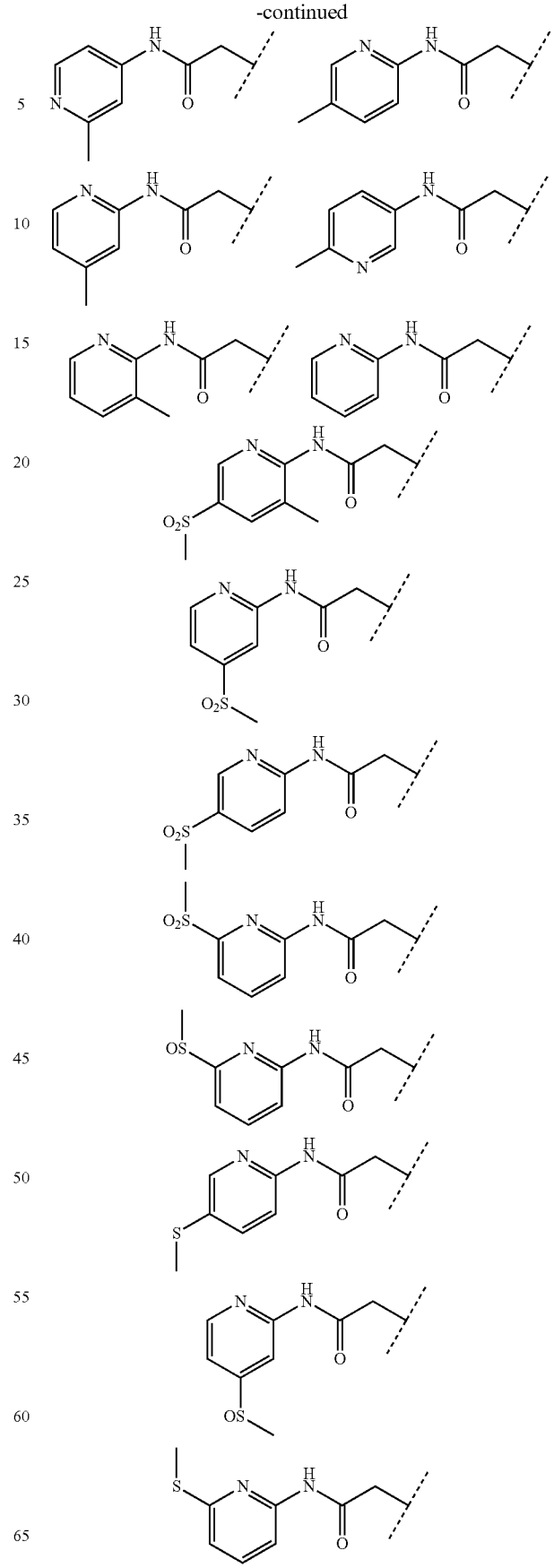

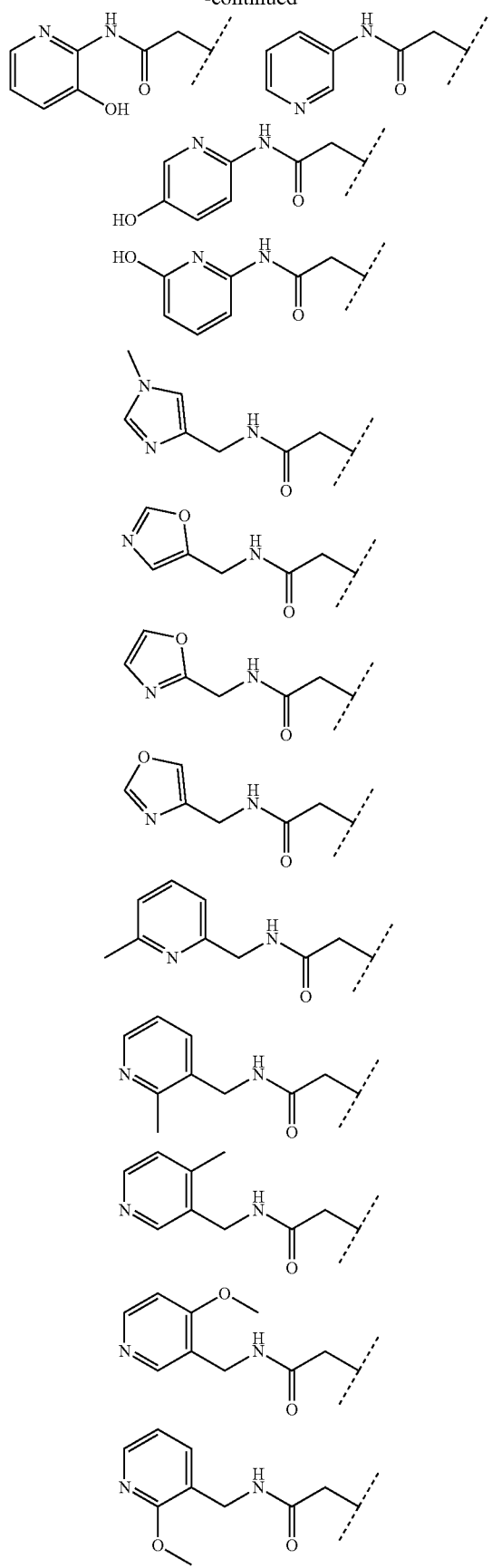
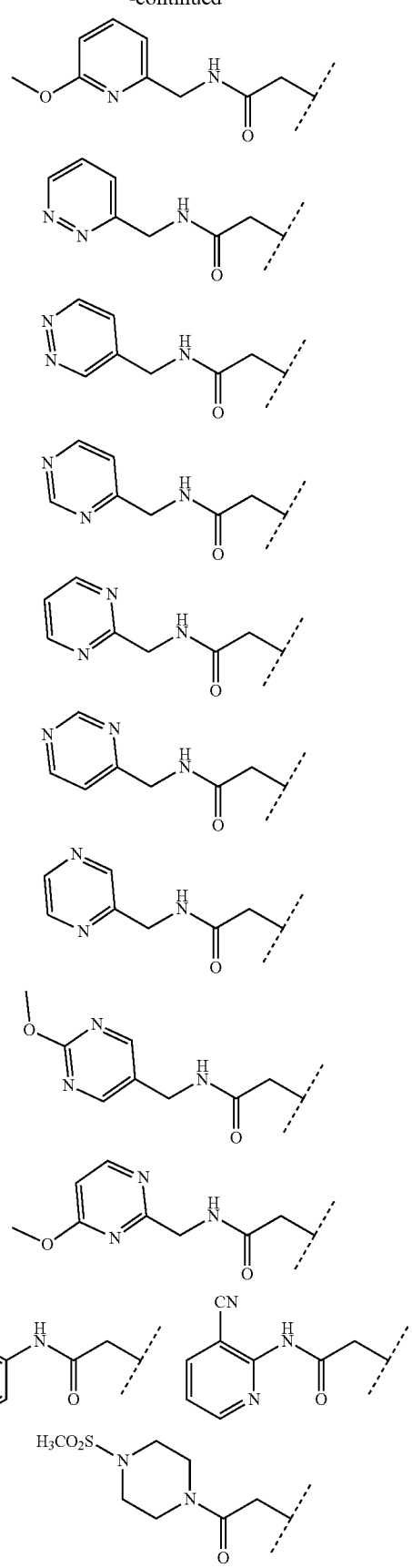

In a particularly preferred embodiment of the compound according to the invention $R^1$ means —H or —$CH_3$;
$R^2$ means —$CH_3$, —$CH_2CH_3$ or —$CH_2$—C(H)($CH_3$)$_2$;
$R^3$ means -phenyl, -thienyl or -pyridinyl, in each case unsubstituted or monosubstituted with —F;
$R^4$ means
—H;
—$C_1$-$C_6$-alkyl, linear or branched, saturated, unsubstituted or substituted with one, two, three or four substituents independently of one another selected from the group consisting of —F, —Cl, —Br, —I, —CN, —OH, =O, —N($CH_3$)$_2$ and —O—$CH_3$; or
-cyclopropyl, -cyclobutyl, -cyclopentyl or -cyclohexyl, unsubstituted or monosubstituted with —F, —OH, —CN or —$CH_3$, wherein said -cyclopropyl, -cyclobutyl, -cyclopentyl or -cyclohexyl is connected through —$CH_2$— or —$CH_2CH_2$—;
-oxetanyl unsubstituted or monosubstituted with —F, —OH, —CN or —$CH_3$, wherein said -oxetanyl is connected through —$CH_2$— or —$CH_2CH_2$—;
X means —O— or —$NR^6$—;
$R^5$ means
—H;
—$C_1$-$C_6$-alkyl, linear or branched, saturated or unsaturated, unsubstituted or substituted with one, two, three or four substituents independently of one another selected from the group consisting of —F, —Cl, —Br, —I, —CN, —O—$CH_3$, —O—($CH_2$—$CH_2$—O)$_{1-10}$—H, —O—($CH_2CH_2$—O)$_{1-10}$—$CH_3$, —C(=O)OH, —C(=O)O$CH_3$, —C(=O)NH$_2$, —C(=O)NHCH$_3$, —C(=O)N($CH_3$)$_2$, —OH, —S(=O)$CH_3$, —S(=O)$_2CH_3$, unsubstituted —C(=O)-morpholinyl, —NH—C(=O)—$CH_3$, —N($CH_3$)$_2$ and NH—S(=O)$_2$—$CH_3$;
-cyclopropyl, -cyclobutyl, -cyclopentyl or -cyclohexyl, unsubstituted or monosubstituted with —F, —OH, —CN or —$CH_3$, wherein said -cyclopropyl, -cyclobutyl, cyclopentyl or cyclohexyl is optionally connected through —$CH_2$— or —$CH_2CH_2$—;
-heterocyclobutyl, -heterocyclopentyl, or -heterocyclohexyl, in each case unsubstituted or substituted with one, two, three or four substituents independently of one another selected from the group consisting of —F, —Cl, —Br, —I, —CN, —O—$CH_3$, —O—($CH_2$—$CH_2$—O)$_{1-10}$—H, —O—($CH_2CH_2$—O)$_{1-10}$—$CH_3$, —$C_1$-$C_4$-alkyl, —C(=O)OH, —C(=O)O$CH_3$, —C(=O)NH$_2$, —C(=O)NHCH$_3$, —C(=O)N($CH_3$)$_2$, =O, —OH, —S$CH_3$, —S(=O)$CH_3$, —S(=O)$_2CH_3$, unsubstituted —C(=O)-morpholinyl, —NH—C(=O)—$CH_3$, —N($CH_3$)$_2$ and NH—S(=O)$_2$—$CH_3$; wherein said -heterocyclobutyl, -heterocyclopentyl, or -heterocyclohexyl is optionally connected through —$CH_2$— or —$CH_2CH_2$—;
-oxazolyl, -isoxazolyl, -pyrazolyl, -pyridinyl, -pyridazinyl, -pyrazinyl, -thiazolyl, -thiadiazolyl, -imidazolyl, -pyrimidinyl, or 5,6,7,8-tetrahydro-[1,2,4]triazolo[1,5-a]pyrazine, in each case unsubstituted or substituted with one, two, three or four substituents independently of one another selected from the group consisting of —F, —Cl, Br, —I, —CN, —OH, —$CH_3$, —O—$CH_3$, —C(=O)OH, —C(=O)O$CH_3$, —C(=O)NH$_2$, —C(=O)NHCH$_3$, —C(=O)N($CH_3$)$_2$, S(=O)$CH_3$, —S(=O)$_2CH_3$ and —S—$CH_3$, wherein said -oxazolyl, -isoxazolyl, -pyrazolyl, -pyridinyl, -pyridazinyl, -pyrazinyl, -thiazolyl, -thiadiazolyl, -imidazolyl, -pyrimidinyl, or 5,6,7,8-tetrahydro-[1,2,4]triazolo[1,5-a]pyrazine is optionally connected through —$CH_2$—; or
-phenyl, unsubstituted or substituted with one, two, three or four substituents independently of one another selected from the group consisting of —F, —Cl, Br, —I, —CN, —OH, —$CH_3$, —O—$CH_3$, —C(=O)OH, —C(=O)O$CH_3$, —C(=O)NH$_2$, —C(=O)NHCH$_3$, —C(=O)N($CH_3$)$_2$, S(=O)$CH_3$, —S(=O)$_2CH_3$ and —S—$CH_3$, wherein said -phenyl is optionally connected through —$CH_2$—;
in case X means $NR^6$, $R^6$ means —H or —$CH_3$;
or in case X means $NR^6$, $R^5$ and $R^6$ together with the nitrogen atom to which they are attached form a -pyrrolidinyl, -piperidinyl, -piperazinyl, -morpholinyl, -thiomorpholinyl, -thiomorpholinyl dioxide or -(methylsulfonyl)piperazinyl, in each case unsubstituted or substituted with one, two, three or four substituents independently of one another selected from the group consisting of =O, —OH, —$CH_2$—OH, —C(=O)NH$_2$, and —S(=O)$_2CH_3$, wherein said -pyrrolidinyl, -piperidinyl, -piperazinyl, -morpholinyl, -thiomorpholinyl, -thiomorpholinyl dioxide or -(methylsulfonyl)piperazinyl is optionally condensed with an imidazole moiety, unsubstituted; and
$R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ mean —H.

In a particularly preferred embodiment of the compound according to the invention
$R^1$ means —H or —$CH_3$; and/or
$R^2$ means —$CH_3$, —$CH_2CH_3$ or —$CH_2$—C(H)($CH_3$)$_2$; and/or
$R^3$ means -phenyl, -thienyl or -pyridinyl, in each case unsubstituted; preferably, $R^3$ means phenyl unsubstituted; and/or
$R^4$ means
—H;
—$C_1$-$C_6$-alkyl, linear or branched, saturated, unsubstituted or substituted with one, two, three or four substituents independently of one another selected from the group consisting of —F, —Cl, —Br, —I, —CN, —OH, =O, —N($CH_3$)$_2$ and —O—$CH_3$; or -cyclopropyl, -cyclobutyl, -cyclopentyl or -cyclohexyl, unsubstituted or monosubstituted with —F, —OH, —CN or —CH$_3$, wherein said -cyclopropyl, -cyclobutyl, -cyclopentyl or -cyclohexyl is connected through —CH$_2$— or —CH$_2$CH$_2$—; preferably, R$^4$ means -cyclobutyl, unsubstituted or monosubstituted with —OH, wherein said -cyclobutyl is connected through —CH$_2$—; and/or X means —O— or —NR$^6$—; and/or R$^5$ means
—H;
—C$_1$-C$_6$-alkyl, linear or branched, saturated or unsaturated, unsubstituted or substituted with one, two, three or four substituents independently of one another selected from the group consisting of —F, —Cl, —Br, —I, —CN, —O—CH$_3$, —O—(CH$_2$—CH$_2$—O)$_{1-10}$—H, —O—(CH$_2$CH$_2$—O)$_{1-10}$—CH$_3$, —C(═O)OH, —C(═O)OCH$_3$, —C(═O)NH$_2$, —C(═O)NHCH$_3$, —C(═O)N(CH$_3$)$_2$, —OH, —S(═O)CH$_3$, —S(═O)$_2$CH$_3$, unsubstituted —C(═O)-morpholinyl, —NH—C(═O)—CH$_3$, —N(CH$_3$)$_2$ and NH—S(═O)$_2$—CH$_3$; preferably, R$^5$ means —C$_1$-C$_6$-alkyl, linear or branched, saturated or unsaturated, unsubstituted or monosubstituted with —OH; -cyclopropyl, -cyclobutyl, -cyclopentyl or -cyclohexyl, unsubstituted or monosubstituted with —F, —OH, —CN or —CH$_3$, wherein said -cyclopropyl, -cyclobutyl, cyclopentyl or cyclohexyl is optionally connected through —CH$_2$— or —CH$_2$CH$_2$—;
-heterocyclobutyl, -tetrahydro-2H-thiopyranyl dioxide, —CH$_2$-heterocyclobutyl or —CH$_2$-tetrahydro-2H-thiopyranyl dioxide, in each case unsubstituted;
-oxazolyl, -isoxazolyl, -pyrazolyl, -pyridinyl, -pyridazinyl, -pyrazinyl, -thiazolyl, -thiadiazolyl, -imidazolyl or -pyrimidinyl, in each case unsubstituted or substituted with one, two, three or four substituents independently of one another selected from the group consisting of —F, —Cl, Br, —I, —CN, —OH, —CH$_3$, —O—CH$_3$, —C(═O)OH, —C(═O)OCH$_3$, —C(═O)NH$_2$, —C(═O)NHCH$_3$, —C(═O)N(CH$_3$)$_2$, S(═O)CH$_3$, —S(═O)$_2$CH$_3$ and —S—CH$_3$, wherein said -oxazolyl, -isoxazolyl, -pyrazolyl, -pyridinyl, -pyridazinyl, -pyrazinyl, -thiazolyl, -thiadiazolyl, -imidazolyl or -pyrimidinyl is optionally connected through —CH$_2$—; preferably, R$^5$ means -pyridinyl unsubstituted; or
-phenyl, unsubstituted or substituted with one, two, three or four substituents independently of one another selected from the group consisting of —F, —Cl, Br, —I, —CN, —OH, —CH$_3$, —O—CH$_3$, —C(═O)OH, —C(═O)OCH$_3$, —C(═O)NH$_2$, —C(═O)NHCH$_3$, —C(═O)N(CH$_3$)$_2$, S(═O)CH$_3$, —S(═O)$_2$CH$_3$ and —S—CH$_3$, wherein said -phenyl is optionally connected through —CH$_2$—; and/or in case X means NR$^6$, R$^6$ means —H or —CH$_3$;
or in case X means NR$^6$, R$^5$ and R$^6$ together with the nitrogen atom to which they are attached form a -pyrrolidinyl, -piperidinyl, -piperazinyl, -morpholinyl, -thiomorpholinyl, -thiomorpholinyl dioxide or -(methylsulfonyl)piperazinyl, in each case unsubstituted or substituted with one, two, three or four substituents independently of one another selected from the group consisting of ═O, —OH, —CH$_2$—OH and —C(═O)NH$_2$, wherein said -pyrrolidinyl, -piperidinyl, -piperazinyl, -morpholinyl, -thiomorpholinyl, -thiomorpholinyl dioxide or -(methylsulfonyl)piperazinyl is optionally condensed with an imidazole moiety, unsubstituted; and/or R$^9$, R$^{10}$, R$^{11}$, R$^{12}$, R$^{13}$, R$^{14}$, R$^{15}$, R$^{16}$, R$^{17}$, R$^{18}$, R$^{19}$, and R$^{20}$ mean —H.

Preferably, the compound according to the invention is selected from the group consisting of

| | |
|---|---|
| SC_1001 | CIS-2-[1-(Cyclobutyl-methyl)-8-dimethylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide |
| SC_1002 | CIS-6-[[2-[1-(Cyclobutyl-methyl)-8-dimethylamino-2-oxo-8-phenyl-1,3-diazaspiro[4.5]decan-3-yl]-acetyl]amino]-pyridine-2-carboxylic acid methyl ester |
| SC_1003 | CIS-2-[1-(Cyclobutyl-methyl)-8-dimethylamino-2-oxo-8-phenyl-1,3-diazaspiro[4.5]decan-3-yl]-N-[(1R)-2-hydroxy-1-methyl-ethyl]-acetamide |
| SC_1004 | CIS-2-[1-(Cyclobutyl-methyl)-8-dimethylamino-2-oxo-8-phenyl-1,3-diazaspiro[4.5]decan-3-yl]-N-[(1S)-2-hydroxy-1-methyl-ethyl]-acetamide |
| SC_1005 | CIS-2-[1-(Cyclobutyl-methyl)-8-dimethylamino-2-oxo-8-phenyl-1,3-diazaspiro[4.5]decan-3-yl]-N-methyl-N-(methylcarbamoyl-methyl)-acetamide |
| SC_1006 | CIS-6-[[2-[1-(Cyclobutyl-methyl)-8-dimethylamino-2-oxo-8-phenyl-1,3-diazaspiro[4.5]decan-3-yl]-acetyl]amino]-nicotinic acid methyl ester |
| SC_1007 | CIS-2-[[2-[1-(Cyclobutyl-methyl)-8-dimethylamino-2-oxo-8-phenyl-1,3-diazaspiro[4.5]decan-3-yl]-acetyl]-methyl-amino]-2-methyl-propionamide |
| SC_1008 | CIS-2-[[2-[1-(Cyclobutyl-methyl)-8-dimethylamino-2-oxo-8-phenyl-1,3-diazaspiro[4.5]decan-3-yl]-acetyl]amino]-N,2-dimethyl-propionamide |
| SC_1009 | CIS-2-[[2-[1-(Cyclobutyl-methyl)-8-dimethylamino-2-oxo-8-phenyl-1,3-diazaspiro[4.5]decan-3-yl]-acetyl]-methyl-amino]-N,2-dimethyl-propionamide |
| SC_1010 | CIS-2-[1-(Cyclobutyl-methyl)-8-dimethylamino-2-oxo-8-phenyl-1,3-diazaspiro[4.5]decan-3-yl]-N-[(dimethyl-carbamoyl)-methyl]-N-methyl-acetamide |
| SC_1011 | CIS-2-[[2-[1-(Cyclobutyl-methyl)-8-dimethylamino-2-oxo-8-phenyl-1,3-diazaspiro[4.5]decan-3-yl]-acetyl]amino]-2-methyl-propionamide |
| SC_1012 | CIS-2-[1-(Cyclobutyl-methyl)-8-dimethylamino-2-oxo-8-phenyl-1,3-diazaspiro[4.5]decan-3-yl]-N-(5-methoxy-pyridin-2-yl)-acetamide |
| SC_1013 | CIS-2-[1-(Cyclobutyl-methyl)-8-dimethylamino-2-oxo-8-phenyl-1,3-diazaspiro[4.5]decan-3-yl]-N-(6-methoxy-pyridin-2-yl)-acetamide |
| SC_1014 | CIS-2-[1-(Cyclobutyl-methyl)-8-dimethylamino-2-oxo-8-phenyl-1,3-diazaspiro[4.5]decan-3-yl]-N-(4-methoxy-pyridin-2-yl)-acetamide |
| SC_1015 | CIS-6-[[2-[1-(Cyclobutyl-methyl)-8-dimethylamino-2-oxo-8-phenyl-1,3-diazaspiro[4.5]decan-3-yl]-acetyl]amino]-N-methyl-pyridine-2-carboxylic acid amide |
| SC_1016 | CIS-2-[1-(Cyclobutyl-methyl)-8-dimethylamino-2-oxo-8-phenyl-1,3-diazaspiro[4.5]decan-3-yl]-N-[(3-hydroxy-cyclobutyl)-methyl]-acetamide |
| SC_1017 | CIS-2-[1-(Cyclobutyl-methyl)-8-dimethylamino-2-oxo-8-phenyl-1,3-diazaspiro[4.5]decan-3-yl]-N-[(3-hydroxy-cyclobutyl)-methyl]-acetamide |
| SC_1018 | CIS-2-[1-(Cyclobutyl-methyl)-8-dimethylamino-2-oxo-8-phenyl-1,3-diazaspiro[4.5]decan-3-yl]-N-[(1-hydroxy-cyclopropyl)-methyl]-acetamide |

-continued

| | |
|---|---|
| SC_1019 | CIS-2-[1-(Cyclobutyl-methyl)-8-dimethylamino-2-oxo-8-phenyl-1,3-diazaspiro[4.5]decan-3-yl]-N-(3-morpholin-4-yl-3-oxo-propyl)-acetamide |
| SC_1020 | CIS-N-(1-Cyano-cyclopropyl)-2-[1-(cyclobutyl-methyl)-8-dimethylamino-2-oxo-8-phenyl-1,3-diazaspiro[4.5]decan-3-yl]-acetamide |
| SC_1021 | CIS-2-[1-(Cyclobutyl-methyl)-8-dimethylamino-2-oxo-8-phenyl-1,3-diazaspiro[4.5]decan-3-yl]-N-[(3-hydroxy-cyclopentyl)-methyl]-acetamide |
| SC_1022 | CIS-2-[1-(Cyclobutyl-methyl)-8-dimethylamino-2-oxo-8-phenyl-1,3-diazaspiro[4.5]decan-3-yl]-N-[[(2R)-2-hydroxy-cyclohexyl]-methyl]-acetamide |
| SC_1023 | CIS-2-[1-(Cyclobutyl-methyl)-8-dimethylamino-2-oxo-8-phenyl-1,3-diazaspiro[4.5]decan-3-yl]-N-[2-[2-[2-(2-methoxy-ethoxy)-ethoxy]-ethoxy]-ethyl]-acetamide |
| SC_1024 | CIS-2-[1-(Cyclobutyl-methyl)-8-dimethylamino-2-oxo-8-phenyl-1,3-diazaspiro[4.5]decan-3-yl]-N-[(1-hydroxy-cyclohexyl)-methyl]-acetamide |
| SC_1025 | CIS-2-[1-(Cyclobutyl-methyl)-8-dimethylamino-2-oxo-8-phenyl-1,3-diazaspiro[4.5]decan-3-yl]-N-[2-[2-[2-[2-(2-methoxy-ethoxy)-ethoxy]-ethoxy]-ethoxy]-ethyl]-acetamide |
| SC_1026 | CIS-N-(6-Cyano-pyridin-2-yl)-2-[1-(cyclobutyl-methyl)-8-dimethylamino-2-oxo-8-phenyl-1,3-diazaspiro[4.5]decan-3-yl]-acetamide |
| SC_1027 | CIS-2-[[2-[1-(Cyclobutyl-methyl)-8-dimethylamino-2-oxo-8-phenyl-1,3-diazaspiro[4.5]decan-3-yl]-acetyl]amino]-nicotinic acid methyl ester |
| SC_1028 | CIS-2-[1-(Cyclobutyl-methyl)-8-dimethylamino-2-oxo-8-phenyl-1,3-diazaspiro[4.5]decan-3-yl]-N-(3-methoxy-pyridin-2-yl)-acetamide |
| SC_1029 | CIS-2-[1-(Cyclobutyl-methyl)-8-dimethylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide |
| SC_1030 | CIS-N-(4-Cyano-pyridin-2-yl)-2-[1-(cyclobutyl-methyl)-8-dimethylamino-2-oxo-8-phenyl-1,3-diazaspiro[4.5]decan-3-yl]-acetamide |
| SC_1031 | CIS-2-[1-(Cyclobutyl-methyl)-8-dimethylamino-2-oxo-8-phenyl-1,3-diazaspiro[4.5]decan-3-yl]-N-(5-methoxy-pyrimidin-2-yl)-acetamide |
| SC_1032 | CIS-2-[[2-[1-(Cyclobutyl-methyl)-8-dimethylamino-2-oxo-8-phenyl-1,3-diazaspiro[4.5]decan-3-yl]-acetyl]amino]-isonicotinic acid methyl ester |
| SC_1033 | CIS-2-[1-(Cyclobutyl-methyl)-8-dimethylamino-2-oxo-8-phenyl-1,3-diazaspiro[4.5]decan-3-yl]-N-(2-methoxy-pyridin-4-yl)-acetamide |
| SC_1034 | CIS-2-[1-(Cyclobutyl-methyl)-8-dimethylamino-2-oxo-8-phenyl-1,3-diazaspiro[4.5]decan-3-yl]-N-(6-fluoro-pyridin-3-yl)-acetamide |
| SC_1035 | CIS-2-[1-(Cyclobutyl-methyl)-8-dimethylamino-2-oxo-8-phenyl-1,3-diazaspiro[4.5]decan-3-yl]-N-(2-methyl-pyrimidin-5-yl)-acetamide |
| SC_1036 | CIS-2-[1-(Cyclobutyl-methyl)-8-dimethylamino-2-oxo-8-phenyl-1,3-diazaspiro[4.5]decan-3-yl]-N-(5-methyl-pyrimidin-2-yl)-acetamide |
| SC_1037 | CIS-2-[1-(Cyclobutyl-methyl)-8-dimethylamino-2-oxo-8-phenyl-1,3-diazaspiro[4.5]decan-3-yl]-N-(3-fluoro-pyridin-2-yl)-acetamide |
| SC_1038 | CIS-2-[1-(Cyclobutyl-methyl)-8-dimethylamino-2-oxo-8-phenyl-1,3-diazaspiro[4.5]decan-3-yl]-N-(3-fluoro-pyridin-4-yl)-acetamide |
| SC_1039 | CIS-2-[1-(Cyclobutyl-methyl)-8-dimethylamino-2-oxo-8-phenyl-1,3-diazaspiro[4.5]decan-3-yl]-N-(6-methoxy-pyridin-3-yl)-acetamide |
| SC_1040 | CIS-2-[1-(Cyclobutyl-methyl)-8-dimethylamino-2-oxo-8-phenyl-1,3-diazaspiro[4.5]decan-3-yl]-N-(2-methyl-pyridin-3-yl)-acetamide |
| SC_1041 | CIS-2-[1-(Cyclobutyl-methyl)-8-dimethylamino-2-oxo-8-phenyl-1,3-diazaspiro[4.5]decan-3-yl]-N-(4-methyl-pyridin-3-yl)-acetamide |
| SC_1042 | CIS-2-[1-(Cyclobutyl-methyl)-8-dimethylamino-2-oxo-8-phenyl-1,3-diazaspiro[4.5]decan-3-yl]-N-(3-methyl-pyridin-4-yl)-acetamide |
| SC_1043 | CIS-2-[1-(Cyclobutyl-methyl)-8-dimethylamino-2-oxo-8-phenyl-1,3-diazaspiro[4.5]decan-3-yl]-N-(6-methyl-pyridin-3-yl)-acetamide |
| SC_1044 | CIS-2-[1-(Cyclobutyl-methyl)-8-dimethylamino-2-oxo-8-phenyl-1,3-diazaspiro[4.5]decan-3-yl]-N-(5-fluoro-pyridin-2-yl)-acetamide |
| SC_1045 | CIS-2-[1-(Cyclobutyl-methyl)-8-dimethylamino-2-oxo-8-phenyl-1,3-diazaspiro[4.5]decan-3-yl]-N-(5-methyl-pyridin-2-yl)-acetamide |
| SC_1046 | CIS-2-[1-(Cyclobutyl-methyl)-8-dimethylamino-2-oxo-8-phenyl-1,3-diazaspiro[4.5]decan-3-yl]-N-(4-methyl-pyridin-2-yl)-acetamide |
| SC_1047 | CIS-2-[1-(Cyclobutyl-methyl)-8-dimethylamino-2-oxo-8-phenyl-1,3-diazaspiro[4.5]decan-3-yl]-N-(3-methyl-pyridin-2-yl)-acetamide |
| SC_1048 | CIS-2-[1-(Cyclobutyl-methyl)-8-dimethylamino-2-oxo-8-phenyl-1,3-diazaspiro[4.5]decan-3-yl]-N-(3-methoxy-pyridin-4-yl)-acetamide |
| SC_1049 | CIS-2-[1-(Cyclobutyl-methyl)-8-dimethylamino-2-oxo-8-phenyl-1,3-diazaspiro[4.5]decan-3-yl]-N-(6-methoxy-pyridazin-3-yl)-acetamide |
| SC_1050 | CIS-2-[1-(Cyclobutyl-methyl)-8-dimethylamino-2-oxo-8-phenyl-1,3-diazaspiro[4.5]decan-3-yl]-N-(5-methylsulfonyl-pyridin-2-yl)-acetamide |
| SC_1051 | CIS-2-[1-(Cyclobutyl-methyl)-8-dimethylamino-2-oxo-8-phenyl-1,3-diazaspiro[4.5]decan-3-yl]-N-(5-methoxy-pyridin-2-yl)-acetamide |
| SC_1052 | CIS-2-[1-(Cyclobutyl-methyl)-8-dimethylamino-2-oxo-8-phenyl-1,3-diazaspiro[4.5]decan-3-yl]-N-(6-methylsulfonyl-pyridin-3-yl)-acetamide |
| SC_1053 | CIS-2-[1-(Cyclobutyl-methyl)-8-dimethylamino-2-oxo-8-phenyl-1,3-diazaspiro[4.5]decan-3-yl]-N-(6-methoxy-pyrazin-2-yl)-acetamide |
| SC_1054 | CIS-2-[1-(Cyclobutyl-methyl)-8-dimethylamino-2-oxo-8-phenyl-1,3-diazaspiro[4.5]decan-3-yl]-N-(4-methoxy-pyridin-2-yl)-acetamide |
| SC_1055 | CIS-2-[1-(Cyclobutyl-methyl)-8-dimethylamino-2-oxo-8-phenyl-1,3-diazaspiro[4.5]decan-3-yl]-N-(4-methoxy-pyrimidin-2-yl)-acetamide |
| SC_1056 | CIS-2-[1-(Cyclobutyl-methyl)-8-dimethylamino-2-oxo-8-phenyl-1,3-diazaspiro[4.5]decan-3-yl]-N-(oxazol-5-yl-methyl)-acetamide |

-continued

| | |
|---|---|
| SC_1057 | CIS-2-[1-(Cyclobutyl-methyl)-8-dimethylamino-2-oxo-8-phenyl-1,3-diazaspiro[4.5]decan-3-yl]-N-(oxazol-2-yl-methyl)-acetamide |
| SC_1058 | CIS-1-(Cyclobutyl-methyl)-3-[2-[(3S,4S)-3,4-dihydroxy-piperidin-1-yl]-2-oxo-ethyl]-8-dimethylamino-8-phenyl-1,3-diazaspiro[4.5]decan-2-one |
| SC_1059 | CIS-1-(Cyclobutyl-methyl)-3-[2-[(3S,4S)-3,4-dihydroxy-pyrrolidin-1-yl]-2-oxo-ethyl]-8-dimethylamino-8-phenyl-1,3-diazaspiro[4.5]decan-2-one |
| SC_1060 | CIS-1-(Cyclobutyl-methyl)-3-[2-[(3S,4R)-3,4-dihydroxy-pyrrolidin-1-yl]-2-oxo-ethyl]-8-dimethylamino-8-phenyl-1,3-diazaspiro[4.5]decan-2-one |
| SC_1061 | CIS-2-[1-(Cyclobutyl-methyl)-8-dimethylamino-2-oxo-8-phenyl-1,3-diazaspiro[4.5]decan-3-yl]-N-cyclopropyl-acetamide |
| SC_1062 | CIS-2-[1-(Cyclobutyl-methyl)-8-dimethylamino-2-oxo-8-phenyl-1,3-diazaspiro[4.5]decan-3-yl]-N-(2-hydroxy-ethyl)-N-methyl-acetamide |
| SC_1063 | CIS-1-(Cyclobutyl-methyl)-8-dimethylamino-3-[2-(3-hydroxy-piperidin-1-yl)-2-oxo-ethyl]-8-phenyl-1,3-diazaspiro[4.5]decan-2-one |
| SC_1064 | CIS-2-[1-(Cyclobutyl-methyl)-8-dimethylamino-2-oxo-8-phenyl-1,3-diazaspiro[4.5]decan-3-yl]-N-[(1-hydroxy-cyclobutyl)-methyl]-acetamide |
| SC_1065 | CIS-2-[[2-[1-(Cyclobutyl-methyl)-8-dimethylamino-2-oxo-8-phenyl-1,3-diazaspiro[4.5]decan-3-yl]-acetyl]amino]-N,N-dimethyl-acetamide |
| SC_1066 | CIS-1-(Cyclobutyl-methyl)-8-dimethylamino-3-[2-oxo-2-(5,6,7,8-tetrahydro-[1,2,4]triazolo[1,5-a]pyrazin-7-yl)-ethyl]-8-phenyl-1,3-diazaspiro[4.5]decan-2-one |
| SC_1067 | CIS-3-[[2-[1-(Cyclobutyl-methyl)-8-dimethylamino-2-oxo-8-phenyl-1,3-diazaspiro[4.5]decan-3-yl]-acetyl]amino]-N,N-dimethyl-propionamide |
| SC_1068 | CIS-2-[1-(Cyclobutyl-methyl)-8-dimethylamino-2-oxo-8-phenyl-1,3-diazaspiro[4.5]decan-3-yl]-N-[2-[2-[2-[2-[2-[2-(2-methoxy-ethoxy)-ethoxy]-ethoxy]-ethoxy]-ethoxy]-ethoxy]-ethyl]-acetamide |
| SC_1069 | CIS-2-[1-(Cyclobutyl-methyl)-8-dimethylamino-2-oxo-8-phenyl-1,3-diazaspiro[4.5]decan-3-yl]-N-(4-methoxy-pyrimidin-5-yl)-acetamide |
| SC_1070 | CIS-2-[1-(Cyclobutyl-methyl)-8-dimethylamino-2-oxo-8-phenyl-1,3-diazaspiro[4.5]decan-3-yl]-N-(2-methoxy-pyrimidin-5-yl)-acetamide |
| SC_1072 | CIS-N-(5-Cyano-pyridin-2-yl)-2-[1-(cyclobutyl-methyl)-8-dimethylamino-2-oxo-8-phenyl-1,3-diazaspiro[4.5]decan-3-yl]-acetamide |
| SC_1073 | CIS-2-[[2-[1-(Cyclobutyl-methyl)-8-dimethylamino-2-oxo-8-phenyl-1,3-diazaspiro[4.5]decan-3-yl]-acetyl]amino]-N-methyl-pyridine-4-carboxylic acid amide |
| SC_1074 | CIS-2-[1-(Cyclobutyl-methyl)-8-dimethylamino-2-oxo-8-phenyl-1,3-diazaspiro[4.5]decan-3-yl]-N-(5-methoxy-pyrimidin-4-yl)-acetamide |
| SC_1075 | CIS-N-(2-Cyano-pyrimidin-5-yl)-2-[1-(cyclobutyl-methyl)-8-dimethylamino-2-oxo-8-phenyl-1,3-diazaspiro[4.5]decan-3-yl]-acetamide |
| SC_1076 | CIS-6-[[2-[1-(Cyclobutyl-methyl)-8-dimethylamino-2-oxo-8-phenyl-1,3-diazaspiro[4.5]decan-3-yl]-acetyl]amino]-pyridine-2-carboxylic acid amide |
| SC_1077 | CIS-N-(3-Cyano-pyridin-2-yl)-2-[1-(cyclobutyl-methyl)-8-dimethylamino-2-oxo-8-phenyl-1,3-diazaspiro[4.5]decan-3-yl]-acetamide |
| SC_1078 | CIS-2-[[2-[1-(Cyclobutyl-methyl)-8-dimethylamino-2-oxo-8-phenyl-1,3-diazaspiro[4.5]decan-3-yl]-acetyl]amino]-acetamide |
| SC_1079 | CIS-6-[[2-[1-(Cyclobutyl-methyl)-8-dimethylamino-2-oxo-8-phenyl-1,3-diazaspiro[4.5]decan-3-yl]-acetyl]amino]-pyridine-3-carboxylic acid amide |
| SC_1080 | CIS-N-(4-Cyano-pyrimidin-2-yl)-2-[1-(cyclobutyl-methyl)-8-dimethylamino-2-oxo-8-phenyl-1,3-diazaspiro[4.5]decan-3-yl]-acetamide |
| SC_1081 | CIS-2-[1-(Cyclobutyl-methyl)-8-dimethylamino-2-oxo-8-phenyl-1,3-diazaspiro[4.5]decan-3-yl]-N-([1,3,4]thiadiazol-2-yl)-acetamide |
| SC_1082 | CIS-2-[1-(Cyclobutyl-methyl)-8-dimethylamino-2-oxo-8-phenyl-1,3-diazaspiro[4.5]decan-3-yl]-N-thiazol-2-yl-acetamide |
| SC_1083 | CIS-2-[1-(Cyclobutyl-methyl)-8-dimethylamino-2-oxo-8-phenyl-1,3-diazaspiro[4.5]decan-3-yl]-N-(5-methyl-isoxazol-3-yl)-acetamide |
| SC_1084 | CIS-2-[1-(Cyclobutyl-methyl)-8-dimethylamino-2-oxo-8-phenyl-1,3-diazaspiro[4.5]decan-3-yl]-N-isoxazol-3-yl-acetamide |
| SC_1085 | CIS-2-[1-(Cyclobutyl-methyl)-8-dimethylamino-2-oxo-8-phenyl-1,3-diazaspiro[4.5]decan-3-yl]-N-(1-methyl-1H-pyrazol-3-yl)-acetamide |
| SC_1086 | CIS-N-(4-Cyano-5-methylsulfanyl-1H-pyrazol-3-yl)-2-[1-(cyclobutyl-methyl)-8-dimethylamino-2-oxo-8-phenyl-1,3-diazaspiro[4.5]decan-3-yl]-acetamide |
| SC_1087 | CIS-2-[1-(Cyclobutyl-methyl)-8-dimethylamino-2-oxo-8-phenyl-1,3-diazaspiro[4.5]decan-3-yl]-N-(5-methoxy-pyrazin-2-yl)-acetamide |
| SC_1088 | CIS-2-[1-(Cyclobutyl-methyl)-8-dimethylamino-2-oxo-8-phenyl-1,3-diazaspiro[4.5]decan-3-yl]-N-(pyridazin-4-yl-methyl)-acetamide |
| SC_1089 | CIS-2-[1-(Cyclobutyl-methyl)-8-dimethylamino-2-oxo-8-phenyl-1,3-diazaspiro[4.5]decan-3-yl]-N-[(2-hydroxyphenyl)-methyl]-acetamide |
| SC_1090 | CIS-2-[1-(Cyclobutyl-methyl)-8-dimethylamino-2-oxo-8-phenyl-1,3-diazaspiro[4.5]decan-3-yl]-N-[(1-methyl-1H-imidazol-4-yl)-methyl]-acetamide |
| SC_1091 | CIS-2-[1-(Cyclobutyl-methyl)-8-dimethylamino-2-oxo-8-phenyl-1,3-diazaspiro[4.5]decan-3-yl]-N-[(4-methyl-pyridin-3-yl)-methyl]-acetamide |
| SC_1092 | CIS-2-[1-(Cyclobutyl-methyl)-8-dimethylamino-2-oxo-8-phenyl-1,3-diazaspiro[4.5]decan-3-yl]-N-(pyrimidin-2-yl-methyl)-acetamide |
| SC_1093 | CIS-2-[1-(Cyclobutyl-methyl)-8-dimethylamino-2-oxo-8-phenyl-1,3-diazaspiro[4.5]decan-3-yl]-N-(pyridazin-3-yl-methyl)-acetamide |
| SC_1094 | CIS-2-[1-(Cyclobutyl-methyl)-8-dimethylamino-2-oxo-8-phenyl-1,3-diazaspiro[4.5]decan-3-yl]-N-(pyrimidin-4-yl-methyl)-acetamide |
| SC_1095 | CIS-2-[1-(Cyclobutyl-methyl)-8-dimethylamino-2-oxo-8-phenyl-1,3-diazaspiro[4.5]decan-3-yl]-N-(pyrazin-2-yl-methyl)-acetamide |

| | -continued |
|---|---|
| SC_1096 | CIS-2-[1-(Cyclobutyl-methyl)-8-dimethylamino-2-oxo-8-phenyl-1,3-diazaspiro[4.5]decan-3-yl]-N-(oxazol-4-yl-methyl)-acetamide |
| SC_1097 | CIS-2-[1-(Cyclobutyl-methyl)-8-dimethylamino-2-oxo-8-phenyl-1,3-diazaspiro[4.5]decan-3-yl]-N-[(2-methyl-pyridin-3-yl)-methyl]-acetamide |
| SC_1098 | CIS-2-[1-(Cyclobutyl-methyl)-8-dimethylamino-2-oxo-8-phenyl-1,3-diazaspiro[4.5]decan-3-yl]-N-[(2-methoxy-pyridin-3-yl)-methyl]-acetamide |
| SC_1099 | CIS-2-[1-(Cyclobutyl-methyl)-8-dimethylamino-2-oxo-8-phenyl-1,3-diazaspiro[4.5]decan-3-yl]-N-[(4-methoxy-pyridin-3-yl)-methyl]-acetamide |
| SC_1100 | CIS-2-[1-(Cyclobutyl-methyl)-8-dimethylamino-2-oxo-8-phenyl-1,3-diazaspiro[4.5]decan-3-yl]-N-[(6-methyl-pyridin-2-yl)-methyl]-acetamide |
| SC_1101 | CIS-2-[1-(Cyclobutyl-methyl)-8-dimethylamino-2-oxo-8-phenyl-1,3-diazaspiro[4.5]decan-3-yl]-N-[(6-methoxy-pyridin-2-yl)-methyl]-acetamide |
| SC_1102 | CIS-2-[1-(Cyclobutyl-methyl)-8-dimethylamino-2-oxo-8-phenyl-1,3-diazaspiro[4.5]decan-3-yl]-N-[(2-methoxyphenyl)-methyl]-acetamide |
| SC_1103 | CIS-2-[1-(Cyclobutyl-methyl)-8-dimethylamino-2-oxo-8-phenyl-1,3-diazaspiro[4.5]decan-3-yl]-N-(o-tolyl-methyl)-acetamide |
| SC_1104 | CIS-6-[[2-[1-(Cyclobutyl-methyl)-8-dimethylamino-2-oxo-8-phenyl-1,3-diazaspiro[4.5]decan-3-yl]-acetyl]amino]-N-methyl-pyridine-3-carboxylic acid amide |
| SC_1105 | CIS-2-[[2-[1-(Cyclobutyl-methyl)-8-dimethylamino-2-oxo-8-phenyl-1,3-diazaspiro[4.5]decan-3-yl]-acetyl]amino]-pyridine-4-carboxylic acid amide |
| SC_1106 | CIS-2-[1-(Cyclobutyl-methyl)-8-dimethylamino-2-oxo-8-phenyl-1,3-diazaspiro[4.5]decan-3-yl]-N-(6-methoxy-pyrimidin-4-yl)-acetamide |
| SC_1107 | CIS-2-[1-(Cyclobutyl-methyl)-8-dimethylamino-2-oxo-8-phenyl-1,3-diazaspiro[4.5]decan-3-yl]-N-(2-methoxy-pyrimidin-4-yl)-acetamide |
| SC_1109 | CIS-2-[1-(Cyclobutyl-methyl)-8-dimethylamino-2-oxo-8-phenyl-1,3-diazaspiro[4.5]decan-3-yl]-N-(4-hydroxy-pyrimidin-5-yl)-acetamide |
| SC_1110 | CIS-2-[1-(Cyclobutyl-methyl)-8-dimethylamino-2-oxo-8-phenyl-1,3-diazaspiro[4.5]decan-3-yl]-N-(2-hydroxy-pyrimidin-5-yl)-acetamide |
| SC_1111 | CIS-2-[1-(Cyclobutyl-methyl)-8-dimethylamino-2-oxo-8-phenyl-1,3-diazaspiro[4.5]decan-3-yl]-N-(5-hydroxy-pyridin-2-yl)-acetamide |
| SC_1112 | CIS-2-[1-(Cyclobutyl-methyl)-8-dimethylamino-2-oxo-8-phenyl-1,3-diazaspiro[4.5]decan-3-yl]-N-(1,1-dioxo-thian-4-yl)-acetamide |
| SC_1113 | CIS-1-(Cyclobutyl-methyl)-8-dimethylamino-3-[2-(1,1-dioxo-[1,4]thiazinan-4-yl)-2-oxo-ethyl]-8-phenyl-1,3-diazaspiro[4.5]decan-2-one |
| SC_1114 | CIS-2-[8-Dimethylamino-1-(2-methoxy-ethyl)-2-oxo-8-phenyl-1,3-diazaspiro[4.5]decan-3-yl]-N-pyrimidin-4-yl-acetamide |
| SC_1115 | CIS-2-[8-Dimethylamino-1-(2-methoxy-ethyl)-2-oxo-8-phenyl-1,3-diazaspiro[4.5]decan-3-yl]-N-methyl-acetamide |
| SC_1117 | CIS-N-(5-Cyano-pyrimidin-4-yl)-2-[1-(cyclobutyl-methyl)-8-dimethylamino-2-oxo-8-phenyl-1,3-diazaspiro[4.5]decan-3-yl]-acetamide |
| SC_1118 | CIS-2-[1-(Cyclobutyl-methyl)-8-dimethylamino-2-oxo-8-phenyl-1,3-diazaspiro[4.5]decan-3-yl]-N-(5-methylsulfanyl-pyridin-2-yl)-acetamide |
| SC_1119 | CIS-2-[1-(Cyclobutyl-methyl)-8-dimethylamino-2-oxo-8-phenyl-1,3-diazaspiro[4.5]decan-3-yl]-N-(4-methoxy-pyrimidin-2-yl)-acetamide |
| SC_1120 | CIS-2-[1-(Cyclobutyl-methyl)-8-dimethylamino-2-oxo-8-phenyl-1,3-diazaspiro[4.5]decan-3-yl]-N-(6-methylsulfanyl-pyridin-2-yl)-acetamide |
| SC_1121 | CIS-2-[8-Dimethylamino-1-(2-methoxy-ethyl)-2-oxo-8-phenyl-1,3-diazaspiro[4.5]decan-3-yl]-N-(2-hydroxy-ethyl)-acetamide |
| SC_1122 | CIS-2-[[2-[8-Dimethylamino-1-(2-methoxy-ethyl)-2-oxo-8-phenyl-1,3-diazaspiro[4.5]decan-3-yl]-acetyl]amino]-acetamide |
| SC_1123 | CIS-2-[1-(Cyclobutyl-methyl)-8-dimethylamino-2-oxo-8-phenyl-1,3-diazaspiro[4.5]decan-3-yl]-N-methyl-acetamide |
| SC_1124 | CIS-2-[1-(Cyclobutyl-methyl)-8-dimethylamino-2-oxo-8-phenyl-1,3-diazaspiro[4.5]decan-3-yl]-N-(2-hydroxy-ethyl)-acetamide |
| SC_1125 | CIS-2-[1-(Cyclobutyl-methyl)-8-dimethylamino-2-oxo-8-phenyl-1,3-diazaspiro[4.5]decan-3-yl]-N-(6-hydroxy-pyridin-2-yl)-acetamide |
| SC_1126 | CIS-2-[1-(Cyclobutyl-methyl)-8-dimethylamino-2-oxo-8-phenyl-1,3-diazaspiro[4.5]decan-3-yl]-N-[(2-methoxy-pyrimidin-5-yl)-methyl]-acetamide |
| SC_1127 | CIS-2-[1-(Cyclobutyl-methyl)-8-dimethylamino-2-oxo-8-phenyl-1,3-diazaspiro[4.5]decan-3-yl]-N-[(4-methoxy-pyrimidin-2-yl)-methyl]-acetamide |
| SC_1128 | CIS-N-(2-Cyano-pyrimidin-4-yl)-2-[1-(cyclobutyl-methyl)-8-dimethylamino-2-oxo-8-phenyl-1,3-diazaspiro[4.5]decan-3-yl]-acetamide |
| SC_1129 | CIS-2-[1-(Cyclobutyl-methyl)-8-dimethylamino-2-oxo-8-phenyl-1,3-diazaspiro[4.5]decan-3-yl]-N-[6-(methylsulfinyl)-pyridin-2-yl]-acetamide |
| SC_1130 | CIS-2-[[2-[1-(Cyclobutyl-methyl)-8-methylamino-2-oxo-8-phenyl-1,3-diazaspiro[4.5]decan-3-yl]-acetyl]amino]-2-methyl-propionamide |
| SC_1131 | CIS-2-[[2-[1-(Cyclobutyl-methyl)-8-methylamino-2-oxo-8-phenyl-1,3-diazaspiro[4.5]decan-3-yl]-acetyl]amino]-N-methyl-acetamide |
| SC_1132 | CIS-2-[[2-[1-(Cyclobutyl-methyl)-8-methylamino-2-oxo-8-phenyl-1,3-diazaspiro[4.5]decan-3-yl]-acetyl]amino]-acetamide |
| SC_1133 | CIS-2-[1-(Cyclobutyl-methyl)-8-dimethylamino-2-oxo-8-phenyl-1,3-diazaspiro[4.5]decan-3-yl]-N-[2-[2-(2-methoxy-ethoxy)-ethoxy]-ethyl]-acetamide |
| SC_1134 | CIS-N-(Carbamoyl-methyl)-2-[1-(cyclobutyl-methyl)-8-methylamino-2-oxo-8-phenyl-1,3-diazaspiro[4.5]decan-3-yl]-N-methyl-acetamide |
| SC_1135 | CIS-2-[1-(Cyclobutyl-methyl)-8-methylamino-2-oxo-8-phenyl-1,3-diazaspiro[4.5]decan-3-yl]-N-methyl-N-(methylcarbamoyl-methyl)-acetamide |
| SC_1136 | CIS-2-[8-Dimethylamino-1-[(1-hydroxy-cyclobutyl)-methyl]-2-oxo-8-phenyl-1,3-diazaspiro[4.5]decan-3-yl]-N-(2-methylsulfonyl-ethyl)-acetamide |

-continued

| | |
|---|---|
| SC_1137 | CIS-2-[8-Dimethylamino-1-[(1-hydroxy-cyclobutyl)-methyl]-2-oxo-8-phenyl-1,3-diazaspiro[4.5]decan-3-yl]-N-pyrimidin-5-yl-acetamide |
| SC_1138 | CIS-2-[1-(Cyclobutyl-methyl)-8-dimethylamino-2-oxo-8-phenyl-1,3-diazaspiro[4.5]decan-3-yl]-N-(6-methylsulfonyl-pyridin-2-yl)-acetamide |
| SC_1139 | CIS-2-[8-Dimethylamino-1-[(dimethyl-carbamoyl)-methyl]-2-oxo-8-phenyl-1,3-diazaspiro[4.5]decan-3-yl]-N-(2-hydroxy-ethyl)-acetamide |
| SC_1140 | CIS-2-[[2-[1-(Cyclobutyl-methyl)-8-methylamino-2-oxo-8-phenyl-1,3-diazaspiro[4.5]decan-3-yl]-acetyl]-methyl-amino]-2-methyl-propionamide |
| SC_1141 | CIS-1-(Cyclobutyl-methyl)-3-[2-(1,1-dioxo-[1,4]thiazinan-4-yl)-2-oxo-ethyl]-8-methylamino-8-phenyl-1,3-diazaspiro[4.5]decan-2-one |
| SC_1142 | CIS-2-[1-(Cyclobutyl-methyl)-8-methylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide |
| SC_1143 | CIS-2-[[2-[1-(Cyclobutyl-methyl)-8-methylamino-2-oxo-8-phenyl-1,3-diazaspiro[4.5]decan-3-yl]-acetyl]amino]-N,N-dimethyl-acetamide |
| SC_1144 | CIS-2-[1-(Cyclobutyl-methyl)-8-dimethylamino-2-oxo-8-phenyl-1,3-diazaspiro[4.5]decan-3-yl]-N-(5-hydroxy-pyrimidin-2-yl)-acetamide |
| SC_1145 | CIS-2-[1-(Cyclobutyl-methyl)-8-dimethylamino-2-oxo-8-phenyl-1,3-diazaspiro[4.5]decan-3-yl]-N-(4-methylsulfonyl-pyridin-2-yl)-acetamide |
| SC_1146 | CIS-2-[[2-[1-(Cyclobutyl-methyl)-8-dimethylamino-2-oxo-8-phenyl-1,3-diazaspiro[4.5]decan-3-yl]-acetyl]amino]-N-methyl-acetamide |
| SC_1147 | CIS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide |
| SC_1148 | CIS-2-(8-Dimethylamino-2-oxo-8-phenyl-1-propyl-1,3-diazaspiro[4.5]decan-3-yl)-N-methyl-acetamide |
| SC_1149 | CIS-2-[8-Dimethylamino-1-(3-methoxy-propyl)-2-oxo-8-phenyl-1,3-diazaspiro[4.5]decan-3-yl]-N-methyl-acetamide |
| SC_1150 | CIS-2-[1-(Cyclobutyl-methyl)-8-dimethylamino-2-oxo-8-phenyl-1,3-diazaspiro[4.5]decan-3-yl]-N-[4-(methylsulfinyl)-pyridin-2-yl]-acetamide |
| SC_1151 | CIS-2-[1-(Cyclobutyl-methyl)-8-dimethylamino-2-oxo-8-phenyl-1,3-diazaspiro[4.5]decan-3-yl]-N-(3-hydroxy-pyridin-2-yl)-acetamide |
| SC_1152 | CIS-2-[1-(Cyclobutyl-methyl)-8-dimethylamino-2-oxo-8-phenyl-1,3-diazaspiro[4.5]decan-3-yl]-N-(2-methylsulfonyl-ethyl)-acetamide |
| SC_1154 | CIS-1-(Cyclobutyl-methyl)-3-[2-[(3S,4R)-3,4-dihydroxy-pyrrolidin-1-yl]-2-oxo-ethyl]-8-dimethylamino-8-phenyl-1,3-diazaspiro[4.5]decan-2-one |
| SC_1155 | CIS-2-[1-(Cyclobutyl-methyl)-8-methylamino-2-oxo-8-phenyl-1,3-diazaspiro[4.5]decan-3-yl]-N-(2-hydroxy-ethyl)-acetamide |
| SC_1156 | CIS-2-[8-Dimethylamino-1-[(dimethyl-carbamoyl)-methyl]-2-oxo-8-phenyl-1,3-diazaspiro[4.5]decan-3-yl]-N-pyrimidin-4-yl-acetamide |
| SC_1157 | CIS-2-[8-Dimethylamino-1-[(dimethyl-carbamoyl)-methyl]-2-oxo-8-phenyl-1,3-diazaspiro[4.5]decan-3-yl]-N-methyl-acetamide |
| SC_1158 | CIS-2-[[2-[8-Dimethylamino-1-(2-methyl-propyl)-2-oxo-8-phenyl-1,3-diazaspiro[4.5]decan-3-yl]-acetyl]amino]-acetamide |
| SC_1159 | CIS-2-[8-Dimethylamino-1-[(1-hydroxy-cyclobutyl)-methyl]-2-oxo-8-phenyl-1,3-diazaspiro[4.5]decan-3-yl]-acetamide |
| SC_1160 | CIS-2-[8-Dimethylamino-1-[(1-hydroxy-cyclobutyl)-methyl]-2-oxo-8-phenyl-1,3-diazaspiro[4.5]decan-3-yl]-N-methyl-acetamide |
| SC_1161 | CIS-2-[[2-[8-Dimethylamino-1-(3-methoxy-propyl)-2-oxo-8-phenyl-1,3-diazaspiro[4.5]decan-3-yl]-acetyl]amino]-acetamide |
| SC_1162 | CIS-2-[8-Dimethylamino-1-(2-methyl-propyl)-2-oxo-8-phenyl-1,3-diazaspiro[4.5]decan-3-yl]-N-methyl-acetamide |
| SC_1163 | CIS-1-(Cyclobutyl-methyl)-3-[2-[(3S,4R)-3,4-dihydroxy-pyrrolidin-1-yl]-2-oxo-ethyl]-8-methylamino-8-phenyl-1,3-diazaspiro[4.5]decan-2-one |
| SC_1164 | CIS-2-[8-Dimethylamino-1-[(1-methyl-cyclobutyl)-methyl]-2-oxo-8-phenyl-1,3-diazaspiro[4.5]decan-3-yl]-N-methyl-acetamide |
| SC_1165 | CIS-2-[8-Dimethylamino-1-[(1-methyl-cyclobutyl)-methyl]-2-oxo-8-phenyl-1,3-diazaspiro[4.5]decan-3-yl]-N-pyrimidin-4-yl-acetamide |
| SC_1166 | CIS-2-[[2-[8-Dimethylamino-1-[(1-methyl-cyclobutyl)-methyl]-2-oxo-8-phenyl-1,3-diazaspiro[4.5]decan-3-yl]-acetyl]amino]-acetamide |
| SC_1167 | CIS-2-[8-Dimethylamino-1-[(1-methyl-cyclobutyl)-methyl]-2-oxo-8-phenyl-1,3-diazaspiro[4.5]decan-3-yl]-N-(2-hydroxy-ethyl)-acetamide |
| SC_1168 | CIS-2-[[2-[1-(Cyclopropyl-methyl)-8-dimethylamino-2-oxo-8-phenyl-1,3-diazaspiro[4.5]decan-3-yl]-acetyl]amino]-acetamide |
| SC_1169 | CIS-2-[1-(Cyclobutyl-methyl)-8-(ethyl-methyl-amino)-2-oxo-8-phenyl-1,3-diazaspiro[4.5]decan-3-yl]-N-methyl-acetamide |
| SC_1171 | CIS-2-[[2-(8-Dimethylamino-2-oxo-8-phenyl-1-propyl-1,3-diazaspiro[4.5]decan-3-yl)-acetyl]amino]-acetamide |
| SC_1172 | CIS-2-[[2-[8-Dimethylamino-1-[(1-hydroxy-cyclobutyl)-methyl]-2-oxo-8-phenyl-1,3-diazaspiro[4.5]decan-3-yl]-acetyl]amino]-acetamide |
| SC_1173 | CIS-2-[8-Dimethylamino-1-[(1-hydroxy-cyclobutyl)-methyl]-2-oxo-8-phenyl-1,3-diazaspiro[4.5]decan-3-yl]-N-(2-hydroxy-ethyl)-acetamide |
| SC_1174 | CIS-2-[8-Dimethylamino-1-[(1-hydroxy-cyclobutyl)-methyl]-2-oxo-8-phenyl-1,3-diazaspiro[4.5]decan-3-yl]-N-(1,1-dioxo-thian-4-yl)-acetamide |
| SC_1175 | CIS-2-[1-(Cyclopropyl-methyl)-8-dimethylamino-2-oxo-8-phenyl-1,3-diazaspiro[4.5]decan-3-yl]-N-methyl-acetamide |
| SC_1176 | CIS-2-[1-[(1-Cyano-cyclobutyl)-methyl]-8-dimethylamino-2-oxo-8-phenyl-1,3-diazaspiro[4.5]decan-3-yl]-N-methyl-acetamide |
| SC_1177 | CIS-2-[1-(Cyclobutyl-methyl)-8-(ethyl-methyl-amino)-2-oxo-8-phenyl-1,3-diazaspiro[4.5]decan-3-yl]-N-(2-hydroxy-ethyl)-acetamide |

| | |
|---|---|
| SC__1178 | CIS-2-[[2-[1-(Cyclobutyl-methyl)-8-(ethyl-methyl-amino)-2-oxo-8-phenyl-1,3-diazaspiro[4.5]decan-3-yl]-acetyl]amino]-acetamide |
| SC__1179 | CIS-2-[[2-[1-(Cyclobutyl-methyl)-8-methylamino-2-oxo-8-phenyl-1,3-diazaspiro[4.5]decan-3-yl]-acetyl]amino]-N,2-dimethyl-propionamide |
| SC__1180 | CIS-2-[8-Dimethylamino-1-(3-methoxy-propyl)-2-oxo-8-phenyl-1,3-diazaspiro[4.5]decan-3-yl]-N-(2-hydroxy-ethyl)-acetamide |
| SC__1181 | CIS-2-[8-Dimethylamino-1-(3-methoxy-propyl)-2-oxo-8-phenyl-1,3-diazaspiro[4.5]decan-3-yl]-N-methyl-N-(methylcarbamoyl-methyl)-acetamide |
| SC__1182 | CIS-8-Dimethylamino-1-(3-methoxy-propyl)-3-[2-oxo-2-(3-oxo-piperazin-1-yl)-ethyl]-8-phenyl-1,3-diazaspiro[4.5]decan-2-one |
| SC__1183 | CIS-N-(Carbamoyl-methyl)-2-[8-dimethylamino-1-(3-methoxy-propyl)-2-oxo-8-phenyl-1,3-diazaspiro[4.5]decan-3-yl]-N-methyl-acetamide |
| SC__1184 | CIS-2-[8-Dimethylamino-1-(3-methoxy-propyl)-2-oxo-8-phenyl-1,3-diazaspiro[4.5]decan-3-yl]-N-[(3-hydroxy-cyclobutyl)-methyl]-acetamide |
| SC__1185 | CIS-2-[8-Dimethylamino-1-(3-methoxy-propyl)-2-oxo-8-phenyl-1,3-diazaspiro[4.5]decan-3-yl]-N-[(3-hydroxy-cyclobutyl)-methyl]-acetamide |
| SC__1186 | CIS-2-[8-Dimethylamino-1-(3-methoxy-propyl)-2-oxo-8-phenyl-1,3-diazaspiro[4.5]decan-3-yl]-N-[(3-hydroxy-cyclopentyl)-methyl]-acetamide |
| SC__1187 | CIS-2-[8-Dimethylamino-1-(3-methoxy-propyl)-2-oxo-8-phenyl-1,3-diazaspiro[4.5]decan-3-yl]-N-pyridazin-4-yl-acetamide |
| SC__1188 | CIS-2-[8-Dimethylamino-1-(3-methoxy-propyl)-2-oxo-8-phenyl-1,3-diazaspiro[4.5]decan-3-yl]-N-(6-methoxy-pyridin-2-yl)-acetamide |
| SC__1189 | CIS-N-(2-Cyanoethyl)-2-[8-dimethylamino-1-(3-methoxy-propyl)-2-oxo-8-phenyl-1,3-diazaspiro[4.5]decan-3-yl]-acetamide |
| SC__1190 | CIS-2-[8-Dimethylamino-1-(3-methoxy-propyl)-2-oxo-8-phenyl-1,3-diazaspiro[4.5]decan-3-yl]-N-pyrimidin-5-yl-acetamide |
| SC__1191 | CIS-2-[8-Dimethylamino-1-(3-methoxy-propyl)-2-oxo-8-phenyl-1,3-diazaspiro[4.5]decan-3-yl]-N-pyrimidin-4-yl-acetamide |
| SC__1192 | CIS-2-[1-(Cyclobutyl-methyl)-8-(ethyl-methyl-amino)-2-oxo-8-phenyl-1,3-diazaspiro[4.5]decan-3-yl]-N-(6-methoxy-pyridin-2-yl)-acetamide |
| SC__1193 | CIS-2-[8-Dimethylamino-1-[(1-hydroxy-cyclobutyl)-methyl]-2-oxo-8-phenyl-1,3-diazaspiro[4.5]decan-3-yl]-N-pyridin-3-yl-acetamide |
| SC__1195 | CIS-2-[1-(Cyclobutyl-methyl)-8-dimethylamino-2-oxo-8-phenyl-1,3-diazaspiro[4.5]decan-3-yl]-acetamide |
| SC__1196 | CIS-2-[1-(Cyclobutyl-methyl)-8-dimethylamino-2-oxo-8-phenyl-1,3-diazaspiro[4.5]decan-3-yl]-N-pyrimidin-4-yl-acetamide |
| SC__1197 | CIS-2-[1-(Cyclobutyl-methyl)-8-dimethylamino-2-oxo-8-phenyl-1,3-diazaspiro[4.5]decan-3-yl]-N-(2-methoxy-ethyl)-acetamide |
| SC__1198 | CIS-2-[1-(Cyclobutyl-methyl)-8-dimethylamino-2-oxo-8-phenyl-1,3-diazaspiro[4.5]decan-3-yl]-N-(2-hydroxy-ethyl)-acetamide |
| SC__1199 | CIS-2-[1-(Cyclobutyl-methyl)-8-dimethylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide |
| SC__1201 | CIS-2-[1-(Cyclobutyl-methyl)-8-methylamino-2-oxo-8-phenyl-1,3-diazaspiro[4.5]decan-3-yl]-N-methyl-acetamide |
| SC__1203 | CIS-(2S)-1-[2-[1-(Cyclobutyl-methyl)-8-dimethylamino-2-oxo-8-phenyl-1,3-diazaspiro[4.5]decan-3-yl]-acetyl]-pyrrolidine-2-carboxylic acid amide |
| SC__1204 | CIS-2-[[2-[1-(Cyclobutyl-methyl)-8-dimethylamino-2-oxo-8-phenyl-1,3-diazaspiro[4.5]decan-3-yl]-acetyl]amino]-N,N-dimethyl-acetamide |
| SC__1205 | CIS-2-[1-(Cyclobutyl-methyl)-8-dimethylamino-2-oxo-8-phenyl-1,3-diazaspiro[4.5]decan-3-yl]-N-(oxetan-3-yl)-acetamide |
| SC__1206 | CIS-2-[[2-[1-(Cyclobutyl-methyl)-8-dimethylamino-2-oxo-8-phenyl-1,3-diazaspiro[4.5]decan-3-yl]-acetyl]amino]-acetamide |
| SC__1207 | CIS-1-(Cyclobutyl-methyl)-8-dimethylamino-3-[2-oxo-2-(3-oxo-piperazin-1-yl)-ethyl]-8-phenyl-1,3-diazaspiro[4.5]decan-2-one |
| SC__1208 | CIS-2-[1-(Cyclobutyl-methyl)-8-dimethylamino-2-oxo-8-phenyl-1,3-diazaspiro[4.5]decan-3-yl]-N-(1,1-dioxo-thian-4-yl)-acetamide |
| SC__1209 | CIS-1-(Cyclobutyl-methyl)-8-dimethylamino-3-[2-[2-(hydroxymethyl)-morpholin-4-yl]-2-oxo-ethyl]-8-phenyl-1,3-diazaspiro[4.5]decan-2-one |
| SC__1210 | CIS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide |
| SC__1211 | CIS-N-(Cyano-methyl)-2-[1-(cyclobutyl-methyl)-8-dimethylamino-2-oxo-8-phenyl-1,3-diazaspiro[4.5]decan-3-yl]-acetamide |
| SC__1212 | CIS-N-(2-Acetylamino-ethyl)-2-[1-(cyclobutyl-methyl)-8-dimethylamino-2-oxo-8-phenyl-1,3-diazaspiro[4.5]decan-3-yl]-acetamide |
| SC__1213 | CIS-2-[1-(Cyclobutyl-methyl)-8-dimethylamino-2-oxo-8-phenyl-1,3-diazaspiro[4.5]decan-3-yl]-N-(2-methylsulfonyl-ethyl)-acetamide |
| SC__1214 | CIS-1-(Cyclobutyl-methyl)-8-dimethylamino-3-[2-(1,1-dioxo-[1,4]thiazinan-4-yl)-2-oxo-ethyl]-8-phenyl-1,3-diazaspiro[4.5]decan-2-one |
| SC__1215 | CIS-2-[1-(Cyclobutyl-methyl)-8-dimethylamino-2-oxo-8-phenyl-1,3-diazaspiro[4.5]decan-3-yl]-N-[(1,1-dioxo-thian-4-yl)-methyl]-acetamide |
| SC__1216 | CIS-1-(Cyclobutyl-methyl)-8-dimethylamino-3-[2-(4-methylsulfonyl-piperazin-1-yl)-2-oxo-ethyl]-8-phenyl-1,3-diazaspiro[4.5]decan-2-one |
| SC__1217 | CIS-N-(2-Cyanoethyl)-2-[1-(cyclobutyl-methyl)-8-dimethylamino-2-oxo-8-phenyl-1,3-diazaspiro[4.5]decan-3-yl]-acetamide |
| SC__1218 | CIS-2-[1-(Cyclobutyl-methyl)-8-dimethylamino-2-oxo-8-phenyl-1,3-diazaspiro[4.5]decan-3-yl]-N-(2-hydroxy-2-methyl-propyl)-acetamide |
| SC__1219 | CIS-2-[1-(Cyclobutyl-methyl)-8-dimethylamino-2-oxo-8-phenyl-1,3-diazaspiro[4.5]decan-3-yl]-N-(2-morpholin-4-yl-2-oxo-ethyl)-acetamide |

-continued

| | |
|---|---|
| SC_1220 | CIS-2-[1-(Cyclobutyl-methyl)-8-dimethylamino-2-oxo-8-phenyl-1,3-diazaspiro[4.5]decan-3-yl]-N-[2-(2-hydroxy-ethoxy)-ethyl]-acetamide |
| SC_1222 | CIS-2-[[2-[1-(Cyclobutyl-methyl)-8-dimethylamino-2-oxo-8-phenyl-1,3-diazaspiro[4.5]decan-3-yl]-acetyl]amino]-N-methyl-acetamide |
| SC_1223 | CIS-2-[1-(Cyclobutyl-methyl)-8-dimethylamino-2-oxo-8-phenyl-1,3-diazaspiro[4.5]decan-3-yl]-N-[2-(methanesulfonamido)-ethyl]-acetamide |
| SC_1224 | CIS-2-[1-(Cyclobutyl-methyl)-8-dimethylamino-2-oxo-8-phenyl-1,3-diazaspiro[4.5]decan-3-yl]-N-[(1-hydroxy-cyclopentyl)-methyl]-acetamide |
| SC_1225 | CIS-2-[1-(Cyclobutyl-methyl)-8-dimethylamino-2-oxo-8-phenyl-1,3-diazaspiro[4.5]decan-3-yl]-N-[(4-hydroxy-cyclohexyl)-methyl]-acetamide |
| SC_1226 | CIS-2-[1-(Cyclobutyl-methyl)-8-dimethylamino-2-oxo-8-phenyl-1,3-diazaspiro[4.5]decan-3-yl]-N-[2-(2-methoxy-ethoxy)-ethyl]-acetamide |
| SC_1227 | CIS-2-[1-(Cyclobutyl-methyl)-8-dimethylamino-2-oxo-8-phenyl-1,3-diazaspiro[4.5]decan-3-yl]-N-[2-(dimethylamino)ethyl]-acetamide |
| SC_1228 | CIS-2-[1-(Cyclobutyl-methyl)-8-[methyl-(2-methyl-propyl)-amino]-2-oxo-8-phenyl-1,3-diazaspiro[4.5]decan-3-yl]-N-methyl-acetamide |
| SC_1229 | CIS-2-[1-(Cyclobutyl-methyl)-8-dimethylamino-2-oxo-8-phenyl-1,3-diazaspiro[4.5]decan-3-yl]-N-methyl-acetamide |
| SC_1230 | CIS-2-[1-(Cyclobutyl-methyl)-8-dimethylamino-2-oxo-8-phenyl-1,3-diazaspiro[4.5]decan-3-yl]-N-pyrimidin-4-yl-acetamide |
| SC_1231 | CIS-2-[1-(Cyclobutyl-methyl)-8-dimethylamino-2-oxo-8-phenyl-1,3-diazaspiro[4.5]decan-3-yl]-N-(6-methyl-pyridin-2-yl)-acetamide |
| SC_1232 | CIS-2-[1-(Cyclobutyl-methyl)-8-dimethylamino-2-oxo-8-phenyl-1,3-diazaspiro[4.5]decan-3-yl]-N-pyridazin-3-yl-acetamide |
| SC_1233 | CIS-2-[1-(Cyclobutyl-methyl)-8-dimethylamino-2-oxo-8-phenyl-1,3-diazaspiro[4.5]decan-3-yl]-N-pyrimidin-5-yl-acetamide |
| SC_1234 | CIS-2-[1-(Cyclobutyl-methyl)-8-dimethylamino-2-oxo-8-phenyl-1,3-diazaspiro[4.5]decan-3-yl]-N-pyridazin-4-yl-acetamide |
| SC_1235 | CIS-2-[1-(Cyclobutyl-methyl)-8-dimethylamino-2-oxo-8-phenyl-1,3-diazaspiro[4.5]decan-3-yl]-N-(6-methoxy-pyrimidin-4-yl)-acetamide |
| SC_1236 | CIS-2-[1-(Cyclobutyl-methyl)-8-dimethylamino-2-oxo-8-phenyl-1,3-diazaspiro[4.5]decan-3-yl]-N-(2-methyl-pyridin-4-yl)-acetamide |
| SC_1300 | CIS-2-[8-Dimethylamino-1-[(1-hydroxy-cyclobutyl)-methyl]-2-oxo-8-phenyl-1,3-diazaspiro[4.5]decan-3-yl]-N-pyridin-4-yl-acetamide |
| SC_1301 | CIS-2-[8-Dimethylamino-1-[(1-hydroxy-cyclobutyl)-methyl]-2-oxo-8-phenyl-1,3-diazaspiro[4.5]decan-3-yl]-N-(oxetan-3-yl)-acetamide |
| SC_1302 | CIS-2-[8-Dimethylamino-1-[(1-hydroxy-cyclobutyl)-methyl]-2-oxo-8-phenyl-1,3-diazaspiro[4.5]decan-3-yl]-N-(2-methoxy-ethyl)-acetamide |
| SC_1303 | CIS-2-[1-[(1-Hydroxy-cyclobutyl)-methyl]-8-methylamino-2-oxo-8-phenyl-1,3-diazaspiro[4.5]decan-3-yl]-N-(oxetan-3-yl)-acetamide |
| SC_1304 | CIS-2-[1-[(1-Hydroxy-cyclobutyl)-methyl]-8-methylamino-2-oxo-8-phenyl-1,3-diazaspiro[4.5]decan-3-yl]-N-(2-methoxy-ethyl)-acetamide |
| SC_1305 | CIS-2-[8-Dimethylamino-1-(3-methoxy-propyl)-2-oxo-8-phenyl-1,3-diazaspiro[4.5]decan-3-yl]-N-(4-methoxy-pyridin-2-yl)-acetamide |
| SC_1306 | CIS-2-[8-Dimethylamino-1-(3-methoxy-propyl)-2-oxo-8-phenyl-1,3-diazaspiro[4.5]decan-3-yl]-N-(pyrimidin-4-yl-methyl)-acetamide |
| SC_1308 | CIS-8-Dimethylamino-3-[2-(1,1-dioxo-[1,4]thiazinan-4-yl)-2-oxo-ethyl]-8-phenyl-1-propyl-1,3-diazaspiro[4.5]decan-2-one |
| SC_1309 | CIS-2-[8-Dimethylamino-1-[(1-hydroxy-cyclobutyl)-methyl]-2-oxo-8-phenyl-1,3-diazaspiro[4.5]decan-3-yl]-N-pyridin-2-yl-acetamide |
| SC_1310 | CIS-2-[1-[(1-Cyano-cyclobutyl)-methyl]-8-dimethylamino-2-oxo-8-phenyl-1,3-diazaspiro[4.5]decan-3-yl]-acetamide |
| SC_1311 | CIS-2-[[2-[1-[(1-Cyano-cyclobutyl)-methyl]-8-dimethylamino-2-oxo-8-phenyl-1,3-diazaspiro[4.5]decan-3-yl]-acetyl]amino]-acetamide |
| SC_1312 | CIS-2-[1-[(1-Hydroxy-cyclobutyl)-methyl]-8-methylamino-2-oxo-8-phenyl-1,3-diazaspiro[4.5]decan-3-yl]-N-methyl-acetamide |
| SC_1313 | CIS-3-[2-(1,1-Dioxo-[1,4]thiazinan-4-yl)-2-oxo-ethyl]-8-methylamino-8-phenyl-1-propyl-1,3-diazaspiro[4.5]decan-2-one |
| SC_1317 | CIS-2-[1-(Cyclobutyl-methyl)-8-dimethylamino-2-oxo-8-phenyl-1,3-diazaspiro[4.5]decan-3-yl]-N-pyridin-2-yl-acetamide |
| SC_1318 | CIS-8-Dimethylamino-1-[(1-hydroxy-cyclobutyl)-methyl]-3-(2-morpholin-4-yl-2-oxo-ethyl)-8-phenyl-1,3-diazaspiro[4.5]decan-2-one |
| SC_1319 | CIS-2-[1-[(1-Hydroxy-cyclobutyl)-methyl]-8-methylamino-2-oxo-8-phenyl-1,3-diazaspiro[4.5]decan-3-yl]-acetamide |
| SC_1320 | CIS-1-(Cyclobutyl-methyl)-8-dimethylamino-3-(2-morpholin-4-yl-2-oxo-ethyl)-8-phenyl-1,3-diazaspiro[4.5]decan-2-one |
| SC_1321 | CIS-2-[1-(Cyclobutyl-methyl)-8-dimethylamino-2-oxo-8-phenyl-1,3-diazaspiro[4.5]decan-3-yl]-N-(4-methylsulfanyl-pyridin-2-yl)-acetamide |
| SC_1322 | CIS-3-[2-(1,1-Dioxo-[1,4]thiazinan-4-yl)-2-oxo-ethyl]-8-methylamino-8-phenyl-1,3-diazaspiro[4.5]decan-2-one |
| SC_1323 | CIS-2-(8-Methylamino-2-oxo-8-phenyl-1,3-diazaspiro[4.5]decan-3-yl)-acetamide |
| SC_1324 | CIS-2-(8-Dimethylamino-2-oxo-8-phenyl-1,3-diazaspiro[4.5]decan-3-yl)-acetamide |
| SC_1325 | CIS-3-[2-(1,1-Dioxo-[1,4]thiazinan-4-yl)-2-oxo-ethyl]-8-ethylamino-8-phenyl-1,3-diazaspiro[4.5]decan-2-one |
| SC_1326 | TRANS-3-[2-(1,1-Dioxo-[1,4]thiazinan-4-yl)-2-oxo-ethyl]-8-ethylamino-8-phenyl-1,3-diazaspiro[4.5]decan-2-one |
| SC_1327 | CIS-2-[1-(Cyclobutyl-methyl)-8-methylamino-2-oxo-8-phenyl-1,3-diazaspiro[4.5]decan-3-yl]-N-methyl-acetamide |
| SC_1328 | CIS-2-(8-Ethylamino-2-oxo-8-phenyl-1,3-diazaspiro[4.5]decan-3-yl)-acetamide |

-continued

| | |
|---|---|
| SC_1329 | TRANS-2-(8-Ethylamino-2-oxo-8-phenyl-1,3-diazaspiro[4.5]decan-3-yl)-acetamide |
| SC_1330 | CIS-2-(8-Dimethylamino-2-oxo-8-phenyl-1,3-diazaspiro[4.5]decan-3-yl)-N-(2-hydroxy-ethyl)-N-methyl-acetamide |
| SC_1331 | CIS-8-Dimethylamino-3-[2-(1,1-dioxo-[1,4]thiazinan-4-yl)-2-oxo-ethyl]-1-[(1-hydroxy-cyclobutyl)-methyl]-8-phenyl-1,3-diazaspiro[4.5]decane-2,4-dione |
| SC_1332 | CIS-2-(8-Dimethylamino-2-oxo-8-phenyl-1,3-diazaspiro[4.5]decan-3-yl)-N-phenyl-acetamide |
| SC_1333 | CIS-N-(Carbamoyl-methyl)-2-[1-(cyclopropyl-methyl)-8-dimethylamino-2-oxo-8-phenyl-1,3-diazaspiro[4.5]decan-3-yl]-N-methyl-acetamide |
| SC_1334 | CIS-2-(8-Dimethylamino-2,4-dioxo-8-phenyl-1,3-diazaspiro[4.5]decan-3-yl)-N-phenyl-acetamide |
| SC_1335 | CIS-2-[1-(Cyclobutyl-methyl)-8-dimethylamino-2-oxo-8-phenyl-1,3-diazaspiro[4.5]decan-3-yl]-acetamide |
| SC_1336 | CIS-2-[8-Dimethylamino-1-[(1-hydroxy-cyclobutyl)-methyl]-2-oxo-8-phenyl-1,3-diazaspiro[4.5]decan-3-yl]-N-[2-[2-[2-(2-methoxy-ethoxy)-ethoxy]-ethoxy]-ethyl]-acetamide |
| SC_1337 | CIS-3-[2-(1,1-Dioxo-[1,4]thiazinan-4-yl)-2-oxo-ethyl]-1-[(1-hydroxy-cyclobutyl)-methyl]-8-methylamino-8-phenyl-1,3-diazaspiro[4.5]decane-2,4-dione |
| SC_1338 | CIS-2-(8-Dimethylamino-2-oxo-8-phenyl-1,3-diazaspiro[4.5]decan-3-yl)-N-[2-[2-[2-(2-methoxy-ethoxy)-ethoxy]-ethoxy]-ethyl]-acetamide |
| SC_1339 | CIS-N-(Carbamoyl-methyl)-N-methyl-2-(8-methylamino-2-oxo-8-phenyl-1,3-diazaspiro[4.5]decan-3-yl)-acetamide |
| SC_1340 | CIS-N-(Carbamoyl-methyl)-2-(8-dimethylamino-2-oxo-8-phenyl-1,3-diazaspiro[4.5]decan-3-yl)-N-methyl-acetamide |
| SC_1341 | CIS-N-(Carbamoyl-methyl)-2-[8-dimethylamino-1-(oxetan-3-yl-methyl)-2-oxo-8-phenyl-1,3-diazaspiro[4.5]decan-3-yl]-N-methyl-acetamide |
| SC_1342 | CIS-N-(2-Hydroxy-ethyl)-N-methyl-2-(8-methylamino-2-oxo-8-phenyl-1,3-diazaspiro[4.5]decan-3-yl)-acetamide |
| SC_1343 | CIS-2-[1-(Cyclopropyl-methyl)-8-dimethylamino-2-oxo-8-phenyl-1,3-diazaspiro[4.5]decan-3-yl]-acetamide |
| SC_1344 | CIS-2-[1-(Cyclopropyl-methyl)-8-dimethylamino-2-oxo-8-phenyl-1,3-diazaspiro[4.5]decan-3-yl]-N-(2-hydroxy-ethyl)-acetamide |
| SC_1345 | CIS-2-[1-(Cyclobutyl-methyl)-8-dimethylamino-8-(3-fluorophenyl)-2-oxo-1,3-diazaspiro[4.5]decan-3-yl]-N-(2-hydroxy-ethyl)-N-methyl-acetamide |
| SC_1346 | CIS-2-[1-(Cyclobutyl-methyl)-8-dimethylamino-8-(3-fluorophenyl)-2-oxo-1,3-diazaspiro[4.5]decan-3-yl]-acetic acid tert-butyl ester |
| SC_1347 | CIS-2-[1-(Cyclopropyl-methyl)-8-dimethylamino-2-oxo-8-phenyl-1,3-diazaspiro[4.5]decan-3-yl]-N-(2-hydroxy-ethyl)-N-methyl-acetamide |
| SC_1348 | CIS-2-[1-(Cyclopropyl-methyl)-8-dimethylamino-2-oxo-8-phenyl-1,3-diazaspiro[4.5]decan-3-yl]-N-(2-methylsulfonyl-ethyl)-acetamide |
| SC_1349 | CIS-N-(Carbamoyl-methyl)-2-[1-(cyclobutyl-methyl)-8-dimethylamino-8-(3-fluorophenyl)-2-oxo-1,3-diazaspiro[4.5]decan-3-yl]-N-methyl-acetamide |
| SC_1350 | CIS-1-[2-[8-Dimethylamino-1-[(1-hydroxy-cyclobutyl)-methyl]-2-oxo-8-phenyl-1,3-diazaspiro[4.5]decan-3-yl]-acetyl]-piperidine-4-carboxylic acid amide |
| SC_1351 | CIS-8-Dimethylamino-1-[(1-hydroxy-cyclobutyl)-methyl]-3-[2-(4-methylsulfonyl-piperidin-1-yl)-2-oxo-ethyl]-8-phenyl-1,3-diazaspiro[4.5]decan-2-one |
| SC_1352 | CIS-2-[1-(Cyclobutyl-methyl)-8-dimethylamino-8-(3-fluorophenyl)-2-oxo-1,3-diazaspiro[4.5]decan-3-yl]-N-(2-hydroxy-ethyl)-acetamide |
| SC_1353 | TRANS-2-[1-(Cyclobutyl-methyl)-8-dimethylamino-2-oxo-8-phenyl-1,3-diazaspiro[4.5]decan-3-yl]-N-(2-hydroxy-ethyl)-acetamide |
| SC_1354 | TRANS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide |
| SC_1355 | CIS-8-Dimethylamino-1-[(1-hydroxy-cyclobutyl)-methyl]-3-[2-(4-hydroxy-4-methyl-piperidin-1-yl)-2-oxo-ethyl]-8-phenyl-1,3-diazaspiro[4.5]decan-2-one |
| SC_1356 | CIS-2-[1-(Cyclobutyl-methyl)-8-dimethylamino-8-(4-fluorophenyl)-2-oxo-1,3-diazaspiro[4.5]decan-3-yl]-N-(2-hydroxy-ethyl)-acetamide |
| SC_1357 | TRANS-1-(Cyclopropyl-methyl)-8-dimethylamino-3-(2-morpholin-4-yl-2-oxo-ethyl)-8-phenyl-1,3-diazaspiro[4.5]decan-2-one |
| SC_1358 | TRANS-8-Dimethylamino-3-(2-morpholin-4-yl-2-oxo-ethyl)-8-phenyl-1,3-diazaspiro[4.5]decan-2-one |
| SC_1359 | CIS-2-[1-(Cyclobutyl-methyl)-8-dimethylamino-8-(4-fluorophenyl)-2-oxo-1,3-diazaspiro[4.5]decan-3-yl]-N-(2-hydroxy-ethyl)-N-methyl-acetamide |
| SC_1360 | CIS-N-(Carbamoyl-methyl)-2-[1-(cyclobutyl-methyl)-8-dimethylamino-8-(4-fluorophenyl)-2-oxo-1,3-diazaspiro[4.5]decan-3-yl]-N-methyl-acetamide |
| SC_1361 | CIS-1-(Cyclopropyl-methyl)-8-dimethylamino-3-[2-(4-hydroxy-4-methyl-piperidin-1-yl)-2-oxo-ethyl]-8-phenyl-1,3-diazaspiro[4.5]decan-2-one |
| SC_1362 | CIS-1-[2-[1-(Cyclopropyl-methyl)-8-dimethylamino-2-oxo-8-phenyl-1,3-diazaspiro[4.5]decan-3-yl]-acetyl]-piperidine-4-carboxylic acid amide |
| SC_1363 | TRANS-2-[1-(Cyclopropyl-methyl)-8-dimethylamino-2-oxo-8-phenyl-1,3-diazaspiro[4.5]decan-3-yl]-acetamide |
| SC_1364 | TRANS-2-[1-(Cyclopropyl-methyl)-8-dimethylamino-2-oxo-8-phenyl-1,3-diazaspiro[4.5]decan-3-yl]-N-methyl-acetamide |
| SC_1365 | TRANS-1-(Cyclopropyl-methyl)-8-dimethylamino-3-[2-(1,1-dioxo-[1,4]thiazinan-4-yl)-2-oxo-ethyl]-8-phenyl-1,3-diazaspiro[4.5]decan-2-one |
| SC_1366 | CIS-1-(Cyclopropyl-methyl)-8-dimethylamino-3-[2-(4-methylsulfonyl-piperidin-1-yl)-2-oxo-ethyl]-8-phenyl-1,3-diazaspiro[4.5]decan-2-one |
| SC_1368 | CIS-8-Dimethylamino-3-[2-(1,1-dioxo-[1,4]thiazinan-4-yl)-2-oxo-ethyl]-1-[(1-hydroxy-cyclobutyl)-methyl]-8-phenyl-1,3-diazaspiro[4.5]decan-2-one |

| | |
|---|---|
| SC_1369 | TRANS-2-(8-Dimethylamino-2-oxo-8-phenyl-1,3-diazaspiro[4.5]decan-3-yl)-acetamide |
| SC_1370 | TRANS-8-Dimethylamino-3-[2-(1,1-dioxo-[1,4]thiazinan-4-yl)-2-oxo-ethyl]-8-phenyl-1,3-diazaspiro[4.5]decan-2-one |
| SC_1371 | CIS-8-(dimethylamino)-8-phenyl-1-(2,2,2-trifluoroethyl)-3-(2-(trifluoromethyl)pyrimidin-5-yl)-1,3-diazaspiro[4.5]decan-2-one |
| SC_1372 | CIS-8-(dimethylamino)-8-phenyl-3-(2-(trifluoromethyl)pyrimidin-5-yl)-1-(3,3,3-trifluoropropyl)-1,3-diazaspiro[4.5]decan-2-one | and the physiologically acceptable salts thereof.

According to the invention, unless expressly stated otherwise, "—$C_1$-$C_4$-alkyl", "—$C_1$-$C_6$-alkyl" and any other alkyl residues can be linear or branched, saturated or unsaturated. Linear saturated alkyl includes methyl, ethyl, n-propyl, n-butyl, n-pentyl and n-hexyl. Examples of branched saturated alkyl include but are not limited to iso-propyl, sec-butyl, and tert-butyl. Examples of linear unsaturated alkyl include but are not limited to vinyl, propenyl, allyl, and propargyl.

According to the invention, unless expressly stated otherwise, "—$C_1$-$C_4$-alkyl", "—$C_1$-$C_6$-alkyl" and any other alkyl residues can be unsubstituted, mono- or polysubstituted. Examples of substituted alkyl include but are not limited to —$CH_2CH_2OH$, —$CH_2CH_2OCH_3$, —$CH_2CH_2CH_2OCH_3$, —$CH_2CH_2S(=O)_2CH_3$, —$CH_2C(=O)NH_2$, —$C(CH_3)_2C(=O)NH_2$, —$CH_2C(CH_3)_2C(=O)NH_2$, and —$CH_2CH_2C(=O)N(CH_3)_2$.

According to the invention, unless expressly stated otherwise, "—$C_1$-$C_6$-alkylene-", "—$C_1$-$C_4$-alkylene" and any other alkylene residue can be unsubstituted, mono- or polysubstituted. Examples of saturated alkylene include but are not limited to —$CH_2$—, —$CH(CH_3)$—, —$C(CH_3)_2$—, —$CH_2CH_2$—, —$CH(CH_3)CH_2$—, —$CH_2CH(CH_3)$—, —$CH(CH_3)$—$CH(CH_3)$—, —$C(CH_3)_2CH_2$—, —$CH_2C(CH_3)_2$—, —$CH(CH_3)C(CH_3)_2$—, —$C(CH_3)_2CH(CH_3)$—, $C(CH_3)_2C(CH_3)_2$—, —$CH_2CH_2CH_2$—, and —$C(CH_3)_2CH_2CH_2$—. Examples of unsaturated alkylene include but are not limited to —$CH=CH$—, —$C\equiv C$—, —$C(CH_3)=CH$—, —$CH=C(CH_3)$—, —$C(CH_3)=C(CH_3)$—, —$CH_2CH=CH$—, —$CH=CHCH_2$—, —$CH=CH$—$CH=CH$—, and —$CH=CH$—$C\equiv C$—.

According to the invention, unless expressly stated otherwise, "—$C_1$-$C_6$-alkylene-", "—$C_1$-$C_4$-alkylene" and any other alkylene residue can be unsubstituted, mono- or polysubstituted. Examples of substituted —$C_1$-$C_6$-alkylene- include but are not limited to —CHF—, —$CF_2$—, —CHOH— and —C(=O)—.

According to the invention, moieties may be connected through —$C_1$-$C_6$-alkylene-, i.e. the moieties may not be directly bound to the core structure of compound according to general formula (I), but may be connected to the core structure of compound according to general formula (I) or its periphery through a —$C_1$-$C_6$-alkylene- linker.

According to the invention, "3-12-membered cycloalkyl moiety" means a non-aromatic, monocyclic, bicyclic or tricyclic moiety comprising 3 to 12 ring carbon atoms but no heteroatoms in the ring. Examples of preferred saturated 3-12-membered cycloalkyl moieties according to the invention include but are not limited to cyclopropane, cyclobutane, cyclopentane, cyclohexane, cycloheptane, cyclooctane, hydrindane, and decaline. Examples of preferred unsaturated 3-12-membered cycloalkyl moiety moieties according to the invention include but are not limited to cyclopropene, cyclobutene, cyclopentene, cyclopentadiene, cyclohexene, 1,3-cyclohexadiene, and 1,4-cyclohexadiene.

The 3-12-membered cycloalkyl moiety, which is bonded to the compound according to the invention, in its periphery may optionally be condensed with a 3-12-membered heterocycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered cycloalkyl moiety. Examples of 3-12-membered cycloalkyl moieties condensed with 3-12-membered heterocycloalkyl moieties include but are not limited to octahydro-1H-indol, decahydroquinoline, decahydroisoquinoline, octahydro-2H-benzo[b][1,4]oxazin, and decahydro-quinoxalin, which in each case are connected through the 3-12-membered cycloalkyl moiety. Examples of 3-12-membered cycloalkyl moieties condensed with 6-14-membered aryl moieties include but are not limited to 2,3-dihydro-1H-indene and tetraline, which in each case are connected through the 3-12-membered cycloalkyl moiety. Examples of 3-12-membered cycloalkyl moieties condensed with 5-14-membered heteroaryl moieties include but are not limited to 5,6,7,8-tetrahydroquinoline and 5,6,7,8-tetrahydroquinazoline, which in each case are connected through the 3-12-membered cycloalkyl moiety.

According to the invention, the 3-12-membered cycloalkyl moiety may optionally be connected through —$C_1$-$C_6$-alkylene-, i.e. the 3-12-membered cycloalkyl moiety may not be directly bound to the compound according to general formula (I) but may be connected thereto through a —$C_1$-$C_6$-alkylene- linker. Examples include but are not limited to —$CH_2$-cyclopropyl, —$CH_2$-cyclobutyl, —$CH_2$-cyclopentyl, —$CH_2$-cyclohexyl, —$CH_2CH_2$-cyclopropyl, —$CH_2CH_2$-cyclobutyl, —$CH_2CH_2$-cyclopentyl, and —$CH_2CH_2$-cyclohexyl.

According to the invention, unless expressly stated otherwise, the 3-12-membered cycloalkyl moiety can be unsubstituted, mono- or polysubstituted. Examples of substituted 3-12-membered cycloalkyl moieties include but are not limited to —$CH_2$-1-hydroxy-cyclobutyl.

According to the invention, "3-12-membered heterocycloalkyl moiety" means a non-aromatic, monocyclic, bicyclic or tricyclic moiety comprising 3 to 12 ring atoms, wherein each cycle comprises independently of one another 1, 2, 3, 4 or more heteroatoms independently of one another selected from the group consisting of nitrogen, oxygen and sulfur, whereas sulfur may be oxidized (S(=O) or S(=O)$_2$), whereas the remaining ring atoms are carbon atoms, and whereas bicyclic or tricyclic systems may share common heteroatom(s). Examples of preferred saturated 3-12-membered heterocycloalkyl moieties according to the invention include but are not limited to aziridin, azetidine, pyrrolidine, imidazolidine, pyrazolidine, piperidine, piperazine, triazolidine, tetrazolidine, oxiran, oxetane, tetrahydrofurane, tetrahydropyrane, thiirane, thietane, tetra-hydrothiophene, diazepane, oxazolidine, isoxazolidine, thiazolidine, isothiazolidine, thiadiazolidine, morpholine, thiomorpholine. Examples of preferred unsaturated 3-12-membered heterocycloalkyl moiety moieties according to the invention include but are not limited to oxazoline, pyrazoline, imidazoline, isoxazoline, thiazoline, isothiazoline, and dihydropyran. The 3-12-membered heterocycloalkyl moiety, which is bonded to the compound according to the invention, in its periphery may optionally be condensed with a 3-12-membered cycloalkyl moiety, saturated or unsaturated, unsubstituted, mono- or polysubstituted; and/or with a 6-14-membered aryl moiety, unsubstituted, mono- or polysubstituted; and/or with a 5-14-membered heteroaryl moiety, unsubstituted, mono- or polysubstituted. Under these circumstances, the ring atoms of the condensed moieties are not included in the 3 to 12 ring atoms of the 3-12-membered heterocycloalkyl moieties. Examples of 3-12-membered heterocycloalkyl moieties condensed with 3-12-membered cycloalkyl moieties include but are not limited to octahydro-1H-indol, decahydroquinoline, decahydroisoquinoline, octahydro-2H-benzo[b][1,4]oxazin, and decahydro-quinoxalin, which in each case are connected through the 3-12-membered heterocycloalkyl moiety. An examples of a 3-12-membered heterocycloalkyl moiety condensed with a 6-14-membered aryl moiety includes but is not limited to 1,2,3,4-tetrahydroquinoline, which is connected through the 3-12-membered heterocycloalkyl moiety. An example of a 3-12-membered heterocycloalkyl moiety condensed with a 5-14-membered heteroaryl moieties includes but is not limited to 5,6,7,8-tetrahydro-[1,2,4]triazolo[1,5-a]pyrazine, which is connected through the 3-12-membered heterocycloalkyl moiety.

According to the invention, the 3-12-membered heterocycloalkyl moiety may optionally be connected through —$C_1$-$C_6$-alkylene-, i.e. the 3-12-membered heterocycloalkyl moiety may not be directly bound to the compound according to general formula (I) but may be connected thereto through a —$C_1$-$C_6$-alkylene- linker. Said linker may be connected to a carbon ring atom or to a hetero ring atom of the 3-12-membered heterocycloalkyl moiety. Examples include but are not limited to —$CH_2$-oxetane, —$CH_2$-pyrrolidine, —$CH_2$-piperidine, —$CH_2$-morpholine, —$CH_2CH_2$-oxetane, —$CH_2CH_2$-pyrrolidine, —$CH_2CH_2$-piperidine, and —$CH_2CH_2$-morpholine.

According to the invention, unless expressly stated otherwise, the 3-12-membered heterocycloalkyl moiety can be unsubstituted, mono- or polysubstituted. Examples of substituted 3-12-membered heterocycloalkyl moieties include but are not limited to 2-carboxamido-N-pyrrolidinyl-, 3,4-dihydroxy-N-pyrrolidinyl, 3-hydroxy-N-pyrimidinyl, 3,4-dihydroxy-N-pyrimidinyl, 3-oxo-N-piperazinyl, -tetrahydro-2H-thiopyranyl dioxide and thiomorpholinyl dioxide.

According to the invention, "6-14-membered aryl moiety" means an aromatic, monocyclic, bicyclic or tricyclic moiety comprising 6 to 14 ring carbon atoms but no heteroatoms in the ring. Examples of preferred 6-14-membered aryl moieties according to the invention include but are not limited to benzene, naphthalene, anthracen, and phenanthren. The 6-14-membered aryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 5-14-membered heteroaryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 6-14-membered aryl moieties condensed with 3-12-membered cycloalkyl moieties include but are not limited to 2,3-dihydro-1H-indene and tetraline, which in each case are connected through the 6-14-membered aryl moiety. An example of a 6-14-membered aryl moiety condensed with a 3-12-membered heterocycloalkyl moiety includes but is not limited to 1,2,3,4-tetrahydroquinoline, which is connected through the 6-14-membered aryl moiety. Examples of 6-14-membered aryl moieties condensed with 5-14-membered heteroaryl moieties include but are not limited to quinoline, isoquinoline, phenazine and phenoxacine, which in each case are connected through the 6-14-membered aryl moiety.

According to the invention, the 6-14-membered aryl moiety may optionally be connected through —$C_1$-$C_6$-alkylene-, i.e. the 6-14-membered aryl moiety may not be directly bound to the compound according to general formula (I) but may be connected thereto through a —$C_1$-$C_6$-alkylene- linker. Said linker may be connected to a carbon ring atom or to a hetero ring atom of the 6-14-membered aryl moiety. Examples include but are not limited to —$CH_2$—$C_6H_5$, —$CH_2CH_2$—$C_6H_5$ and —CH=CH—$C_6H_5$.

According to the invention, unless expressly stated otherwise, the 6-14-membered aryl moiety can be unsubstituted, mono- or polysubstituted. Examples of substituted 6-14-membered aryl moieties include but are not limited to 2-fluorophenyl, 3-fluorophenyl, 2-methoxyphenyl and 3-methoxyphenyl.

According to the invention, "5-14-membered heteroaryl moiety" means an aromatic, monocyclic, bicyclic or tricyclic moiety comprising 6 to 14 ring atoms, wherein each cycle comprises independently of one another 1, 2, 3, 4 or more heteroatoms independently of one another selected from the group consisting of nitrogen, oxygen and sulfur, whereas the remaining ring atoms are carbon atoms, and whereas bicyclic or tricyclic systems may share common heteroatom(s). Examples of preferred 5-14-membered heteroaryl moieties according to the invention include but are not limited to pyrrole, pyrazole, imidazole, triazole, tetrazole, furane, thiophene, oxazole, isoxazole, thiazole, isothiazole, pyridine, pyridazine, pyrimidine, pyrazine, indolicine, 9H-chinolicine, 1,8-naphthyridine, purine, imidazo[1,2-a]pyrazine, and pteridine. The 5-14-membered heteroaryl moiety, which is bonded to the compound according to the invention, in its periphery may optionally be condensed with a 3-12-membered cycloalkyl moiety, saturated or unsaturated, unsubstituted, mono- or polysubstituted; and/or with a 3-12-membered heterocycloalkyl moiety, saturated or unsaturated, unsubstituted, mono- or polysubstituted; and/or with a 6-14-membered aryl moiety, unsubstituted, mono- or polysubstituted. Under these circumstances, the ring atoms of the condensed moieties are not included in the 6 to 14 ring carbon atoms of the 6-14-membered heterocycloalkyl moieties. Examples of 5-14-membered heteroaryl moieties condensed with 3-12-membered cycloalkyl moieties include but are not limited to 5,6,7,8-tetrahydroquinoline and 5,6,7,8-tetrahydroquinazoline, which in each case are connected through the 5-14-membered heteroaryl moiety. An examples of a 5-14-membered heteroaryl moiety condensed with a 3-12-membered heterocycloalkyl moiety includes but is not limited to 5,6,7,8-tetrahydro-[1,2,4]triazolo[1,5-a]pyrazine, which is connected through the 5-14-membered heteroaryl moiety. Examples of 5-14-membered heteroaryl moieties condensed with 6-14-membered aryl moieties include but are not limited to quinoline, isoquinoline, phenazine and phenoxacine, which in each case are connected through the 5-14-membered heteroaryl moiety.

According to the invention, the 5-14-membered heteroaryl moiety may optionally be connected through —$C_1$-$C_6$-alkylene-, i.e. the 5-14-membered heteroaryl moiety may not be directly bound to the compound according to general formula (I) but may be connected thereto through a —$C_1$-$C_6$-alkylene- linker. Said linker may be connected to a carbon ring atom or to a hetero ring atom of the 5-14-membered heteroaryl moiety. Examples include but are not limited to —$CH_2$-oxazole, —$CH_2$-isoxazole, —$CH_2$-imidazole, —$CH_2$-pyridine, —$CH_2$-pyrimidine, —$CH_2$-pyridazine, —$CH_2CH_2$-oxazole, —$CH_2CH_2$-isoxazole, —$CH_2CH_2$-imidazole, —$CH_2CH_2$-pyridine, —$CH_2CH_2$-pyrimidine, and —$CH_2CH_2$-pyridazine.

According to the invention, unless expressly stated otherwise, the 5-14-membered heteroaryl moiety can be unsubstituted, mono- or polysubstituted. Examples of 5-14-membered heteroaryl moieties include but are not limited to 2-methoxy-4-pyridinyl, 2-methoxy-5-pyridinyl, 3-methoxy-4-pyridinyl, 3-methoxy-6-pyridinyl, 4-methoxy-2-pyridinyl, 2-methylsulfonyl-5-pyridinyl, 3-methylsulfonyl-6-pyridinyl, 3-methoxy-6-pyridazinyl, 2-nitrilo-5-pyrimidinyl, 4-hydroxy-2-pyrimidinyl, 4-methoxy-pyrimidinyl, and 2-methoxy-6-pyrazinyl.

Preferably, the compounds according to the invention have a structure according to general formula (I')

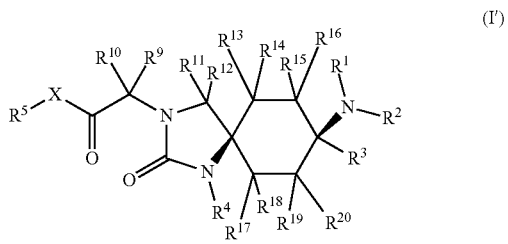

(I')

wherein $R^1$ to $R^5$, $R^9$ to $R^{20}$, and X are defined as above, or a physiologically acceptable salt thereof.

In one preferred embodiment, the excess of the cis-isomer so designated is at least 50% de, more preferably at least 75% de, yet more preferably at least 90% de, most preferably at least 95% de and in particular at least 99% de.

Preferably, the compounds according to the invention have a structure according to general formula (IX)

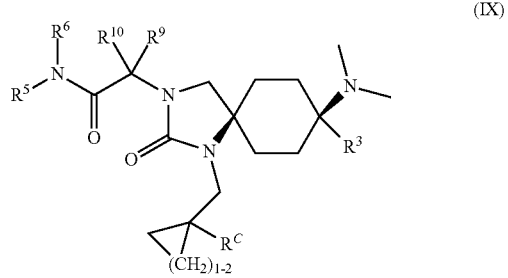

(IX)

wherein
$R^C$ means —H or —OH;
$R^3$ means -phenyl or -3-fluorophenyl;
$R^5$ means —H, —$CH_3$, —$CH_2CH_2OH$, or —$CH_2C(=O)NH_2$;
$R^6$ means —H or —$CH_3$;
or $R^5$ and $R^6$ together with the nitrogen atom to which they are attached form a ring and mean —$(CH_2)_5$—, wherein said ring is unsubstituted or substituted with one or two substituents independently of one another selected from the group consisting of —$CH_3$, —OH, —$S(=O)_2CH_3$ and —$C(=O)NH_2$;
$R^9$ and $R^{10}$ independently of one another mean —H or —$CH_3$;
or a physiologically acceptable salt thereof.

In a preferred embodiment, the compounds according to the invention are in the form of the free bases.

In another preferred embodiment, the compounds according to the invention are in the form of the physiologically acceptable salts.

For the purposes of the description, a "salt" is to be understood as being any form of the compound in which it assumes an ionic form or is charged and is coupled with a counter-ion (a cation or anion) or is in solution. The term is also to be understood as meaning complexes of the compound with other molecules and ions, in particular complexes which are associated via ionic interactions. Preferred salts are physiologically acceptable, in particular physiologically acceptable salts with anions or acids or also a salt formed with a physiologically acceptable acid.

Physiologically acceptable salts with anions or acids are salts of the particular compound in question with inorganic or organic acids which are physiologically acceptable, in particular when used in humans and/or mammals. Examples of physiologically acceptable salts of particular acids include but are not limited to salts of hydrochloric acid, sulfuric acid, and acetic acid.

The invention also includes isotopic isomers of a compound according to the invention, wherein at least one atom of the compound is replaced by an isotope of the respective atom which is different from the naturally predominantly occurring isotope, as well as any mixtures of isotopic isomers of such a compound. Preferred isotopes are $^2$H (deuterium), $^3$H (tritium), $^{13}$C and $^{14}$C.

Certain compounds according to the invention are useful for modulating a pharmacodynamic response from one or more opioid receptors (mu, delta, kappa, NOP/ORL-1) either centrally or peripherally, or both. The pharmacodynamic response may be attributed to the compound either stimulating (agonizing) or inhibiting (antagonizing) the one or more receptors. Certain compounds according to the invention may antagonize one opioid receptor, while also agonizing one or more other receptors. Compounds according to the invention having agonist activity may be either full agonists or partial agonists.

As used herein, compounds that bind to receptors and mimic the regulatory effects of endogenous ligands are defined as "agonists". Compounds that bind to a receptor but produce no regulatory effect, but rather block the binding of ligands to the receptor, are defined as "antagonists".

In certain embodiments, the compounds according to the invention are agonists at the mu opioid (MOP) and/or kappa opioid (KOP) and/or delta opioid (DOP) and/or nociceptin opioid (NOP/ORL-1) receptors.

The compounds according to the invention potently bind to the MOP and/or KOP and/or DOP and/or NOP receptors.

The compounds according to the invention can be modulators at the MOP and/or KOP and/or DOP and/or NOP receptors, and therefore the compounds according to the invention can be used/administered to treat, ameliorate, or prevent pain.

In some embodiments, the compounds according to the invention are agonists of one or more opioid receptors. In some embodiments, the compounds according to the invention are agonists of the MOP and/or KOP and/or DOP and/or NOP receptors.

In some embodiments, the compounds according to the invention are antagonists of one or more opioid receptors. In some embodiments, the compounds according to the invention are antagonists of the MOP and/or KOP and/or DOP and/or NOP receptors.

In some embodiments, the compounds according to the invention have both, (i) agonist activity at the NOP receptor; and (ii) agonist activity at one or more of the MOP, KOP, and DOP receptors.

In some embodiments, the compounds according to the invention have both, (i) agonist activity at the NOP receptor; and (ii) antagonist activity at one or more of the MOP, KOP, and DOP receptors.

In some embodiments, the compounds according to the invention have both, (i) antagonist activity at the NOP receptor; and (ii) agonist activity at one or more of the MOP, KOP, and DOP receptors.

In some embodiments, the compounds according to the invention have both, (i) antagonist activity at the NOP receptor; and (ii) antagonist activity at one or more of the MOP, KOP, and DOP receptors.

In some embodiments, preferably with respect to receptors of the peripheral nervous system, the compounds according to the invention have selective agonist activity at the NOP receptor. In some embodiments, preferably with respect to receptors of the peripheral nervous system, the compounds according to the invention
- have agonist activity at the NOP receptor, but no significant activity at the MOP receptor;
- have agonist activity at the NOP receptor, but no significant activity at the KOP receptor;
- have agonist activity at the NOP receptor, but no significant activity at the DOP receptor;
- have agonist activity at the NOP receptor, but no significant activity at the MOP receptor as well as no significant activity at the KOP receptor;
- have agonist activity at the NOP receptor, but no significant activity at the MOP receptor as well as no significant activity at the DOP receptor; or
- have agonist activity at the NOP receptor, but no significant activity at the MOP receptor as well as no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the MOP receptor. In some embodiments, preferably with respect to receptors of the peripheral nervous system, the compounds according to the invention
- have agonist activity at the NOP receptor as well as agonist activity at the MOP receptor;
- have agonist activity at the NOP receptor as well as agonist activity at the MOP receptor as well as agonist activity at the KOP receptor;
- have agonist activity at the NOP receptor as well as agonist activity at the MOP receptor as well as agonist activity at the DOP receptor;
- can be regarded as opioid pan agonists, i.e. have agonist activity at the NOP receptor as well as agonist activity at the MOP receptor as well as agonist activity at the KOP receptor as well as agonist activity at the DOP receptor;
- have agonist activity at the NOP receptor as well as agonist activity at the MOP receptor, but no significant activity at the KOP receptor;
- have agonist activity at the NOP receptor as well as agonist activity at the MOP receptor, but no significant activity at the DOP receptor; or
- have agonist activity at the NOP receptor as well as agonist activity at the MOP receptor, but no significant activity at the KOP receptor as well as no significant activity at the DOP receptor.

In some embodiments, preferably with respect to receptors of the peripheral nervous system, the compounds according to the invention have balanced agonist activity at the NOP receptor as well as at the KOP receptor. In some embodiments, preferably with respect to receptors of the peripheral nervous system, the compounds according to the invention
- have agonist activity at the NOP receptor as well as agonist activity at the KOP receptor;
- have agonist activity at the NOP receptor as well as agonist activity at the KOP receptor as well as agonist activity at the MOP receptor;
- have agonist activity at the NOP receptor as well as agonist activity at the KOP receptor as well as agonist activity at the DOP receptor;
- have agonist activity at the NOP receptor as well as agonist activity at the KOP receptor, but no significant activity at the MOP receptor;
- have agonist activity at the NOP receptor as well as agonist activity at the KOP receptor, but no significant activity at the DOP receptor; or
- have agonist activity at the NOP receptor as well as agonist activity at the KOP receptor, but no significant activity at the MOP receptor as well as no significant activity at the DOP receptor.

In some embodiments, preferably with respect to receptors of the peripheral nervous system, the compounds according to the invention have balanced agonist activity at the NOP receptor as well as at the DOP receptor. In some embodiments, preferably with respect to receptors of the peripheral nervous system, the compounds according to the invention
- have agonist activity at the NOP receptor as well as agonist activity at the DOP receptor;
- have agonist activity at the NOP receptor as well as agonist activity at the DOP receptor, but no significant activity at the MOP receptor;
- have agonist activity at the NOP receptor as well as agonist activity at the DOP receptor, but no significant activity at the KOP receptor; or
- have agonist activity at the NOP receptor as well as agonist activity at the DOP receptor, but no significant activity at the MOP receptor as well as no significant activity at the KOP receptor.

In some embodiments, preferably with respect to receptors of the peripheral nervous system, the compounds according to the invention have selective agonist activity at the KOP receptor. In some embodiments, preferably with respect to receptors of the peripheral nervous system, the compounds according to the invention
- have agonist activity at the KOP receptor, but no significant activity at the MOP receptor;
- have agonist activity at the KOP receptor, but no significant activity at the NOP receptor;

have agonist activity at the KOP receptor, but no significant activity at the DOP receptor;

have agonist activity at the KOP receptor, but no significant activity at the MOP receptor as well as no significant activity at the NOP receptor;

have agonist activity at the KOP receptor, but no significant activity at the MOP receptor as well as no significant activity at the DOP receptor; or have agonist activity at the KOP receptor, but no significant activity at the MOP receptor as well as no significant activity at the NOP receptor as well as no significant activity at the DOP receptor.

In some embodiments, preferably with respect to receptors of the peripheral nervous system, the compounds according to the invention have agonist activity at the MOP receptor, agonist activity at the KOP receptor, and antagonist activity at the DOP receptor. In some embodiments, preferably with respect to receptors of the peripheral nervous system, the compounds according to the invention have agonist activity at the MOP receptor as well as agonist activity at the KOP receptor as well as antagonist activity at the DOP receptor;

have agonist activity at the MOP receptor as well as agonist activity at the KOP receptor as well as antagonist activity at the DOP receptor as well as agonist activity at the NOP receptor;

have agonist activity at the MOP receptor as well as agonist activity at the KOP receptor as well as antagonist activity at the DOP receptor as well as antagonist activity at the NOP receptor; or have agonist activity at the MOP receptor as well as agonist activity at the KOP receptor as well as antagonist activity at the DOP receptor, no significant activity at the NOP receptor.

In some embodiments, preferably with respect to receptors of the central nervous system, the compounds according to the invention have selective agonist activity at the NOP receptor. In some embodiments, preferably with respect to receptors of the central nervous system, the compounds according to the invention have agonist activity at the NOP receptor, but no significant activity at the MOP receptor;

have agonist activity at the NOP receptor, but no significant activity at the KOP receptor;

have agonist activity at the NOP receptor, but no significant activity at the DOP receptor;

have agonist activity at the NOP receptor, but no significant activity at the MOP receptor as well as no significant activity at the KOP receptor;

have agonist activity at the NOP receptor, but no significant activity at the MOP receptor as well as no significant activity at the DOP receptor; or have agonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have selective antagonist activity at the NOP receptor. In some embodiments, preferably with respect to receptors of the central nervous system, the compounds according to the invention have antagonist activity at the NOP receptor, but no significant activity at the MOP receptor;

have antagonist activity at the NOP receptor, but no significant activity at the KOP receptor;

have antagonist activity at the NOP receptor, but no significant activity at the DOP receptor;

have antagonist activity at the NOP receptor, but no significant activity at the MOP receptor as well as no significant activity at the KOP receptor;

have antagonist activity at the NOP receptor, but no significant activity at the MOP receptor as well as no significant activity at the DOP receptor; or have antagonist activity at the NOP receptor, but no significant activity at the MOP receptor as well as no significant activity at the KOP receptor as well as no significant activity at the DOP receptor.

In some embodiments, preferably with respect to receptors of the central nervous system, the compounds according to the invention have antagonist activity at the NOP receptor as well as agonist activity at the DOP receptor. In some embodiments, preferably with respect to receptors of the central nervous system, the compounds according to the invention antagonist activity at the NOP receptor as well as agonist activity at the DOP receptor;

have antagonist activity at the NOP receptor as well as agonist activity at the DOP receptor, but no significant activity at the MOP receptor;

have antagonist activity at the NOP receptor as well as agonist activity at the DOP receptor, but no significant activity at the KOP receptor; or have antagonist activity at the NOP receptor as well as agonist activity at the DOP receptor, but no significant activity at the MOP receptor as well as no significant activity at the KOP receptor.

For the purpose of the specification, "no significant activity" means that the activity (agonist/antagonist) of the given compound at this receptor is lower by a factor of 1000 or more compared to its activity (agonist/antagonist) at one or more of the other opioid receptors.

A further aspect of the invention relates to the compounds according to the invention as medicaments.

A further aspect of the invention relates to the compounds according to the invention for use in the treatment of pain. A further aspect of the invention relates to a method of treating pain comprising the administration of a pain alleviating amount of a compound according to the invention to a subject in need thereof, preferably to a human. The pain is preferably acute or chronic. The pain is preferably nociceptive or neuropathic.

A further aspect of the invention relates to the compounds according to the invention for use in the treatment of neurodegenerative disorders, neuroinflammatory disorders, neuropsychiatric disorders, and substance abuse/dependence. A further aspect of the invention relates to a method of treating any one of the aforementioned disorders, diseases or conditions comprising the administration of a therapeutically effective amount of a compound according to the invention to a subject in need thereof, preferably to a human.

Another aspect of the invention relates to a pharmaceutical composition which contains a physiologically acceptable carrier and at least one compound according to the invention.

Preferably, the composition according to the invention is solid, liquid or pasty; and/or contains the compound according to the invention in an amount of from 0.001 to 99 wt. %, preferably from 1.0 to 70 wt. %, based on the total weight of the composition.

The pharmaceutical composition according to the invention can optionally contain suitable additives and/or auxiliary substances and/or optionally further active ingredients.

Examples of suitable physiologically acceptable carriers, additives and/or auxiliary substances are fillers, solvents, diluents, colorings and/or binders. These substances are known to the person skilled in the art (see H. P. Fiedler, Lexikon der Hilfsstoffe fur Pharmazie, Kosmetik and angrenzende Gebiete, Editio Cantor Aulendoff).

The pharmaceutical composition according to the invention contains the compound according to the invention in an amount of preferably from 0.001 to 99 wt. %, more preferably from 0.1 to 90 wt. %, yet more preferably from 0.5 to 80 wt. %, most preferably from 1.0 to 70 wt. % and in particular from 2.5 to 60 wt. %, based on the total weight of the pharmaceutical composition.

The pharmaceutical composition according to the invention is preferably for systemic, topical or local administration, preferably for oral administration.

Another aspect of the invention relates to a pharmaceutical dosage form which contains the pharmaceutical composition according to the invention.

In one preferred embodiment, the pharmaceutical dosage form according to the invention is produced for administration twice daily, for administration once daily or for administration less frequently than once daily. Administration is preferably systemic, in particular oral.

The pharmaceutical dosage form according to the invention can be administered, for example, as a liquid dosage form in the form of injection solutions, drops or juices, or as a semi-solid dosage form in the form of granules, tablets, pellets, patches, capsules, plasters/spray-on plasters or aerosols. The choice of auxiliary substances etc. and the amounts thereof to be used depend on whether the form of administration is to be administered orally, perorally, parenterally, intravenously, intraperitoneally, intradermally, intramuscularly, intranasally, buccally, rectally or locally, for example to the skin, the mucosa or into the eyes.

Pharmaceutical dosage forms in the form of tablets, dragees, capsules, granules, drops, juices and syrups are suitable for oral administration, and solutions, suspensions, readily reconstitutable dry preparations and also sprays are suitable for parenteral, topical and inhalatory administration. Compounds according to the invention in a depot, in dissolved form or in a plaster, optionally with the addition of agents promoting penetration through the skin, are suitable percutaneous administration preparations.

The amount of the compounds according to the invention to be administered to the patient varies in dependence on the weight of the patient, on the type of administration, on the indication and on the severity of the disease. Usually, from 0.00005 mg/kg to 50 mg/kg, preferably from 0.001 mg/kg to 10 mg/kg, of at least one compound according to the invention is administered.

Another aspect of the invention relates to a process for the preparation of the compounds according to the invention. Suitable processes for the synthesis of the compounds according to the invention are known in principle to the person skilled in the art.

Preferred synthesis routes are described below:

The compounds according to the invention can be obtained via different synthesis routes. Depending on the synthesis route, different intermediates are prepared and subsequently further reacted.

In a preferred embodiment, the synthesis of the compounds according to the invention proceeds via a synthesis route which comprises the preparation of an intermediate according to general formula (IIIa):

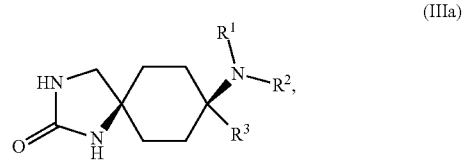

(IIIa)

wherein $R^1$, $R^2$ and $R^3$ are defined as above.

In another preferred embodiment, the synthesis of the compounds according to the invention proceeds via a synthesis route which comprises the preparation of an intermediate according to general formula (IIIb):

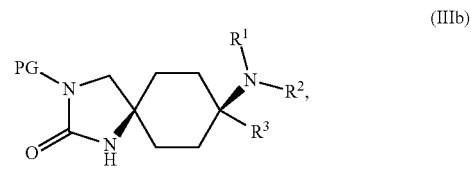

(IIIb)

wherein $R^1$, $R^2$ and $R^3$ are defined as above and PG is a protecting group.

Preferably the protecting group is -p-methoxybenzyl. Therefore, in another preferred embodiment, the synthesis of the compounds according to the invention proceeds via a synthesis route which comprises the preparation of an intermediate according to general formula (IIIc):

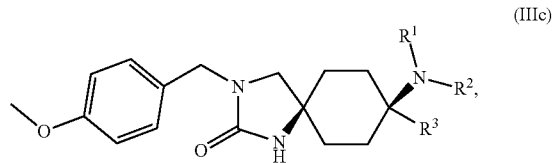

(IIIc)

wherein $R^1$, $R^2$ and $R^3$ are defined as above.

As already indicated, in general formula (IIIc), the -p-methoxybenzyl moiety represents a protecting group which can be cleaved in the course of the synthesis route.

In yet another preferred embodiment, the synthesis of the compounds according to the invention proceeds via a synthesis route which comprises the preparation of

- an intermediate according to general formula (IIIa) and according to general formula (IIIb); or
- an intermediate according to general formula (IIIa) and according to general formula (IIIc); or
- an intermediate according to general formula (IIIb) and according to general formula (IIIc); or
- an intermediate according to general formula (IIIa), according to general formula (IIIb) and according to general formula (IIIc).

The following examples further illustrate the invention but are not to be construed as limiting its scope.

EXAMPLES

"RT" means room temperature (23±7° C.), "M" are indications of concentration in mol/l, "aq." means aqueous, "anhydr." means anhydrous, "sat." means saturated, "sol." means solution, "conc." means concentrated.

Further Abbreviations brine saturated aqueous sodium chloride solution
CC column chromatography
cHex cyclohexane
DCM dichloromethane
DIPEA N,N-diisopropylethylamine
DMF N,N-dimethylformamide
EDCl 1-ethyl-3-(3-dimethylaminopropyl)carbodiimide
Et ethyl
ether diethyl ether
EE ethyl acetate
EtOAc ethyl acetate
EtOH ethanol
h hour(s)
H$_2$O water
HATU O-(7-aza-benzotriazol-1-yl)-N,N,N',N'-tetramethyl-uroniumhexafluorophosphate
LDA Lithium-di-isoproyl-amid
Me methyl
m/z mass-to-charge ratio
MeOH methanol
MeCN acetonitrile
min minutes
MS mass spectrometry
NBS N-bromo-succinimide
NEt$_3$ triethylamine
Pd$_2$(dba)$_3$ tris(dibenzylideneacetone)dipalladium(0)
PE petroleum ether (60-80° C.)
RM reaction mixture
RT room temperature
T3P 2,4,6-tripropyl-1,3,5,2,4,6-trioxatriphosphorinane-2,4,6-trioxide
tBME tert-butyl methyl ether
THF tetrahydrofuran
TFA trifluoroacetic acid
v/v volume to volume
w/w weight to weight
XantPhos 4,5-bis(diphenylphosphino)-9,9-dimethylxanthene The yields of the compounds prepared were not optimised. All temperatures are uncorrected.

All starting materials, which are not explicitly described, were either commercially available (the details of suppliers such as for example Acros, Aldrich, Bachem, Butt park, Enamine, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The mixing ratios of solvents or eluents for chromatography are specified in v/v.

All the intermediate products and exemplary compounds were analytically characterised by mass spectrometry (MS, m/z for [M+H]+). In addition $^1$H-NMR and $^{13}$C spectroscopy was carried out for all the exemplary compounds and selected intermediate products.

Remark Regarding Stereochemistry

CIS refers to the relative configuration of compounds described herein, in which both nitrogen atoms are drawn on the same face of the cyclohexane ring as described in the following exemplary structure. Two depictions are possible:

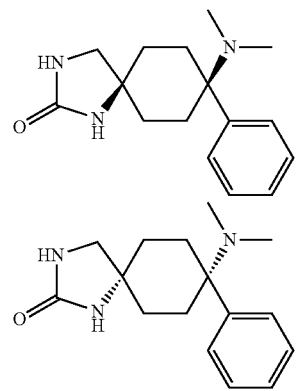

CIS configuration

TRANS refers to compounds, in which both nitrogen atoms are on opposite faces of the cyclohexane ring as described in the following exemplary structure. Two depictions are possible:

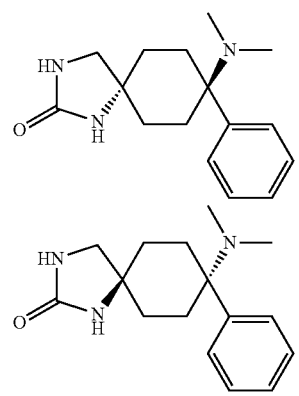

TRANS configuration

Synthesis of Intermediates

Synthesis of INT-799: CIS-8-Dimethylamino-1-[(1-hydroxy-cyclobutyl)-methyl]-8-phenyl-1,3-diaz-aspiro[4.5]decan-2-one

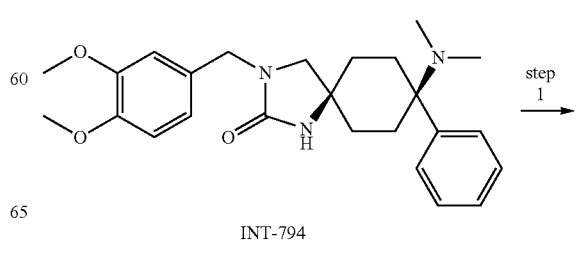

INT-794

-continued

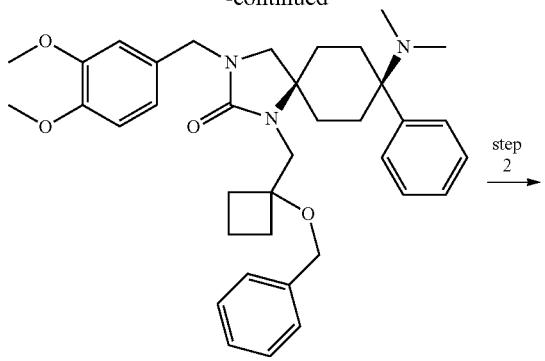

step 2

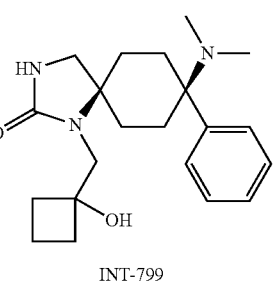

INT-799

Step 1: CIS-1-((1-(benzyloxy)cyclobutyl)methyl)-3-(3,4-dimethoxybenzyl)-8-(dimethylamino)-8-phenyl-1,3-diazaspiro[4.5]decan-2-one NaOH (1.42 g, 35.5 mmol) was added to a solution of CIS-3-(3,4-dimethoxybenzyl)-8-(dimethylamino)-8-phenyl-1,3-diazaspiro[4.5]decan-2-one (INT-794) (3 g, 7.09 mmol) in DMSO (90 mL) under argon atmosphere and the reaction mixture was stirred at 80° C. for 30 min. ((1-(Bromomethyl)cyclobutoxy)methyl)benzene (5.4 g, 21.3 mmol) was added and stirring was continued for 2 days at 80° C. The reaction completion was monitored by TLC. The reaction mixture was diluted with water (500 mL) and extracted with diethyl ether (4×300 mL). The combined organic extracts were dried over anhydrous $Na_2SO_4$ and concentrated under reduced pressure. The residue was purified by column chromatography (230-400 mesh silica gel; 65-70% EtOAc in petroleum ether as eluent) to afford 2.5 g (59%) of CIS-1-((1-(benzyloxy)cyclobutyl)methyl)-3-(3,4-dimethoxybenzyl)-8-(dimethylamino)-8-phenyl-1,3-diazaspiro[4.5]decan-2-one (TLC system: 10% MeOH in DCM; Rf: 0.8).

Step 2: CIS-8-Dimethylamino-1-[(1-hydroxy-cyclobutyl)-methyl]-8-phenyl-1,3-diazaspiro[4.5]decan-2-one TFA (12 mL) was added to CIS-1-((1-(benzyloxy)cyclobutyl)methyl)-3-(3,4-dimethoxybenzyl)-8-(dimethylamino)-8-phenyl-1,3-diazaspiro[4.5]decan-2-one (2.5 g, 4.18 mmol) at 0° C. and the resulting mixture was stirred at 70° C. for 6 h. The reaction completion was monitored by LCMS. The reaction mixture was concentrated under reduced pressure. To the residue sat. aq. $NaHCO_3$ was added (until pH 10) and the organic product was extracted with DCM (3×150 mL). The combined organic extracts were dried over anhydrous $Na_2SO_4$ and concentrated under reduced pressure. The residue was purified by column chromatography (230-400 mesh silica gel; 5% MeOH in DCM as eluent) to afford 500 mg (33%) of CIS-8-dimethylamino-1-[(1-hydroxy-cyclobutyl)-methyl]-8-phenyl-1,3-diazaspiro[4.5]decan-2-one (INT-799) (TLC system: 10% MeOH in DCM; Rf: 0.5). $[M+H]^+$ 358.2

Synthesis of INT-951: CIS-1-[(8-Dimethylamino-2-oxo-8-phenyl-1,3-diazaspiro[4.5]decan-1-yl)-methyl]-cyclobutane-1-carbonitrile

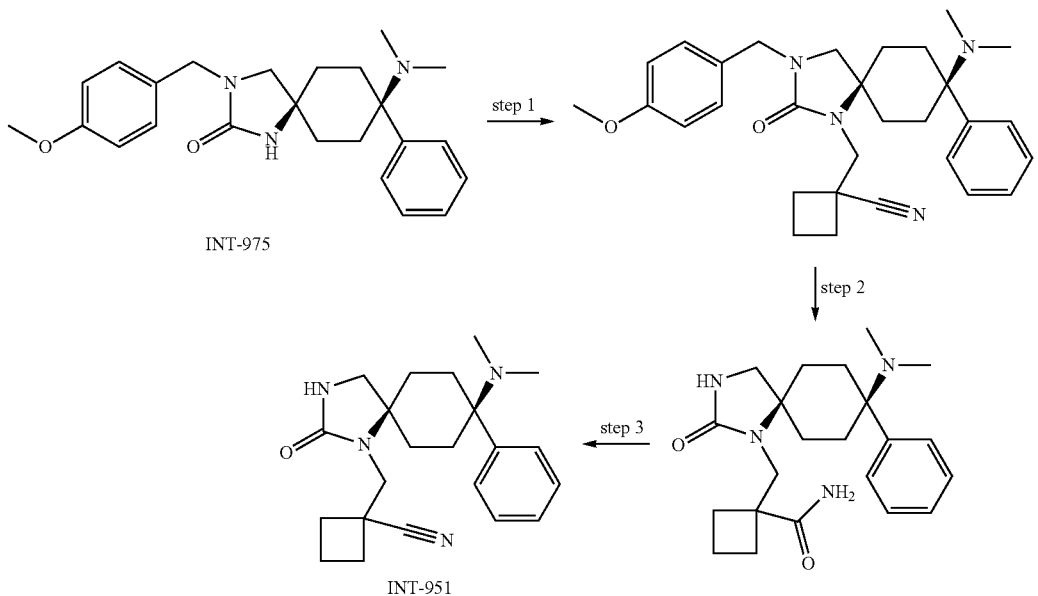

Step 1: 1—((CIS-8-(dimethylamino)-3-(4-methoxybenzyl)-2-oxo-8-phenyl-1,3-diazaspiro[4.5]decan-1-yl)methyl)cyclobutanecarbonitrile NaH (50% in mineral oil) (2.44 g, 50.89 mmol) was added to a solution of CIS-8-dimethylamino-3-[(4-methoxyphenyl)-methyl]-8-phenyl-1,3-diazaspiro[4.5]decan-2-one (INT-975) (5 g, 12.72 mmol) in DMF (100 mL) at 0° C. portionwise over 10 min. 1-(Bromomethyl)cyclobutanecarbonitrile (4.4 g, 25.44 mmol) was added dropwise over 10 minutes at 0° C. The reaction mixture was allowed to stir at RT for 3 h, then quenched with water and the organic product was extracted with ethyl acetate (3×200 mL). The combined organic extracts were dried over anhydrous Na$_2$SO$_4$ and concentrated under reduced pressure to afford 5 g (crude) of 1-((CIS-8-(dimethylamino)-3-(4-methoxybenzyl)-2-oxo-8-phenyl-1,3-diazaspiro[4.5]decan-1-yl)methyl) cyclobutane-carbonitrile as gummy brown liquid. The material was used for the next step without further purification.

Step 2: 1-((CIS-8-(dimethylamino)-2-oxo-8-phenyl-1,3-diazaspiro[4.5]decan-1-yl)methyl) cyclobutanecarboxamide TFA (100 mL) was added to 1-((CIS-8-(dimethylamino)-3-(4-methoxybenzyl)-2-oxo-8-phenyl-1,3-diazaspiro[4.5]decan-1-yl)methyl)cyclobutanecarbonitrile (5 g, 10.28 mmol) at 0° C. and the reaction mixture at mixture was stirred at RT for 2 days. The reaction mixture was concentrated in vacuo. To the residue sat. aq. NaHCO$_3$ was added (until pH 10) and the organic product was extracted with dichloromethane (3×150 mL). The combined organic extracts were dried over anhydrous Na$_2$SO$_4$ and concentrated under reduced pressure to afford 3.5 g (crude) of 1-((CIS-8-(dimethylamino)-2-oxo-8-phenyl-1,3-diazaspiro[4.5]decan-1-yl)methyl) cyclobutanecarboxamide. The material was used for the next step without further purification.

Step 3: 1-((cis-8-(dimethylamino)-2-oxo-8-phenyl-1,3-diazaspiro[4.5]decan-1-yl)methyl)cyclobutane carbonitrile Thionyl chloride (35 mL) was added to 1-((cis-8-(dimethylamino)-2-oxo-8-phenyl-1,3-diazaspiro[4.5]decan-1-yl)methyl)cyclobutanecarboxamide (3.5 g, 9.11 mmol) at RT and the resulting mixture was stirred at reflux for 2 h. The reaction mixture was concentrated in vacuo. To the residue sat. aq. NaHCO$_3$ was added (until pH 10) and the organic product was extracted with dichloromethane (3×150 mL). The combined organic layer was dried over anhydrous Na$_2$SO$_4$ and concentrated in vacuo. The residue was purified by column chromatography to afford 1.3 g (34% after three steps) of CIS-1-[(8-dimethylamino-2-oxo-8-phenyl-1,3-diazaspiro[4.5]decan-1-yl)-methyl]-cyclobutane-1-carbonitrile (INT-951). [M+H]$^+$ 367.2.

Synthesis of INT-952: CIS-1-(Cyclobutyl-methyl)-8-dimethylamino-8-phenyl-3-[(4-methoxyphenyl)-methyl]-1,3-diazaspiro[4.5]decan-2-one

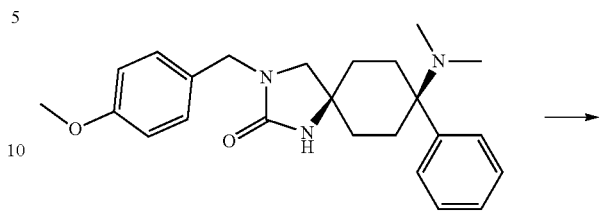

INT-975

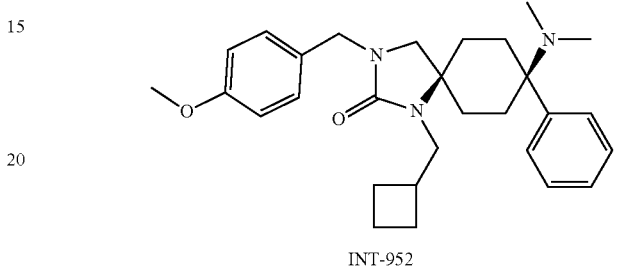

INT-952

To a solution of CIS-8-dimethylamino-3-[(4-methoxyphenyl)-methyl]-8-phenyl-1,3-diazaspiro[4.5]decan-2-one (INT-975) (10 g, 25 mmol) in THF (500 mL) was added KOtBu (7.1 g, 63 mmol) at 50° C. The reaction mixture was heated up to reflux, cyclobutylmethylbromide (11.3 g, 76 mmol) was added in one portion, and stirring was continued at reflux for 12 h. KOtBu (7.1 g) and cyclobutylmethylbromide (11.3 g) were added again. The reaction mixture was allowed to stir another 2 h at reflux, then cooled to RT, diluted with water (150 mL) and the layers partitioned. The aqueous layer was extracted with EtOAc (3×300 mL). The combined organic layers were dried over Na$_2$SO$_4$ and then concentrated in vacuo. The residue was filtered through a plug of silica gel using a DCM/MeOH (19/1 v/v) mixture. The filtrate was concentrated in vacuo and the resulting solid was recrystallized from hot ethanol to yield 7.8 g of CIS-1-(cyclobutyl-methyl)-8-dimethylamino-8-phenyl-3-[(4-methoxyphenyl)-methyl]-1,3-diazaspiro[4.5]decan-2-one (INT-952). [M+H]$^+$ 461.3.

Synthesis of INT-953: CIS-1-(Cyclobutyl-methyl)-8-(methyl-(2-methyl-propyl)-amino)-8-phenyl-1,3-diazaspiro[4.5]decan-2-one

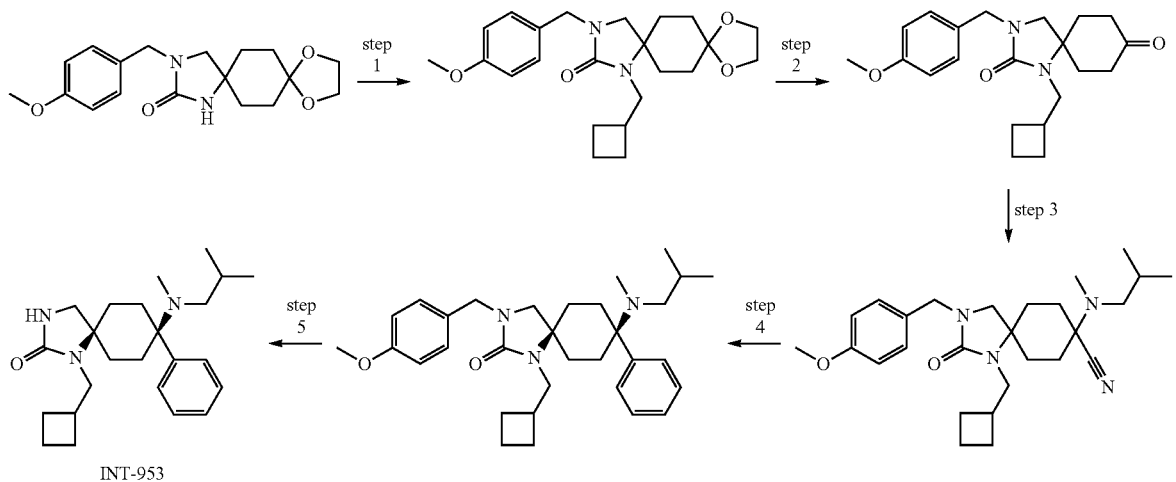

INT-953

Step 1: 1-Cyclobutylmethyl-3-(4-methoxy-benzyl)-9,12-dioxa-1,3-diazadispiro[4.2.4.2]tetradecan-2-one To a stirred solution of 3-(4-methoxy-benzyl)-9,12-dioxa-1,3-diazadispiro[4.2.4.2]tetradecan-2-one (4 g, 12.04 mmol) in anhydrous DMF (60 ml) was added NaH (1.38 g, 60% dispersion in oil, 36.14 mmol) at RT. The reaction mixture was stirred for 10 min, bromomethylcyclobutane (3 ml, 26.5 mmol) was added dropwise and stirring was continued for 50 h. TLC analysis showed complete consumption of the starting material. The reaction mixture was quenched with sat. aq. NH₄Cl (50 ml) and extracted with EtOAc (3×200 ml). The combined organic phase was dried over Na₂SO₄ and concentrated under reduced pressure. The resulting residue was purified column chromatography (neutral aluminum oxide, EtOAc-petroleum ether (2:8)) to give 1-cyclobutylmethyl-3-(4-methoxy-benzyl)-9,12-dioxa-1,3-diazadispiro[4.2.4.2]tetradecan-2-one (2.4 g, 50%, white solid). TLC system: EtOAc-pet ether (6:4); $R_f$=0.48.

Step 2: 1-Cyclobutylmethyl-3-(4-methoxy-benzyl)-1,3-diaza-spiro[4.5]decane-2,8-dione To a stirred solution of 1-cyclobutylmethyl-3-(4-methoxy-benzyl)-9,12-dioxa-1,3-diazadispiro[4.2.4.2]tetradecan-2-one (1 g, 2.5 mmol) in MeOH (7 ml) was added 10% aq. HCl (8 ml) at 0° C. The reaction mixture was warmed up to RT and stirred for 16 h. TLC analysis showed complete consumption of the starting material. The reaction mixture was quenched with sat. aq. NaHCO₃ (30 ml) and extracted with EtOAc (3×50 ml). The combined organic phase was dried over Na₂SO₄ and concentrated under reduced pressure. The resulting residue was purified by column chromatography (silica gel, 230-400 mesh, EtOAc-pet ether (1:3)→(3:7)) to give 1-cyclobutylmethyl-3-(4-methoxy-benzyl)-1,3-diaza-spiro[4.5]decane-2,8-dione (650 mg, 73%, colorless viscous oil). TLC system: EtOAc-pet ether (6:4); $R_f$=0.40.

Step 3: 1-(cyclobutylmethyl)-8-(isobutyl(methyl)amino)-3-(4-methoxybenzyl)-2-oxo-1,3-diazaspiro[4.5]decane-8-carbonitrile To a stirred solution of N-isobutyl-N-methylamine (1.34 ml, 11.23 mmol) and MeOH/H₂O (8 ml, 1:1, v/v) was added 4N aq. HCl (1.5 ml) and the reaction mixture was stirred for 10 min at 0° C. (ice bath). A solution of 1-cyclobutylmethyl-3-(4-methoxy-benzyl)-1,3-diaza-spiro[4.5]decane-2,8-dione (1 g, 2.80 mmol) in MeOH (7 ml) and KCN (548 mg, 8.42 mmol) were added and the reaction mixture was stirred at 45° C. for 20 h. TLC analysis showed complete consumption of the starting material. The reaction mixture was diluted with water (30 ml), extracted with EtOAc (3×30 ml), the combined organic phase was dried over Na₂SO₄ and concentrated under reduced pressure to give 1-(cyclobutylmethyl)-8-(isobutyl(methyl)amino)-3-(4-methoxybenzyl)-2-oxo-1,3-diazaspiro[4.5]decane-8-carbonitrile (1.3 g, viscous yellow oil). TLC system: EtOAc-pet ether (1:1); $R_f$=0.45. The product was used for the next step without additional purification.

Step 4: CIS-1-(cyclobutylmethyl)-8-(isobutyl(methyl)amino)-3-(4-methoxybenzyl)-8-phenyl-1,3-diazaspiro[4.5]decan-2-one A round bottom flask containing 1-(cyclobutylmethyl)-8-(isobutyl(methyl)amino)-3-(4-methoxybenzyl)-2-oxo-1,3-diazaspiro[4.5]decane-8-carbonitrile (1.3 g, 2.81 mmol) was cooled in an ice bath (~0° C.) and a solution of phenylmagnesium bromide (26 ml, -2M in THF) was added slowly at 0° C.-5° C. The ice bath was removed and the reaction mixture was stirred for 30 min, then diluted with sat. aq. NH₄Cl (25 ml) and extracted with EtOAc (4×30 ml). The combined organic phase was dried over Na₂SO₄ and concentrated under reduced pressure to give pale yellow viscous oil. This residue was purified by column chromatography (silica gel, 230-400 mesh, eluent: EtOAc-pet ether (15:85)→(2:4)) to give CIS-1-(cyclobutylmethyl)-8-(isobutyl(methyl)amino)-3-(4-methoxybenzyl)-8-phenyl-1,3-diazaspiro[4.5]decan-2-one (135 mg, 10%, white solid). TLC system: EtOAc-pet ether (1:1); $R_f$=0.6

Step 5: CIS-1-(Cyclobutyl-methyl)-8-(methyl-(2-methyl-propyl)-amino)-8-phenyl-1,3-diazaspiro[4.5]decan-2-one A round bottom flask containing CIS-1-(cyclobutylmethyl)-8-(isobutyl(methyl)amino)-3-(4-methoxybenzyl)-8-phenyl-1,3-diazaspiro[4.5]decan-2-one (130 mg, 0.25 mmol) was cooled in an ice bath and a mixture of TFA/CH₂Cl₂ (2.6 ml, 1:1, v/v) was added slowly at 0° C.-5° C. The reaction mixture was warmed to RT and stirred for 20 h, then quenched with methanolic NH₃ (10 ml, ~10% in MeOH) and concentrated under reduced pressure to give pale yellow viscous oil. This residue was purified twice by column chromatography (silica gel, 230-400 mesh, eluent: MeOH—CHCl₃ (1:99)→(2:98)) to give CIS-1-(cyclobutyl-methyl)-8-(methyl-(2-methyl-propyl)-amino)-8-phenyl-1,3-diazaspiro[4.5]decan-2-one (INT-953) (65 mg, 66%, white solid). TLC system: MeOH—CHCl₃ (5:95); $R_f$=0.25; [M+H]⁺ 384.3

Synthesis of INT-958: 4-Oxo-1-pyridin-2-yl-cyclohexane-1-carbonitrile

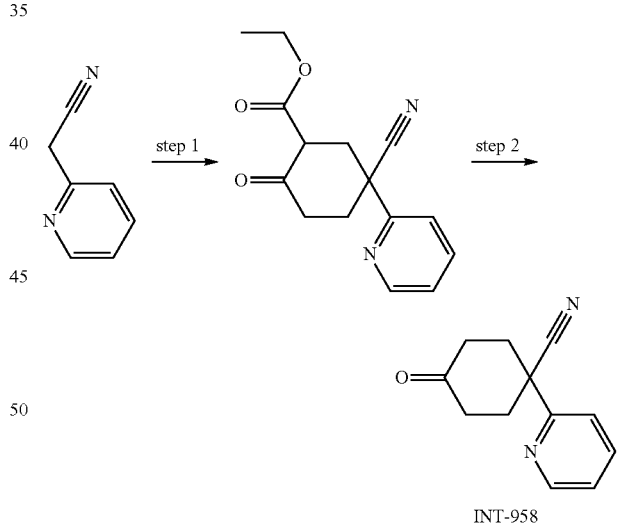

Step 1: Ethyl 5-cyano-2-oxo-5-(pyridin-2-Yl)cyclohexanecarboxylate

KOtBu (57.0 g, 508.4 mmol) was added to the solution of 2-(pyridin-2-yl)acetonitrile (50.0 g, 423.7 mmol) and ethyl acrylate (89.0 g, 889.8 mmol) in THF (500 mL) at 0° C. and stirred for 16 h at RT. The reaction mixture was quenched with sat. aq. NH₄Cl and extracted with EtOAc (2×500 mL). The combined organic layer was washed with brine, dried over Na₂SO₄ and concentrated under reduced pressure to afford 68.0 g (60%; crude) of ethyl 5-cyano-2-oxo-5-(pyridin-2-yl)cyclohexanecarboxylate as a brown liquid (TLC system: 50% ethyl acetate in petroleum ether; Rf: 0.65).

Step 2:
4-Oxo-1-pyridin-2-yl-cyclohexane-1-carbonitrile

A solution of ethyl 5-cyano-2-oxo-5-(pyridin-2-yl)cyclohexanecarboxylate (68.0 g, 250.0 mmol) was added to a mixture of conc. aq. HCl and glacial acetic acid (170 mL/510 mL) at 0° C. The reaction mixture was heated to 100° C. for 16 h. All volatiles were evaporated under reduced pressure. The residue was diluted with sat. aq. NaHCO₃ and extracted with ethyl acetate (3×300 mL). The combined organic layer was washed with brine, dried over Na₂SO₄ and concentrated under reduced pressure to afford 44.0 g (88%) of 4-oxo-1-pyridin-2-yl-cyclohexane-1-carbonitrile INT-958 as a brown solid (TLC system: 50% ethyl acetate in pet ether; Rf: 0.45). [M+H]⁺ 201.1

Synthesis of INT-961:
4-Dimethylamino-4-pyridin-2-yl-cyclohexan-1-one of 8-(pyridin-2-yl)-1,4-dioxaspiro[4.5]decane-8-carbonitrile (45.0 g, 184.42 mmol) in DMSO (450 mL) at 0° C. and the resulting mixture was stirred at RT for 14 h. The reaction mixture was diluted with water (1.5 L) and stirred for 1 h. The precipitated solid was separated by filtration, washed with water, petroleum ether and dried under reduced pressure to get 32.0 g (66%) of 8-(pyridin-2-yl)-1,4-dioxaspiro[4.5]decane-8-carboxamide as a white solid. (TLC system: 10% MeOH in DCM Rf: 0.35).

Step 3: methyl 8-(pyridin-2-yl)-1,4-dioxaspiro[4.5]decan-8-ylcarbamate

A mixture of 8-(pyridin-2-yl)-1,4-dioxaspiro[4.5]decane-8-carboxamide (25.0 g, 95.41 mmol), sodium hypochlorite (5 wt % aq. solution, 700 mL, 477.09 mmol) and KF—Al₂O₃ (125.0 g) in methanol (500 mL) was heated to 80° C. for 16 h. The reaction mixture was filtered through celite and the solid residue was washed with methanol. The combined filtrate was concentrated under reduced pressure. The residue was diluted with water and extracted with ethyl

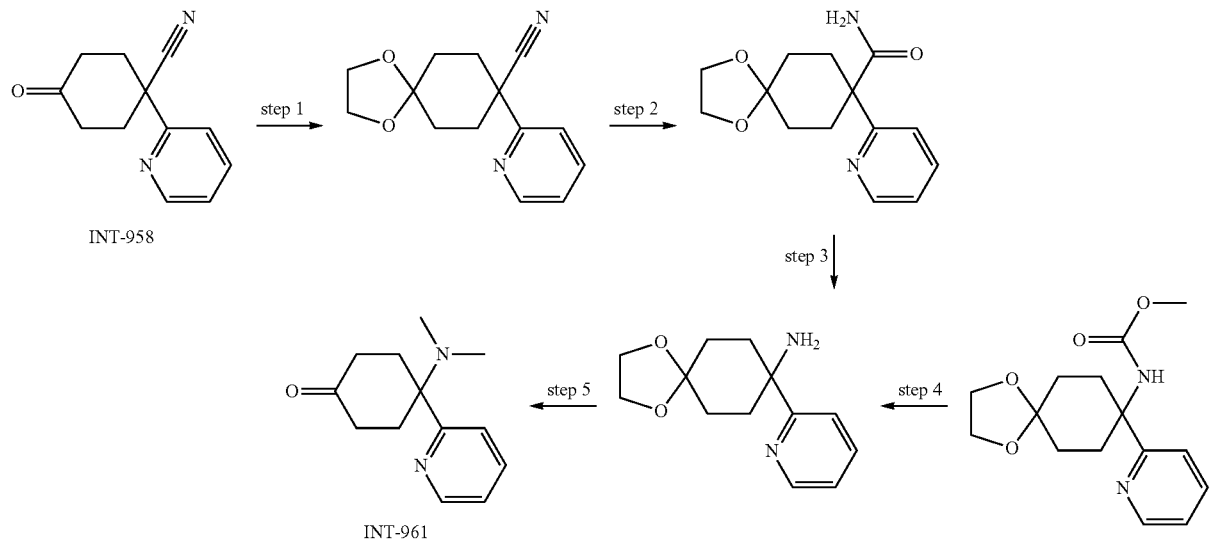

INT-958

INT-961

Step 1: 8-(pyridin-2-yl)-1,4-dioxaspiro[4.5]decane-8-carbonitrile

A solution of 4-oxo-1-pyridin-2-yl-cyclohexane-1-carbonitrile (INT-958) (44.0 g, 220.0 mmol), ethylene glycol (27.0 g, 440.0 mmol) and PTSA (4.2 g, 22.0 mmol) in toluene (450 mL) was heated to 120° C. for 16 h using Dean Stark apparatus. All volatiles were evaporated under reduced pressure. The residue was diluted with sat. aq. NaHCO₃ and extracted with ethyl acetate (3×300 mL). The combined organic layer was washed with brine, dried over Na₂SO₄ and concentrated under reduced pressure to afford 45.0 g (85%) of 8-(pyridin-2-yl)-1,4-dioxaspiro[4.5]decane-8-carbonitrile as a light brown solid (TLC system: 50% ethyl acetate in petroleum ether; Rf: 0.55).

Step 2: 8-(pyridin-2-yl)-1,4-dioxaspiro[4.5]decane-8-carboxamide

Potassium carbonate (50.0 g, 368.84 mmol) and 30% aq. H₂O₂ (210.0 mL, 1844.2 mmol) were added to the solution acetate (3×500 mL). The combined organic layer was washed with brine, dried over Na₂SO₄ and concentrated under reduced pressure to afford 18.0 g (66%) of methyl 8-(pyridin-2-yl)-1,4-dioxaspiro[4.5]decan-8-ylcarbamate as a light brown solid. (TLC system: 5% MeOH in DCM Rf: 0.52.)

Step 4: 8-(pyridin-2-yl)-1,4-dioxaspiro[4.5]decan-8-amine

A suspension of methyl 8-(pyridin-2-yl)-1,4-dioxaspiro[4.5]decan-8-ylcarbamate (18.0 g, 61.64 mmol) in 10 wt % aq. NaOH (200 mL) was heated to 100° C. for 24 h. The reaction mixture was filtered through celite pad, the solid residue was washed with water and the combined filtrate was extracted with EtOAc (4×200 mL). The combined organic layer washed with brine, dried over Na₂SO₄ and concentrated under reduced pressure to afford 12.5 g (88%) of 8-(pyridin-2-yl)-1,4-dioxaspiro[4.5]decan-8-amine as a light brown semi-solid. (TLC system: 5% MeOH in DCM Rf: 0.22.).

Step 5: 4-Dimethylamino-4-pyridin-2-yl-cyclohexan-1-one

Sodium cyanoborohydride (13.7 g, 0.213 mol) was added portionwise to a solution of 8-(pyridin-2-yl)-1,4-dioxaspiro [4.5]decan-8-amine (12.5 g, 53.418 mmol) and 35 wt % aq. formaldehyde (45 mL, 0.534 mol) in acetonitrile (130 mL) at 0° C. The reaction mixture was warmed up to room temperature and stirred for 16 h. The reaction mixture was quenched with sat. aq. NH$_4$Cl and concentrated under reduced pressure. The residue was dissolved in water and extracted with EtOAc (3×200 mL). The combined organic layer was washed with brine, dried over Na$_2$SO$_4$ and concentrated under reduced pressure to afford 10.5 g (72%) of 4-dimethylamino-4-pyridin-2-yl-cyclohexan-1-one (INT-961) as a light brown solid. (TLC system: 5% MeOH in DCM R$_f$: 0.32.). [M+H]$^+$ 219.1

Synthesis of INT-965: 4-Dimethylamino-4-phenyl-cyclohexan-1-one

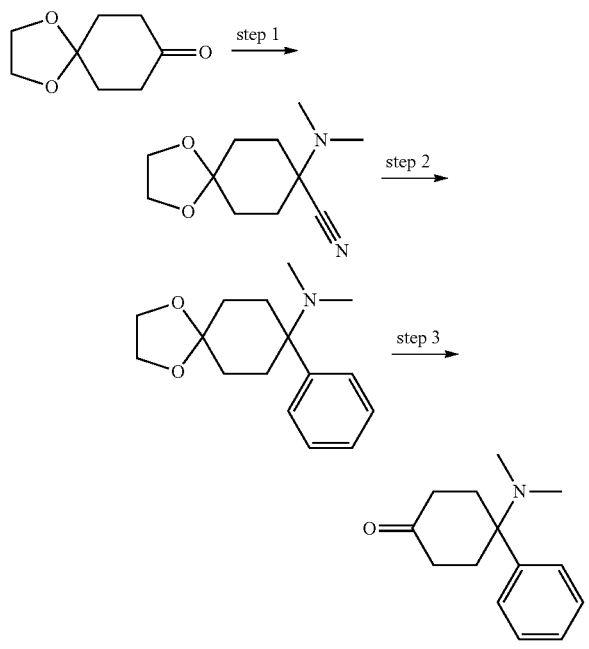

Step 1: 8-(Dimethylamino)-1,4-dioxaspiro 4.5]decane-8-carbonitrile

Dimethylamine hydrochloride (52 g, 0.645 mol) was added to the solution of 1,4-dioxaspiro-[4.5]-decan-8-one (35 g, 0.224 mmol) in MeOH (35 mL) at RT under argon atmosphere. The solution was stirred for 10 min and 40 wt % aq. dimethylamine (280 mL, 2.5 mol) and KCN (32 g, 0.492 mol) were sequentially added. The reaction mixture was stirred for 48 h at RT, then diluted with water (100 mL) and extracted with EtOAc (2×200 mL). The combined organic layer was dried over anhydrous Na$_2$SO$_4$ and concentrated under reduced pressure to afford 44 g of 8-(dimethylamino)-1,4-dioxaspiro-[4.5]-decane-8-carbonitrile (93%) as a white solid.

Step 2: N,N-dimethyl-8-phenyl-1,4-dioxaspiro [4.5]decan-8-amine 8-(Dimethylamino)-1,4-dioxaspiro[4.5]decane-8-carbonitrile (35 g, 0.167 mol) in THF (350 mL) was added to the solution of 3M phenylmagnesium bromide in diethyl ether (556 mL, 1.67 mol) dropwise at −10° C. under argon atmosphere. The reaction mixture was stirred for 4 h at -10° C. to 0° C. and then at RT for 18 h. The reaction completion was monitored by TLC. The reaction mixture was cooled to 0° C., diluted with sat. aq. NH$_4$Cl (1 L) and extracted with EtOAc (2×600 mL). The combined organic layer was dried over anhydrous Na$_2$SO$_4$ and concentrated under reduced pressure to afford 60 g of, N N-dimethyl-8-phenyl-1,4-dioxaspiro-[4.5]-decan-8-amine as a liquid.

Step 3: 4-(dimethylamino)-4-phenylcyclohexanone

A solution of N,N-dimethyl-8-phenyl-1,4-dioxaspiro[4.5] decan-8-amine (32 g, 0.123 mol) in 6N aq. HCl (320 mL) was stirred at 0° C. for 2 h and then at RT for 18 h. The reaction completion was monitored by TLC. The reaction mixture was extracted with DCM (2×150 mL). The aqueous layer was basified to pH 10 with solid NaOH and extracted with ethyl acetate (2×200 mL). The combined organic layer was dried over anhydrous Na$_2$SO$_4$ and concentrated under reduced pressure. The solid residue was washed with hexane and dried in vacuo to afford 7 g of 4-dimethylamino-4-phenyl-cyclohexan-1-one (INT-965) (25% over 2 steps) as a brown solid. [M+H]$^+$ 218.1

Synthesis of INT-966: 3-[(4-Methoxyphenyl)-methyl]-1,3-diazaspiro[4.5]decane-2,8-dione

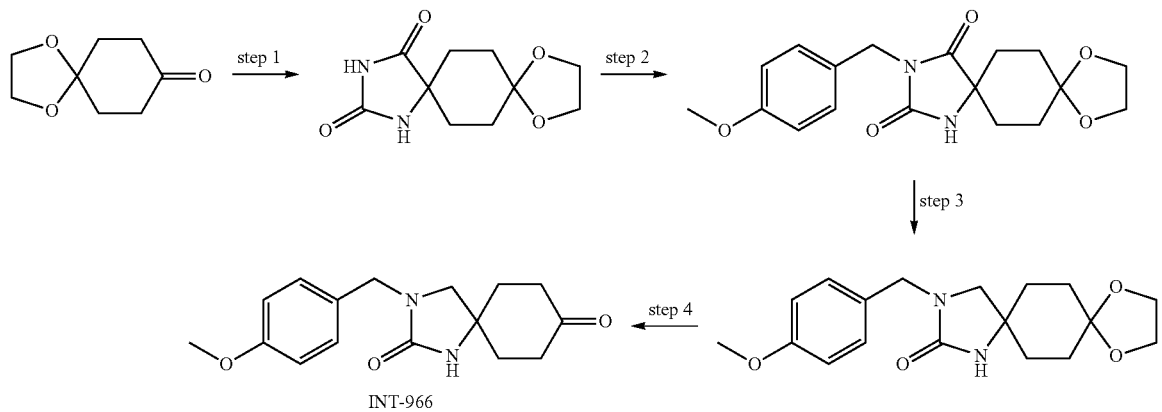

INT-966

Step 1: 9,12-Dioxa-2,4-diazadispiro[4.2.4^{8}.2^{5}]tetradecane-1,3-dione

KCN (93.8 g, 1441.6 mmol) and (NH$_4$)$_2$CO$_3$ (271.8 g, 1729.9 mmol) were added to the solution of 1,4-dioxaspiro[4.5]decan-8-one (150 g, 961 mmol) in MeOH:H$_2$O (1:1 v/v) (1.92 L) at RT under argon atmosphere. The reaction mixture was stirred at 60° C. for 16 h. The reaction completion was monitored by TLC. The reaction mixture was cooled to 0° C., the precipitated solid was filtered off and dried in vacuo to afford 120 g (55%) of 9,12-dioxa-2,4-diazadispiro[4.2.4^{8}.2^{5}]tetradecane-1,3-dione. The filtrate was extracted with DCM (2×1.5 L). The combined organic layer was dried over anhydrous Na$_2$SO$_4$ and concentrated under reduced pressure to afford additional 30 g (14%) of 9,12-dioxa-2,4-diazadispiro[4.2.4^{8}.2^{5}]tetradecane-1,3-dione (TLC system: 10% Methanol in DCM; Rf: 0.4).

Step 2: 2-[(4-Methoxyphenyl)-methyl]-9,12-dioxa-2,4-diazadispiro[4.2.4^{8}.2^{5}]tetradecane-1,3-dione Cs$_2$CO$_3$ (258.7 g, 796.1 mmol) was added to the solution of 73a (150 g, 663.4 mmol) in MeCN (1.5 L) under argon atmosphere and the reaction mixture was stirred for 30 min. A solution of p-methoxybenzyl bromide (96 mL, 663.4 mmol) was added. The reaction mixture was stirred at RT for 48 h. The reaction completion was monitored by TLC. The reaction mixture was quenched with sat. aq. NH$_4$Cl (1.0 L) and the organic product was extracted with EtOAc (2×1.5 L). The combined organic layer was dried over anhydrous Na$_2$SO$_4$ and concentrated under reduced pressure. The residue was washed with diethyl ether and pentane and dried under reduced pressure to afford 151 g (65%) of 2-[(4-Methoxyphenyl)-methyl]-9,12-dioxa-2,4-diazadispiro[4.2.4^{8}.2^{5}]tetradecane-1,3-dione as an off white solid (TLC system: 10% MeOH in DCM; Rf: 0.6).

Step 3: 2-[(4-Methoxyphenyl)-methyl]-9,12-dioxa-2,4-diazadispiro[4.2.4^{8}.2^{5}]tetradecan-3-one AlCl$_3$ (144.3 g, 1082.6 mmol) was added to a solution of LiAlH$_4$ (2M in THF) (433 mL, 866.10 mmol) in THF (4.5 L) at 0° C. under argon atmosphere and the resulting mixture was stirred at RT for 1 h. 2-[(4-Methoxyphenyl)-methyl]-9,12-dioxa-2,4-diazadispiro[4.2.4^{8}.2^{5}]tetradecane-1,3-dione (150 g, 433.05 mmol) was added at 0° C. The reaction mixture was stirred at RT for 16 h. The reaction completion was monitored by TLC. The reaction mixture was cooled to 0° C., quenched with sat. aq. NaHCO$_3$ (500 mL) and filtered through celite pad. The filtrate was extracted with EtOAc (2×2.0 L). The combined organic layer was dried over anhydrous Na$_2$SO$_4$ and concentrated in vacuo to afford 120 g (84%) of 2-[(4-methoxyphenyl)-methyl]-9,12-dioxa-2,4-diazadispiro[4.2.4^{8}.2^{5}]tetradecan-3-one as an off-white solid. (TLC system: 10% MeOH in DCM, Rf: 0.5).

Step 4: 3-[(4-Methoxyphenyl)-methyl]-1,3-diazaspiro[4.5]decane-2,8-dione

A solution of 2-[(4-methoxyphenyl)-methyl]-9,12-dioxa-2,4-diazadispiro[4.2.4^{8}.2^{5}]tetradecan-3-one (120 g, 361.03 mmol) in 6N aq. HCl (2.4 L) was stirred at 0° C. for 2 h and then at RT for 18 h. The reaction completion was monitored by TLC. The reaction mixture was extracted with DCM (2×2.0 L). The aqueous layer was basified to pH 10 with 50% aq. NaOH and then extracted with DCM (2×2.0 L). Combined organic extracts were dried over anhydrous Na$_2$SO$_4$ and concentrated under reduced pressure. The solid residue was washed with hexane and dried in vacuo to afford 90 g of 3-[(4-Methoxyphenyl)-methyl]-1,3-diazaspiro[4.5]decane-2,8-dione (INT-966) as an off-white solid (TLC system: 10% MeOH in DCM; Rf: 0.4) [M+H]$^+$ 289.11.

Synthesis of INT-971: CIS-1-(Cyclobutyl-methyl)-8-dimethylamino-8-(3-hydroxyphenyl)-3-[(4-methoxyphenyl)-methyl]-1,3-diazaspiro[4.5]decan-2-one

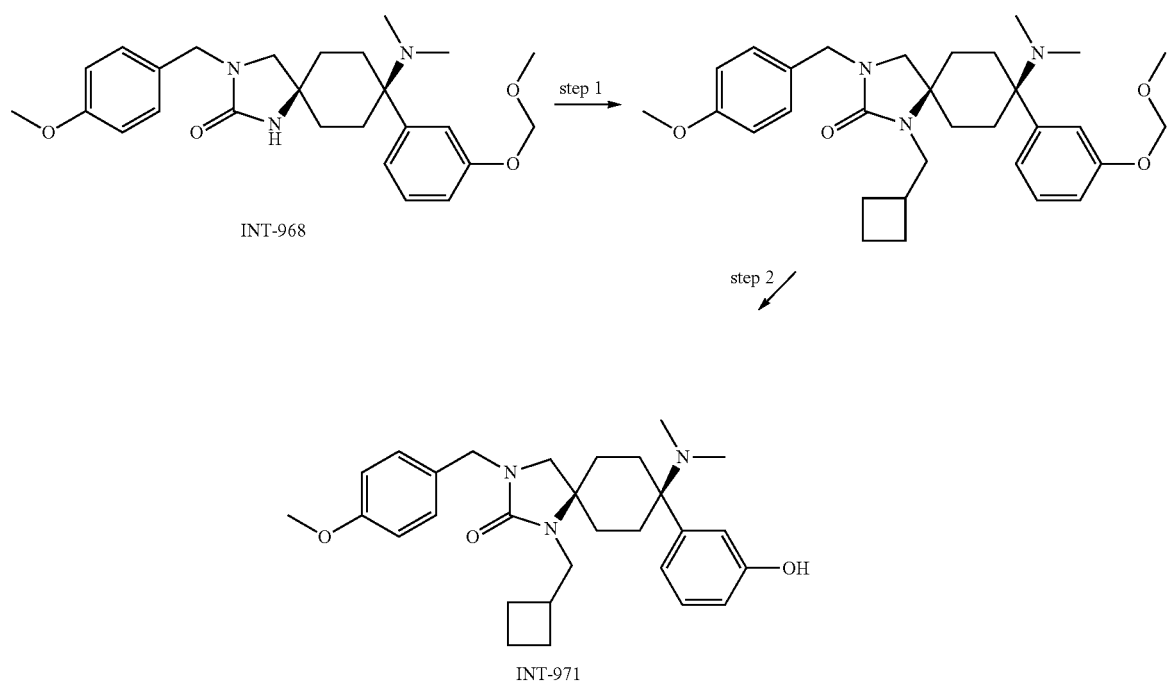

Step 1: CIS-8-(dimethylamino)-1-isobutyl-3-(4-methoxybenzyl)-8-phenyl-1,3-diazaspiro[4.5]decan-2-one In analogy to the method described for INT-951 step 1 CIS-8-Dimethylamino-8-[3-(methoxymethyloxy)-phenyl]-3-[(4-methoxyphenyl)-methyl]-1,3-diazaspiro[4.5]decan-2-one (INT-968) was converted into CIS-1-(cyclobutylmethyl)-8-(dimethylamino)-3-(4-methoxybenzyl)-8-(3-(methoxymethoxy)phenyl)-1,3-diazaspiro[4.5]decan-2-one.

Step 2: CIS-1-(Cyclobutyl-methyl)-8-dimethylamino-8-(3-hydroxyphenyl)-3-[(4-methoxyphenyl)-methyl]-1,3-diazaspiro[4.5]decan-2-one TFA (0.2 mL) was added to the solution of CIS-1-(cyclobutylmethyl)-8-(dimethylamino)-3-(4-methoxybenzyl)-8-(3-methoxyphenyl)-1,3-diazaspiro[4.5]decan-2-one (300 mg, 0.57 mmol) in DCM (1.5 mL) at 0° C. The reaction mixture was stirred at 0° C. for 3 h. The reaction completion was monitored by TLC. The reaction mixture was quenched with sat. aq. NaHCO₃ and the organic product was extracted with DCM (3×10 mL). The combined organic extracts were dried over anhydrous Na$_2$SO$_4$ and concentrated under reduced pressure. Purification of the residue by preparative TLC (3% MeOH in DCM as mobile phase) yielded 50 mg (18%) of CIS-1-(Cyclobutyl-methyl)-8-dimethylamino-8-(3-hydroxyphenyl)-3-[(4-methoxyphenyl)-methyl]-1,3-diazaspiro[4.5]decan-2-one (INT-971) as an off white solid. (TLC system: 10% MeOH in DCM; Rf: 0.20) [M+H]$^+$ 478.3

Synthesis of INT-974: CIS-8-Dimethylamino-8-(3-fluorophenyl)-3-[(4-methoxyphenyl)-methyl]-1,3-diazaspiro[4.5]decan-2-one

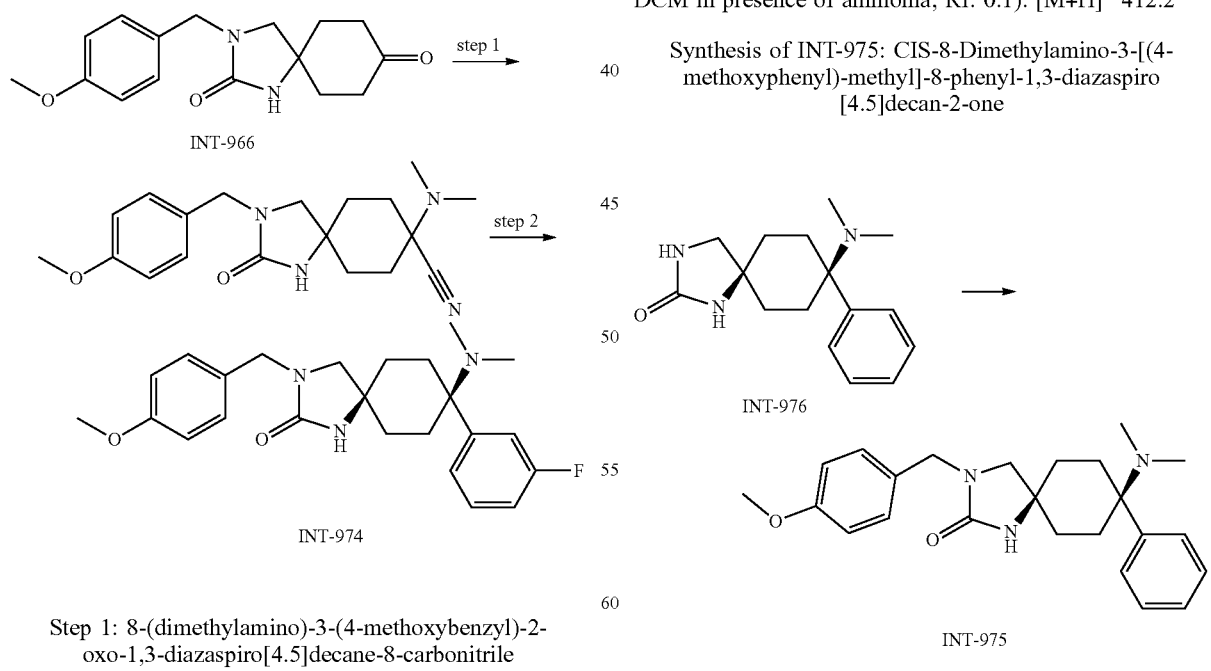

Step 1: 8-(dimethylamino)-3-(4-methoxybenzyl)-2-oxo-1,3-diazaspiro[4.5]decane-8-carbonitrile Dimethylamine hydrochloride (76.4 g, 936.4 mmol) was added to a solution of 3-[(4-methoxyphenyl)-methyl]-1,3-diazaspiro[4.5]decane-2,8-dione (INT-966) (90 g, 312.13 mmol) in MeOH (180 mL) at RT under argon atmosphere. The solution was stirred for 15 min and 40 wt % aq. dimethylamine (780 mL) and KCN (48.76 g, 749.11 mmol) were sequentially added. The reaction mixture was stirred for 48 h and the completion of the reaction was monitored by NMR. The reaction mixture was diluted with water (1.0 L) and the organic product was extracted with ethyl acetate (2×2.0 L). The combined organic layer was dried over anhydrous Na$_2$SO$_4$ and concentrated under reduced pressure to afford 90 g (85%) of 8-(dimethylamino)-3-(4-methoxybenzyl)-2-oxo-1,3-diazaspiro[4.5]decane-8-carbonitrile as an off white solid (TLC system: TLC system: 10% MeOH in DCM; Rf: 0.35, 0.30).

Step 2: CIS-8-Dimethylamino-8-(3-fluorophenyl)-3-[(4-methoxyphenyl)-methyl]-1,3-diazaspiro[4.5]decan-2-one 3-Fluorophenylmagnesium bromide (1M in THF) (220 mL, 219.17 mmol) was added dropwise to a solution of 8-(dimethylamino)-3-(4-methoxybenzyl)-2-oxo-1,3-diazaspiro[4.5]decane-8-carbonitrile (15 g, 43.83 mmol) in THF (300 mL) at 0° C. under argon atmosphere. The reaction mixture was stirred for 16 h at RT. The reaction completion was monitored by TLC. The reaction mixture was cooled to 0° C., quenched with sat. aq. NH$_4$Cl (200 mL) and the organic product was extracted with EtOAc (2×200 mL). The combined organic layer was dried over anhydrous Na$_2$SO$_4$ and concentrated under reduced pressure. The reaction was carried out in 4 batches (15 g×2 and 5 g×2) and the batches were combined for purification. Purification of the crude product by flash column chromatography on silica gel (230-400 mesh) (2 times) (0-20% methanol in DCM) eluent and subsequently by washing with pentane yielded 5.6 g (11%) of CIS-8-dimethylamino-8-(3-fluorophenyl)-3-[(4-methoxyphenyl)-methyl]-1,3-diazaspiro[4.5]decan-2-one (INT-974) as an off-white solid. (TLC system: 5% MeOH in DCM in presence of ammonia; Rf: 0.1). [M+H]$^+$ 412.2

Synthesis of INT-975: CIS-8-Dimethylamino-3-[(4-methoxyphenyl)-methyl]-8-phenyl-1,3-diazaspiro[4.5]decan-2-one KOtBu (1M in THF) (29.30 mL, 29.30 mmol) was added to the solution of CIS-8-Dimethylamino-8-phenyl-1,3-diazaspiro[4.5]decan-2-one INT-976 (8.0 g, 29.30 mmol) in THF (160 mL) under argon atmosphere and the reaction mixture was stirred for 30 min. 4-Methoxybenzyl bromide (4.23 mL, 29.30 mmol) was added and stirring was continued at RT for 4 h. The reaction completion was monitored by TLC. The reaction mixture was diluted with sat. aq. NH₄Cl (150 mL) and the organic product was extracted with EtOAc (2×150 mL). The combined organic layer was dried over anhydrous Na₂SO₄ and concentrated in vacuo. The reaction was carried out in 2 batches (8 g×2) and the batches were combined for purification. Purification of the crude product by flash column chromatography on silica gel (0-10% methanol in DCM) and subsequently by washing with pentane yielded 11 g (47%) of CIS-8-Dimethylamino-3-[(4-methoxyphenyl)-methyl]-8-phenyl-1,3-diazaspiro[4.5]decan-2-one (INT-975) as a white solid. [M+H]⁺ 394.2

Synthesis of INT-976: CIS-8-Dimethylamino-8-phenyl-1,3-diazaspiro[4.5]decan-2-one

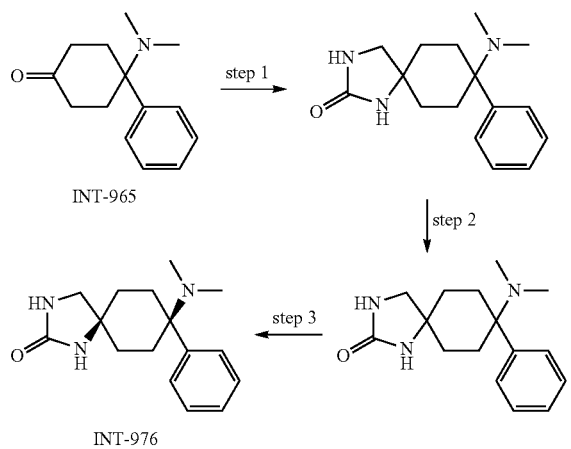

INT-965

INT-976

Step 1: 8-(dimethylamino)-8-phenyl-1,3-diazaspiro [4,5]decane-2,4-dione

In a sealed tube 4-dimethylamino-4-phenyl-cyclohexan-1-one (INT-965) (2 g, 9.22 mmol) was suspended in 40 mL EtOH/H₂O (1:1 v/v) at RT under argon atmosphere. (NH₄)₂CO₃ (3.62 g, 23.04 mmol) and KCN (0.6 g, 9.22 mmol) were added. The reaction mixture was stirred at 60° C. for 18 h. The reaction mixture was cooled to 0° C. and diluted with ice-water and filtered through a glass filter. The solid residue was dried under reduced pressure to afford 8-(dimethylamino)-8-phenyl-1,3-diazaspiro[4,5]decane-2,4-dione (1.8 g, 86%) as an off white crystalline solid (TLC: 80% EtOAc in hexane; Rf: 0.25).

Step 2: 8-(dimethylamino)-8-phenyl-1,3-diazaspiro [4,5] decan-2-one

LiAlH₄ (2M in THF) (70 mL, 139.4 mmol) was added to the solution of 8-(dimethylamino)-8-phenyl-1,3-diazaspiro [4,5]decane-2,4-dione (10 g, 34.8 mmol) in THF/Et₂O (2:1 v/v) (400 mL) at 0° C. under argon atmosphere. The reaction mixture was stirred for 4 h at 60° C. The reaction completion was monitored by TLC. The reaction mixture was cooled to 0° C., quenched with saturated Na₂SO₄ solution (100 mL) and filtered through Celite pad. The filtrate was dried over anhydrous Na₂SO₄ and concentrated in vacuo to afford 5.7 g (59%) of 8-(dimethylamino)-8-phenyl-1, 3-diazaspiro [4, 5] decan-2-one as an off white solid. (TLC system: 10% MeOH in DCM, Rf: 0.3).

Step 3: CIS-8-Dimethylamino-8-phenyl-1,3-diazaspiro[4.5]decan-2-one

A mixture of CIS- and TRANS-8-(dimethylamino)-8-phenyl-1,3-diazaspiro[4,5]decan-2-one (8 g, 29.30 mmol) was purified by preparative chiral SFC (column: Chiralcel AS-H, 60% CO₂, 40% (0.5% DEA in MeOH)) to get 5 g of CIS-8-Dimethylamino-8-phenyl-1,3-diazaspiro[4.5]decan-2-one (INT-976) as a white solid. [M+H]⁺ 274.2.

Synthesis of INT-977: CIS-2-(8-Dimethylamino-2-oxo-8-phenyl-1,3-diazaspiro[4.5]decan-1-yl)-acetic acid; 2,2,2-trifluoro-acetic Acid Salt

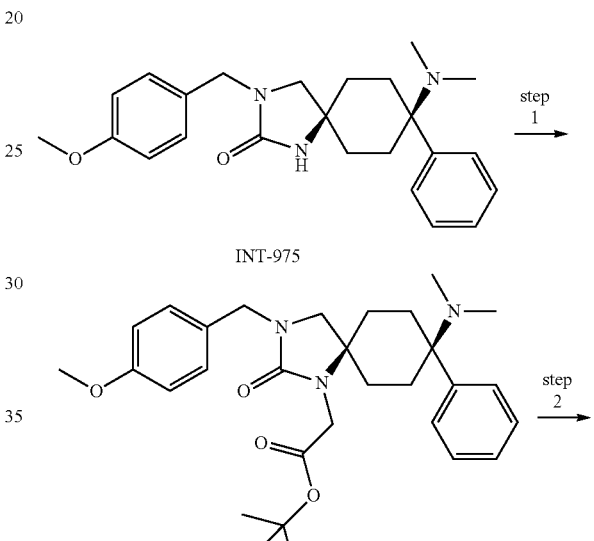

INT-975

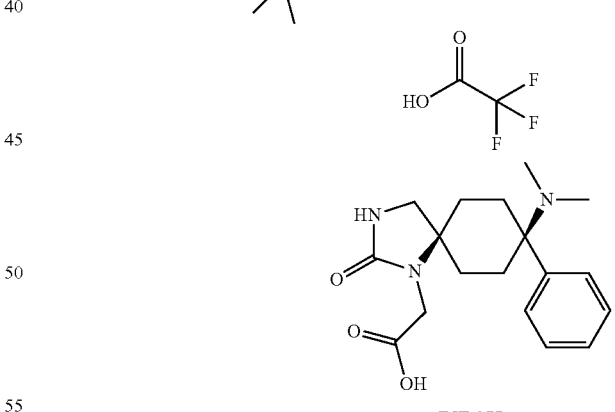

INT-977

Step 1: CIS-2-[8-Dimethylamino-3-[(4-methoxyphenyl)-methyl]-2-oxo-8-phenyl-1,3-diazaspiro[4.5] decan-1-yl]-acetic Acid Tert-Butyl Ester A solution of CIS-8-Dimethylamino-3-[(4-methoxyphenyl)-methyl]-8-phenyl-1,3-diazaspiro[4.5]decan-2-one (INT-975) (5.0 g, 12.7 mmol) in THF (18 mL) was cooled to 0° C. and treated with LDA solution (2M in THF/heptane/ether, 25.4 mL, 50.8 mmol). The resulting mixture was allowed to warm up to RT over 30 min. The solution was then cooled to 0° C. again and tert-butyl-bromoacetate (5.63 mL, 38.1 mmol) was added. The reaction mixture was stirred at RT for 16 h, quenched with water and extracted with DCM (3×). The combined organic layers were dried over $Na_2SO_4$, filtered and concentrated under reduced pressure. Purification of the residue by column chromatography on silica gel provided CIS-2-[8-dimethylamino-3-[(4-methoxyphenyl)-methyl]-2-oxo-8-phenyl-1,3-diazaspiro[4.5]decan-1-yl]-acetic acid tert-butyl ester (4.4 g).

Step 2: cis-2-(8-Dimethylamino-2-oxo-8-phenyl-1,3-diazaspiro[4.5]decan-1-yl)-acetic Acid Trifluoroacetic Acid Salt CIS-2-[8-Dimethylamino-3-[(4-methoxyphenyl)-methyl]-2-oxo-8-phenyl-1,3-diazaspiro[4.5]decan-1-yl]-acetic acid tert-butyl ester (200 mg, 0.4 mmol) was dissolved in TFA (5 mL) and heated to reflux overnight. After cooling to RT all volatiles are removed in vacuo. The residue was taken up in THF (1 mL) and added dropwise to diethyl ether (20 mL). The resulting precipitate was filtered off and dried under reduced pressure to give CIS-2-(8-dimethylamino-2-oxo-8-phenyl-1,3-diazaspiro[4.5]decan-1-yl)-acetic acid; 2,2,2-trifluoro-acetic acid salt (INT-977) (119 mg) as a white solid. $[M+H]^+$ 332.2

Synthesis of INT-978: CIS-2-(8-Dimethylamino-2-oxo-8-phenyl-1,3-diazaspiro[4.5]decan-1-yl)-N,N-dimethyl-acetamide

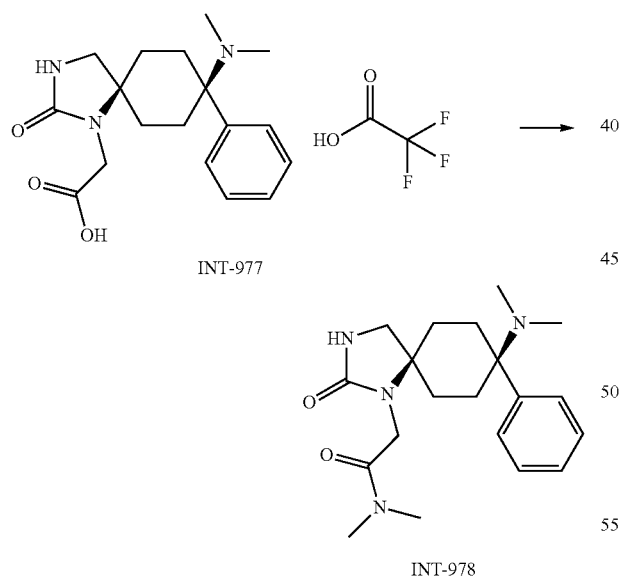

CIS-2-(8-Dimethylamino-2-oxo-8-phenyl-1,3-diazaspiro[4.5]decan-1-yl)-acetic acid (INT-977) trifluoroacetic acid salt (119 mg, 0.35 mmol) was dissolved in DCM (5 mL). Triethylamine (0.21 mL, 1.6 mmol), dimethylamine (0.54 mL, 1.1 mmol) and T3P (0.63 mL, 1.1 mmol) were sequentially added. The reaction mixture was stirred at RT overnight, then diluted with 1 M aq. $Na_2CO_3$ (5 mL). The aqueous layer was extracted with DCM (3×5 mL), the combined organic layers were dried over $Na_2SO_4$ and concentrated under reduced pressure. The residue was purified by flash chromatography on silica gel to yield CIS-2-(8-dimethylamino-2-oxo-8-phenyl-1,3-diazaspiro[4.5]decan-1-yl)-N,N-dimethyl-acetamide (INT-978) (39 mg) as a white solid. $[M+H]^+$ 359.2

Synthesis of INT-982: CIS-8-Dimethylamino-1-[(1-methyl-cyclobutyl)-methyl]-8-phenyl-1,3-diazaspiro[4.5]decan-2-one

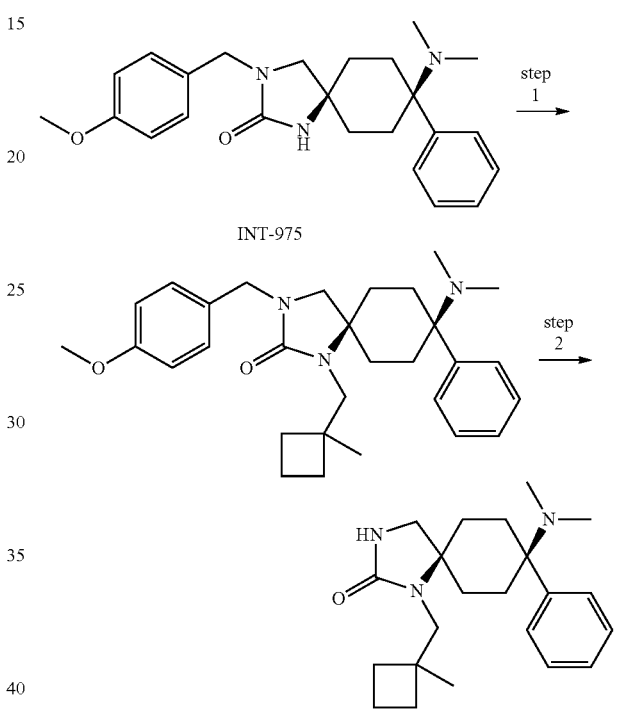

Step 1: CIS-8-(dimethylamino)-3-(4-methoxybenzyl)-1-((1-methylcyclobutyl)methyl)-8-phenyl-1,3-diazaspiro[4.5]decan-2-one A solution of NaOH (2.85 g, 71.2 mmol) in DMSO (25 mL) was stirred at RT for 10 min. CIS-8-Dimethylamino-3-[(4-methoxyphenyl)-methyl]-8-phenyl-1,3-diazaspiro[4.5]decan-2-one (INT-975) (7.00 g, 17.8 mmol) was added and stirring was continued for 15 min. 1-(Bromo-methyl)-1-methyl-cyclobutane (8.7 g, 53.4 mmol) was added at 0° C. The reaction mixture was heated to 60° C. for 16 h. After cooling down to RT, water (100 mL) was added and the mixture was extracted with DCM (3×150 mL). The combined organic layers were washed with water (70 mL), brine (100 mL), dried over $Na_2SO_4$ and concentrated under reduced pressure. Purification of the residue by column chromatography on silica gel provided CIS-8-(dimethylamino)-3-(4-methoxybenzyl)-1-((1-methylcyclobutyl)methyl)-8-phenyl-1,3-diazaspiro[4.5]decan-2-one (6.5 g) as a light yellow solid.

Step 2: CIS-8-Dimethylamino-1-[(1-methyl-cyclobutyl)-methyl]-8-phenyl-1,3-diazaspiro[4.5]decan-2-one To the solution of CIS-8-Dimethylamino-1-[(1-methyl-cyclobutyl)-methyl]-8-phenyl-1,3-diazaspiro[4.5]decan-2-one (6.66 g, 14.0 mmol) in DCM (65 mL) was added TFA (65 mL) and the resulting mixture was stirred at RT for 16 h. The reaction mixture was concentrated under reduced pressure. The residue was taken up in DCM (100 mL) and water (60 mL) and basified with 2M aq. NaOH to pH 10. The organic layer was separated and washed with brine (40 mL), dried over MgSO₄, filtered and concentrated under reduced pressure. Crystallization of the residue from EtOAc provided CIS-8-Dimethylamino-1-[(1-methyl-cyclobutyl)-methyl]-8-phenyl-1,3-diazaspiro[4.5]decan-2-one (INT-982) (3.41 g) as an off-white solid. [M+H]+ 356.3

Synthesis of INT-984: CIS-1-(Cyclobutyl-methyl)-8-(ethyl-methyl-amino)-8-phenyl-1,3-diazaspiro[4.5]decan-2-one

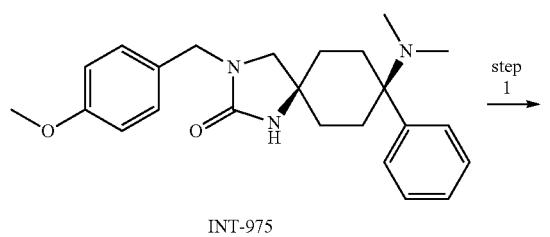

INT-975 step 1

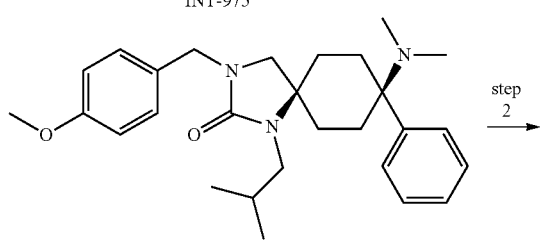

step 2

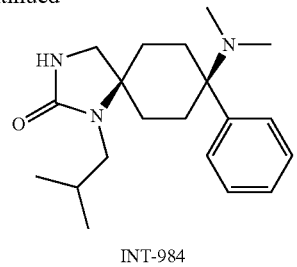

INT-984

Step 1: CIS-8-(dimethylamino)-1-isobutyl-3-(4-methoxybenzyl)-8-phenyl-1,3-diazaspiro[4.5]decan-2-one In analogy to the method described for INT-951 step 1 CIS-8-Dimethylamino-3-[(4-methoxyphenyl)-methyl]-8-phenyl-1,3-diazaspiro[4.5]decan-2-one (INT-975) was converted into CIS-8-(dimethylamino)-1-isobutyl-3-(4-methoxybenzyl)-8-phenyl-1,3-diazaspiro[4.5]decan-2-one.

Step 2: CIS-1-(Cyclobutyl-methyl)-8-(ethyl-methyl-amino)-8-phenyl-1,3-diazaspiro[4.5]decan-2-one In analogy to the method described for INT-982 step 2 CIS-8-(dimethylamino)-1-isobutyl-3-(4-methoxybenzyl)-8-phenyl-1,3-diazaspiro[4.5] decan-2-one was converted into CIS-1-(Cyclobutyl-methyl)-8-(ethyl-methyl-amino)-8-phenyl-1,3-diazaspiro[4.5]decan-2-one (INT-984).

Synthesis of INT-986: CIS-1-(Cyclobutyl-methyl)-8-(ethyl-methyl-amino)-8-phenyl-1,3-diazaspiro[4.5]decan-2-one

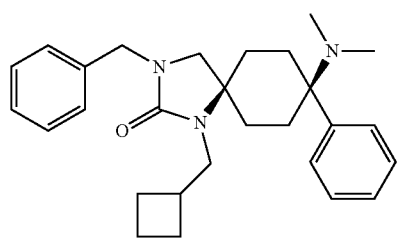

INT-950 step 1

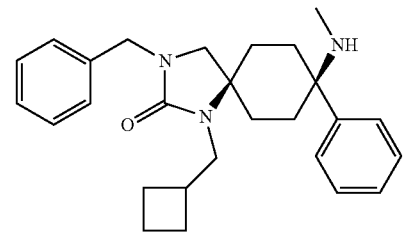

step 2

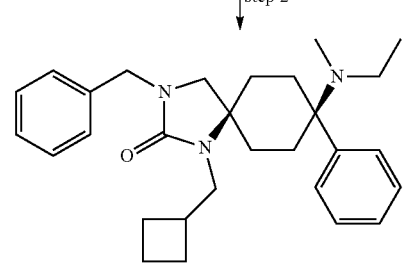

step 3

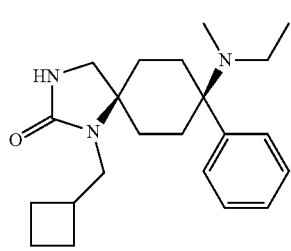

INT-986

Step 1: CIS-3-benzyl-1-(cyclobutylmethyl)-8-(methylamino)-8-phenyl-1,3-diazaspiro[4.5]decan-2-one N-Iodosuccinimide (3.11 g, 13.92 mmol) was added to the solution of CIS-1-(Cyclobutyl-methyl)-8-dimethylamino-8-phenyl-3-[phenyl-methyl]-1,3-diazaspiro[4.5]decan-2-one (INT-950) (4 g, 9.28 mmol) in a mixture of acetonitrile and THF (1:1 v/v, 80 mL) and the resulting mixture was stirred at RT for 16 h. The reaction mixture was basified with 2N aq. NaOH to pH-10 and the organic product was extracted with DCM (3×10 mL). The combined organic extracts were dried over anhydrous Na$_2$SO$_4$ and concentrated in vacuo. The residue was stirred vigorously with a mixture of 10 wt % aq. citric acid (5 mL) and DCM (10 mL) at RT for 10 min. The reaction mixture was basified with 5N aq. NaOH to pH~10 and extracted with DCM (3×10 mL). The combined organic layer was dried over anhydrous Na$_2$SO$_4$ and concentrated in vacuo to give 3.5 g (crude) of CIS-3-benzyl-1-(cyclobutylmethyl)-8-(methylamino)-8-phenyl-1,3-diazaspiro[4.5]decan-2-one as semi solid (TLC system: 10% MeOH in DCM; R$_f$: 0.60.).

Step 2: CIS-3-benzyl-1-(cyclobutylmethyl)-8-(ethyl(methyl)amino)-8-phenyl-1,3-diazaspiro[4.5]decan-2-one Sodium cyanoborohydride (1.56 g, 25.17 mmol, 3 equiv.) was added to the solution of CIS-3-benzyl-1-(cyclobutylmethyl)-8-(methylamino)-8-phenyl-1,3-diazaspiro[4.5]decan-2-one (3.5 g, 8.39 mmol), acetaldehyde (738 mg, 16.78 mmol, 2 equiv.) and acetic acid (0.5 mL) in methanol (20 mL). The reaction mixture was stirred at RT for 3 h, then quenched with sat. aq. NaHCO$_3$ and the organic product was extracted with DCM (3×50 mL). The combined organic extracts were dried over anhydrous Na$_2$SO$_4$ and concentrated in vacuo. Purification of the residue by flash column chromatography on silica gel (230-400 mesh) (20-25% ethyl acetate in petroleum ether) yielded 2.3 g (62%) of CIS-3-benzyl-1-(cyclobutylmethyl)-8-(ethyl(methyl)amino)-8-phenyl-1,3-diazaspiro[4.5]decan-2-one as a solid. (TLC system: 50% EtOAc in Pet. Ether; R$_f$: 0.65).

Step 3: CIS-1-(Cyclobutyl-methyl)-8-(ethyl-methyl-amino)-8-phenyl-1,3-diazaspiro[4.5]decan-2-one (INT-986)

Sodium metal (1.18 g, 51.68 mmol, 10 equiv.) was added to liquid ammonia (~25 mL) at -78° C. The resulting mixture was stirred for 10 min at -78° C. A solution of CIS-3-benzyl-1-(cyclobutylmethyl)-8-(ethyl(methyl)amino)-8-phenyl-1,3-diazaspiro[4.5]decan-2-one (2.3 g, 5.16 mmol) in THF (25 mL) was added at -78° C. The reaction mixture was stirred for 15 min, then quenched with sat. aq. NH$_4$Cl, warmed to RT and stirred for 1 h. The organic product was extracted with DCM (3×50 mL). The combined organic layer was washed with water, brine and concentrated under reduced pressure to afford 1.30 g (72%) of CIS-1-(cyclobutylmethyl)-8-(ethyl(methyl)amino)-8-phenyl-1,3-diazaspiro[4.5]decan-2-one (INT-986) as an off-white solid. (TLC system: 10% MeOH in DCM R$_f$: 0.15.). [M+H]$^+$ 356.3

Synthesis of INT-987: CIS-1-(Cyclobutyl-methyl)-8-dimethylamino-8-phenyl-1,3-diazaspiro[4.5]decan-2-one

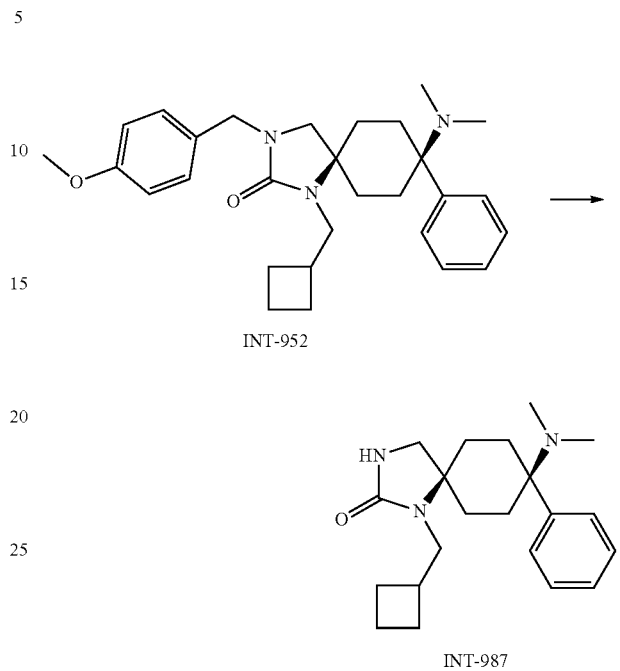

INT-952

INT-987

In analogy to the method as described for INT-982 step 2 CIS-1-(Cyclobutyl-methyl)-8-dimethylamino-8-phenyl-3-[(4-methoxyphenyl)-methyl]-1,3-diazaspiro[4.5]decan-2-one (INT-952) was converted into CIS-1-(Cyclobutyl-methyl)-8-dimethylamino-8-phenyl-1,3-diazaspiro[4.5]decan-2-one (INT-987).

Synthesis of INT-988: CIS-8-(dimethylamino)-1-(2-(1-methoxycyclobutyl)ethyl)-8-phenyl-1,3-diazaspiro[4.5]decan-2-one

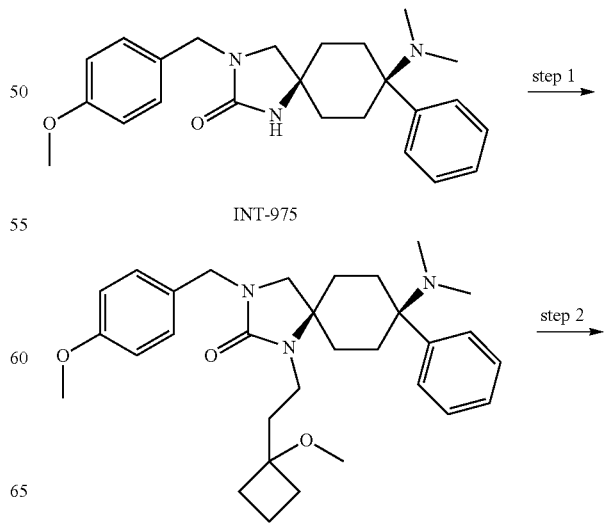

INT-975

-continued

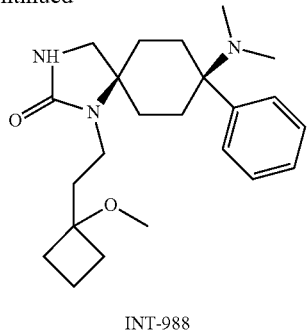

INT-988

Step 1: CIS-8-(dimethylamino)-1-[2-(1-methoxycyclobutyl)ethyl]-3-[(4-methoxyphenyl)methyl]-8-phenyl-1,3-diazaspiro[4.5]decan-2-one Sodium hydroxide (78.06 mg, 4.0 equiv.) was suspended in DMSO (3.5 mL), stirred for 10 minutes, 8-(dimethylamino)-3-[(4-methoxyphenyl)methyl]-8-phenyl-1,3-diazaspiro[4.5]decan-2-one (INT-975) (192.0 mg, 1.0 equiv.) was added, the reaction mixture was stirred for 5 min followed by addition of 2-(1-methoxycyclobutyl)ethyl 4-methylbenzenesulfonate (416.2 mg, 3.0 equiv.) in DMSO (1.5 mL). The resulting mixture was stirred overnight at 50° C. The reaction mixture was quenched with water and extracted with DCM (3×20 mL). The combined organic phases were washed with brine, dried over $Na_2SO_4$ and concentrated under reduced pressure. The residue (283 mg yellow oil) was purified by column chromatography on silica gel (eluent DCM/EtOH 98/2 to 96/4) to give 8-(dimethylamino)-1-[2-(1-methoxycyclobutyl)ethyl]-3-[(4-methoxyphenyl)methyl]-8-phenyl-1,3-diazaspiro[4.5]decan-2-one 163 mg (66%).

Step 2: CIS-8-(dimethylamino)-1-(2-(1-methoxycyclobutyl)ethyl)-8-phenyl-1,3-diazaspiro[4.5]decan-2-one (INT-988)

In analogy to the method described for INT-982 step 2 CIS-8-(dimethylamino)-1-[2-(1-methoxycyclobutyl)ethyl]-3-[(4-methoxyphenyl)methyl]-8-phenyl-1,3-diazaspiro[4.5]decan-2-one was converted into CIS-8-(dimethylamino)-1-(2-(1-methoxycyclobutyl)ethyl)-8-phenyl-1,3-diazaspiro[4.5]decan-2-one (INT-988). Mass: m/z 386.3 $(M+H)^+$.

Synthesis of INT-992: CIS-2-[8-Dimethylamino-1l-(2-methyl-propyl)-2-oxo-8-phenyl-1,3-diazaspiro[4.5]decan-3-yl]-acetic acid

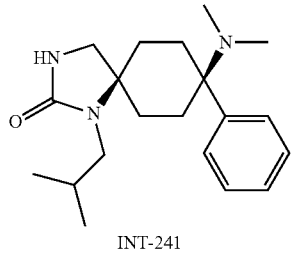

INT-241

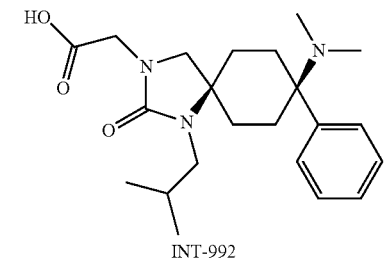

INT-992

CIS-8-Dimethylamino-1-(2-methyl-propyl)-8-phenyl-1,3-diazaspiro[4.5]decan-2-one (INT-241) (0.9 g, 2.73 mmol) was added to a solution of NaH (60 wt % in mineral oil, 1.64 g, 41.03 mmol) in DMF (20 mL) at RT. The reaction mixture was stirred at RT for 15 min, then cooled to 0° C. and ethyl 2-bromoacetate (4.56 g, 27.35 mmol) was added dropwise. The resulting mixture was stirred at RT for 2 days. The reaction completion was monitored by TLC. The reaction mixture was quenched with water and concentrated under reduced pressure. The residue was diluted with small amount of water and acidified by acetic acid. The resulting mixture was concentrated under reduced pressure again. The crude product was purified by silica gel flash chromatography using 230-400 mesh (25 vol % MeOH in DCM) to afford 1.1 g of CIS-2-[8-dimethylamino-1-(2-methyl-propyl)-2-oxo-8-phenyl-1,3-diazaspiro[4.5]decan-3-yl]-acetic acid (INT-992) as a solid. $[M+H]^+$ 388.3

Synthesis of INT-994: CIS-2-[8-Dimethylamino-1-[(1-hydroxy-cyclobutyl)-methyl]-2-oxo-8-phenyl-1,3-diazaspiro[4.5]decan-3-yl]-acetic Acid

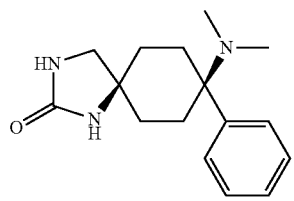

INT-976 step 1 →

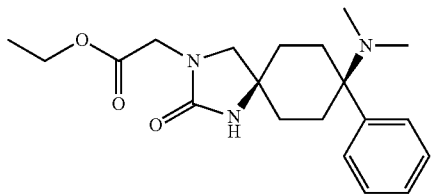

| step 2
↓

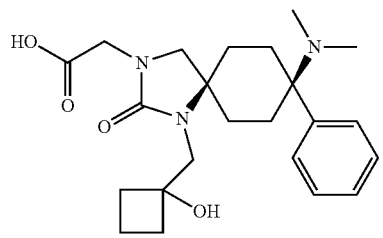

INT-994

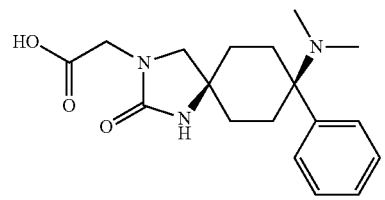

Step 1: ethyl 2-(cis-8-(dimethylamino)-2-oxo-8-phenyl-1,3-diazaspiro[4.5]decan-3yl)acetate KOtBu (1M in THF) (54.90 mL, 54.95 mmol) was added to a solution of CIS-8-dimethylamino-8-phenyl-1,3-diazaspiro[4.5]decan-2-one (INT-976) (10 g, 36.63 mmol) in THF (950 mL) under argon atmosphere at 0° C. and the reaction mixture was stirred for 15 min. A solution of ethyl bromoacetate (5.06 mL, 43.96 mmol) in THF (50 mL) was added. The reaction mixture was warmed up to RT and stirred for 48 h. The reaction completion was monitored by TLC. Solvent was evaporated under reduced pressure and the crude product was purified by column chromatography to yield the desired product in 2 fractions: fraction 1: 2.2 g ethyl 2-(cis-8-(dimethylamino)-2-oxo-8-phenyl-1,3-diazaspiro[4.5]decan-3-yl)acetate (68% pure according to LCMS) as an off-white solid and Fraction 2: 3.2 g of ethyl 2-(cis-8-(dimethylamino)-2-oxo-8-phenyl-1,3-diazaspiro [4.5]decan-3-yl)acetate (32% pure according to LCMS) as well as 1.1 g of unreacted starting material. Fraction 1 was used further without additional purification.

Step 2: 2-(cis-8-(dimethylamino)-2-oxo-8-phenyl-1,3-diazaspiro[4.5]decan-3-yl)acetic Acid A mixture of ethyl-2-(CIS-8-(dimethylamino)-2-oxo-8-phenyl-1,3-diazaspiro[4.5]decan-3-yl)acetate (68% pure, 2.2 g, 6.128 mmol) and powdered NaOH (981 mg, 24.513 mmol) in toluene (40 mL) was stirred at 80° C. for 3 h under argon atmosphere. Ester hydrolysis was monitored by LCMS. Toluene was evaporated under reduced pressure and the resulting crude product (2.4 g) was further purified by reverse phase prep. HPLC to yield 0.93 g of 2-(CIS-8-(dimethylamino)-2-oxo-8-phenyl-1,3-diazaspiro[4.5]decan-3-yl)acetic acid.

Step 3: 2-(cis-8-(dimethylamino)-1-((1-hydroxycyclobutyl)methyl)-2-oxo-8-phenyl-1,3-diazaspiro[4.5]decan-3-yl)acetic Acid To a solution of 2-(CIS-8-(dimethylamino)-2-oxo-8-phenyl-1,3-diazaspiro[4.5]decan-3-yl)acetic acid (1.5 g, 4.532 mmol) in toluene (45 mL) was added in one portion powdered NaOH (725.08 mg, 18.127 mmol) under argon atmosphere at RT. The reaction mixture was stirred at 80° C. for 4 h. Toluene was evaporated under reduced pressure to get the residue which was dissolved in DMSO (45 mL) under argon atmosphere. The solution was stirred at 55° C. for 1 h. To the reaction mixture was added dropwise a solution of 1-oxaspiro[2.3]hexane (1.144 g, 13.596 mmol) in DMSO (12 mL) via syringe pump (flow rate 10 mL/h). The reaction mixture was stirred at 55° C. for 65 h. The reaction progress was monitored by LCMS. DMSO was evaporated in vacuo. The residue was dissolved in water (50 mL), cooled to 0° C. and pH was adjusted to 3-4 with acetic acid. The resulting mixture was concentrated under reduced pressure and the crude product was purified by column chromatography (elution with 8-10% MeOH in DCM) to yield 750 mg (78%) of 2-(cis-8-(dimethylamino)-1-((1-hydroxycyclobutyl)methyl)-2-oxo-8-phenyl-1,3-diazaspiro[4.5]decan-3-yl)acetic acid (INT-994) as an off-white solid. [M+H]$^+$ 416.2

Synthesis of INT-998: CIS-2-[8-Dimethylamino-1-[(1-methyl-cyclobutyl)-methyl]-2-oxo-8-phenyl-1,3-diazaspiro[4.5]decan-3-yl]-acetic acid; 2,2,2-trifluoro-acetic Acid Salt

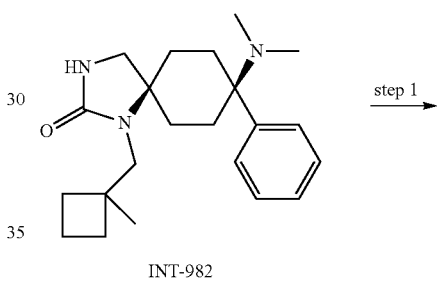

INT-982

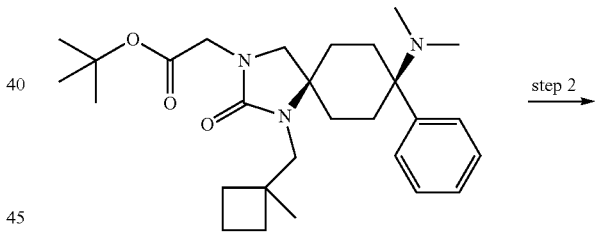

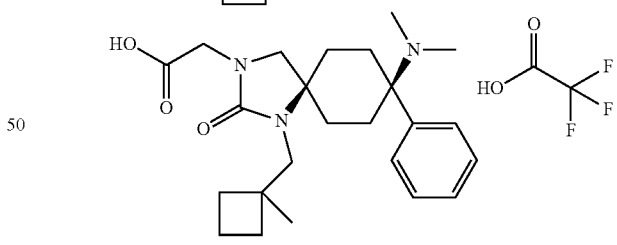

INT-998

Step 1: CIS-tert-butyl 2-[8-(dimethylamino)-1-[(1-methylcyclobutyl)methyl]-2-oxo-8-phenyl-1,3-diazaspiro[4.5]decan-3-yl]acetate CIS-8-Dimethylamino-1-[(1-methyl-cyclobutyl)-methyl]-8-phenyl-1,3-diazaspiro[4.5]decan-2-one (INT-982) (2.8 g, 7.9 mmol) was dissolved in THF (110 mL) and the solution was cooled to 0° C. Lithium diisopropylamide solution in THF/heptane/ethylbenzene (2M, 16 mL) was added dropwise. The reaction mixture was stirred for 30 min and t-butyl-bromoacetate was added dropwise at the same temperature. The reaction mixture was concentrated in vacuo, water was added and the resulting mixture was extracted with DCM (3×250 mL). The combined organic layers were dried over Na$_2$SO$_4$, concentrated in vacuo and the residue was purified by flash chromatography to yield CIS-tert-butyl 2-[8-(dimethylamino)-1-[(1-methylcyclobutyl)methyl]-2-oxo-8-phenyl-1,3-diazaspiro[4.5]decan-3-yl]acetate (1670 mg) as a white solid.

Step 2: CIS-2-[8-Dimethylamino-1-[(1-methyl-cyclobutyl)-methyl]-2-oxo-8-phenyl-1,3-diazaspiro [4.5]decan-3-yl]-acetic Acid; 2,2,2-trifluoro-acetic Acid Salt CIS-tert-butyl 2-[8-(dimethylamino)-1-[(1-methylcyclobutyl)methyl]-2-oxo-8-phenyl-1,3-diaza-spiro[4.5]decan-3-yl]acetate (2250 mg, 4.8 mmol) was treated with TFA (18 mL) at RT. After stirring for 10 min, all volatiles were removed in vacuo. The residue was triturated with diethyl ether (30 mL) using ultrasonic bath, the solid rest was dried under reduced pressure to yield CIS-2-[8-dimethylamino-1-[(1-methyl-cyclobutyl)-methyl]-2-oxo-8-phenyl-1,3-diaz-aspiro[4.5]decan-3-yl]-acetic acid; 2,2,2-trifluoro-acetic acid salt (INT-998) (2.2 g) as a brown solid. [M+H]$^+$ 413.3

Synthesis of INT-1008: CIS-8-ethylamino-8-phenyl-1,3-diaza-spiro[4.5]decan-2-one Step 1 and step 2: ethyl-(8-phenyl-1,4-dioxa-spiro [4.5]dec-8-yl)-amine Hydrochloride (INT-1004)

A mixture of 1,4-dioxa-spiro[4.5]decan-8-one (25.0 g, 160.25 mmol, 1.0 eq.) and 2M solution of EtNH$_2$ in THF (200 ml, 2.5 eq. 400.64 mmol) in EtOH (30 mL) was stirred at RT for 48 h. The reaction mixture was concentrated under argon atmosphere. The residue was diluted with ether (60 mL) and added to the freshly prepared PhLi solution [prepared by addition of 2.5M n-BuLi in THF (70.5 mL, 1.1 eq. 176.27 mmol) to a solution of bromobenzene (27.675 g, 1.1 eq. 176.275 mmol) in ether (100 mL) at -30° C. and stirred at RT for 1 h] at RT. The reaction mixture was stirred at RT for 1.5 h, then cooled down to 0° C. and quenched with sat. aq. NH$_4$Cl (100 mL). The resulting mixture was extracted with EtOAc (2×750 mL), combined organic extracts were washed with water (3×350 mL), brine (300 mL), dried over Na$_2$SO$_4$ and concentrated under reduced pressure. The crude product was dissolved in ethylmethyl ketone (100 mL) and TMSCl (37.5 mL) was added at 0° C. The reaction mixture was stirred at RT for 16 h, the precipitate formed was filtered off and washed with acetone and THF to give ethyl-(8-phenyl-1,4-dioxa-spiro[4.5]dec-8-yl)-amine hydrochloride as an off-white solid. This reaction was done in 2 batches of 25 g scale and the yield is given for 2 combined batches. Yield: 18% (17.1 g, 57.575 mmol). LCMS: m/z 262.2 (M+H)$^+$.

Step 3: 4-ethylamino-4-phenyl-cyclohexanone (INT-1005)

To a solution of ethyl-(8-phenyl-1,4-dioxa-spiro[4.5]dec-8-yl)-amine hydrochloride (10.1 g, 34.0 mmol, 1 eq.) in

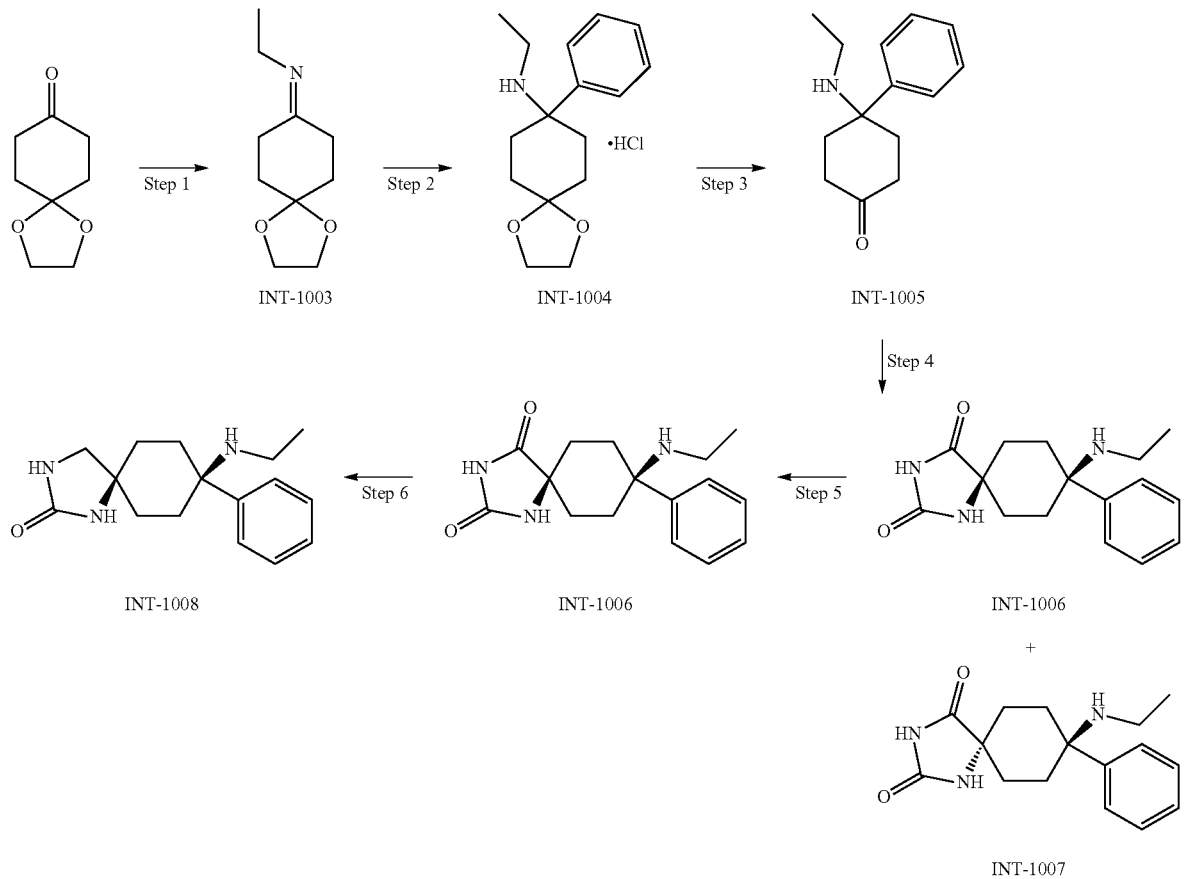

water (37.5 mL) was added conc. HCl (62.5 mL) at 0° C. and the reaction mixture was stirred at RT for 16 h. The reaction mixture was basified with 1N aq. NaOH to pH ~14 at 0° C. and extracted with DCM (2×750 mL). Organic layer was washed with water (400 mL), brine (400 mL), dried over $Na_2SO_4$ and concentrated under reduced pressure to yield 4-ethylamino-4-phenyl-cyclohexanone which was used in the next step without further purification. This reaction was carried out in another batch of 15.1 g scale and yield is given for 2 combined batches. Yield: 92% (17.0 g, 78.34 mmol).

Step 4: mixture of CIS- and TRANS-8-ethylamino-8-phenyl-1,3-diaza-spiro[4.5]decane-2,4-dione (INT-1006 and INT-1007)

To a solution of 4-ethylamino-4-phenyl-cyclohexanone (17 g, 78.341 mmol, 1.0 eq.) in EtOH (250 mL) and water (200 mL) was added $(NH_4)_2CO_3$ (18.8 g, 195.85 mmol, 2.5 eq.) and the reaction mixture was stirred at RT for 15 min. KCN (5.09 g, 78.341 mmol, 1.0 eq.) was and the resulting mixture was stirred at 60° C. for 18 h. The reaction mixture was cooled to RT, the precipitate was filtered off, washed with water (250 mL), EtOH (300 mL), hexane (200 mL) and dried under reduced pressure to yield CIS- and TRANS-mixture 8-ethylamino-8-phenyl-1,3-diaza-spiro[4.5]decane-2,4-dione (13.0 g, 45.29 mmol, 58%) as a white solid. Yield: 58% (13 g, 45.296 mmol). LC-MS: m/z $[M+1]^+=288.2$.

Step 5: CIS-8-ethylamino-8-phenyl-1,3-diaza-spiro[4.5]decane-2,4-dione (INT-1006)

To a solution of cis and trans mixture of 8-ethylamino-8-phenyl-1,3-diaza-spiro[4.5]decane-2,4-dione (12 g) in MeOH/DCM (1:1 v/v, 960 mL) was added a solution of L-tartaric acid in MeOH (25 mL). The resulting mixture was stirred at RT for 2 h and then kept in refrigerator for 16 h. The solid material was filtered off and washed with MeOH/DCM (1:5, 50 ml) to get 8-ethylamino-8-phenyl-1,3-diaza-spiro[4.5]decane-2,4-dione tartrate (7.5 g) as a white solid. The solid was suspended in sat. aq. $NaHCO_3$ (pH-8) and the resulting mixture was extracted with 25% MeOH-DCM (2×800 ml). Combined organic extracts were washed with water (300 ml), brine (300 ml) and dried over anhydrous $Na_2SO_4$. The solvent was evaporated under reduced pressure and the residue was triturated with 20% DCM-hexane to afford CIS-8-ethylamino-8-phenyl-1,3-diaza-spiro[4.5] decane-2,4-dione as a white solid. This step was done in 2 batches (12 g & 2.4 g) and yield is given for 2 combined batches. Yield: 31.2% (5.0 g, 17.421 mmol). LC-MS: m/z $[M+1]^+=288.0$.

Step 6: CIS-8-ethylamino-8-phenyl-1,3-diaza-spiro[4.5]decan-2-one (INT-1008)

To a slurry of $LiAlH_4$ (793 mg, 20.905 mmol, 3.0 eq.) in THF (15 mL) was added a suspension of cis-8-ethylamino-8-phenyl-1,3-diaza-spiro[4.5]decane-2,4-dione (2.0 g, 6.968 mmol, 1.0 eq.) in THF (60 mL) at 0° C. and the reaction mixture was stirred at 65° C. for 16 h. The resulting mixture was cooled to 0° C., quenched with sat. aq. $Na_2SO_4$ (20 ml), stirred at RT for 1 h and filtered through celite. The celite layer was washed with 15% MeOH-DCM (500 ml). The combined filtrate was dried over anhydrous $Na_2SO_4$ and concentrated under reduced pressure. The resulting crude product was triturated with 15% DCM-Hexane to afford CIS-8-ethylamino-8-phenyl-1,3-diaza-spiro[4.5]decan-2-one (INT-1008) (1.6 g, 5.86 mmol, 84%) as a white solid. Yield: 84% (1.6 g, 5.86 mmol). LC-MS: m/z $[M+H]^+=274.2$.

Synthesis of INT-1019: CIS-2-(8-(dimethylamino)-1-((1-hydroxycyclobutyl)methyl)-2-oxo-8-phenyl-1,3-diazaspiro[4.5]decan-3-yl)acetic Acid Hydrochloride

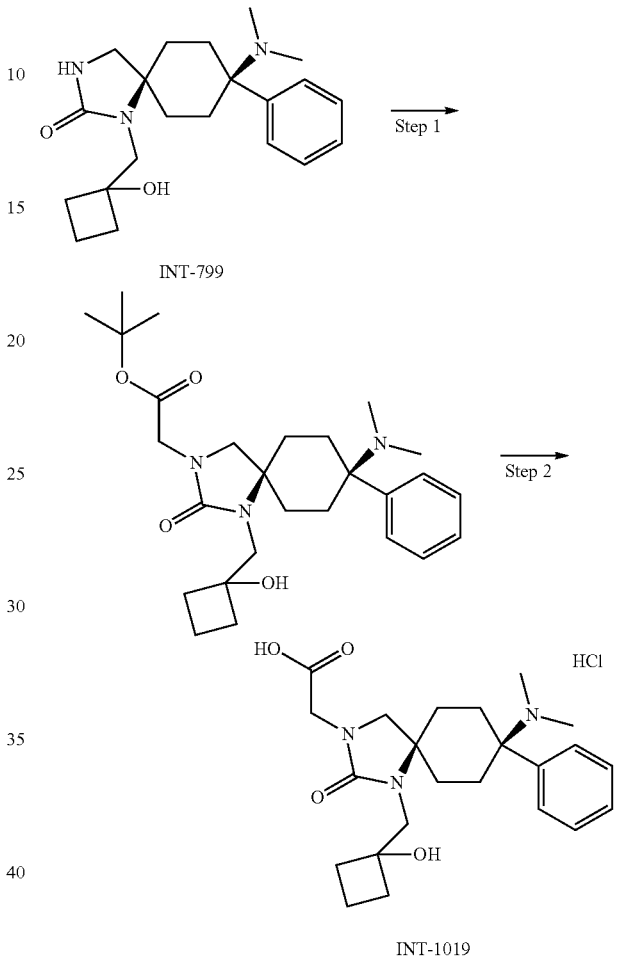

Step 1: tert-butyl CIS-2-(8-(dimethylamino)-1-((1-hydroxycyclobutyl)methyl)-2-oxo-8-phenyl-1,3-diazaspiro[4.5]decan-3-yl)acetate The solution of CIS-8-(dimethylamino)-1-((1-hydroxycyclobutyl)methyl)-8-phenyl-1,3-diazaspiro[4.5]decan-2-one (INT-799) (1.8 g, 5.042 mmol) in THF (40 mL) was cooled down to 0° C. and KOtBu (1 M in THF, 5.55 mL, 5.546 mmol) was added. The resulting mixture was stirred for 10 min followed by the dropwise addition of tert-butyl bromoacetate (1.081 g, 5.546 mmol). The ice bath was removed and the reaction mixture was stirred for 2 h, then quenched with sat. aq. $NH_4Cl$ (40 mL) and extracted with EtOAc (2×80 mL). The combined organic extracts were dried over anhydr. $Na_2SO_4$ and concentrated under reduced pressure. Crude product was purified by column chromatography (silica gel 100-200 mesh, 0-4% MeOH in DCM as eluent) to afford 1.7 g of tert-butyl CIS-2-(8-(dimethylamino)-1-((1-hydroxycyclobutyl)methyl)-2-oxo-8-phenyl-1,3-diazaspiro[4.5]decan-3-yl)acetate as an off white solid.

Step 2: CIS-2-(8-(dimethylamino)-1-((1-hydroxycyclobutyl)methyl)-2-oxo-8-phenyl-1,3-diazaspiro[4.5]decan-3-yl)acetic Acid Hydrochloride 4N HCl in dioxane (30 mL) was added to the solution of tert-butyl CIS-2-(8-(dimethylamino)-1-((1-hydroxycyclobutyl)methyl)-2-oxo-8-phenyl-1,3-diazaspiro[4.5]decan-3-yl)acetate (1.7 g, 3.609 mmol) in 1,4 dioxane (10 mL). The resulting mixture was stirred at RT for 16 h and then concentrated under reduced pressure to afford 1.5 g of CIS-2-(8-(dimethylamino)-1-((1-hydroxycyclobutyl)methyl)-2-oxo-8-phenyl-1,3-diazaspiro[4.5]decan-3-yl)acetic acid hydrochloride (INT-1019) as a hygroscopic solid. TLC $R_f$ (10% MeOH in DCM)=0.2. LC-MS: m/z [M+H]$^+$= 416.3.

Synthesis of INT-1020: sodium CIS-2-(8-(dimethylamino)-1-((1-hydroxycyclobutyl)methyl)-2,4-dioxo-8-phenyl-1,3-diazaspiro[4.5]decan-3-yl)acetate

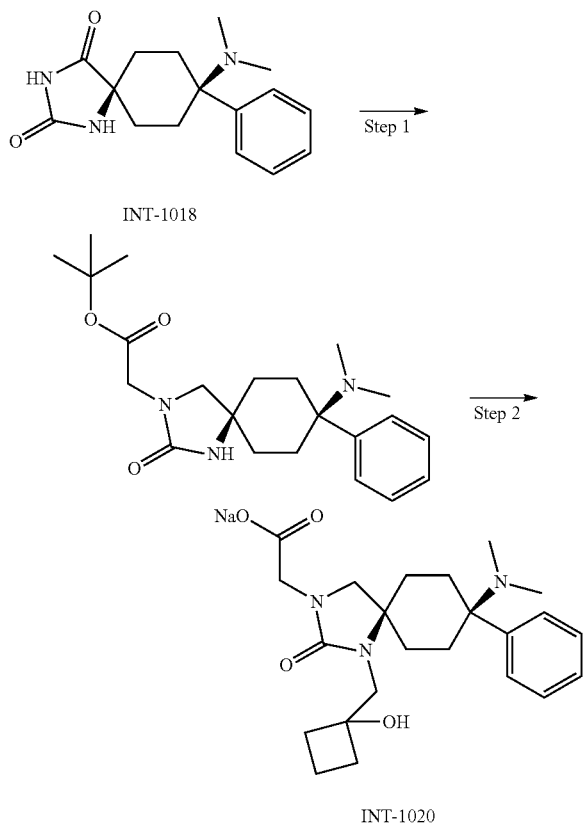

Step 1: tert-butyl CIS-2-(8-(dimethylamino)-2,4-dioxo-8-phenyl-1,3-diazaspiro[4.5]decan-3-yl)acetate To the suspension of tert-butyl CIS-2-(8-(dimethylamino)-2,4-dioxo-8-phenyl-1,3-diazaspiro[4.5]decan-3-yl)acetate (INT-1018) (0.5 g, 1.74 mmol) in DMF (11 mL) was added portionwise sodium hydride (60% in mineral oil, 70 mg, 1.74 mmol, 1 equiv.). The reaction mixture was stirred until the evolution of hydrogen was over and a clear solution was formed (ca. 40 min). Tert-butyl bromoacetate (257 µL, 1.74 mmol, 1 equiv.) was added, the reaction mixture was stirred at RT overnight, quenched with ca. 40 mL water and stirred for 2 h. The precipitate was filtered off, washed with water, hexane and dried under reduced pressure to give tert-butyl CIS-2-(8-(dimethylamino)-2,4-dioxo-8-phenyl-1,3-diazaspiro[4.5]decan-3-yl)acetate (653 mg, 93%) which was used further without additional purification. LC-MS: m/z [M+H]$^+$=402.2.

Step 2: sodium CIS-2-(8-(dimethylamino)-1-((1-hydroxycyclobutyl)methyl)-2,4-dioxo-8-phenyl-1,3-diazaspiro[4.5]decan-3-yl)acetate (INT-1020)

Sodium hydroxide (135 mg, 3.37 mmol, 4 equiv.) was suspended in dimethyl sulfoxide (1.8 mL, 25.26 mmol, 30 equiv.) and the mixture was stirred at RT for 10 min. Tert-butyl CIS-2-(8-(dimethylamino)-2,4-dioxo-8-phenyl-1,3-diazaspiro[4.5]decan-3-yl)acetate (338 mg, 0.84 mmol, 1 equiv.) was added, the reaction mixture was stirred 5 min at RT and then heated up to 50° C. [1-[Tert-butyl(dimethyl)silyl]oxycyclobutyl]methyl 4-methylbenzenesulfonate (936 mg, 2.53 mmol, 3 equiv.) was added and the reaction mixture was stirred at 60° C. for 3 days. The resulting mixture was cooled down to RT, diluted with water (5 mL), extracted with EtOAc (1×10 mL) and the aqueous phase was concentrated under reduced pressure to give crude sodium CIS-2-(8-(dimethylamino)-1-((1-hydroxycyclobutyl)methyl)-2,4-dioxo-8-phenyl-1,3-diazaspiro[4.5]decan-3-yl)acetate (INT-1020) (473 mg) which was used in the next step without further purification. LC-MS: m/z [M+H]$^+$=452.2.

Synthesis of INT-1026: CIS-8-(methyl((tetrahydrofuran-3-yl)methyl)amino)-8-phenyl-1,3-diazaspiro[4.5]decan-2-one

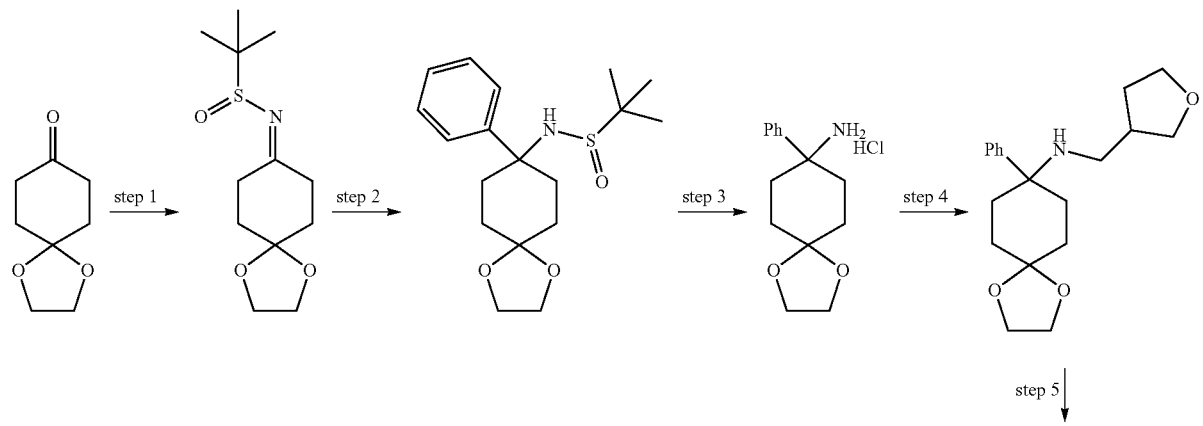

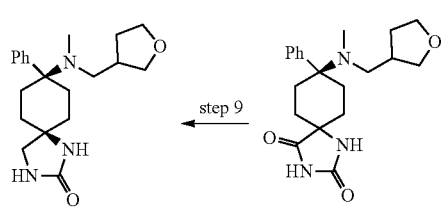
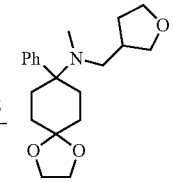

INT-1026

Step 1: 2-methyl-N-(1,4-dioxaspiro[4.5]decan-8-ylidene)propane-2-sulfinamide Titanium ethoxide (58.45 g, 256.4 mmol) was added to a solution of 1,4-dioxaspiro[4.5]decan-8-one (20 g, 128.20 mmol) and 2-methylpropane-2-sulfinamide (15.51 g, 128.20 mmol) in THF (200 mL) at RT and the reaction mixture was stirred at RT for 18 h. The reaction mixture was cooled to 0° C. and quenched by dropwise addition of sat. aq. NaHCO₃ (500 mL) over a period of 30 min. The organic product was extracted with EtOAc (3×100 mL). The combined organic extracts were dried over anhydrous Na₂SO₄ and concentrated in vacuo to afford 10 g (crude) of 2-methyl-N-(1,4-dioxaspiro[4.5]decan-8-ylidene)propane-2-sulfinamide as a white solid (TLC system: 30% Ethyl acetate in hexane; Rf: 0.30).

Step 2: 2-methyl-N-(8-phenyl-1,4-dioxaspiro[4.5]decan-8-yl)propane-2-sulfinamide Phenylmagnesium bromide (1M in THF, 116 mL, 116 mmol) was added dropwise to a solution of 2-methyl-N-(1,4-dioxaspiro[4.5]decan-8-ylidene)propane-2-sulfinamide (10 g, 38.61 mmol) in THF (500 mL) at −10° C. under argon atmosphere. The reaction mixture was stirred for 2 h at −10° C. to 0° C. The reaction completion was monitored by TLC. The reaction mixture was quenched with sat. aq. NH₄Cl (50 mL) at 0° C. and the organic product was extracted with EtOAc (3×100 mL). The combined organic extracts were dried over anhydrous Na₂SO₄ and concentrated in vacuo. The residue was purified by column chromatography (silica gel 230-400 mesh; 40-60% ethyl acetate in hexane) to yield 6.0 g (46%) of 2-methyl-N-(8-phenyl-1,4-dioxaspiro[4.5]decan-8-yl)propane-2-sulfinamide as a liquid (TLC system: 70% Ethyl acetate in hexane; Rf: 0.30).

Step 3: 8-phenyl-1,4-dioxaspiro[4.5]decan-8-amine Hydrochloride 2N solution of HCl in diethyl ether (17.80 mL, 35.60 mmol) was added to a solution of 2-methyl-N-(8-phenyl-1,4-dioxaspiro[4.5]decan-8-yl)propane-2-sulfinamide (6.0 g, 17.80 mmol) in DCM (60 mL) at 0° C. The reaction mixture was stirred at RT for 2 h. The reaction mixture was concentrated in vacuo. The residue was washed with diethyl ether to yield 3 g (crude) of 8-phenyl-1,4-dioxaspiro[4.5]decan-8-amine hydrochloride as a brown solid (TLC system: 5% MeOH in DCM; Rf: 0.10).

Step 4: 8-phenyl-N-((tetrahydrofuran-3-yl)methyl)-1,4-dioxaspiro[4.5]decan-8-amine Sodium cyanoborohydride (2.17 g, 33.45 mmol) was added to a solution of 8-phenyl-1,4-dioxaspiro[4.5]decan-8-amine hydrochloride (3.0 g, 11.15 mmol) and tetrahydrofuran-3-carbaldehyde (4.46 mL, 22.30 mmol) and acetic acid (0.05 mL) in methanol (30 mL) at 0° C. The reaction mixture was stirred at RT for 16 h. The reaction mixture was concentrated in vacuo at 30° C. and to the residue sat. aq. NaHCO₃ was added. The organic product was extracted with DCM (3×30 mL). The combined organic extracts were dried over anhydrous Na₂SO₄ and solvent was concentrated under reduced pressure to get 3 g (crude) of 8-phenyl-N-((tetrahydrofuran-3-yl)methyl)-1,4-dioxaspiro[4.5]decan-8-amine as a semi-solid (TLC system: 10% MeOH in DCM; Rf: 0.22).

Step 5: N-methyl-8-phenyl-N-((tetrahydrofuran-3-yl)methyl)-1,4-dioxaspiro[4.5]decan-8-amine)

Sodium cyanoborohydride (1.76 g, 28.39 mmol) was added to a solution of 8-phenyl-N-((tetrahydrofuran-3-yl)methyl)-1,4-dioxaspiro[4.5]decan-8-amine (3.0 g, 9.46 mmol), 37% formaldehyde in water (7.70 mL, 94.60 mmol) and acetic acid (0.05 mL) in methanol (30 mL) at 0° C. The reaction mixture was stirred at RT for 16 h. The reaction mixture was concentrated in vacuo and to the residue sat. aq. NaHCO₃ was added. The organic product was extracted with DCM (3×30 mL). The combined organic extracts were dried over anhydrous Na₂SO₄ and solvent was concentrated under reduced pressure. The resulting residue was purified by column chromatography (silica gel 230-400 mesh; 5-6% MeOH in DCM) to yield 2.50 g (83%) of N-methyl-8-phenyl-N-((tetrahydrofuran-3-yl)methyl)-1,4-dioxaspiro[4.5]decan-8-amine as a semi solid (TLC system: 10% MeOH in DCM; Rf: 0.25).

Step 6: 4-(methyl((tetrahydrofuran-3-yl)methyl)amino)-4-phenylcyclohexanone

5% sulfuric acid in water (25 mL) was added to N-methyl-8-phenyl-N-((tetrahydrofuran-3-yl)methyl)-1,4-dioxaspiro[4.5]decan-8-amine (2.50 g, 7.55 mmol) at 0° C. and the resulting mixture was stirred at RT for 24 h. The reaction mixture was quenched with sat. aq. NaHCO₃ and the organic product was extracted with DCM (2×50 mL). The combined organic layers were dried over anhydrous Na₂SO₄ and concentrated in vacuo to afford 2.0 g (crude) of 4-(methyl((tetrahydrofuran-3-yl)methyl)amino)-4-phenylcyclohexanone as a thick liquid (TLC system: 10% MeOH in DCM, Rf: 0.20).

Step 7: 8-(methyl((tetrahydrofuran-3-yl)methyl)amino)-8-phenyl-1,3-diazaspiro[4.5]decane-2,4-dione 4-(methyl((tetrahydrofuran-3-yl)methyl)amino)-4-phenylcyclohexanone (1.50 g, 5.22 mmol) was suspended in 30 mL of EtOH:H₂O (1:1 v/v) at RT under argon atmosphere. (NH₄)₂CO₃ (1.9 g, 13.05 mmol) and KCN (0.34 g, 5.22 mmol) were added. The reaction mixture was heated to 70° C. for 16 h. The reaction mixture was diluted with ice-water and the organic product was extracted with DCM (2×50 mL). The combined organic layer was dried over anhydrous Na₂SO₄ and concentrated in vacuo to give 1.0 g (crude) of 8-(methyl((tetrahydrofuran-3-yl)methyl)amino)-8-phenyl-1,3-diazaspiro[4.5]decane-2,4-dione as a solid (TLC system: 70% Ethyl acetate in hexane; Rf: 0.18).

Step 8: CIS-8-(methyl((tetrahydrofuran-3-yl)methyl)amino)-8-phenyl-1,3-diazaspiro[4.5]decane-2,4-dione Diastereomeric mixture of 8-(methyl((tetrahydrofuran-3-yl)methyl)amino)-8-phenyl-1,3-diazaspiro[4.5]decane-2,4-dione (1.0 g) was separated by reverse phase preparative HPLC to afford 400 mg of isomer 1 (CIS-8-(methyl((tetrahydrofuran-3-yl)methyl)amino)-8-phenyl-1,3-diazaspiro[4.5]decane-2,4-dione) and 60 mg of isomer 2 (TRANS-8-(methyl((tetrahydrofuran-3-yl)methyl)amino)-8-phenyl-1,3-diazaspiro[4.5]decane-2,4-dione) and 300 mg of mixture of both isomers. Reverse phase preparative HPLC conditions: mobile phase: 10 mM ammonium bicarbonate in H₂O/acetonitrile, column: X-BRIDGE-C18 (150*30), 5 µm, gradient (T/B %): 0/35, 8/55, 8.1/98, 10/98, 10.1/35, 13/35, flow rate: 25 ml/min, diluent: mobile phase+ THF.

Step 9: CIS-8-(methyl((tetrahydrofuran-3-yl)methyl)amino)-8-phenyl-1,3-diazaspiro[4.5]decan-2-one (INT-1026)

LiAlH₄ (1M in THF) (4.48 mL, 4.48 mmol) was added to a solution of CIS-8-(methyl((tetrahydrofuran-3-yl)methyl)amino)-8-phenyl-1,3-diazaspiro[4.5]decane-2,4-dione (isomer-1) (0.4 g, 1.12 mmol) in THF:Et₂O (2:1 v/v, 15 mL) at 0° C. under argon atmosphere. The reaction mixture was stirred at 65° C. for 16 h. The mixture was cooled to 0° C., quenched with sat. aq. Na₂SO₄ (1000 mL) and filtered through celite pad. The filtrate was dried over anhydrous Na₂SO₄ and concentrated in vacuo. The residue was purified by column chromatography (silica gel 230-400 mesh; 5-6% MeOH in DCM) to yield 0.3 g (78%) of CIS-8-(methyl((tetrahydrofuran-3-yl)methyl)amino)-8-phenyl-1,3-diazaspiro[4.5]decan-2-one (INT-1026) as an off white solid. (TLC system: 10% MeOH in DCM, Rf: 0.2). LC-MS: m/z [M+1]⁺=344.2.

Synthesis of INT-1031: CIS-1-(Cyclobutyl-methyl)-8-dimethylamino-8-(3-fluorophenyl)-1,3-diazaspiro[4.5]decan-2-one

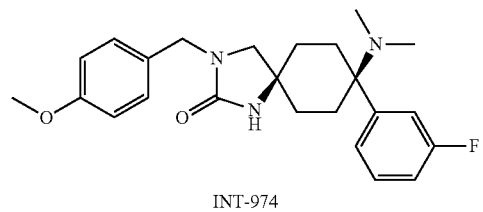

INT-974

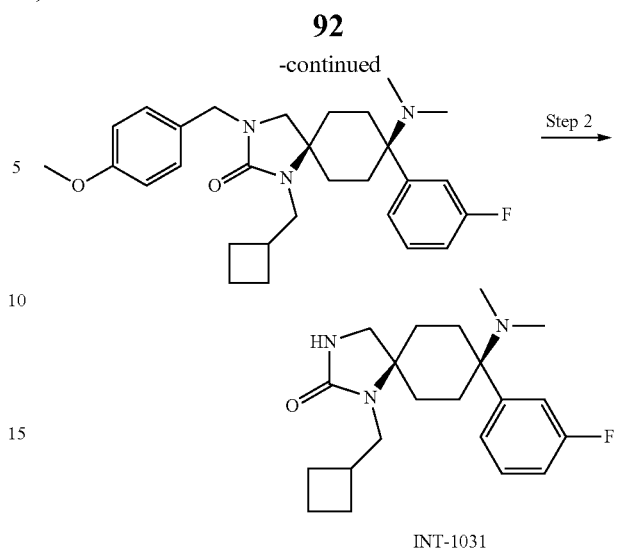

INT-1031

Step 1: CIS-1-(Cyclobutyl-methyl)-8-dimethylamino-8-(3-fluorophenyl)-3-[(4-methoxyphenyl)-methyl]-1,3-diazaspiro[4.5]decan-2-one In analogy to the method described for INT-952 CIS-8-dimethylamino-8-(3-fluorophenyl)-3-[(4-methoxyphenyl)-methyl]-1,3-diazaspiro[4.5]decan-2-one (INT-974) was converted into CIS-1-(cyclobutyl-methyl)-8-dimethylamino-8-(3-fluorophenyl)-3-[(4-methoxyphenyl)-methyl]-1,3-diazaspiro[4.5]decan-2-one.

Step 2: CIS-1-(Cyclobutyl-methyl)-8-dimethylamino-8-(3-fluorophenyl)-1,3-diazaspiro[4.5] decan-2-one In analogy to the method described for INT-982 step 2 1-(cyclobutyl-methyl)-8-dimethylamino-8-(3-fluorophenyl)-3-[(4-methoxyphenyl)-methyl]-1,3-diazaspiro[4.5]decan-2-one was converted into 1-(cyclobutyl-methyl)-8-dimethylamino-8-(3-fluorophenyl)-1,3-diazaspiro[4.5]decan-2-one (INT-1031).

Synthesis of INT-1032: CIS-2-[1-(cyclobutylmethyl)-8-(dimethylamino)-8-(3-fluorophenyl)-2-oxo-1,3-diazaspiro[4.5]decan-3-yl]acetic acid trifluoroacetate

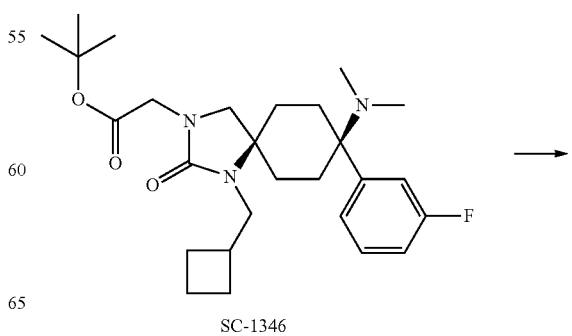

SC-1346

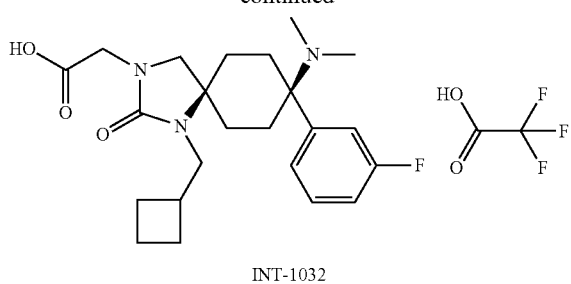

INT-1032

In analogy to the method described for INT-998 step 2 2-[1-(cyclobutyl-methyl)-8-dimethylamino-8-(3-fluorophenyl)-2-oxo-1,3-diazaspiro[4.5]decan-3-yl]-acetic acid tert-butyl ester (SC_1346) was converted into 2-[1-(cyclobutyl-methyl)-8-(dimethylamino)-8-(3-fluorophenyl)-2-oxo-1,3-diazaspiro[4.5]decan-3-yl]acetic acid trifluoroacetate (INT-10322).

Synthesis of INT-1034: CIS-(8-methylamino-2-oxo-8-phenyl-1,3-diaza-spiro[4.5]dec-3-yl)-acetic Acid

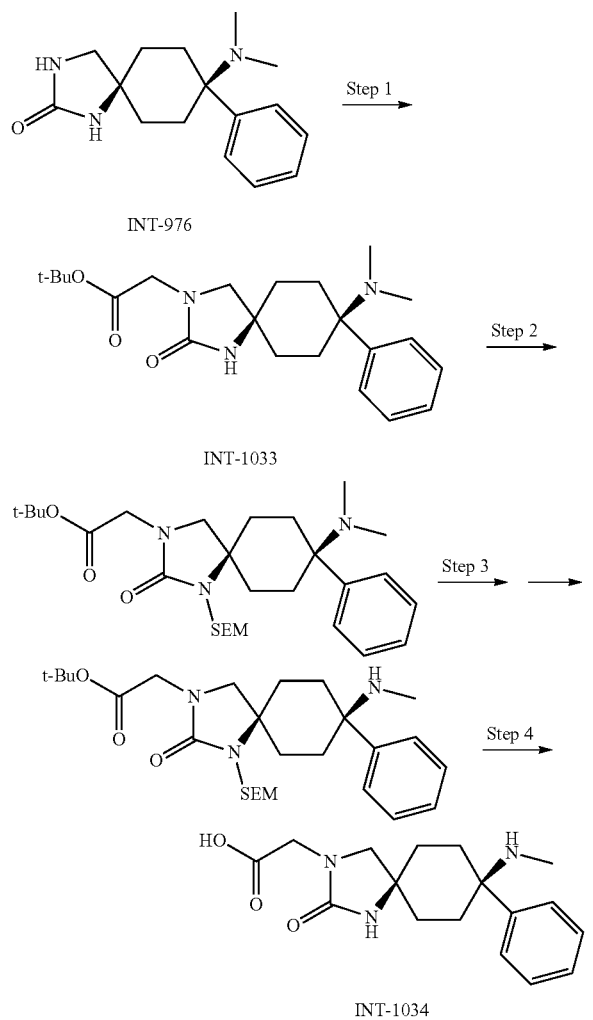

Step 1: CIS-[8-dimethylamino-2-oxo-8-phenyl-1-(2-trimethylsilanyl-ethoxymethyl)-1,3-diaza-spiro[4.5]dec-3-yl]-acetic Acid Tert-Butyl Ester In analogy to the method described for INT-988 Step 1 CIS-8-dimethylamino-8-phenyl-1,3-diaza-spiro[4.5]decan-2-one (INT-967) was converted into CIS-[8-dimethylamino-2-oxo-8-phenyl-1-(2-trimethylsilanyl-ethoxymethyl)-1,3-diaza-spiro[4.5]dec-3-yl]-acetic acid tert-butyl ester (INT-1033). LC-MS: m/z $[M+H]^+=388.3$

Step 2: CIS-[8-dimethylamino-2-oxo-8-phenyl-1l-(2-trimethylsilanyl-ethoxymethyl)-1,3-diaza-spiro[4.5]dec-3-yl]-acetic Acid Tert-Butyl Ester To a suspension of CIS-(8-dimethylamino-2-oxo-8-phenyl-1,3-diaza-spiro[4.5]dec-3-yl)-acetic acid tert-butyl ester (INT-1033) (8.1 g, 20.90 mmol, 1.0 eq.) in DMF (300 mL) was added NaH (603 mg, 25.11 mmol, 1.2 eq.) at RT and the reaction mixture was stirred for 40 min. Trimethylsilylethoxymethyl chloride (SEMCl) was added (4.06 ml, 23.02 mmol, 1.1 eq). The resulting mixture was stirred at RT for 16 h, then diluted with ice-water (100 mL) and extracted with ethyl acetate (2×500 mL). The combined organic layer was washed with water (150 mL), brine (200 mL), dried over $Na_2SO_4$ and concentrated under reduced pressure. The resulting crude product was purified by column chromatography (silica gel, 30% ethyl acetate/hexane) to yield CIS-[8-dimethylamino-2-oxo-8-phenyl-1-(2-trimethylsilanyl-ethoxymethyl)-1,3-diaza-spiro[4.5]dec-3-yl]-acetic acid tert-butyl ester (4.0 g, 7.736 mmol, 37%) as a light yellow dense sticky liquid. LC-MS: m/z $[M+H]^+=518.3$

Step 3: CIS-[8-methylamino-2-oxo-8-phenyl-1l-(2-trimethylsilanyl-ethoxymethyl)-1,3-diaza-spiro[4.5]dec-3-yl]-acetic Acid Tert-Butyl Ester In analogy to the method described for INT-986 Step 1 CIS-[8-dimethylamino-2-oxo-8-phenyl-1-(2-trimethylsilanyl-ethoxymethyl)-1,3-diaza-spiro[4.5]dec-3-yl]-acetic acid tert-butyl ester was converted into CIS-[8-methylamino-2-oxo-8-phenyl-1l-(2-trimethylsilanyl-ethoxymethyl)-1,3-diaza-spiro[4.5]dec-3-yl]-acetic acid tert-butyl ester. LC-MS: m/z $[M+H]^+=504.2$

Step 4: CIS-(8-methylamino-2-oxo-8-phenyl-1,3-diaza-spiro[4.5]dec-3-yl)-acetic Acid (INT-1034)

To a solution of CIS-[8-methylamino-2-oxo-8-phenyl-1-(2-trimethylsilanyl-ethoxymethyl)-1,3-diaza-spiro[4.5]dec-3-yl]-acetic acid tert-butyl ester (1.6 g, 3.180 mmol, 1.0 eq.) in MeOH (48 mL) was added 2N aq. HCl (48 mL) and the mixture was stirred at RT for 16 h. The reaction mixture concentrated under reduced pressure, diluted with MeOH (40 mL), basified with 1M aq. LiOH (pH~12) and stirred at RT for 16 h. The reaction mixture was concentrated under reduced pressure and acidified to pH~6 with aq. $NaHSO_4$. The reaction mixture was extracted with 20% MeOH/DCM (5×200 ml). The combined organic layer was dried over anhydr. $Na_2SO_4$ and concentrated under reduced pressure to yield CIS-(8-methylamino-2-oxo-8-phenyl-1,3-diaza-spiro[4.5]dec-3-yl)-acetic acid (INT-1034) (850 mg, 0.681 mmol, 84%) as an off white solid. The product was used in the next step without further purification. LC-MS: m/z $[M+H]^+=318.2$

Synthesis of INT-1035: CIS-(8-dimethylamino-1-oxetan-3-ylmethyl-2-oxo-8-phenyl-1,3-diaza-spiro[4.5]dec-3-yl)-acetic Acid

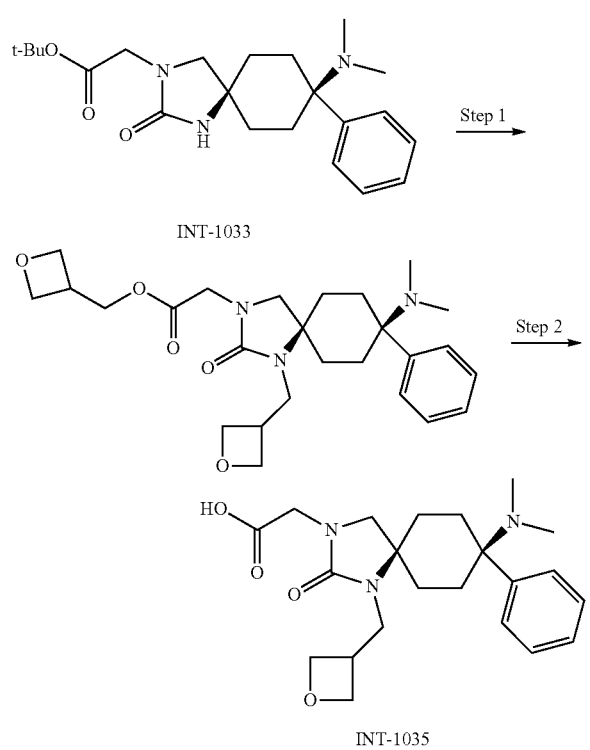

Step 1: CIS-(8-dimethylamino-1-oxetan-3-ylmethyl-2-oxo-8-phenyl-1,3-diaza-spiro[4.5]dec-3-yl)-acetic Acid oxetan-3-ylmethyl Ester In analogy to the method described for INT-986 Step 1 CIS-(8-dimethylamino-2-oxo-8-phenyl-1,3-diaza-spiro[4.5]dec-3-yl)-acetic acid tert-butyl ester (INT-1033) was converted into CIS-(8-dimethylamino-1-oxetan-3-ylmethyl-2-oxo-8-phenyl-1,3-diaza-spiro[4.5]dec-3-yl)-acetic acid oxetan-3-ylmethyl ester.

Step 2: CIS-(8-dimethylamino-1-oxetan-3-ylmethyl-2-oxo-8-phenyl-1,3-diaza-spiro[4.5]dec-3-yl)-acetic acid (INT-1035)

Synthesis of INT-1037: 8-(dimethylamino)-2-oxo-1,3-diazaspiro[4.5]decane-8-carbonitrile

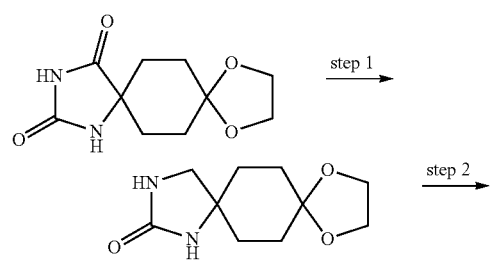

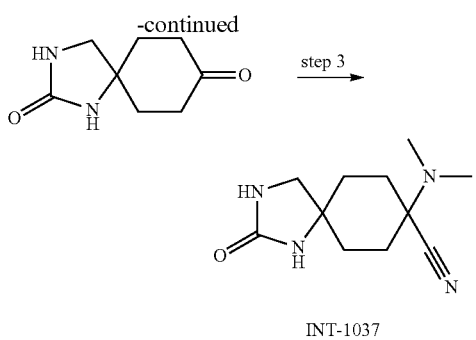

Step 1: 9,12-dioxa-2,4-diazadispiro[4.2.4^{8}.2^{5}]tetradecan-3-one

Lithiumaluminiumhydride (2.2 equiv., 292 mmol) was suspended in THF (400 mL) and the suspension was cooled to 0° C. 8-(Dimethylamino)-8-(m-tolyl)-1,3-diazaspiro[4.5]decan-2-one (B, 75 mg, 0,261 mmol) (step 1 of INT-965) was added portionwise at 0° C. The reaction mixture was stirred 1.5 h at 0° C., then overnight at RT and then 2 h at 40° C. The reaction mixture was cooled down to 0° C., quenched carefully with sat. aq. $Na_2SO_4$, EtOAc (400 mL) was added and the resulting mixture was stirred for 2 h and then left without stirring for 2 h at RT. The precipitate was filtered off and washed with EtOAc and MeOH. The resulting solid residue was suspended in methanol and stirred at RT overnight. The precipitate was filtered off and disposed. The filtrate was concentrated under reduced pressure, the residue was suspended thoroughly in water (50 mL) at 40° C., the precipitate was filtered off and dried under reduced pressure to yield 9,12-dioxa-2,4-diazadispiro[4.2.4^{8}.2^{5}]tetradecan-3-one (11.4 g, 41%). Mass: m/z 213.2 $(M+H)^+$.

Step 2: 1,3-diazaspiro[4.5]decane-2,8-dione

In analogy to the method described for INT-1003 step 3 9,12-dioxa-2,4-diazadispiro[4.2.4^{8}.2^{5}]tetradecan-3-one was treated with conc. aq. HCl to be converted into 1,3-diazaspiro[4.5]decane-2,8-dione. Mass: m/z 169.1 $(M+H)^+$.

Step 3: 8-(dimethylamino)-2-oxo-1,3-diazaspiro[4.5]decane-8-carbonitrile (INT-1037)

In analogy to the method described for INT-965 step 1 1,3-diazaspiro[4.5]decane-2,8-dione was treated with dimethyl amine and potassium cyanide to be converted into 8-(dimethylamino)-2-oxo-1,3-diazaspiro[4.5]decane-8-carbonitrile (INT-1037). Mass: m/z 223.2 $(M+H)^+$.

Synthesis of INT-1038: CIS-8-(dimethylamino)-8-(m-tolyl)-1,3-diazaspiro[4.5]decan-2-one

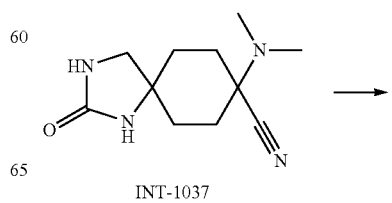

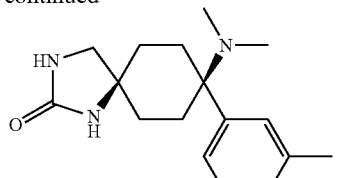

INT-1038

To the suspension of 8-(dimethylamino)-2-oxo-1,3-diazaspiro[4.5]decane-8-carbonitrile (200 mg, 0.90 mmol) in THF (4 mL) at RT was added dropwise 1M bromo(m-tolyl) magnesium in THF (4 equiv., 3.6 mmol, 3.6 mL) and the reaction mixture was stirred for 1 h at RT. Additional portion of 1M bromo(m-tolyl)magnesium in THF (1 equiv., 0.8 mL) was added. The reaction mixture was stirred at RT overnight, then quenched with methanol/water. Solid $NH_4Cl$ and DCM were added to the resulting mixture and the precipitate was filtered off. The organic phase of the filtrate was separated and the aqueous phase was extracted with DCM (3×). The combined organic phases were dried over anhydr. $Na_2SO_4$ and concentrated under reduced pressure. The residue was purified by flash chromatography on silica gel (DCM/MeOH, 100/0 to 65/35) to yield CIS-8-(dimethylamino)-8-(m-tolyl)-1,3-diazaspiro[4.5]decan-2-one (INT-1038) (81 mg, 31%). Mass: m/z 288.2 (M+H)$^+$.

Synthesis of INT-1059: TRANS-8-(dimethylamino)-8-phenyl-1,3-diazaspiro[4.5]decan-2-one

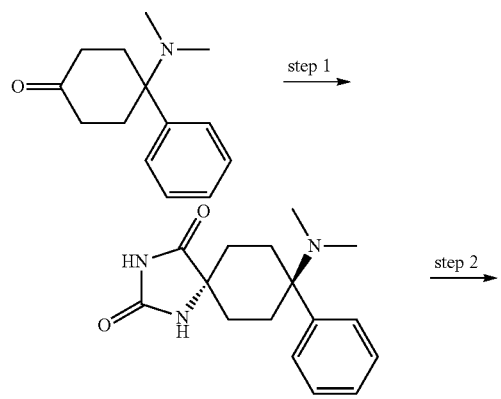

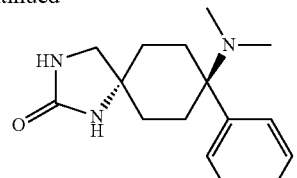

INT-1059

Step 1: TRANS-8-(dimethylamino)-8-phenyl-1,3-diazaspiro[4.5]decane-2,4-dione

To a stirred solution of 4-dimethylamino-4-phenyl-cyclohexanone (250.0 g, 1.15 mol, 1.0 eq.) in EtOH (2.5 L) and water (2.1 L) was added $(NH_4)_2CO_3$ (276.2 g, 2.87 mol, 2.5 eq.) and the reaction mixture was stirred at RT for 15 min. KCN (74.92 g, 1.15 mol, 1.0 eq.) was added. The reaction mixture was stirred at 60° C. for 18 h and then filtered in hot condition to get white solid which was washed with water (2.5 L), ethanol (1 L) and hexane (2.5 L). The resulting solid was dried under reduced pressure to get CIS-8-dimethylamino-8-phenyl-1,3-diaza-spiro[4.5]decane-2,4-dione (223 g, 0.776 mol, 65%) as a white solid. The filtrate was collected from multiple batches (~450 g) which contained a mixture of cis and trans isomers. The filtrate was concentrated under reduced pressure and solid obtained was filtered and washed with water (1 L) and hexane (1 L). Solid material was dried under reduced pressure to get ~100 g of a mixture of cis and trans (major) isomers. Crude material was partially dissolved in hot MeOH (600 mL) and cooled to RT, filtered through sintered funnel, washed with MeOH (200 mL) followed by ether (150 mL) and dried to get TRANS-8-dimethylamino-8-phenyl-1,3-diaza-spiro[4.5]decane-2,4-dione (50 g, 0.174 mmol, ~9-10%).

Step 2: TRANS-8-(dimethylamino)-8-phenyl-1,3-diazaspiro[4.5]decan-2-one (INT-1059)

In analogy to the method described for INT-976 step 2 TRANS-8-dimethylamino-8-phenyl-1,3-diaza-spiro[4.5]decane-2,4-dione was treated with $LiAlH_4$ to be converted into TRANS-8-(dimethylamino)-8-phenyl-1,3-diazaspiro[4.5]decan-2-one (INT-1059). Mass: m/z 274.2 (M+H)$^+$.

Synthesis of INT-1068 and INT-1069: CIS- and TRANS-8-(dimethylamino)-8-phenyl-1-(2,2,2-trifluoroethyl)-1,3-diazaspiro[4.5]decan-2-one

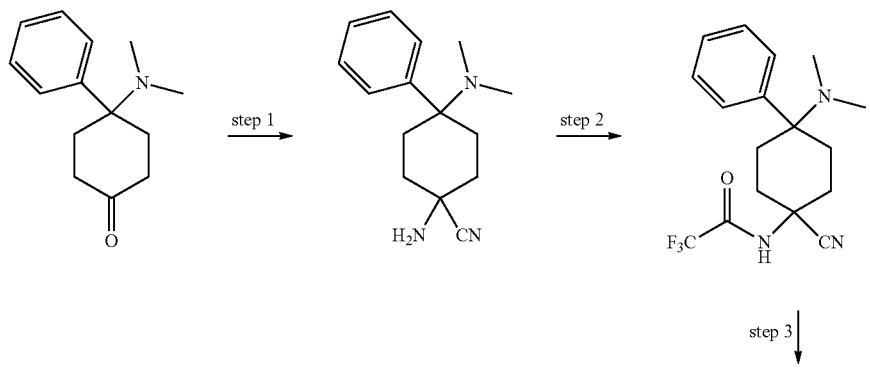

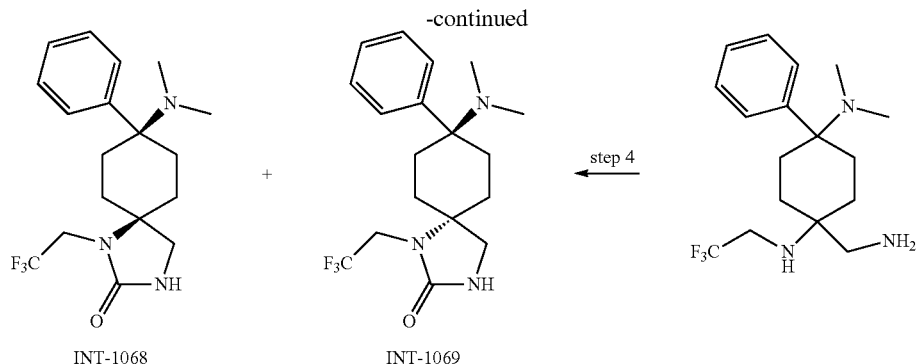

INT-1068    INT-1069

Step 1: 1-amino-4-dimethylamino-4-phenyl-cyclohexanecarbonitrile

To a stirred solution of 4-dimethylamino-4-phenyl-cyclohexanone (50 g, 230.096 mmol) in MeOH (400 mL) was added $NH_4Cl$ (24.6 g, 460.8 mmol) followed by $NH_4OH$ (400 mL) at RT and the reaction mixture was stirred for 15 min. NaCN (22.5 g, 460.83 mmol) was added and the resulting mixture was stirred for 16 h at RT. The reaction mixture was extracted with DCM (3×750 mL). Combined organic layer was washed with water (750 mL), brine (750 mL), dried over $Na_2SO_4$ and concentrated under reduced pressure. The residue was triturated with DCM/hexane to get crude 1-amino-4-dimethylamino-4-phenyl-cyclohexanecarbonitrile (50 g, 90%) as an off white solid which was used in next step without further purification. LC-MS: m/z $[M+H]^+$=244.2 (MW calc. 244.09).

Step 2: N-(1-cyano-4-dimethylamino-4-phenyl-cyclohexyl)-2,2,2-trifluoroacetamide To a solution of 1-amino-4-dimethylamino-4-phenyl-cyclohexanecarbonitrile (5.0 g, 20.57 mmol, 1.0 eq.) in THF (100 ml) were added DIPEA (10.72 ml, 61.71 mmol, 3.0 eq), trifluoroacetic acid (1.89 ml, 24.69 mmol, 1.2 eq) and T3P (18.2 ml, 30.85 mmol, 1.5 eq) at 0° C. The reaction mixture was stirred at RT for 16 h, then diluted with water (100 ml) and extracted with 10% MeOH in DCM (2×250 mL). Combined organic layer was washed with brine (100 mL), dried over $Na_2SO_4$ and concentrated under reduced pressure to get crude N-(1-cyano-4-dimethylamino-4-phenyl-cyclohexyl)-2,2,2-trifluoroacetamide as a light yellow sticky material which was used in the next step without further purification. LC-MS: m/z $[M+1]^+$=339.9 (MW calc. 339.36).

Step 3: 1-aminomethyl-N',N'-dimethyl-4-phenyl-N-(2,2,2-trifluoroethyl)cyclohexane-1,4-diamine To suspension of $LiAlH_4$ (4.03 g, 106.19 mmol, 6.0 eq.) in dry THF (40 mL) was added N-(1-cyano-4-dimethylamino-4-phenyl-cyclohexyl)-2,2,2-trifluoro-acetamide (6.0 g, 17.69 mmol, 1.0 eq.) in dry THF (100 mL) dropwise at 0° C. The reaction mixture was stirred at RT for 16 h, then quenched with sat. aq. $Na_2SO_4$ at 0° C., excess THF was added and the resulting mixture was stirred at RT for 2 h. The resulting suspension was filtered through celite and the filter cake was washed with 10% MeOH in DCM (150 mL). Combined filtrate was concentrated under reduced pressure to yield crude 1-aminomethyl-N',N'-dimethyl-4-phenyl-N-(2,2,2-trifluoro-ethyl)-cyclohexane-1,4-diamine (4.2 g, crude) as a light yellow sticky material which was directly used in the next step without further purification. LC-MS: m/z $[M+1]^+$=330.0 (MW calc. 329.40).

Step 4: CIS- and TRANS-8-dimethylamino-8-phenyl-1-(2,2,2-trifluoro-ethyl)-1,3-diaza-spiro[4.5]decan-2-one (INT-1068 and INT-1069)

To a solution of 1-aminomethyl-N',N'-dimethyl-4-phenyl-N-(2,2,2-trifluoro-ethyl)-cyclohexane-1,4-diamine (4.2 g, 12.76 mmol, 1.0 eq.) in toluene (60 ml) was added KOH (4.29 g, 76.56 mmol, 6.0 eq.) in water (120 ml) at 0° C. followed by addition of $COCl_2$ (15.6 ml, 44.66 mmol, 3.5 eq., 20% in toluene) at 0° C. and stirred at RT for 16 h. Reaction mixture was basified with sat $NaHCO_3$ solution and extracted with DCM (2×200 ml). Combined organic layer was dried over $Na_2SO_4$ and concentrated under reduced pressure to get crude product which was purified by prep HPLC to get CIS-8-dimethylamino-8-phenyl-1-(2,2,2-trifluoro-ethyl)-1,3-diaza-spiro[4.5]decan-2-one (INT-1068) (1.5 g) (major isomer, polar spot on TLC) and TRANS-8-dimethylamino-8-phenyl-1-(2,2,2-trifluoro-ethyl)-1,3-diaza-spiro[4.5]decan-2-one (INT-1069) as minor isomer (non-polar spot on TLC) (120 mg, 92.93% by HPLC) as off-white solids. CIS-isomer: LC-MS: m/z $[M+1]^+$=356.2 (MW calc.=355.40). HPLC: 98.53%, Column: Xbridge C-18 (100×4.6), 5 µ, Diluent: MeOH, Mobile phase: A) 0.05% TFA in water; B) ACN flow rate: 1 ml/min, Rt=5.17 min. $^1$HNMR (DMSO-$d_6$, 400 MHz), δ (ppm)=7.43-7.27 (m, 5H), 6.84 (s, 1H), 3.30-3.25 (m, 4H), 2.66-2.63 (d, 2H, J=12.72 Hz), 1.89 (s, 6H), 1.58-1.51 (m, 2H), 1.46-1.43 (m, 2H), 1.33-1.23 (m, 2H).

To a solution of CIS-(8-dimethylamino-1-oxetan-3-ylmethyl-2-oxo-8-phenyl-1,3-diaza-spiro[4.5]dec-3-yl)-acetic acid oxetan-3-ylmethyl ester (300 mg, 0.636 mmol, 1.0 eq.) in $THF/H_2O$ (8 mL, 1.5:1) was added LiOH (160 mg, 3.821 mmol, 6.0 eq.). The reaction mixture was stirred at RT for 16 h, concentrated under reduced pressure, neutralized with aq. $NaHSO_4$ to pH~6 and extracted with 5% MeOH/DCM (3×200 mL). the combined organic extract was dried over $Na_2SO_4$ and concentrated under reduced pressure. The residue was triturated with 15% DCM-Hexane to yield CIS-(8-dimethylamino-1-oxetan-3-ylmethyl-2-oxo-8-phenyl-1,3-diaza-spiro[4.5]dec-3-yl)-acetic acid (INT-1035) (210 mg, 0.523 mmol, 82%) as an off-white solid.

For further intermediates the synthesis in analogy to previously described methods is given in the following table. The syntheses of the building blocks and intermediates have either been described previously within this application or can be performed in analogy to the herein described methods or by methods known to the person, skilled in the art. Such a person will also know which building blocks and intermediates need to be chosen for synthesis of each exemplary compound.

| Intermediate | Chemical Name | Chemical structure | in analogy to method | m/z [M + H]+ |
|---|---|---|---|---|
| INT-241 | CIS-8-(dimethylamino)-1-isobutyl-8-phenyl-1,3-diazaspiro[4.5]decan-2-one | 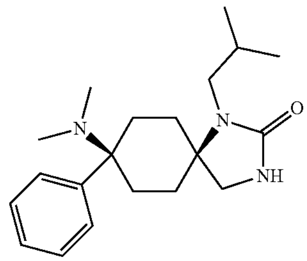 [SMILES: CC(C)CN1C(=O)NC[C@]12CC[C@](c1ccccc1)(N(C)C)CC2] | INT-982 | 330.3 |
| INT-794 | CIS-3-(3,4-dimethoxybenzyl)-8-(dimethylamino)-8-phenyl-1,3-diazaspiro[4.5]decan-2-one | 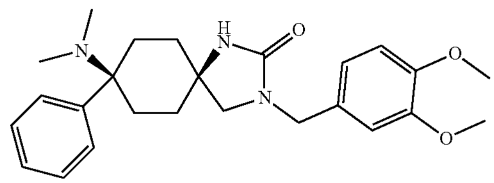 [SMILES: COc1ccc(CN2C[C@]3(CC[C@](c4ccccc4)(N(C)C)CC3)NC2=O)cc1OC] | INT-975 | 424.3 |
| INT-796 | CIS-8-Dimethylamino-3-[(4-methoxyphenyl)-methyl]-8-(3-methoxy-propyl)-1,3-diazaspiro[4.5]decan-2-one | 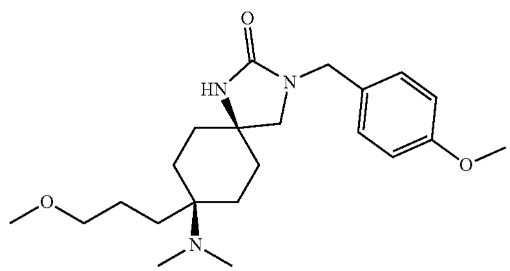 | INT-974 | 390.3 |
| INT-797 | CIS-8-(Ethyl-methyl-amino)-8-phenyl-1,3-diazaspiro[4.5]decan-2-one | 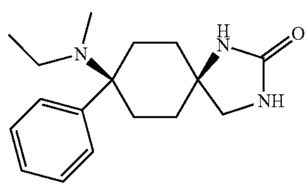 [SMILES: CCN(C)[C@]1(c2ccccc2)CC[C@]2(CC1)CNC(=O)N2] | INT-976 | 288.2 |
| INT-949 | CIS-8-Dimethylamino-1-ethyl-8-phenyl-1,3-diazaspiro[4.5]decan-2-one | 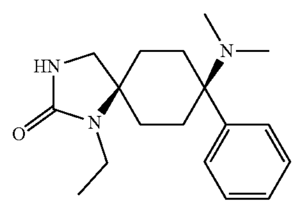 [SMILES: CCN1C(=O)NC[C@]12CC[C@](c1ccccc1)(N(C)C)CC2] | INT-984 | 302.2 |
| INT-950 | CIS-1-(Cyclobutyl-methyl)-8-dimethylamino-8-phenyl-3-[phenyl-methyl]-1,3-diazaspiro[4.5]decan-2-one | 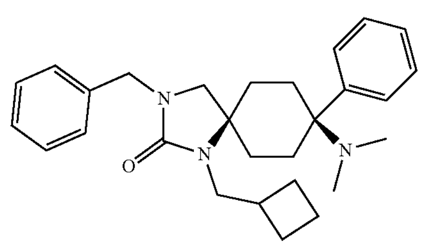 [SMILES: CN(C)[C@]1(c2ccccc2)CC[C@]2(CC1)CN(Cc1ccccc1)C(=O)N2CC1CCC1] | INT-952 | 432.3 |
| INT-954 | 4-Dimethylamino-4-(5-methyl-thiophen-2-yl)-cyclohexan-1-one | 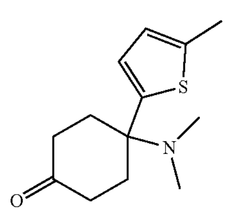 [SMILES: Cc1ccc(C2(N(C)C)CCC(=O)CC2)s1] | INT-965 | 238.1 |

-continued

| Intermediate | Chemical Name | Chemical structure | in analogy to method | m/z [M + H]+ |
|---|---|---|---|---|
| INT-955 | 4-Dimethylamino-4-thiophen-2-yl-cyclohexan-1-one | 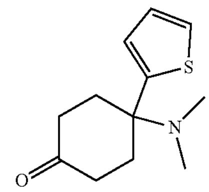 | INT-965 | 224.1 |
| INT-956 | 1-(1-Methyl-1H-pyrazol-3-yl)-4-oxo-cyclohexane-1-carbonitrile | 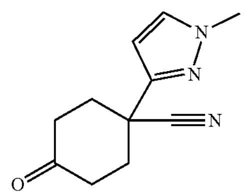 | INT-958 | 204.1 |
| INT-957 | 4-Oxo-1-pyrazin-2-yl-cyclohexane-1-carbonitrile | 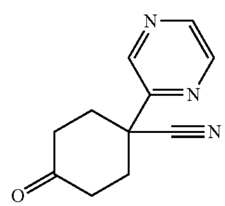 [SMILES: N#CC1(c2cnccn2)CCC(=O)CC1] | INT-958 | 202.1 |
| INT-959 | 4-Dimethylamino-4-(1-methyl-1H-pyrazol-3-yl)-cyclohexan-1-one | 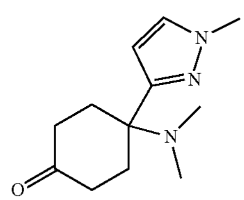 [SMILES: CN(C)C1(c2ccn(C)n2)CCC(=O)CC1] | INT-961 | 222.2 |
| INT-960 | 4-Dimethylamino-4-pyrazin-2-yl-cyclohexan-1-one | 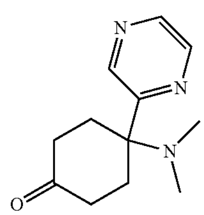 [SMILES: CN(C)C1(c2cnccn2)CCC(=O)CC1] | INT-961 | 220.1 |
| INT-962 | 4-Dimethylamino-4-(3-methoxyphenyl)-cyclohexan-1-one | 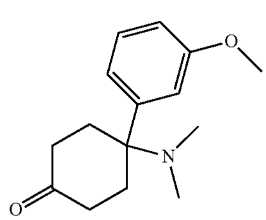 [SMILES: COc1cccc(C2(N(C)C)CCC(=O)CC2)c1] | INT-965 | 248.2 |
| INT-963 | CIS-3-Benzyl-8-dimethylamino-8-phenyl-1,3-diazaspiro[4.5]decan-2-one | 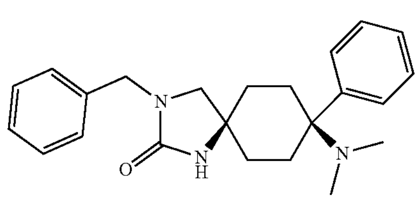 [SMILES: CN(C)[C@]1(c2ccccc2)CC[C@]2(CC1)CN(Cc1ccccc1)C(=O)N2] | INT-975 | 364.2 |

-continued

| Intermediate | Chemical Name | Chemical structure | in analogy to method | m/z [M + H]+ |
|---|---|---|---|---|
| INT-964 | 4-(Ethyl-methyl-amino)-4-phenyl-cyclohexan-1-one | 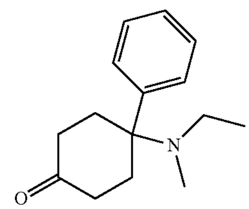 [SMILES: CCN(C)C1(c2ccccc2)CCC(=O)CC1] | INT-965 | 232.2 |
| INT-967 | CIS-8-Dimethylamino-8-[4-(methoxymethyloxy)-phenyl]-3-[(4-methoxyphenyl)-methyl]-1,3-diazaspiro[4.5]decan-2-one | 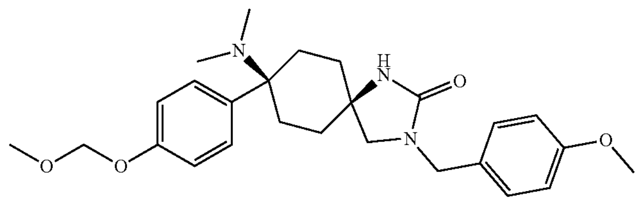 | INT-974 | 454.3 |
| INT-968 | CIS-8-Dimethylamino-8-[3-(methoxymethyloxy)-phenyl]-3-[(4-methoxyphenyl)-methyl]-1,3-diazaspiro[4.5]decan-2-one | 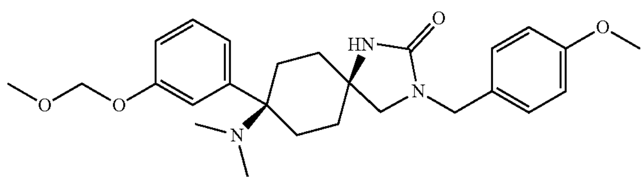 | INT-974 | 454.3 |
| INT-969 | CIS-1-(Cyclobutyl-methyl)-8-dimethylamino-8-(4-hydroxyphenyl)-3-[(4-methoxyphenyl)-methyl]-1,3-diazaspiro[4.5]decan-2-one | 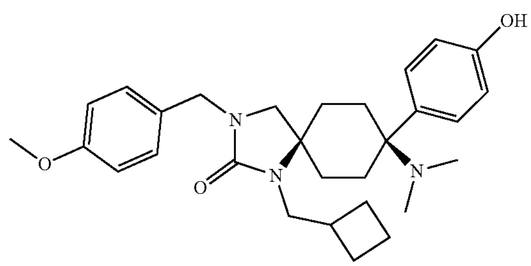 [SMILES: COc1ccc(CN2C[C@]3(CC[C@](c4ccc(O)cc4)(N(C)C)CC3)N(CC3CCC3)C2=O)cc1] | INT-971 | 478.3 |
| INT-970 | CIS-8-Dimethylamino-8-(4-methoxyphenyl)-3-[(4-methoxyphenyl)-methyl]-1,3-diazaspiro[4.5]decan-2-one | 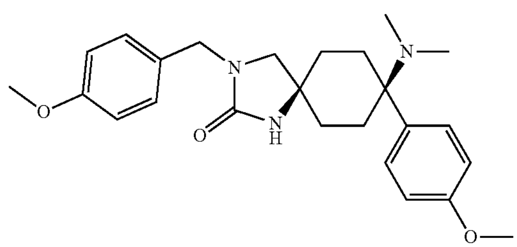 | SC_2017 | 424.3 |
| INT-972 | CIS-8-Dimethylamino-8-(3-methoxyphenyl)-3-[(4-methoxyphenyl)-methyl]-1,3-diazaspiro[4.5]decan-2-one | 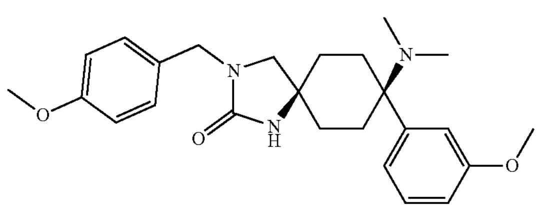 | SC_2017 | 424.3 |
| INT-973 | CIS-8-Dimethylamino-8-(4-fluorophenyl)-3-[(4-methoxyphenyl)-methyl]-1,3-diazaspiro[4.5]decan-2-one | 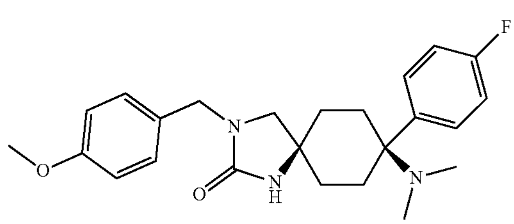 [SMILES: COc1ccc(CN2C[C@]3(CC[C@](c4ccc(F)cc4)(N(C)C)CC3)NC2=O)cc1] | INT-974 | 412.2 |

-continued

| Inter-mediate | Chemical Name | Chemical structure | in analogy to method | m/z [M + H]+ |
|---|---|---|---|---|
| INT-979 | CIS-8-Dimethylamino-1-(3-methoxy-propyl)-8-phenyl-1,3-diazaspiro[4.5]decan-2-one | 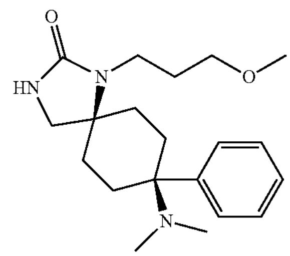 [SMILES: COCCCN1C(=O)NC[C@]12CC[C@](c1ccccc1)(N(C)C)CC2] | INT-984 | 346.2 |
| INT-980 | CIS-8-Dimethylamino-1-(2-methoxy-ethyl)-8-phenyl-1,3-diazaspiro[4.5]decan-2-one | 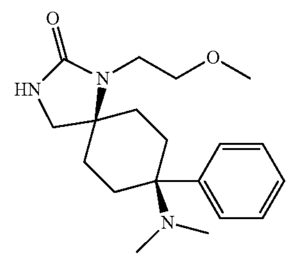 [SMILES: COCCN1C(=O)NC[C@]12CC[C@](c1ccccc1)(N(C)C)CC2] | INT-984 | 332.2 |
| INT-981 | CIS-8-Dimethylamino-8-phenyl-1-propyl-1,3-diazaspiro[4.5]decan-2-one | 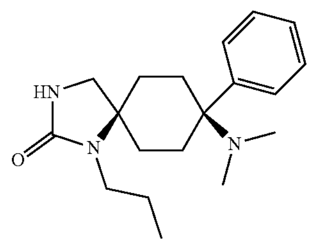 [SMILES: CCCN1C(=O)NC[C@]12CC[C@](c1ccccc1)(N(C)C)CC2] | INT-984 | 316.2 |
| INT-983 | CIS-1-(Cyclopropyl-methyl)-8-dimethylamino-8-phenyl-1,3-diazaspiro[4.5]decan-2-one | 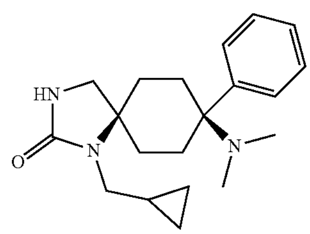 [SMILES: CN(C)[C@]1(c2ccccc2)CC[C@]2(CC1)CNC(=O)N2CC1CC1] | INT-984 | 328.2 |
| INT-985 | CIS-1-(Cyclobutyl-methyl)-8-(methyl-propyl-amino)-8-phenyl-1,3-diazaspiro[4.5]decan-2-one | 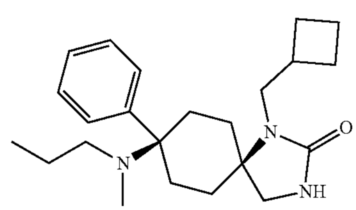 [SMILES: CCCN(C)[C@]1(c2ccccc2)CC[C@]2(CC1)CNC(=O)N2CC1CCC1] | INT-986 | 370.3 |
| INT-989 | CIS-2-[1-[(1-Cyano-cyclobutyl)-methyl]-8-dimethylamino-2-oxo-8-phenyl-1,3-diazaspiro[4.5]decan-3-yl]-acetic acid | 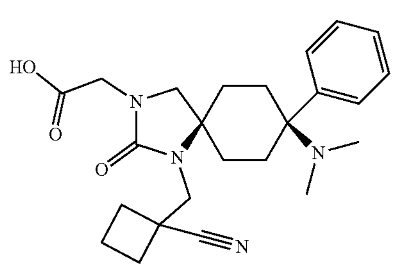 [SMILES: CN(C)[C@]1(c2ccccc2)CC[C@]2(CC1)CN(CC(=O)O)C(=O)N2CC1(C#N)CCC1] | INT-992 | 425.2 |

-continued

| Intermediate | Chemical Name | Chemical structure | in analogy to method | m/z [M + H]+ |
|---|---|---|---|---|
| INT-990 | CIS-2-[8-Dimethylamino-1-(3-methoxy-propyl)-2-oxo-8-phenyl-1,3-diazaspiro[4.5]decan-3-yl]-acetic acid | 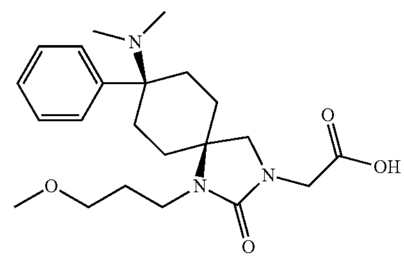 [SMILES: COCCCN1C(=O)N(CC(=O)O)C[C@]12CC[C@](c1ccccc1)(N(C)C)CC2] | INT-992 | 404.2 |
| INT-991 | CIS-2-[1-(Cyclopropyl-methyl)-8-dimethylamino-2-oxo-8-phenyl-1,3-diazaspiro[4.5]decan-3-yl]-acetic acid | 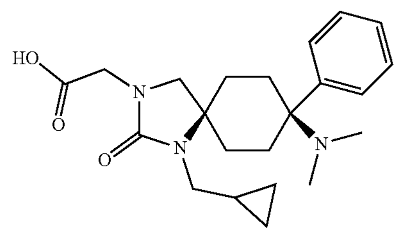 [SMILES: CN(C)[C@]1(c2ccccc2)CC[C@]2(CC1)CN(CC(=O)O)C(=O)N2CC1CC1] | INT-992 | 386.2 |
| INT-993 | CIS-2-[1-(Cyclobutyl-methyl)-8-dimethylamino-2-oxo-8-phenyl-1,3-diazaspiro[4.5]decan-3-yl]-acetic acid | 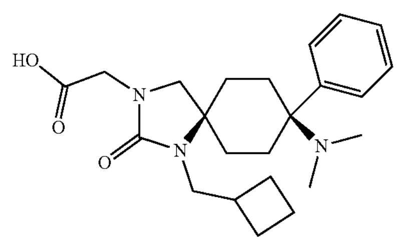 [SMILES: CN(C)[C@]1(c2ccccc2)CC[C@]2(CC1)CN(CC(=O)O)C(=O)N2CC1CCC1] | INT-992 | 400.3 |
| INT-995 | CIS-2-(8-Dimethylamino-2-oxo-8-phenyl-1-propyl-1,3-diazaspiro[4.5]decan-3-yl)-acetic acid | 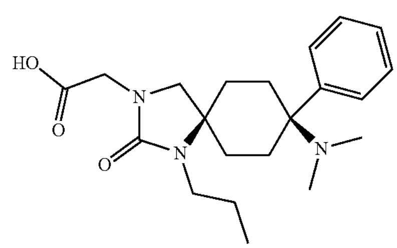 [SMILES: CCCN1C(=O)N(CC(=O)O)C[C@]12CC[C@](c1ccccc1)(N(C)C)CC2] | INT-992 | 374.2 |
| INT-996 | CIS-2-[8-Dimethylamino-1-[(dimethyl-carbamoyl)-methyl]-2-oxo-8-phenyl-1,3-diazaspiro[4.5]decan-3-yl]-acetic acid; 2,2,2-trifluoro-acetic acid salt | 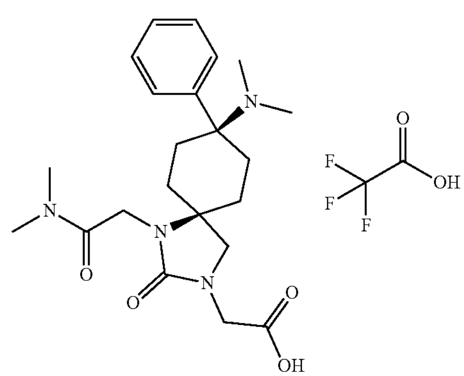 | INT-998 | 417.2 |

-continued

| Intermediate | Chemical Name | Chemical structure | in analogy to method | m/z [M + H]+ |
|---|---|---|---|---|
| INT-997 | CIS-2-[8-Dimethylamino-1-(2-methoxy-ethyl)-2-oxo-8-phenyl-1,3-diazaspiro[4.5]decan-3-yl]-acetic acid; 2,2,2-trifluoro-acetic acid | 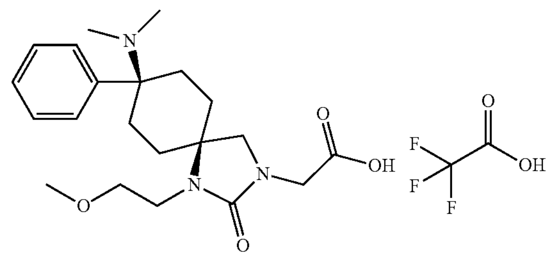 | INT-998 | 390.2 |
| INT-999 | CIS-2-[1-(Cyclobutyl-methyl)-8-dimethylamino-2-oxo-8-phenyl-1,3-diazaspiro[4.5]decan-3-yl]-acetic acid; 2,2,2-trifluoro-acetic acid salt | 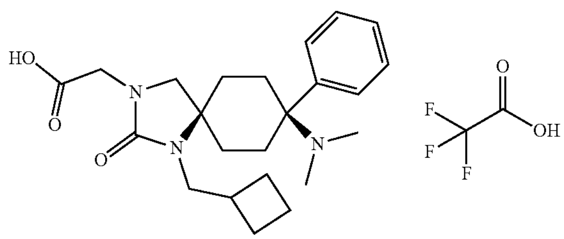 [SMILES: CN(C)[C@]1(c2ccccc2)CC[C@]2(CC1)CN(CC(=O)O)C(=O)N2CC1CCC1 ; O=C(O)C(F)(F)F] | INT-998 | 400.3 |
| INT-1000 | 4-benzyl-4-(dimethylamino)cyclohexanone | 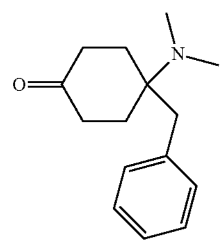 [SMILES: CN(C)C1(Cc2ccccc2)CCC(=O)CC1] | INT-965 | 232.3 |
| INT-1001 | CIS-8-benzyl-8-(dimethylamino)-1,3-diazaspiro[4.5]decan-2-one | 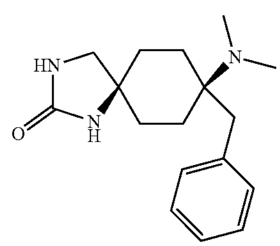 [SMILES: CN(C)[C@]1(Cc2ccccc2)CC[C@]2(CC1)CNC(=O)N2] | INT-976 | 288.2 |
| INT-1002 | TRANS-8-benzyl-8-(dimethylamino)-1,3-diazaspiro[4.5]decan-2-one | 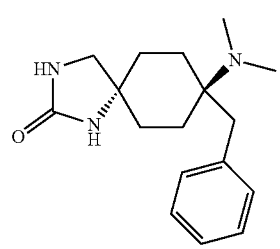 [SMILES: CN(C)[C@]1(Cc2ccccc2)CC[C@@]2(CC1)CNC(=O)N2] | INT-976 | 288.2 |
| INT-1009 | CIS-8-(dimethylamino)-8-(thiophen-2-yl)-1,3-diazaspiro[4.5]decan-2-one | 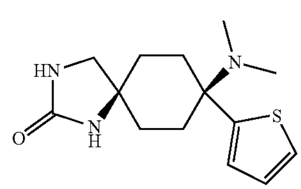 [SMILES: CN(C)[C@]1(c2cccs2)CC[C@]2(CC1)CNC(=O)N2] | INT-976 | 280.1 |

-continued

| Intermediate | Chemical Name | Chemical structure | in analogy to method | m/z [M + H]+ |
|---|---|---|---|---|
| INT-1010 | TRANS-8-(dimethylamino)-8-(thiophen-2-yl)-1,3-diazaspiro[4.5]decan-2-one | 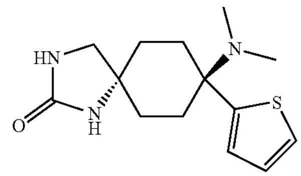 [SMILES: CN(C)[C@]1(c2cccs2)CC[C@@]2(CC1)CNC(=O)N2] | INT-976 | 280.1 |
| INT-1011 | 4-(dimethylamino)-4-(1-methyl-1H-benzo[d]imidazol-2-yl)cyclohexanone | 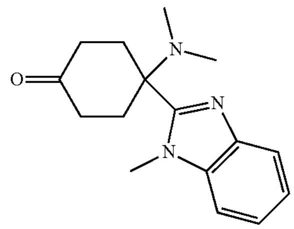 [SMILES: CN(C)C1(c2nc3ccccc3n2C)CCC(=O)CC1] | INT-965 | 272.2 |
| INT-1012 | CIS-8-(dimethylamino)-8-(1-methyl-1H-benzo[d]imidazol-2-yl)-1,3-diazaspiro[4.5]decan-2-one | 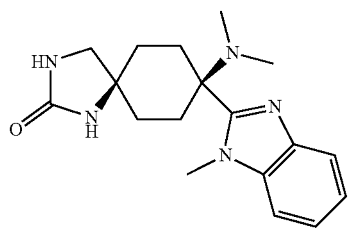 [SMILES: Cn1c2ccccc2nc1[C@]1(N(C)C)CC[C@@]2(CC1)CNC(=O)N2] | INT-976 | 328.2 |
| INT-1013 | TRANS-8-(dimethylamino)-8-(1-methyl-1H-benzo[d]imidazol-2-yl)-1,3-diazaspiro[4.5]decan-2-one | 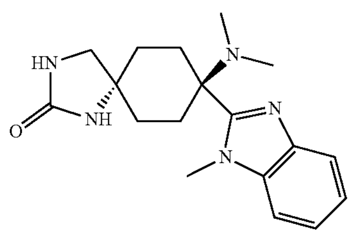 [SMILES: Cn1c2ccccc2nc1[C@]1(N(C)C)CC[C@]2(CC1)CNC(=O)N2] | INT-976 | 328.2 |
| INT-1014 | CIS-2-(8-(dimethylamino)-2-oxo-8-phenyl-1,3-diazaspiro[4.5]decan-3-yl)acetic acid trifluoroacetate salt | 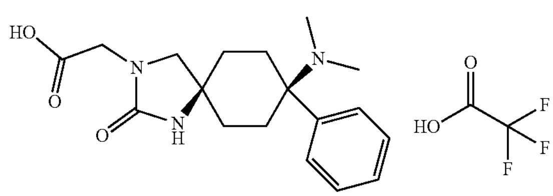 | steps 1 and 2 of INT-994 | 332.2 |
| INT-1015 | CIS-2-(8-(ethylamino)-2-oxo-8-phenyl-1,3-diazaspiro[4.5]decan-3-yl)acetic acid trifluoroacetate salt | 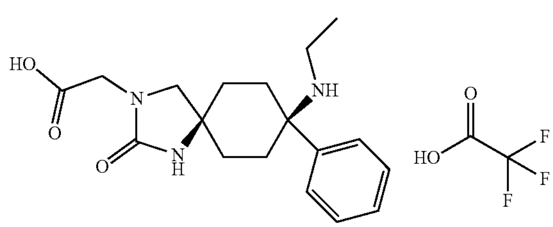 | steps 1 and 2 of INT-994 | 332.2 |
| INT-1016 | TRANS-8-(ethylamino)-8-phenyl-1,3-diazaspiro[4.5]decan-2-one | 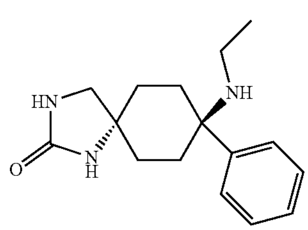 [SMILES: CCN[C@]1(c2ccccc2)CC[C@@]2(CC1)CNC(=O)N2] | INT-1008 | 274.2 |

-continued

| Intermediate | Chemical Name | Chemical structure | in analogy to method | m/z [M + H]+ |
|---|---|---|---|---|
| INT-1017 | TRANS-2-(8-(ethylamino)-2-oxo-8-phenyl-1,3-diazaspiro[4.5]decan-3-yl)acetic acid trifluoroacetate salt | 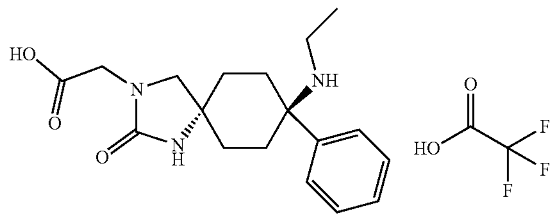 | steps 1 and 2 of INT-994 | 332.2 |
| INT-1018 | CIS-8-(dimethylamino)-8-phenyl-1,3-diazaspiro[4.5]decane-2,4-dione | 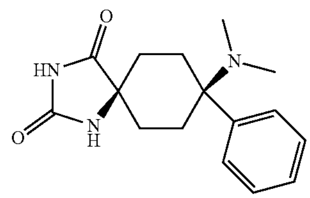 [SMILES: CN(C)[C@]1(c2ccccc2)CC[C@@]2(CC1)NC(=O)NC2=O] | INT-976 | 288.2 |
| INT-1024 | CIS-8-(dimethylamino)-8-(3-fluorophenyl)-1,3-diazaspiro[4.5]decan-2-one | 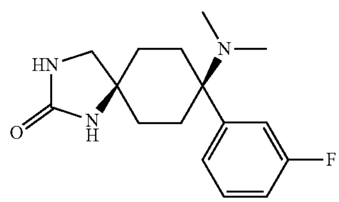 [SMILES: CN(C)[C@]1(c2cccc(F)c2)CC[C@]2(CC1)CNC(=O)N2] | INT-977 (step 2) | 292.2 |
| INT-1025 | CIS-8-(dimethylamino)-8-(4-fluorophenyl)-1,3-diazaspiro[4.5]decan-2-one | 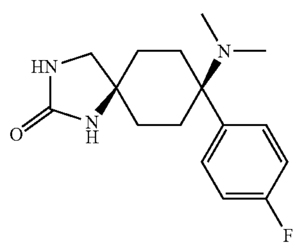 [SMILES: CN(C)[C@]1(c2ccc(F)cc2)CC[C@]2(CC1)CNC(=O)N2] | INT-974, INT-977 (step 2) | 292.2 |
| INT-1039 | CIS-8-(dimethylamino)-8-(3-(trifluoromethoxy)phenyl)-1,3-diazaspiro[4.5]decan-2-one | 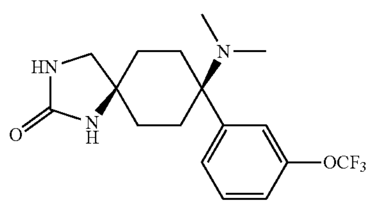 [SMILES: CN(C)[C@]1(c2cccc(OC(F)(F)F)c2)CC[C@]2(CC1)CNC(=O)N2] | INT-1038 | 358.2 |
| INT-1040 | (CIS)-8-(dimethylamino)-8-(3-(trifluoromethyl)phenyl)-1,3-diazaspiro[4.5]decan-2-one | 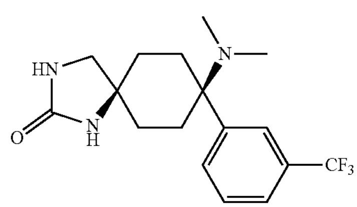 [SMILES: CN(C)[C@]1(c2cccc(C(F)(F)F)c2)CC[C@]2(CC1)CNC(=O)N2] | INT-1038 | 342.2 |
| INT-1041 | (CIS)-8-(dimethylamino)-8-(3-methoxyphenyl)-1,3-diazaspiro[4.5]decan-2-one | 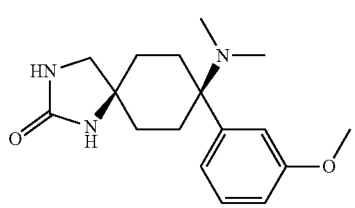 [SMILES: COc1cccc([C@]2(N(C)C)CC[C@@]3(CC2)CNC(=O)N3)c1] | INT-1038 | 304.2 |

| Intermediate | Chemical Name | Chemical structure | in analogy to method | m/z [M + H]+ |
|---|---|---|---|---|
| INT-1042 | (CIS)-8-(5-chlorothiophen-2-yl)-8-(dimethylamino)-1,3-diazaspiro[4.5]decan-2-one | 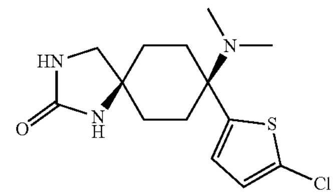 [SMILES: CN(C)[C@]1(c2ccc(Cl)s2)CC[C@]2(CC1)CNC(=O)N2] | INT-1038 | 314.1 |
| INT-1043 | (CIS)-8-(dimethylamino)-8-(3-fluoro-5-methylphenyl)-1,3-diazaspiro[4.5]decan-2-one | 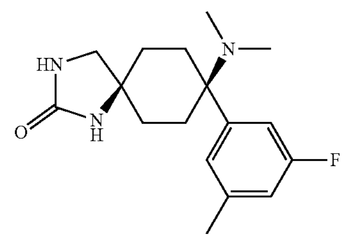 [SMILES: Cc1cc(F)cc([C@]2(N(C)C)CC[C@@]3(CC2)CNC(=O)N3)c1] | INT-1038 | 306.2 |
| INT-1044 | (CIS)-8-(3-chlorophenyl)-8-(dimethylamino)-1,3-diazaspiro[4.5]decan-2-one | 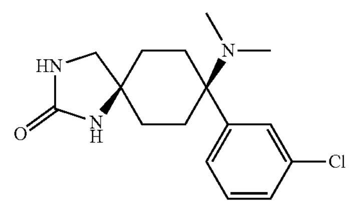 [SMILES: CN(C)[C@]1(c2cccc(Cl)c2)CC[C@]2(CC1)CNC(=O)N2] | INT-1038 | 308.2 |
| INT-1047 | (CIS)-8-(methyl(oxetan-3-ylmethyl)amino)-8-phenyl-1,3-diazaspiro[4.5]decan-2-one | 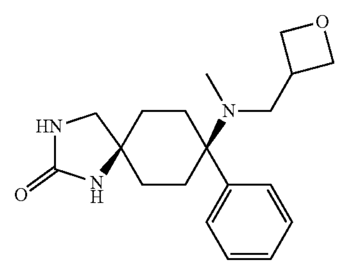 [SMILES: CN(CC1COC1)[C@]1(c2ccccc2)CC[C@]2(CC1)CNC(=O)N2] | INT-1026 | 330.5 |
| INT-1057 | CIS-1-(cyclobutylmethyl)-8-(dimethylamino)-8-(4-fluorophenyl)-1,3-diazaspiro[4.5]decan-2-one | 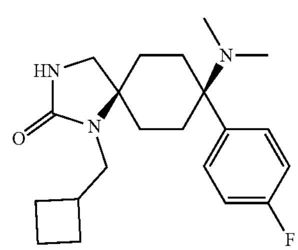 [SMILES: CN(C)[C@]1(c2ccc(F)cc2)CC[C@]2(CC1)CNC(=O)N2CC1CCC1] | INT-1031 | 360.3 |
| INT-1058 | CIS-2-(1-(cyclobutylmethyl)-8-(dimethylamino)-8-(4-fluorophenyl)-2-oxo-1,3-diazaspiro[4.5]decan-3-yl)acetic acid trifluoroacetate | 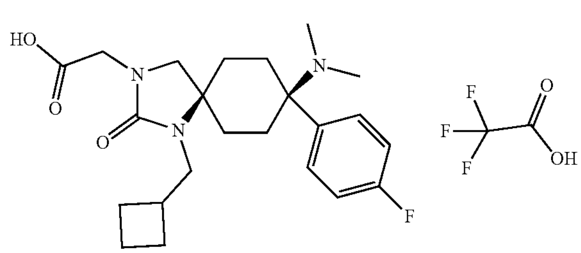 | INT-998 | 418.3 |

-continued

| Intermediate | Chemical Name | Chemical structure | in analogy to method | m/z [M + H]+ |
|---|---|---|---|---|
| INT-1060 | TRANS-2-(8-(dimethylamino)-2-oxo-8-phenyl-1,3-diazaspiro[4.5]decan-3-yl)acetic acid trifluoroacetate salt | 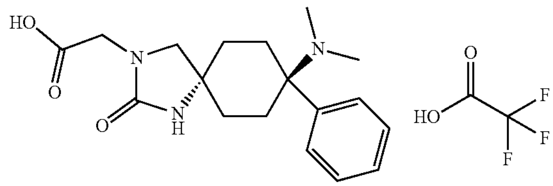 | steps 1 and 2 of INT-994 | 332.2 |
| INT-1061 | TRANS-1-(cyclopropyl-methyl)-8-dimethylamino-8-phenyl-1,3-diazaspiro[4.5]decan-2-one | 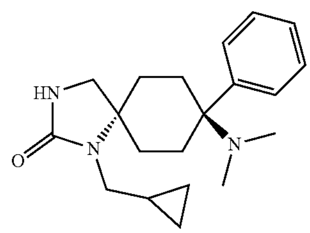 [SMILES: CN(C)[C@]1(c2ccccc2)CC[C@@]2(CC1)CNC(=O)N2CC1CC1] | INT-984 | 328.2 |
| INT-1062 | TRANS-2-[1-(cyclopropyl-methyl)-8-dimethylamino-2-oxo-8-phenyl-1,3-diazaspiro[4.5]decan-3-yl]-acetic acid trifluoroacetate salt | 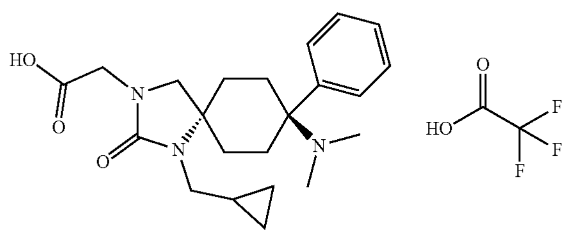 [SMILES: CN(C)[C@]1(c2ccccc2)CC[C@@]2(CC1)CN(CC(=O)O)C(=O)N2CC1CC1 ; O=C(O)C(F)(F)F] | INT-998 | 386.2 |
| INT-1063 | CIS-1-(cyclopropylmethyl)-8-(dimethylamino)-8-(3-fluorophenyl)-1,3-diazaspiro[4.5]decan-2-one | 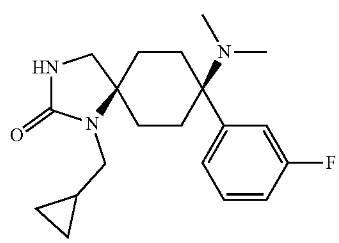 [SMILES: CN(C)[C@]1(c2cccc(F)c2)CC[C@]2(CC1)CNC(=O)N2CC1CC1] | INT-1031 | 346.2 |
| INT-1066 | TRANS-1-(cyclobutylmethyl)-8-(dimethylamino)-8-phenyl-1,3-diazaspiro[4.5]decan-2-one | 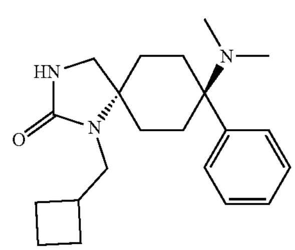 [SMILES: CN(C)[C@]1(c2ccccc2)CC[C@@]2(CC1)CNC(=O)N2CC1CCC1] | INT-987 | 342.3 |
| INT-1067 | TRANS-2-[1-(cyclobutyl-methyl)-8-dimethylamino-2-oxo-8-phenyl-1,3-diazaspiro[4.5]decan-3-yl]-acetic acid; 2,2,2-trifluoro-acetic acid salt | 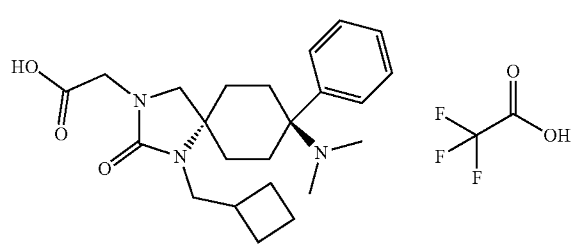 [SMILES: CN(C)[C@]1(c2ccccc2)CC[C@@]2(CC1)CN(CC(=O)O)C(=O)N2CC1CCC1 ; O=C(O)C(F)(F)F] | INT-998 | 400.3 |

| Intermediate | Chemical Name | Chemical structure | in analogy to method | m/z [M + H]+ |
|---|---|---|---|---|
| INT-1070 | CIS-8-(dimethylamino)-8-phenyl-1-(3,3,3-trifluoropropyl)-1,3-diazaspiro[4.5]decan-2-one | 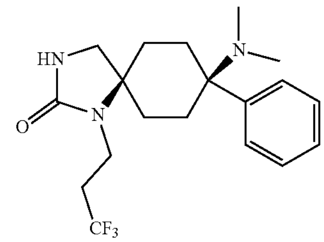 [SMILES: CN(C)[C@]1(c2ccccc2)CC[C@]2(CC1)CNC(=O)N2CCC(F)(F)F] | INT-1068 | 360.2 |
| INT-1074 | CIS-8-(dimethylamino)-8-(3-fluorophenyl)-1-((1-hydroxycyclobutyl)methyl)-1,3-diazaspiro[4.5]decan-2-one | 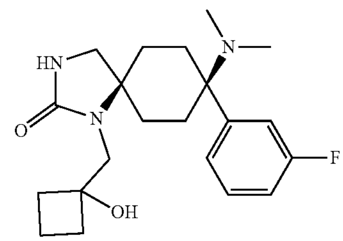 [SMILES: CN(C)[C@]1(c2cccc(F)c2)CC[C@]2(CC1)CNC(=O)N2CC1(O)CCC1] | INT-1031 | 376.2 |

Synthesis of Exemplary Compounds

Synthesis of SC_1051: CIS-2-[1-(Cyclobutyl-methyl)-8-dimethylamino-2-oxo-8-phenyl-1,3-diazaspiro[4.5]decan-3-yl]-N-(5-methoxy-pyridin-2-yl)-acetamide

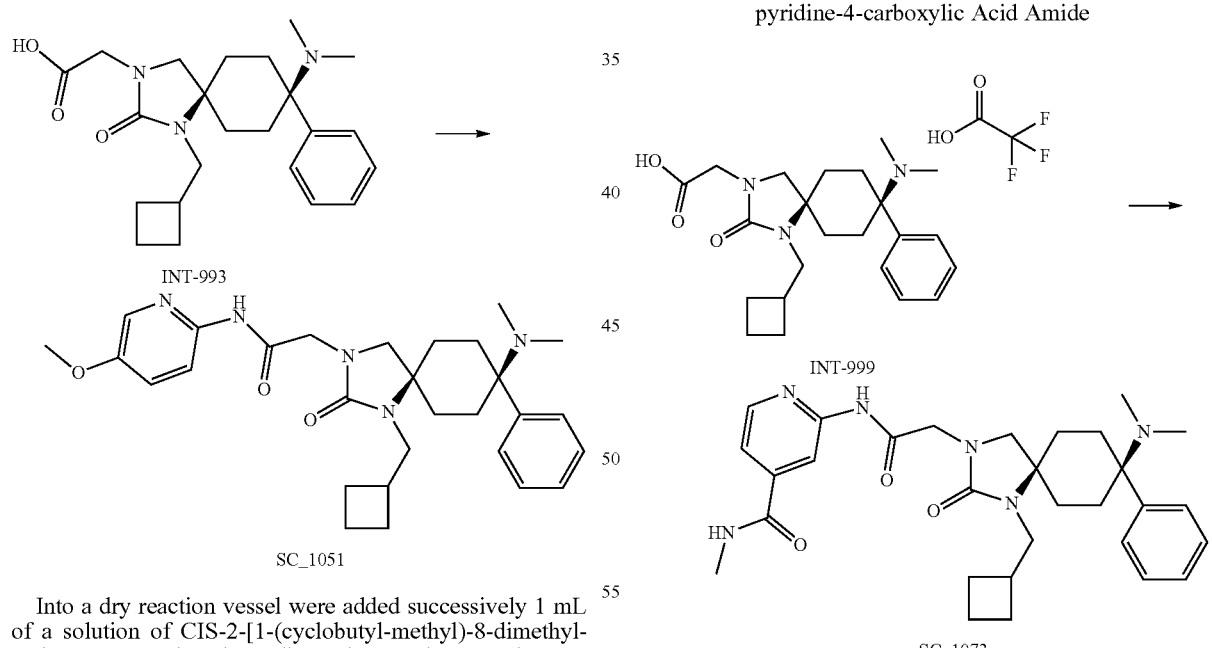

Into a dry reaction vessel were added successively 1 mL of a solution of CIS-2-[1-(cyclobutyl-methyl)-8-dimethyl-amino-2-oxo-8-phenyl-1,3-diazaspiro[4.5]decan-3-yl]-acetic acid (INT-993) (0.1 M in DCM), 2 mL of a solution of 5-methoxy-pyridin-2-amine (0.2 M in DCM), 0.07 ml of triethylamine and 0.118 mL of a solution of T3P (1.7 M, 50% in EtOAc). The reaction mixture was stirred at RT overnight, then quenched with 3 mL aq. Na₂CO₃ (1 M) and stirred at RT for 1 h. The organic layer was separated and the aq. layer was extracted with DCM (2×). The combined organic layers were concentrated under reduced pressure and the resulting crude product was purified by HPLC to obtain CIS-2-[1-(cyclobutyl-methyl)-8-dimethylamino-2-oxo-8-phenyl-1,3-diazaspiro[4.5]decan-3-yl]-N-(5-methoxy-pyridin-2-yl)-acetamide (SC_1051). [M+H]+ 506.3

Synthesis of SC_1073: CIS-2-[[2-[1-(Cyclobutyl-methyl)-8-dimethylamino-2-oxo-8-phenyl-1,3-diazaspiro[4.5]decan-3-yl]-acetyl]amino]-N-methyl-pyridine-4-carboxylic Acid Amide To a mixture of CIS-2-[1-(cyclobutyl-methyl)-8-dimethylamino-2-oxo-8-phenyl-1,3-diazaspiro[4.5]decan-3-yl]-acetic acid trifluoroacetate (INT-999) (100 mg, 0.19 mmol) and 2-amino-N-methylisonicotinamide (118 mg, 0.78 mmol) in DCM (6 ml) were added HATU (148 mg, 0.39 mmol) and DIPEA (0.13 ml, 0.78 mmol) at RT and the reaction mixture was stirred at same temperature for 16 h. The reaction mixture was washed with 1M aq. Na₂CO₃ (1 mL) and 2M aq. NaOH (1 mL). The combined aqueous layers were extracted with DCM (3×5 mL). The combined organic layers were washed with water (3 mL) and brine (3 ml), dried over magnesium sulfate, filtered and concentrated in vacuum. Column chromatography (silica gel, cHex/tBuOMe/1N methanolic ammonia 1:1:0.05) of the crude product provided CIS-2-[[2-[1-(cyclobutyl-methyl)-8-dimethylamino-2-oxo-8-phenyl-1,3-diazaspiro[4.5]decan-3-yl]-acetyl]amino]-N-methyl-pyridine-4-carboxylic acid amide (SC_1073) (27 mg). [M+H]+ 533.3

Synthesis of SC_1076: CIS-6-[[2-[1-(Cyclobutyl-methyl)-8-dimethylamino-2-oxo-8-phenyl-1,3-diazaspiro[4.5]decan-3-yl]-acetyl]amino]-pyridine-2-carboxylic Acid Amide

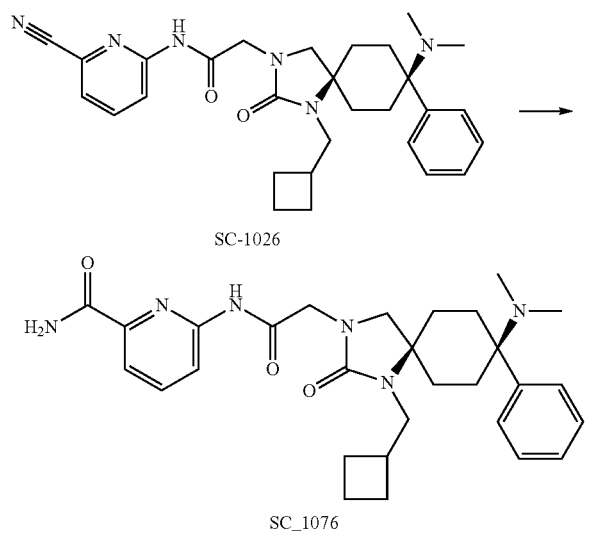

CIS-N-(6-Cyano-pyridin-2-yl)-2-[1-(cyclobutyl-methyl)-8-dimethylamino-2-oxo-8-phenyl-1,3-diazaspiro[4.5]decan-3-yl]-acetamide (SC_1026) (30 mg, 0.06 mmol) was dissolved in DMSO (0.2 mL) and potassium carbonate (17 mg, 0.12 mmol) and hydrogen peroxide (30% in water, 0.12 mmol) were added at 0° C. The resulting mixture was stirred for 18 h, then water was added and the reaction mixture was extracted with DCM (3×5 mL). The combined organic layers were dried over Na2SO4, concentrated in vacuo and the resulting crude product was purified by flash chromatography to yield CIS-6-[[2-[1-(cyclobutyl-methyl)-8-dimethylamino-2-oxo-8-phenyl-1,3-diazaspiro[4.5]decan-3-yl]-acetyl]amino]-pyridine-2-carboxylic acid amide SC_1076 (14 mg) as a white solid. [M+H]+ 519.3

Synthesis of SC_1110: CIS-2-[1-(cyclobutyl-methyl)-8-dimethylamino-2-oxo-8-phenyl-1,3-diazaspiro[4.5]decan-3-yl]-N-(2-hydroxy-pyrimidin-5-yl)-acetamide

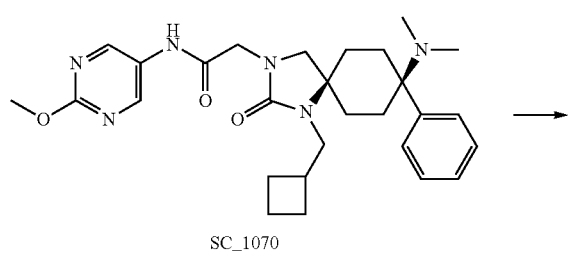

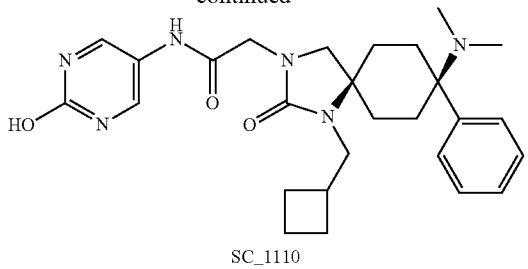

A solution of CIS-2-[1-(cyclobutyl-methyl)-8-dimethylamino-2-oxo-8-phenyl-1,3-diazaspiro[4.5]decan-3-yl]-N-(2-methoxy-pyrimidin-5-yl)-acetamide (SC_1070) (80 mg, 0.16 mmol) in DCM (12 mL) was cooled to 0° C. and treated with a boron tribromide solution (1M in DCM, 1.26 mL, 1.26 mmol). After stirring at RT for 16 h the reaction mixture was quenched with MeOH, diluted with water and extracted with DCM (3×). The combined organic layers were dried over Na2SO4, filtered and concentrated in vacuum. The resulting crude product was purified by column chromatography (reversed phase silica gel C18, water/MeCN 100:0→20:80) to yield CIS-2-[1-(cyclobutyl-methyl)-8-dimethylamino-2-oxo-8-phenyl-1,3-diazaspiro[4.5]decan-3-yl]-N-(2-hydroxy-pyrimidin-5-yl)-acetamide (SC_1110) (17 mg). [M+H]+ 493.3

Synthesis of SC_1128: CIS-N-(2-Cyano-pyrimidin-4-yl)-2-[1-(cyclobutyl-methyl)-8-dimethylamino-2-oxo-8-phenyl-1,3-diazaspiro[4.5]decan-3-yl]-acetamide

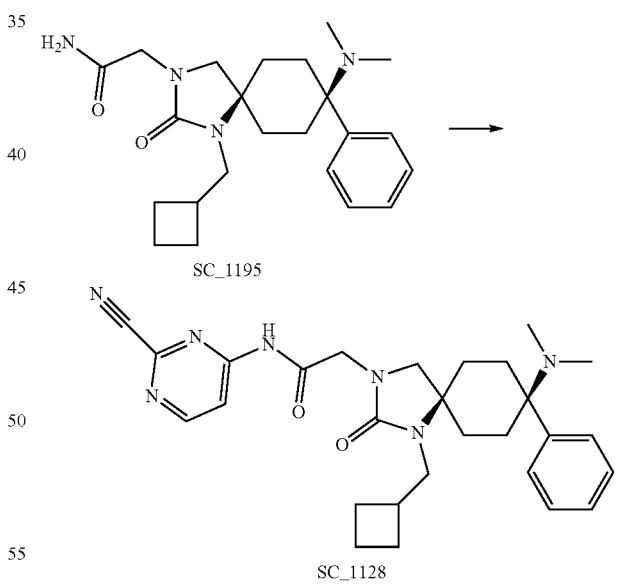

CIS-2-[1-(cyclobutyl-methyl)-8-dimethylamino-2-oxo-8-phenyl-1,3-diazaspiro[4.5]decan-3-yl]-acetamide (SC_1195) (50 mg, 0.1255 mmol), 4-bromopyrimidine-2-carbonitrile (0.1882 mmol), 4,5-XantPhos (0.0188 mmol), Cs2CO3 (0.2509 mmol) and Pd2(dba)3 (0.0063 mmol) were dissolved in 1,4-dioxane (6 mL). The reaction mixture was degassed by three consecutive vacuum/nitrogen-refill cycles and then stirred at 90° C. for 18 h. Water (2 mL) was added and the resulting mixture was extracted with ethyl acetate (3×6 mL). The combined organic layers were dried over Na2SO4, concentrated in vacuo and purified by flash chromatography to yield CIS-N-(2-cyano-pyrimidin-4-yl)-2-[1-(cyclobutyl-methyl)-8-dimethylamino-2-oxo-8-phenyl-1,3-diazaspiro[4.5]decan-3-yl]-acetamide (SC_1128) (43 mg) as a white solid. [M+H]+ 502.3

Synthesis of SC_1129: CIS-2-[1-(Cyclobutyl-methyl)-8-dimethylamino-2-oxo-8-phenyl-1,3-diazaspiro[4.5]decan-3-yl]-N-[6-(methylsulfinyl)-pyridin-2-yl]-acetamide

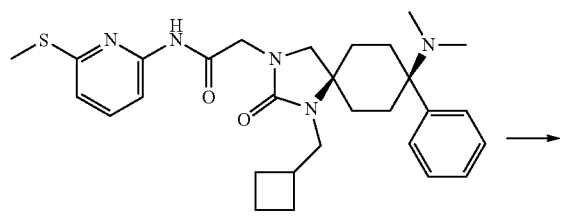

SC_1120

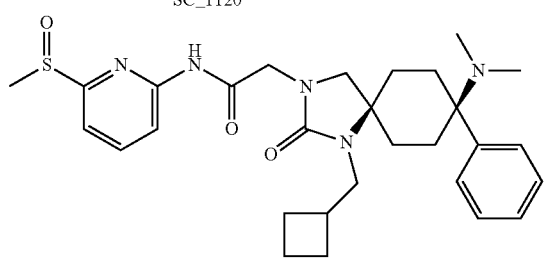

SC_1129

CIS-2-[1-(Cyclobutyl-methyl)-8-dimethylamino-2-oxo-8-phenyl-1,3-diazaspiro[4.5]decan-3-yl]-N-(6-methylsulfanyl-pyridin-2-yl)-acetamide SC_1120 (30.0 mg) was dissolved in 1,1,1,3,3,3-hexafluoropropan-2-ol (0.303 mL) and hydrogen peroxide (30% in water, 12 µL) was added. The resulting mixture was stirred at 60° C. for 1 h. Then sat. aq. Na2S2O3 (2 mL) was added and the aqueous layer was extracted with DCM (3×5 mL). The combined organic layers were dried over Na2SO4, concentrated in vacuo and purified by flash chromatography to yield CIS-2-[1-(cyclobutyl-methyl)-8-dimethylamino-2-oxo-8-phenyl-1,3-diazaspiro[4.5]decan-3-yl]-N-[6-(methylsulfinyl)-pyridin-2-yl]-acetamide (SC_1129) (8 mg) as a white solid. [M+H]+ 538.3

Synthesis of SC_1136: CIS-2-[8-dimethylamino-1-[(1-hydroxy-cyclobutyl)-methyl]-2-oxo-8-phenyl-1,3-diazaspiro[4.5]decan-3-yl]-N-(2-methylsulfonyl-ethyl)-acetamide

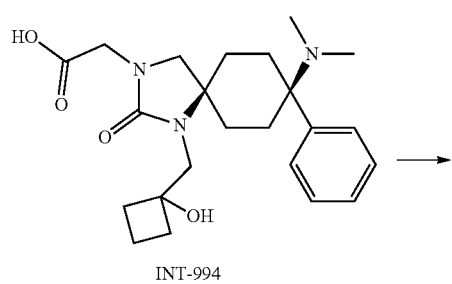

INT-994

-continued

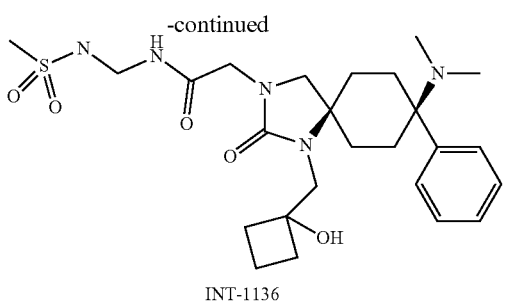

INT-1136

50% Propylphosphonic anhydride (T3P) solution in EtOAc (0.766 mL, 1.204 mmol) was added to a solution of crude CIS-2-[8-dimethylamino-1-[(1-hydroxy-cyclobutyl)-methyl]-2-oxo-8-phenyl-1,3-diazaspiro[4.5]decan-3-yl]-acetic acid (INT-994) (250 mg, 0.602 mmol), 2-(methylsulfonyl)ethanamine hydrochloride (115.4 mg, 0.723 mmol) and diisopropylethylamine (0.410 mL, 2.408 mmol) in DCM (15 mL) at 0° C. The reaction mixture was warmed to RT and stirred for 4 h. The reaction mixture was quenched with water and the organic product was extracted with DCM (3×20 mL). The combined organic layer was washed with sat. aq. NaHCO3 (10 mL), brine (10 mL) and dried over anhydr. Na2SO4 and concentrated under reduced pressure The crude product was purified by preparative HPLC to give 56 mg (25%) of CIS-2-[8-dimethylamino-1-[(1-hydroxy-cyclobutyl)-methyl]-2-oxo-8-phenyl-1,3-diazaspiro[4.5]decan-3-yl]-N-(2-methylsulfonyl-ethyl)-acetamide (SC_1136) as an off-white solid. (TLC system: 10% MeOH in DCM Rf: 0.62). [M+H]+ 521.3

Synthesis of SC_1138: CIS-2-[1-(Cyclobutyl-methyl)-8-dimethylamino-2-oxo-8-phenyl-1,3-diazaspiro[4.5]decan-3-yl]-N-(6-methylsulfonyl-pyridin-2-yl)-acetamide

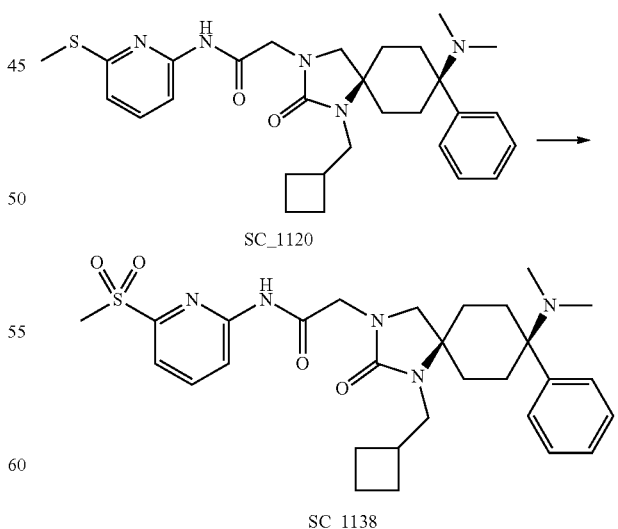

SC_1120

SC_1138

CIS-2-[1-(Cyclobutyl-methyl)-8-dimethylamino-2-oxo-8-phenyl-1,3-diazaspiro[4.5]decan-3-yl]-N-(6-methylsulfanyl-pyridin-2-yl)-acetamide (SC_1120) (22 mg) was dissolved in a water/methanol (500 μL/500 μL) and oxone (39 mg) was added. The resulting mixture was stirred at RT for 18 h. Then 2N aq. NaOH (2 mL) was added and the aqueous layer was extracted with DCM (3×5 mL). The combined organic layers were dried over Na$_2$SO$_4$, concentrated in vacuo and the residue was purified by flash chromatography to yield CIS-2-[1-(cyclobutyl-methyl)-8-dimethylamino-2-oxo-8-phenyl-1,3-diazaspiro[4.5]decan-3-yl]-N-(6-methyl-sulfonyl-pyridin-2-yl)-acetamide (SC_1138) (14 mg) as a white solid. [M+H]$^+$ 554.3

Synthesis of SC_1149: CIS-2-[8-Dimethylamino-1l-(3-methoxy-propyl)-2-oxo-8-phenyl-1,3-diazaspiro[4.5]decan-3-yl]-N-methyl-acetamide

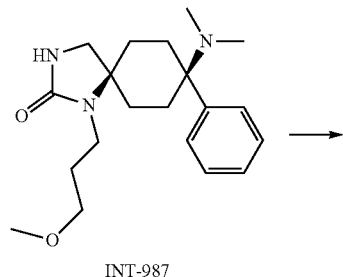

INT-987

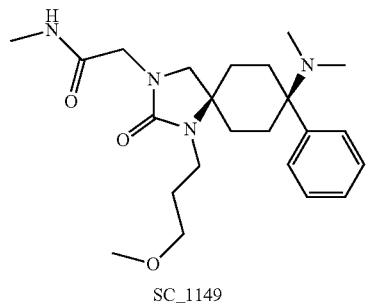

SC_1149

CIS-1-(Cyclobutyl-methyl)-8-dimethylamino-8-phenyl-1,3-diazaspiro[4.5]decan-2-one (INT-987) (0.2 g, 0.57 mmol) was added to a solution of NaH (60% in mineral oil) (0.15 g, 3.47 mmol) in DMF (5 mL) at RT and the reaction mixture was stirred at RT for 1 h. The reaction mixture was cooled to 0° C. and 2-bromo-N-methylacetamide (0.52 g, 3.47 mmol) in DMF (2 mL) was added dropwise. the resulting mixture was stirred for 30 min at 0° C. and then at RT for 16 h. The reaction completion was monitored by TLC. The reaction mixture was quenched with sat. aq. NH$_4$Cl and the organic product was extracted with EtOAc (2×10 mL). The combined organic extracts were dried over anhydrous Na$_2$SO$_4$ and concentrated under reduced pressure. Purified of the crude product by preparative TLC using 5% MeOH in DCM as a mobile phase gave 45 g (18%) of CIS-2-[8-dimethylamino-1-(3-methoxy-propyl)-2-oxo-8-phenyl-1,3-diazaspiro[4.5]decan-3-yl]-N-methyl-acetamide (SC_1149) as an off-white solid. (TLC system: 10% MeOH in DCM; Rf: 0.3). [M+H]$^+$ 417.3

Synthesis of SC_1303: CIS-2-[1-[(1-Hydroxy-cyclobutyl)-methyl]-8-methylamino-2-oxo-8-phenyl-1,3-diazaspiro[4.5]decan-3-yl]-N-(oxetan-3-yl)-acetamide

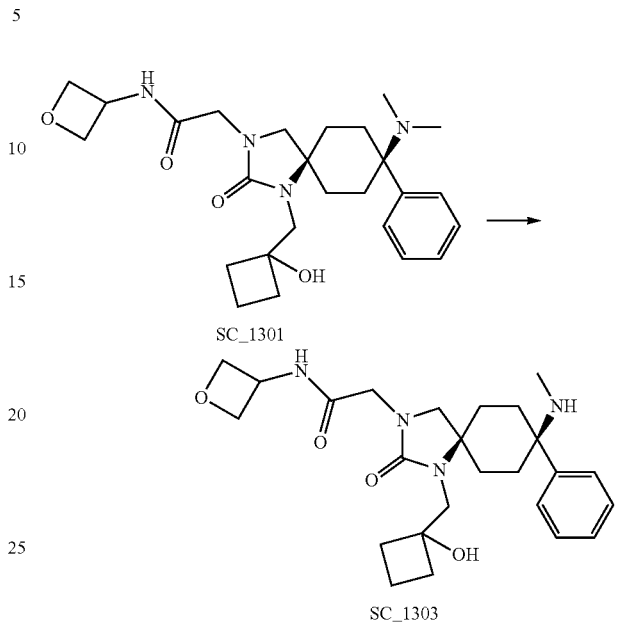

N-Iodosuccinimide (71.8 mg, 0.319 mmol) was added to a solution of CIS-2-[8-dimethylamino-1-[(1-hydroxy-cyclobutyl)-methyl]-2-oxo-8-phenyl-1,3-diazaspiro[4.5]decan-3-yl]-N-(oxetan-3-yl)-acetamide (SC_1301) (100 mg, 0.213 mmol) in a mixture of acetonitrile and THF (1:1 v/v, 5 mL) at 0° C. and the resulting mixture was stirred at RT for 16 h. The reaction mixture was basified with 2N NaOH solution to pH~10 and the organic product was extracted with ethyl acetate (10 mL×3). The combined organic extracts were dried over anhydr. Na$_2$SO$_4$ and concentrated under reduced pressure. The resulting crude product was purified by preparative reverse phase HPLC to give 50 mg of the desired product as a formiate. The isolated product was diluted with water (5 mL) and basified with sat. aq. NaHCO$_3$. The product was extracted with EtOAc (10 mL×2), combined organic layer was dried over anhydr. Na$_2$SO$_4$ and concentrated in vacuo to yield 42 mg (43%) of CIS-2-[1-[(1-hydroxy-cyclobutyl)-methyl]-8-methylamino-2-oxo-8-phenyl-1,3-diazaspiro[4.5]decan-3-yl]-N-(oxetan-3-yl)-acetamide (SC_1303) as an off-white solid (TLC system: 5% MeOH in DCM; R$_f$: 0.42.). [M+H]$^+$ 457.3

Synthesis of SC_1308: CIS-8-Dimethylamino-3-[2-(1,1-dioxo-[1,4]thiazinan-4-yl)-2-oxo-ethyl]-8-phenyl-1-propyl-1,3-diazaspiro[4.5]decan-2-one

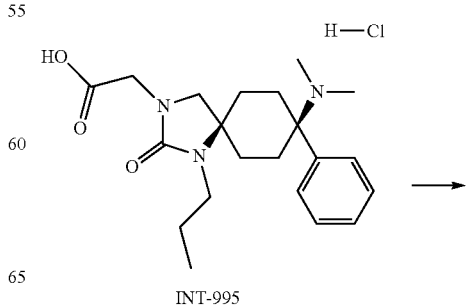

INT-995

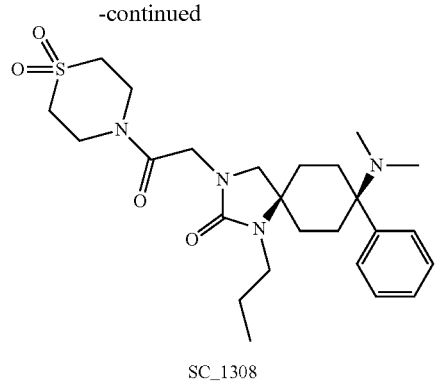

SC_1308

50 wt % solution of T3P (2.32 g, 3.65 mmol) in EtOAc was added to a suspension of CIS-2-(8-dimethylamino-2-oxo-8-phenyl-1-propyl-1,3-diazaspiro[4.5]decan-3-yl)-acetic acid hydrochlorid (INT-995) (600 mg, 1.46 mmol), thiomorpholin-1,1-dioxide (237 mg, 1.76 mmol) and diisopropylethylamine (1.27 mL, 7.30 mmol) in THF (10 mL) at 0° C. The reaction mixture was warmed to RT and stirred for 16 h. The reaction mixture was quenched with water, the organic product was extracted with EtOAc (3×25 mL). The combined organic extracts were washed with water, brine, dried over anhydrous $Na_2SO_4$ and concentrated under reduced pressure to give the crude compound. Purification by flash silica column chromatography using 4-5% methanol in DCM as eluent yielded 250 mg (34%) of CIS-8-dimethylamino-3-[2-(1,1-dioxo-[1,4]thiazinan-4-yl)-2-oxo-ethyl]-8-phenyl-1-propyl-1,3-diazaspiro[4.5]decan-2-one (SC_1308) as a solid (TLC system: 10% MeOH in DCM $R_f$: 0.30). $[M+H]^+$ 491.3

Synthesis of SC_1324: CIS-2-(8-(dimethylamino)-2-oxo-8-phenyl-1,3-diazaspiro[4.5]decan-3-yl)acetamide

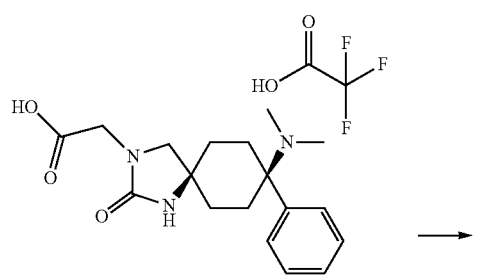

SC_1324

The suspension of TFA salt of CIS-(8-dimethylamino-2-oxo-8-phenyl-1,3-diaza-spiro[4.5]dec-3-yl)-acetic acid (500 mg, 1.12 mmol, 1.0 eq.) in THF (40 ml) was cooled to 0° C. and DIPEA (0.78 ml, 4.48 mmol, 4.0 eq.), 1-hydroxy-1H-benzotriazole ammonium salt (287 mg, 1.68 mmol, 1.5 eq.) and EDCl (321 mg, 1.68 mmol, 1.5 eq.) were sequentially added. The resulting mixture was stirred at RT for 16 h and then concentrated under reduced pressure. Crude product was purified by column chromatography (neutral alumina; 0.5% $NH_3$ in 20% MeOH/DCM) to yield CIS-2-(8-dimethylamino-2-oxo-8-phenyl-1,3-diaza-spiro[4.5]dec-3-yl)-acetamide (SC_1324) (250 mg, 0.75 mmol, 67%) as an off-white solid. $[M+H]^+$ 331.2

Synthesis of SC_1332: CIS-2-(8-(dimethylamino)-2-oxo-8-phenyl-1,3-diazaspiro[4.5]decan-3-yl)-N-phenylacetamide

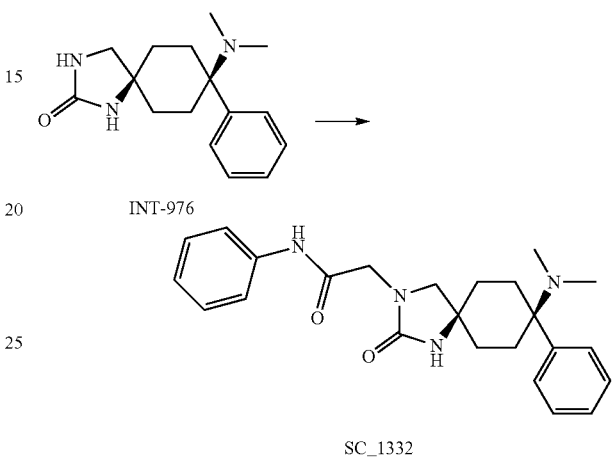

KOtBu (1M in THF) (1.4 mL, 1.37 mmol) was added to the solution of CIS-8-(dimethylamino)-8-phenyl-1,3-diazaspiro[4.5]decan-2-one (250 mg, 0.915 mmol) in THF (15 mL) under argon atmosphere at 0° C. and the reaction mixture was stirred for 30 min. 2-Bromo-N-phenylacetamide (312 mg, 1.46 mmol) was added, the ice bath was removed and the reaction mixture was stirred for 4 h. Sat. aq. $NH_4Cl$ (10 mL) was added and the resulting mixture was extracted with EtOAc (2×50 mL). The combined organic extracts were dried over anhydr. $Na_2SO_4$ and concentrated under reduced pressure. The crude product was purified by reverse phase preparative HPLC to give 60 mg (16%) of CIS-2-(8-(dimethylamino)-2-oxo-8-phenyl-1,3-diazaspiro[4.5]decan-3-yl)-N-phenylacetamide (SC_1332) as a white solid. $^1H$ NMR ($CDCl_3$): δ 8.32 (br s, 1H), 7.50-7.48 (d, 2H), 7.39-7.36 (m, 2H), 7.33-7.26 (m, 5H), 7.12-7.08 (t, 1H), 5.90 (br s, 1H), 3.90 (s, 2H), 3.25 (s, 2H), 2.12 (m, 4H), 1.99 (s, 6H), 1.94-1.91 (m, 2H), 1.58-1.53 (m, 2H). $[M+H]^+$ 407.2

Synthesis of SC-1346: CIS-2-[1-(Cyclobutyl-methyl)-8-dimethylamino-8-(3-fluorophenyl)-2-oxo-1,3-diazaspiro[4.5]decan-3-yl]-acetic Acid Tert-Butyl Ester

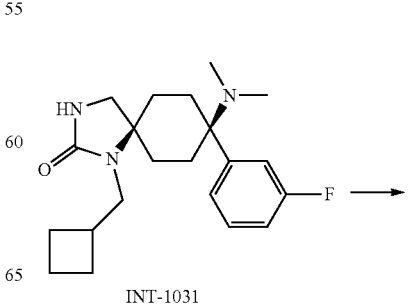

INT-1031

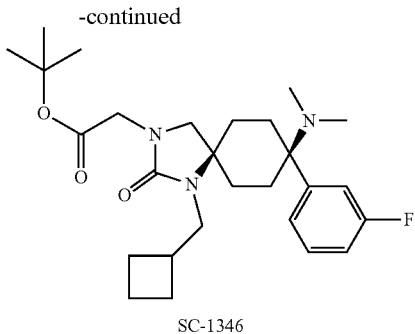

SC-1346

KOtBu (187 mg, 1.67 mmol) was added to a solution of CIS-1-(cyclobutyl-methyl)-8-dimethylamino-8-(3-fluorophenyl)-1,3-diazaspiro[4.5]decan-2-one (INT-1031) (400 mg, 1.1 mmol) in dry THF (9 mL) at 0° C. The mixture was stirred for 15 min at this temperature and t-butyl-bromoacetate (0.246 mL, 1.67 mmol) was added subsequently. After stirring for 1 h at 0° C., the reaction was quenched with water, diluted with EtOAc and stirred for 5 min at RT. The layers were separated and the aqueous layer was extracted two times with ethyl acetate. The combined organic extracts were dried over anhydrous $Na_2SO_4$ and concentrated under reduced pressure. The crude product was purified by flash chromatography (silica, 0.5 M $NH_3$ in MeOH/DCM gradient) to yield 395 mg (75%) of CIS-2-[1-(cyclobutyl-methyl)-8-dimethylamino-8-(3-fluorophenyl)-2-oxo-1,3-diazaspiro[4.5]decan-3-yl]-acetic acid tert-butyl ester (SC_1346) as a white solid. $^1$H NMR (600 MHz, DMSO) δ 7.43-7.36 (m, 1H), 7.17 (d, 1H), 7.13 (dt, 1H), 7.09 (td, 1H), 3.75 (d, 2H), 3.21 (s, 2H), 3.05 (d, 2H), 2.67-2.61 (m, 2H), 2.08-2.00 (m, 2H), 1.99 (d, 7H), 1.98-1.93 (m, 2H), 1.83-1.75 (m, 2H), 1.75-1.65 (m, 2H), 1.39 (d, 8H), 1.38-1.29 (m, 5H). [M+H]$^+$ 474.3

Of SC-1357: TRANS-1-(cyclopropylmethyl)-8-(dimethylamino)-3-(2-morpholino-2-oxoethyl)-8-phenyl-1,3-diazaspiro[4.5]decan-2-one

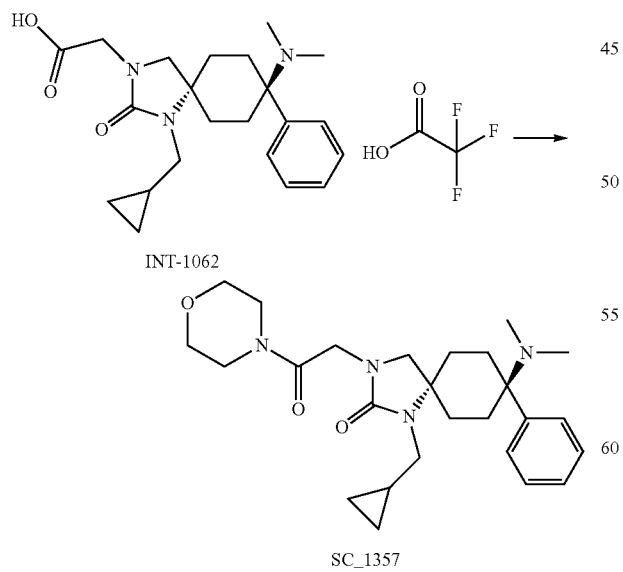

INT-1062

SC_1357

To a solution of TRANS-2-(1-(cyclopropylmethyl)-8-(dimethylamino)-2-oxo-8-phenyl-1,3-diazaspiro[4.5]decan-3-yl)acetic acid trifluoroacetate (300 mg, 0.6 mmol, 1.0 eq.) in DCM (10 mL) were added DIPEA (0.62 mL, 3.6 mmol, 6.0 eq.) and HATU (296 mg, 0.78 mmol, 1.3 eq.) followed by morpholine (102 mg, 1.08 mmol, 1.8 eq.) at 0° C. The reaction mixture was stirred at RT for 16 h, then quenched with water (25 mL) and extracted with DCM (50 mL×2). Combined organic layer was washed with brine (25 mL), dried over $Na_2SO_4$, filtered and concentrated under reduced pressure. The resulting crude product was purified by prep HPLC to get TRANS-1-cyclopropylmethyl-8-dimethylamino-3-(2-morpholin-4-yl-2-oxo-ethyl)-8-phenyl-1,3-diaza-spiro[4.5]decan-2-one (SC-1357) (55 mg, 0.12 mmol, 20%) as a white solid. $^1$HNMR (DMSO-$d_6$, 400 MHz), δ (ppm)=7.44-7.29 (m, 5H), 3.96 (s, 2H), 3.56 (bs, 4H), 3.42-3.40 (m, 4H), 3.29 (s, 2H), 2.67 (bs, 2H), 2.55-2.54 (d, 2H, J=6.36 Hz), 1.92 (s, 6H), 1.56-.144 (m, 6H), 0.51-0.48 (m, 1H), 0.16-0.14 (m, 2H), (−0.26)-(−0.27) (m, 2H). [M+H]$^+$ 455.1

Synthesis of INT-1363: TRANS-2-(1-(cyclopropylmethyl)-8-(dimethylamino)-2-oxo-8-phenyl-1,3-diazaspiro[4.5]decan-3-yl)acetamide

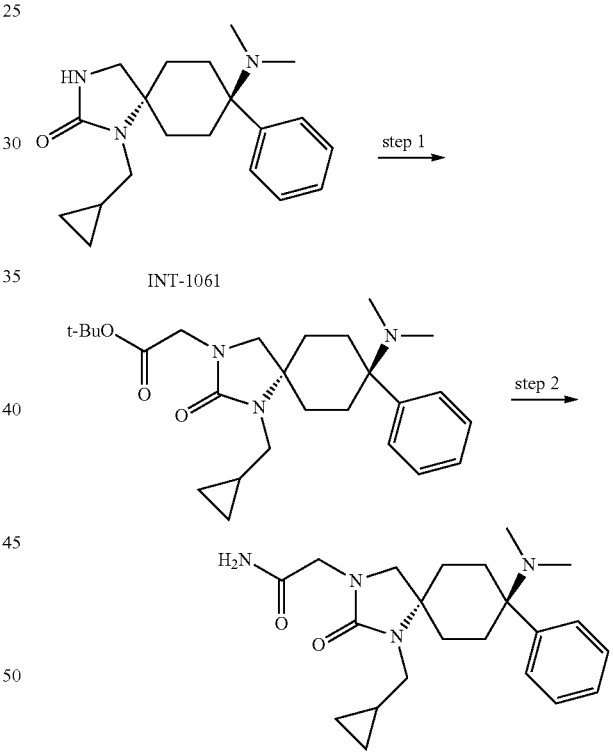

Step 1: tert-butyl TRANS-2-(1-(cyclopropylmethyl)-8-(dimethylamino)-2-oxo-8-phenyl-1,3-diazaspiro[4.5]decan-3-yl)acetate In analogy to the method described for INT-1019 step 1 TRANS-1-(cyclopropylmethyl)-8-(dimethylamino)-8-phenyl-1,3-diazaspiro[4.5]decan-2-one (INT-1061) was converted into tert-butyl TRANS-2-(1-(cyclopropylmethyl)-8-(dimethylamino)-2-oxo-8-phenyl-1,3-diazaspiro[4.5]decan-3-yl)acetate. LC-MS: m/z [M+H]$^+$=442.3

Step 2: TRANS-2-(1-(cyclopropylmethyl)-8-(dimethylamino)-2-oxo-8-phenyl-1,3-diazaspiro[4.5]decan-3-yl)acetamide (INT-1363)

A mixture of TRANS-(1-cyclopropylmethyl-8-dimethylamino-2-oxo-8-phenyl-1,3-diaza-spiro[4.5]dec-3-yl)-acetic acid tert-butyl ester (250 mg, 0.56 mmol, 1.0 eq.) and 7M $NH_3$ in MeOH (5 mL) was heated in sealed tube at 90° C. for 16 h, then cooled down to RT and concentrated under reduced pressure. The residue was purified by column chromatography (silica gel basified with aq. $NH_3$; 10% MeOH in DCM) to yield 2-(1-cyclopropylmethyl-8-dimethylamino-2-oxo-8-phenyl-1,3-diaza-spiro[4.5]dec-3-yl)-acetamide (77 mg, 0.2 mmol, 35%) as a white solid. LC-MS: m/z $[M+1]^+$=385.2 (MW calc. 384.52); $^1$H NMR at 100° C. (DMSO-d6, 400 MHz), δ (ppm)=7.40-7.29 (m, 5H), 6.76 (bs, 2H), 3.68 (s, 2H), 3.33 (s, 2H), 2.61-2.60 (m, 4H), 2.00 (s, 6H), 1.61-0.153 (m, 6H), 0.58-0.56 (m, 1H), 0.22-0.20 (m, 2H), (−0.16)-(−0.18) (m, 2H).

For further exemplary compounds the last synthesis step in analogy to previously described methods is given in the following table. The syntheses of the building blocks and intermediates have either been described previously within this application or can be performed in analogy to the herein described methods or by methods known to the person, skilled in the art. Such a person will also know which building blocks and intermediates need to be chosen for synthesis of each exemplary compound.

| Example | Chemical Name | Reactant I | Reactant II | in analogy to method | m/z [M + H]$^+$ |
|---|---|---|---|---|---|
| SC_1001 | CIS-2-[1-(Cyclobutyl-methyl)-8-dimethylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide | INT 993 | 2,5,8,11,14,17,20-heptaoxadocosan-22-amine | SC_1308 | 721.5 |
| SC_1002 | CIS-6-[[2-[1-(Cyclobutyl-methyl)-8-dimethylamino-2-oxo-8-phenyl-1,3-diazaspiro[4.5]decan-3-yl]-acetyl]amino]-pyridine-2-carboxylic acid methyl ester | INT 993 | methyl 6-aminopicolinate | SC_1308 | 534.3 |
| SC_1003 | CIS-2-[1-(Cyclobutyl-methyl)-8-dimethylamino-2-oxo-8-phenyl-1,3-diazaspiro[4.5]decan-3-yl]-N-[(1R)-2-hydroxy-1-methyl-ethyl]-acetamide | INT 993 | (R)-2-aminopropan-1-ol | SC_1308 | 457.3 |
| SC_1004 | CIS-2-[1-(Cyclobutyl-methyl)-8-dimethylamino-2-oxo-8-phenyl-1,3-diazaspiro[4.5]decan-3-yl]-N-[(1S)-2-hydroxy-1-methyl-ethyl]-acetamide | INT 993 | (S)-2-aminopropan-1-ol | SC_1308 | 457.3 |
| SC_1005 | CIS-2-[1-(Cyclobutyl-methyl)-8-dimethylamino-2-oxo-8-phenyl-1,3-diazaspiro[4.5]decan-3-yl]-N-methyl-N-(methylcarbamoyl-methyl)-acetamide | INT 993 | N-methyl-2-(methylamino)acetamide | SC_1308 | 484.3 |
| SC_1006 | CIS-6-[[2-[1-(Cyclobutyl-methyl)-8-dimethylamino-2-oxo-8-phenyl-1,3-diazaspiro[4.5]decan-3-yl]-acetyl]amino]-nicotinic acid methyl ester | INT 993 | methyl 6-aminonicotinate | SC_1308 | 534.3 |
| SC_1007 | CIS-2-[[2-[1-(Cyclobutyl-methyl)-8-dimethylamino-2-oxo-8-phenyl-1,3-diazaspiro[4.5]decan-3-yl]-acetyl]-methyl-amino]-2-methyl-propionamide | INT 993 | 2-methyl-2-(methylamino)propanamide | SC_1308 | 498.3 |
| SC_1008 | CIS-2-[[2-[1-(Cyclobutyl-methyl)-8-dimethylamino-2-oxo-8-phenyl-1,3-diazaspiro[4.5]decan-3-yl]-acetyl]amino]-N,2-dimethyl-propionamide | INT 993 | 2-amino-N,2-dimethylpropanamide | SC_1308 | 498.3 |
| SC_1009 | CIS-2-[[2-[1-(Cyclobutyl-methyl)-8-dimethylamino-2-oxo-8-phenyl-1,3-diazaspiro[4.5]decan-3-yl]-acetyl]-methyl-amino]-N,2-dimethyl-propionamide | INT 993 | N,2-dimethyl-2-(methylamino)propanamide | SC_1308 | 512.4 |

-continued

| Example | Chemical Name | Reactant I | Reactant II | in analogy to method | m/z [M + H]+ |
|---|---|---|---|---|---|
| SC_1010 | CIS-2-[1-(Cyclobutyl-methyl)-8-dimethylamino-2-oxo-8-phenyl-1,3-diazaspiro[4.5]decan-3-yl]-N-[(dimethyl-carbamoyl)-methyl]-N-methyl-acetamide | INT 993 | N,N-dimethyl-2-(methylamino)acetamide | SC_1308 | 498.3 |
| SC_1011 | CIS-2-[[2-[1-(Cyclobutyl-methyl)-8-dimethylamino-2-oxo-8-phenyl-1,3-diazaspiro[4.5]decan-3-yl]-acetyl]amino]-2-methyl-propionamide | INT 993 | 2-amino-2-methylpropanamide | SC_1308 | 484.3 |
| SC_1012 | CIS-2-[1-(Cyclobutyl-methyl)-8-dimethylamino-2-oxo-8-phenyl-1,3-diazaspiro[4.5]decan-3-yl]-N-(5-methoxy-pyridin-2-yl)-acetamide | INT 993 | 5-methoxypyridin-2-amine | SC_1308 | 506.3 |
| SC_1013 | CIS-2-[1-(Cyclobutyl-methyl)-8-dimethylamino-2-oxo-8-phenyl-1,3-diazaspiro[4.5]decan-3-yl]-N-(6-methoxy-pyridin-2-yl)-acetamide | INT 993 | 6-methoxypyridin-2-amine | SC_1308 | 506.3 |
| SC_1014 | CIS-2-[1-(Cyclobutyl-methyl)-8-dimethylamino-2-oxo-8-phenyl-1,3-diazaspiro[4.5]decan-3-yl]-N-(4-methoxy-pyridin-2-yl)-acetamide | INT 993 | 4-methoxypyridin-2-amine | SC_1308 | 506.3 |
| SC_1015 | CIS-6-[[2-[1-(Cyclobutyl-methyl)-8-dimethylamino-2-oxo-8-phenyl-1,3-diazaspiro[4.5]decan-3-yl]-acetyl]amino]-N-methyl-pyridine-2-carboxylic acid amide | INT 999 | 6-amino-N-methylpicolinamide | SC_1073 | 533.3 |
| SC_1016 | CIS-2-[1-(Cyclobutyl-methyl)-8-dimethylamino-2-oxo-8-phenyl-1,3-diazaspiro[4.5]decan-3-yl]-N-[(3-hydroxy-cyclobutyl)-methyl]-acetamide | INT 993 | cis-3-(aminomethyl)cyclobutanol | SC_1308 | 483.3 |
| SC_1017 | CIS-2-[1-(Cyclobutyl-methyl)-8-dimethylamino-2-oxo-8-phenyl-1,3-diazaspiro[4.5]decan-3-yl]-N-[(3-hydroxy-cyclobutyl)-methyl]-acetamide | INT 993 | trans-3-(aminomethyl)cyclobutanol | SC_1308 | 483.3 |
| SC_1018 | CIS-2-[1-(Cyclobutyl-methyl)-8-dimethylamino-2-oxo-8-phenyl-1,3-diazaspiro[4.5]decan-3-yl]-N-[(1-hydroxy-cyclopropyl)-methyl]-acetamide | INT 993 | 1-(aminomethyl)cyclopropanol | SC_1308 | 469.3 |
| SC_1019 | CIS-2-[1-(Cyclobutyl-methyl)-8-dimethylamino-2-oxo-8-phenyl-1,3-diazaspiro[4.5]decan-3-yl]-N-(3-morpholin-4-yl-3-oxo-propyl)-acetamide | INT 993 | 3-amino-1-morpholinopropan-1-one | SC_1308 | 540.3 |
| SC_1020 | CIS-N-(1-Cyano-cyclopropyl)-2-[1-(cyclobutyl-methyl)-8-dimethylamino-2-oxo-8-phenyl-1,3-diazaspiro[4.5]decan-3-yl]-acetamide | INT 993 | 1-aminocyclopropanecarbonitrile | SC_1308 | 464.3 |
| SC_1021 | CIS-2-[1-(Cyclobutyl-methyl)-8-dimethylamino-2-oxo-8-phenyl-1,3-diazaspiro[4.5]decan-3-yl]-N-[(3-hydroxy-cyclopentyl)-methyl]-acetamide | INT 993 | 3-(aminomethyl)cyclopentanol | SC_1308 | 497.3 |

-continued

| Example | Chemical Name | Reactant I | Reactant II | in analogy to method | m/z [M + H]+ |
|---|---|---|---|---|---|
| SC_1022 | CIS-2-[1-(Cyclobutyl-methyl)-8-dimethylamino-2-oxo-8-phenyl-1,3-diazaspiro[4.5]decan-3-yl]-N-[[(2R)-2-hydroxy-cyclohexyl]-methyl]-acetamide | INT 993 | (1R)-2-(aminomethyl)cyclohexanol | SC_1308 | 511.4 |
| SC_1023 | CIS-2-[1-(Cyclobutyl-methyl)-8-dimethylamino-2-oxo-8-phenyl-1,3-diazaspiro[4.5]decan-3-yl]-N-[2-[2-[2-(2-methoxy-ethoxy)-ethoxy]-ethoxy]-ethyl]-acetamide | INT 993 | 2,5,8,11-tetraoxatridecan-13-amine | SC_1308 | 589.4 |
| SC_1024 | CIS-2-[1-(Cyclobutyl-methyl)-8-dimethylamino-2-oxo-8-phenyl-1,3-diazaspiro[4.5]decan-3-yl]-N-[(1-hydroxy-cyclohexyl)-methyl]-acetamide | INT 993 | 1-(aminomethyl)cyclohexanol | SC_1308 | 511.4 |
| SC_1025 | CIS-2-[1-(Cyclobutyl-methyl)-8-dimethylamino-2-oxo-8-phenyl-1,3-diazaspiro[4.5]decan-3-yl]-N-[2-[2-[2-[2-(2-methoxy-ethoxy)-ethoxy]-ethoxy]-ethoxy]-ethyl]-acetamide | INT 993 | 2,5,8,11,14-pentaoxahexadecan-16-amine | SC_1308 | 633.4 |
| SC_1026 | CIS-N-(6-Cyano-pyridin-2-yl)-2-[1-(cyclobutyl-methyl)-8-dimethylamino-2-oxo-8-phenyl-1,3-diazaspiro[4.5]decan-3-yl]-acetamide | INT 993 | 6-aminopicolinonitrile | SC_1308 | 501.3 |
| SC_1027 | CIS-2-[[2-[1-(Cyclobutyl-methyl)-8-dimethylamino-2-oxo-8-phenyl-1,3-diazaspiro[4.5]decan-3-yl]-acetyl]amino]-nicotinic acid methyl ester | INT 993 | methyl 2-aminonicotinate | SC_1308 | 534.3 |
| SC_1028 | CIS-2-[1-(Cyclobutyl-methyl)-8-dimethylamino-2-oxo-8-phenyl-1,3-diazaspiro[4.5]decan-3-yl]-N-(3-methoxy-pyridin-2-yl)-acetamide | INT 993 | 3-methoxypyridin-2-amine | SC_1308 | 506.3 |
| SC_1029 | CIS-2-[1-(Cyclobutyl-methyl)-8-dimethylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide | INT 993 | 2,5,8,11,14,17-hexaoxanonadecan-19-amine | SC_1308 | 677.4 |
| SC_1030 | CIS-N-(4-Cyano-pyridin-2-yl)-2-[1-(cyclobutyl-methyl)-8-dimethylamino-2-oxo-8-phenyl-1,3-diazaspiro[4.5]decan-3-yl]-acetamide | INT 993 | 2-aminoisonicotinonitrile | SC_1308 | 501.3 |
| SC_1031 | CIS-2-[1-(Cyclobutyl-methyl)-8-dimethylamino-2-oxo-8-phenyl-1,3-diazaspiro[4.5]decan-3-yl]-N-(5-methoxy-pyrimidin-2-yl)-acetamide | INT 993 | 5-methoxypyrimidin-2-amine | SC_1308 | 507.3 |
| SC_1032 | CIS-2-[[2-[1-(Cyclobutyl-methyl)-8-dimethylamino-2-oxo-8-phenyl-1,3-diazaspiro[4.5]decan-3-yl]-acetyl]amino]-isonicotinic acid methyl ester | INT 993 | methyl 2-aminoisonicotinate | SC_1308 | 534.3 |
| SC_1033 | CIS-2-[1-(Cyclobutyl-methyl)-8-dimethylamino-2-oxo-8-phenyl-1,3-diazaspiro[4.5]decan-3-yl]-N-(2-methoxy-pyridin-4-yl)-acetamide | INT 993 | 2-methoxypyridin-4-amine | SC_1051 | 506.3 |

-continued

| Example | Chemical Name | Reactant I | Reactant II | in analogy to method | m/z [M + H]+ |
|---|---|---|---|---|---|
| SC_1034 | CIS-2-[1-(Cyclobutyl-methyl)-8-dimethylamino-2-oxo-8-phenyl-1,3-diazaspiro[4.5]decan-3-yl]-N-(6-fluoro-pyridin-3-yl)-acetamide | INT 993 | 6-fluoropyridin-3-amine | SC_1051 | 494.3 |
| SC_1035 | CIS-2-[1-(Cyclobutyl-methyl)-8-dimethylamino-2-oxo-8-phenyl-1,3-diazaspiro[4.5]decan-3-yl]-N-(2-methyl-pyrimidin-5-yl)-acetamide | INT 993 | 2-methylpyrimidin-5-amine | SC_1051 | 491.3 |
| SC_1036 | CIS-2-[1-(Cyclobutyl-methyl)-8-dimethylamino-2-oxo-8-phenyl-1,3-diazaspiro[4.5]decan-3-yl]-N-(5-methyl-pyrimidin-2-yl)-acetamide | INT 993 | 5-methylpyrimidin-2-amine | SC_1051 | 491.3 |
| SC_1037 | CIS-2-[1-(Cyclobutyl-methyl)-8-dimethylamino-2-oxo-8-phenyl-1,3-diazaspiro[4.5]decan-3-yl]-N-(3-fluoro-pyridin-2-yl)-acetamide | INT 993 | 3-fluoropyridin-2-amine | SC_1051 | 494.3 |
| SC_1038 | CIS-2-[1-(Cyclobutyl-methyl)-8-dimethylamino-2-oxo-8-phenyl-1,3-diazaspiro[4.5]decan-3-yl]-N-(3-fluoro-pyridin-4-yl)-acetamide | INT 993 | 3-fluoropyridin-4-amine | SC_1051 | 494.3 |
| SC_1039 | CIS-2-[1-(Cyclobutyl-methyl)-8-dimethylamino-2-oxo-8-phenyl-1,3-diazaspiro[4.5]decan-3-yl]-N-(6-methoxy-pyridin-3-yl)-acetamide | INT 993 | 6-methoxypyridin-3-amine | SC_1051 | 506.3 |
| SC_1040 | CIS-2-[1-(Cyclobutyl-methyl)-8-dimethylamino-2-oxo-8-phenyl-1,3-diazaspiro[4.5]decan-3-yl]-N-(2-methyl-pyridin-3-yl)-acetamide | INT 993 | 2-methylpyridin-3-amine | SC_1051 | 490.3 |
| SC_1041 | CIS-2-[1-(Cyclobutyl-methyl)-8-dimethylamino-2-oxo-8-phenyl-1,3-diazaspiro[4.5]decan-3-yl]-N-(4-methyl-pyridin-3-yl)-acetamide | INT 993 | 4-methylpyridin-3-amine | SC_1051 | 490.3 |
| SC_1042 | CIS-2-[1-(Cyclobutyl-methyl)-8-dimethylamino-2-oxo-8-phenyl-1,3-diazaspiro[4.5]decan-3-yl]-N-(3-methyl-pyridin-4-yl)-acetamide | INT 993 | 3-methylpyridin-4-amine | SC_1051 | 490.3 |
| SC_1043 | CIS-2-[1-(Cyclobutyl-methyl)-8-dimethylamino-2-oxo-8-phenyl-1,3-diazaspiro[4.5]decan-3-yl]-N-(6-methyl-pyridin-3-yl)-acetamide | INT 993 | 6-methylpyridin-3-amine | SC_1051 | 490.3 |
| SC_1044 | CIS-2-[1-(Cyclobutyl-methyl)-8-dimethylamino-2-oxo-8-phenyl-1,3-diazaspiro[4.5]decan-3-yl]-N-(5-fluoro-pyridin-2-yl)-acetamide | INT 993 | 5-fluoropyridin-2-amine | SC_1051 | 494.3 |
| SC_1045 | CIS-2-[1-(Cyclobutyl-methyl)-8-dimethylamino-2-oxo-8-phenyl-1,3-diazaspiro[4.5]decan-3-yl]-N-(5-methyl-pyridin-2-yl)-acetamide | INT 993 | 5-methylpyridin-2-amine | SC_1051 | 490.3 |

-continued

| Example | Chemical Name | Reactant I | Reactant II | in analogy to method | m/z [M + H]+ |
|---|---|---|---|---|---|
| SC_1046 | CIS-2-[1-(Cyclobutyl-methyl)-8-dimethylamino-2-oxo-8-phenyl-1,3-diazaspiro[4.5]decan-3-yl]-N-(4-methyl-pyridin-2-yl)-acetamide | INT 993 | 4-methylpyridin-2-amine | SC_1051 | 490.3 |
| SC_1047 | CIS-2-[1-(Cyclobutyl-methyl)-8-dimethylamino-2-oxo-8-phenyl-1,3-diazaspiro[4.5]decan-3-yl]-N-(3-methyl-pyridin-2-yl)-acetamide | INT 993 | 3-methylpyridin-2-amine | SC_1051 | 490.3 |
| SC_1048 | CIS-2-[1-(Cyclobutyl-methyl)-8-dimethylamino-2-oxo-8-phenyl-1,3-diazaspiro[4.5]decan-3-yl]-N-(3-methoxy-pyridin-4-yl)-acetamide | INT 993 | 3-methoxypyridin-4-amine | SC_1051 | 506.3 |
| SC_1049 | CIS-2-[1-(Cyclobutyl-methyl)-8-dimethylamino-2-oxo-8-phenyl-1,3-diazaspiro[4.5]decan-3-yl]-N-(6-methoxy-pyridazin-3-yl)-acetamide | INT 993 | 6-methoxypyridazin-3-amine | SC_1051 | 507.3 |
| SC_1050 | CIS-2-[1-(Cyclobutyl-methyl)-8-dimethylamino-2-oxo-8-phenyl-1,3-diazaspiro[4.5]decan-3-yl]-N-(5-methylsulfonyl-pyridin-2-yl)-acetamide | INT 993 | 5-(methylsulfonyl)pyridin-2-amine | SC_1051 | 554.3 |
| SC_1052 | CIS-2-[1-(Cyclobutyl-methyl)-8-dimethylamino-2-oxo-8-phenyl-1,3-diazaspiro[4.5]decan-3-yl]-N-(6-methylsulfonyl-pyridin-3-yl)-acetamide | INT 993 | 6-(methylsulfonyl)pyridin-3-amine | SC_1051 | 554.3 |
| SC_1053 | CIS-2-[1-(Cyclobutyl-methyl)-8-dimethylamino-2-oxo-8-phenyl-1,3-diazaspiro[4.5]decan-3-yl]-N-(6-methoxy-pyrazin-2-yl)-acetamide | INT 993 | 6-methoxypyrazin-2-amine | SC_1051 | 507.3 |
| SC_1054 | CIS-2-[1-(Cyclobutyl-methyl)-8-dimethylamino-2-oxo-8-phenyl-1,3-diazaspiro[4.5]decan-3-yl]-N-(4-methoxy-pyridin-2-yl)-acetamide | INT 993 | 4-methoxypyridin-2-amine | SC_1051 | 506.3 |
| SC_1055 | CIS-2-[1-(Cyclobutyl-methyl)-8-dimethylamino-2-oxo-8-phenyl-1,3-diazaspiro[4.5]decan-3-yl]-N-(4-methoxy-pyrimidin-2-yl)-acetamide | INT 993 | 4-methoxypyrimidin-2-amine | SC_1051 | 507.3 |
| SC_1056 | CIS-2-[1-(Cyclobutyl-methyl)-8-dimethylamino-2-oxo-8-phenyl-1,3-diazaspiro[4.5]decan-3-yl]-N-(oxazol-5-yl-methyl)-acetamide | INT 993 | oxazol-5-ylmethanamine | SC_1051 | 480.3 |
| SC_1057 | CIS-2-[1-(Cyclobutyl-methyl)-8-dimethylamino-2-oxo-8-phenyl-1,3-diazaspiro[4.5]decan-3-yl]-N-(oxazol-2-yl-methyl)-acetamide | INT 993 | oxazol-2-ylmethanamine | SC_1051 | 480.3 |
| SC_1058 | CIS-1-(Cyclobutyl-methyl)-3-[2-[(3S,4S)-3,4-dihydroxy-piperidin-1-yl]-2-oxo-ethyl]-8-dimethylamino-8-phenyl-1,3-diazaspiro[4.5]decan-2-one | INT 993 | (3S,4S)-piperidine-3,4-diol | SC_1051 | 499.3 |
| SC_1059 | CIS-1-(Cyclobutyl-methyl)-3-[2-[(3S,4S)-3,4-dihydroxy-pyrrolidin-1-yl]-2-oxo-ethyl]-8-dimethylamino-8-phenyl-1,3-diazaspiro[4.5]decan-2-one | INT 993 | (3S,4S)-pyrrolidine-3,4-diol | SC_1051 | 485.3 |

-continued

| Example | Chemical Name | Reactant I | Reactant II | in analogy to method | m/z [M + H]+ |
|---|---|---|---|---|---|
| SC_1060 | CIS-1-(Cyclobutyl-methyl)-3-[2-[(3S,4R)-3,4-dihydroxy-pyrrolidin-1-yl]-2-oxo-ethyl]-8-dimethylamino-8-phenyl-1,3-diazaspiro[4.5]decan-2-one | INT 993 | (3S,4R)-pyrrolidine-3,4-diol | SC_1051 | 485.3 |
| SC_1061 | CIS-2-[1-(Cyclobutyl-methyl)-8-dimethylamino-2-oxo-8-phenyl-1,3-diazaspiro[4.5]decan-3-yl]-N-cyclopropyl-acetamide | INT 993 | cyclopropanamine | SC_1051 | 439.3 |
| SC_1062 | CIS-2-[1-(Cyclobutyl-methyl)-8-dimethylamino-2-oxo-8-phenyl-1,3-diazaspiro[4.5]decan-3-yl]-N-(2-hydroxy-ethyl)-N-methyl-acetamide | INT 993 | 2-(methylamino)ethanol | SC_1051 | 457.3 |
| SC_1063 | CIS-1-(Cyclobutyl-methyl)-8-dimethylamino-3-[2-(3-hydroxy-piperidin-1-yl)-2-oxo-ethyl]-8-phenyl-1,3-diazaspiro[4.5]decan-2-one | INT 993 | piperidin-3-ol | SC_1051 | 483.3 |
| SC_1064 | CIS-2-[1-(Cyclobutyl-methyl)-8-dimethylamino-2-oxo-8-phenyl-1,3-diazaspiro[4.5]decan-3-yl]-N-[(1-hydroxy-cyclobutyl)-methyl]-acetamide | INT 993 | 1-(aminomethyl)cyclobutanol | SC_1051 | 483.3 |
| SC_1065 | CIS-2-[[2-[1-(Cyclobutyl-methyl)-8-dimethylamino-2-oxo-8-phenyl-1,3-diazaspiro[4.5]decan-3-yl]-acetyl]amino]-N,N-dimethyl-acetamide | INT 993 | 2-amino-N,N-dimethylacetamide | SC_1051 | 484.3 |
| SC_1066 | CIS-1-(Cyclobutyl-methyl)-8-dimethylamino-3-[2-oxo-2-(5,6,7,8-tetrahydro-[1,2,4]triazolo[1,5-a]pyrazin-7-yl)-ethyl]-8-phenyl-1,3-diazaspiro[4.5]decan-2-one | INT 993 | 5,6,7,8-tetrahydro-[1,2,4]triazolo[1,5-a]pyrazine | SC_1051 | 506.3 |
| SC_1067 | CIS-3-[[2-[1-(Cyclobutyl-methyl)-8-dimethylamino-2-oxo-8-phenyl-1,3-diazaspiro[4.5]decan-3-yl]-acetyl]amino]-N,N-dimethyl-propionamide | INT 993 | 3-amino-N,N-dimethylpropanamide | SC_1051 | 498.3 |
| SC_1068 | CIS-2-[1-(Cyclobutyl-methyl)-8-dimethylamino-2-oxo-8-phenyl-1,3-diazaspiro[4.5]decan-3-yl]-N-[2-[2-[2-[2-[2-[2-(2-methoxy-ethoxy)-ethoxy]-ethoxy]-ethoxy]-ethoxy]-ethyl]-acetamide | INT 993 | 2,5,8,11,14,17,20,23-octa-oxapentacosan-25-amine | SC_1308 | 765.5 |
| SC_1069 | CIS-2-[1-(Cyclobutyl-methyl)-8-dimethylamino-2-oxo-8-phenyl-1,3-diazaspiro[4.5]decan-3-yl]-N-(4-methoxy-pyrimidin-5-yl)-acetamide | INT 993 | 4-methoxypyrimidin-5-amine | SC_1308 | 507.3 |
| SC_1070 | CIS-2-[1-(Cyclobutyl-methyl)-8-dimethylamino-2-oxo-8-phenyl-1,3-diazaspiro[4.5]decan-3-yl]-N-(2-methoxy-pyrimidin-5-yl)-acetamide | INT 993 | 2-methoxypyrimidin-5-amine | SC_1308 | 507.3 |
| SC_1072 | CIS-N-(5-Cyano-pyridin-2-yl)-2-[1-(cyclobutyl-methyl)-8-dimethylamino-2-oxo-8-phenyl-1,3-diazaspiro[4.5]decan-3-yl]-acetamide | INT 993 | 6-aminonicotinonitrile | SC_1308 | 501.3 |

-continued

| Example | Chemical Name | Reactant I | Reactant II | in analogy to method | m/z [M + H]+ |
|---|---|---|---|---|---|
| SC_1074 | CIS-2-[1-(Cyclobutyl-methyl)-8-dimethylamino-2-oxo-8-phenyl-1,3-diazaspiro[4.5]decan-3-yl]-N-(5-methoxy-pyrimidin-4-yl)-acetamide | INT 993 | 5-methoxypyrimidin-4-amine | SC_1308 | 507.3 |
| SC_1075 | CIS-N-(2-Cyano-pyrimidin-5-yl)-2-[1-(cyclobutyl-methyl)-8-dimethylamino-2-oxo-8-phenyl-1,3-diazaspiro[4.5]decan-3-yl]-acetamide | INT 993 | 5-aminopyrimidine-2-carbonitrile | SC_1308 | 502.3 |
| SC_1077 | CIS-N-(3-Cyano-pyridin-2-yl)-2-[1-(cyclobutyl-methyl)-8-dimethylamino-2-oxo-8-phenyl-1,3-diazaspiro[4.5]decan-3-yl]-acetamide | INT 993 | 2-aminonicotinonitrile | SC_1308 | 501.3 |
| SC_1078 | CIS-2-[[2-[1-(Cyclobutyl-methyl)-8-dimethylamino-2-oxo-8-phenyl-1,3-diazaspiro[4.5]decan-3-yl]-acetyl]amino]-acetamide | INT 993 | 2-aminoacetamide | SC_1308 | 456.3 |
| SC_1079 | CIS-6-[[2-[1-(Cyclobutyl-methyl)-8-dimethylamino-2-oxo-8-phenyl-1,3-diazaspiro[4.5]decan-3-yl]-acetyl]amino]-pyridine-3-carboxylic acid amide | SC_1072 | — | SC_1076 | 519.3 |
| SC_1080 | CIS-N-(4-Cyano-pyrimidin-2-yl)-2-[1-(cyclobutyl-methyl)-8-dimethylamino-2-oxo-8-phenyl-1,3-diazaspiro[4.5]decan-3-yl]-acetamide | INT 993 | 2-aminopyrimidine-4-carbonitrile | SC_1308 | 502.3 |
| SC_1081 | CIS-2-[1-(Cyclobutyl-methyl)-8-dimethylamino-2-oxo-8-phenyl-1,3-diazaspiro[4.5]decan-3-yl]-N-([1,3,4]thiadiazol-2-yl)-acetamide | INT 993 | 1,3,4-thiadiazol-2-amine | SC_1051 | 483.2 |
| SC_1082 | CIS-2-[1-(Cyclobutyl-methyl)-8-dimethylamino-2-oxo-8-phenyl-1,3-diazaspiro[4.5]decan-3-yl]-N-thiazol-2-yl-acetamide | INT 993 | thiazol-2-amine | SC_1051 | 482.3 |
| SC_1083 | CIS-2-[1-(Cyclobutyl-methyl)-8-dimethylamino-2-oxo-8-phenyl-1,3-diazaspiro[4.5]decan-3-yl]-N-(5-methyl-isoxazol-3-yl)-acetamide | INT 993 | 5-methylisoxazol-3-amine | SC_1051 | 480.3 |
| SC_1084 | CIS-2-[1-(Cyclobutyl-methyl)-8-dimethylamino-2-oxo-8-phenyl-1,3-diazaspiro[4.5]decan-3-yl]-N-isoxazol-3-yl-acetamide | INT 993 | isoxazol-3-amine | SC_1051 | 466.3 |
| SC_1085 | CIS-2-[1-(Cyclobutyl-methyl)-8-dimethylamino-2-oxo-8-phenyl-1,3-diazaspiro[4.5]decan-3-yl]-N-(1-methyl-1H-pyrazol-3-yl)-acetamide | INT 993 | 1-methyl-1H-pyrazol-3-amine | SC_1051 | 479.3 |
| SC_1086 | CIS-N-(4-Cyano-5-methylsulfanyl-1H-pyrazol-3-yl)-2-[1-(cyclobutyl-methyl)-8-dimethylamino-2-oxo-8-phenyl-1,3-diazaspiro[4.5]decan-3-yl]-acetamide | INT 993 | 3-amino-5-(methylthio)-1H-pyrazole-4-carbonitrile | SC_1051 | 536.3 |
| SC_1087 | CIS-2-[1-(Cyclobutyl-methyl)-8-dimethylamino-2-oxo-8-phenyl-1,3-diazaspiro[4.5]decan-3-yl]-N-(5-methoxy-pyrazin-2-yl)-acetamide | INT 993 | 5-methoxypyrazin-2-amine | SC_1051 | 507.3 |

-continued

| Example | Chemical Name | Reactant I | Reactant II | in analogy to method | m/z [M + H]+ |
|---|---|---|---|---|---|
| SC_1088 | CIS-2-[1-(Cyclobutyl-methyl)-8-dimethylamino-2-oxo-8-phenyl-1,3-diazaspiro[4.5]decan-3-yl]-N-(pyridazin-4-yl-methyl)-acetamide | INT 993 | pyridazin-4-ylmethanamine | SC_1051 | 491.3 |
| SC_1089 | CIS-2-[1-(Cyclobutyl-methyl)-8-dimethylamino-2-oxo-8-phenyl-1,3-diazaspiro[4.5]decan-3-yl]-N-[(2-hydroxyphenyl)-methyl]-acetamide | INT 993 | 2-(aminomethyl)phenol | SC_1051 | 505.3 |
| SC_1090 | CIS-2-[1-(Cyclobutyl-methyl)-8-dimethylamino-2-oxo-8-phenyl-1,3-diazaspiro[4.5]decan-3-yl]-N-[(1-methyl-1H-imidazol-4-yl)-methyl]-acetamide | INT 993 | (1-methyl-1H-imidazol-4-yl)methanamine | SC_1051 | 493.3 |
| SC_1091 | CIS-2-[1-(Cyclobutyl-methyl)-8-dimethylamino-2-oxo-8-phenyl-1,3-diazaspiro[4.5]decan-3-yl]-N-[(4-methyl-pyridin-3-yl)-methyl]-acetamide | INT 993 | (4-methylpyridin-3-yl)methanamine | SC_1051 | 504.3 |
| SC_1092 | CIS-2-[1-(Cyclobutyl-methyl)-8-dimethylamino-2-oxo-8-phenyl-1,3-diazaspiro[4.5]decan-3-yl]-N-(pyrimidin-2-yl-methyl)-acetamide | INT 993 | pyrimidin-2-ylmethanamine | SC_1051 | 491.3 |
| SC_1093 | CIS-2-[1-(Cyclobutyl-methyl)-8-dimethylamino-2-oxo-8-phenyl-1,3-diazaspiro[4.5]decan-3-yl]-N-(pyridazin-3-yl-methyl)-acetamide | INT 993 | pyridazin-3-ylmethanamine | SC_1051 | 491.3 |
| SC_1094 | CIS-2-[1-(Cyclobutyl-methyl)-8-dimethylamino-2-oxo-8-phenyl-1,3-diazaspiro[4.5]decan-3-yl]-N-(pyrimidin-4-yl-methyl)-acetamide | INT 993 | pyrimidin-4-ylmethanamine | SC_1051 | 491.3 |
| SC_1095 | CIS-2-[1-(Cyclobutyl-methyl)-8-dimethylamino-2-oxo-8-phenyl-1,3-diazaspiro[4.5]decan-3-yl]-N-(pyrazin-2-yl-methyl)-acetamide | INT 993 | pyrazin-2-ylmethanamine | SC_1051 | 491.3 |
| SC_1096 | CIS-2-[1-(Cyclobutyl-methyl)-8-dimethylamino-2-oxo-8-phenyl-1,3-diazaspiro[4.5]decan-3-yl]-N-(oxazol-4-yl-methyl)-acetamide | INT 993 | oxazol-4-ylmethanamine | SC_1051 | 480.3 |
| SC_1097 | CIS-2-[1-(Cyclobutyl-methyl)-8-dimethylamino-2-oxo-8-phenyl-1,3-diazaspiro[4.5]decan-3-yl]-N-[(2-methyl-pyridin-3-yl)-methyl]-acetamide | INT 993 | (2-methylpyridin-3-yl)methanamine | SC_1051 | 504.3 |
| SC_1098 | CIS-2-[1-(Cyclobutyl-methyl)-8-dimethylamino-2-oxo-8-phenyl-1,3-diazaspiro[4.5]decan-3-yl]-N-[(2-methoxy-pyridin-3-yl)-methyl]-acetamide | INT 993 | (2-methoxypyridin-3-yl)methanamine | SC_1051 | 520.3 |
| SC_1099 | CIS-2-[1-(Cyclobutyl-methyl)-8-dimethylamino-2-oxo-8-phenyl-1,3-diazaspiro[4.5]decan-3-yl]-N-[(4-methoxy-pyridin-3-yl)-methyl]-acetamide | INT 993 | (4-methoxypyridin-3-yl)methanamine | SC_1051 | 520.3 |
| SC_1100 | CIS-2-[1-(Cyclobutyl-methyl)-8-dimethylamino-2-oxo-8-phenyl-1,3-diazaspiro[4.5]decan-3-yl]-N-[(6-methyl-pyridin-2-yl)-methyl]-acetamide | INT 993 | (6-methylpyridin-2-yl)methanamine | SC_1051 | 504.3 |

-continued

| Example | Chemical Name | Reactant I | Reactant II | in analogy to method | m/z [M + H]+ |
|---|---|---|---|---|---|
| SC_1101 | CIS-2-[1-(Cyclobutyl-methyl)-8-dimethylamino-2-oxo-8-phenyl-1,3-diazaspiro[4.5]decan-3-yl]-N-[(6-methoxy-pyridin-2-yl)-methyl]-acetamide | INT 993 | (6-methoxypyridin-2-yl)methanamine | SC_1051 | 520.3 |
| SC_1102 | CIS-2-[1-(Cyclobutyl-methyl)-8-dimethylamino-2-oxo-8-phenyl-1,3-diazaspiro[4.5]decan-3-yl]-N-[(2-methoxyphenyl)-methyl]-acetamide | INT 993 | (2-methoxyphenyl)methanamine | SC_1051 | 519.3 |
| SC_1103 | CIS-2-[1-(Cyclobutyl-methyl)-8-dimethylamino-2-oxo-8-phenyl-1,3-diazaspiro[4.5]decan-3-yl]-N-(o-tolyl-methyl)-acetamide | INT 993 | o-tolylmethanamine | SC_1051 | 503.3 |
| SC_1104 | CIS-6-[[2-[1-(Cyclobutyl-methyl)-8-dimethylamino-2-oxo-8-phenyl-1,3-diazaspiro[4.5]decan-3-yl]-acetyl]amino]-N-methyl-pyridine-3-carboxylic acid amide | INT 999 | 6-amino-N-methylnicotinamide | SC_1073 | 533.3 |
| SC_1105 | CIS-2-[[2-[1-(Cyclobutyl-methyl)-8-dimethylamino-2-oxo-8-phenyl-1,3-diazaspiro[4.5]decan-3-yl]-acetyl]amino]-pyridine-4-carboxylic acid amide | SC 1030 | — | SC_1076 | 519.3 |
| SC_1106 | CIS-2-[1-(Cyclobutyl-methyl)-8-dimethylamino-2-oxo-8-phenyl-1,3-diazaspiro[4.5]decan-3-yl]-N-(6-methoxy-pyrimidin-4-yl)-acetamide | INT 993 | 6-methoxypyrimidin-4-amine | SC_1308 | 507.3 |
| SC_1107 | CIS-2-[1-(Cyclobutyl-methyl)-8-dimethylamino-2-oxo-8-phenyl-1,3-diazaspiro[4.5]decan-3-yl]-N-(2-methoxy-pyrimidin-4-yl)-acetamide | INT 993 | 2-methoxypyrimidin-4-amine | SC_1308 | 507.3 |
| SC_1109 | CIS-2-[1-(Cyclobutyl-methyl)-8-dimethylamino-2-oxo-8-phenyl-1,3-diazaspiro[4.5]decan-3-yl]-N-(4-hydroxy-pyrimidin-5-yl)-acetamide | SC 1069 | | SC_1110 | 493.3 |
| SC_1111 | CIS-2-[1-(Cyclobutyl-methyl)-8-dimethylamino-2-oxo-8-phenyl-1,3-diazaspiro[4.5]decan-3-yl]-N-(5-hydroxy-pyridin-2-yl)-acetamide | INT 993 | 6-aminopyridin-3-ol | SC_1308 | 492.3 |
| SC_1112 | CIS-2-[1-(Cyclobutyl-methyl)-8-dimethylamino-2-oxo-8-phenyl-1,3-diazaspiro[4.5]decan-3-yl]-N-(1,1-dioxo-thian-4-yl)-acetamide | INT 993 | 4-aminotetrahydro-2H-thiopyran 1,1-dioxide | SC_1308 | 531.3 |
| SC_1113 | CIS-1-(Cyclobutyl-methyl)-8-dimethylamino-3-[2-(1,1-dioxo-[1,4]thiazinan-4-yl)-2-oxo-ethyl]-8-phenyl-1,3-diazaspiro[4.5]decan-2-one | INT 993 | thiomorpholine 1,1-dioxide | SC_1308 | 517.3 |
| SC_1114 | CIS-2-[8-Dimethylamino-1-(2-methoxy-ethyl)-2-oxo-8-phenyl-1,3-diazaspiro[4.5]decan-3-yl]-N-pyrimidin-4-yl-acetamide | INT 997 | pyrimidin-4-amine | SC_1308 | 467.3 |
| SC_1115 | CIS-2-[8-Dimethylamino-1-(2-methoxy-ethyl)-2-oxo-8-phenyl-1,3-diazaspiro[4.5]decan-3-yl]-N-methyl-acetamide | INT 997 | methylamine | SC_1308 | 403.3 |

-continued

| Example | Chemical Name | Reactant I | Reactant II | in analogy to method | m/z [M + H]+ |
|---|---|---|---|---|---|
| SC_1117 | CIS-N-(5-Cyano-pyrimidin-4-yl)-2-[1-(cyclobutyl-methyl)-8-dimethylamino-2-oxo-8-phenyl-1,3-diazaspiro[4.5]decan-3-yl]-acetamide | INT 993 | 4-aminopyrimidine-5-carbonitrile | SC_1308 | 502.3 |
| SC_1118 | CIS-2-[1-(Cyclobutyl-methyl)-8-dimethylamino-2-oxo-8-phenyl-1,3-diazaspiro[4.5]decan-3-yl]-N-(5-methylsulfanyl-pyridin-2-yl)-acetamide | INT 993 | 5-(methylthio)pyridin-2-amine | SC_1308 | 522.3 |
| SC_1119 | CIS-2-[1-(Cyclobutyl-methyl)-8-dimethylamino-2-oxo-8-phenyl-1,3-diazaspiro[4.5]decan-3-yl]-N-(4-methoxy-pyrimidin-2-yl)-acetamide | INT 993 | 4-methoxypyrimidin-2-amine | SC_1308 | 507.3 |
| SC_1120 | CIS-2-[1-(Cyclobutyl-methyl)-8-dimethylamino-2-oxo-8-phenyl-1,3-diazaspiro[4.5]decan-3-yl]-N-(6-methylsulfanyl-pyridin-2-yl)-acetamide | INT 993 | 6-(methylthio)pyridin-2-amine | SC_1308 | 522.3 |
| SC_1121 | CIS-2-[8-Dimethylamino-1-(2-methoxy-ethyl)-2-oxo-8-phenyl-1,3-diazaspiro[4.5]decan-3-yl]-N-(2-hydroxy-ethyl)-acetamide | INT 997 | 2-aminoethanol | SC_1308 | 433.3 |
| SC_1122 | CIS-2-[[2-8-Dimethylamino-1-(2-methoxy-ethyl)-2-oxo-8-phenyl-1,3-diazaspiro[4.5]decan-3-yl]-acetyl]amino]-acetamide | INT 997 | 2-aminoacetamide | SC_1308 | 446.3 |
| SC_1123 | CIS-2-[1-(Cyclobutyl-methyl)-8-dimethylamino-2-oxo-8-phenyl-1,3-diazaspiro[4.5]decan-3-yl]-N-methyl-acetamide | INT 993 | methylamine | SC_1308 | 413.3 |
| SC_1124 | CIS-2-[1-(Cyclobutyl-methyl)-8-dimethylamino-2-oxo-8-phenyl-1,3-diazaspiro[4.5]decan-3-yl]-N-(2-hydroxy-ethyl)-acetamide | INT 993 | 2-aminoethanol | SC_1308 | 443.3 |
| SC_1125 | CIS-2-[1-(Cyclobutyl-methyl)-8-dimethylamino-2-oxo-8-phenyl-1,3-diazaspiro[4.5]decan-3-yl]-N-(6-hydroxy-pyridin-2-yl)-acetamide | INT 993 | 6-aminopyridin-2-ol | SC_1308 | 492.3 |
| SC_1126 | CIS-2-[1-(Cyclobutyl-methyl)-8-dimethylamino-2-oxo-8-phenyl-1,3-diazaspiro[4.5]decan-3-yl]-N-[(2-methoxy-pyrimidin-5-yl)-methyl]-acetamide | INT 993 | (2-methoxypyrimidin-5-yl)methanamine | SC_1308 | 521.3 |
| SC_1127 | CIS-2-[1-(Cyclobutyl-methyl)-8-dimethylamino-2-oxo-8-phenyl-1,3-diazaspiro[4.5]decan-3-yl]-N-[(4-methoxy-pyrimidin-2-yl)-methyl]-acetamide | INT 993 | (4-methoxypyrimidin-2-yl)methanamine | SC_1308 | 521.3 |
| SC_1130 | CIS-2-[[2-1-(Cyclobutyl-methyl)-8-methylamino-2-oxo-8-phenyl-1,3-diazaspiro[4.5]decan-3-yl]-acetyl]amino]-2-methyl-propionamide | SC 1011 | 2-amino-2-methylpropanamide | SC_1303 | 470.3 |
| SC_1131 | CIS-2-[[2-[1-(Cyclobutyl-methyl)-8-methylamino-2-oxo-8-phenyl-1,3-diazaspiro[4.5]decan-3-yl]-acetyl]amino]-N-methyl-acetamide | SC 1222 | — | SC_1303 | 456.3 |

-continued

| Example | Chemical Name | Reactant I | Reactant II | in analogy to method | m/z [M + H]+ |
|---|---|---|---|---|---|
| SC__1132 | CIS-2-[[2-[1-(Cyclobutyl-methyl)-8-methylamino-2-oxo-8-phenyl-1,3-diazaspiro[4.5]decan-3-yl]-acetyl]amino]-acetamide | SC 1078 | — | SC__1303 | 442.3 |
| SC__1133 | CIS-2-[1-(Cyclobutyl-methyl)-8-dimethylamino-2-oxo-8-phenyl-1,3-diazaspiro[4.5]decan-3-yl]-N-[2-[2-(2-methoxy-ethoxy)-ethoxy]-ethyl]-acetamide | INT 993 | 2-(2-(2-methoxyethoxy)ethoxy)-ethanamine | SC__1308 | 545.4 |
| SC__1134 | CIS-N-(Carbamoyl-methyl)-2-[1-(cyclobutyl-methyl)-8-methylamino-2-oxo-8-phenyl-1,3-diazaspiro[4.5]decan-3-yl]-N-methyl-acetamide | SC 1146 | 2-(methylamino)acetamide | SC__1303 | 456.3 |
| SC__1135 | CIS-2-[1-(Cyclobutyl-methyl)-8-methylamino-2-oxo-8-phenyl-1,3-diazaspiro[4.5]decan-3-yl]-N-methyl-N-(methylcarbamoyl-methyl)-acetamide | SC 1005 | N-methyl-2-(methylamino)acetamide | SC__1303 | 470.3 |
| SC__1137 | CIS-2-[8-Dimethylamino-1-[(1-hydroxy-cyclobutyl)-methyl]-2-oxo-8-phenyl-1,3-diazaspiro[4.5]decan-3-yl]-N-pyrimidin-5-yl-acetamide | INT 994 | pyrimidin-5-amine | SC__1136 | 493.3 |
| SC__1139 | CIS-2-[8-Dimethylamino-1-[(dimethyl-carbamoyl)-methyl]-2-oxo-8-phenyl-1,3-diazaspiro[4.5]decan-3-yl]-N-(2-hydroxy-ethyl)-acetamide | INT 996 | 2-aminoethanol | SC__1308 | 460.3 |
| SC__1140 | CIS-2-[[2-[1-(Cyclobutyl-methyl)-8-methylamino-2-oxo-8-phenyl-1,3-diazaspiro[4.5]decan-3-yl]-acetyl]-methyl-amino]-2-methyl-propionamide | SC 1007 | — | SC__1303 | 484.3 |
| SC__1141 | CIS-1-(Cyclobutyl-methyl)-3-[2-(1,1-dioxo-[1,4]thiazinan-4-yl)-2-oxo-ethyl]-8-methylamino-8-phenyl-1,3-diazaspiro[4.5]decan-2-one | SC 1214 | — | SC__1303 | 503.3 |
| SC__1142 | CIS-2-[1-(Cyclobutyl-methyl)-8-methylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide | SC 1199 | — | SC__1303 | 707.5 |
| SC__1143 | CIS-2-[[2-[1-(Cyclobutyl-methyl)-8-methylamino-2-oxo-8-phenyl-1,3-diazaspiro[4.5]decan-3-yl]-acetyl]amino]-N,N-dimethyl-acetamide | SC 1065 | — | SC__1303 | 470.3 |
| SC__1144 | CIS-2-[1-(Cyclobutyl-methyl)-8-dimethylamino-2-oxo-8-phenyl-1,3-diazaspiro[4.5]decan-3-yl]-N-(5-hydroxy-pyrimidin-2-yl)-acetamide | SC 1070 | — | SC__1110 | 493.3 |
| SC__1145 | CIS-2-[1-(Cyclobutyl-methyl)-8-dimethylamino-2-oxo-8-phenyl-1,3-diazaspiro[4.5]decan-3-yl]-N-(4-methylsulfonyl-pyridin-2-yl)-acetamide | SC 1321 | — | SC__1138 | 554.3 |
| SC__1146 | CIS-2-[[2-[1-(Cyclobutyl-methyl)-8-dimethylamino-2-oxo-8-phenyl-1,3-diazaspiro[4.5]decan-3-yl]-acetyl]amino]-N-methyl-acetamide | INT 993 | 2-amino-N-methylacetamide | SC__1308 | 470.3 |

-continued

| Example | Chemical Name | Reactant I | Reactant II | in analogy to method | m/z [M + H]+ |
|---|---|---|---|---|---|
| SC_1147 | CIS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide | INT 993 | 2-(methylamino)acetamide | SC_1308 | 470.3 |
| SC_1148 | CIS-2-(8-Dimethylamino-2-oxo-8-phenyl-1-propyl-1,3-diazaspiro[4.5]decan-3-yl)-N-methyl-acetamide | INT 995 | methylamine | SC_1136 | 387.3 |
| SC_1150 | CIS-2-[1-(Cyclobutyl-methyl)-8-dimethylamino-2-oxo-8-phenyl-1,3-diazaspiro[4.5]decan-3-yl]-N-[4-(methylsulfinyl)-pyridin-2-yl]-acetamide | SC_1321 | — | SC_1129 | 538.3 |
| SC_1151 | CIS-2-[1-(Cyclobutyl-methyl)-8-dimethylamino-2-oxo-8-phenyl-1,3-diazaspiro[4.5]decan-3-yl]-N-(3-hydroxy-pyridin-2-yl)-acetamide | INT 993 | 2-aminopyridin-3-ol | SC_1308 | 492.3 |
| SC_1152 | CIS-2-[1-(Cyclobutyl-methyl)-8-dimethylamino-2-oxo-8-phenyl-1,3-diazaspiro[4.5]decan-3-yl]-N-(2-methylsulfonyl-ethyl)-acetamide | INT 993 | 2-(methylsulfonyl)ethanamine | SC_1308 | 505.3 |
| SC_1154 | CIS-1-(Cyclobutyl-methyl)-3-[2-[(3S,4R)-3,4-dihydroxy-pyrrolidin-1-yl]-2-oxo-ethyl]-8-dimethylamino-8-phenyl-1,3-diazaspiro[4.5]decan-2-one | INT 993 | (3S,4R)-pyrrolidine-3,4-diol | SC_1308 | 485.3 |
| SC_1155 | CIS-2-[1-(Cyclobutyl-methyl)-8-methylamino-2-oxo-8-phenyl-1,3-diazaspiro[4.5]decan-3-yl]-N-(2-hydroxy-ethyl)-acetamide | SC 1198 | — | SC_1303 | 429.3 |
| SC_1156 | CIS-2-[8-Dimethylamino-1-[(dimethyl-carbamoyl)-methyl]-2-oxo-8-phenyl-1,3-diazaspiro[4.5]decan-3-yl]-N-pyrimidin-4-yl-acetamide | INT 996 | pyrimidin-4-amine | SC_1308 | 494.3 |
| SC_1157 | CIS-2-[8-Dimethylamino-1-[(dimethyl-carbamoyl)-methyl]-2-oxo-8-phenyl-1,3-diazaspiro[4.5]decan-3-yl]-N-methyl-acetamide | INT 996 | methylamine | SC_1308 | 430.3 |
| SC_1158 | CIS-2-[[2-[8-Dimethylamino-1-(2-methyl-propyl)-2-oxo-8-phenyl-1,3-diazaspiro[4.5]decan-3-yl]-acetyl]amino]-acetamide | INT 992 | 2-aminoacetamide | SC_1136 | 444.3 |
| SC_1159 | CIS-2-[8-Dimethylamino-1-[(1-hydroxy-cyclobutyl)-methyl]-2-oxo-8-phenyl-1,3-diazaspiro[4.5]decan-3-yl]-acetamide | INT 994 | NH4Cl | SC_1136 | 415.3 |
| SC_1160 | CIS-2-[8-Dimethylamino-1-[(1-hydroxy-cyclobutyl)-methyl]-2-oxo-8-phenyl-1,3-diazaspiro[4.5]decan-3-yl]-N-methyl-acetamide | INT 994 | methylamine | SC_1136 | 429.3 |
| SC_1161 | CIS-2-[[2-[8-Dimethylamino-1-(3-methoxy-propyl)-2-oxo-8-phenyl-1,3-diazaspiro[4.5]decan-3-yl]-acetyl]amino]-acetamide | INT 987 | N-(2-amino-2-oxoethyl)-2-bromoacetamide | SC_1149 | 460.3 |
| SC_1162 | CIS-2-[8-Dimethylamino-1-(2-methyl-propyl)-2-oxo-8-phenyl-1,3-diazaspiro[4.5]decan-3-yl]-N-methyl-acetamide | INT 984 | 2-bromo-N-methylacetamide | SC_1149 | 401.3 |
| SC_1163 | CIS-1-(Cyclobutyl-methyl)-3-[2-[(3S,4R)-3,4-dihydroxy-pyrrolidin-1-yl]-2-oxo-ethyl]-8-methylamino-8-phenyl-1,3-diazaspiro[4.5]decan-2-one | SC 1154 | — | SC_1303 | 471.3 |

-continued

| Example | Chemical Name | Reactant I | Reactant II | in analogy to method | m/z [M + H]+ |
|---|---|---|---|---|---|
| SC_1164 | CIS-2-[8-Dimethylamino-1-[(1-methyl-cyclobutyl)-methyl]-2-oxo-8-phenyl-1,3-diazaspiro[4.5]decan-3-yl]-N-methyl-acetamide | INT 998 | methylamine | SC_1308 | 427.3 |
| SC_1165 | CIS-2-[8-Dimethylamino-1-[(1-methyl-cyclobutyl)-methyl]-2-oxo-8-phenyl-1,3-diazaspiro[4.5]decan-3-yl]-N-pyrimidin-4-yl-acetamide | INT 998 | pyrimidin-4-amine | SC_1308 | 491.3 |
| SC_1166 | CIS-2-[[2-[8-Dimethylamino-1-[(1-methyl-cyclobutyl)-methyl]-2-oxo-8-phenyl-1,3-diazaspiro[4.5]decan-3-yl]-acetyl]amino]-acetamide | INT 998 | 2-aminoacetamide | SC_1308 | 470.3 |
| SC_1167 | CIS-2-[8-Dimethylamino-1-[(1-methyl-cyclobutyl)-methyl]-2-oxo-8-phenyl-1,3-diazaspiro[4.5]decan-3-yl]-N-(2-hydroxy-ethyl)-acetamide | INT 998 | 2-aminoethanol | SC_1308 | 457.3 |
| SC_1168 | CIS-2-[[2-[1-(Cyclopropyl-methyl)-8-dimethylamino-2-oxo-8-diazaspiro[4.5]decan-3-yl]-acetyl]amino]-acetamide | INT 983 | N-(2-amino-2-oxoethyl)-2-bromoacetamide | SC_1149 | 442.3 |
| SC_1169 | CIS-2-[1-(Cyclobutyl-methyl)-8-(ethyl-methyl-amino)-2-oxo-8-phenyl-1,3-diazaspiro[4.5]decan-3-yl]-N-methyl-acetamide | INT 986 | 2-bromo-N-methylacetamide | SC_1149 | 427.3 |
| SC_1171 | CIS-2-[[2-(8-Dimethylamino-2-oxo-8-phenyl-1-propyl-1,3-diazaspiro[4.5]decan-3-yl)-acetyl]amino]-acetamide | INT 995 | 2-aminoacetamide | SC_1308 | 430.3 |
| SC_1172 | CIS-2-[[2-[8-Dimethylamino-1-[(1-hydroxy-cyclobutyl)-methyl]-2-oxo-8-phenyl-1,3-diazaspiro[4.5]decan-3-yl]-acetyl]amino]-acetamide | INT 994 | 2-aminoacetamide | SC_1308 | 472.3 |
| SC_1173 | CIS-2-[8-Dimethylamino-1-[(1-hydroxy-cyclobutyl)-methyl]-2-oxo-8-phenyl-1,3-diazaspiro[4.5]decan-3-yl]-N-(2-hydroxy-ethyl)-acetamide | INT 994 | 2-aminoethanol | SC_1308 | 459.3 |
| SC_1174 | CIS-2-[8-Dimethylamino-1-[(1-hydroxy-cyclobutyl)-methyl]-2-oxo-8-phenyl-1,3-diazaspiro[4.5]decan-3-yl]-N-(1,1-dioxo-thian-4-yl)-acetamide | INT 994 | 4-aminotetrahydro-2H-thiopyran 1,1-dioxide | SC_1308 | 547.3 |
| SC_1175 | CIS-2-[1-(Cyclopropyl-methyl)-8-dimethylamino-2-oxo-8-phenyl-1,3-diazaspiro[4.5]decan-3-yl]-N-methyl-acetamide | INT 983 | 2-bromo-N-methylacetamide | SC_1149 | 399.3 |
| SC_1176 | CIS-2-[1-[(1-Cyano-cyclobutyl)-methyl]-8-dimethylamino-2-oxo-8-phenyl-1,3-diazaspiro[4.5]decan-3-yl]-N-methyl-acetamide | INT 951 | 2-bromo-N-methylacetamide | SC_1149 | 438.3 |
| SC_1177 | CIS-2-[1-(Cyclobutyl-methyl)-8-(ethyl-methyl-amino)-2-oxo-8-phenyl-1,3-diazaspiro[4.5]decan-3-yl]-N-(2-hydroxy-ethyl)-acetamide | INT 998 | 2-aminoethanol | SC_1308 | 457.3 |
| SC_1178 | CIS-2-[[2-[1-(Cyclobutyl-methyl)-8-(ethyl-methyl-amino)-2-oxo-8-phenyl-1,3-diazaspiro[4.5]decan-3-yl]-acetyl]amino]-acetamide | INT 998 | 2-aminoacetamide | SC_1308 | 470.3 |
| SC_1179 | CIS-2-[[2-[1-(Cyclobutyl-methyl)-8-methylamino-2-oxo-8-phenyl-1,3-diazaspiro[4.5]decan-3-yl]-acetyl]amino]-N,2-dimethyl-propionamide | SC 1008 | — | SC_1303 | 484.3 |

-continued

| Example | Chemical Name | Reactant I | Reactant II | in analogy to method | m/z [M + H]+ |
|---|---|---|---|---|---|
| SC_1180 | CIS-2-[8-Dimethylamino-1-(3-methoxy-propyl)-2-oxo-8-phenyl-1,3-diazaspiro[4.5]decan-3-yl]-N-(2-hydroxy-ethyl)-acetamide | INT 990 | 2-aminoethanol | SC_1308 | 447.3 |
| SC_1181 | CIS-2-[8-Dimethylamino-1-(3-methoxy-propyl)-2-oxo-8-phenyl-1,3-diazaspiro[4.5]decan-3-yl]-N-methyl-N-(methylcarbamoyl-methyl)-acetamide | INT 990 | N-methyl-2-(methylamino)acetamide | SC_1308 | 488.3 |
| SC_1182 | CIS-8-Dimethylamino-1-(3-methoxy-propyl)-3-[2-oxo-2-(3-oxo-piperazin-1-yl)-ethyl]-8-phenyl-1,3-diazaspiro[4.5]decan-2-one | INT 990 | piperazin-2-one | SC_1308 | 486.3 |
| SC_1183 | CIS-N-(Carbamoyl-methyl)-2-[8-dimethylamino-1-(3-methoxy-propyl)-2-oxo-8-phenyl-1,3-diazaspiro[4.5]decan-3-yl]-N-methyl-acetamide | INT 990 | 2-(methylamino)acetamide | SC_1308 | 474.3 |
| SC_1184 | CIS-2-[8-Dimethylamino-1-(3-methoxy-propyl)-2-oxo-8-phenyl-1,3-diazaspiro[4.5]decan-3-yl]-N-[(3-hydroxy-cyclobutyl)-methyl]-acetamide | INT 990 | cis-3-(aminomethyl)cyclobutanol | SC_1073 | 487.3 |
| SC_1185 | CIS-2-[8-Dimethylamino-1-(3-methoxy-propyl)-2-oxo-8-phenyl-1,3-diazaspiro[4.5]decan-3-yl]-N-[(3-hydroxy-cyclobutyl)-methyl]-acetamide | INT 990 | trans-3-(aminomethyl)cyclobutanol | SC_1073 | 487.3 |
| SC_1186 | CIS-2-[8-Dimethylamino-1-(3-methoxy-propyl)-2-oxo-8-phenyl-1,3-diazaspiro[4.5]decan-3-yl]-N-[(3-hydroxy-cyclopentyl)-methyl]-acetamide | INT 990 | 3-(aminomethyl)cyclopentanol | SC_1073 | 501.3 |
| SC_1187 | CIS-2-[8-Dimethylamino-1-(3-methoxy-propyl)-2-oxo-8-phenyl-1,3-diazaspiro[4.5]decan-3-yl]-N-pyridazin-4-yl-acetamide | INT 990 | pyridazin-4-amine | SC_1308 | 481.3 |
| SC_1188 | CIS-2-[8-Dimethylamino-1-(3-methoxy-propyl)-2-oxo-8-phenyl-1,3-diazaspiro[4.5]decan-3-yl]-N-(6-methoxy-pyridin-2-yl)-acetamide | INT 990 | 6-methoxypyridin-2-amine | SC_1308 | 510.3 |
| SC_1189 | CIS-N-(2-Cyanoethyl)-2-[8-dimethylamino-1-(3-methoxy-propyl)-2-oxo-8-phenyl-1,3-diazaspiro[4.5]decan-3-yl]-acetamide | INT 990 | 3-aminopropanenitrile | SC_1308 | 456.3 |
| SC_1190 | CIS-2-[8-Dimethylamino-1-(3-methoxy-propyl)-2-oxo-8-phenyl-1,3-diazaspiro[4.5]decan-3-yl]-N-pyrimidin-5-yl-acetamide | INT 990 | pyrimidin-5-amine | SC_1308 | 481.3 |
| SC_1191 | CIS-2-[8-Dimethylamino-1-(3-methoxy-propyl)-2-oxo-8-phenyl-1,3-diazaspiro[4.5]decan-3-yl]-N-pyrimidin-4-yl-acetamide | INT 990 | pyrimidin-4-amine | SC_1308 | 481.3 |
| SC_1192 | CIS-2-[1-(Cyclobutyl-methyl)-8-(ethyl-methyl-amino)-2-oxo-8-phenyl-1,3-diazaspiro[4.5]decan-3-yl]-N-(6-methoxy-pyridin-2-yl)-acetamide | INT 999 | 6-methoxypyridin-2-amine | SC_1073 | 520.3 |

-continued

| Example | Chemical Name | Reactant I | Reactant II | in analogy to method | m/z [M + H]+ |
|---|---|---|---|---|---|
| SC_1193 | CIS-2-[8-Dimethylamino-1-[(1-hydroxy-cyclobutyl)-methyl]-2-oxo-8-phenyl-1,3-diazaspiro[4.5]decan-3-yl]-N-pyridin-3-yl-acetamide | INT 995 | pyridin-3-amine | SC_1308 | 492.3 |
| SC_1195 | CIS-2-[1-(Cyclobutyl-methyl)-8-dimethylamino-2-oxo-8-phenyl-1,3-diazaspiro[4.5]decan-3-yl]-acetamide | INT 999 | NH4Cl | SC_1073 | 399.3 |
| SC_1196 | CIS-2-[1-(Cyclobutyl-methyl)-8-dimethylamino-2-oxo-8-phenyl-1,3-diazaspiro[4.5]decan-3-yl]-N-pyrimidin-4-yl-acetamide | INT 999 | pyrimidin-4-amine | SC_1073 | 477.3 |
| SC_1197 | CIS-2-[1-(Cyclobutyl-methyl)-8-dimethylamino-2-oxo-8-phenyl-1,3-diazaspiro[4.5]decan-3-yl]-N-(2-methoxy-ethyl)-acetamide | INT 999 | 2-methoxyethanamine | SC_1073 | 457.3 |
| SC_1198 | CIS-2-[1-(Cyclobutyl-methyl)-8-dimethylamino-2-oxo-8-phenyl-1,3-diazaspiro[4.5]decan-3-yl]-N-(2-hydroxy-ethyl)-acetamide | INT 999 | 2-aminoethanol | SC_1073 | 443.3 |
| SC_1199 | CIS-2-[1-(Cyclobutyl-methyl)-8-dimethylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide | INT 993 | 2,5,8,11,14,17,20-heptaoxadocosan-22-amine | SC_1308 | 721.5 |
| SC_1201 | CIS-2-[1-(Cyclobutyl-methyl)-8-methylamino-2-oxo-8-phenyl-1,3-diazaspiro[4.5]decan-3-yl]-N-methyl-acetamide | SC 1229 | — | SC_1303 | 399.3 |
| SC_1203 | CIS-(2S)-1-[2-[1-(Cyclobutyl-methyl)-8-dimethylamino-2-oxo-8-phenyl-1,3-diazaspiro[4.5]decan-3-yl]-acetyl]-pyrrolidine-2-carboxylic acid amide | INT 993 | (S)-pyrrolidine-2-carboxamide | SC_1308 | 496.3 |
| SC_1204 | CIS-2-[[2-[1-(Cyclobutyl-methyl)-8-dimethylamino-2-oxo-8-phenyl-1,3-diazaspiro[4.5]decan-3-yl]-acetyl]amino]-N,N-dimethyl-acetamide | INT 993 | 2-amino-N,N-dimethylacetamide | SC_1308 | 484.3 |
| SC_1205 | CIS-2-[1-(Cyclobutyl-methyl)-8-dimethylamino-2-oxo-8-phenyl-1,3-diazaspiro[4.5]decan-3-yl]-N-(oxetan-3-yl)-acetamide | INT 993 | oxetan-3-amine | SC_1308 | 455.3 |
| SC_1206 | CIS-2-[[2-[1-(Cyclobutyl-methyl)-8-dimethylamino-2-oxo-8-phenyl-1,3-diazaspiro[4.5]decan-3-yl]-acetyl]amino]-acetamide | INT 993 | 2-aminoacetamide | SC_1308 | 456.3 |
| SC_1207 | CIS-1-(Cyclobutyl-methyl)-8-dimethylamino-3-[2-oxo-2-(3-oxo-piperazin-1-yl)-ethyl]-8-phenyl-1,3-diazaspiro[4.5]decan-2-one | INT 999 | piperazin-2-one | SC_1073 | 482.3 |
| SC_1208 | CIS-2-[1-(Cyclobutyl-methyl)-8-dimethylamino-2-oxo-8-phenyl-1,3-diazaspiro[4.5]decan-3-yl]-N-(1,1-dioxo-thian-4-yl)-acetamide | INT 999 | 4-aminotetrahydro-2H-thiopyran 1,1-dioxide | SC_1073 | 531.3 |
| SC_1209 | CIS-1-(Cyclobutyl-methyl)-8-dimethylamino-3-[2-[2-(hydroxymethyl)-morpholin-4-yl]-2-oxo-ethyl]-8-phenyl-1,3-diazaspiro[4.5]decan-2-one | INT 999 | morpholin-2-ylmethanol | SC_1073 | 499.3 |

-continued

| Example | Chemical Name | Reactant I | Reactant II | in analogy to method | m/z [M + H]+ |
|---|---|---|---|---|---|
| SC_1210 | CIS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide | INT 993 | 2-(methylamino)acetamide | SC_1308 | 470.3 |
| SC_1211 | CIS-N-(Cyano-methyl)-2-[1-(cyclobutyl-methyl)-8-dimethylamino-2-oxo-8-phenyl-1,3-diazaspiro[4.5]decan-3-yl]-acetamide | INT 993 | 2-aminoacetonitrile | SC_1308 | 438.3 |
| SC_1212 | CIS-N-(2-Acetylamino-ethyl)-2-[1-(cyclobutyl-methyl)-8-dimethylamino-2-oxo-8-phenyl-1,3-diazaspiro[4.5]decan-3-yl]-acetamide | INT 993 | N-(2-aminoethyl)acetamide | SC_1308 | 484.3 |
| SC_1213 | CIS-2-[1-(Cyclobutyl-methyl)-8-dimethylamino-2-oxo-8-phenyl-1,3-diazaspiro[4.5]decan-3-yl]-N-(2-methylsulfonyl-ethyl)-acetamide | INT 999 | 2-(methylsulfonyl)ethan-amine | SC_1073 | 505.3 |
| SC_1214 | CIS-1-(Cyclobutyl-methyl)-8-dimethylamino-3-[2-(1,1-dioxo-[1,4]thiazinan-4-yl)-2-oxo-ethyl]-8-phenyl-1,3-diazaspiro[4.5]decan-2-one | INT 999 | thiomorpholine 1,1-dioxide | SC_1073 | 517.3 |
| SC_1215 | CIS-2-[1-(Cyclobutyl-methyl)-8-dimethylamino-2-oxo-8-phenyl-1,3-diazaspiro[4.5]decan-3-yl]-N-[(1,1-dioxo-thian-4-yl)-methyl]-acetamide | INT 999 | 4-(aminomethyl)tetra-hydro-2H-thiopyran 1,1-dioxide | SC_1073 | 545.3 |
| SC_1216 | CIS-1-(Cyclobutyl-methyl)-8-dimethylamino-3-[2-(4-methylsulfonyl-piperazin-1-yl)-2-oxo-ethyl]-8-phenyl-1,3-diazaspiro[4.5]decan-2-one | INT 999 | 1-(methylsulfonyl)-piperazine | SC_1073 | 546.3 |
| SC_1217 | CIS-N-(2-Cyanoethyl)-2-[1-(cyclobutyl-methyl)-8-dimethylamino-2-oxo-8-phenyl-1,3-diazaspiro[4.5]decan-3-yl]-acetamide | INT 993 | 3-aminopropanenitrile | SC_1308 | 452.3 |
| SC_1218 | CIS-2-[1-(Cyclobutyl-methyl)-8-dimethylamino-2-oxo-8-phenyl-1,3-diazaspiro[4.5]decan-3-yl]-N-(2-hydroxy-2-methyl-propyl)-acetamide | INT 993 | 1-amino-2-methylpropan-2-ol | SC_1308 | 471.3 |
| SC_1219 | CIS-2-[1-(Cyclobutyl-methyl)-8-dimethylamino-2-oxo-8-phenyl-1,3-diazaspiro[4.5]decan-3-yl]-N-(2-morpholin-4-yl-2-oxo-ethyl)-acetamide | INT 993 | 2-amino-1-morpholinoethanone | SC_1308 | 526.3 |
| SC_1220 | CIS-2-[1-(Cyclobutyl-methyl)-8-dimethylamino-2-oxo-8-phenyl-1,3-diazaspiro[4.5]decan-3-yl]-N-[2-(2-hydroxy-ethoxy)-ethyl]-acetamide | INT 993 | 2-(2-aminoethoxy)ethanol | SC_1308 | 487.3 |
| SC_1222 | CIS-2-[[2-[1-(Cyclobutyl-methyl)-8-dimethylamino-2-oxo-8-phenyl-1,3-diazaspiro[4.5]decan-3-yl]-acetyl]amino]-N-methyl-acetamide | INT 993 | 2-amino-N-methylacetamide | SC_1308 | 470.3 |
| SC_1223 | CIS-2-[1-(Cyclobutyl-methyl)-8-dimethylamino-2-oxo-8-phenyl-1,3-diazaspiro[4.5]decan-3-yl]-N-[2-(methanesulfonamido)-ethyl]-acetamide | INT 993 | N-(2-aminoethyl)-methanesulfonamide | SC_1308 | 520.3 |

-continued

| Example | Chemical Name | Reactant I | Reactant II | in analogy to method | m/z [M + H]+ |
|---|---|---|---|---|---|
| SC_1224 | CIS-2-[1-(Cyclobutyl-methyl)-8-dimethylamino-2-oxo-8-phenyl-1,3-diazaspiro[4.5]decan-3-yl]-N-[(1-hydroxy-cyclopentyl)-methyl]-acetamide | INT 993 | 1-(aminomethyl)-cyclopentanol | SC_1308 | 497.3 |
| SC_1225 | CIS-2-[1-(Cyclobutyl-methyl)-8-dimethylamino-2-oxo-8-phenyl-1,3-diazaspiro[4.5]decan-3-yl]-N-[(4-hydroxy-cyclohexyl)-methyl]-acetamide | INT 993 | 4-(aminomethyl)cyclohexanol | SC_1308 | 511.4 |
| SC_1226 | CIS-2-[1-(Cyclobutyl-methyl)-8-dimethylamino-2-oxo-8-phenyl-1,3-diazaspiro[4.5]decan-3-yl]-N-[2-(2-methoxy-ethoxy)-ethyl]-acetamide | INT 993 | 2-(2-methoxyethoxy)-ethanamine | SC_1308 | 501.3 |
| SC_1227 | CIS-2-[1-(Cyclobutyl-methyl)-8-dimethylamino-2-oxo-8-phenyl-1,3-diazaspiro[4.5]decan-3-yl]-N-[2-(dimethylamino)ethyl]-acetamide | INT 993 | $N^1,N^1$-dimethylethane-1,2-diamine | SC_1308 | 470.3 |
| SC_1228 | CIS-2-[1-(Cyclobutyl-methyl)-8-[methyl-(2-methyl-propyl)-amino]-2-oxo-8-phenyl-1,3-diazaspiro[4.5]decan-3-yl]-N-methyl-acetamide | INT 953 | 2-bromo-N-methylacetamide | SC_1149 | 455.3 |
| SC_1229 | CIS-2-[1-(Cyclobutyl-methyl)-8-dimethylamino-2-oxo-8-phenyl-1,3-diazaspiro[4.5]decan-3-yl]-N-methyl-acetamide | INT 999 | methylamine | SC_1073 | 413.3 |
| SC_1230 | CIS-2-[1-(Cyclobutyl-methyl)-8-dimethylamino-2-oxo-8-phenyl-1,3-diazaspiro[4.5]decan-3-yl]-N-pyrimidin-4-yl-acetamide | INT 993 | pyrimidin-4-amine | SC_1051 | 477.3 |
| SC_1231 | CIS-2-[1-(Cyclobutyl-methyl)-8-dimethylamino-2-oxo-8-phenyl-1,3-diazaspiro[4.5]decan-3-yl]-N-(6-methyl-pyridin-2-yl)-acetamide | INT 993 | 6-methylpyridin-2-amine | SC_1051 | 490.3 |
| SC_1232 | CIS-2-[1-(Cyclobutyl-methyl)-8-dimethylamino-2-oxo-8-phenyl-1,3-diazaspiro[4.5]decan-3-yl]-N-pyridazin-3-yl-acetamide | INT 993 | pyridazin-3-amine | SC_1051 | 477.3 |
| SC_1233 | CIS-2-[1-(Cyclobutyl-methyl)-8-dimethylamino-2-oxo-8-phenyl-1,3-diazaspiro[4.5]decan-3-yl]-N-pyrimidin-5-yl-acetamide | INT 993 | pyrimidin-5-amine | SC_1051 | 477.3 |
| SC_1234 | CIS-2-[1-(Cyclobutyl-methyl)-8-dimethylamino-2-oxo-8-phenyl-1,3-diazaspiro[4.5]decan-3-yl]-N-pyridazin-4-yl-acetamide | INT 993 | pyridazin-4-amine | SC_1051 | 477.3 |
| SC_1235 | CIS-2-[1-(Cyclobutyl-methyl)-8-dimethylamino-2-oxo-8-phenyl-1,3-diazaspiro[4.5]decan-3-yl]-N-(6-methoxy-pyrimidin-4-yl)-acetamide | INT 993 | 6-methoxypyrimidin-4-amine | SC_1051 | 507.3 |
| SC_1236 | CIS-2-[1-(Cyclobutyl-methyl)-8-dimethylamino-2-oxo-8-phenyl-1,3-diazaspiro[4.5]decan-3-yl]-N-(2-methyl-pyridin-4-yl)-acetamide | INT 993 | 2-methylpyridin-4-amine | SC_1051 | 490.3 |

-continued

| Example | Chemical Name | Reactant I | Reactant II | in analogy to method | m/z [M + H]+ |
|---|---|---|---|---|---|
| SC_1300 | CIS-2-[8-Dimethylamino-1-[(1-hydroxy-cyclobutyl)-methyl]-2-oxo-8-phenyl-1,3-diazaspiro[4.5]decan-3-yl]-N-pyridin-4-yl-acetamide | INT 994 | pyridin-4-amine | SC_1308 | 492.3 |
| SC_1301 | CIS-2-[8-Dimethylamino-1-[(1-hydroxy-cyclobutyl)-methyl]-2-oxo-8-phenyl-1,3-diazaspiro[4.5]decan-3-yl]-N-(oxetan-3-yl)-acetamide | INT 994 | oxetan-3-amine | SC_1308 | 471.3 |
| SC_1302 | CIS-2-[8-Dimethylamino-1-[(1-hydroxy-cyclobutyl)-methyl]-2-oxo-8-phenyl-1,3-diazaspiro[4.5]decan-3-yl]-N-(2-methoxy-ethyl)-acetamide | INT 994 | 2-methoxyethanamine | SC_1308 | 473.3 |
| SC_1304 | CIS-2-[1-[(1-Hydroxy-cyclobutyl)-methyl]-8-methylamino-2-oxo-8-phenyl-1,3-diazaspiro[4.5]decan-3-yl]-N-(2-methoxy-ethyl)-acetamide | SC 1301 | — | SC_1303 | 459.3 |
| SC_1305 | CIS-2-[8-Dimethylamino-1-(3-methoxy-propyl)-2-oxo-8-phenyl-1,3-diazaspiro[4.5]decan-3-yl]-N-(4-methoxy-pyridin-2-yl)-acetamide | SC 1302 | — | SC_1308 | 510.3 |
| SC_1306 | CIS-2-[8-Dimethylamino-1-(3-methoxy-propyl)-2-oxo-8-phenyl-1,3-diazaspiro[4.5]decan-3-yl]-N-(pyrimidin-4-yl-methyl)-acetamide | INT 990 | pyrimidin-4-ylmethanamine | SC_1073 | 495.3 |
| SC_1309 | CIS-2-[8-Dimethylamino-1-[(1-hydroxy-cyclobutyl)-methyl]-2-oxo-8-phenyl-1,3-diazaspiro[4.5]decan-3-yl]-N-pyridin-2-yl-acetamide | SC 1159 | — | SC_1128 | 492.3 |
| SC_1310 | CIS-2-[1-[(1-Cyano-cyclobutyl)-methyl]-8-dimethylamino-2-oxo-8-phenyl-1,3-diazaspiro[4.5]decan-3-yl]-acetamide | INT 989 | NH4Cl | SC_1308 | 424.3 |
| SC_1311 | CIS-2-[[2-[1-[(1-Cyano-cyclobutyl)-methyl]-8-dimethylamino-2-oxo-8-phenyl-1,3-diazaspiro[4.5]decan-3-yl]-acetyl]amino]-acetamide | INT 989 | 2-aminoacetamide | SC_1308 | 481.3 |
| SC_1312 | CIS-2-[1-[(1-Hydroxy-cyclobutyl)-methyl]-8-methylamino-2-oxo-8-phenyl-1,3-diazaspiro[4.5]decan-3-yl]-N-methyl-acetamide | SC 1160 | — | SC_1303 | 415.3 |
| SC_1313 | CIS-3-[2-(1,1-Dioxo-[1,4]thiazinan-4-yl)-2-oxo-ethyl]-8-methylamino-8-phenyl-1-propyl-1,3-diazaspiro[4.5]decan-2-one | SC 1308 | — | SC_1303 | 477.2 |
| SC_1317 | CIS-2-[1-(Cyclobutyl-methyl)-8-dimethylamino-2-oxo-8-phenyl-1,3-diazaspiro[4.5]decan-3-yl]-N-pyridin-2-yl-acetamide | INT 993 | pyridin-2-amine | SC_1051 | 476.3 |
| SC_1318 | CIS-8-Dimethylamino-1-[(1-hydroxy-cyclobutyl)-methyl]-3-(2-morpholin-4-yl-2-oxo-ethyl)-8-phenyl-1,3-diazaspiro[4.5]decan-2-one | INT 994 | morpholine | SC_1136 | 485.3 |
| SC_1319 | CIS-2-[1-[(1-Hydroxy-cyclobutyl)-methyl]-8-methylamino-2-oxo-8-phenyl-1,3-diazaspiro[4.5]decan-3-yl]-acetamide | SC 1159 | — | SC_1303 | 401.2 |
| SC_1320 | CIS-1-(Cyclobutyl-methyl)-8-dimethylamino-3-(2-morpholin-4-yl-2-oxo-ethyl)-8-phenyl-1,3-diazaspiro[4.5]decan-2-one | INT 993 | morpholine | SC_1308 | 469.3 |

-continued

| Example | Chemical Name | Reactant I | Reactant II | in analogy to method | m/z [M + H]+ |
|---|---|---|---|---|---|
| SC_1321 | CIS-2-[1-(Cyclobutyl-methyl)-8-dimethylamino-2-oxo-8-phenyl-1,3-diazaspiro[4.5]decan-3-yl]-N-(4-methylsulfanyl-pyridin-2-yl)-acetamide | INT 993 | 4-(methylthio)pyridin-2-amine | SC_1073 | 522.3 |

| Example | Chemical name | Reactant I | Reactant II | in analogy to method | 1H NMR data | m/z (M + H)+ |
|---|---|---|---|---|---|---|
| SC_1322 | CIS-3-[2-(1,1-Dioxo-[1,4]thiazinan-4-yl)-2-oxo-ethyl]-8-methylamino-8-phenyl-1,3-diazaspiro[4.5]decan-2-one | INT-1014 | thiomorpholin-1,1-dioxide | SC_1308 (for step 1), SC_1303 (for step 2) | 1HNMR (DMSO-d6, 400 MHz), δ (ppm) = 7.40 (d, 2H, J = 7.2 Hz), 7.31 (t, 2H, J = 7.44 Hz), 7.18 (t, 1H, J = 6.78 Hz), 6.61 (bs, 1H), 3.98 (s, 2H), 3.82 (bs, 4H), 3.21 (bs, 4H), 3.09 (s, 2H), 1.95 (t, 2H, J = 11.74 Hz), 1.85 (bs, 5H), 1.65 (bs, 2H), 1.48 (bs, 2H). | 435.3 |
| SC_1323 | CIS-2-(8-Methylamino-2-oxo-8-phenyl-1,3-diazaspiro[4.5]decan-3-yl)-acetamide | SC-1324 | | SC_1303 | 1HNMR (DMSO-d6, 400 MHz), δ (ppm) = 7.41 (d, 2H, J = 7.60 Hz), 7.30 (t, 2H, J = 7.60 Hz), 7.23 (s, 1H), 7.18 (t, 1H, J = 7.08 Hz), 6.95 (s, 1H), 6.58 (s, 1H), 3.58 (s, 2H), 3.21 (s, 2H), 1.96-1.80 (m, 7H), 1.69-1.66 (m, 2H), 1.47 (d, 2H, J = 11.76 Hz). | 317.2 |
| SC_1324 | CIS-2-(8-Dimethylamino-2-oxo-8-phenyl-1,3-diazaspiro[4.5]decan-3-yl)-acetamide | INT-1014 | | procedure described | — | 331.2 |
| SC_1325 | CIS-3-[2-(1,1-Dioxo-[1,4]thiazinan-4-yl)-2-oxo-ethyl]-8-ethylamino-8-phenyl-1,3-diazaspiro[4.5]decan-2-one | INT-1015 | thiomorpholin-1,1-dioxide | SC_1308 (for step 1), SC_1303 (for step 2) | 1HNMR (DMSO-d6, 400 MHz), δ (ppm) = 7.42 (d, 2H, J = 7.2 Hz), 7.29 (t, 2H, J = 7.2 Hz), 7.17 (t, 1H), 6.61 (s, 1H), 5.75 (s, 1H), 3.98 (s, 2H), 3.82 (s, 4H), 3.21 (s, 4H), 3.09 (s, 2H), 2.07-1.93 (m, 4H), 1.87-1.83 (m, 2H), 1.69-1.66 (m, 2H), 1.48-1.45 (m, 2H), 0.92 (t, 3H, J = 6.8 Hz). | 449.4 |
| SC_1326 | TRANS-3-[2-(1,1-Dioxo-[1,4]thiazinan-4-yl)-2-oxo-ethyl]-8-ethylamino-8-phenyl-1,3-diazaspiro[4.5]decan-2-one | INT-1017 | thiomorpholin-1,1-dioxide | SC_1308 (for step 1), SC_1303 (for step 2) | 1HNMR (DMSO-d6, 400 MHz), δ (ppm) = 7.50 (d, 2H, J = 7.4 Hz), 7.30 (t, 2H, J = 7.2 Hz), 7.18-7.15 (m, 2H), 4.00 (s, 2H), 3.84 (bs, 4H), 3.24 (s, 2H), 3.19 (s, 2H), 3.11 (s, 2H), 2.07-1.44 (m, 11H), 0.91 (t, 3H, J = 6.6 Hz). | 449.2 |
| SC_1327 | CIS-2-[1-(Cyclobutyl-methyl)-8-methylamino-2-oxo-8-phenyl-1,3-diazaspiro[4.5]decan-3-yl]-N-methyl-acetamide | INT-998 | methylamine (step 1) | SC_1308 (for step 1), SC_1303 (for step 2) | 1H NMR (DMSO-d6): δ 7.71-7.70 (m, 1H), 7.43 (d, 2H), 7.30 (t, 2H), 7.18 (t, 1H), 3.64 (s, 2H), 3.21 (s, 2H), 3.08 (d, 2H), 2.57-2.54 (m, 4H), 2.25 (m, 1H), 2.11-2.06 (m, 2H), 1.97-1.82 (m, 7H), 1.80-1.67 (m, 4H), 1.59 (m, 2H), 1.36-1.35 (m, 2H). | 399.3 |

-continued

| Example | Chemical name | Reactant I | Reactant II | in analogy to method | $^1$H NMR data | m/z (M + H)$^+$ |
|---|---|---|---|---|---|---|
| SC__1328 | CIS-2-(8-Ethylamino-2-oxo-8-phenyl-1,3-diazaspiro[4.5]decan-3-yl)-acetamide | INT-1015 | | SC__1324 | $^1$HNMR (DMSO-d6, 400 MHz), (ppm) = 7.43 (d, 2H, J = 7.6 Hz), 7.29 (t, 2H, J = 7.2 Hz), 7.22 (s, 1H), 7.17 (t, 1H, J = 6.8 Hz), 6.95 (s, 1H), 6.58 (s, 1H), 3.58 (s, 2H), 3.20 (s, 2H), 2.07-2.05 (m, 2H), 1.93 (t, 2H, J = 11.2), 1.85-1.82 (m, 2H), 1.69-1.67 (m, 2H,), 1.48-1.45 (m, 2H), 0.92 (t, 3H, J = 6.8 Hz). | 331.1 |
| SC__1329 | TRANS-2-(8-Ethylamino-2-oxo-8-phenyl-1,3-diazaspiro[4.5]decan-3-yl)-acetamide | INT-1017 | | SC__1324 | $^1$HNMR (DMSO-d6, 400 MHz), δ (ppm) = 7.49 (d, 2H, J = 7.56 Hz), 7.29 (t, 2H, J = 7.66 Hz), 7.24 (s, 1H), 7.16 (t, 1H, 7.24 Hz), 7.11 (bs, 1H), 6.98 (bs, 1H), 3.59 (s, 2H), 3.17 (s, 2H), 2.09-1.95 (m, 4H). | 331.2 |
| SC__1330 | CIS-2-(8-Dimethylamino-2-oxo-8-phenyl-1,3-diazaspiro[4.5]decan-3-yl)-N-(2-hydroxy-ethyl)-N-methyl-acetamide | INT-1014 | 2-(methylamino)-ethanol | SC__1308 | $^1$HNMR (DMSO-d6, 400 MHz at 100° C.), δ (ppm) = 7.34-7.23 (m, 5H), 6.41 (s, 1H), 4.4 (bs, 1H), 3.89 (s, 2H), 3.53-3.52 (m, 2H), 3.34 (t, 2H, J = 5.56 Hz), 3.13 (s, 2H), 2.89 (s, 2H), 2.31-2.27 (m, 2H), 2.01 (s, 6H), 1.89-1.78 (m, 4H), 1.46-1.41 (m, 2H). | 389.2 |
| SC__1331 | CIS-8-Dimethylamino-3-[2-(1,1-dioxo-[1,4]thiazinan-4-yl)-2-oxo-ethyl]-1-[(1-hydroxy-cyclobutyl)-methyl]-8-phenyl-1,3-diazaspiro[4.5]decane-2,4-dione | INT-1020 | 1,4-thiazinane 1,1-dioxide | SC__1308 | $^1$H NMR (600 MHz, DMSO) δ 7.35 (qd, 4H), 7.26 (tt, 1H), 4.40 (s, 2H), 3.89 (dt, 4H), 3.26 (t, 2H), 3.11 (d, 2H), 2.64-2.58 (m, 2H), 2.45 (td, 2H), 2.14 (tt, 2H), 2.03 (td, 2H), 1.98 (s, 6H), 1.97-1.88 (m, 2H), 1.70-1.63 (m, 1H), 1.58-1.47 (m, 3H). | 547.3 |
| SC__1332 | CIS-2-(8-Dimethylamino-2-oxo-8-phenyl-1,3-diazaspiro[4.5]decan-3-yl)-N-phenyl-acetamide | INT-976 | | procedure described | $^1$H NMR (CDCl3): δ 8.32 (br s, 1H), 7.50-7.48 (d, 2H), 7.39-7.36 (m, 2H), 7.33-7.26 (m, 5H), 7.12-7.08 (t, 1H), 5.90 (br s, 1H), 3.90 (s, 2H), 3.25 (s, 2H), 2.12 (m, 4H), 1.99 (s, 6H), 1.94-1.91 (m, 2H), 1.58-1.53 (m, 2H). | 407.2 |
| SC__1333 | CIS-N-(Carbamoyl-methyl)-2-[1-(cyclopropyl-methyl)-8-dimethylamino-2-oxo-8-phenyl-1,3-diazaspiro[4.5]decan-3-yl]-N-methyl-acetamide | INT-991 | 2-methylamino-acetamide•HCl | SC__1308 | $^1$HNMR (DMSO-d6, 400 MHz at 100° C.), δ (ppm) = 7.34-7.23 (m, 5H), 6.85 (bs, 2H), 3.94 (s, 2H), 3.88 (s, 2H), 3.26 (s, 2H), 3.00-2.99 (m, 2H), 2.95 (s, 3H), 2.61 (d, 2H, J = 13.2 Hz), 2.22 (t, 2H, J = 12 Hz), 2.06 (s, 6H), 1.47-1.38 (m, 4H), 0.98 (m, 1H), 0.48 (d, 2H, J = 7.6 Hz), 0.28 (d, 2H, 4.8 Hz). | 388.3 |
| SC__1334 | CIS-2-(8-Dimethylamino-2,4-dioxo-8-phenyl-1,3-diazaspiro[4.5]decan-3-yl)-N-phenyl-acetamide | INT-1018 | 2-Bromo-N-phenylacetamide | SC__1332 | $^1$H NMR (DMSO-d6): δ 10.19 (s, 1H), 8.80 (br s, 1H), 7.52-7.520 (d, 2H), 7.42-7.34 (m, 4H), 7.31-7.27 (m, 3H), 7.06-7.02 (t, 1H), 4.11 (s, 2H), 2.49-2.45 (m, 2H), 2.03-1.93 (m, 8H), 1.71-1.68 (m, 2H), 1.60-1.54 (m, 2H). | 421.2 |

| Example | Chemical name | Reactant I | Reactant II | in analogy to method | $^1$H NMR data | m/z (M + H)$^+$ |
|---|---|---|---|---|---|---|
| SC_1335 | CIS-2-[1-(Cyclobutyl-methyl)-8-dimethylamino-2-oxo-8-phenyl-1,3-diazaspiro[4.5]decan-3-yl]-acetamide | INT-998 | NH$_4$Cl | SC_1308 | $^1$H NMR (DMSO-d6): δ 7.36-7.22 (m, 6H), 6.93 (br s, 1H), 3.61 (s, 2H), 3.18 (s, 2H), 3.04 (d, 2H), 2.66-2.63 (m, 2H), 2.54-2.52 (m, 1H), 2.07-1.93 (m, 10H), 1.81-1.67 (m, 4H), 1.39-1.29 (m, 4H). | 399.3 |
| SC_1336 | CIS-2-[8-Dimethylamino-1-[(1-hydroxy-cyclobutyl)-methyl]-2-oxo-8-phenyl-1,3-diazaspiro[4.5]decan-3-yl]-N-[2-[2-[2-(2-methoxy-ethoxy)-ethoxy]-ethoxy]-ethyl]-acetamide | INT-1019 | 2,5,8,11-tetraoxatridecan-13-amine | SC_1308 | $^1$H NMR (DMSO-d6): δ 7.37-7.33 (m, 2H), 7.28-7.26 (m, 3H), 6.67 (t, 1H), 6.31 (br, s, 1H), 3.83 (s, 2H), 3.65-3.59 (m, 10H), 3.55-3.52 (m, 4H), 3.46-3.42 (m, 2H), 3.37 (s, 5H), 3.29 (s, 2H), 2.68-2.65 (m, 2H), 2.20-2.06 (m, 12H), 1.78-1.71 (m, 1H), 1.59-1.56 (m, 2H), 1.48-1.37 (m, 3H). | 605.3 |
| SC_1337 | CIS-3-[2-(1,1-Dioxo-[1,4]thiazinan-4-yl)-2-oxo-ethyl]-1-[(1-hydroxy-cyclobutyl)-methyl]-8-methylamino-8-phenyl-1,3-diazaspiro[4.5]decane-2,4-dione | SC_1331 | | SC_1303 | $^1$H NMR (600 MHz, DMSO) δ 7.46 (d, 2H), 7.33 (t, 2H), 7.21 (t, 1H), 4.42 (s, 2H), 3.90 (dt, 4H), 3.49 (s, 2H), 3.28 (t, 2H), 3.12 (t, 2H), 2.47 (dd, 2H), 2.35-2.25 (m, 2H), 2.15-2.08 (m, 2H), 1.98-1.89 (m, 6H), 1.84 (d, 2H), 1.71-1.63 (m, 1H), 1.58-1.48 (m, 3H). | 533.3 |
| SC_1338 | CIS-2-(8-Dimethylamino-2-oxo-8-phenyl-1,3-diazaspiro[4.5]decan-3-yl)-N-[2-[2-[2-(2-methoxy-ethoxy)-ethoxy]-ethoxy]-ethyl]-acetamide | INT-976 | 2-bromo-N-(2,5,8,11-tetraoxatridecan-13-yl)acetamide | SC_1332 | $^1$H NMR (DMSO-d6): δ 7.78 (t, 1H), 7.37-7.23 (m, 5H), 6.89 (br s, 1H), 3.60 (s, 2H), 3.49-3.47 (m, 10H), 3.43-3.37 (m, 4H), 3.22-3.17 (m, 5H), 3.08 (s, 2H), 2.30 (br m, 2H), 1.92-1.74 (m, 10H), 1.38 (br m, 2H). | 521.3 |
| SC_1339 | CIS-N-(Carbamoyl-methyl)-N-methyl-2-(8-methylamino-2-oxo-8-phenyl-1,3-diazaspiro[4.5]decan-3-yl)-acetamide | INT-1034 | 2-methylamino-acetamide•HCl | SC_1308 | $^1$HNMR (DMSO-d6, 400 MHz at 100° C.), δ (ppm) = 7.43 (d, 2H, J = 7.52 Hz), 7.31 (t, 2H, J = 7.44 Hz), 7.18 (t, 1H, J = 7.20 Hz), 6.8 (bs, 2H), 3.88 (s, 4H), 3.25 (s, 2H), 2.95 (3H, merged with DMSO water), 1.97-1.85 (m, 7H), 1.77-1.50 (m, 4H). | 388.3 |
| SC_1340 | CIS-N-(Carbamoyl-methyl)-2-(8-dimethylamino-2-oxo-8-phenyl-1,3-diazaspiro[4.5]decan-3-yl)-N-methyl-acetamide | INT-1014 | 2-methylamino-acetamide•HCl | SC_1308 | $^1$HNMR (DMSO-d6, 400 MHz at 100° C.), δ (ppm) = 7.33-7.23 (m, 5H), 6.84 (bs, 2H), 6.45 (s, 1H), 3.87 (s, 4H), 3.13 (s, 2H), 2.95 (3H, merged with DMSO water), 2.32-2.27 (m, 2H), 2.01 (s, 6H), 1.88-1.77 (m, 4H), 1.46-1.41 (m, 2H). | 402.1 |
| SC_1341 | CIS-N-(Carbamoyl-methyl)-2-[8-dimethylamino-1-(oxetan-3-yl-methyl)-2-oxo-8-phenyl-1,3-diazaspiro[4.5]decan-3-yl]-N-methyl-acetamide | INT-1035 | 2-methylamino-acetamide•HCl | SC_1308 | $^1$HNMR (DMSO-d6, 400 MHz at 100° C.), δ (ppm) = 7.33-7.24 (m, 5H), 6.8 (bs, 2H), 4.63 (t, 2H, J = 5.6 Hz), 4.39 (s, 2H), 3.93-3.87 (m, 4H), 3.36 (d, 2H, J = 6.8 Hz), 3.24 (m, 3H), 2.95 (s, 3H), 2.66-2.60 (m, 2H), 2.06-2.03 (m, 8H), 1.44-1.37 (m, 4H). | 472.3 |

-continued

| Example | Chemical name | Reactant I | Reactant II | in analogy to method | ¹H NMR data | m/z (M + H)⁺ |
|---|---|---|---|---|---|---|
| SC_1342 | CIS-N-(2-Hydroxy-ethyl)-N-methyl-2-(8-methylamino-2-oxo-8-phenyl-1,3-diazaspiro[4.5]decan-3-yl)-acetamide | INT-1034 | 2-(methylamino)-ethanol | SC_1308 | ¹HNMR (DMSO-d6, 400 MHz at 100° C.), δ (ppm) = 7.41 (d, 2H, J = 7.48 Hz), 7.31 (t, 2H, J = 7.60 Hz), 7.18 (t, 1H, J = 7.18 Hz), 6.24 (s, 1H), 4.58-4.36 (m, 1H), 3.92 (bs, 2H), 3.52 (bs, 2H), 3.34 (t, 2H, J = 5.72 Hz), 3.24 (s, 2H), 2.96-2.84 (m, 3H), 1.97-1.84 (m, 7H), 1.74-1.49 (m, 4H). | 375.0 |
| SC_1343 | CIS-2-[1-(Cyclopropyl-methyl)-8-dimethylamino-2-oxo-8-phenyl-1,3-diazaspiro[4.5]decan-3-yl]-acetamide | INT-991 | ammonium chloride | SC_1308 | ¹H NMR (DMSO d6): δ 7.34-7.25 (m, 6H), 6.96 (s, 1H), 3.63 (s, 2H), 3.22 (m, 2H), 2.93 (d, 2H), 2.67-2.64 (m, 2H), 2.16 (t, 2H), 1.97 (s, 6H), 1.43-1.31 (m, 4H), 0.93 (m, 1H), 0.46-0.45 (m, 2H), 0.26 (m, 2H). | 385.3 |
| SC_1344 | CIS-2-[1-(Cyclopropyl-methyl)-8-dimethylamino-2-oxo-8-phenyl-1,3-diazaspiro[4.5]decan-3-yl]-N-(2-hydroxy-ethyl)-acetamide | INT-991 | 2-aminoethanol | SC_1308 | ¹H NMR (DMSO d6): δ 7.77-7.75 (m, 1H), 7.36-7.33 (m, 4H), 7.26-7.23 (m, 1H), 4.65-4.63 (m, 1H), 3.67 (s, 2H), 3.39-3.35 (m, 2H), 3.21 (s, 2H), 3.12-3.09 (m, 2H), 2.94-2.93 (m, 2H), 2.67-2.64 (m, 2H), 2.19-2.14 (t, 2H), 1.97 (s, 6H), 1.42-1.31 (m, 4H), 0.93-0.92 (s, 1H), 0.48-0.44 (m, 2H), 0.27-0.25 (m, 2H). | 429.3 |
| SC_1345 | CIS-2-[1-(Cyclobutyl-methyl)-8-dimethylamino-8-(3-fluorophenyl)-2-oxo-1,3-diazaspiro[4.5]decan-3-yl]-N-(2-hydroxy-ethyl)-N-methyl-acetamide | INT-1032 | 2-(methylamino)-ethanol | SC_1308 | ¹H NMR (600 MHz, DMSO) δ 7.39 (td, 1H), 7.16 (dd, 1H), 7.13 (dt, 2H), 7.08 (td, 1H), 3.99 (s, 1H), 3.91 (s, 1H), 3.52 (q, 1H), 3.45 (d, 1H), 3.40-3.36 (m, 0H), 3.34-3.28 (m, 2H), 3.19 (d, 2H), 3.05 (dd, 2H), 2.96 (s, 2H), 2.80 (s, 2H), 2.66-2.60 (m, 3H), 2.07-1.93 (m, 3H), 1.99 (s, 7H), 1.85-1.74 (m, 2H), 1.75-1.65 (m, 3H), 1.40-1.28 (m, 5H). | 475.3 |
| SC_1346 | CIS-2-[1-(Cyclobutyl-methyl)-8-dimethylamino-8-(3-fluorophenyl)-2-oxo-1,3-diazaspiro[4.5]decan-3-yl]-acetic acid tert-butyl ester | INT-1031 | tert-butyl-bromo acetate | procedure described | ¹H NMR (600 MHz, DMSO) δ 7.43-7.36 (m, 1H), 7.17 (d, 1H), 7.13 (dt, 1H), 7.09 (td, 1H), 3.75 (d, 2H), 3.21 (s, 2H), 3.05 (d, 2H), 2.67-2.61 (m, 2H), 2.08-2.00 (m, 2H), 1.99 (d, 7H), 1.98-1.93 (m, 2H), 1.83-1.75 (m, 2H), 1.75-1.65 (m, 2H), 1.39 (d, 8H), 1.38-1.29 (m, 5H). | 474.3 |
| SC_1347 | CIS-2-[1-(Cyclopropyl-methyl)-8-dimethylamino-2-oxo-8-phenyl-1,3-diazaspiro[4.5]decan-3-yl]-N-(2-hydroxy-ethyl)-N-methyl-acetamide | INT-991 | 2-(methylamino)-ethanol | SC_1308 | ¹H NMR (DMSO): δ 7.36-7.32 (m, 4H), 7.26-7.23 (m, 1H), 4.83-4.63 (m, 1H), 3.99-3.91 (m, 2H), 3.50-3.44 (m, 2H), 3.32-3.28 (m, 2H), 3.22-3.20 (m, 2H), 2.95-2.92 (m, 3H), 2.79 (s, 2H), 2.67-2.65 (m, 2H), 2.20-2.15 (m, 2H), 1.97 (s, 6H), 1.42-1.30 (m, 4H), 0.93-0.90 (s, 1H), 0.47-0.43 (m, 2H), 0.27-0.25 (m, 2H). | 444.3 |

-continued

| Example | Chemical name | Reactant I | Reactant II | in analogy to method | ¹H NMR data | m/z (M + H)⁺ |
|---|---|---|---|---|---|---|
| SC_1348 | CIS-2-[1-(Cyclopropyl-methyl)-8-dimethylamino-2-oxo-8-phenyl-1,3-diazaspiro[4.5]decan-3-yl]-N-(2-methylsulfonyl-ethyl)-acetamide | INT-991 | 2-(methylsulfonyl)-ethanamine | SC_1308 | ¹H NMR (DMSO): δ 8.05-8.02 (m, 1H), 7.37-7.32 (m, 4H), 7.26-7.22 (m, 1H), 3.67 (s, 2H), 3.49-3.44 (m, 2H), 3.25-3.21 (m, 4H), 2.98-2.93 (m, 5H), 2.67-2.64 (m, 2H), 2.19-2.13 (m, 2H), 1.97 (s, 6H), 1.45-1.31 (m, 4H), 0.95-0.91 (s, 1H), 0.48-0.44 (m, 2H), 0.28-0.24 (m, 2H). | 491.3 |
| SC_1349 | CIS-N-(Carbamoyl-methyl)-2-[1-(cyclobutyl-methyl)-8-dimethylamino-8-(3-fluorophenyl)-2-oxo-1,3-diazaspiro[4.5]decan-3-yl]-N-methyl-acetamide | INT-1032 | 2-methylamino-acetamide hydrochloride | SC_1308 | 1H NMR (600 MHz, DMSO) δ 7.39 (td, 1H), 7.31 (s, 1H), 7.19-7.05 (m, 3H), 6.99 (s, 1H), 4.00-3.78 (m, 4H), 3.18 (d, 2H), 3.07-3.02 (m, 2H), 2.94 (s, 2H), 2.76 (s, 1H), 2.66-2.59 (m, 2H), 2.06-1.93 (m, 9H), 1.84-1.73 (m, 2H), 1.70 (dt, 2H), 1.43-1.28 (m, 4H) (mixture of amide rotamers) | 488.3 |
| SC_1350 | CIS-1-[2-[8-Dimethylamino-1-[(1-hydroxy-cyclobutyl)-methyl]-2-oxo-8-phenyl-1,3-diazaspiro[4.5]decan-3-yl]-acetyl]-piperidine-4-carboxylic acid amide | INT-1019 | piperidine-4-carboxamide | SC_1308 | 1H NMR (DMSO d6): δ 7.37-7.25 (m, 6H), 6.77 (s, 1H), 6.02 (s, 1H), 4.26-4.23 (m, 1H), 4.02-3.91 (m, 2H), 3.79-3.75 (m, 2H), 3.31 (m, 2H), 3.10 (s, 2H), 3.00-2.93 (t, 1H), 2.68-2.65 (m, 2H), 2.60-2.58 (m, 2H), 2.32-2.27 (m, 2H), 2.06-2.03 (m, 4H), 1.91-1.83 (m, 8H), 1.67-1.61 (m, 2H), 1.49-1.40 (m, 2H), 1.36-1.30 (m, 4H). | 526.4 |
| SC_1351 | CIS-8-Dimethylamino-1-[(1-hydroxy-cyclobutyl)-methyl]-3-[2-(4-methylsulfonyl-piperidin-1-yl)-2-oxo-ethyl]-8-phenyl-1,3-diazaspiro[4.5]decan-2-one | INT-1019 | 4-(methylsulfonyl)-piperidine | SC_1308 | 1H NMR (DMSO d6): δ 7.37-7.23 (m, 5H), 6.00 (s, 1H), 4.45-4.41 (m, 1H), 4.08-3.91 (m, 3H), 3.17 (s, 3H), 3.10-2.99 (m, 2H), 2.92 (s, 3H), 2.73-2.65 (m, 3H), 2.06-1.83 (m, 15H), 1.64-1.46 (m, 4H), 1.40-1.30 (m, 4H). | 561.3 |
| SC_1352 | CIS-2-[1-(Cyclobutyl-methyl)-8-dimethylamino-8-(3-fluorophenyl)-2-oxo-1,3-diazaspiro[4.5]decan-3-yl]-N-(2-hydroxy-ethyl)-acetamide | INT-1032 | 2-aminoethanol | SC_1308 | 1H NMR (600 MHz, DMSO) δ 7.73 (t, 1H), 7.39 (td, 1H), 7.19-7.05 (m, 3H), 4.66 (t, 1H), 3.67 (s, 2H), 3.43-3.35 (m, 2H), 3.18 (s, 2H), 3.11 (q, 2H), 3.05 (d, 2H), 2.65-2.58 (m, 2H), 2.55-2.45 (m, 1H), 2.07-1.93 (m, 10H), 1.84-1.73 (m, 2H), 1.74-1.64 (m, 2H), 1.41-1.29 (m, 4H). | 461.3 |
| SC_1353 | TRANS-2-[1-(Cyclobutyl-methyl)-8-dimethylamino-2-oxo-8-phenyl-1,3-diazaspiro[4.5]decan-3-yl]-N-(2-hydroxy-ethyl)-acetamide | INT-1067 | 2-aminoethanol | SC_1357 | 1HNMR at 100° C. (DMSO-d6, 400 MHz), δ (ppm) = 7.44-7.38 (m, 5H), 7.29 (t, 1H, J = 6.48 Hz), 4.29 (bs, 1H), 3.69 (s, 2H), 3.48-3.44 (m, 2H), 3.28 (s, 2H), 3.21-3.17 (m, 2H), 2.69-2.67 (m, 2H), 2.58-2.55 (d, 2H, J = 11.6 Hz), 2.19-2.12 (m, 1H), 1.98 (s, 6H), 1.82-1.74 (m, 2H), 1.71-1.60 (m, 4H), 1.58-1.46 (m, 6H). | 443.1 |

-continued

| Example | Chemical name | Reactant I | Reactant II | in analogy to method | $^1$H NMR data | m/z (M + H)$^+$ |
|---|---|---|---|---|---|---|
| SC_1354 | TRANS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide | INT-1067 | 2-methylamino-acetamide hydrochloride | SC_1357 | 1HNMR at 100° C. (DMSO-d6, 400 MHz), δ (ppm) = 7.40-7.28 (m, 5H), 6.87 (bs, 2H), 3.94-3.90 (m, 4H), 3.29 (s, 2H), 3.68-3.66 (m, 2H), 2.58-2.55 (m, 2H), 2.15-2.13 (m, 1H), 1.98 (s, 6H), 1.77 (bs, 2H), 1.64-1.61 (m, 4H), 1.46-1.27 (m, 6H). | 470.4 |
| SC_1355 | CIS-8-Dimethylamino-1-[(1-hydroxy-cyclobutyl)-methyl]-3-[2-(4-hydroxy-4-methyl-piperidin-1-yl)-2-oxo-ethyl]-8-phenyl-1,3-diazaspiro[4.5]decan-2-one | INT-1019 | 4-methylpiperidin-4-ol | SC_1308 | 1H NMR (DMSO d6): δ 7.36-7.32 (m, 4H), 7.26-7.23 (m, 1H), 6.02 (s, 1H), 4.37 (s, 1H), 3.96-3.95 (m, 2H), 3.90-3.80 (m, 1H), 3.50-3.40 (m, 1H), 3.30 (m, 1H), 3.10 (s, 2H), 3.00-2.93 (m, 1H), 2.68-2.65 (m, 2H), 2.09-2.04 (m, 4H), 1.97 (s, 6H), 1.90-1.86 (m, 2H), 1.64-1.61 (m, 1H), 1.48-1.40 (m, 5H), 1.37-1.30 (m, 4H), 1.22 (m, 2H), 1.11 (s, 3H). | 513.4 |
| SC_1356 | CIS-2-[1-(Cyclobutyl-methyl)-8-dimethylamino-8-(4-fluorophenyl)-2-oxo-1,3-diazaspiro[4.5]decan-3-yl]-N-(2-hydroxy-ethyl)-acetamide | INT-1058 | 2-aminoethanol | SC_1308 | 1H NMR (600 MHz, DMSO) δ 7.72 (t, 1H), 7.40-7.33 (m, 2H), 7.15 (t, 2H), 4.81 (tdd, 0.15H), 4.65 (ddq, 0.75H), 3.66 (s, 2H), 3.48 (q), 3.25 (q), 3.17 (s, 2H), 3.11 (q, 2H), 3.05 (d, 2H), 2.66-2.60 (m, 2H), 2.57-2.47 (m, 1H), 2.06-1.92 (m, 10H), 1.85-1.73 (m, 2H), 1.75-1.63 (m, 2H), 1.40-1.28 (m, 4H). Not all signals could be intergrated due to overlap with solvent peaks; two rotamers observed in spectrum. | 461.3 |
| SC_1357 | TRANS-1-(Cyclopropyl-methyl)-8-dimethylamino-3-(2-morpholin-4-yl-2-oxo-ethyl)-8-phenyl-1,3-diazaspiro[4.5]decan-2-one | INT-1062 | morpholine | procedure described | 1HNMR (DMSO-d6, 400 MHz), δ (ppm) = 7.44-7.29 (m, 5H), 3.96 (s, 2H), 3.56 (bs, 4H), 3.42-3.40 (m, 4H), 3.29 (s, 2H), 2.67 (bs, 2H), 2.55-2.54 (d, 2H, J = 6.36 Hz), 1.92 (s, 6H), 1.56-.144 (m, 6H), 0.51-0.48 (m, 1H), 0.16-0.14 (m, 2H), (−0.26)-(−0.27) (m, 2H). | 455.1 |
| SC_1358 | TRANS-8-Dimethylamino-3-(2-morpholin-4-yl-2-oxo-ethyl)-8-phenyl-1,3-diazaspiro[4.5]decan-2-one | INT-1060 | morpholine | SC_1357 | 1HNMR (DMSO-d6, 400 MHz at 100° C.), δ (ppm) = 7.39-7.36 (m, 4H), 7.26-7.23 (m, 1H), 6.35 (m, 1H), 3.91 (s, 2H), 3.59 (t, 4H, J = 4.8 Hz), 3.45 (t, 4H, J = 4.8 Hz), 3.27 (s, 2H), 2.18-2.15 (m, 2H), 2.0-1.99 (m, 8H), 1.78-1.73 (m, 2H), 1.48-1.43 (m, 2H). | 401.3 |
| SC_1359 | CIS-2-[1-(Cyclobutyl-methyl)-8-dimethylamino-8-(4-fluorophenyl)-2-oxo-1,3-diazaspiro[4.5]decan-3-yl]-N-(2-hydroxy-ethyl)-N-methyl-acetamide | INT-1058 | 2-(methylamino)-ethanol | SC_1308 | 1H NMR (600 MHz, DMSO) δ 7.37 (dd, 2H), 7.15 (t, 2H), 4.82 (t, 0.2H), 4.63 (t, 0.2H), 3.98 (s, 1H), 3.91 (s, 1H), 3.51 (q, 1H), 3.45 (q, 1H), 3.37-3.26 (m, 2H), 3.18 (d, 2H), 3.04 (dd, 2H), 2.96 (s, 1H), 2.80 (s, 2H), 2.64 (d, 2H), 2.56-2.47 (m, 1H), 2.08-2.00 (m, 2H), 2.00-1.91 (m, 8H), 1.79 (ddt, 2H), 1.75-1.65 (m, 2H), 1.37 (d, 2H), 1.31 (td, 2H). Two rotamers are observed. | 475.3 |

-continued

| Example | Chemical name | Reactant I | Reactant II | in analogy to method | ¹H NMR data | m/z (M + H)⁺ |
|---|---|---|---|---|---|---|
| SC_1360 | CIS-N-(Carbamoyl-methyl)-2-[1-(cyclobutyl-methyl)-8-dimethylamino-8-(4-fluorophenyl)-2-oxo-1,3-diazaspiro[4.5]decan-3-yl]-N-methyl-acetamide | INT-1058 | 2-methylamino-acetamide hydrochloride | SC_1308 | 1H NMR (600 MHz, DMSO) δ 7.46 (s, 0.4H), 7.37 (dd, 2H), 7.30 (s, 0.6H), 7.20-7.12 (m, 2H), 6.99 (s, 0.6H), 3.97 (s, 1H), 3.90 (s, 1H), 3.83 (d, 2H), 3.18 (d, 2H), 3.04 (dd, 2H), 2.94 (s, 2H), 2.76 (s, 1H), 2.67-2.60 (m, 2H), 2.57-2.47 (m, 1H), 2.07-1.92 (m, 10H), 1.83-1.74 (m, 2H), 1.74-1.63 (m, 2H), 1.40-1.27 (m, 4H). Two rotamers are observed. | 488.3 |
| SC_1361 | CIS-1-(Cyclopropyl-methyl)-8-dimethylamino-3-[2-(4-hydroxy-4-methyl-piperidin-1-yl)-2-oxo-ethyl]-8-phenyl-1,3-diazaspiro[4.5]decan-2-one | INT-991 hydrochloride | 4-methylpiperidin-4-ol | SC_1308 | 1H NMR (DMSO d6): δ 7.36-7.33 (m, 4H), 7.25-7.23 (m, 1H), 4.37 (s, 1H), 3.92-3.84 (m, 3H), 3.48-3.46 (m, 1H), 3.25-3.21 (m, 3H), 2.99-2.92 (m, 3H), 2.67-2.64 (m, 2H), 2.20-2.15 (t, 2H), 1.97 (s, 6H), 1.44-1.21 (m, 8H), 1.11 (s, 3H), 0.93-0.92 (m, 1H), 0.47-0.45 (m, 2H), 0.44-0.43 (m, 2H). | 483.4 |
| SC_1362 | CIS-1-[2-[1-(Cyclopropyl-methyl)-8-dimethylamino-2-oxo-8-phenyl-1,3-diazaspiro[4.5]decan-3-yl]-acetyl]-piperidine-4-carboxylic acid amide | INT-991 hydrochloride | piperidine-4-carboxamide | SC_1308 | 1H NMR (DMSO): δ 7.34-7.32 (m, 4H), 7.25-7.24 (m, 2H), 6.77 (s, 1H), 4.21-4.29 (m, 1H), 3.94-3.86 (m, 2H), 3.78 (m, 1H), 3.22 (s, 2H), 2.96-2.93 (m, 3H), 2.67-2.57 (m, 2H), 2.50 (t, 1H), 2.30 (m, 1H), 2.20-2.15 (m, 2H), 1.97 (s, 6H), 1.69-1.67 (m, 2H), 1.42-1.31 (m, 6H), 0.92 (m, 1H), 0.47-0.43 (m, 2H), 0.27-0.24 (m, 2H). | 496.4 |
| SC_1363 | TRANS-2-[1-(Cyclopropyl-methyl)-8-dimethylamino-2-oxo-8-phenyl-1,3-diazaspiro[4.5]decan-3-yl]-acetamide | INT-1061 | t-butyl-bromoacetate (step 1), 7N ammonia in methanol (step 2) | procedure described | 1HNMR at 100° C. (DMSO-d6, 400 MHz), δ (ppm) = 7.40-7.29 (m, 5H), 6.76 (bs, 2H), 3.68 (s, 2H), 3.33 (s, 2H), 2.61-2.60 (m, 4H), 2.00 (s, 6H), 1.61-153 (m, 6H), 0.58-0.56 (m, 1H), 0.22-0.20 (m, 2H), (−0.16)-(−0.18) (m, 2H). | 385.2 |
| SC_1364 | TRANS-2-[1-(Cyclopropyl-methyl)-8-dimethylamino-2-oxo-8-phenyl-1,3-diazaspiro[4.5]decan-3-yl]-N-methyl-acetamide | INT-1062 | methylamine | SC_1357 | 1HNMR at 100° C. (DMSO-d6, 400 MHz), δ (ppm) = 7.43-7.27 (m, 6H), 3.68 (s, 2H), 3.32 (s, 2H), 2.64-2.58 (m, 7H), 1.99 (s, 6H), 1.66-.152 (m, 6H), 0.58-0.56 (m, 1H), 0.23-0.19 (m, 2H), (−0.15)-(−0.17) (m, 2H). | 399.2 |
| SC_1365 | TRANS-1-(Cyclopropyl-methyl)-8-dimethylamino-3-[2-(1,1-dioxo-[1,4]thiazinan-4-yl)-2-oxo-ethyl]-8-phenyl-1,3-diazaspiro[4.5]decan-2-one | INT-1062 | 1,4-thiazinane 1,1-dioxide | SC_1357 | 1HNMR at 100° C. (DMSO-d6, 400 MHz), δ (ppm) = 7.40-7.28 (m, 5H), 4.06 (s, 2H), 3.90-3.88 (m, 4H), 3.34 (s, 2H), 3.14 (bs, 4H), 2.66-2.60 (m, 4H), 1.99 (s, 6H), 1.63-.152 (m, 6H), 0.58-0.56 (m, 1H), 0.23-0.20 (m, 2H), (−0.16)-(−0.17) (m, 2H). | 503.3 |

-continued

| Example | Chemical name | Reactant I | Reactant II | in analogy to method | $^1$H NMR data | m/z (M + H)$^+$ |
|---|---|---|---|---|---|---|
| SC_1366 | CIS-1-(Cyclopropyl-methyl)-8-dimethylamino-3-[2-(4-methylsulfonyl-piperidin-1-yl)-2-oxo-ethyl]-8-phenyl-1,3-diazaspiro[4.5]decan-2-one | INT-991 hydrochloride | 4-(methylsulfonyl)-piperidine | SC_1308 | 1H NMR (DMSO d6): δ 7.36-7.32 (m, 4H), 7.26-7.23 (m, 1H), 4.40 (m, 1H), 4.04-3.88 (m, 3H), 3.31 (m, 1H), 3.02 (s, 2H), 2.94 (t, 1H), 2.94-2.92 (m, 5H), 2.67-2.50 (m, 3H), 2.20-2.15 (m, 2H), 2.08-1.97 (m, 8H), 1.56 (m, 1H), 1.42-1.31 (m, 5H), 0.92 (m, 1H), 0.47-0.43 (m, 2H), 0.27-0.24 (m, 2H). | 531.4 |
| SC_1368 | CIS-8-Dimethylamino-3-[2-(1,1-dioxo-[1,4]thiazinan-4-yl)-2-oxo-ethyl]-1-[(1-hydroxy-cyclobutyl)-methyl]-8-phenyl-1,3-diazaspiro[4.5]decan-2-one | INT-1019 | 1,4-thiazinane 1,1-dioxide | SC_1308 | 1H NMR (600 MHz, DMSO) δ 7.35 (d, 4H), 7.29-7.22 (m, 2H), 3.83 (dt, 4H), 3.25-3.19 (m, 2H), 3.15-3.05 (m, 4H), 2.72-2.65 (m, 2H), 2.12-2.04 (m, 6H), 1.99 (s, 6H), 1.88 (dt, 2H), 1.68-1.59 (m, 1H), 1.50 (d, 2H), 1.43-1.29 (m, 3H). | 533.3 |
| SC_1369 | TRANS-2-(8-Dimethylamino-2-oxo-8-phenyl-1,3-diazaspiro[4.5]decan-3-yl)-acetamide | INT-1060 | t-butyl-bromoacetate (step 1), 7N ammonia in methanol (step 2) | SC_1363 | 1HNMR (DMSO-d6, 400 MHz at 100° C.), δ (ppm) = 7.37-7.24 (m, 5H), 6.74 (bs, 2H), 6.38 (s, 1H), 3.62 (s, 2H), 3.27 (s, 2H), 2.19-2.14 (m, 2H), 2.01-1.96 (m, 8H), 1.78-1.73 (m, 2H), 1.48-1.43 (m, 2H). | 331.2 |
| SC_1370 | TRANS-8-Dimethylamino-3-[2-(1,1-dioxo-[1,4]thiazinan-4-yl)-2-oxo-ethyl]-8-phenyl-1,3-diazaspiro[4.5]decan-2-one | INT-1060 | 1,4-thiazinane 1,1-dioxide | SC_1357 | 1HNMR (DMSO-d6, 400 MHz at 100° C.), δ (ppm) = 7.37-7.24 (m, 5H), 6.41 (s, 1H), 4.0 (s, 2H), 3.89 (bs, 4H), 3.28 (s, 2H), 3.14 (bs, 4H), 2.15 (m, 2H), 1.99 (m, 8H), 1.78-1.73 (m, 2H), 1.48-1.43 (m 2H). | 449.2 |
| SC_1371 | CIS-8-(dimethylamino)-8-phenyl-1-(2,2,2-trifluoroethyl)-3-(2-(trifluoromethyl)pyrimidin-5-yl)-1,3-diazaspiro[4.5]decan-2-one | INT-1068 | t-butyl-bromoacetate (step 1), 7N ammonia in methanol (step 2) | SC_1363 | | 413.2 |
| SC_1372 | CIS-8-(dimethylamino)-8-phenyl-3-(2-(trifluoromethyl)pyrimidin-5-yl)-1-(3,3,3-trifluoropropyl)-1,3-diazaspiro[4.5]decan-2-one | INT-1070 | t-butyl-bromoacetate (step 1), 7N ammonia in methanol (step 2) | SC_1363 | | |

Chemical Structure of all Examples

SC_1001

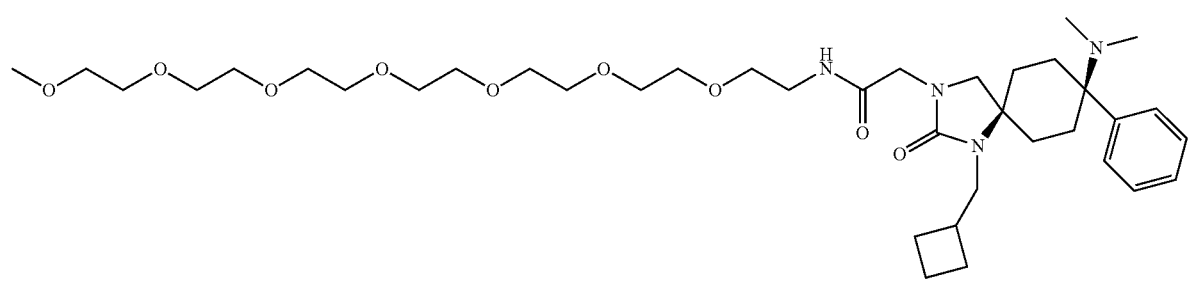

-continued
SC_1002
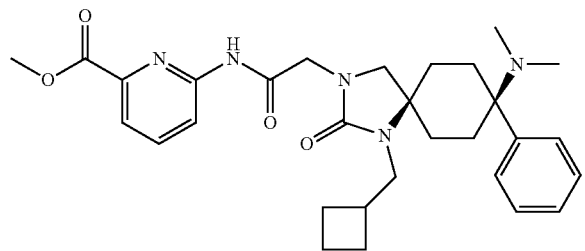
SC_1003
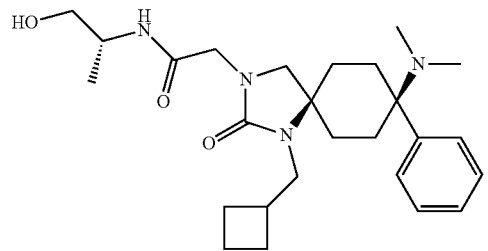
SC_1004
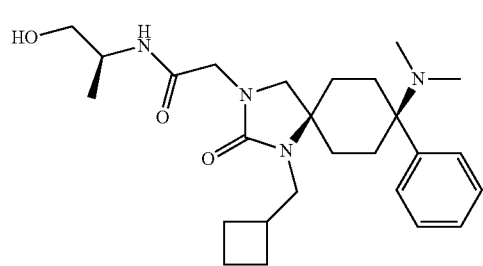
SC_1005
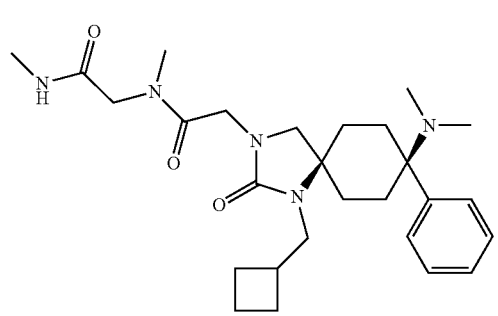
SC-1006
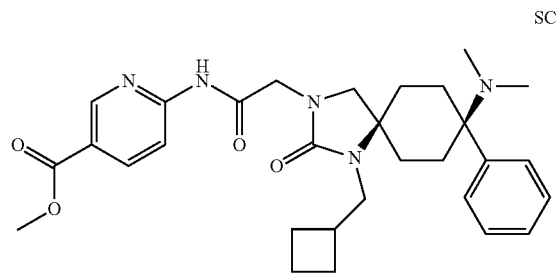
SC-1007
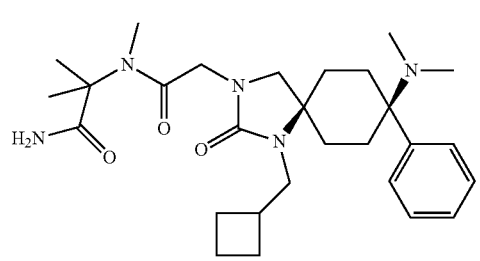
SC-1008
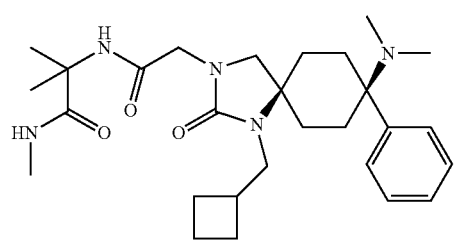
SC-1009
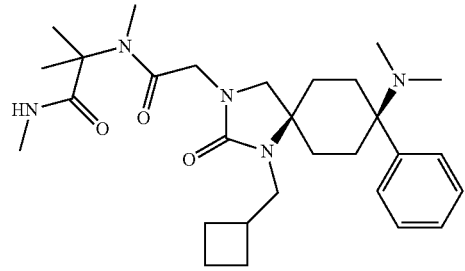
SC_1010
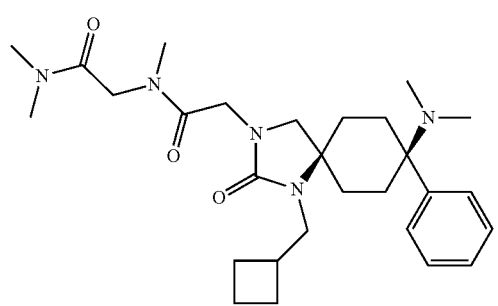
SC_1011
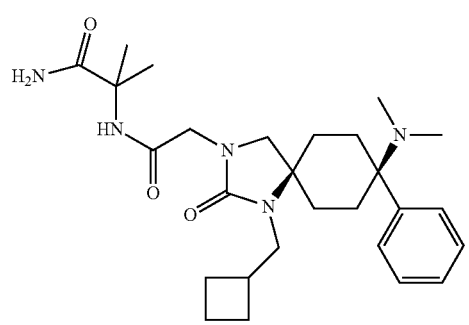

-continued
SC_1012
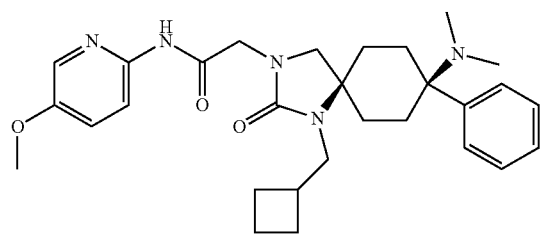
SC_1013
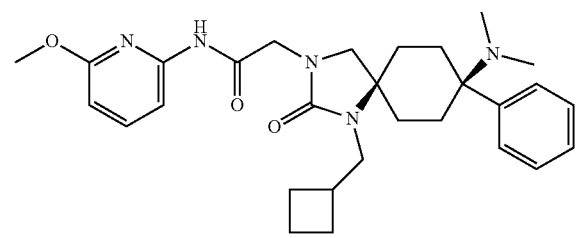
SC_1014
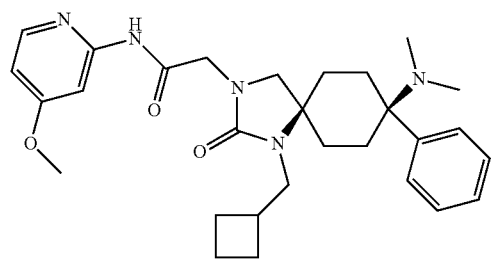
SC_1015
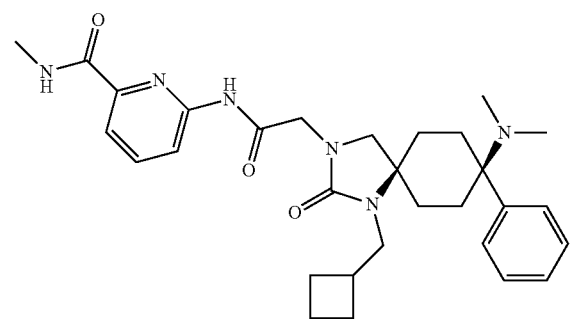
SC_1016
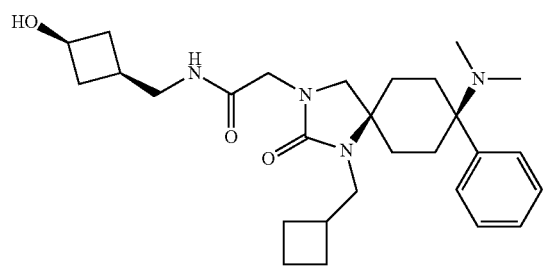
SC_1017
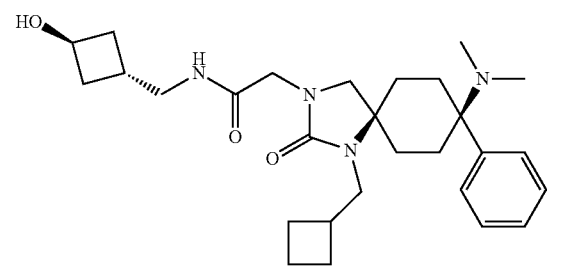
SC_1018
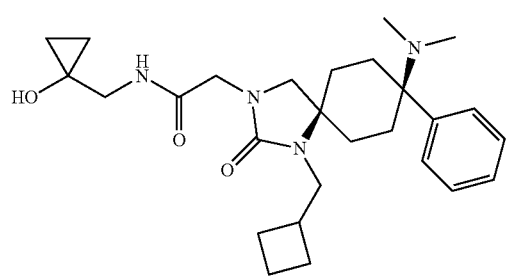
SC_1019
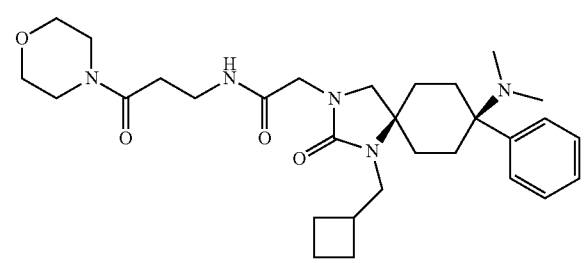
SC_1020
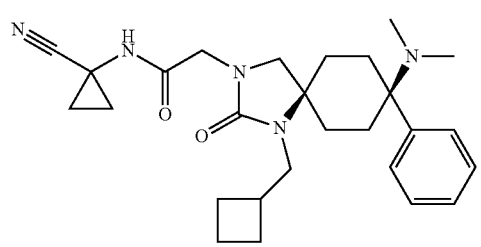
SC_1021
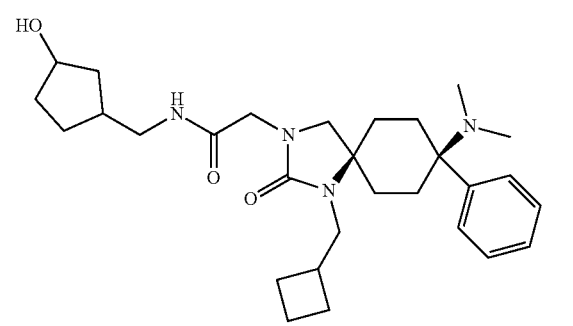

-continued
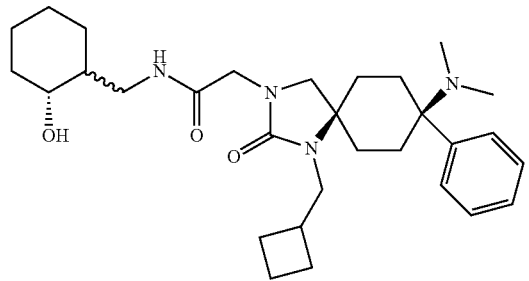
SC_1022
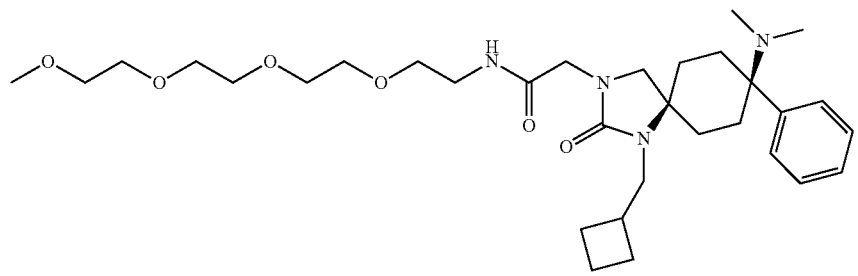
SC_1023
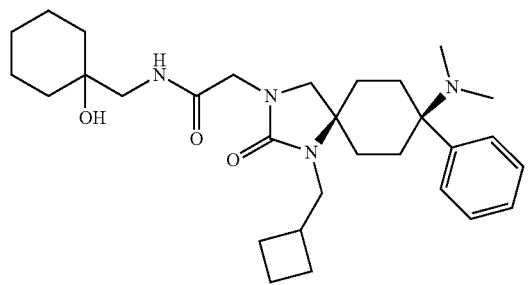
SC_1024
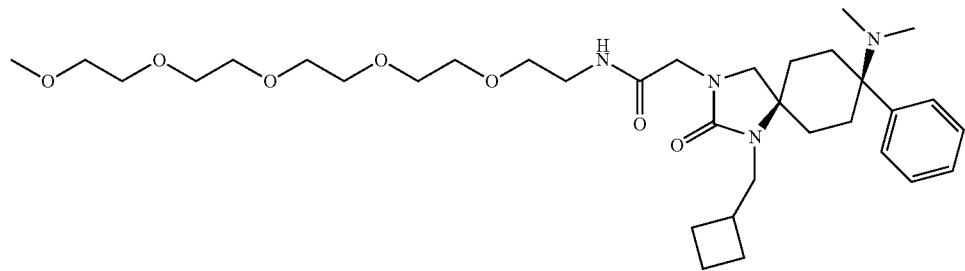
SC_1025
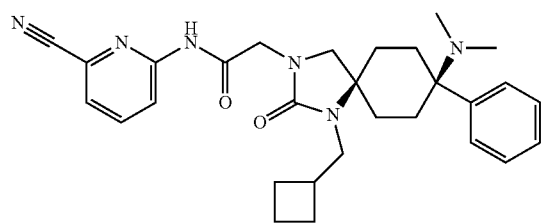
SC_1026
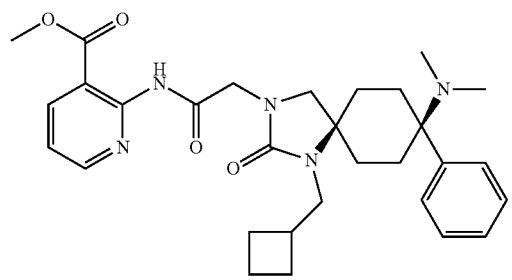
SC_1027

-continued
SC_1028
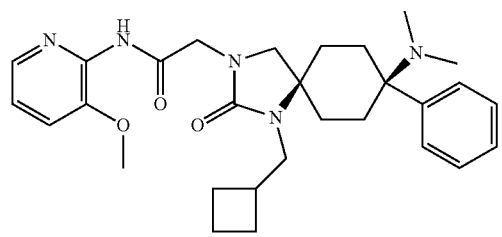
SC_1029
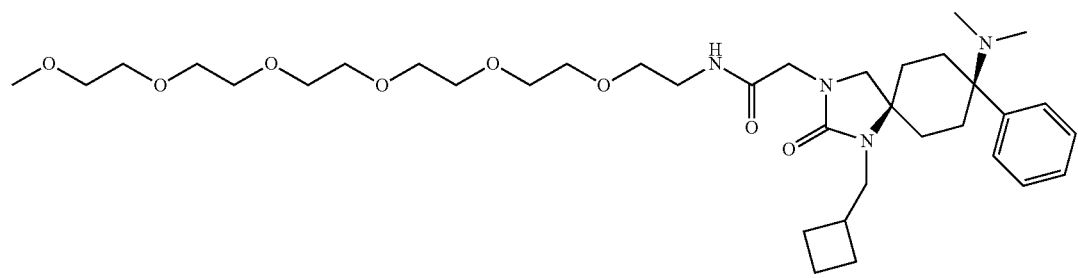
SC_1030
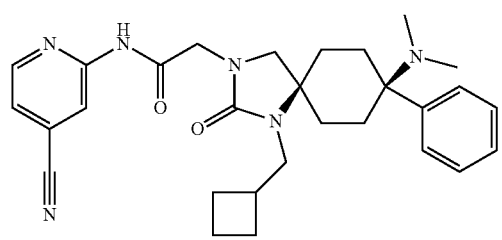
SC_1031
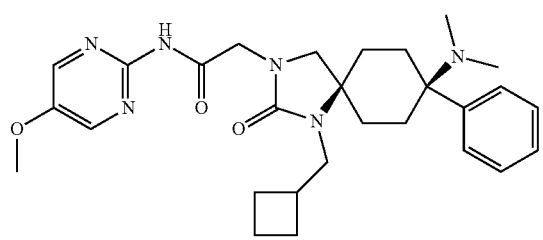
SC_1032
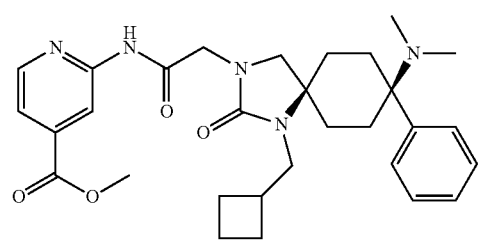
SC_1033
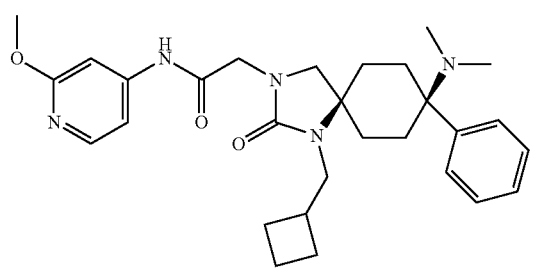
SC_1034
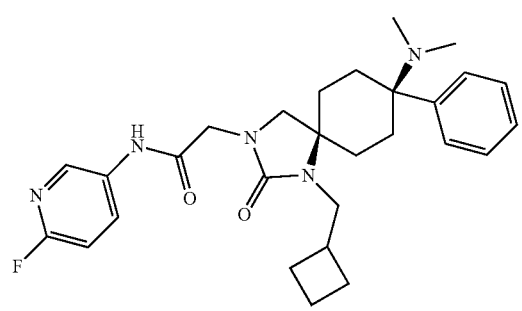
SC_1035
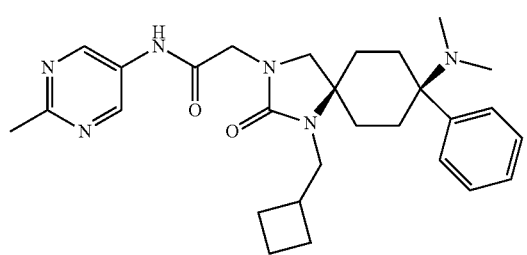

-continued
SC_1036
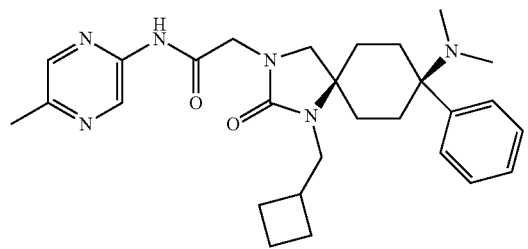
SC_1037
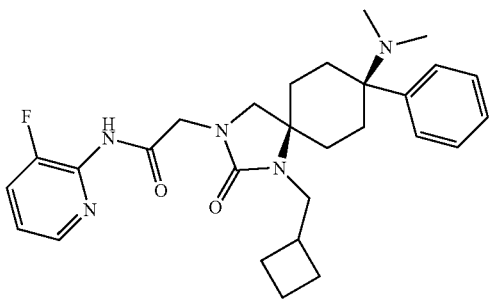
SC_1038
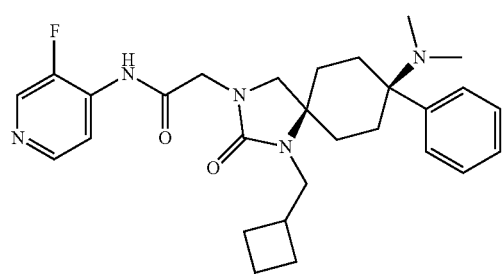
SC_1039
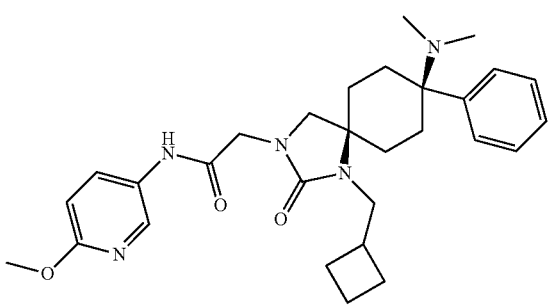
SC_1040
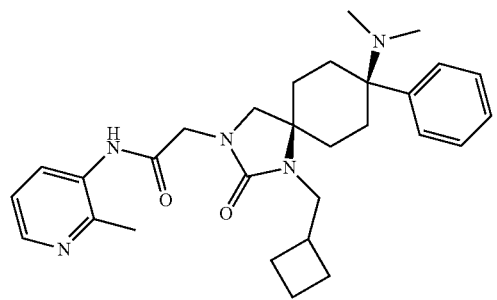
SC_1041
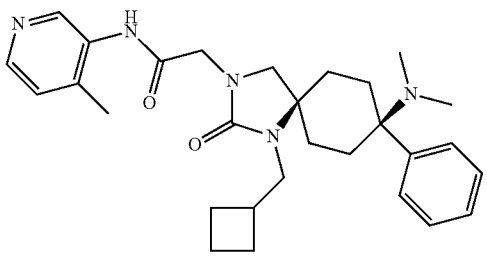
SC_1042
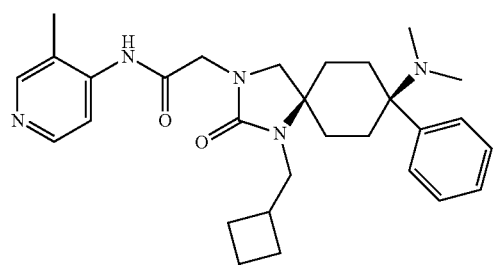
SC_1043
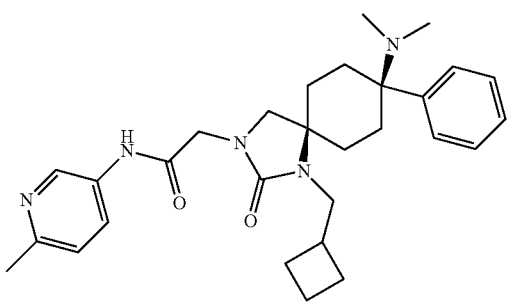
SC_1044
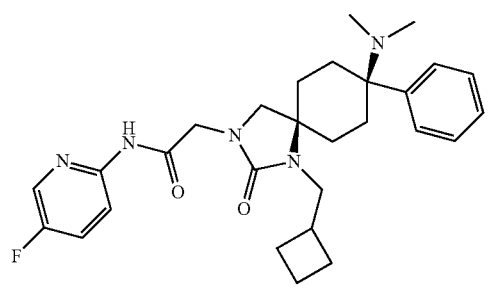
SC_1045
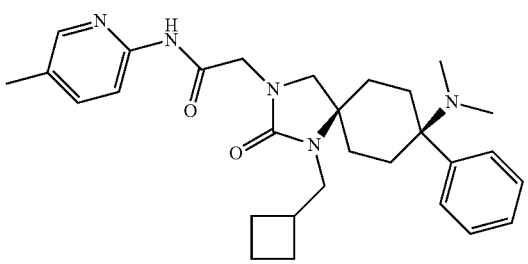

-continued
SC_1046
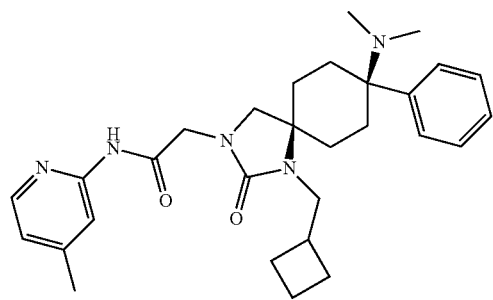
SC_1047
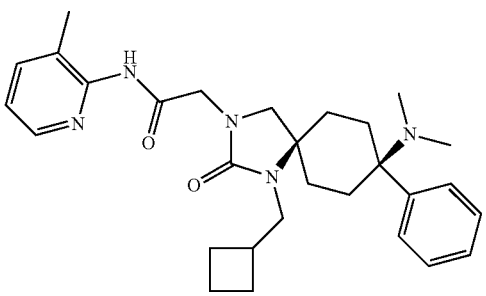
SC_1048
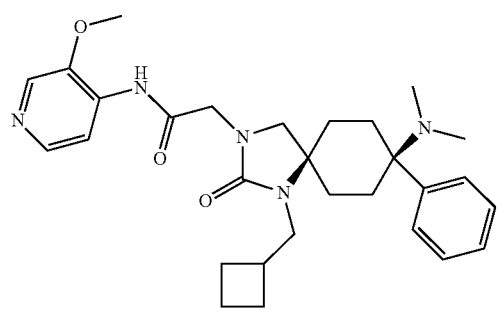
SC_1049
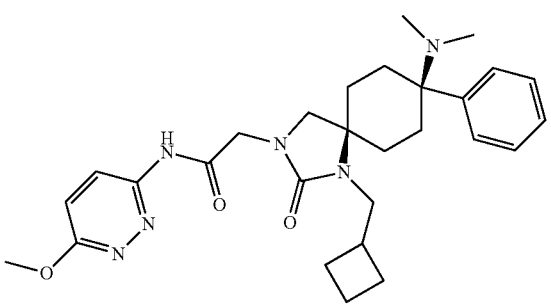
SC_1050
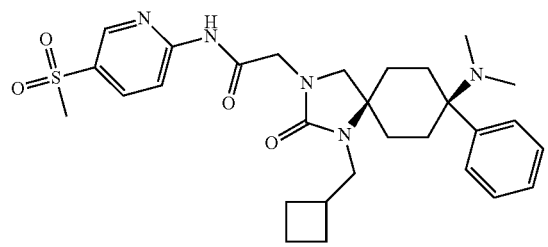
SC_1051
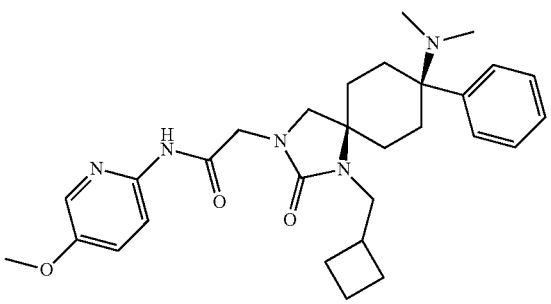
SC_1052
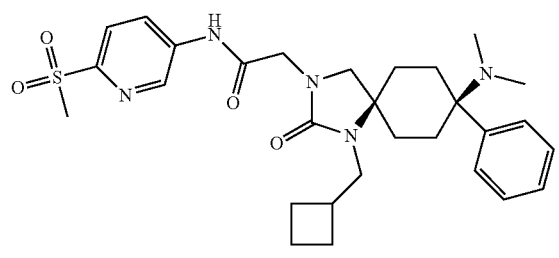
SC_1053
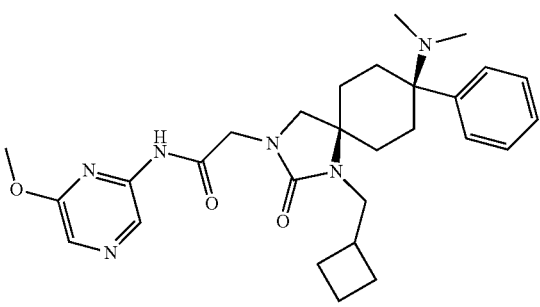
SC_1054
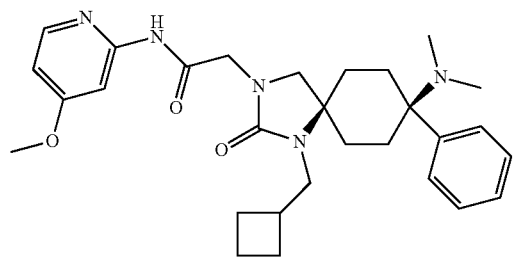
SC_1055
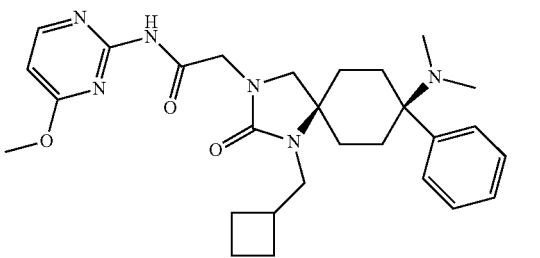

-continued
SC_1056
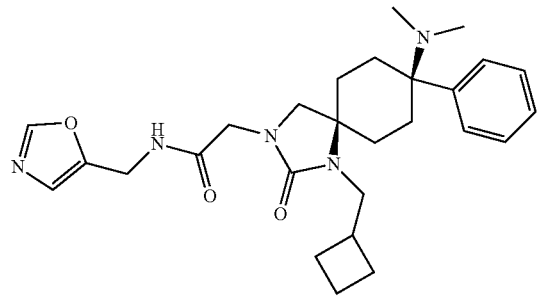
SC_1057
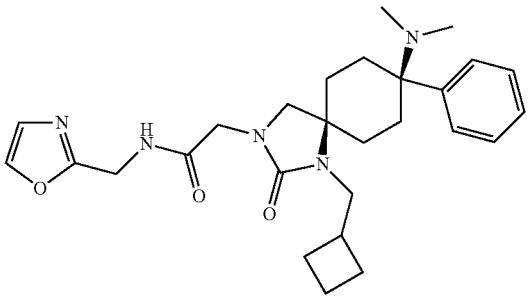
SC_1058
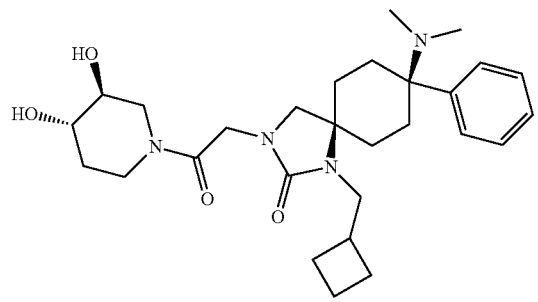
SC_1059
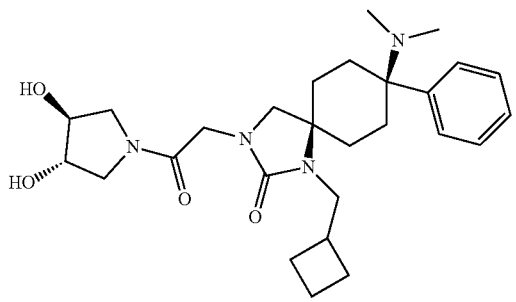
SC_1060
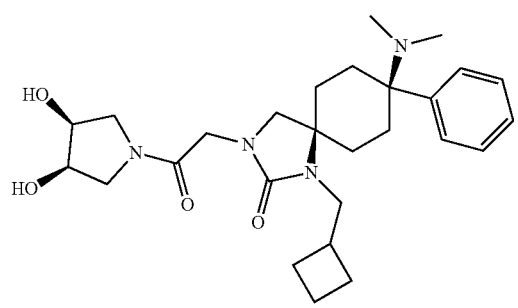
SC_1061
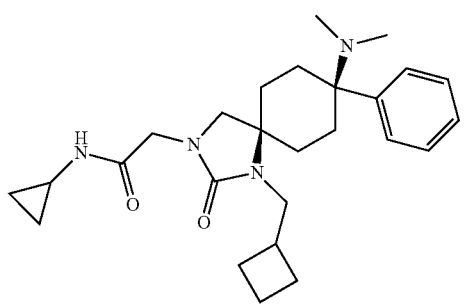
SC_1062
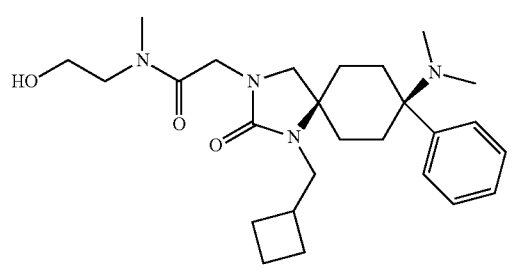
SC_1063
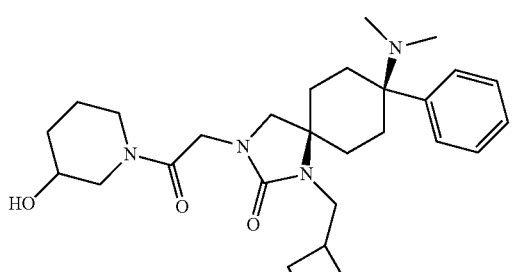
SC_1064
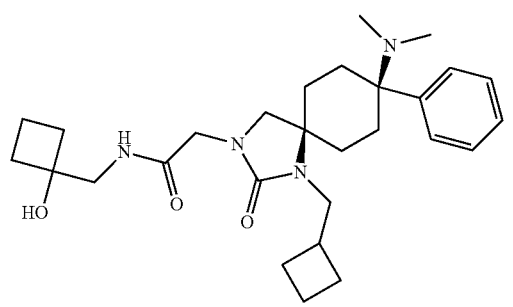
SC_1065
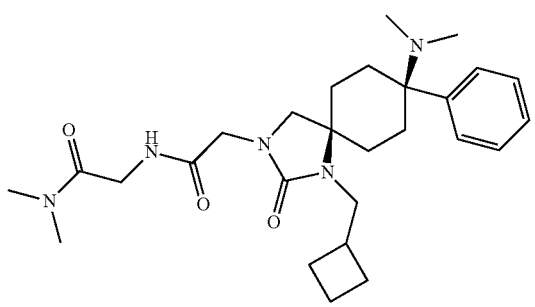

-continued
SC_1066
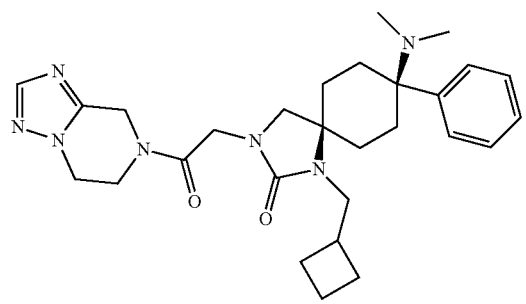
SC_1067
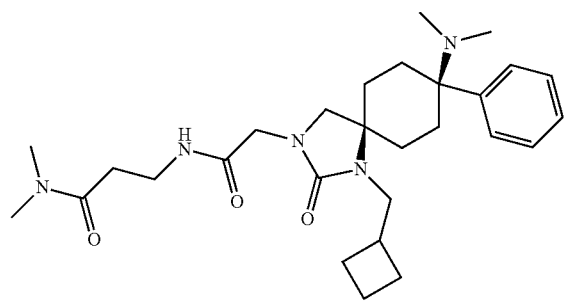
SC_1068
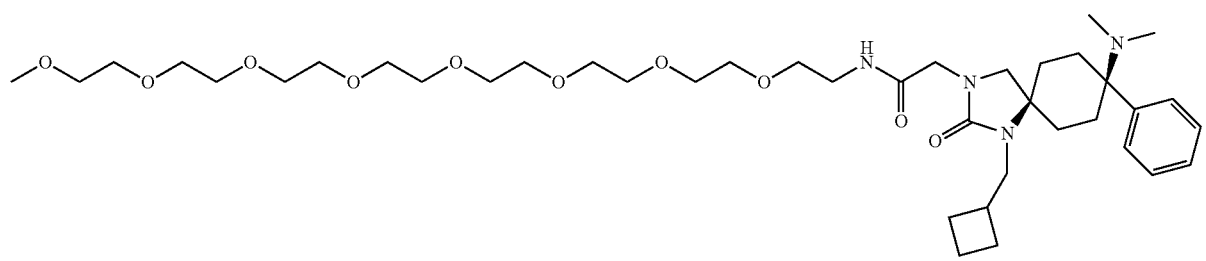
SC_1069
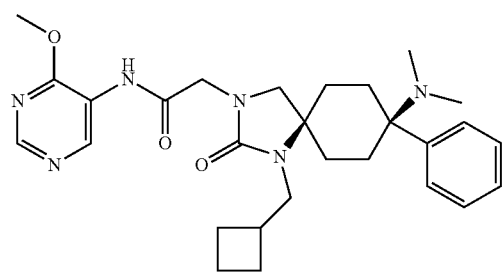
SC_1070
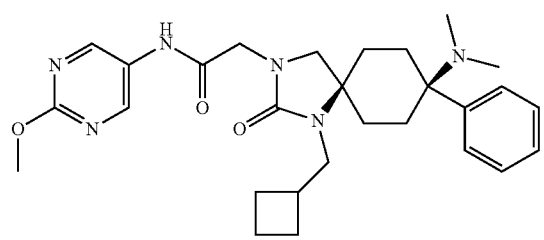
SC_1071
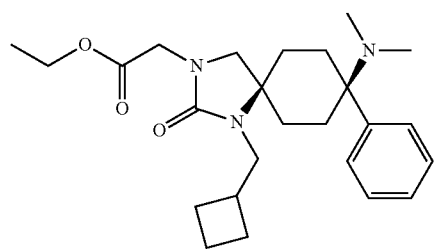
SC_1072
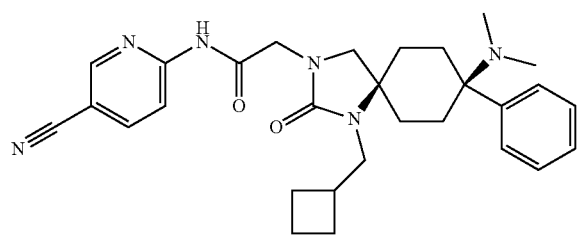
SC_1073
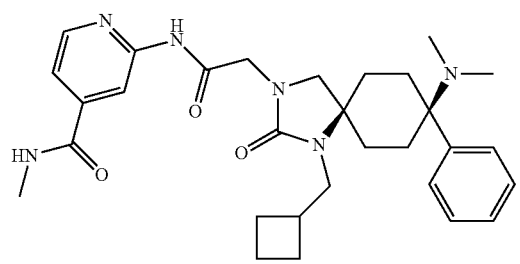
SC_1074
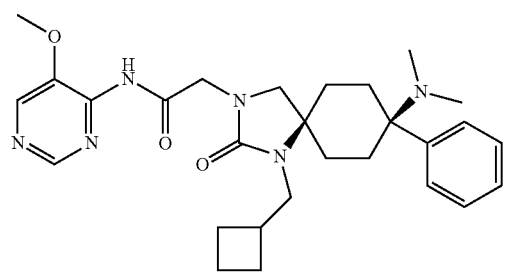

-continued
SC_1075
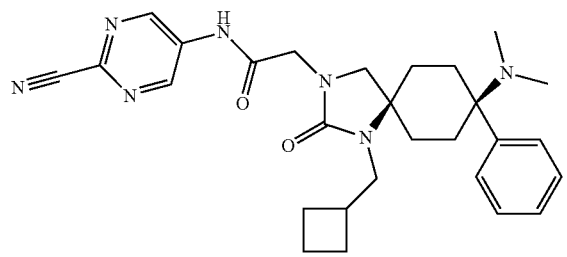
SC_1076
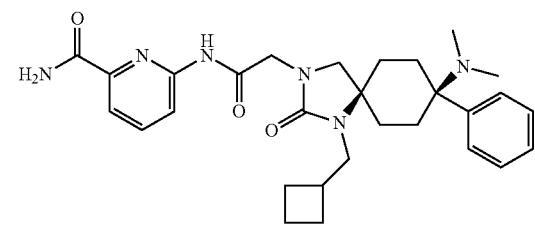
SC_1077
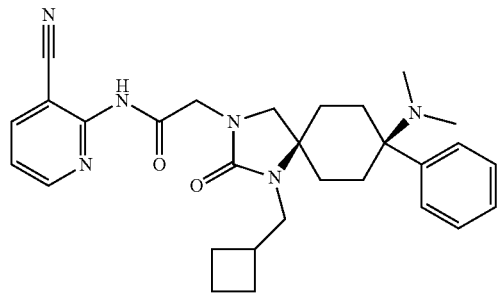
SC_1078
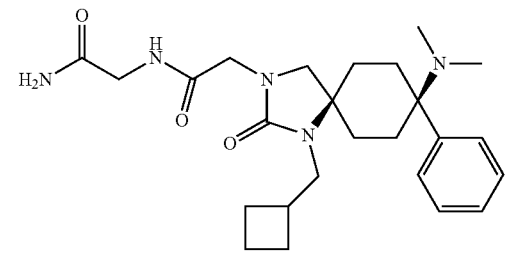
SC_1079
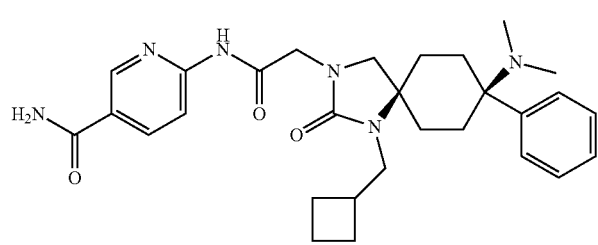
SC_1080
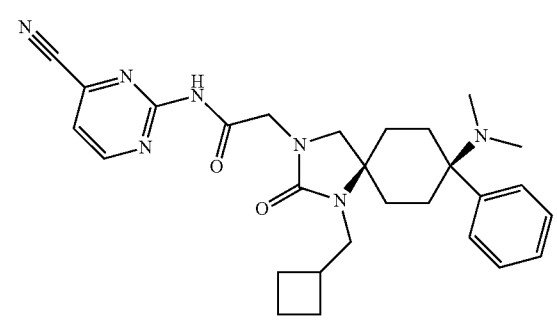
SC_1081
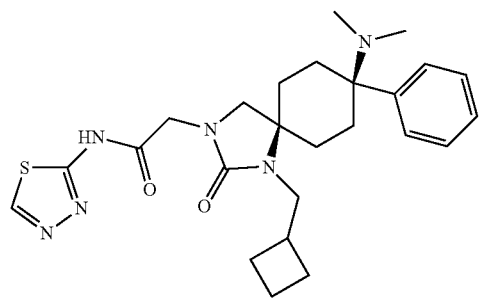
SC_1082
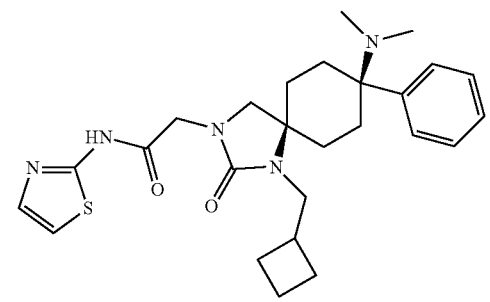
SC_1083
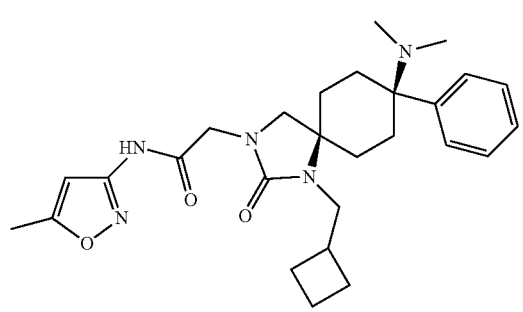
SC_1084
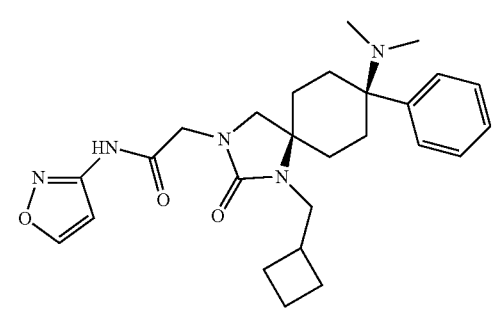

-continued
SC_1085
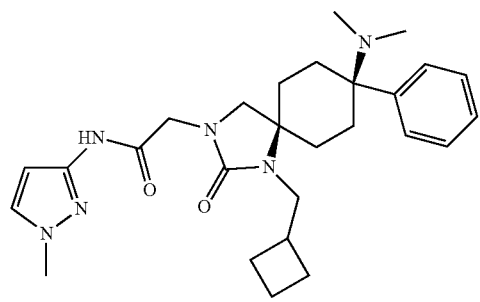
SC_1086
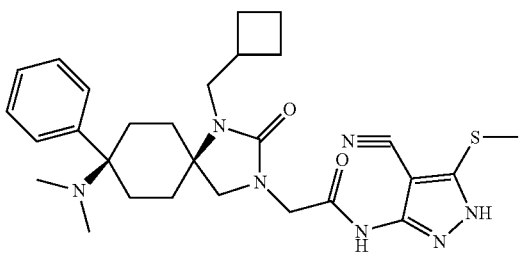
SC_1087
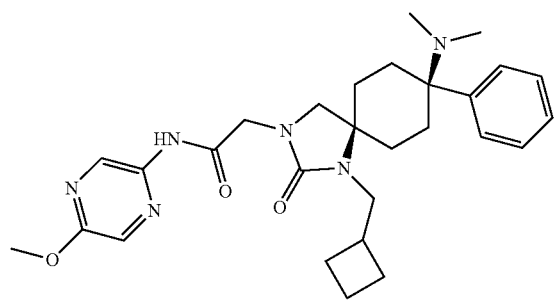
SC_1088
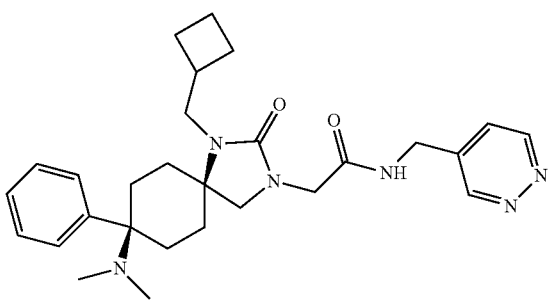
SC_1089
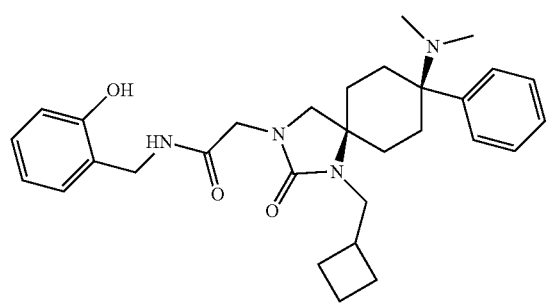
SC_1090
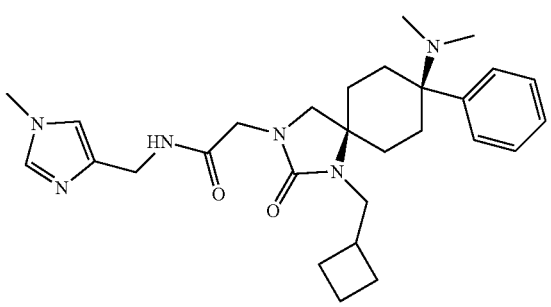
SC_1091
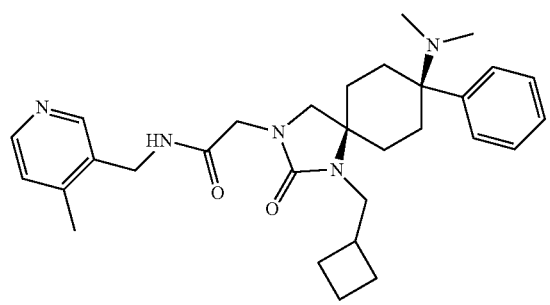
SC_1092
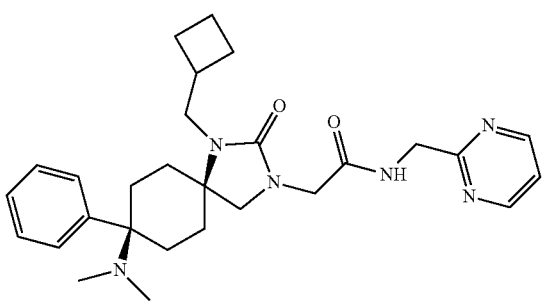
SC_1093
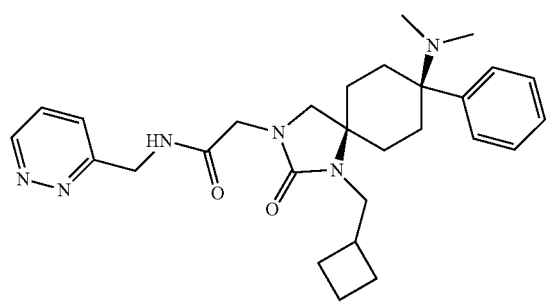
SC_1094
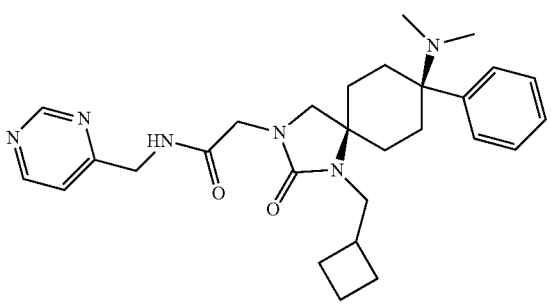

SC_1095
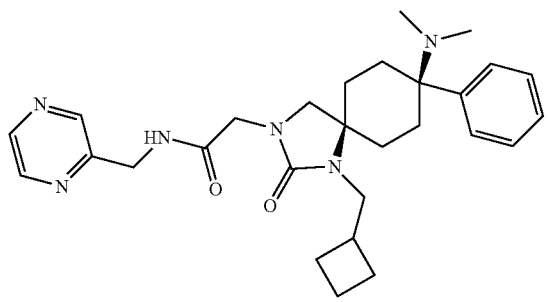
SC_1096
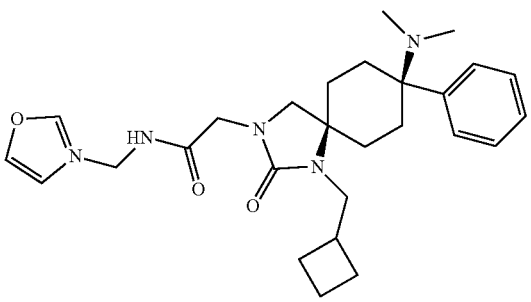
SC_1097
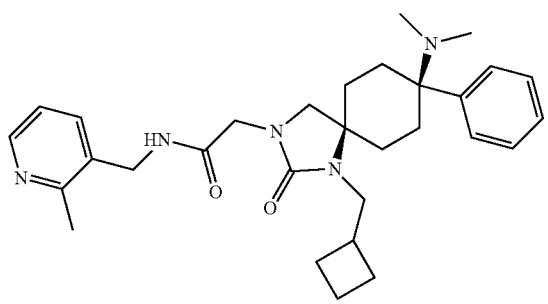
SC_1098
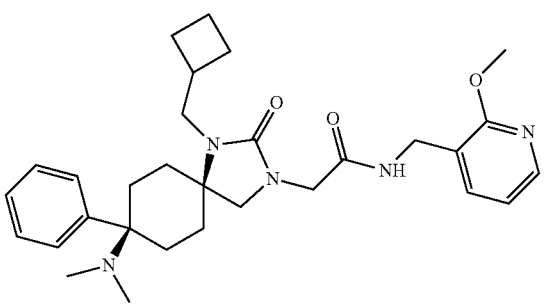
SC_1099
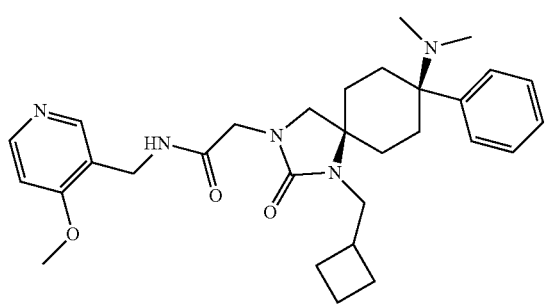
SC_1100
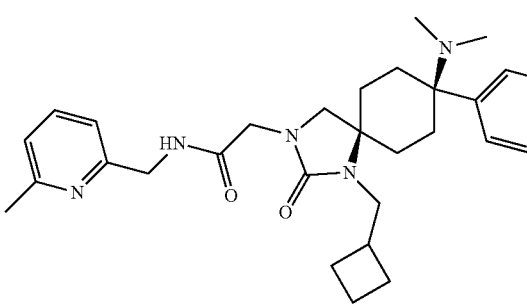
SC_1101
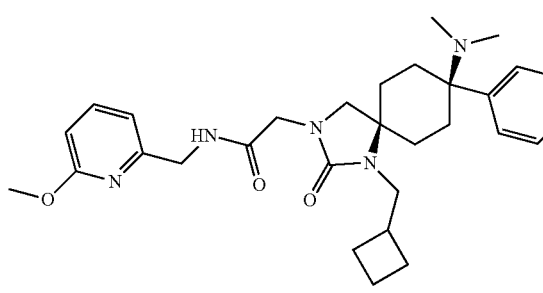
SC_1102
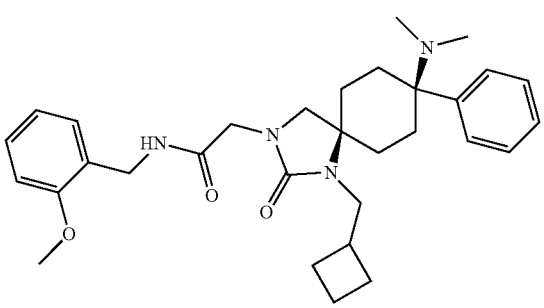
SC_1103
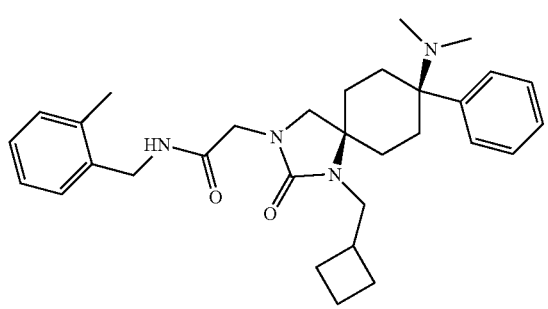
SC_1104
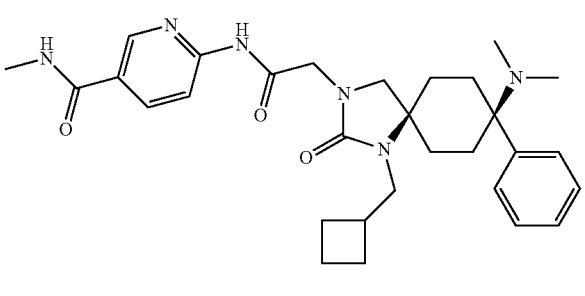

-continued
SC_1105
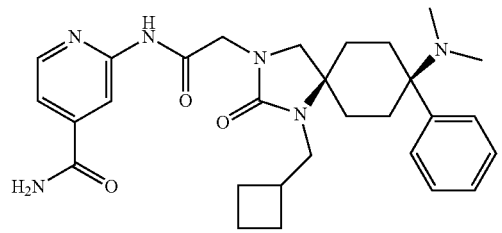
SC_1106
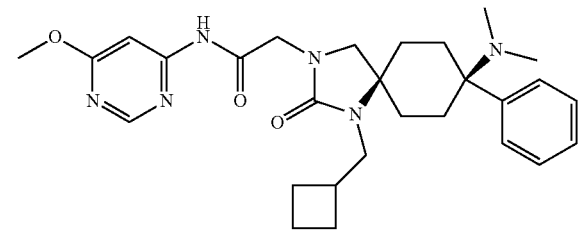
SC_1107
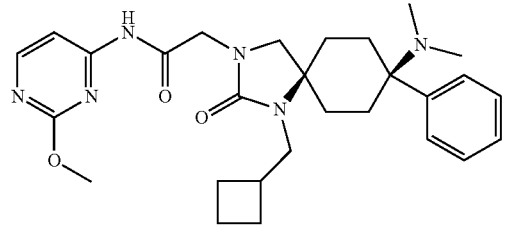
SC_1109
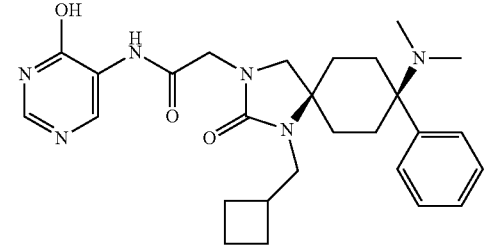
SC_1110
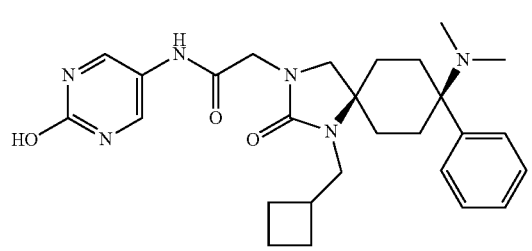
SC_1111
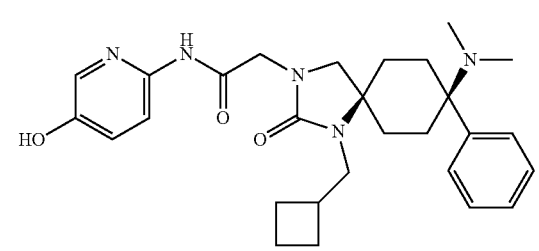
SC_1112
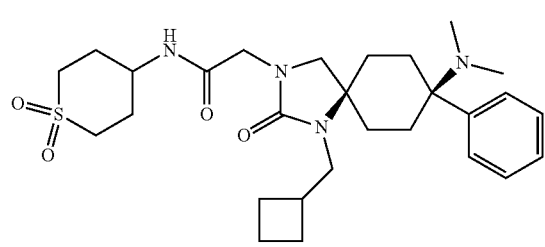
SC_1113
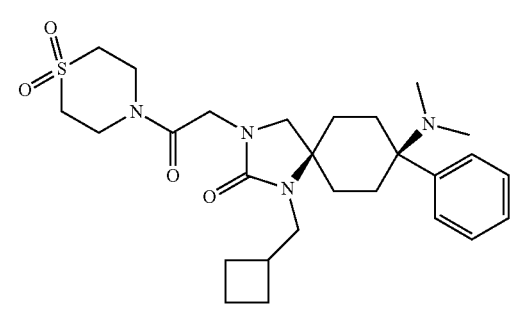
SC_1114
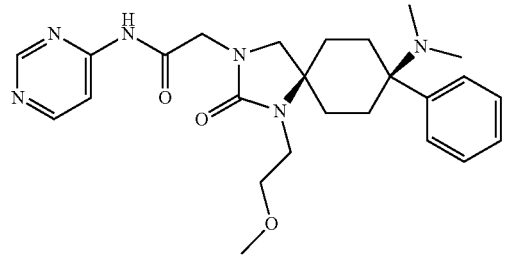
SC_1115
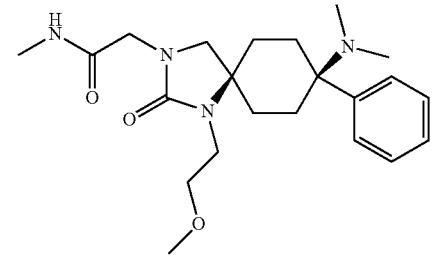

-continued
SC_1117
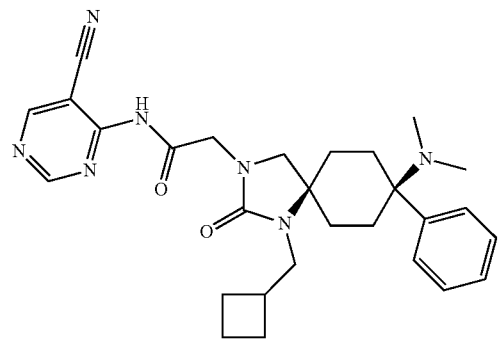
SC_1118
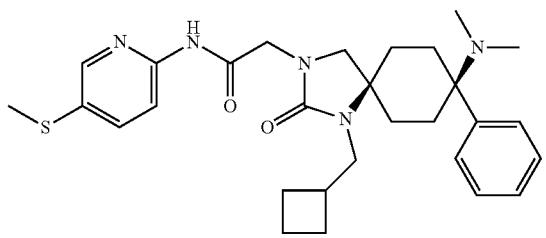
SC_1119
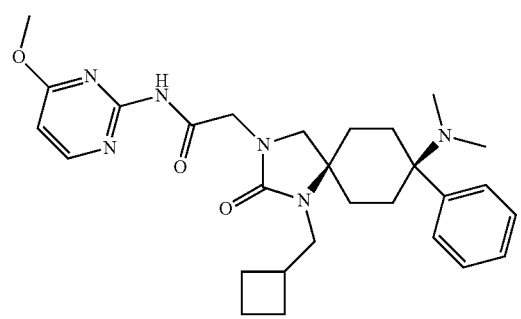
SC_1120
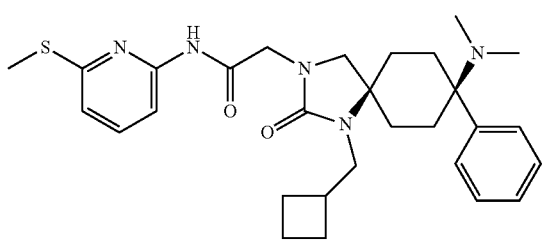
SC_1121
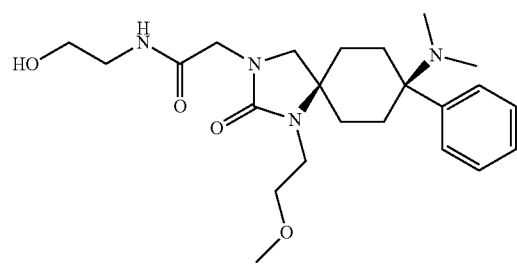
SC_1122
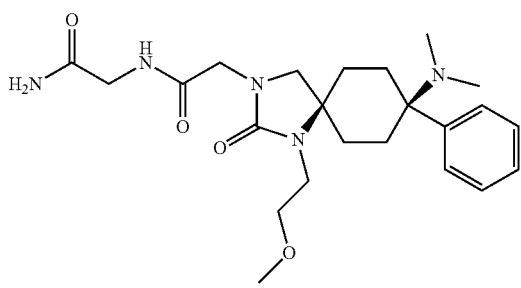
SC_1123
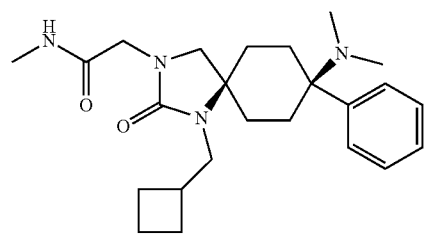
SC_1124
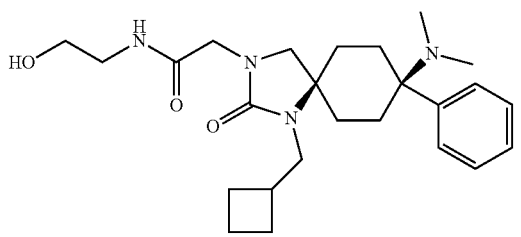
SC_1125
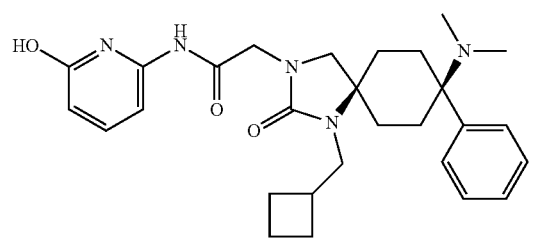
SC_1126
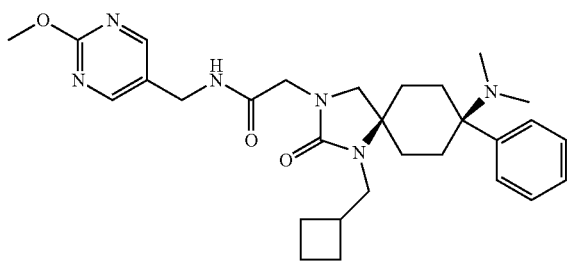

-continued
SC_1127
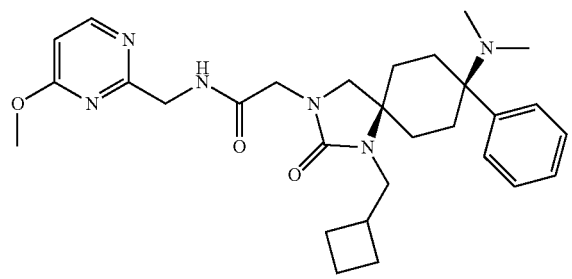
SC_1128
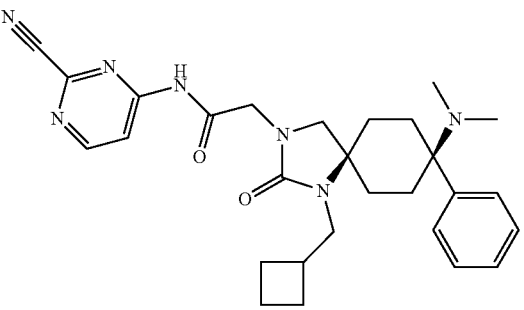
SC_1129
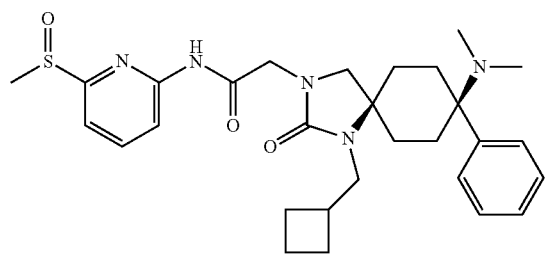
SC_1130
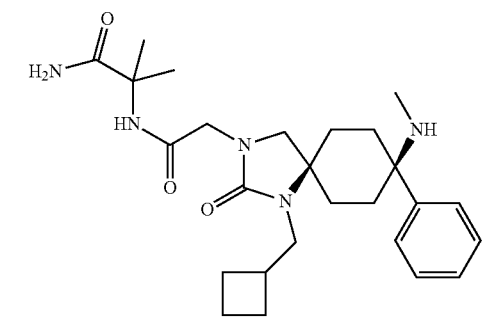
SC_1131
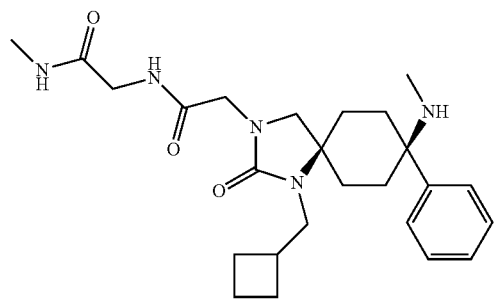
SC_1132
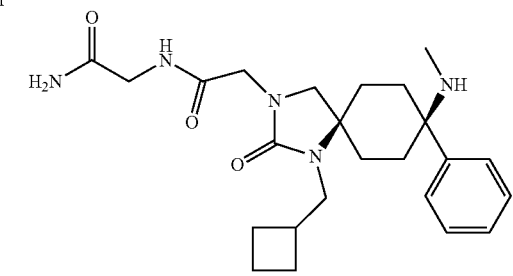
SC_1133
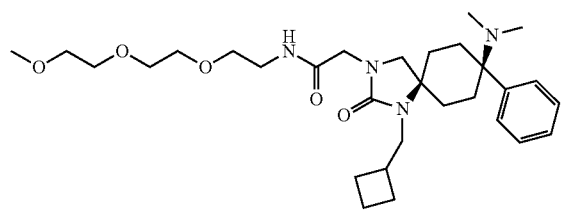
SC_1134
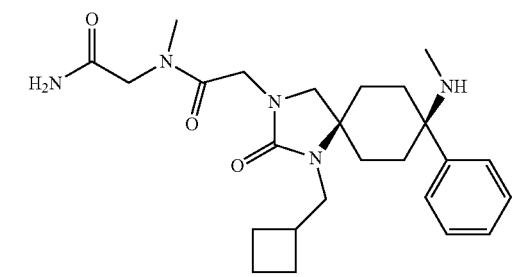
SC_1135
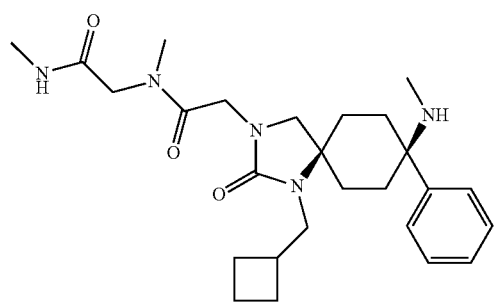
SC_1136
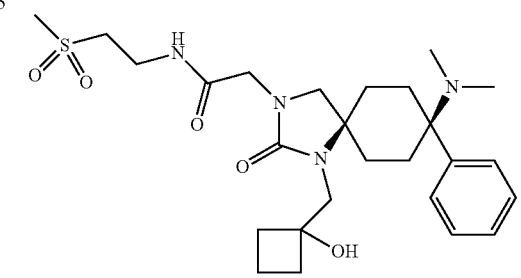

-continued
SC_1137
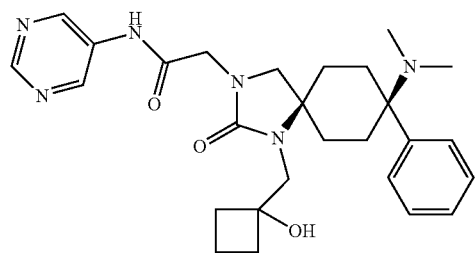
SC_1138
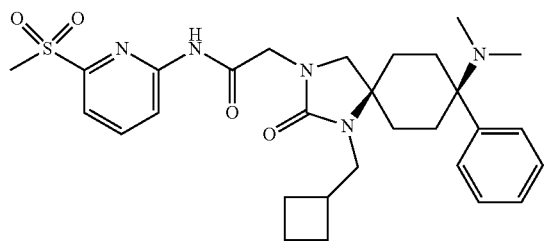
SC_1139
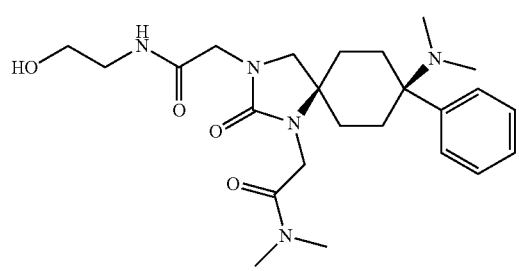
SC_1140
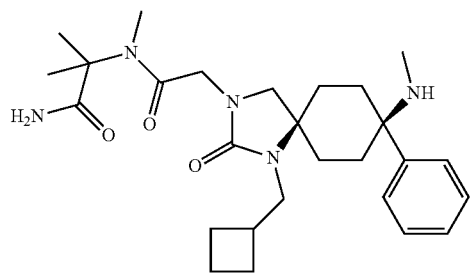
SC_1141
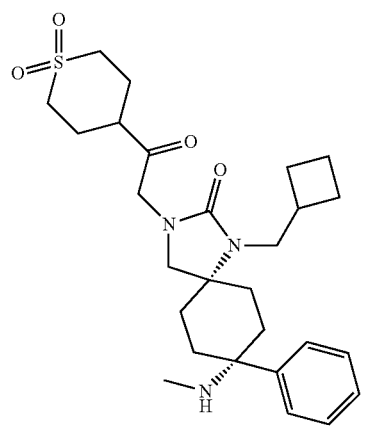
SC_1142
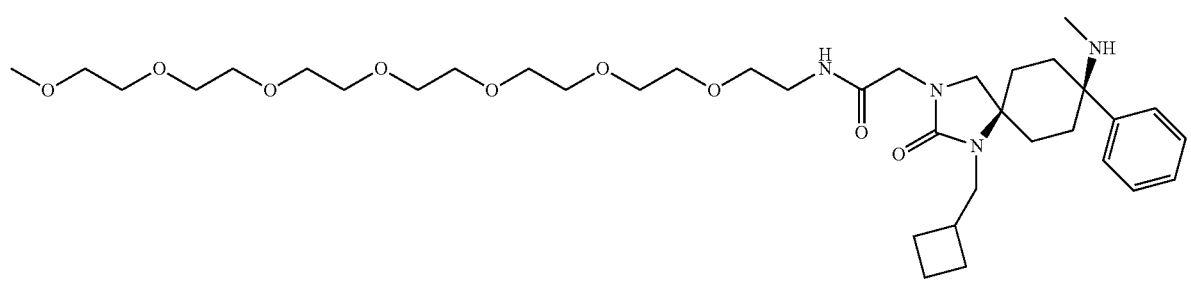
SC_1143
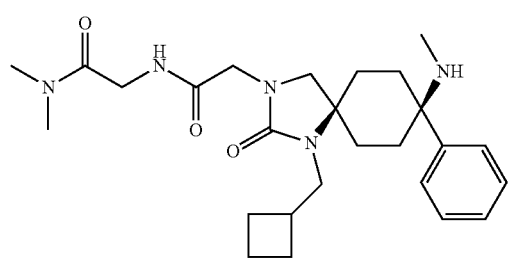
SC_1144
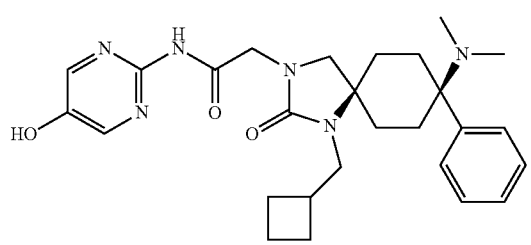

-continued
SC_1145
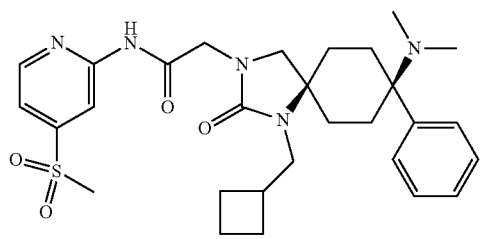
SC_1146
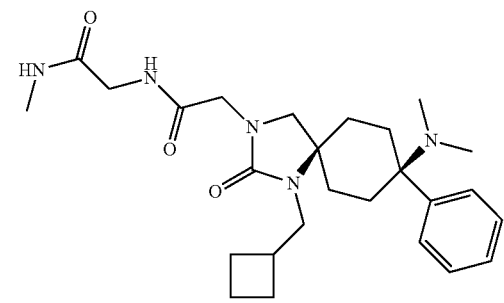
SC_1147
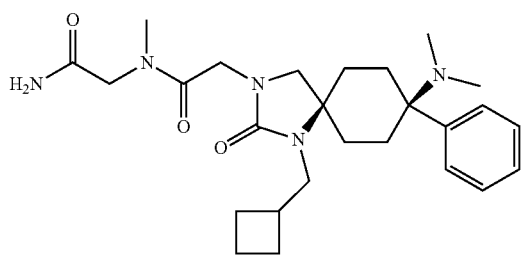
SC_1148
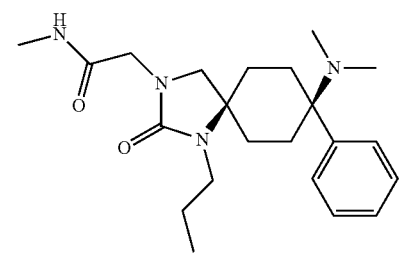
SC_1149
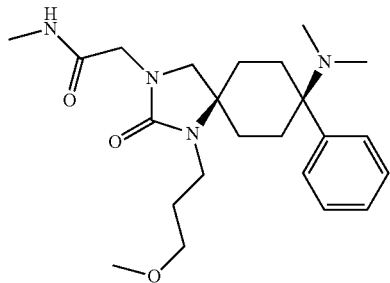
SC_1150
SC_1151
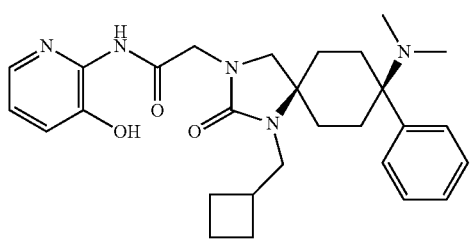
SC_1152
SC_1153
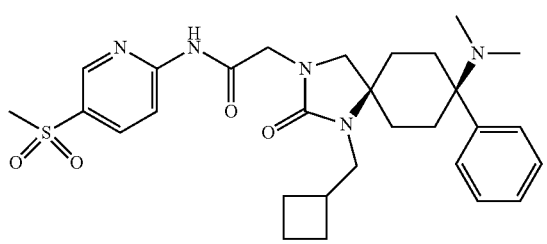
SC_1154
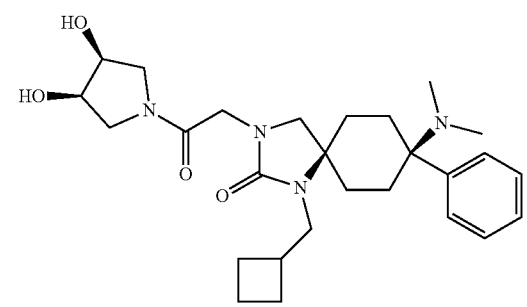

-continued
SC_1155
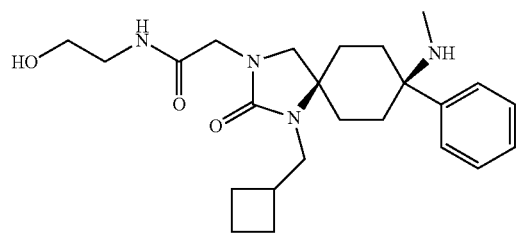
SC_1156
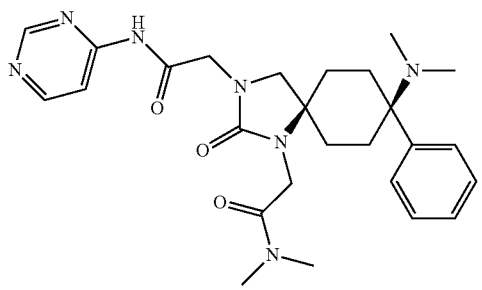
SC_1157
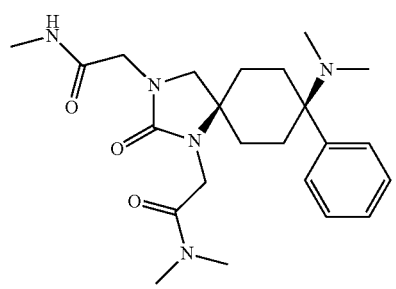
SC_1158
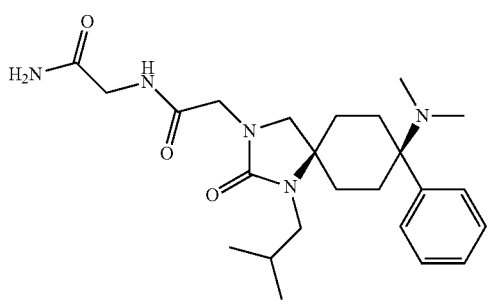
SC_1159
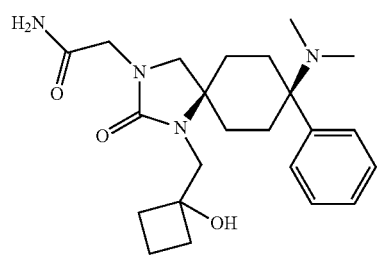
SC_1160
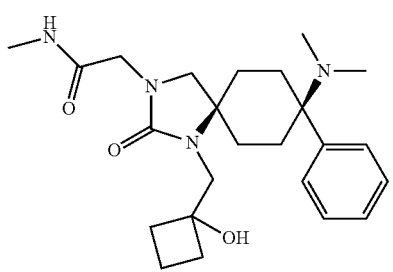
SC_1161
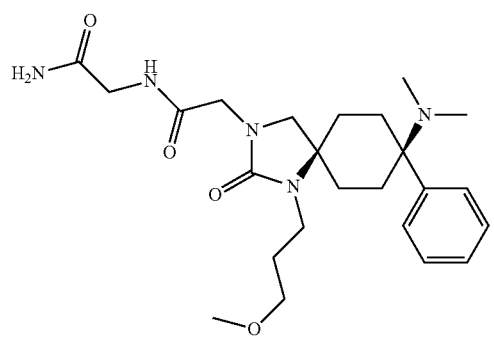
SC_1162
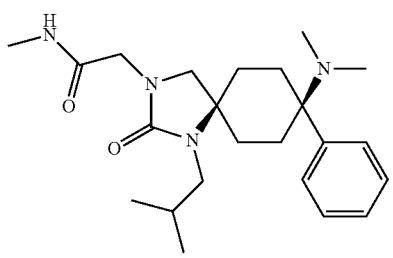
SC_1163
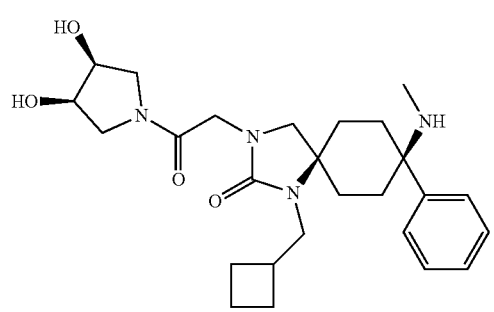
SC_1164
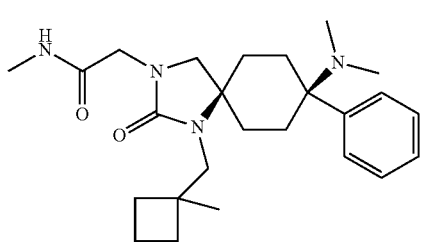

-continued
SC_1165
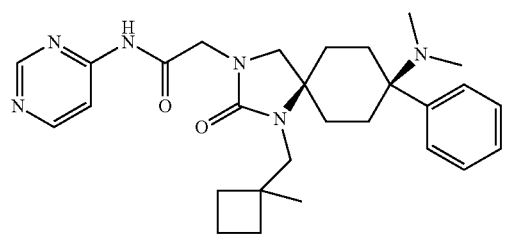
SC_1166
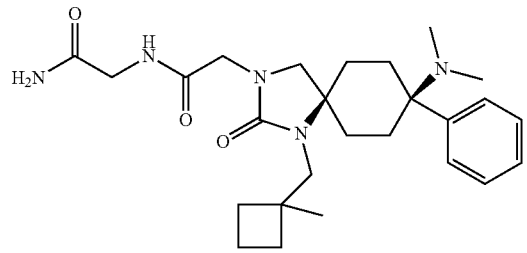
SC_1167
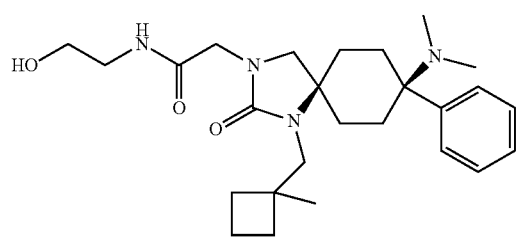
SC_1168
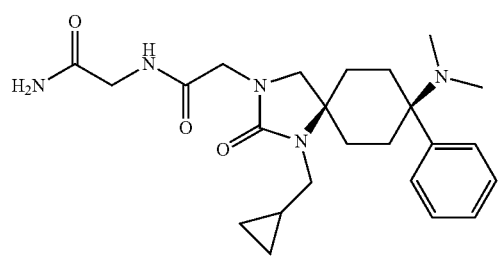
SC_1169
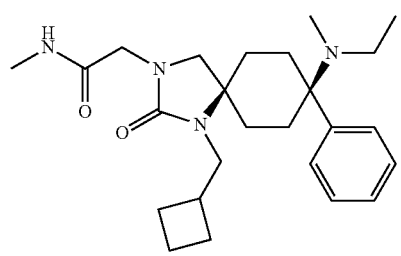
SC_1171
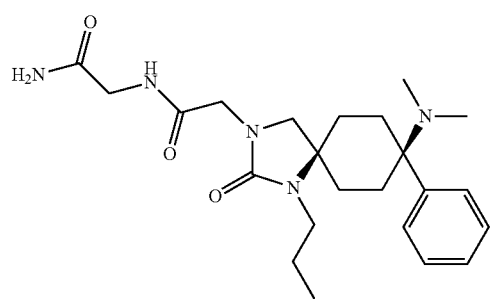
SC_1172
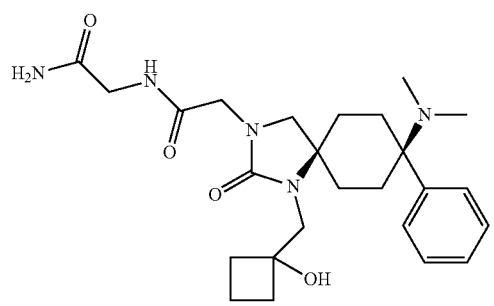
SC_1173
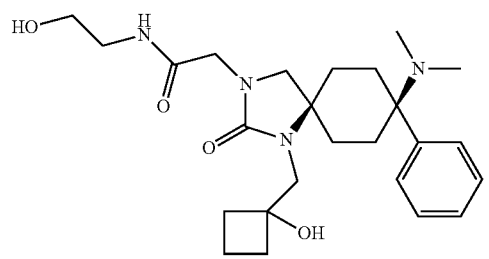
SC_1174
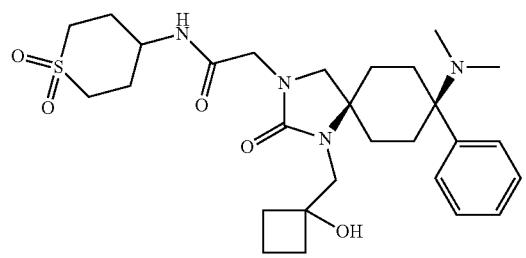
SC_1175
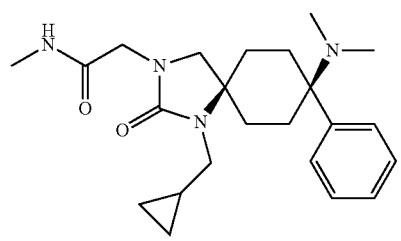

-continued
SC_1176
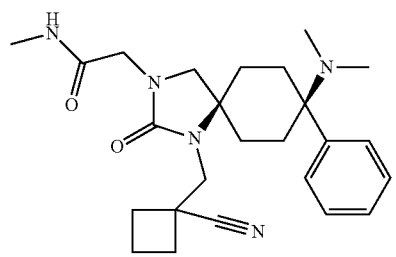
SC_1177
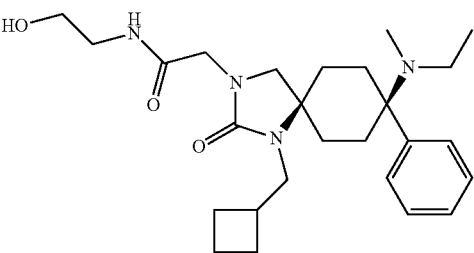
SC_1178
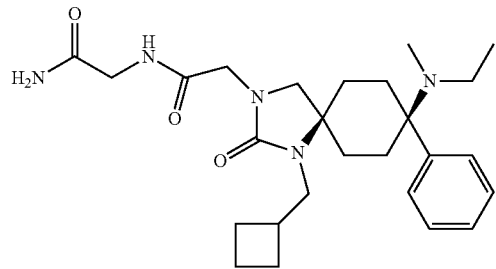
SC_1179
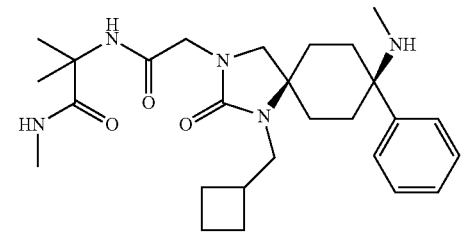
SC_1180
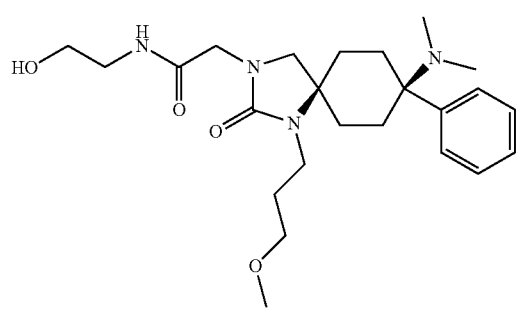
SC_1181
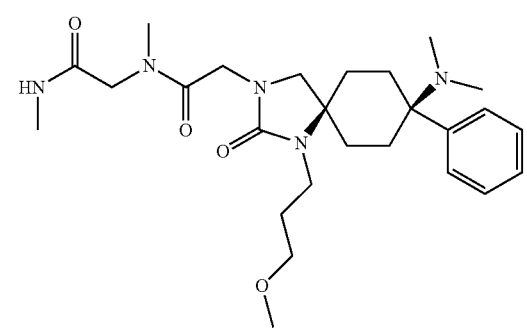
SC_1182
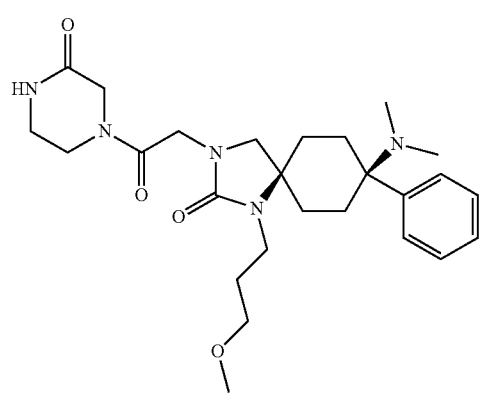
SC_1183
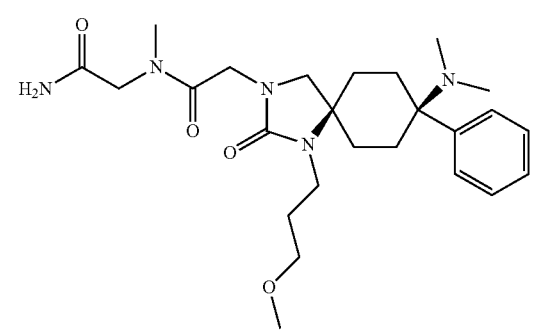
SC_1184
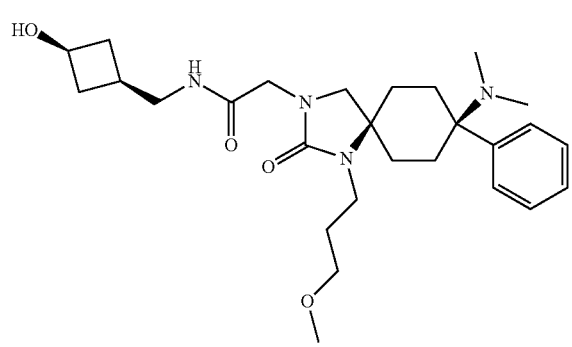
SC_1185
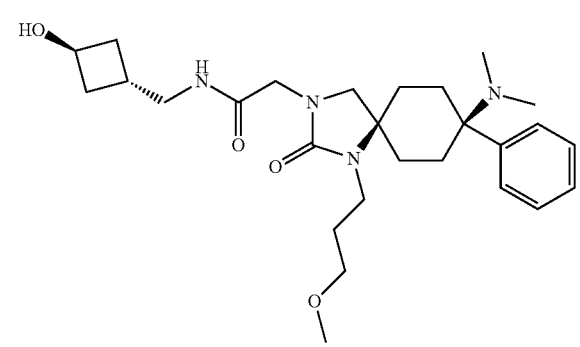

-continued
SC_1186
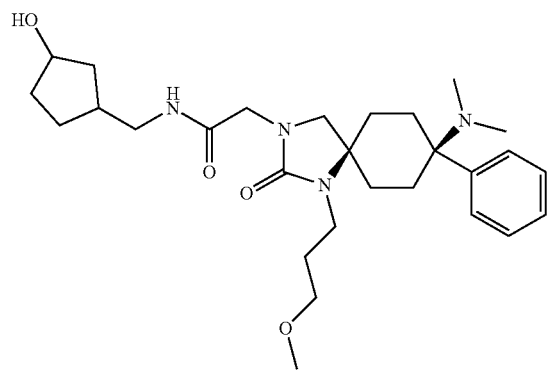
SC_1187
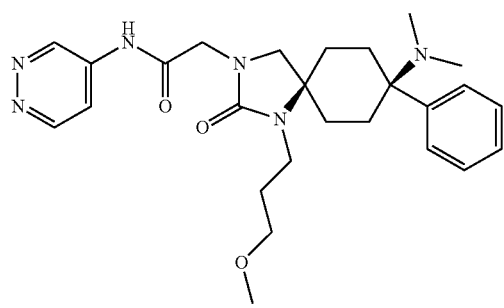
SC_1188
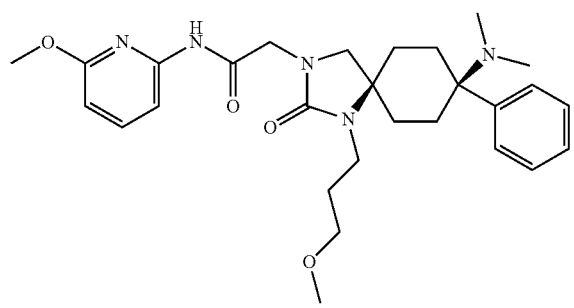
SC_1189
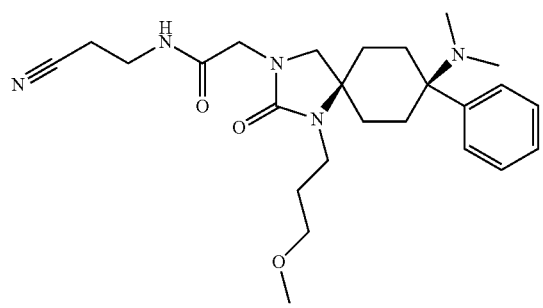
SC_1190
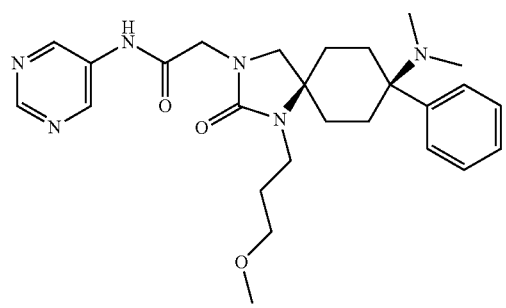
SC_1191
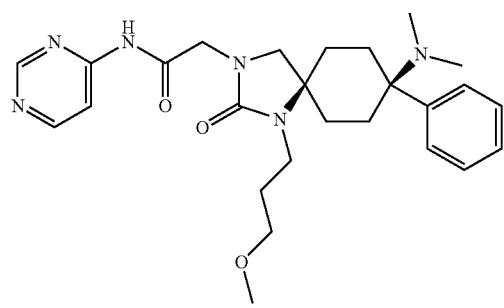
SC_1192
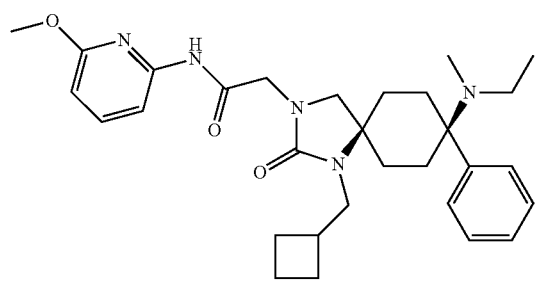
SC_1193
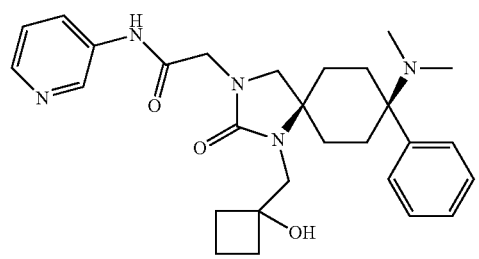
SC_1195
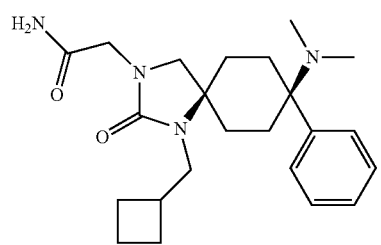
SC_1196
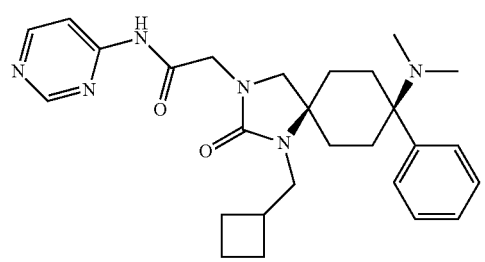

-continued
SC_1197
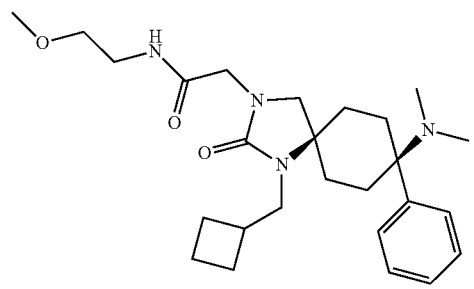
SC_1198
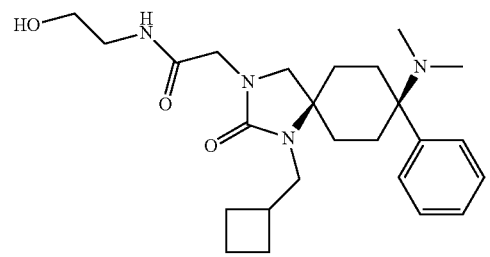
SC_1199
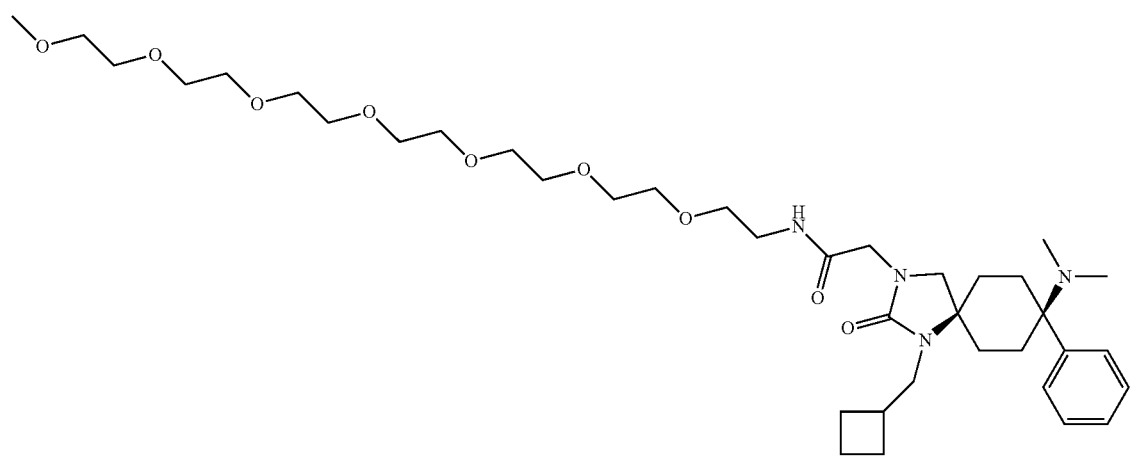
SC_1201
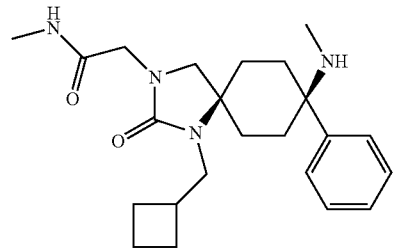
SC_1203
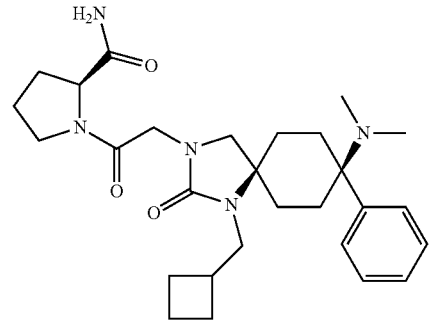
SC_1204
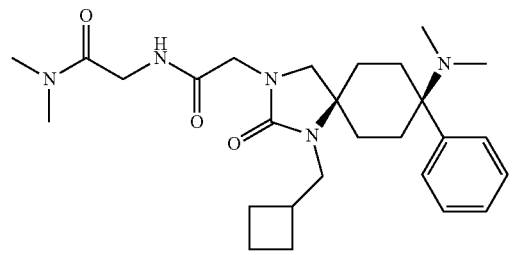
SC_1205
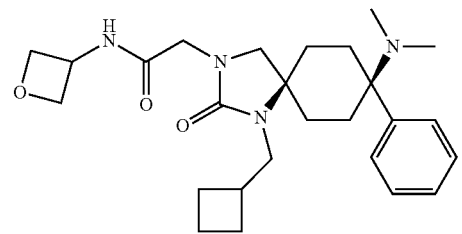

-continued
SC_1206
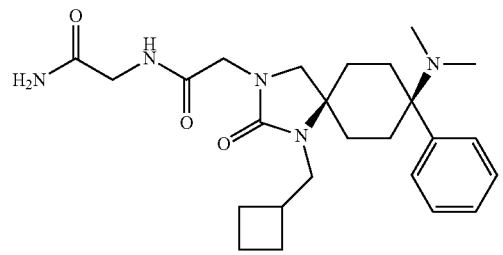
SC_1207
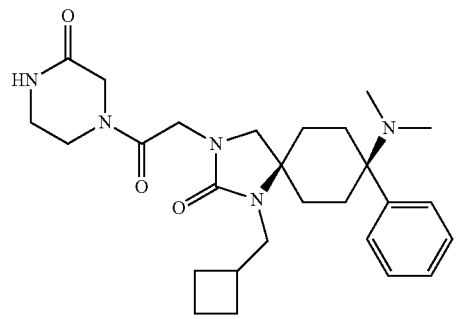
SC_1208
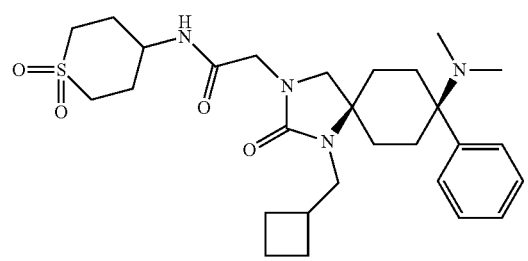
SC_1209
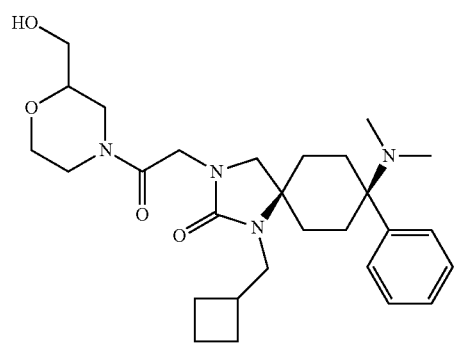
SC_1210
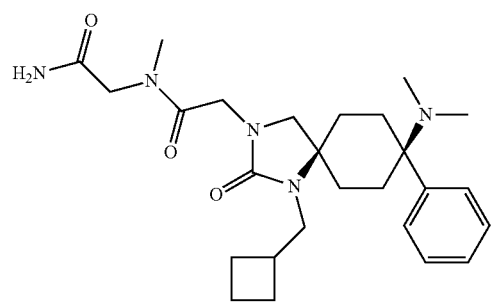
SC_1211
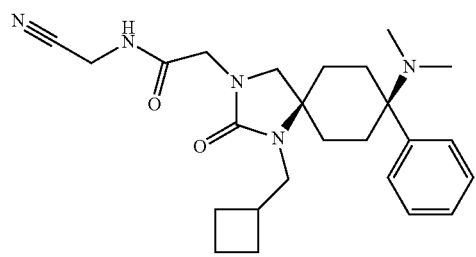
SC_1212
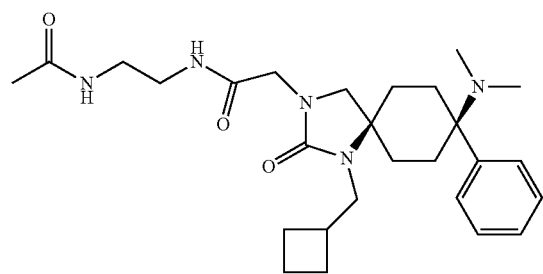
SC_1213
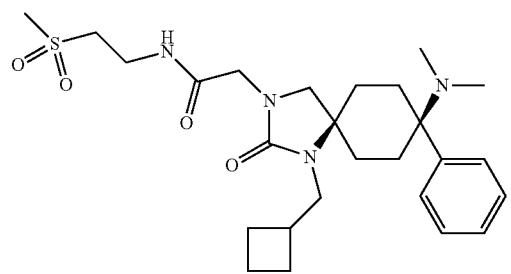

-continued
SC_1214
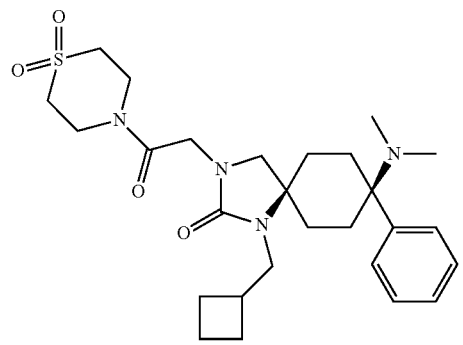
SC_1215
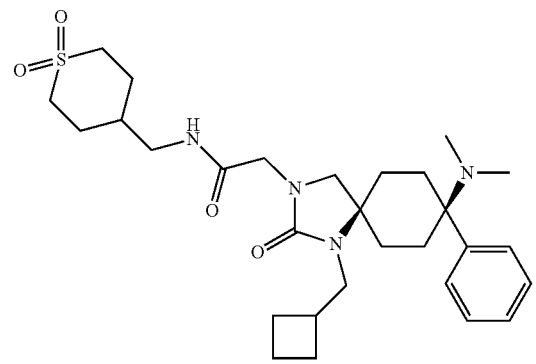
SC_1216
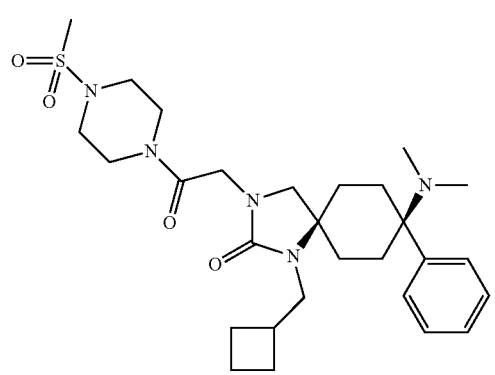
SC_1217
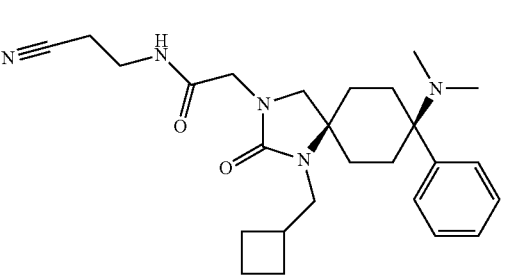
SC_1218
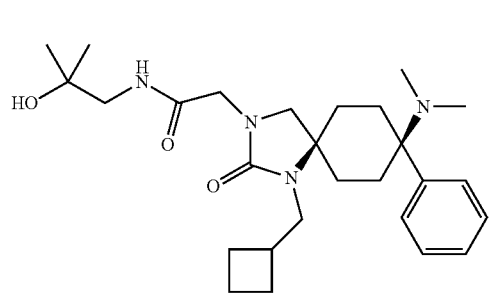
SC_1219
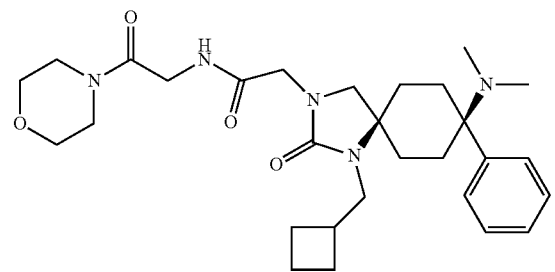
SC_1220
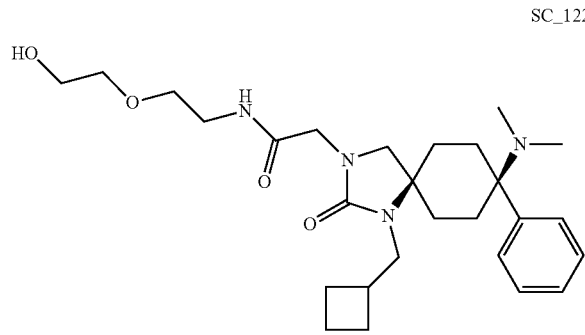
SC_1222
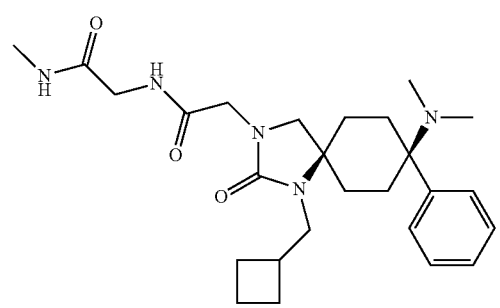

-continued
SC_1223
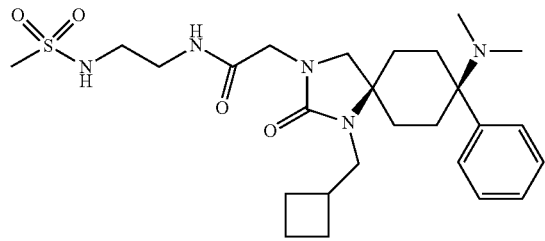
SC_1224
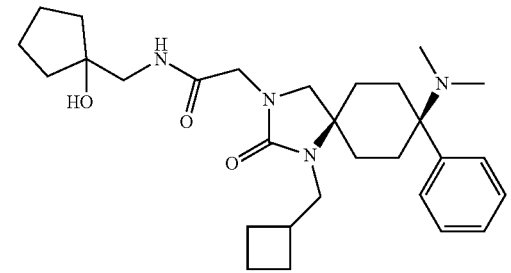
SC_1225
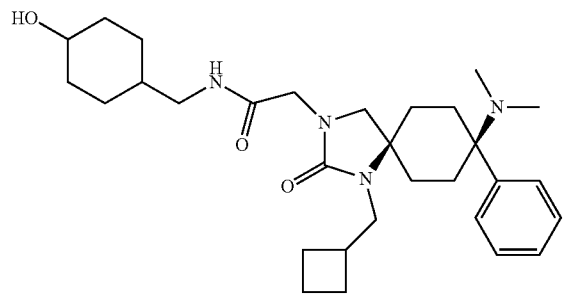
SC_1226
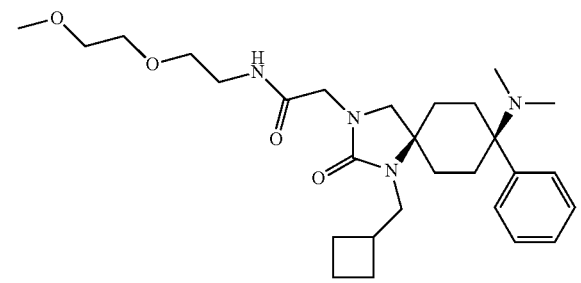
SC_1227
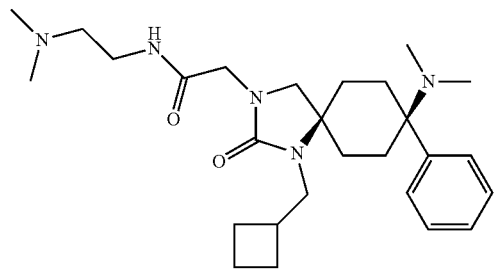
SC_1228
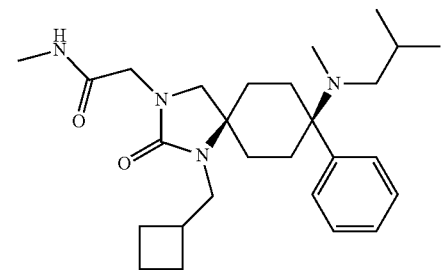
SC_1229
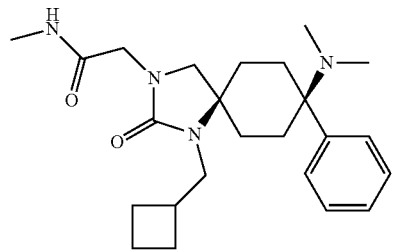
SC_1230
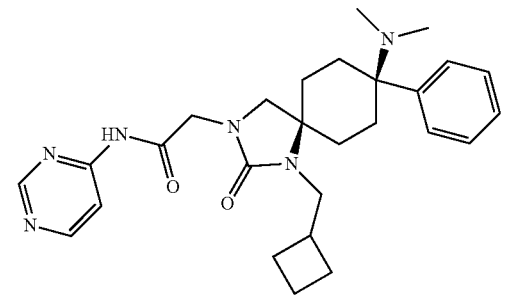
SC_1231
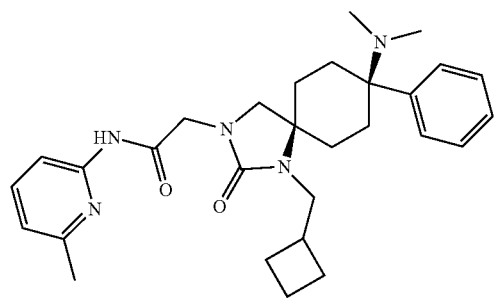
SC_1232
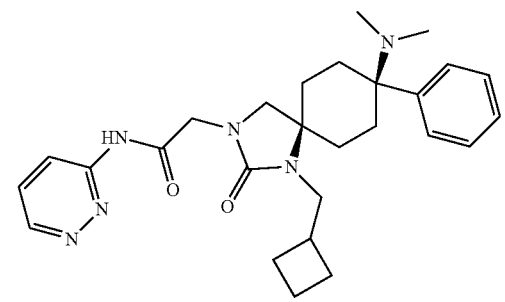

-continued
SC_1233
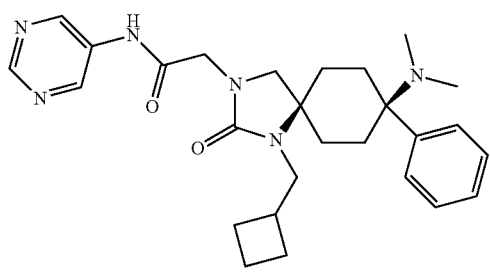
SC_1234
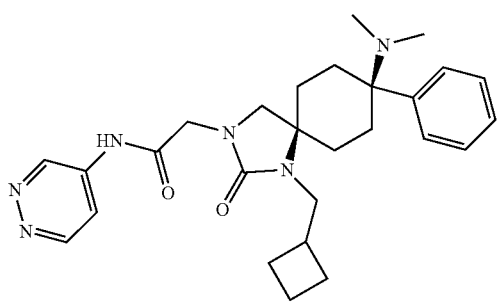
SC_1235
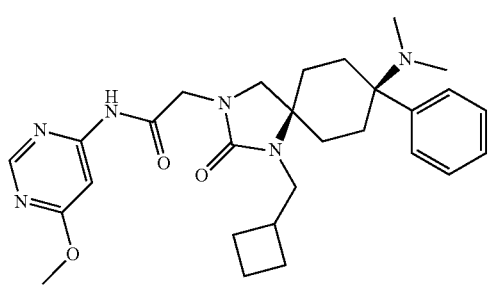
SC_1236
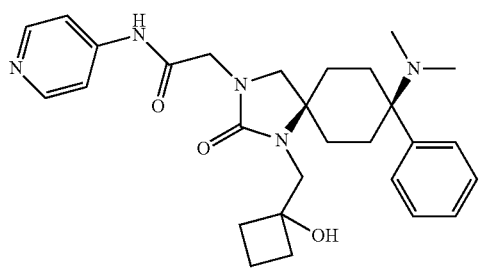
SC_1300
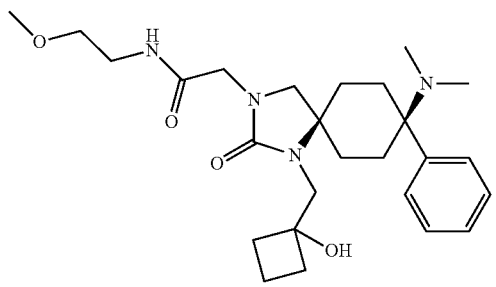
SC_1301
SC_1302
SC_1303
SC_1304
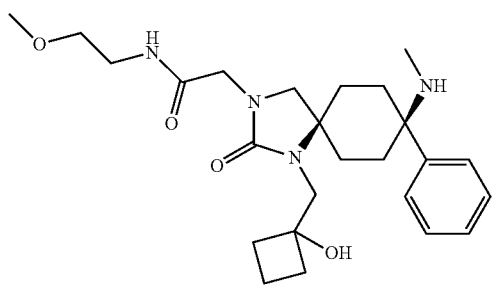
SC_1305
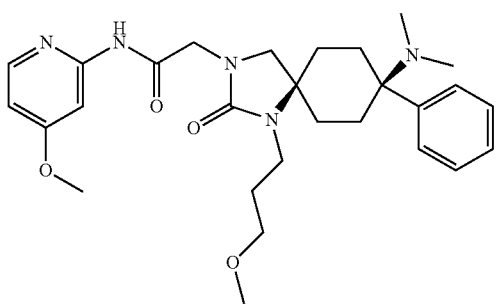

-continued
SC_1306
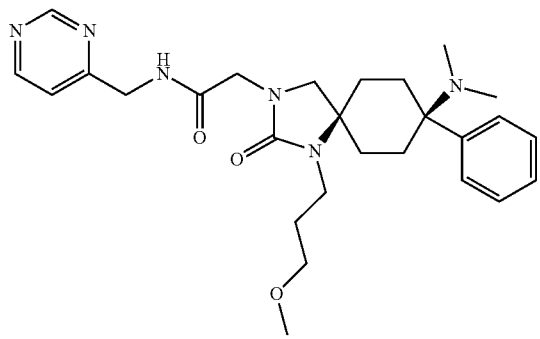
SC_1308
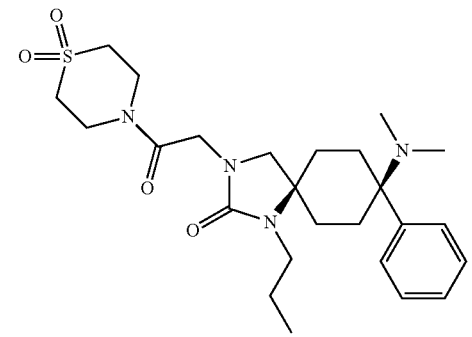
SC_1309
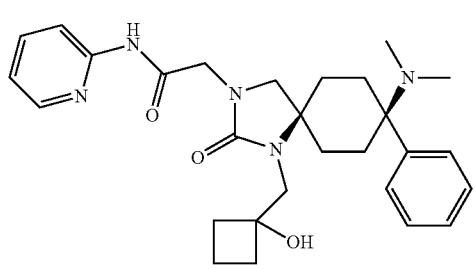
SC_1310
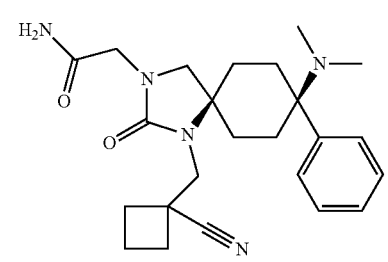
SC_1311
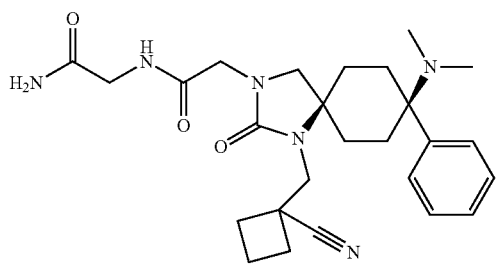
SC_1312
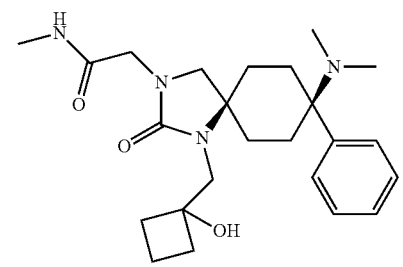
SC_1313
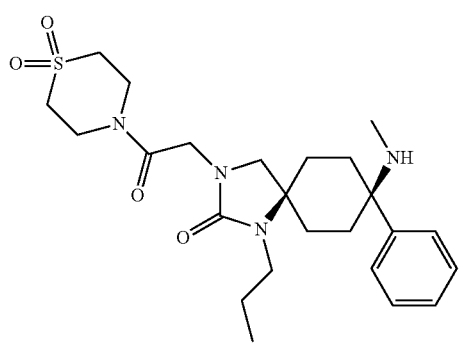
SC_1317
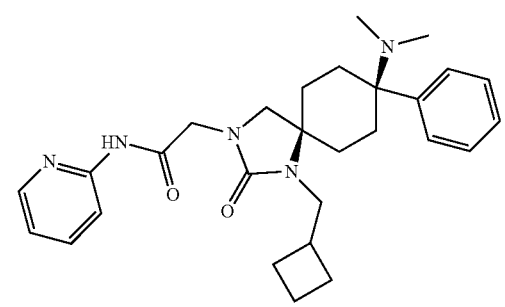
SC_1318
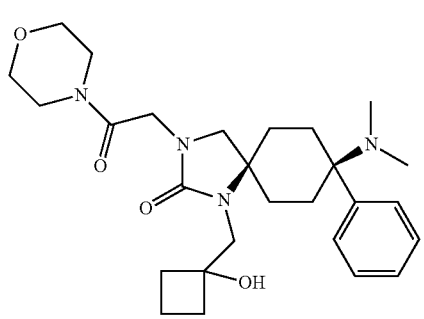
SC_1319
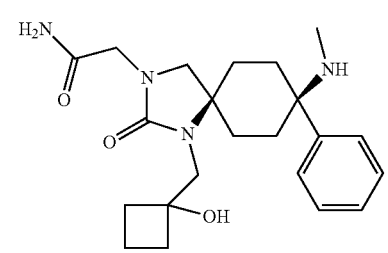

SC_1320 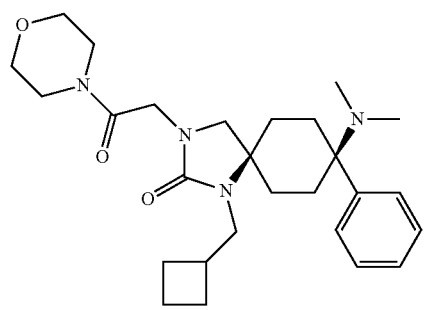
SC_1321 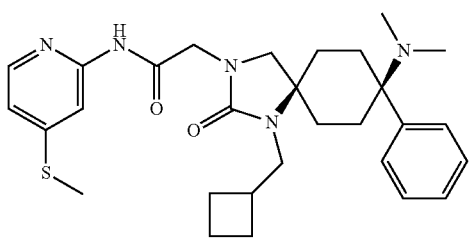
SC_1322 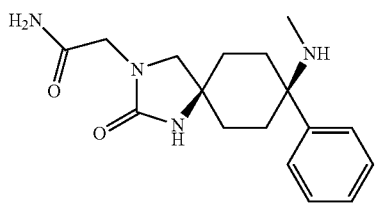
SC_1323 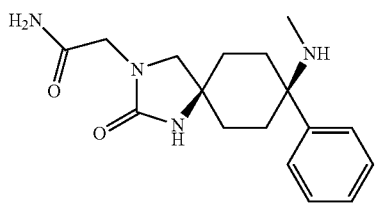
SC_1324 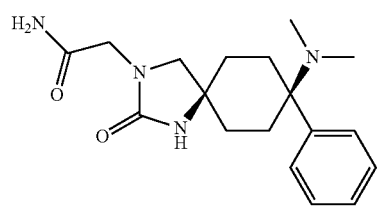
SC_1325 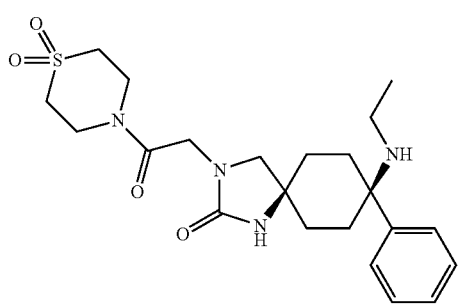
SC_1326 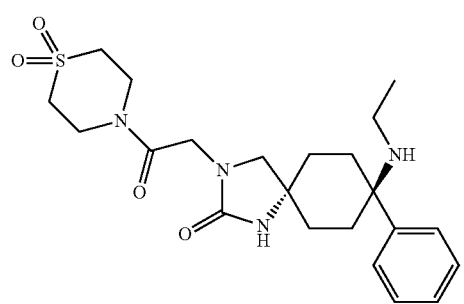
SC_1327 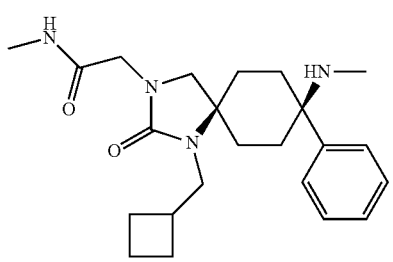
SC_1328 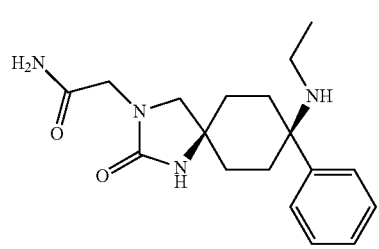
SC_1329 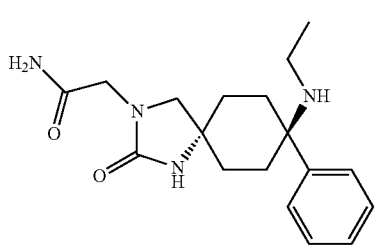

-continued
SC_1330
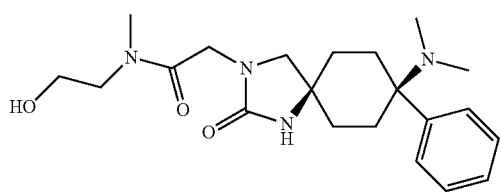
SC_1331
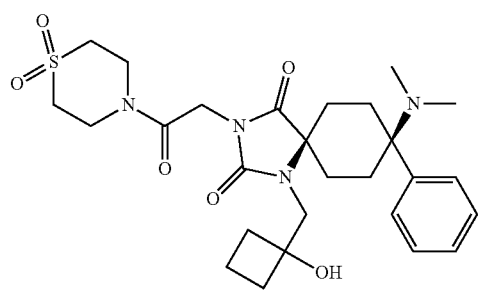
SC_1332
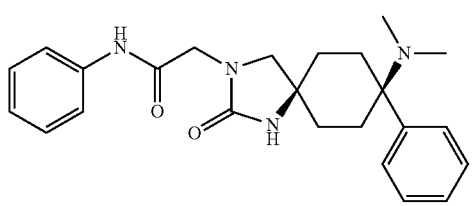
SC-1333
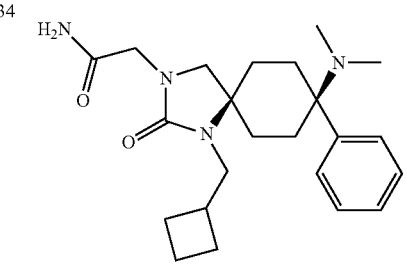
SC_1334
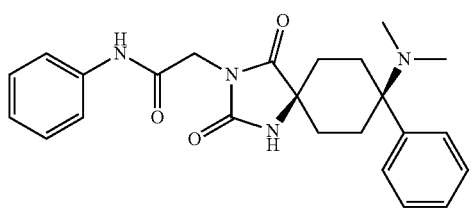
SC_1335
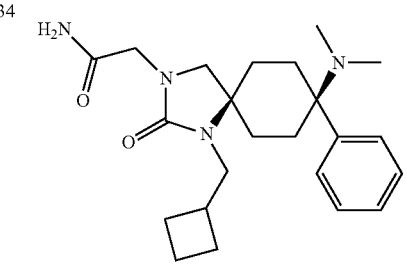
SC_1336
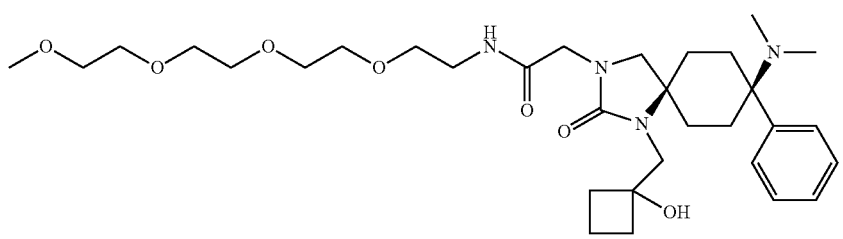
SC_1337
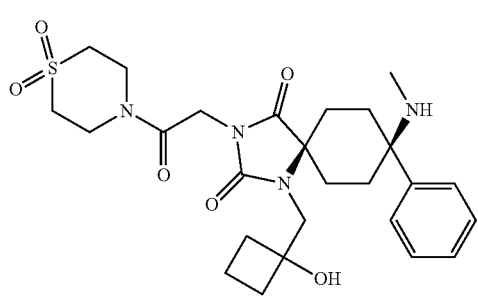
SC_1338
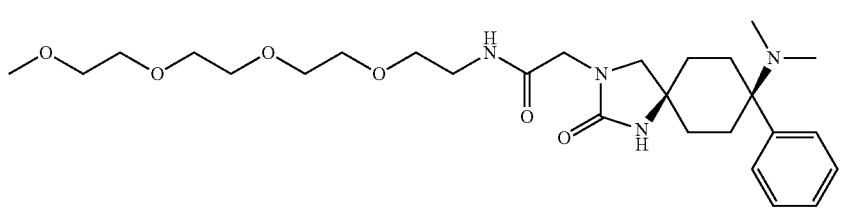

-continued
241
SC_1339
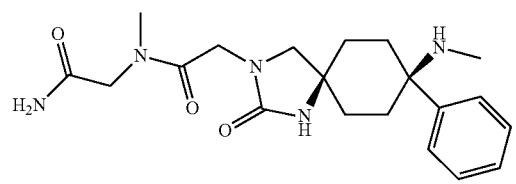
242
SC_1340
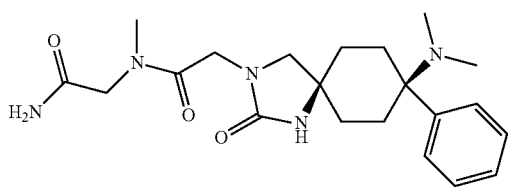
SC_1341
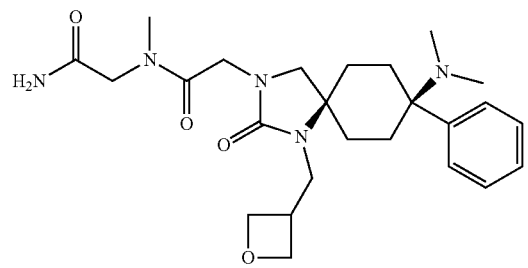
SC_1342
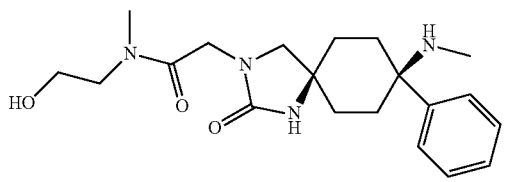
SC_1343
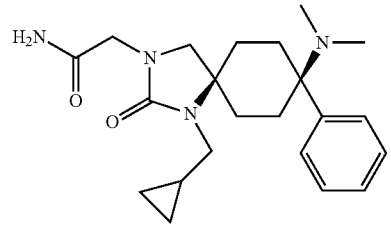
SC_1344
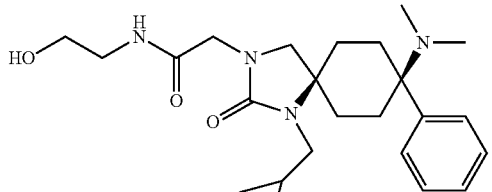
SC_1345
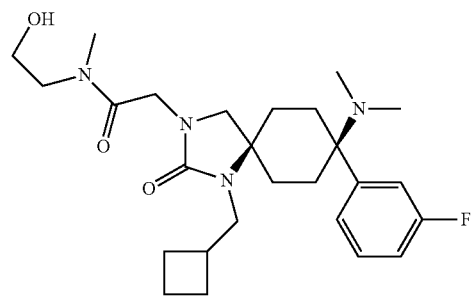
SC_1346
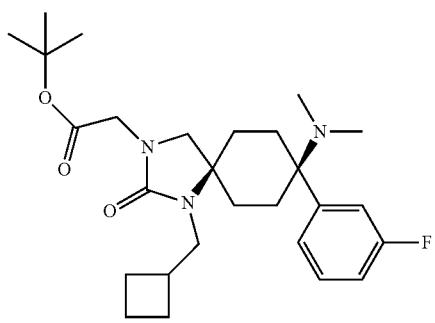
SC_1347
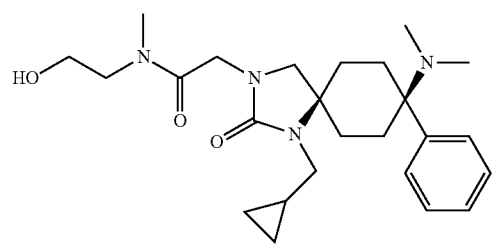
SC_1348
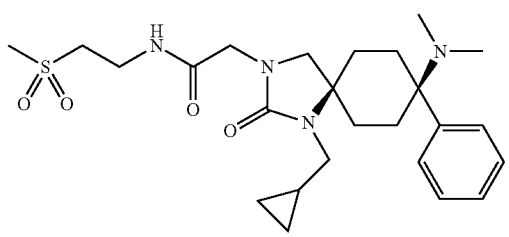
SC_1349
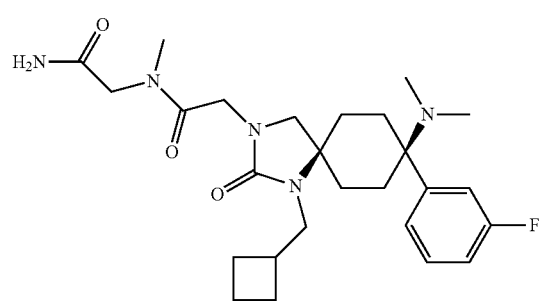
SC_1350
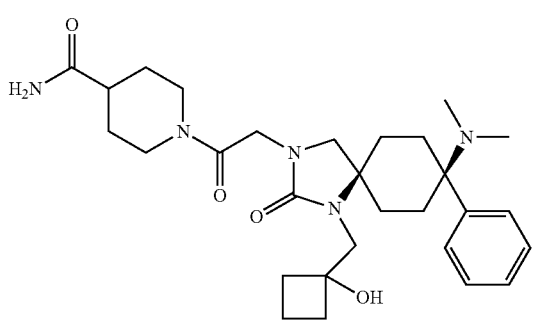

-continued
SC_1351
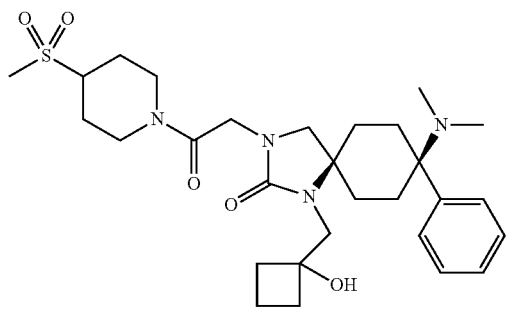
SC_1352
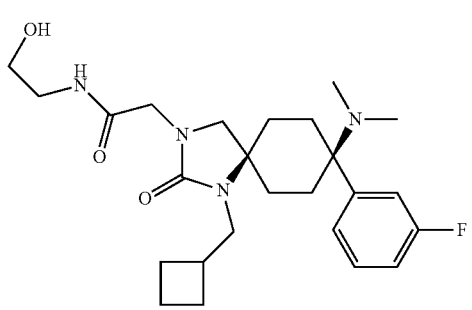
SC_1353
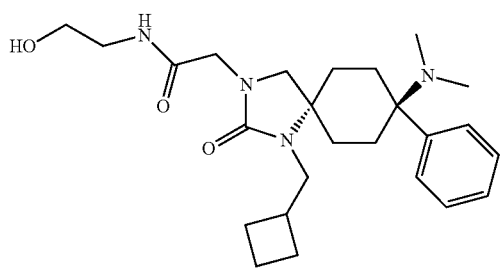
SC_1354
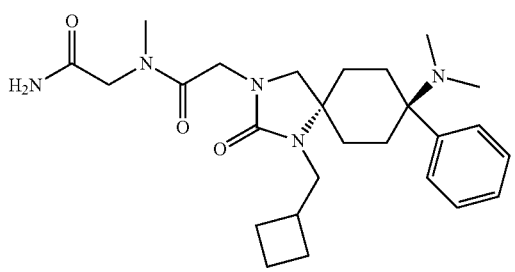
SC_1355
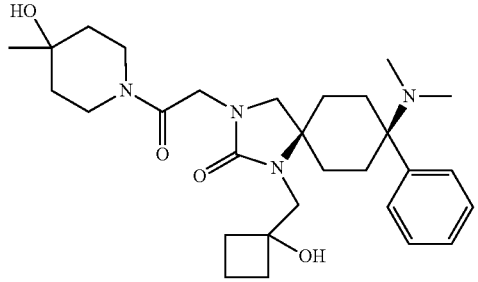
SC_1356
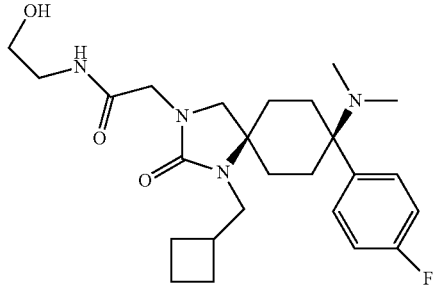
SC_1357
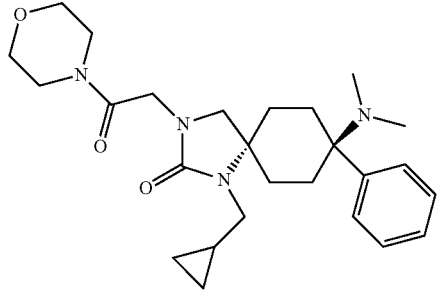
SC_1358
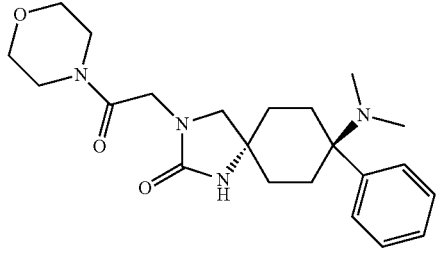
SC_1359
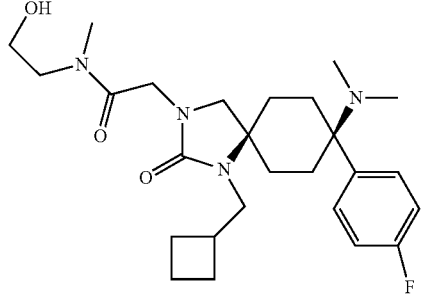
SC_1360
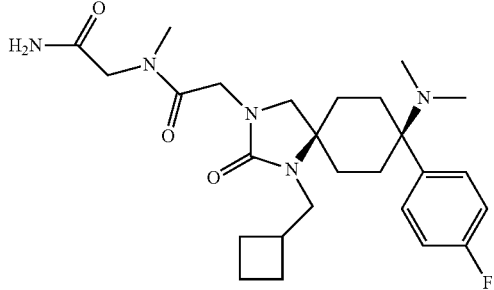

-continued
SC_1361
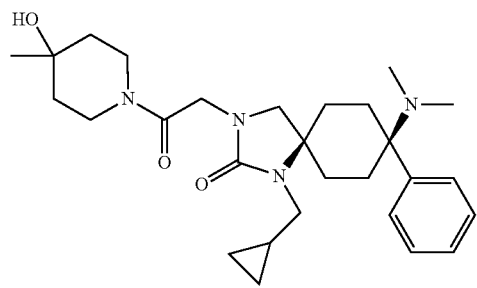
SC_1362
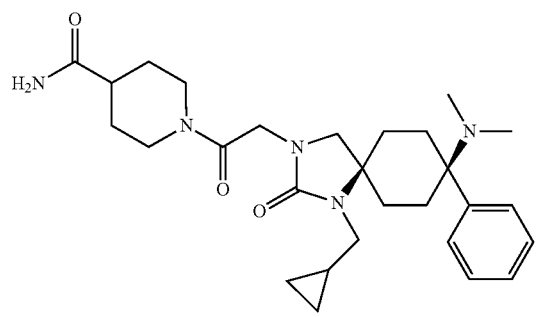
SC_1363
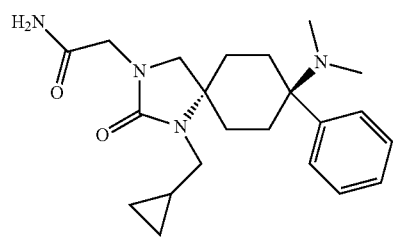
SC_1364
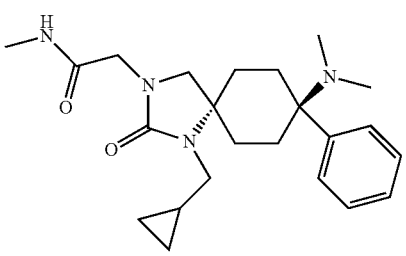
SC_1365
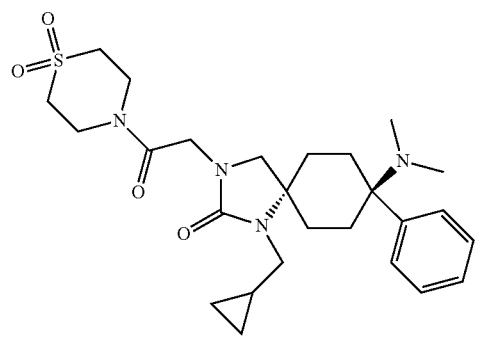
SC_1366
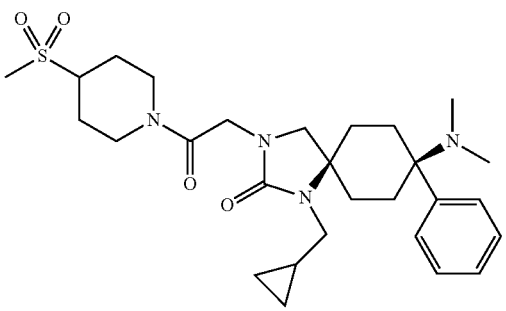
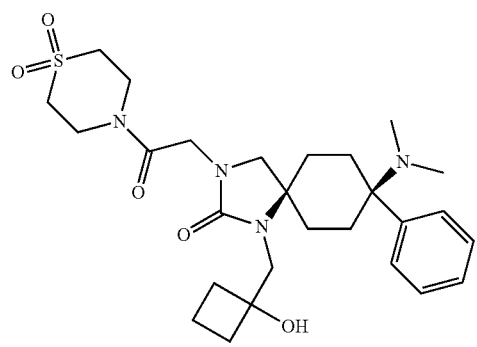
SC_1368
SC_1369
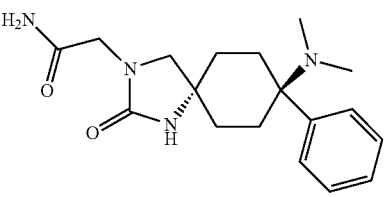
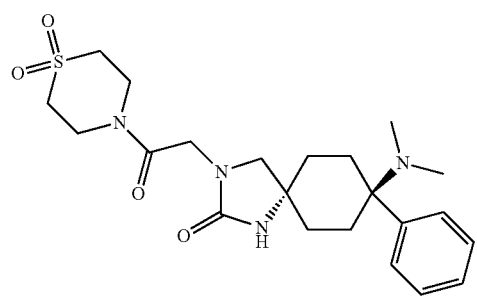
SC_1370
SC_1371
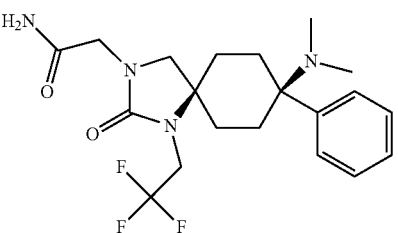

-continued

SC_1372

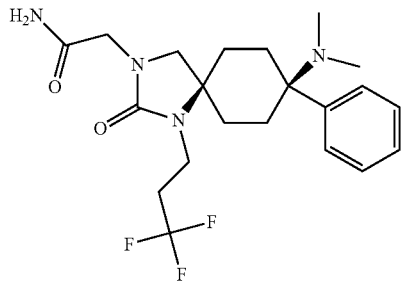

Pharmacological Investigations

Functional investigation on the human mu-opioid receptor (hMOP), human kappa-opioid receptor (hKOP), human delta-opioid receptor (hDOP), and human nociceptin/orphanin FQ peptide receptor (hNOP)

Human Mu-Opioid Peptide (hMOP) Receptor Binding Assay

The hMOP receptor binding assay was performed as homogeneous SPA-assay (scintillation proximity assay) using the assay buffer 50 mM TRIS-HCl (pH 7.4) supplemented with 0.052 mg/ml bovine serum albumin (Sigma-Aldrich Co., St. Louis, Mo.). The final assay volume (250 µl/well) included 1 nM of [N-allyl-2,3-$^3$H]naloxone as ligand (PerkinElmer Life Sciences, Inc. Boston, Mass., USA), and either test compound in dilution series or 25 µM unlabelled naloxone for determination of unspecific binding. The test compound was diluted with 25% DMSO in $H_2O$ to yield a final 0.5% DMSO concentration, which also served as a respective vehicle control. The assay was started by adding wheat germ agglutinin coated SPA beads (GE Healthcare UK Ltd., Buckinghamshire, UK) which had been preloaded with hMOP receptor membranes (PerkinElmer Life Sciences, Inc. Boston, Mass., USA). After incubation for 90 minutes at RT and centrifugation for 20 minutes at 500 rpm the signal rate was measured by means of a 1450 Microbeta Trilux ß-counter (PerkinElmer Life Sciences/Wallac, Turku, Finland). Half-maximal inhibitory concentration (IC50) values reflecting 50% displacement of [$^3$H] naloxone-specific receptor binding were calculated by nonlinear regression analysis and Ki values were calculated by using the Cheng-Prusoff equation, (Cheng and Prusoff, 1973).

Human Kappa-Opioid Peptide (hKOP) Receptor Binding Assay

The hKOP receptor binding assay is run as homogeneous SPA-assay (scintillation proximity assay) using the assay buffer 50 mM TRIS-HCl (pH 7.4) supplemented with 0.076 mg BSA/ml. The final assay volume of 250 µl per well includes 2 nM of [$^3$H]U69,593 as ligand, and either test compound in dilution series or 100 µM unlabelled naloxone for determination of unspecific binding. The test compound is diluted with 25% DMSO in $H_2O$ to yield a final 0.5% DMSO concentration which serves as respective vehicle control, as well. The assays are started by the addition of wheat germ agglutinin coated SPA beads (1 mg SPA beads/250 µl final assay volume per well) which has been preloaded for 15 minutes at room temperature with hKOP receptor membranes (14.8 µg/250 µl final assay volume per well). After short mixing on a mini-shaker, the microtiter plates are covered with a lid and the assay plates are incubated for 90 minutes at room temperature. After this incubation, the microtiter plates are sealed with a topseal and centrifuged for 20 minutes at 500 rpm. The signal rate is measured after a short delay of 5 minutes by means of a 1450 Microbeta Trilux ß-counter (PerkinElmer Life Sciences/Wallac, Turku, Finland). Half-maximal inhibitory concentration (IC50) values reflecting 50% displacement of [$^3$H] U69.593-specific receptor binding are calculated by nonlinear regression analysis and $K_i$ values are calculated by using the Cheng-Prusoff equation, (Cheng and Prusoff, 1973).

Human Delta-Opioid Peptide (hDOP) Receptor Binding Assay

The hDOP receptor binding assay is performed as homogeneous SPA-assay using the assay buffer 50 mM TRIS-HCl, 5 mM $MgCl_2$ (pH 7.4). The final assay volume (250 µl/well) includes 1 nM of [Tyrosyl-3,5-$^3$H]2-D-Ala-deltorphin II as ligand, and either test compound in dilution series or 10 µM unlabelled naloxone for determination of unspecific binding. The test compound is diluted with 25% DMSO in $H_2O$ to yield a final 0.5% DMSO concentration which serves as respective vehicle control, as well. The assays are started by the addition of wheat germ agglutinin coated SPA beads (1 mg SPA beads/250 µl final assay volume per well) which has been preloaded for 15 minutes at room temperature with hDOP receptor membranes (15.2 µg/250 µl final assay volume per well). After short mixing on a mini-shaker, the microtiter plates are covered with a lid and the assay plates are incubated for 120 minutes at room temperature and centrifuged for 20 minutes at 500 rpm. The signal rate is measured by means of a 1450 Microbeta Trilux ß-counter (PerkinElmer Life Sciences/Wallac, Turku, Finland). Half-maximal inhibitory concentration (IC50) values reflecting 50% displacement of [Tyrosyl-3,5-$^3$H]2-D-Ala-deltorphin II-specific receptor binding are calculated by nonlinear regression analysis and $K_i$ values are calculated by using the Cheng-Prusoff equation, (Cheng and Prusoff, 1973).

Human Nociceptin/Orphanin FQ Peptide (hNOP) Receptor Binding Assay

The hNOP receptor binding assay was performed as homogeneous SPA-assay (scintillation proximity assay) using the assay buffer 50 mM TRIS-HCl, 10 mM $MgCl_2$, 1 mM EDTA (pH 7.4). The final assay volume (250 µl/well) included 0.5 nM of [leucyl-$^3$H]nociceptin as ligand (PerkinElmer Life Sciences, Inc. Boston, Mass., USA), and either test compound in dilution series or 1 µM unlabelled nociceptin for determination of unspecific binding. The test compound was diluted with 25% DMSO in $H_2O$ to yield a final 0.5% DMSO concentration, which also served as a respective vehicle control. The assay was started by adding wheat germ agglutinin coated SPA beads (GE Healthcare UK Ltd., Buckinghamshire, UK) which had been preloaded with hMOP receptor membranes (PerkinElmer Life Sciences, Inc. Boston, Mass., USA). After incubation for 60 minutes at RT and centrifugation for 20 minutes at 500 rpm the signal rate was measured by means of a 1450 Microbeta Trilux ß-counter (PerkinElmer Life Sciences/Wallac, Turku, Finland). Half-maximal inhibitory concentration (IC50) values reflecting 50% displacement of [$^3$H]nociceptin-specific receptor binding were calculated by nonlinear regression analysis and Ki values were calculated by using the Cheng-Prusoff equation, (Cheng and Prusoff, 1973).

| Example | hNOP Ki [nM] | hMOP Ki [nM] |
| --- | --- | --- |
| SC_1001 | 33 | 206 |
| SC_1002 | 2.1 | 160 |
| SC_1003 | 3.7 | 102 |
| SC_1004 | 3.6 | 84 |
| SC_1005 | 6.3 | 115.5 |
| SC_1006 | 2.2 | 150 |
| SC_1007 | 29.5 | 190 |
| SC_1008 | 5.4 | 117.5 |
| SC_1009 | 17 | 390 |
| SC_1010 | 9.8 | 175 |
| SC_1011 | 9.1 | 112.5 |
| SC_1012 | 1.8 | 47.5 |
| SC_1013 | 1 | 220 |
| SC_1014 | 2.6 | 175 |
| SC_1015 | 1.3 | 140 |
| SC_1016 | 3.1 | 76.5 |
| SC_1017 | 2.6 | 130 |
| SC_1018 | 2.8 | 106.5 |
| SC_1019 | 4.6 | 170 |
| SC_1020 | 2 | 86 |
| SC_1021 | 1.6 | 94 |
| SC_1022 | 2.1 | 20.5 |
| SC_1023 | 13 | 270 |
| SC_1024 | 3.7 | 26.5 |
| SC_1025 | 22 | 125 |
| SC_1026 | 2 | 67.3 |
| SC_1027 | 7.6 | 55 |
| SC_1028 | 4.8 | 104 |
| SC_1029 | 52.3 | 303.3 |
| SC_1030 | 3.1 | 74.5 |
| SC_1031 | 3.6 | 43 |
| SC_1032 | 4.9 | 69.5 |
| SC_1033 | 3.9 | 75.5 |
| SC_1034 | 2.1 | 47 |
| SC_1035 | 1.3 | 21.5 |
| SC_1036 | 2.7 | 39 |
| SC_1037 | 1.8 | 45 |
| SC_1038 | 1.6 | 41.5 |
| SC_1039 | 1.3 | 34.5 |
| SC_1040 | 1.1 | 15 |
| SC_1041 | 1.7 | 20.5 |
| SC_1042 | 1.8 | 57 |
| SC_1043 | 1.1 | 21.5 |
| SC_1044 | 1.7 | 43 |
| SC_1045 | 1.6 | 44.5 |
| SC_1046 | 2.3 | 54 |
| SC_1047 | 2.5 | 49 |
| SC_1048 | 1 | 43.5 |
| SC_1049 | 2.9 | 48.5 |
| SC_1050 | 0.8 | 40 |
| SC_1051 | 1.6 | 36.5 |
| SC_1052 | 1.6 | 24.5 |
| SC_1053 | 2.7 | 53 |
| SC_1054 | 2.6 | 74.5 |
| SC_1055 | 2.5 | 29 |
| SC_1056 | 3.3 | 10 |
| SC_1057 | 1.9 | 11 |
| SC_1058 | 2.9 | 78 |
| SC_1059 | 7.4 | 45 |
| SC_1060 | 5.1 | 40.5 |
| SC_1061 | 2.2 | 12.6 |
| SC_1062 | 2.6 | 47.5 |
| SC_1063 | 1.6 | 22 |
| SC_1064 | 4.2 | 33 |
| SC_1065 | 4.8 | 26.5 |
| SC_1066 | 1.9 | 23 |
| SC_1067 | 7.5 | 31.5 |
| SC_1068 | 68.5 | 360 |
| SC_1069 | 1.4 | 16.5 |
| SC_1070 | 1 | 13.5 |
| SC_1071 | 3.6 | 38.5 |
| SC_1072 | 2.8 | 62 |
| SC_1073 | 3.5 | 25 |
| SC_1074 | 5.9 | 37 |
| SC_1075 | 1.5 | 19.5 |
| SC_1076 | 0.8 | 72 |
| SC_1077 | 1.8 | 20.5 |
| SC_1078 | 1.3 | 23.3 |
| SC_1079 | 1.7 | 26.2 |
| SC_1080 | 6.4 | 19.5 |
| SC_1081 | 1.9 | 64 |
| SC_1082 | 1 | 81.5 |
| SC_1083 | 1.5 | 44 |
| SC_1084 | 1.1 | 59 |
| SC_1085 | 3.8 | 71 |
| SC_1086 | 0.8 | 16.5 |
| SC_1087 | 2.4 | 28.2 |
| SC_1088 | 2 | 19.5 |
| SC_1089 | 1.4 | 16.5 |
| SC_1090 | 3 | 27.5 |
| SC_1091 | 1.3 | 15.5 |
| SC_1092 | 1.8 | 26.5 |
| SC_1093 | 4.2 | 43 |
| SC_1094 | 2.8 | 10.4 |
| SC_1095 | 1.8 | 12.5 |
| SC_1096 | 1.6 | 12 |
| SC_1097 | 1.6 | 15 |
| SC_1098 | 1.5 | 10 |
| SC_1099 | 1.5 | 4.5 |
| SC_1100 | 1 | 2.3 |
| SC_1101 | 3.4 | 6 |
| SC_1102 | 2 | 4.4 |
| SC_1103 | 0.4 | 7.2 |
| SC_1104 | 1.2 | 23 |
| SC_1105 | 4 | 50.5 |
| SC_1106 | 11 | 122 |
| SC_1107 | 1.8 | 45 |
| SC_1109 | 2.8 | 16 |
| SC_1110 | 9.8 | 31.5 |
| SC_1111 | 1.6 | 30 |
| SC_1112 | 1.3 | 30.5 |
| SC_1113 | 0.8 | 30 |
| SC_1114 | 109.5 | 850 |
| SC_1115 | 140 | 145 |
| SC_1117 | 4.1 | 37.5 |
| SC_1118 | 2.4 | 114.3 |
| SC_1119 | 6.5 | 73.5 |
| SC_1120 | 2.9 | 125 |
| SC_1121 | 115 | 630 |
| SC_1122 | 124.5 | 480 |
| SC_1123 | 2.6 | 24.8 |
| SC_1124 | 1.8 | 33.8 |
| SC_1125 | 2.2 | 23 |
| SC_1126 | 3.5 | 29.5 |
| SC_1127 | 2.6 | 2.7 |
| SC_1128 | 1.9 | 72 |
| SC_1129 | 1.7 | 37.3 |
| SC_1130 | 68.5 | 160 |
| SC_1131 | 34.5 | 215 |
| SC_1132 | 23.5 | 410 |
| SC_1133 | 6.4 | 25.5 |
| SC_1134 | 26 | 140 |
| SC_1135 | 73 | 370 |
| SC_1136 | 14 | 57.5 |
| SC_1137 | 5.8 | 99 |
| SC_1138 | 0.9 | 23.5 |
| SC_1139 | 215 | 515 |
| SC_1140 | 51.5 | 150 |
| SC_1141 | 4.8 | 165 |
| SC_1142 | 265 | 1200 |
| SC_1143 | 17 | 200 |
| SC_1144 | 9.8 | 73.5 |
| SC_1145 | 3.4 | 60.5 |
| SC_1146 | 2.2 | 21.2 |
| SC_1147 | 2.6 | 34.2 |

| Example | hNOP Ki [nM] | hMOP Ki [nM] |
| --- | --- | --- |
| SC_1148 | 40 | 18.8 |
| SC_1149 | 62 | 102.5 |
| SC_1150 | 4.9 | 55.5 |
| SC_1151 | 1.6 | 13.5 |
| SC_1152 | 0.9 | 13.7 |
| SC_1153 | 1.6 | 37 |
| SC_1154 | 4.5 | 29 |
| SC_1155 | 14.1 | 114.5 |
| SC_1156 | 155 | 1215 |
| SC_1157 | 170 | 1120 |
| SC_1158 | 12.5 | 144.5 |
| SC_1159 | 22.5 | 81.5 |
| SC_1160 | 20 | 84.5 |
| SC_1161 | 60 | 86 |
| SC_1162 | 15.3 | 47.5 |
| SC_1163 | 30.5 | 119 |
| SC_1164 | 8.2 | 16.5 |
| SC_1165 | 5.7 | 63.5 |
| SC_1166 | 17 | 72.5 |
| SC_1167 | 18 | 92 |
| SC_1168 | 37 | 125 |
| SC_1169 | 36.5 | 370 |
| SC_1171 | 43 | 130 |
| SC_1172 | 27.5 | 106 |
| SC_1173 | 38.5 | 120 |
| SC_1174 | 12.9 | 195 |
| SC_1175 | 28.5 | 9.6 |
| SC_1176 | 9 | 56 |
| SC_1177 | 39 | 660 |
| SC_1178 | 16 | 390 |
| SC_1179 | 87.5 | 180 |
| SC_1180 | 80 | 230 |
| SC_1181 | 125 | 435 |
| SC_1182 | 47.5 | 320 |
| SC_1183 | 130 | 185 |
| SC_1184 | 110 | 153.3 |
| SC_1185 | 47 | 165 |
| SC_1186 | 95.5 | 355 |
| SC_1187 | 43 | 127.5 |
| SC_1188 | 9.1 | 175 |
| SC_1189 | 70.5 | 75.5 |
| SC_1190 | 11.2 | 123.5 |
| SC_1191 | 29 | 150 |
| SC_1192 | 17 | 680 |
| SC_1193 | 9.9 | 41 |
| SC_1195 | 4.4 | 6.2 |
| SC_1196 | 2.1 | 64.8 |
| SC_1197 | 5.4 | 60 |
| SC_1198 | 4.9 | 47 |
| SC_1199 | 35 | 230 |
| SC_1201 | 13.3 | 123.7 |
| SC_1203 | 5.2 | 47.5 |
| SC_1204 | 2.5 | 77.2 |
| SC_1205 | 2.2 | 37 |
| SC_1206 | 1.2 | 61.5 |
| SC_1207 | 2.9 | 38 |
| SC_1208 | 1.8 | 90 |
| SC_1209 | 3.2 | 46 |
| SC_1210 | 4.4 | 83.5 |
| SC_1211 | 2.4 | 18.7 |
| SC_1212 | 4.8 | 37.7 |
| SC_1213 | 1.8 | 31.7 |
| SC_1214 | 1 | 56.7 |
| SC_1215 | 3.9 | 25 |
| SC_1216 | 1.2 | 49 |
| SC_1217 | 2.2 | 25.7 |
| SC_1218 | 5.2 | 59 |
| SC_1219 | 4.2 | 73.7 |
| SC_1220 | 4 | 51 |
| SC_1221 | 17 | 180 |
| SC_1222 | 2.6 | 63 |
| SC_1223 | 2.5 | 43.5 |
| SC_1224 | 1.6 | 15 |
| SC_1225 | 1.8 | 49.5 |
| SC_1226 | 2.6 | 12.5 |
| SC_1227 | 4.6 | 63 |
| SC_1228 | 665 | 1740 |
| SC_1229 | 2.8 | 22.5 |
| SC_1230 | 1.5 | 36.5 |
| SC_1231 | 2 | 51.5 |
| SC_1232 | 1.4 | 32.5 |
| SC_1233 | 0.5 | 26.5 |
| SC_1234 | 1.8 | 53.5 |
| SC_1236 | 3.3 | 83 |
| SC_1300 | 13 | 130 |
| SC_1301 | 23 | 44 |
| SC_1302 | 27 | 66.5 |
| SC_1303 | 145 | 215 |
| SC_1304 | 280 | 400 |
| SC_1305 | 19 | 105.5 |
| SC_1306 | 59 | 45 |
| SC_1308 | 22 | 97 |
| SC_1309 | 12.5 | 100 |
| SC_1310 | 8.1 | 17 |
| SC_1311 | 11.5 | 44 |
| SC_1312 | 295 | 520 |
| SC_1313 | 305 | 1015 |
| SC_1317 | 1.4 | 53.5 |
| SC_1318 | 89 | 960 |
| SC_1319 | 4 | 71 |
| SC_1320 | 4 | 51 |
| SC_1321 | 17 | 180 |
| SC_1322 | 6%@1 μM | 9%@1 μM |
| SC_1323 | 12%@1 μM | 7%@1 μM |
| SC_1324 | 330 | 6025 |
| SC_1325 | 0%@1 μM | 5%@1 μM |
| SC_1326 | 0%@1 μM | 625 |
| SC_1327 | 11 | 120 |
| SC_1328 | 2%@1 μM | 6%@1 μM |
| SC_1329 | 0%@1 μM | 4%@1 μM |
| SC_1330 | 465 | 18%@1 μM |
| SC_1331 | 10 | 38 |
| SC_1332 | 52 | 1950 |
| SC_1333 | 36 | 300 |
| SC_1334 | 195 | 1605 |
| SC_1335 | 2 | 24 |
| SC_1336 | — | — |
| SC_1337 | 23 | — |
| SC_1338 | 475 | 14%@1 μM |
| SC_1339 | 1110 | 9%@1 μM |
| SC_1340 | 230 | 14%@1 μM |
| SC_1341 | 170 | 2905 |
| SC_1342 | 1140 | 10%@1 μM |
| SC_1343 | 12 | 95 |
| SC_1344 | 13 | 145 |
| SC_1345 | 1 | 185 |
| SC_1346 | 2 | 400 |
| SC_1347 | 31 | 615 |
| SC_1348 | 8 | 97 |
| SC_1349 | 1 | 165 |
| SC_1350 | 8 | 510 |
| SC_1351 | 1 | 235 |
| SC_1352 | 1 | 135 |
| SC_1353 | 66 | 80.5 |
| SC_1354 | 465 | 210 |
| SC_1355 | 7 | 325 |
| SC_1356 | 11 | 86 |
| SC_1357 | 100 | 15.5 |
| SC_1358 | 73 | 51.5 |
| SC_1359 | 10 | 260 |
| SC_1360 | 15 | 180 |
| SC_1361 | 13 | 255 |
| SC_1362 | 6 | 240 |
| SC_1363 | 185 | 225 |
| SC_1364 | 230 | 73.5 |
| SC_1365 | 160 | 4.4 |
| SC_1366 | 1 | 205 |
| SC_1368 | 7 | 360 |
| SC_1369 | 465 | 1805 |
| SC_1370 | 100 | 11 |

Protocol for [$^{35}$S]GTPγS Functional NOP/MOP/KOP/DOP Assays

Cell membrane preparations of CHO— K1 cells transfected with the human MOP receptor (Art.-No. RBHOMM) or the human DOP receptor (Art.-No. RBHODM), and HEK293 cells transfected with the human NOP receptor (Art.-No. RBHORLM) or the human KOP receptor (Art.-No. 6110558) are available from PerkinElmer (Waltham, Mass.). Membranes from CHO-K1 cells transfected with the human nociceptin/orphanin FQ peptide (hNOP) receptor (Art.-No. 93-0264C2, DiscoveRx Corporation, Freemont, Calif.) are also used. [$^{35}$S]GTPγS (Art.-No. NEG030H; Lot-No. #0112, #0913, #1113 calibrated to 46.25 TBq/mmol) is available from PerkinElmer (Waltham, Mass.).

The [$^{35}$S]GTPγS assays are carried out essentially as described by Gillen et al (2000). They are run as homogeneous scintillation proximity (SPA) assays in microtiter luminescence plates, where each well contains 1.5 mg of WGA-coated SPA-beads. To test the agonistic activity of test compounds on recombinant hNOP, hMOP, hDOP, and hKOP receptor expressing cell membranes from CHO-K1 or HEK293 cells, 10 or 5 μg membrane protein per assay are incubated with 0.4 nM [$^{35}$S]GTPγS and serial concentrations of receptor-specific agonists in buffer containing 20 mM HEPES pH 7.4, 100 mM NaCl, 10 mM MgCl2, 1 mM EDTA, 1 mM dithiothreitol, 1.28 mM NaN$_3$, and 10 μM GDP for 45 min at room temperature. The microtiter plates are then centrifuged for 10 min at 830 to sediment the SPA beads. The microtiter plates are sealed and the bound radioactivity [cpm] is determined after a delay of 15 min by means of a 1450 Microbeta Trilux (PerkinElmer, Waltham, Mass.).

The unstimulated basal binding activity (UBS$_{obs}$ [cpm]) is determined from 12 unstimulated incubates and is set as 100% basal binding. For determination of the potency and the efficacy, the arithmetic mean of the observed total [$^{35}$S]GTPγS binding (TB$_{obs}$ [cpm]) of all incubates (duplicates) stimulated by the receptor-specific agonists (i.e. N/OFQ, SNC80, DAMGO, or U69,593) are transformed in percent total binding (TB$_{obs}$ [%]) relative to the basal binding activity (i.e. 100% binding). The potency (EC$_{50}$) of the respective agonist and its maximal achievable total [$^{35}$S]GTPγS binding (TB$_{calc}$ [%]) above its calculated basal binding (UBS$_{calc}$ [%]) are determined from its transformed data (TB$_{obs}$ [%]) by means of nonlinear regression analysis with XLfit for each individual concentration series. Then the difference between the calculated unstimulated [$^{35}$S]GTPγS binding (UBS$_{calc}$ [%]) and the maximal achievable total [$^{35}$S]GTPγS binding (TB$_{calc}$ [%]) by each tested agonist is determined (i.e. B1$_{calc}$ [%]). This difference (B1$_{calc}$[%]) as a measure of the maximal achievable enhancement of [$^{35}$S]GTPγS binding by a given agonist is used to calculate the relative efficacy of test compounds versus the maximal achievable enhancement by a receptor-specific full agonist, e.g. N/OFQ (B1$_{calc-N/OFQ}$ [%]) which is set as 100% relative efficacy for the hNOP receptor. Likewise, the percentage efficacies of test compounds at the hDOP, hMOP, or hKOP receptor are determined versus the calculated maximal enhancement of [$^{35}$S]GTPγS binding by the full agonists SNC80 (B1$_{calc-SNC80}$ [%]), DAMGO (B1$_{calc-DAMGO}$ [%]) and U69,593 (B1$_{calc-U69,593}$ [%]) which are set as 100% relative efficacy at each receptor, respectively.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound according to general formula (I)

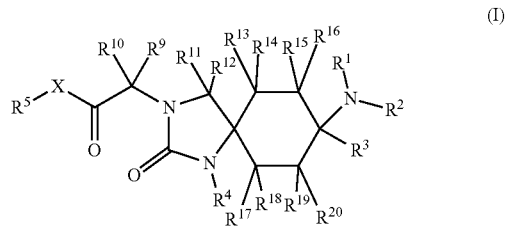

wherein
R$^1$ and R$^2$ independently of one another mean
—H;
—C$_1$-C$_6$-alkyl, linear or branched, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$;
a 3-12-membered cycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered cycloalkyl moiety is optionally connected through —C$_1$-C$_6$-alkylene-, linear or branched, saturated or unsaturated, unsubstituted; or
a 3-12-membered heterocycloalkyl moiety, saturated or unsaturated, unsubstituted or substituted with one, two, three or four substituents independently of one another selected from the group consisting of —F, —Cl, —Br, —I, —OH, —OCH$_3$, —CN and —CO$_2$CH$_3$; wherein said 3-12-membered heterocycloalkyl moiety is optionally connected through —C$_1$-C$_6$-alkylene-, linear or branched, saturated or unsaturated, unsubstituted;
or
R$^1$ and R$^2$ together with the nitrogen atom to which they are attached form a ring and mean —(CH$_2$)$_{3-6}$—; —(CH$_2$)$_2$—O—(CH$_2$)$_2$—; or —(CH$_2$)$_2$—NR$^4$—(CH$_2$)$_2$—, wherein R$^4$ means —H or —C$_1$-C$_6$-alkyl, linear or branched, saturated or unsaturated, unsubstituted or substituted with one, two, three or four substituents independently of one another selected from the group consisting of —F, —Cl, —Br and —I;
R$^3$ means
—C$_1$-C$_6$-alkyl, linear or branched, saturated or unsaturated, unsubstituted, mono- or polysubstituted;
a 3-12-membered cycloalkyl moiety, saturated or unsaturated, unsubstituted, mono- or polysubstituted; wherein said 3-12-membered cycloalkyl moiety is optionally connected through —C$_1$-C$_6$-alkylene-, linear or branched, saturated or unsaturated, unsubstituted, mono- or polysubstituted;
a 3-12-membered heterocycloalkyl moiety, saturated or unsaturated, unsubstituted, mono- or polysubstituted; wherein said 3-12-membered heterocycloalkyl moiety is optionally connected through —C$_1$-C$_6$-alkylene-, linear or branched, saturated or unsaturated, unsubstituted, mono- or polysubstituted;
a 6-14-membered aryl moiety, unsubstituted, mono- or polysubstituted; wherein said 6-14-membered aryl moiety is optionally connected through —C$_1$-C$_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

$R^4$ means

—H;

—$C_1$-$C_6$-alkyl, linear or branched, saturated or unsaturated, unsubstituted, mono- or polysubstituted; wherein said —$C_1$-$C_6$-alkyl is optionally connected through —C(=O)—, —C(=O)O—, or —S(=O)$_2$—;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted; or wherein said 3-12-membered cycloalkyl moiety is optionally connected through —C(=O)—, —C(=O)O—, —C(=O)O—CH$_2$—, or —S(=O)$_2$—;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted; or wherein said 3-12-membered heterocycloalkyl moiety is optionally connected through —C(=O)—, —C(=O)O—, —C(=O)O—CH$_2$—, or —S(=O)$_2$—;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or wherein said 6-14-membered aryl moiety is optionally connected through —C(=O)—, —C(=O)O—, —C(=O)O—CH$_2$—, or —S(=O)$_2$—; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted; or wherein said 5-14-membered heteroaryl moiety is optionally connected through —C(=O)—, —C(=O)O—, —C(=O)O—CH$_2$—, or —S(=O)$_2$—;

X means —O—, —S— or —NR$^6$—;

$R^5$ means

—H;

—$C_1$-$C_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

in case X means NR$^6$, $R^6$ means

—H;

—$C_1$-$C_6$-alkyl, linear or branched, saturated or unsaturated, unsubstituted, mono- or polysubstituted;

a 3-12-membered cycloalkyl moiety, saturated or unsaturated, unsubstituted, mono- or polysubstituted; wherein said 3-12-membered cycloalkyl moiety is optionally connected through —$C_1$-$C_6$-alkylene-, linear or branched, saturated or unsaturated, unsubstituted, mono- or polysubstituted;

a 3-12-membered heterocycloalkyl moiety, saturated or unsaturated, unsubstituted, mono- or polysubstituted; wherein said 3-12-membered heterocycloalkyl moiety is optionally connected through —$C_1$-$C_6$-alkylene-, linear or branched, saturated or unsaturated, unsubstituted, mono- or polysubstituted;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted, mono- or polysubstituted; or a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted;

or in case X means NR$^6$, $R^5$ and $R^6$ together with the nitrogen atom to which they are attached form a 3-12-membered heterocycloalkyl moiety, saturated or unsaturated, unsubstituted, mono- or polysubstituted;

$R^9$, $R_{10}$, $R_{11}$, $R_{12}$, $R_{13}$, $R_{14}$, $R_{15}$, $R_{16}$, $R_{17}$, $R_{18}$, $R_{19}$, and $R^{20}$ independently of one another mean —H, —F, —Cl, —Br, —I, —OH, or —$C_1$-$C_6$-alkyl, linear or branched, saturated or unsaturated, unsubstituted, mono- or polysubstituted;

wherein "mono- or polysubstituted" means that one or more hydrogen atoms are replaced by a substituent independently of one another selected from the group consisting of —F, —Cl, —Br, —I, —CN, —R$^{21}$, —C(=O)R$^{21}$, —C(=O)OR$^{21}$, —C(=O)NR$^{21}$R$^{22}$, —O—(CH$_2$CH$_2$—O)$_{1-30}$—H, —O—(CH$_2$CH$_2$—O)$_{1-30}$—CH$_3$, =O, —OR$^{21}$, —OC(=O)R$^{21}$, —OC(=O)OR$^{21}$, —OC(=O)NR$^{21}$R$^{22}$, —NO$_2$, —NR$^{21}$R$^{22}$, —NR$^{21}$—(CH$_2$)$_{1-6}$—C(=O)R$^{22}$, —NR$^{21}$—(CH$_2$)$_{1-6}$—C(=O)OR$^{22}$, —NR$^{23}$—(CH$_2$)$_{1-6}$—C(=O)NR$^{21}$R$^{22}$, —NR$^{21}$C(=O)R$^{22}$, —NR$^{21}$C(=O)—OR$^{22}$, —NR$^{23}$C(=O)NR$^{21}$R$^{22}$, —NR$^{21}$S(=O)$_2$R$^{22}$, —SR$^{21}$, —S(=O)R$^{21}$, —S(=O)$_2$R$^{21}$, —S(=O)$_2$OR$^{21}$, and —S(=O)$_2$NR$^{21}$R$^{22}$;

wherein $R^{21}$, $R^{22}$ and $R^{23}$ independently of one another mean

—H;

—$C_1$-$C_6$-alkyl, linear or branched, saturated or unsaturated, unsubstituted or substituted with one, two, three or four substituents independently of one another selected from the group consisting of —F, —Cl, —Br, —I, —CN, —OH, —NH$_2$, and —O—$C_1$-$C_6$-alkyl;

a 3-12-membered cycloalkyl moiety, saturated or unsaturated, unsubstituted; wherein said 3-12-membered cycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 3-12-membered heterocycloalkyl moiety, saturated or unsaturated, unsubstituted; wherein said 3-12-membered heterocycloalkyl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 6-14-membered aryl moiety, unsubstituted, mono- or polysubstituted; wherein said 6-14-membered aryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted or substituted with one, two, three or four substituents independently of one another selected from the group consisting of —F, —Cl, —Br, —I, —CN, —OH, —$NH_2$, —$C_1$-$C_6$-alkyl and —O—$C_1$-$C_6$-alkyl;

or $R^{21}$ and $R^{22}$ within —C(=O)$NR^{21}R^{22}$, —OC(=O)$NR^{21}R^{22}$, —$NR^{21}R^{22}$, —$NR^{23}$—$(CH_2)_{1-6}$—C(=O)$NR^{21}R^{22}$, —$NR^{23}$C(=O)$NR^{21}R^{22}$, or —S(=O)$_2$$NR^{21}R^{22}$ together with the nitrogen atom to which they are attached form a ring and mean —$(CH_2)_{3-6}$—; —$(CH_2)_2$—O—$(CH_2)_2$—; or —$(CH_2)_2$—$NR^B$—$(CH_2)_2$—, wherein $R^B$ means —H or —$C_1$-$C_6$-alkyl, linear or branched, saturated or unsaturated, unsubstituted or substituted with one, two, three or four substituents independently of one another selected from the group consisting of —F, —Cl, —Br and —I;

or a physiologically acceptable salt thereof.

2. The compound according to claim 1, wherein $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{20}$ independently of one another mean —H, —F, —OH, or —$C_1$-$C_6$-alkyl.

3. The compound according to claim 1, wherein $R^1$ means —H; and $R^2$ means —$C_1$-$C_6$-alkyl, linear or branched, saturated or unsaturated, unsubstituted, mono- or polysubstituted.

4. The compound according to claim 1, wherein $R^1$ means —$CH_3$; and $R^2$ means —$C_1$-$C_6$-alkyl, linear or branched, saturated or unsaturated, unsubstituted, mono- or polysubstituted.

5. The compound according to claim 1, wherein $R^1$ means —H or —$CH_3$; and
wherein $R^2$ means —$CH_2$-cycloalkyl, —$CH_2$-cyclobutyl, —$CH_2$-cyclopentyl, —$CH_2$-oxetanyl or —$CH_2$-tetrahydrofuranyl.

6. The compound according to claim 1, wherein $R^1$ and $R^2$ together with the nitrogen atom to which they are attached form a ring and mean —$(CH_2)_{3-6}$—.

7. The compound according to claim 1, wherein $R^3$ means —$C_1$-$C_6$-alkyl, linear or branched, saturated or unsaturated, unsubstituted, mono- or polysubstituted.

8. The compound according to claim 1, wherein $R^3$ means a 6-14-membered aryl moiety, unsubstituted, mono- or polysubstituted.

9. The compound according to claim 1, wherein $R^3$ means a 5-14-membered heteroaryl moiety, unsubstituted, mono- or polysubstituted.

10. The compound according to claim 1, wherein $R^4$ means —H.

11. The compound according to claim 1, wherein $R^4$ means —$C_1$-$C_6$-alkyl, linear or branched, saturated or unsaturated, unsubstituted, mono- or polysubstituted.

12. The compound according to claim 1, wherein $R^4$ means a 3-12-membered cycloalkyl moiety, saturated or unsaturated, unsubstituted, mono- or polysubstituted; wherein the 3-12-membered cycloalkyl moiety is connected through —$C_1$-$C_6$-alkylene-, linear or branched, saturated or unsaturated, unsubstituted, mono- or polysubstituted.

13. The compound according to claim 1, wherein $R^4$ means a 3-12-membered heterocycloalkyl moiety, saturated or unsaturated, unsubstituted, mono- or polysubstituted;
wherein said 3-12-membered heterocycloalkyl moiety is connected through —$C_1$-$C_6$-alkylene-, linear or branched, saturated or unsaturated, unsubstituted, mono- or polysubstituted.

14. The compound according to claim 1, wherein $R^4$ means a 6-14-membered aryl moiety, unsubstituted, mono- or polysubstituted; wherein said 6-14-membered aryl moiety is connected through —$C_1$-$C_6$-alkylene-, linear or branched, saturated or unsaturated, unsubstituted, mono- or polysubstituted.

15. The compound according to claim 1, wherein $R^4$ means a 5-14-membered heteroaryl moiety, unsubstituted, mono- or polysubstituted; wherein said 5-14-membered heteroaryl moiety is connected through —$C_1$-$C_6$-alkylene-, linear or branched, saturated or unsaturated, unsubstituted, mono- or polysubstituted.

16. The compound according to claim 1, wherein $R^5$ means —H.

17. The compound according to claim 1, wherein $R^5$ means —$C_1$-$C_6$-alkyl, linear or branched, saturated or unsaturated, unsubstituted, mono- or polysubstituted.

18. The compound according to claim 1, wherein $R^5$ means a 3-12-membered cycloalkyl moiety, saturated or unsaturated, unsubstituted, mono- or polysubstituted, wherein said 3-12-membered cycloalkyl moiety is optionally connected through —$C_1$-$C_6$-alkylene-, linear or branched, saturated or unsaturated, unsubstituted, mono- or polysubstituted.

19. The compound according to claim 1, wherein $R^5$ means a 3-12-membered heterocycloalkyl moiety, saturated or unsaturated, unsubstituted, mono- or polysubstituted;
wherein said 3-12-membered heterocycloalkyl moiety is optionally connected through —$C_1$-$C_6$-alkylene-, linear or branched, saturated or unsaturated, unsubstituted, mono- or polysubstituted.

20. The compound according to claim 1, wherein $R^5$ means a 5-14-membered heteroaryl moiety, unsubstituted, mono- or polysubstituted; wherein said 5-14-membered heteroaryl moiety is optionally connected through —$C_1$-$C_6$-alkylene-, linear or branched, saturated or unsaturated, unsubstituted, mono- or polysubstituted.

21. The compound according to claim 1, wherein X means $NR^6$ and $R^5$ and $R^6$ together with the nitrogen atom to which they are attached form a 3-12-membered heterocycloalkyl moiety, saturated or unsaturated, unsubstituted, mono- or polysubstituted.

22. The compound according to claim 1, wherein X means $NR^6$ and $R^6$ means —H or —$C_1$-$C_6$-alkyl, linear or branched, saturated or unsaturated, unsubstituted, mono- or polysubstituted.

23. The compound according to claim 1, which has a structure according to any of general formulas (II-A) to (VIII-C):

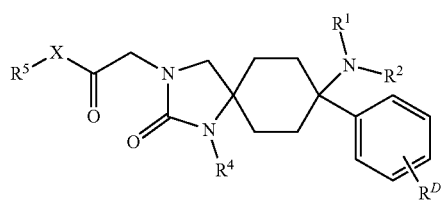
(II-A)

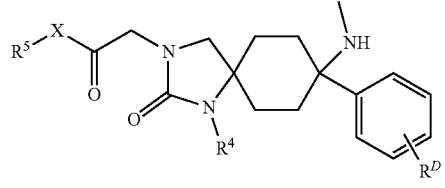
(II-B)

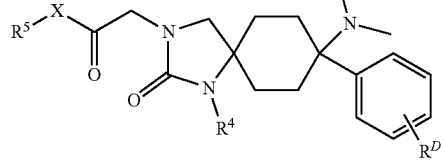
(II-C)

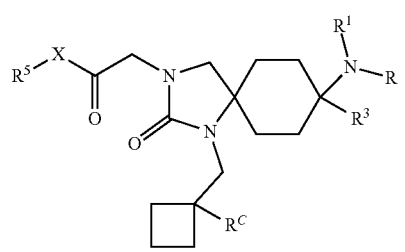
(III-A)

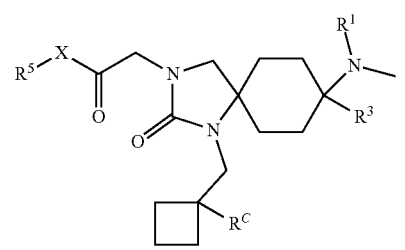
(III-B)

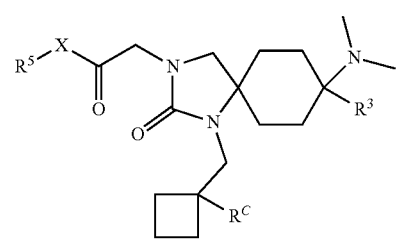
(III-C)

-continued

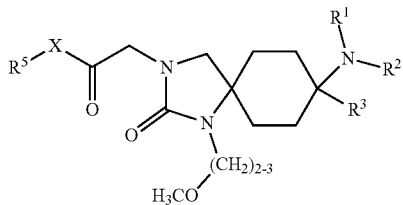
(IV-A)

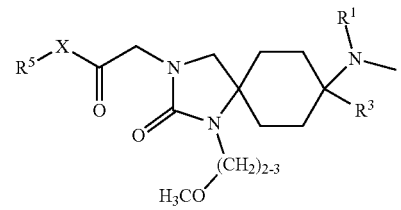
(IV-B)

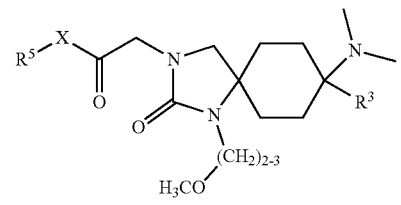
(IV-C)

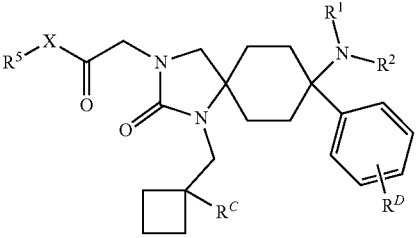
(V-A)

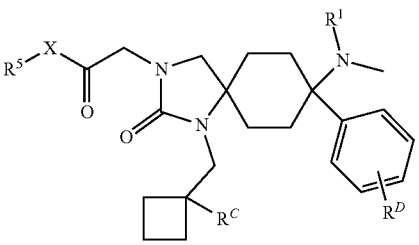
(V-B)

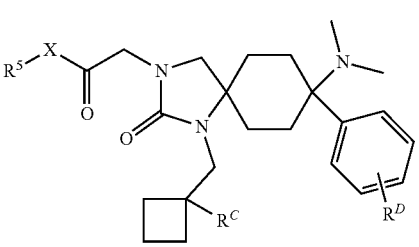
(V-C)

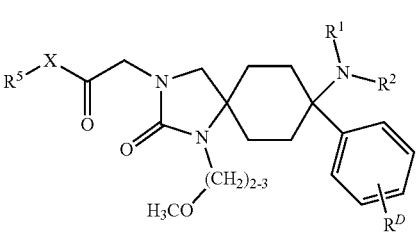
(VI-A)

(VI-B)
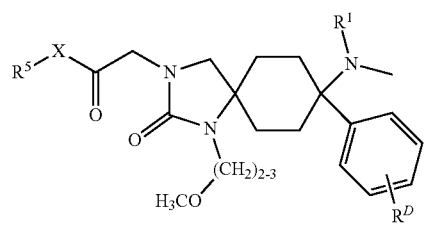
(VI-C)
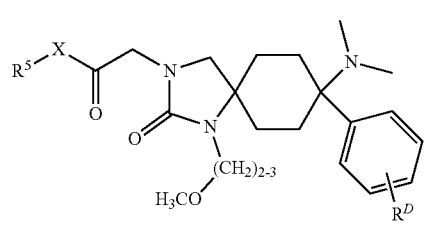
(VII-A)
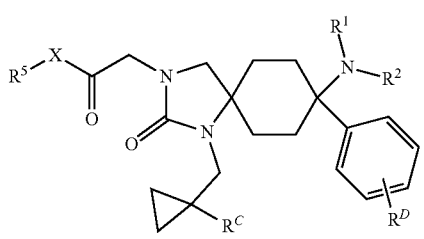
(VII-B)
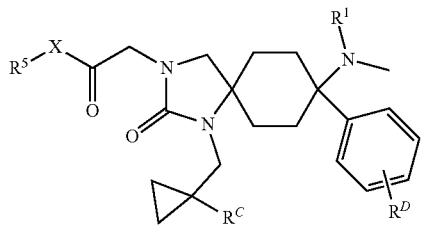
(VII-C)
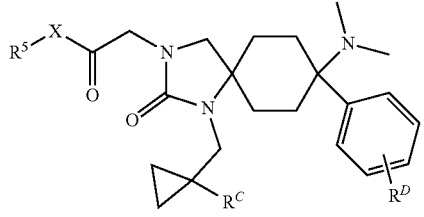
(VIII-A)
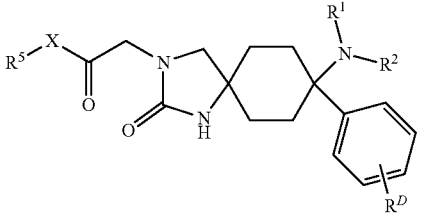
(VIII-B)
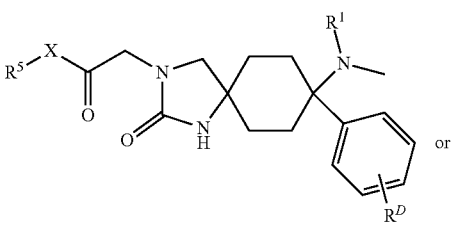 or
(VIII-C)
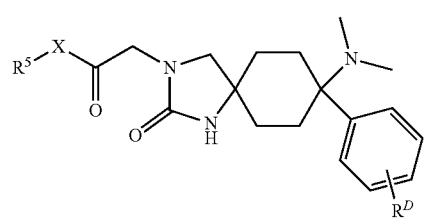
wherein in each case
$R^1$, $R^2$, $R^3$, $R^4$, $R^5$, $R^6$ and X are defined as in claim 1,
$R^C$ means —H, —OH, —F, —CN or —$C_1$-$C_4$-alkyl;
$R^D$ means —H or —F;
or a physiologically acceptable salt thereof.
24. The compound according to claim 1, wherein the substructure
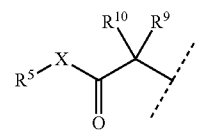
has a meaning selected from the group consisting of:
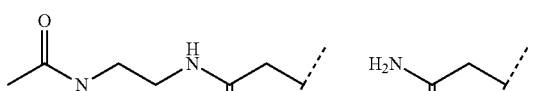
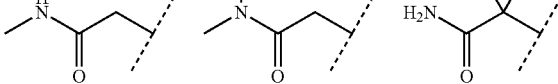
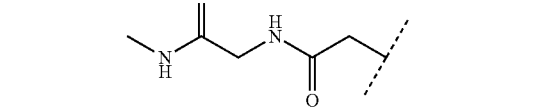
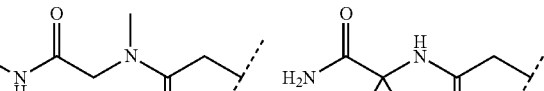

263
-continued
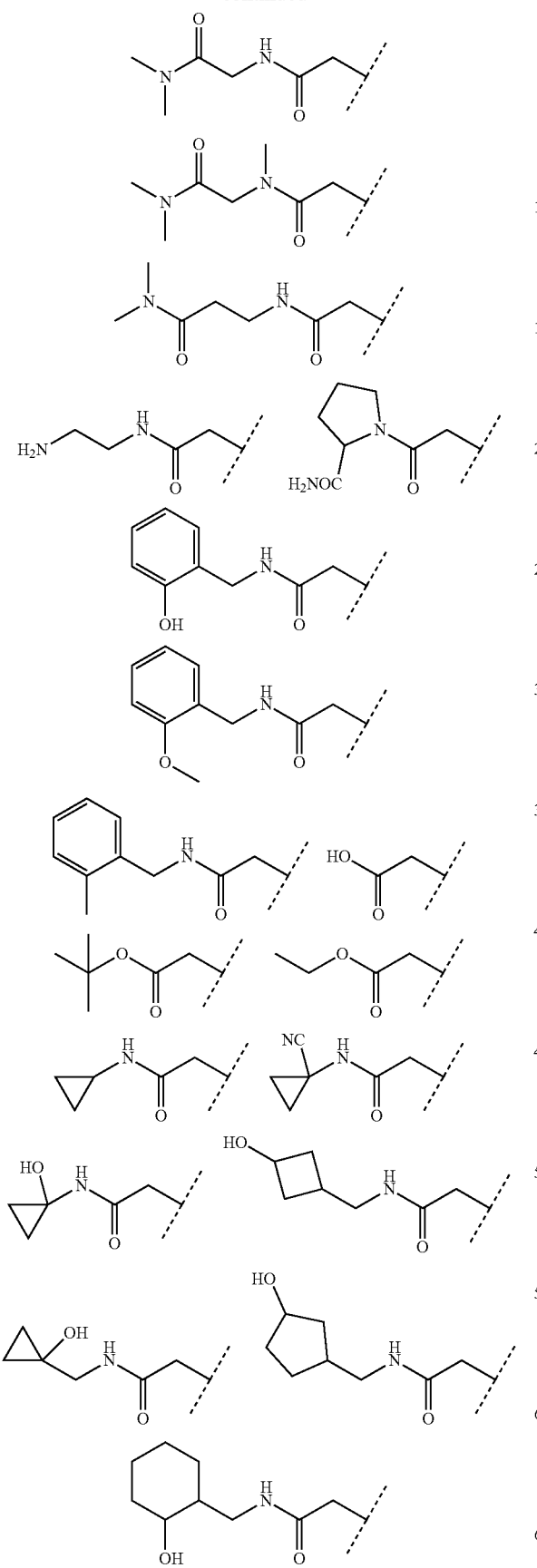
264
-continued
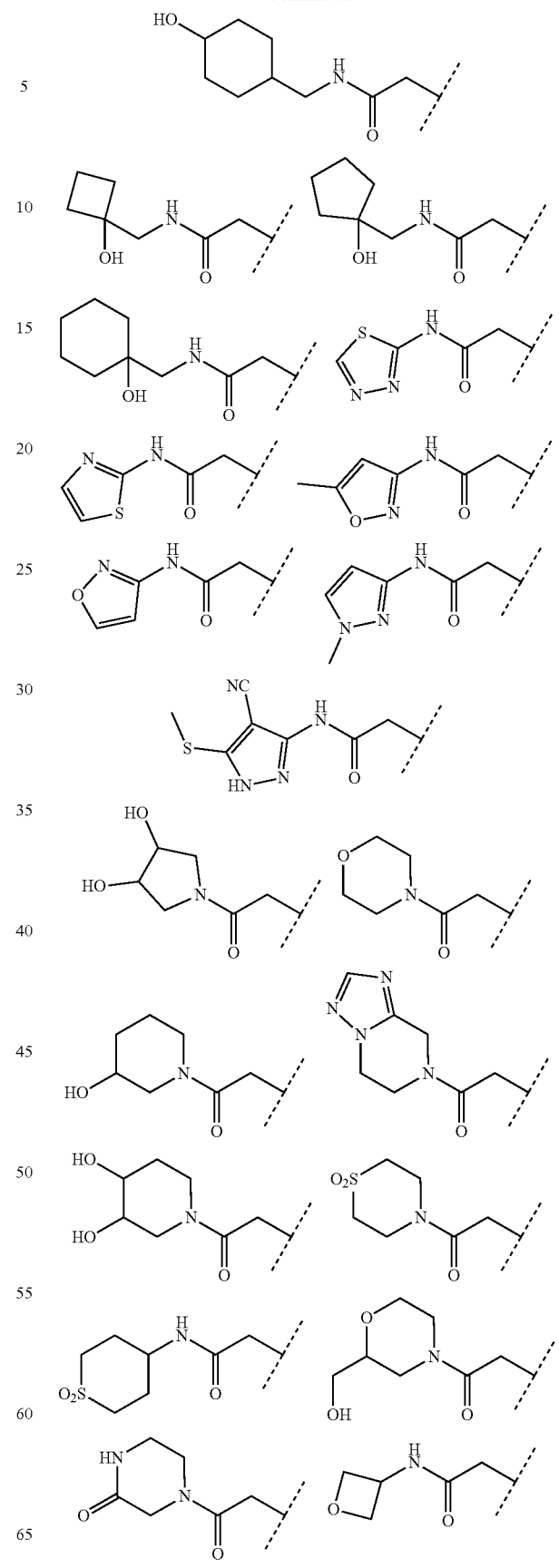

-continued
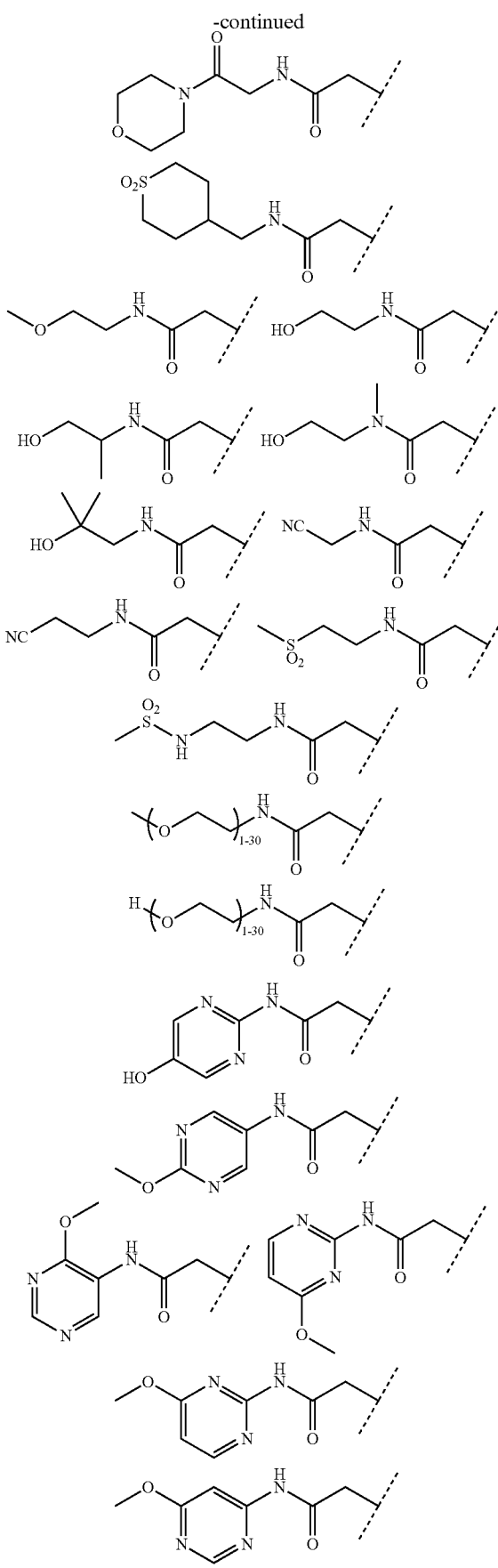
-continued
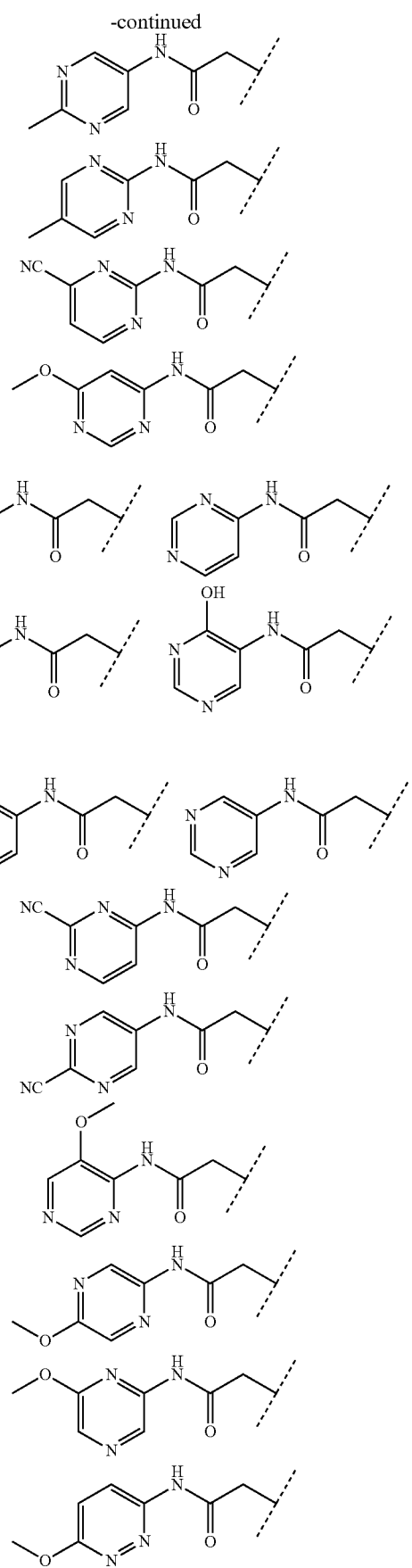

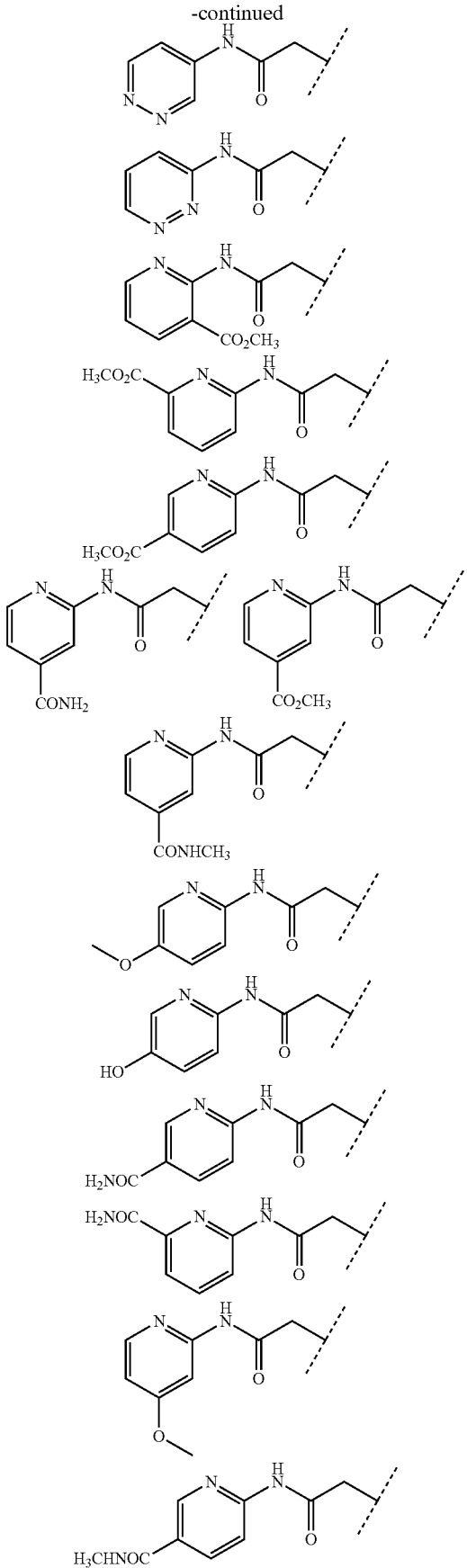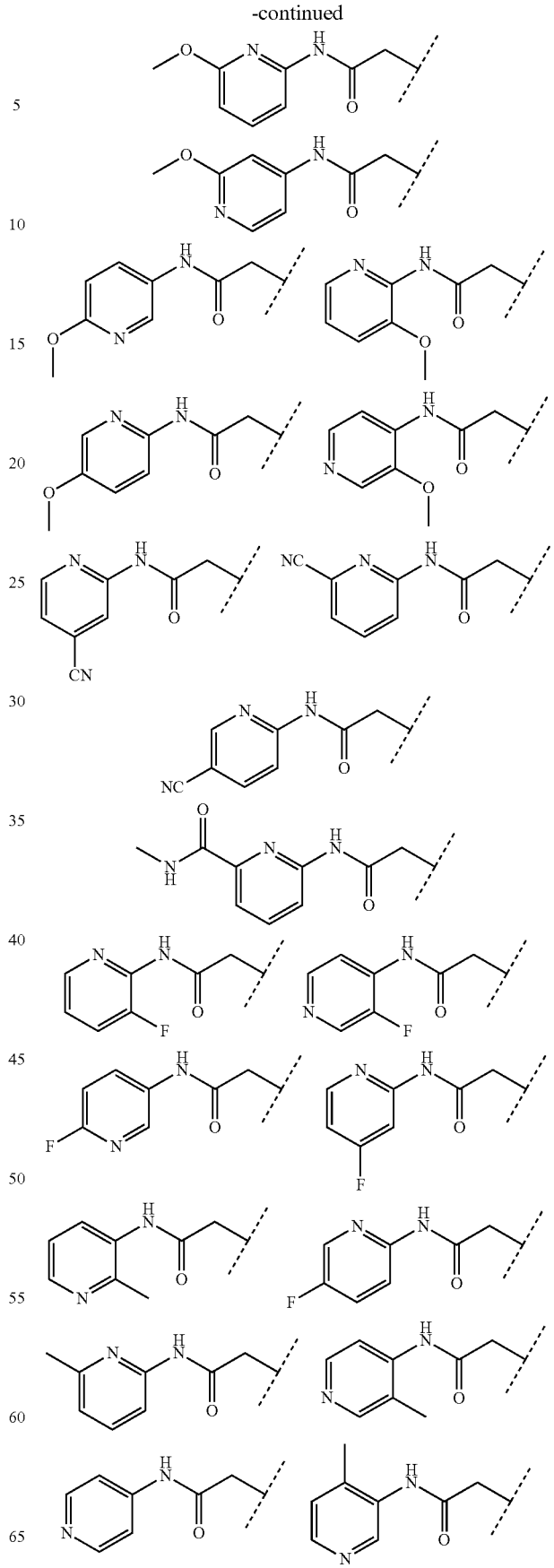

269
-continued
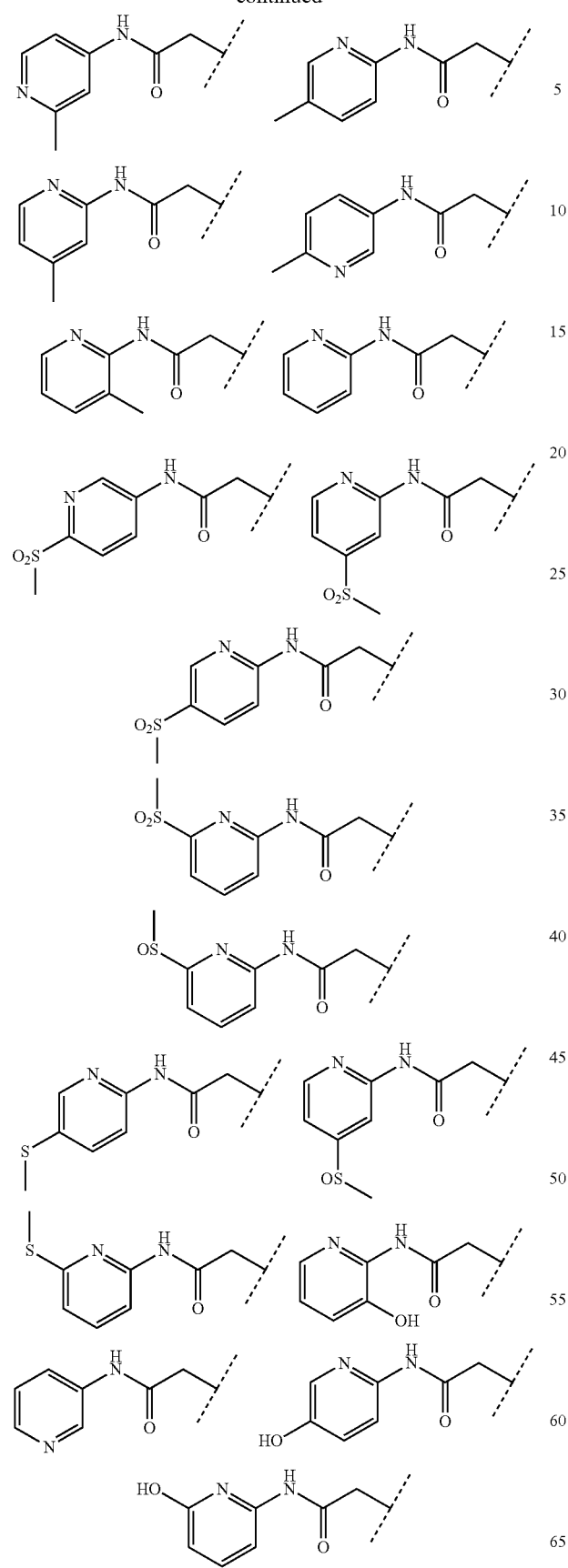
270
-continued
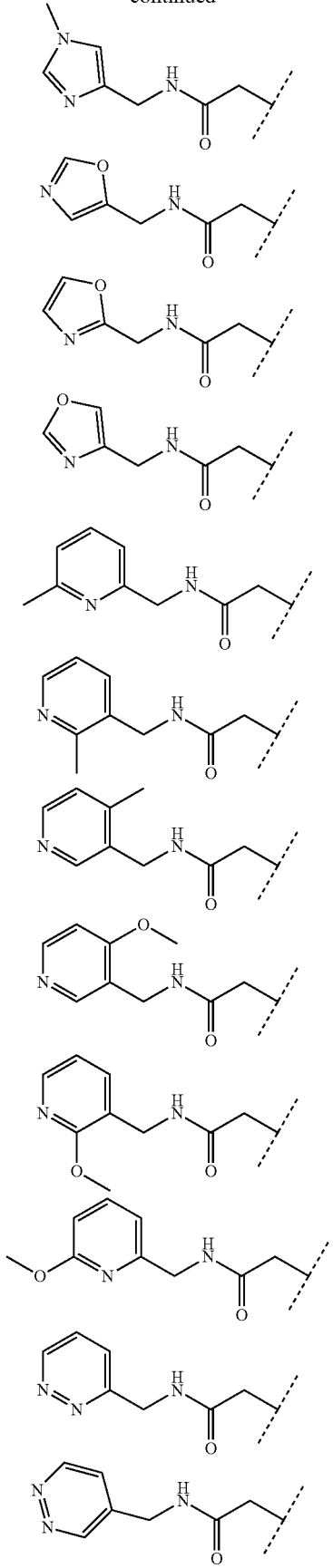

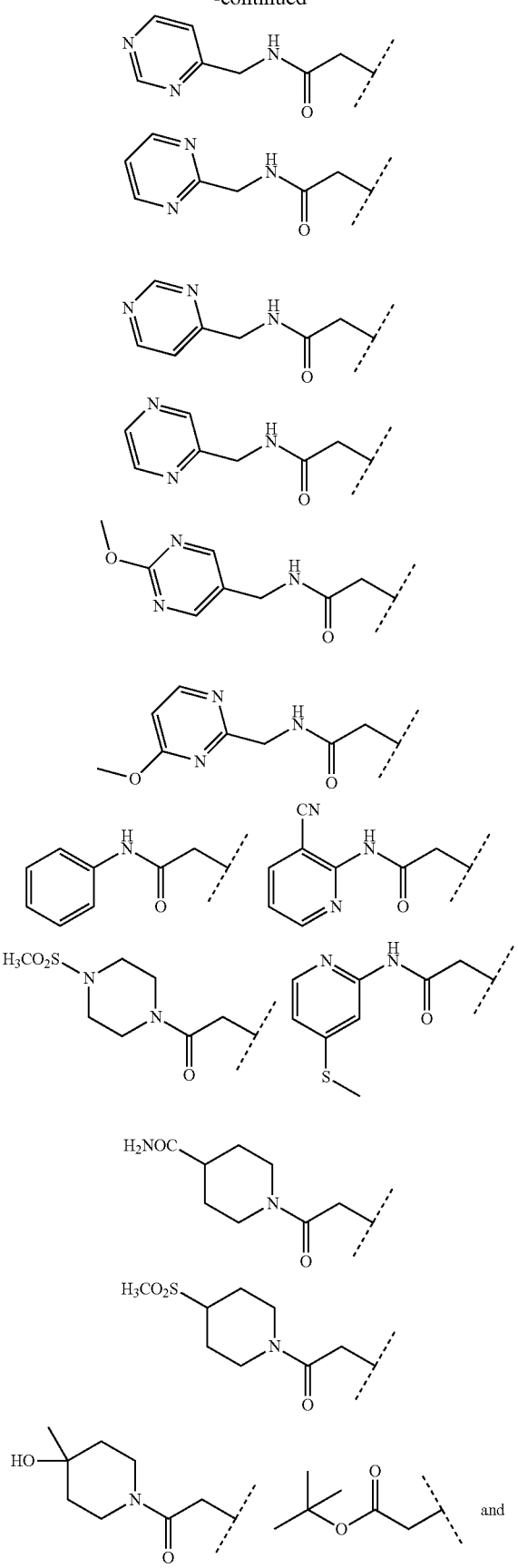

25. The compound according to claim 1, wherein
R¹ means —H or —CH₃;
R² means —CH₃, —CH₂CH₃ or —CH₂—C(H)(CH₃)₂;
R³ means -phenyl, -thienyl or -pyridinyl, in each case unsubstituted or monosubstituted with —F;
R⁴ means
—H;
—C₁-C₆-alkyl, linear or branched, saturated, unsubstituted or substituted with one, two, three or four substituents independently of one another selected from the group consisting of —F, —Cl, —Br, —I, —CN, —OH, =O, —N(CH₃)₂ and —O—CH₃; or -cyclopropyl, -cyclobutyl, -cyclopentyl or -cyclohexyl, unsubstituted or monosubstituted with —F, —OH, —CN or —CH₃, wherein said -cyclopropyl, -cyclobutyl, -cyclopentyl or -cyclohexyl is connected through —CH₂— or —CH₂CH₂—;
-oxetanyl unsubstituted or monosubstituted with —F, —OH, —CN or —CH₃, wherein said -oxetanyl is connected through —CH₂— or —CH₂CH₂—;
X means —O— or —NR⁶—;
R⁵ means
—H;
—C₁-C₆-alkyl, linear or branched, saturated or unsaturated, unsubstituted or substituted with one, two, three or four substituents independently of one another selected from the group consisting of —F, —Cl, —Br, —I, —CN, —O—CH₃, —O—(CH₂—CH₂—O)₁₋₁₀—H, —O—(CH₂CH₂—O)₁₋₁₀—CH₃, —C(=O)OH, —C(=O)OCH₃, —C(=O)NH₂, —C(=O)NHCH₃, —C(=O)N(CH₃)₂, —OH, —S(=O)CH₃, —S(=O)₂CH₃, unsubstituted —C(=O)-morpholinyl, —NH—C(=O)—CH₃, —N(CH₃)₂ and NH—S(=O)₂—CH₃;
-cyclopropyl, -cyclobutyl, -cyclopentyl or -cyclohexyl, unsubstituted or monosubstituted with —F, —OH, —CN or —CH₃, wherein said -cyclopropyl, -cyclobutyl, cyclopentyl or cyclohexyl is optionally connected through —CH₂— or —CH₂CH₂—;
-heterocyclobutyl, -heterocyclopentyl, or -heterocyclohexyl, in each case unsubstituted or substituted with one, two, three or four substituents independently of one another selected from the group consisting of —F, —Cl, —Br, —I, —CN, —O—CH₃, —O—(CH₂—CH₂—O)₁₋₁₀—H, —O—(CH₂CH₂—O)₁₋₁₀—CH₃, —C₁-C₄-alkyl, —C(=O)OH, —C(=O)OCH₃, —C(=O)NH₂, —C(=O)NHCH₃, —C(=O)N(CH₃)₂, =O, —OH, —SCH₃, —S(=O)CH₃, —S(=O)₂CH₃, unsubstituted —C(=O)-morpholinyl, —NH—C(=O)—CH₃, —N(CH₃)₂ and NH—S(=O)₂—CH₃; wherein said -heterocyclobutyl, -heterocyclopentyl, or -heterocyclohexyl is optionally connected through —CH₂— or —CH₂CH₂—;
-oxazolyl, -isoxazolyl, -pyrazolyl, -pyridinyl, -pyridazinyl, -pyrazinyl, -thiazolyl, -thiadiazolyl, -imidazolyl, -pyrimidinyl, or 5,6,7,8-tetrahydro-[1,2,4]triazolo[1,5-a]pyrazine, in each case unsubstituted or substituted with one, two, three or four substituents independently of one another selected from the group consisting of —F, —Cl, Br, —I, —CN, —OH, —CH$_3$, —O—CH$_3$, —C(=O)OH, —C(=O)OCH$_3$, —C(=O)NH$_2$, —C(=O)NHCH$_3$, —C(=O)N(CH$_3$)$_2$, S(=O)CH$_3$, —S(=O)$_2$CH$_3$ and —S—CH$_3$, wherein said -oxazolyl, -isoxazolyl, -pyrazolyl, -pyridinyl, -pyridazinyl, -pyrazinyl, -thiazolyl, -thiadiazolyl, -imidazolyl, -pyrimidinyl, or 5,6,7,8-tetrahydro-[1,2,4]triazolo[1,5-a]pyrazine is optionally connected through —CH$_2$—; or
-phenyl, unsubstituted or substituted with one, two, three or four substituents independently of one another selected from the group consisting of —F, —Cl, Br, —I, —CN, —OH, —CH$_3$, —O—CH$_3$, —C(=O)OH, —C(=O)OCH$_3$, —C(=O)NH$_2$, —C(=O)NHCH$_3$, —C(=O)N(CH$_3$)$_2$, S(=O)CH$_3$, —S(=O)$_2$CH$_3$ and —S—CH$_3$, wherein said -phenyl is optionally connected through —CH$_2$—;
in case X means NR$^6$, R$^6$ means —H or —CH$_3$;
or in case X means NR$^6$, R$^5$ and R$^6$ together with the nitrogen atom to which they are attached form a -pyrrolidinyl, -piperidinyl, -piperazinyl, -morpholinyl, -thiomorpholinyl, -thio-morpholinyl dioxide or -(methylsulfonyl)piperazinyl, in each case unsubstituted or substituted with one, two, three or four substituents independently of one another selected from the group consisting of =O, —OH, —CH$_2$—OH, —C(=O)NH$_2$, and —S(=O)$_2$CH$_3$, wherein said -pyrrolidinyl, -piperidinyl, -piperazinyl, -morpholinyl, -thiomorpholinyl,- thiomorpholinyl dioxide or -(methylsulfonyl)piperazinyl is optionally condensed with an imidazole moiety, unsubstituted; and
R$^9$, R$^{10}$, R$^{11}$, R$^{12}$, R$^{13}$, R$^{14}$, R$^{15}$, R$^{16}$, R$^{17}$, R$^{18}$, R$^{19}$, and R$^{20}$ mean —H.

26. The compound according to claim 1, which has a structure according to general formula (I')

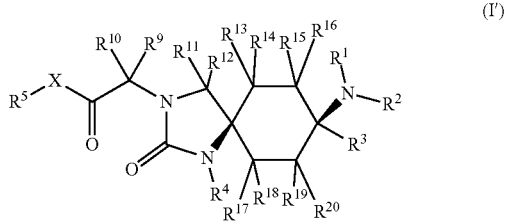

(I')

wherein R$^1$ to R$^5$, R$^9$ to R$^{20}$, and X are defined as in claim 1,
or a physiologically acceptable salt thereof.

27. The compound according to claim 1, which has a structure according to general formula (IX)

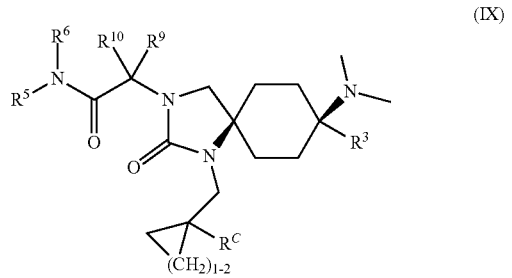

(IX)

wherein
R$^C$ means —H or —OH;
R$^3$ means -phenyl or -3-fluorophenyl;

R$^5$ means —H, —CH$_3$, —CH$_2$CH$_2$OH, or —CH$_2$C(=O)NH$_2$;
R$^6$ means —H or —CH$_3$;
or R$^5$ and R$^6$ together with the nitrogen atom to which they are attached form a ring and mean —(CH$_2$)$_5$—, wherein said ring is unsubstituted or substituted with one or two substituents independently of one another selected from the group consisting of —CH$_3$, —OH, —S(=O)$_2$CH$_3$ and —C(=O)NH$_2$;
R$^9$ and R$^{10}$ independently of one another mean —H or —CH$_3$;
or a physiologically acceptable salt thereof.

28. The compound according to claim 1, which is selected from the group consisting of
CIS-2-[1-(Cyclobutyl-methyl)-8-dimethylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide;
CIS-6-[[2-[1-(Cyclobutyl-methyl)-8-dimethylamino-2-oxo-8-phenyl-1,3-diazaspiro[4.5]decan-3-yl]acetyl]amino]-pyridine-2-carboxylic acid methyl ester;
CIS-2-[1-(Cyclobutyl-methyl)-8-dimethylamino-2-oxo-8-phenyl-1,3-diazaspiro[4.5] decan-3-yl]-N-[(1R)-2-hydroxy-1-methyl-ethyl]-acetamide;
CIS-2-[1-(Cyclobutyl-methyl)-8-dimethylamino-2-oxo-8-phenyl-1,3-diazaspiro[4.5]decan-3-yl]-N-[(1S)-2-hydroxy-1-methyl-ethyl]-acetamide;
CIS-2-[1-(Cyclobutyl-methyl)-8-dimethylamino-2-oxo-8-phenyl-1,3-diazaspiro[4.5]decan-3-yl]-N-methyl-N-(methylcarbamoyl-methyl)-acetamide;
CIS-6-[[2-[1-(Cyclobutyl-methyl)-8-dimethylamino-2-oxo-8-phenyl-1,3-diazaspiro[4.5]decan-3-yl]-acetyl]amino]-nicotinic acid methyl ester;
CIS-2-[[2-[1-(Cyclobutyl-methyl)-8-dimethylamino-2-oxo-8-phenyl-1,3-diazaspiro[4.5]decan-3-yl]-acetyl]-methyl-amino]-2-methyl-propionamide;
CIS-2-[[2-[1-(Cyclobutyl-methyl)-8-dimethylamino-2-oxo-8-phenyl-1,3-diazaspiro[4.5]decan-3-yl]-acetyl]amino]-N,2-dimethyl-propionamide;
CIS-2-[[2-[1-(Cyclobutyl-methyl)-8-dimethylamino-2-oxo-8-phenyl-1,3-diazaspiro[4.5]decan-3-yl]-acetyl]-methyl-amino]-N,2-dimethyl-propionamide;
CIS-2-[1-(Cyclobutyl-methyl)-8-dimethylamino-2-oxo-8-phenyl-1,3-diazaspiro[4.5]decan-3-yl]-N-[(dimethyl-carbamoyl)-methyl]-N-methyl-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-2-methyl-propionamide;
CIS-2-[1-(Cyclobutyl-methyl)-8-dimethylamino-2-oxo-8-phenyl-1,3-diazaspiro[4.5]decan-3-yl]-N-(5-methoxy-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(6-methoxy-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(4-methoxy-pyridin-2-yl)-acetamide;
CIS-6-[[2-[1-(Cyclobutyl-methyl)-8-dimethylamino-2-oxo-8-phenyl-1,3-diazaspiro[4.5]decan-3-yl]-acetyl]amino]-N-methyl-pyridine-2-carboxylic acid amide;
CIS-2-[1-(Cyclobutyl-methyl)-8-dimethylamino-2-oxo-8-phenyl-1,3-diazaspiro[4.5]decan-3-yl]-N-[(3-hydroxy-cyclobutyl)-methyl]-acetamide;
CIS-2-[1-(Cyclobutyl-methyl)-8-dimethylamino-2-oxo-8-phenyl-1,3-diazaspiro[4.5]decan-3-yl]-N-[(3-hydroxy-cyclobutyl)-methyl]-acetamide;

CIS-2-[1-(Cyclobutyl-methyl)-8-dimethylamino-2-oxo-8-phenyl-1,3-diazaspiro[4.5]decan-3-yl]-N-[(1-hydroxy-cyclopropyl)-methyl]-acetamide;
CIS-2-[1-(Cyclobutyl-methyl)-8-dimethylamino-2-oxo-8-phenyl-1,3-diazaspiro[4.5]decan-3-yl]-N-(3-morpholin-4-yl-3-oxo-propyl)-acetamide;
CIS—N-(1-Cyano-cyclopropyl)-2-[1-(cyclobutyl-methyl)-8-dimethylamino-2-oxo-8-phenyl-1,3-diazaspiro[4.5]decan-3-yl]-acetamide;
CIS-2-[1-(Cyclobutyl-methyl)-8-dimethylamino-2-oxo-8-phenyl-1,3-diazaspiro[4.5]decan-3-yl]-N-[(3-hydroxy-cyclopentyl)-methyl]-acetamide;
CIS-2-[1-(Cyclobutyl-methyl)-8-dimethylamino-2-oxo-8-phenyl-1,3-diazaspiro[4.5]decan-3-yl]-N-[[(2R)-2-hydroxy-cyclohexyl]-methyl]-acetamide;
CIS-2-[1-(Cyclobutyl-methyl)-8-dimethylamino-2-oxo-8-phenyl-1,3-diazaspiro[4.5]decan-3-yl]-N-[2-[2-[2-(2-methoxy-ethoxy)-ethoxy]-ethoxy]-ethyl]-acetamide;
CIS-2-[1-(Cyclobutyl-methyl)-8-dimethylamino-2-oxo-8-phenyl-1,3-diazaspiro[4.5]decan-3-yl]-N-[(1-hydroxy-cyclohexyl)-methyl]-acetamide;
CIS-2-[1-(Cyclobutyl-methyl)-8-dimethylamino-2-oxo-8-phenyl-1,3-diazaspiro[4.5]decan-3-yl]-N-[2-[2-[2-[2-(2-methoxy-ethoxy)-ethoxy]-ethoxy]-ethoxy]-ethyl]-acetamide;
CIS-N-(6-Cyano-pyridin-2-yl)-2-[1-(cyclobutyl-methyl)-8-dimethylamino-2-oxo-8-phenyl-1,3-diazaspiro[4.5]decan-3-yl]-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-nicotinic acid methyl ester;
CIS-2-[1-(Cyclobutyl-methyl)-8-dimethylamino-2-oxo-8-phenyl-1,3-diazaspiro[4.5]decan-3-yl]-N-(3-methoxy-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide;
CIS-N-(4-Cyano-pyridin-2-yl)-2-[1-(cyclobutyl-methyl)-8-dimethylamino-2-oxo-8-phenyl-1,3-diazaspiro [4.5]decan-3-yl]-acetamide;
CIS-2-[1-(Cyclobutyl-methyl)-8-dimethylamino-2-oxo-8-phenyl-1,3-diazaspiro[4.5]decan-3-yl]-N-(5-methoxy-pyrimidin-2-yl)-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-isonicotinic acid methyl ester;
CIS-2-[1-(Cyclobutyl-methyl)-8-dimethylamino-2-oxo-8-phenyl-1,3-diazaspiro[4.5]decan-3-yl]-N-(2-methoxy-pyridin-4-yl)-acetamide;
CIS -2-[1-(Cyclobutyl-methyl)-8-dimethylamino-2-oxo-8-phenyl-1,3-diazaspiro[4.5]decan-3-yl]-N-(6-fluoro-pyridin-3-yl)-acetamide;
CIS-2-[1-(Cyclobutyl-methyl)-8-dimethylamino-2-oxo-8-phenyl-1,3-diazaspiro[4.5]decan-3-yl]-N-(2-methyl-pyrimidin-5-yl)-acetamide;
CIS-2-[1-(Cyclobutyl-methyl)-8-dimethylamino-2-oxo-8-phenyl-1,3-diazaspiro[4.5]decan-3-yl]-N-(5-methyl-pyrimidin-2-yl)-acetamide;
CIS-2-[1-(Cyclobutyl-methyl)-8-dimethylamino-2-oxo-8-phenyl-1,3-diazaspiro[4.5]decan-3-yl]-N-(3-fluoro-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(3-fluoro-pyridin-4-yl)-acetamide;
CIS-2-[1-(Cyclobutyl-methyl)-8-dimethylamino-2-oxo-8-phenyl-1,3-diazaspiro[4.5]decan-3-yl]-N-(6-methoxy-pyridin-3-yl)-acetamide;
CIS-2-[1-(Cyclobutyl-methyl)-8-dimethylamino-2-oxo-8-phenyl-1,3-diazaspiro[4.5]decan-3-yl]-N-(2-methyl-pyridin-3-yl)-acetamide;
CIS-2-[1-(Cyclobutyl-methyl)-8-dimethylamino-2-oxo-8-phenyl-1,3-diazaspiro[4.5]decan-3-yl]-N-(4-methyl-pyridin-3-yl)-acetamide;
CIS-2-[1-(Cyclobutyl-methyl)-8-dimethylamino-2-oxo-8-phenyl-1,3-diazaspiro[4.5]decan-3-yl]-N-(3-methyl-pyridin-4-yl)-acetamide;
CIS-2-[1-(Cyclobutyl-methyl)-8-dimethylamino-2-oxo-8-phenyl-1,3-diazaspiro[4.5]decan-3-yl]-N-(6-methyl-pyridin-3-yl)-acetamide;
CIS-2-[1-(Cyclobutyl-methyl)-8-dimethylamino-2-oxo-8-phenyl-1,3-diazaspiro[4.5]decan-3-yl]-N-(5-fluoro-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(5-methyl-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(4-methyl-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(3-methyl-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(3-methoxy-pyridin-4-yl)-acetamide;
CIS-2-[1-(Cyclobutyl-methyl)-8-dimethylamino-2-oxo-8-phenyl-1,3-diazaspiro[4.5]decan-3-yl]-N-(6-methoxy-pyridazin-3-yl)-acetamide;
CIS-2-[1-(Cyclobutyl-methyl)-8-dimethylamino-2-oxo-8-phenyl-1,3-diazaspiro[4.5]decan-3-yl]-N-(5-methylsulfonyl-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(5-methoxy-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(6-methylsulfonyl-pyridin-3-yl)-acetamide;
CIS-2-[1-(Cyclobutyl-methyl)-8-dimethylamino-2-oxo-8-phenyl-1,3-diazaspiro[4.5]decan-3-yl]-N-(6-methoxy-pyrazin-2-yl)-acetamide;
CIS-2-[1-(Cyclobutyl-methyl)-8-dimethylamino-2-oxo-8-phenyl-1,3-diazaspiro[4.5]decan-3-yl]-N-(4-methoxy-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(4-methoxy-pyrimidin-2-yl)-acetamide;
CIS-2-[1-(Cyclobutyl-methyl)-8-dimethylamino-2-oxo-8-phenyl-1,3-diazaspiro[4.5]decan-3-yl]-N-(oxazol-5-yl-methyl)-acetamide;
CIS-2-[1-(Cyclobutyl-methyl)-8-dimethylamino-2-oxo-8-phenyl-1,3-diazaspiro[4.5]decan-3-yl]-N-(oxazol-2-yl-methyl)-acetamide;
CIS-1-(Cyclobutyl-methyl)-3-[2-[(3S,4S)-3,4-dihydroxy-piperidin-1-yl]-2-oxo-ethyl]-8-dimethylamino-8-phenyl-1,3-diazaspiro[4.5]decan-2-one;
CIS-1-(Cyclobutyl-methyl)-3-[2-[(3S,4S)-3,4-dihydroxy-pyrrolidin-1-yl]-2-oxo-ethyl]-8-dimethylamino-8-phenyl-1,3-diazaspiro[4.5]decan-2-one;
CIS-1-(Cyclobutyl-methyl)-3-[2-[(3S,4R)-3,4-dihydroxy-pyrrolidin-1-yl]-2-oxo-ethyl]-8-dimethylamino-8-phenyl-1,3-diazaspiro[4.5]decan-2-one;

CIS-2-[1-(Cyclobutyl-methyl)-8-dimethylamino-2-oxo-8-phenyl-1,3-diazaspiro[4.5]decan-3-yl]-N-cyclopropyl-acetamide;
CIS-2-[1-(Cyclobutyl-methyl)-8-dimethylamino-2-oxo-8-phenyl-1,3-diazaspiro[4.5]decan-3-yl]-N-(2-hydroxy-ethyl)-N-methyl-acetamide;
CIS-1-(Cyclobutyl-methyl)-8-dimethylamino-3-[2-(3-hydroxy-piperidin-1-yl)-2-oxo-ethyl]-8-phenyl-1,3-diazaspiro[4.5]decan-2-one;
CIS-2-[1-(Cyclobutyl-methyl)-8-dimethylamino-2-oxo-8-phenyl-1,3-diazaspiro[4.5]decan-3-yl]-N-[(1-hydroxy-cyclobutyl)-methyl]-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-N,N-dimethyl-acetamide;
CIS-1-(Cyclobutyl-methyl)-8-dimethylamino-3-[2-oxo-2-(5,6,7,8-tetrahydro-[1,2,4]triazolo[1,5-a]pyrazin-7-yl)-ethyl]-8-phenyl-1,3-diazaspiro[4.5]decan-2-one;
CIS-3-[[2-[1-(Cyclobutyl-methyl)-8-dimethylamino-2-oxo-8-phenyl-1,3-diazaspiro[4.5]decan-3-yl]-acetyl]amino]-N,N-dimethyl-propionamide;
CIS-2-[1-(Cyclobutyl-methyl)-8-dimethylamino-2-oxo-8-phenyl-1,3-diazaspiro[4.5]decan-3-yl]-N-[2-[2-[2-[2-[2-[2-(2-methoxy-ethoxy)-ethoxy]-ethoxy]-ethoxy]-ethoxy]-ethoxy]-ethyl]-acetamide;
CIS-2-[1-(Cyclobutyl-methyl)-8-dimethylamino-2-oxo-8-phenyl-1,3-diazaspiro[4.5]decan-3-yl]-N-(4-methoxy-pyrimidin-5-yl)-acetamide;
CIS-2-[1-(Cyclobutyl-methyl)-8-dimethylamino-2-oxo-8-phenyl-1,3-diazaspiro[4.5]decan-3-yl]-N-(2-methoxy-pyrimidin-5-yl)-acetamide;
CIS-N-(5-Cyano-pyridin-2-yl)-2-[1-(cyclobutyl-methyl)-8-dimethylamino-2-oxo-8-phenyl-1,3-diazaspiro[4.5]decan-3-yl]-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-N-methyl-pyridine-4-carboxylic acid amide;
CIS-2-[1-(Cyclobutyl-methyl)-8-dimethylamino-2-oxo-8-phenyl-1,3-diazaspiro[4.5]decan-3-yl]-N-(5-methoxy-pyrimidin-4-yl)-acetamide;
CIS-N-(2-Cyano-pyrimidin-5-yl)-2-[1-(cyclobutyl-methyl)-8-dimethylamino-2-oxo-8-phenyl-1,3-diazaspiro[4.5]decan-3-yl]-acetamide;
CIS-6-[[2-[1-(Cyclobutyl-methyl)-8-dimethylamino-2-oxo-8-phenyl-1,3-diazaspiro[4.5]decan-3-yl]-acetyl]amino]-pyridine-2-carboxylic acid amide;
CIS-N-(3-Cyano-pyridin-2-yl)-2-[1-(cyclobutyl-methyl)-8-dimethylamino-2-oxo-8-phenyl-1,3-diazaspiro[4.5]decan-3-yl]-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-acetamide;
CIS-6-[[2-[1-(Cyclobutyl-methyl)-8-dimethylamino-2-oxo-8-phenyl-1,3-diazaspiro[4.5]decan-3-yl]-acetyl]amino]-pyridine-3-carboxylic acid amide;
CIS-N-(4-Cyano-pyrimidin-2-yl)-2-[1-(cyclobutyl-methyl)-8-dimethylamino-2-oxo-8-phenyl-1,3-diazaspiro[4.5]decan-3-yl]-acetamide;
CIS-2-[1-(Cyclobutyl-methyl)-8-dimethylamino-2-oxo-8-phenyl-1,3-diazaspiro[4.5]decan-3-yl]-N-([1,3,4]thiadiazol-2-yl)-acetamide;
CIS-2-[1-(Cyclobutyl-methyl)-8-dimethylamino-2-oxo-8-phenyl-1,3-diazaspiro[4.5]decan-3-yl]-N-thiazol-2-yl-acetamide;
CIS-2-[1-(Cyclobutyl-methyl)-8-dimethylamino-2-oxo-8-phenyl-1,3-diazaspiro[4.5]decan-3-yl]-N-(5-methyl-isoxazol-3-yl)-acetamide;
CIS-2-[1-(Cyclobutyl-methyl)-8-dimethylamino-2-oxo-8-phenyl-1,3-diazaspiro[4.5]decan-3-yl]-N-isoxazol-3-yl-acetamide;
CIS-2-[1-(Cyclobutyl-methyl)-8-dimethylamino-2-oxo-8-phenyl-1,3-diazaspiro[4.5]decan-3-yl]-N-(1-methyl-1H-pyrazol-3-yl)-acetamide;
CIS-N-(4-Cyano-5-methylsulfanyl-1H-pyrazol-3-yl)-2-[1-(cyclobutyl-methyl)-8-dimethylamino-2-oxo-8-phenyl-1,3-diazaspiro[4.5]decan-3-yl]-acetamide;
CIS-2-[1-(Cyclobutyl-methyl)-8-dimethylamino-2-oxo-8-phenyl-1,3-diazaspiro[4.5]decan-3-yl]-N-(5-methoxy-pyrazin-2-yl)-acetamide;
CIS-2-[1-(Cyclobutyl-methyl)-8-dimethylamino-2-oxo-8-phenyl-1,3-diazaspiro[4.5]decan-3-yl]-N-(pyridazin-4-yl-methyl)-acetamide;
CIS-2-[1-(Cyclobutyl-methyl)-8-dimethylamino-2-oxo-8-phenyl-1,3-diazaspiro[4.5]decan-3-yl]-N-[(2-hydroxyphenyl)-methyl]-acetamide;
CIS-2-[1-(Cyclobutyl-methyl)-8-dimethylamino-2-oxo-8-phenyl-1,3-diazaspiro[4.5]decan-3-yl]-N-[(1-methyl-1H-imidazol-4-yl)-methyl]-acetamide;
CIS-2-[1-(Cyclobutyl-methyl)-8-dimethylamino-2-oxo-8-phenyl-1,3-diazaspiro[4.5]decan-3-yl]-N-[(4-methyl-pyridin-3-yl)-methyl]-acetamide;
CIS-2-[1-(Cyclobutyl-methyl)-8-dimethylamino-2-oxo-8-phenyl-1,3-diazaspiro[4.5]decan-3-yl]-N-(pyrimidin-2-yl-methyl)-acetamide;
CIS-2-[1-(Cyclobutyl-methyl)-8-dimethylamino-2-oxo-8-phenyl-1,3-diazaspiro[4.5]decan-3-yl]-N-(pyridazin-3-yl-methyl)-acetamide;
CIS-2-[1-(Cyclobutyl-methyl)-8-dimethylamino-2-oxo-8-phenyl-1,3-diazaspiro[4.5]decan-3-yl]-N-(pyrimidin-4-yl-methyl)-acetamide;
CIS-2-[1-(Cyclobutyl-methyl)-8-dimethylamino-2-oxo-8-phenyl-1,3-diazaspiro[4.5]decan-3-yl]-N-(pyrazin-2-yl-methyl)-acetamide;
CIS-2-[1-(Cyclobutyl-methyl)-8-dimethylamino-2-oxo-8-phenyl-1,3-diazaspiro[4.5]decan-3-yl]-N-(oxazol-4-yl-methyl)-acetamide;
CIS-2-[1-(Cyclobutyl-methyl)-8-dimethylamino-2-oxo-8-phenyl-1,3-diazaspiro[4.5]decan-3-yl]-N-[(2-methyl-pyridin-3-yl)-methyl]-acetamide;
CIS-2-[1-(Cyclobutyl-methyl)-8-dimethylamino-2-oxo-8-phenyl-1,3-diazaspiro[4.5]decan-3-yl]-N-[(2-methoxy-pyridin-3-yl)-methyl]-acetamide;
CIS-2-[1-(Cyclobutyl-methyl)-8-dimethylamino-2-oxo-8-phenyl-1,3-diazaspiro[4.5]decan-3-yl]-N-[(4-methoxy-pyridin-3-yl)-methyl]-acetamide;
CIS-2-[1-(Cyclobutyl-methyl)-8-dimethylamino-2-oxo-8-phenyl-1,3-diazaspiro[4.5]decan-3-yl]-N-[(6-methyl-pyridin-2-yl)-methyl]-acetamide;
CIS-2-[1-(Cyclobutyl-methyl)-8-dimethylamino-2-oxo-8-phenyl-1,3-diazaspiro[4.5]decan-3-yl]-N-[(6-methoxy-pyridin-2-yl)-methyl]-acetamide;
CIS-2-[1-(Cyclobutyl-methyl)-8-dimethylamino-2-oxo-8-phenyl-1,3-diazaspiro[4.5]decan-3-yl]-N-[(2-methoxyphenyl)-methyl]-acetamide;
CIS-2-[1-(Cyclobutyl-methyl)-8-dimethylamino-2-oxo-8-phenyl-1,3-diazaspiro[4.5]decan-3-yl]-N-(o-tolyl-methyl)-acetamide;
CIS-6-[[2-[1-(Cyclobutyl-methyl)-8-dimethylamino-2-oxo-8-phenyl-1,3-diazaspiro[4.5] decan-3-yl]-acetyl]amino]-N-methyl-pyridine-3-carboxylic acid amide;
CIS-2-[[2-[1-(Cyclobutyl-methyl)-8-dimethylamino-2-oxo-8-phenyl-1,3-diazaspiro[4.5]decan-3-yl]-acetyl]amino]-pyridine-4-carboxylic acid amide;

CIS-2-[1-(Cyclobutyl-methyl)-8-dimethylamino-2-oxo-8-phenyl-1,3-diazaspiro[4.5]decan-3-yl]-N-(6-methoxy-pyrimidin-4-yl)-acetamide;
CIS-2-[1-(Cyclobutyl-methyl)-8-dimethylamino-2-oxo-8-phenyl-1,3-diazaspiro[4.5]decan-3-yl]-N-(2-methoxy-pyrimidin-4-yl)-acetamide;
CIS-2-[1-(Cyclobutyl-methyl)-8-dimethylamino-2-oxo-8-phenyl-1,3-diazaspiro[4.5]decan-3-yl]-N-(4-hydroxy-pyrimidin-5-yl)-acetamide;
CIS-2-[1-(Cyclobutyl-methyl)-8-dimethylamino-2-oxo-8-phenyl-1,3-diazaspiro[4.5]decan-3-yl]-N-(2-hydroxy-pyrimidin-5-yl)-acetamide;
CIS-2-[1-(Cyclobutyl-methyl)-8-dimethylamino-2-oxo-8-phenyl-1,3-diazaspiro[4.5]decan-3-yl]-N-(5-hydroxy-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(1,1-dioxo-thian-4-yl)-acetamide;
CIS-1-(Cyclobutyl-methyl)-8-dimethylamino-3-[2-(1,1-dioxo-[1,4]thiazinan-4-yl)-2-oxo-ethyl]-8-phenyl-1,3-diazaspiro[4.5]decan-2-one;
CIS-2-[8-Dimethylamino-1-(2-methoxy-ethyl)-2-oxo-8-phenyl-1,3-diazaspiro[4.5]decan-3-yl]-N-pyrimidin-4-yl-acetamide;
CIS-2-[8-Dimethylamino-1-(2-methoxy-ethyl)-2-oxo-8-phenyl-1,3-diazaspiro[4.5]decan-3-yl]-N-methyl-acetamide;
CIS-N-(5-Cyano-pyrimidin-4-yl)-2-[1-(cyclobutyl-methyl)-8-dimethylamino-2-oxo-8-phenyl-1,3-diazaspiro[4.5]decan-3-yl]-acetamide;
CIS-2-[1-(Cyclobutyl-methyl)-8-dimethylamino-2-oxo-8-phenyl-1,3-diazaspiro[4.5]decan-3-yl]-N-(5-methylsulfanyl-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-(4-methoxy-pyrimidin-2-yl)-acetamide;
CIS-2-[1-(Cyclobutyl-methyl)-8-dimethylamino-2-oxo-8-phenyl-1,3-diazaspiro[4.5]decan-3-yl]-N-(6-methylsulfanyl-pyridin-2-yl)-acetamide;
CIS-2-[8-Dimethylamino-1-(2-methoxy-ethyl)-2-oxo-8-phenyl-1,3-diazaspiro[4.5]decan-3-yl]-N-(2-hydroxy-ethyl)-acetamide;
CIS-2-[[2-[8-Dimethylamino-1-(2-methoxy-ethyl)-2-oxo-8-phenyl-1,3-diazaspiro[4.5]decan-3-yl]-acetyl]amino]-acetamide;
CIS-2-[1-(Cyclobutyl-methyl)-8-dimethylamino-2-oxo-8-phenyl-1,3-diazaspiro[4.5]decan-3-yl]-N-methyl-acetamide;
CIS-2-[1-(Cyclobutyl-methyl)-8-dimethylamino-2-oxo-8-phenyl-1,3-diazaspiro[4.5]decan-3-yl]-N-(2-hydroxy-ethyl)-acetamide;
CIS-2-[1-(Cyclobutyl-methyl)-8-dimethylamino-2-oxo-8-phenyl-1,3-diazaspiro[4.5]decan-3-yl]-N-(6-hydroxy-pyridin-2-yl)-acetamide;
CIS-2-[1-(Cyclobutyl-methyl)-8-dimethylamino-2-oxo-8-phenyl-1,3-diazaspiro[4.5]decan-3-yl]-N-[(2-methoxy-pyrimidin-5-yl)-methyl]-acetamide;
CIS-2-[1-(Cyclobutyl-methyl)-8-dimethylamino-2-oxo-8-phenyl-1,3-diazaspiro[4.5]decan-3-yl]-N-[(4-methoxy-pyrimidin-2-yl)-methyl]-acetamide;
CIS-N-(2-Cyano-pyrimidin-4-yl)-2-[1-(cyclobutyl-methyl)-8-dimethylamino-2-oxo-8-phenyl-1,3-diazaspiro[4.5]decan-3-yl]-acetamide;
CIS-2-[1-(Cyclobutyl-methyl)-8-dimethylamino-2-oxo-8-phenyl-1,3-diazaspiro[4.5]decan-3-yl]-N-[6-(methylsulfinyl)-pyridin-2-yl]-acetamide;
CIS-2-[[2-[1-(Cyclobutyl-methyl)-8-methylamino-2-oxo-8-phenyl-1,3-diazaspiro[4.5]decan-3-yl]-acetyl]amino]-2-methyl-propionamide;
CIS-2-[[2-[1-(Cyclobutyl-methyl)-8-methylamino-2-oxo-8-phenyl-1,3-diazaspiro[4.5]decan-3-yl]-acetyl]amino]-N-methyl-acetamide;
CIS-2-[[2-[1-(Cyclobutyl-methyl)-8-methylamino-2-oxo-8-phenyl-1,3-diazaspiro[4.5]decan-3-yl]-acetyl]amino]-acetamide;
CIS-2-[1-(Cyclobutyl-methyl)-8-dimethylamino-2-oxo-8-phenyl-1,3-diazaspiro[4.5]decan-3-yl]-N-[2-[2-(2-methoxy-ethoxy)-ethoxy]-ethyl]-acetamide;
CIS-N-(Carbamoyl-methyl)-2-[1-(cyclobutyl-methyl)-8-methylamino-2-oxo-8-phenyl-1,3-diazaspiro[4.5]decan-3-yl]-N-methyl-acetamide;
CIS-2-[1-(Cyclobutyl-methyl)-8-methylamino-2-oxo-8-phenyl-1,3-diazaspiro[4.5]decan-3-yl]-N-methyl-N-(methylcarbamoyl-methyl)-acetamide;
CIS-2-[8-Dimethylamino-1-[(1-hydroxy-cyclobutyl)-methyl]-2-oxo-8-phenyl-1,3-diazaspiro[4.5]decan-3-yl]-N-(2-methylsulfonyl-ethyl)-acetamide;
CIS-2-[8-Dimethylamino-1-[(1-hydroxy-cyclobutyl)-methyl]-2-oxo-8-phenyl-1,3-diazaspiro[4.5]decan-3-yl]-N-pyrimidin-5-yl-acetamide;
CIS-2-[1-(Cyclobutyl-methyl)-8-dimethylamino-2-oxo-8-phenyl-1,3-diazaspiro[4.5]decan-3-yl]-N-(6-methylsulfonyl-pyridin-2-yl)-acetamide;
CIS-2-[8-Dimethylamino-1-[(dimethyl-carbamoyl)-methyl]-2-oxo-8-phenyl-1,3-diazaspiro[4.5]decan-3-yl]-N-(2-hydroxy-ethyl)-acetamide;
CIS-2-[[2-[1-(Cyclobutyl-methyl)-8-methylamino-2-oxo-8-phenyl-1,3-diazaspiro[4.5]decan-3-yl]-acetyl]-methyl-amino]-2-methyl-propionamide;
CIS-1-(Cyclobutyl-methyl)-3-[2-(1,1-dioxo-[1,4]thiazinan-4-yl)-2-oxo-ethyl]-8-methylamino-8-phenyl-1,3-diazaspiro[4.5]decan-2-one;
CIS-2-[1-(Cyclobutyl-methyl)-8-methylamino-2-oxo-8-phenyl-1,3-diazaspiro[4.5]decan-3-yl]-N-[2-[2-[2-[2-[2-(2-methoxy-ethoxy)-ethoxy]-ethoxy]-ethoxy]-ethoxy]-ethyl]-acetamide;
CIS-2-[[2-[1-(Cyclobutyl-methyl)-8-methylamino-2-oxo-8-phenyl-1,3-diazaspiro[4.5]decan-3-yl]-acetyl]amino]-N,N-dimethyl-acetamide;
CIS-2-[1-(Cyclobutyl-methyl)-8-dimethylamino-2-oxo-8-phenyl-1,3-diazaspiro[4.5]decan-3-yl]-N-(5-hydroxy-pyrimidin-2-yl)-acetamide;
CIS-2-[1-(Cyclobutyl-methyl)-8-dimethylamino-2-oxo-8-phenyl-1,3-diazaspiro[4.5]decan-3-yl]-N-(4-methylsulfonyl-pyridin-2-yl)-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-N-methyl-acetamide;
CIS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide;
CIS-2-(8-Dimethylamino-2-oxo-8-phenyl-1-propyl-1,3-diazaspiro[4.5]decan-3-yl)-N-methyl-acetamide;
CIS-2-[8-Dimethylamino-1-(3-methoxy-propyl)-2-oxo-8-phenyl-1,3-diazaspiro[4.5]decan-3-yl]-N-methyl-acetamide;
CIS-2-[1-(Cyclobutyl-methyl)-8-dimethylamino-2-oxo-8-phenyl-1,3-diazaspiro[4.5]decan-3-yl]-N-[4-(methylsulfinyl)-pyridin-2-yl]-acetamide;
CIS-2-[1-(Cyclobutyl-methyl)-8-dimethylamino-2-oxo-8-phenyl-1,3-diazaspiro[4.5]decan-3-yl]-N-(3-hydroxy-pyridin-2-yl)-acetamide;

CIS-2-[1-(Cyclobutyl-methyl)-8-dimethylamino-2-oxo-8-phenyl-1,3-diazaspiro[4.5]decan-3-yl]-N-(2-methylsulfonyl-ethyl)-acetamide;

CIS-1-(Cyclobutyl-methyl)-3-[2-[(3S,4R)-3,4-dihydroxy-pyrrolidin-1-yl]-2-oxo-ethyl]-8-dimethylamino-8-phenyl-1,3-diazaspiro[4.5]decan-2-one;

CIS-2-[1-(Cyclobutyl-methyl)-8-methylamino-2-oxo-8-phenyl-1,3-diazaspiro[4.5]decan-3-yl]-N-(2-hydroxyethyl)-acetamide;

CIS-2-[8-Dimethylamino-1-[(dimethyl-carbamoyl)-methyl]-2-oxo-8-phenyl-1,3-diazaspiro[4.5]decan-3-yl]-N-pyrimidin-4-yl-acetamide;

CIS-2-[8-Dimethylamino-1-[(dimethyl-carbamoyl)-methyl]-2-oxo-8-phenyl-1,3-diazaspiro[4.5]decan-3-yl]-N-methyl-acetamide;

CIS-2-[[2-[8-Dimethylamino-1-(2-methyl-propyl)-2-oxo-8-phenyl-1,3-diazaspiro[4.5]decan-3-yl]-acetyl]amino]-acetamide;

CIS-2-[8-Dimethylamino-1-[(1-hydroxy-cyclobutyl)-methyl]-2-oxo-8-phenyl-1,3-diazaspiro[4.5]decan-3-yl]-acetamide;

CIS-2-[8-Dimethylamino-1-[(1-hydroxy-cyclobutyl)-methyl]-2-oxo-8-phenyl-1,3-diazaspiro[4.5]decan-3-yl]-N-methyl-acetamide;

CIS-2-[ [2-[8-Dimethylamino-1-(3-methoxy-propyl)-2-oxo-8-phenyl-1,3-diazaspiro[4.5]decan-3-yl]-acetyl]amino]-acetamide;

CIS-2-[8-Dimethylamino-1-(2-methyl-propyl)-2-oxo-8-phenyl-1,3-diazaspiro[4.5]decan-3-yl]-N-methyl-acetamide;

CIS-1-(Cyclobutyl-methyl)-3-[2-[(3S,4R)-3,4-dihydroxy-pyrrolidin-1-yl]-2-oxo-ethyl]-8-methylamino-8-phenyl-1,3-diazaspiro[4.5]decan-2-one;

CIS-2-[8-Dimethylamino-1-[(1-methyl-cyclobutyl)-methyl]-2-oxo-8-phenyl-1,3-diazaspiro[4.5]decan-3-yl]-N-methyl-acetamide;

CIS-2-[8-Dimethylamino-1-[(1-methyl-cyclobutyl)-methyl]-2-oxo-8-phenyl-1,3-diazaspiro[4.5]decan-3-yl]-N-pyrimidin-4-yl-acetamide;

CIS-2-[[2-[8-Dimethylamino-1-[(1-methyl-cyclobutyl)-methyl]-2-oxo-8-phenyl-1,3-diazaspiro[4.5]decan-3-yl]-acetyl]amino]-acetamide;

CIS-2-[8-Dimethylamino-1-[(1-methyl-cyclobutyl)-methyl]-2-oxo-8-phenyl-1,3-diazaspiro[4.5]decan-3-yl]-N-(2-hydroxy-ethyl)-acetamide;

CIS-2-[[2-[1-(Cyclopropyl-methyl)-8-dimethylamino-2-oxo-8-phenyl-1,3-diazaspiro[4.5]decan-3-yl]-acetyl]amino]-acetamide;

CIS-2-[1-(Cyclobutyl-methyl)-8-(ethyl-methyl-amino)-2-oxo-8-phenyl-1,3-diazaspiro[4.5]decan-3-yl]-N-methyl-acetamide;

CIS-2-[[2-(8-Dimethylamino-2-oxo-8-phenyl-1-propyl-1,3-diazaspiro[4.5]decan-3-yl)-acetyl]amino]-acetamide;

CIS-2-[[2-[8-Dimethylamino-1-[(1-hydroxy-cyclobutyl)-methyl]-2-oxo-8-phenyl-1,3-diazaspiro[4.5]decan-3-yl]-acetyl]amino]-acetamide;

CIS-2-[8-Dimethylamino-1-[(1-hydroxy-cyclobutyl)-methyl]-2-oxo-8-phenyl-1,3-diazaspiro[4.5]decan-3-yl]-N-(2-hydroxy-ethyl)-acetamide;

CIS-2-[8-Dimethylamino-1-[(1-hydroxy-cyclobutyl)-methyl]-2-oxo-8-phenyl-1,3-diazaspiro[4.5]decan-3-yl]-N-(1,1-dioxo-thian-4-yl)-acetamide;

CIS-2-[1-(Cyclopropyl-methyl)-8-dimethylamino-2-oxo-8-phenyl-1,3-diazaspiro[4.5]decan-3-yl]-N-methyl-acetamide;

CIS-2-[1-[(1-Cyano-cyclobutyl)-methyl]-8-dimethylamino-2-oxo-8-phenyl-1,3-diazaspiro[4.5]decan-3-yl]-N-methyl-acetamide;

CIS-2-[1-(Cyclobutyl-methyl)-8-(ethyl-methyl-amino)-2-oxo-8-phenyl-1,3-diazaspiro[4.5]decan-3-yl]-N-(2-hydroxy-ethyl)-acetamide;

CIS-2-[[2-[1-(Cyclobutyl-methyl)-8-(ethyl-methyl-amino)-2-oxo-8-phenyl-1,3-diazaspiro[4.5]decan-3-yl]-acetyl]amino]-acetamide;

CIS-2-[[2-[1-(Cyclobutyl-methyl)-8-methylamino-2-oxo-8-phenyl-1,3-diazaspiro[4.5]decan-3-yl]-acetyl]amino]-N,2-dimethyl-propionamide;

CIS-2-[8-Dimethylamino-1-(3-methoxy-propyl)-2-oxo-8-phenyl-1,3-diazaspiro[4.5]decan-3-yl]-N-(2-hydroxy-ethyl)-acetamide;

CIS-2-[8-Dimethylamino-1-(3-methoxy-propyl)-2-oxo-8-phenyl-1,3-diazaspiro[4.5]decan-3-yl]-N-methyl-N-(methylcarbamoyl-methyl)-acetamide;

CIS-8-Dimethylamino-1-(3-methoxy-propyl)-3-[2-oxo-2-(3-oxo-piperazin-1-yl)-ethyl]-8-phenyl-1,3-diazaspiro[4.5]decan-2-one;

CIS-N-(Carbamoyl-methyl)-2-[8-dimethylamino-1-(3-methoxy-propyl)-2-oxo-8-phenyl-1,3-diazaspiro[4.5]decan-3-yl]-N-methyl-acetamide;

CIS-2-[8-Dimethylamino-1-(3-methoxy-propyl)-2-oxo-8-phenyl-1,3-diazaspiro[4.5]decan-3-yl]-N-[(3-hydroxy-cyclobutyl)-methyl]-acetamide;

CIS-2-[8-Dimethylamino-1-(3-methoxy-propyl)-2-oxo-8-phenyl-1,3-diazaspiro[4.5]decan-3-yl]-N-[(3-hydroxy-cyclobutyl)-methyl]-acetamide;

CIS-2-[8-Dimethylamino-1-(3-methoxy-propyl)-2-oxo-8-phenyl-1,3-diazaspiro[4.5]decan-3-yl]-N-[(3-hydroxy-cyclopentyl)-methyl]-acetamide;

CIS-2-[8-Dimethylamino-1-(3-methoxy-propyl)-2-oxo-8-phenyl-1,3-diazaspiro[4.5]decan-3-yl]-N-pyridazin-4-yl-acetamide;

CIS-2-[8-Dimethylamino-1-(3-methoxy-propyl)-2-oxo-8-phenyl-1,3-diazaspiro[4.5]decan-3-yl]-N-(6-methoxy-pyridin-2-yl)-acetamide;

CIS-N-(2-Cyanoethyl)-2-[8-dimethylamino-1-(3-methoxy-propyl)-2-oxo-8-phenyl-1,3-diazaspiro[4.5]decan-3-yl]-acetamide;

CIS-2-[8-Dimethylamino-1-(3-methoxy-propyl)-2-oxo-8-phenyl-1,3-diazaspiro[4.5]decan-3-yl]-N-pyrimidin-5-yl-acetamide;

CIS-2-[8-Dimethylamino-1-(3-methoxy-propyl)-2-oxo-8-phenyl-1,3-diazaspiro[4.5]decan-3-yl]-N-pyrimidin-4-yl-acetamide;

CIS-2-[1-(Cyclobutyl-methyl)-8-(ethyl-methyl-amino)-2-oxo-8-phenyl-1,3-diazaspiro[4.5]decan-3-yl]-N-(6-methoxy-pyridin-2-yl)-acetamide;

CIS-2-[8-Dimethylamino-1-[(1-hydroxy-cyclobutyl)-methyl]-2-oxo-8-phenyl-1,3-diazaspiro[4.5]decan-3-yl]-N-pyridin-3-yl-acetamide;

CIS-2-[1-(Cyclobutyl-methyl)-8-dimethylamino-2-oxo-8-phenyl-1,3-diazaspiro[4.5]decan-3-yl]-acetamide;

CIS-2-[1-(Cyclobutyl-methyl)-8-dimethylamino-2-oxo-8-phenyl-1,3-diazaspiro[4.5]decan-3-yl]-N-pyrimidin-4-yl-acetamide;

CIS-2-[1-(Cyclobutyl-methyl)-8-dimethylamino-2-oxo-8-phenyl-1,3-diazaspiro[4.5]decan-3-yl]-N-(2-methoxy-ethyl)-acetamide;

CIS-2-[1-(Cyclobutyl-methyl)-8-dimethylamino-2-oxo-8-phenyl-1,3-diazaspiro[4.5]decan-3-yl]-N-(2-hydroxy-ethyl)-acetamide;

CIS-2-[1-(Cyclobutyl-methyl)-8-dimethylamino-2-oxo-8-phenyl-1,3-diazaspiro[4.5]decan-3-yl]-N-[2-[2-[2-

[2-[2-[2-(2-methoxy-ethoxy)-ethoxy]-ethoxy]-ethoxy]-ethoxy]-ethyl]-acetamide;
CIS-2-[1-(Cyclobutyl-methyl)-8-methylamino-2-oxo-8-phenyl-1,3-diazaspiro[4.5]decan-3-yl]-N-methyl-acetamide;
CIS-(2S)-1-[2-[1-(Cyclobutyl-methyl)-8-dimethylamino-2-oxo-8-phenyl-1,3-diazaspiro[4.5]decan-3-yl]-acetyl]-pyrrolidine-2-carboxylic acid amide;
CIS-2-[[2-[1-(Cyclobutyl-methyl)-8-dimethylamino-2-oxo-8-phenyl-1,3-diazaspiro[4.5]decan-3-yl]-acetyl]amino]-N,N-dimethyl-acetamide;
CIS-2-[1-(Cyclobutyl-methyl)-8-dimethylamino-2-oxo-8-phenyl-1,3-diazaspiro[4.5]decan-3-yl]-N-(oxetan-3-yl)-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-acetamide;
CIS-1-(Cyclobutyl-methyl)-8-dimethylamino-3-[2-oxo-2-(3-oxo-piperazin-1-yl)-ethyl]-8-phenyl-1,3-diazaspiro[4.5]decan-2-one;
CIS-2-[1-(Cyclobutyl-methyl)-8-dimethylamino-2-oxo-8-phenyl-1,3-diazaspiro[4.5]decan-3-yl]-N-(1,1-dioxo-thian-4-yl)-acetamide;
CIS-1-(Cyclobutyl-methyl)-8-dimethylamino-3-[2-[2-(hydroxymethyl)-morpholin-4-yl]-2-oxo-ethyl]-8-phenyl-1,3-diazaspiro[4.5] decan-2-one;
CIS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide;
CIS-N-(Cyano-methyl)-2-[1-(cyclobutyl-methyl)-8-dimethylamino-2-oxo-8-phenyl-1,3-diazaspiro[4.5]decan-3-yl]-acetamide;
CIS-N-(2-Acetylamino-ethyl)-2-[1-(cyclobutyl-methyl)-8-dimethylamino-2-oxo-8-phenyl-1,3-diazaspiro[4.5]decan-3-yl]-acetamide;
CIS-2-[1-(Cyclobutyl-methyl)-8-dimethylamino-2-oxo-8-phenyl-1,3-diazaspiro[4.5]decan-3-yl]-N-(2-methylsulfonyl-ethyl)-acetamide;
CIS-1-(Cyclobutyl-methyl)-8-dimethylamino-3-[2-(1,1-dioxo-[1,4]thiazinan-4-yl)-2-oxo-ethyl]-8-phenyl-1,3-diazaspiro[4.5]decan-2-one;
CIS-2-[1-(Cyclobutyl-methyl)-8-dimethylamino-2-oxo-8-phenyl-1,3-diazaspiro[4.5]decan-3-yl]-N-[(1,1-dioxo-thian-4-yl)-methyl]-acetamide;
CIS-1-(Cyclobutyl-methyl)-8-dimethylamino-3-[2-(4-methylsulfonyl-piperazin-1-yl)-2-oxo-ethyl]-8-phenyl-1,3-diazaspiro[4.5]decan-2-one;
CIS-N-(2-Cyanoethyl)-2-[1-(cyclobutyl-methyl)-8-dimethylamino-2-oxo-8-phenyl-1,3-diazaspiro[4.5]decan-3-yl]-acetamide;
CIS-2-[1-(Cyclobutyl-methyl)-8-dimethylamino-2-oxo-8-phenyl-1,3-diazaspiro[4.5]decan-3-yl]-N-(2-hydroxy-2-methyl-propyl)-acetamide;
CIS-2-[1-(Cyclobutyl-methyl)-8-dimethylamino-2-oxo-8-phenyl-1,3-diazaspiro[4.5]decan-3-yl]-N-(2-morpholin-4-yl-2-oxo-ethyl)-acetamide;
CIS-2-[1-(Cyclobutyl-methyl)-8-dimethylamino-2-oxo-8-phenyl-1,3-diazaspiro[4.5]decan-3-yl]-N-[2-(2-hydroxy-ethoxy)-ethyl]-acetamide;
CIS-2-[[2-[1-(Cyclobutyl-methyl)-8-dimethylamino-2-oxo-8-phenyl-1,3-diazaspiro[4.5]decan-3-yl]-acetyl]amino]-N-methyl-acetamide;
CIS-2-[1-(Cyclobutyl-methyl)-8-dimethylamino-2-oxo-8-phenyl-1,3-diazaspiro[4.5]decan-3-yl]-N-[2-(methanesulfonamido)-ethyl]-acetamide;
CIS-2-[1-(Cyclobutyl-methyl)-8-dimethylamino-2-oxo-8-phenyl-1,3-diazaspiro[4.5]decan-3-yl]-N-[(1-hydroxy-cyclopentyl)-methyl]-acetamide;
CIS-2-[1-(Cyclobutyl-methyl)-8-dimethylamino-2-oxo-8-phenyl-1,3-diazaspiro[4.5]decan-3-yl]-N-[(4-hydroxy-cyclohexyl)-methyl]-acetamide;
CIS-2-[1-(Cyclobutyl-methyl)-8-dimethylamino-2-oxo-8-phenyl-1,3-diazaspiro[4.5]decan-3-yl]-N-[2-(2-methoxy-ethoxy)-ethyl]-acetamide;
CIS-2-[1-(Cyclobutyl-methyl)-8-dimethylamino-2-oxo-8-phenyl-1,3-diazaspiro[4.5]decan-3-yl]-N-[2-(dimethylamino)ethyl]-acetamide;
CIS-2-[1-(Cyclobutyl-methyl)-8-[methyl-(2-methyl-propyl)-amino]-2-oxo-8-phenyl-1,3-diazaspiro[4.5]decan-3-yl]-N-methyl-acetamide;
CIS-2-[1-(Cyclobutyl-methyl)-8-dimethylamino-2-oxo-8-phenyl-1,3-diazaspiro[4.5]decan-3-yl]-N-methyl-acetamide;
CIS-2-[1-(Cyclobutyl-methyl)-8-dimethylamino-2-oxo-8-phenyl-1,3-diazaspiro[4.5]decan-3-yl]-N-pyrimidin-4-yl-acetamide;
CIS-2-[1-(Cyclobutyl-methyl)-8-dimethylamino-2-oxo-8-phenyl-1,3-diazaspiro[4.5]decan-3-yl]-N-(6-methylpyridin-2-yl)-acetamide;
CIS-2-[1-(Cyclobutyl-methyl)-8-dimethylamino-2-oxo-8-phenyl-1,3-diazaspiro[4.5]decan-3-yl]-N-pyridazin-3-yl-acetamide;
CIS-2-[1-(Cyclobutyl-methyl)-8-dimethylamino-2-oxo-8-phenyl-1,3-diazaspiro[4.5]decan-3-yl]-N-pyrimidin-5-yl-acetamide;
CIS-2-[1-(Cyclobutyl-methyl)-8-dimethylamino-2-oxo-8-phenyl-1,3-diazaspiro[4.5]decan-3-yl]-N-pyridazin-4-yl-acetamide;
CIS-2-[1-(Cyclobutyl-methyl)-8-dimethylamino-2-oxo-8-phenyl-1,3-diazaspiro[4.5]decan-3-yl]-N-(6-methoxy-pyrimidin-4-yl)-acetamide;
CIS-2-[1-(Cyclobutyl-methyl)-8-dimethylamino-2-oxo-8-phenyl-1,3-diazaspiro[4.5]decan-3-yl]-N-(2-methylpyridin-4-yl)-acetamide;
CIS-2-[8-Dimethylamino-1-[(1-hydroxy-cyclobutyl)-methyl]-2-oxo-8-phenyl-1,3-diazaspiro[4.5]decan-3-yl]-N-pyridin-4-yl-acetamide;
CIS-2-[8-Dimethylamino-1-[(1-hydroxy-cyclobutyl)-methyl]-2-oxo-8-phenyl-1,3-diazaspiro[4.5]decan-3-yl]-N-(oxetan-3-yl)-acetamide;
CIS-2-[8-Dimethylamino-1-[(1-hydroxy-cyclobutyl)-methyl]-2-oxo-8-phenyl-1,3-diazaspiro[4.5]decan-3-yl]-N-(2-methoxy-ethyl)-acetamide;
CIS-2-[1-[(1-Hydroxy-cyclobutyl)-methyl]-8-methylamino-2-oxo-8-phenyl-1,3-diazaspiro[4.5]decan-3-yl]-N-(oxetan-3-yl)-acetamide;
CIS-2-[1-[(1-Hydroxy-cyclobutyl)-methyl]-8-methylamino-2-oxo-8-phenyl-1,3-diazaspiro[4.5]decan-3-yl]-N-(2-methoxy-ethyl)-acetamide;
CIS-2-[8-Dimethylamino-1-(3-methoxy-propyl)-2-oxo-8-phenyl-1,3-diazaspiro[4.5]decan-3-yl]-N-(4-methoxy-pyridin-2-yl)-acetamide;
CIS-2-[8-Dimethylamino-1-(3-methoxy-propyl)-2-oxo-8-phenyl-1,3-diazaspiro[4.5]decan-3-yl]-N-(pyrimidin-4-yl-methyl)-acetamide;
CIS-8-Dimethylamino-3-[2-(1,1-dioxo-[1,4]thiazinan-4-yl)-2-oxo-ethyl]-8-phenyl-1-propyl-1,3-diazaspiro[4.5]decan-2-one;
CIS-2-[8-Dimethylamino-1-[(1-hydroxy-cyclobutyl)-methyl]-2-oxo-8-phenyl-1,3-diazaspiro[4.5]decan-3-yl]-N-pyridin-2-yl-acetamide;

CIS-2-[1-[(1-Cyano-cyclobutyl)-methyl]-8-dimethyl-amino-2-oxo-8-phenyl-1,3-diazaspiro[4.5]decan-3-yl]-acetamide;
CIS-2-[[2-[1-[(1-Cyano-cyclobutyl)-methyl]-8-dimethyl-amino-2-oxo-8-phenyl-1,3-diazaspiro[4.5]decan-3-yl]-acetyl]amino]-acetamide;
CIS-2-[1-[(1-Hydroxy-cyclobutyl)-methyl]-8-methyl-amino-2-oxo-8-phenyl-1,3-diazaspiro[4.5]decan-3-yl]-N-methyl-acetamide;
CIS-3-[2-(1,1-Dioxo-[1,4]thiazinan-4-yl)-2-oxo-ethyl]-8-methylamino-8-phenyl-1-propyl-1,3-diazaspiro[4.5]decan-2-one;
CIS-2-[1-(Cyclobutyl-methyl)-8-dimethylamino-2-oxo-8-phenyl-1,3-diazaspiro[4.5]decan-3-yl]-N-pyridin-2-yl-acetamide;
CIS-8-Dimethylamino-1-[(1-hydroxy-cyclobutyl)-methyl]-3-(2-morpholin-4-yl-2-oxo-ethyl)-8-phenyl-1,3-diazaspiro[4.5]decan-2-one;
CIS-2-[1-[(1-Hydroxy-cyclobutyl)-methyl]-8-methyl-amino-2-oxo-8-phenyl-1,3-diazaspiro[4.5]decan-3-yl]-acetamide;
CIS-1-(Cyclobutyl-methyl)-8-dimethylamino-3-(2-morpholin-4-yl-2-oxo-ethyl)-8-phenyl-1,3-diazaspiro[4.5]decan-2-one;
CIS-2-[1-(Cyclobutyl-methyl)-8-dimethylamino-2-oxo-8-phenyl-1,3-diazaspiro[4.5]decan-3-yl]-N-(4-methyl-sulfanyl-pyridin-2-yl)-acetamide;
CIS-3-[2-(1,1-Dioxo-[1,4]thiazinan-4-yl)-2-oxo-ethyl]-8-methylamino-8-phenyl-1,3-diazaspiro[4.5]decan-2-one;
CIS-2-(8-Methylamino-2-oxo-8-phenyl-1,3-diazaspiro[4.5]decan-3-yl)-acetamide;
CIS-2-(8-Dimethylamino-2-oxo-8-phenyl-1,3-diazaspiro[4.5]decan-3-yl)-acetamide;
CIS-3-[2-(1,1-Dioxo-[1,4]thiazinan-4-yl)-2-oxo-ethyl]-8-ethylamino-8-phenyl-1,3-diazaspiro[4.5]decan-2-one;
TRANS-3-[2-(1,1-Dioxo-[1,4]thiazinan-4-yl)-2-oxo-ethyl]-8-ethylamino-8-phenyl-1,3-diazaspiro[4.5]decan-2-one;
CIS-2-[1-(Cyclobutyl-methyl)-8-methylamino-2-oxo-8-phenyl-1,3-diazaspiro[4.5]decan-3-yl]-N-methyl-acetamide;
CIS-2-(8-Ethylamino-2-oxo-8-phenyl-1,3-diazaspiro[4.5]decan-3-yl)-acetamide;
TRANS-2-(8-Ethylamino-2-oxo-8-phenyl-1,3-diazaspiro[4.5]decan-3-yl)-acetamide;
CIS-2-(8-Dimethylamino-2-oxo-8-phenyl-1,3-diazaspiro[4.5]decan-3-yl)-N-(2-hydroxy-ethyl)-N-methyl-acetamide;
CIS-8-Dimethylamino-3-[2-(1,1-dioxo-[1,4]thiazinan-4-yl)-2-oxo-ethyl]-1-[(1-hydroxy-cyclobutyl)-methyl]-8-phenyl-1,3-diazaspiro[4.5]decane-2,4-dione;
CIS-2-(8-Dimethylamino-2-oxo-8-phenyl-1,3-diazaspiro[4.5]decan-3-yl)-N-phenyl-acetamide;
CIS-N-(Carbamoyl-methyl)-2-[1-(cyclopropyl-methyl)-8-dimethylamino-2-oxo-8-phenyl-1,3-diazaspiro[4.5]decan-3-yl]-N-methyl-acetamide;
CIS-2-(8-Dimethylamino-2,4-dioxo-8-phenyl-1,3-diazaspiro[4.5]decan-3-yl)-N-phenyl-acetamide;
CIS-2-[1-(Cyclobutyl-methyl)-8-dimethylamino-2-oxo-8-phenyl-1,3-diazaspiro[4.5]decan-3-yl]-acetamide;
CIS-2-[8-Dimethylamino-1-[(1-hydroxy-cyclobutyl)-methyl]-2-oxo-8-phenyl-1,3-diazaspiro[4.5]decan-3-yl]-N-[2-[2-[2-(2-methoxy-ethoxy)-ethoxy]-ethoxy]-ethyl]-acetamide;
CIS-3-[2-(1,1-Dioxo-[1,4]thiazinan-4-yl)-2-oxo-ethyl]-1-[(1-hydroxy-cyclobutyl)-methyl]-8-methyl amino-8-phenyl-1,3-diazaspiro[4.5]decane-2,4-dione;
CIS-2-(8-Dimethylamino-2-oxo-8-phenyl-1,3-diazaspiro[4.5]decan-3-yl)-N-[2-[2-[2-(2-methoxy-ethoxy)-ethoxy]-ethoxy]-ethyl]-acetamide;
CIS-N-(Carbamoyl-methyl)-N-methyl-2-(8-methyl-amino-2-oxo-8-phenyl-1,3-diazaspiro[4.5]decan-3-yl)-acetamide;
CIS-N-(Carbamoyl-methyl)-2-(8-dimethylamino-2-oxo-8-phenyl-1,3-diazaspiro[4.5]decan-3-yl)-N-methyl-acetamide;
CIS-N-(Carbamoyl-methyl)-2-[8-dimethylamino-1-(oxetan-3-yl-methyl)-2-oxo-8-phenyl-1,3-diazaspiro[4.5]decan-3-yl]-N-methyl-acetamide;
CIS-N-(2-Hydroxy-ethyl)-N-methyl-2-(8-methylamino-2-oxo-8-phenyl-1,3-diazaspiro[4.5]decan-3-yl)-acetamide;
CIS-2-[1-(Cyclopropyl-methyl)-8-dimethylamino-2-oxo-8-phenyl-1,3-diazaspiro[4.5]decan-3-yl]-acetamide;
CIS-2-[1-(Cyclopropyl-methyl)-8-dimethylamino-2-oxo-8-phenyl-1,3-diazaspiro[4.5]decan-3-yl]-N-(2-hydroxy-ethyl)-acetamide;
CIS-2-[1-(Cyclobutyl-methyl)-8-dimethylamino-8-(3-fluorophenyl)-2-oxo-1,3-diazaspiro[4.5]decan-3-yl]-N-(2-hydroxy-ethyl)-N-methyl-acetamide;
CIS-2-[1-(Cyclobutyl-methyl)-8-dimethylamino-8-(3-fluorophenyl)-2-oxo-1,3-diazaspiro[4.5]decan-3-yl]-acetic acid tert-butyl ester;
CIS-2-[1-(Cyclopropyl-methyl)-8-dimethylamino-2-oxo-8-phenyl-1,3-diazaspiro[4.5]decan-3-yl]-N-(2-hydroxy-ethyl)-N-methyl-acetamide;
CIS-2-[1-(Cyclopropyl-methyl)-8-dimethylamino-2-oxo-8-phenyl-1,3-diazaspiro[4.5]decan-3-yl]-N-(2-methyl-sulfonyl-ethyl)-acetamide;
CIS-N-(Carbamoyl-methyl)-2-[1-(cyclobutyl-methyl)-8-dimethylamino-8-(3-fluorophenyl)-2-oxo-1,3-diazaspiro[4.5]decan-3-yl]-N-methyl-acetamide;
CIS-1-[2-[8-Dimethylamino-1-[(1-hydroxy-cyclobutyl)-methyl]-2-oxo-8-phenyl-1,3-diazaspiro[4.5]decan-3-yl]-acetyl]-piperidine-4-carboxylic acid amide;
CIS-8-Dimethylamino-1-[(1-hydroxy-cyclobutyl)-methyl]-3-[2-(4-methylsulfonyl-piperidin-1-yl)-2-oxo-ethyl]-8-phenyl-1,3-diazaspiro[4.5]decan-2-one;
CIS-2-[1-(Cyclobutyl-methyl)-8-dimethylamino-8-(3-fluorophenyl)-2-oxo-1,3-diazaspiro[4.5]decan-3-yl]-N-(2-hydroxy-ethyl)-acetamide;
TRANS-2-[1-(Cyclobutyl-methyl)-8-dimethylamino-2-oxo-8-phenyl-1,3-diazaspiro[4.5]decan-3-yl]-N-(2-hydroxy-ethyl)-acetamide;
TRANS-N-(Carbamoyl-methyl)-2-[1-(cyclobutyl-methyl)-8-dimethylamino-2-oxo-8-phenyl-1,3-diazaspiro[4.5]decan-3-yl]-N-methyl-acetamide;
CIS-8-Dimethylamino-1-[(1-hydroxy-cyclobutyl)-methyl]-3-[2-(4-hydroxy-4-methyl-piperidin-1-yl)-2-oxo-ethyl]-8-phenyl-1,3-diazaspiro[4.5]decan-2-one;
CIS-2-[1-(Cyclobutyl-methyl)-8-dimethylamino-8-(4-fluorophenyl)-2-oxo-1,3-diazaspiro[4.5]decan-3-yl]-N-(2-hydroxy-ethyl)-acetamide;
TRANS-1-(Cyclopropyl-methyl)-8-dimethylamino-3-(2-morpholin-4-yl-2-oxo-ethyl)-8-phenyl-1,3-diazaspiro[4.5]decan-2-one;
TRANS-8-Dimethylamino-3-(2-morpholin-4-yl-2-oxo-ethyl)-8-phenyl-1,3-diazaspiro[4.5]decan-2-one;
CIS-2-[1-(Cyclobutyl-methyl)-8-dimethylamino-8-(4-fluorophenyl)-2-oxo-1,3-diazaspiro[4.5]decan-3-yl]-N-(2-hydroxy-ethyl)-N-methyl-acetamide;

CIS-N-(Carbamoyl-methyl)-2-[1-(cyclobutyl-methyl)-8-dimethylamino-8-(4-fluorophenyl)-2-oxo-1,3-diaz-aspiro[4.5]decan-3-yl]-N-methyl-acetamide;

CIS-1-(Cyclopropyl-methyl)-8-dimethylamino-3-[2-(4-hydroxy-4-methyl-piperidin-1-yl)-2-oxo-ethyl]-8-phenyl-1,3-diazaspiro[4.5]decan-2-one;

CIS-1-[2-[1-(Cyclopropyl-methyl)-8-dimethylamino-2-oxo-8-phenyl-1,3-diazaspiro[4.5]decan-3-yl]-acetyl]-piperidine-4-carboxylic acid amide;

TRANS-2-[1-(Cyclopropyl-methyl)-8-dimethylamino-2-oxo-8-phenyl-1,3-diazaspiro[4.5]decan-3-yl]-acetamide;

TRANS-2-[1-(Cyclopropyl-methyl)-8-dimethylamino-2-oxo-8-phenyl-1,3-diazaspiro[4.5]decan-3-yl]-N-methyl-acetamide;

TRANS-1-(Cyclopropyl-methyl)-8-dimethylamino-3-[2-(1,1-dioxo-[1,4]thiazinan-4-yl)-2-oxo-ethyl]-8-phenyl-1,3-diazaspiro[4.5]decan-2-one;

CIS-1-(Cyclopropyl-methyl)-8-dimethylamino-3-[2-(4-methylsulfonyl-piperidin-1-yl)-2-oxo-ethyl]-8-phenyl-1,3-diazaspiro[4.5]decan-2-one;

CIS-8-Dimethylamino-3-[2-(1,1-dioxo-[1,4]thiazinan-4-yl)-2-oxo-ethyl]-1-[(1-hydroxy-cyclobutyl)-methyl]-8-phenyl-1,3-diazaspiro[4.5]decan-2-one;

TRANS-2-(8-Dimethylamino-2-oxo-8-phenyl-1,3-diazaspiro[4.5]decan-3-yl)-acetamide;

TRANS-8-Dimethylamino-3-[2-(1,1-dioxo-[1,4]thiazinan-4-yl)-2-oxo-ethyl]-8-phenyl-1,3-diazaspiro[4.5]decan-2-one;

CIS-8-(dimethylamino)-8-phenyl-1-(2,2,2-trifluoroethyl)-3-(2-(trifluoromethyl)pyrimidin-5-yl)-1,3-diazaspiro[4.5]decan-2-one; and CIS-8-(dimethylamino)-8-phenyl-3-(2-(trifluoromethyl)pyrimidin-5-yl)-1-(3,3,3-trifluoropropyl)-1,3-diazaspiro[4.5]decan-2-one;

and the physiologically acceptable salts thereof.

29. A medicament comprising a compound according to claim 1.

30. A method of treating pain in a patient in need thereof, said method comprising administering to said patient an effective amount therefor of at least one compound according to claim 1.

31. A method of treating a disorder selected from the group consisting of neurodegenerative disorders, neuroinflammatory disorders, neuropsychiatric disorders, and substance abuse/dependence, said method comprising administering to a patient in need thereof an effective amount therefor of at least one compound according to claim 1.

* * * * *